US012714730B2

(12) United States Patent
Culler et al.

(10) Patent No.: US 12,714,730 B2
(45) Date of Patent: Aug. 25, 2026

(54) COMPOSITIONS FOR MODULATING GUT MICROFLORA POPULATIONS, ENHANCING DRUG POTENCY AND TREATING CANCER, AND METHODS FOR MAKING AND USING SAME

(71) Applicant: PERSEPHONE BIOSCIENCES, San Diego, CA (US)

(72) Inventors: Stephanie J. Culler, Del Mar, CA (US); Robert J. Haselbeck, San Diego, CA (US); Steven Van Dien, San Diego, CA (US); Anandh Swaminathan, San Diego, CA (US)

(73) Assignee: PERSEPHONE BIOSCIENCES, San Diego, CA (US)

( * ) Notice: Subject to any disclaimer, the term of this patent is extended or adjusted under 35 U.S.C. 154(b) by 1168 days.

(21) Appl. No.: 16/981,605

(22) PCT Filed: Mar. 15, 2019

(86) PCT No.: PCT/US2019/022583
§ 371 (c)(1),
(2) Date: Sep. 16, 2020

(87) PCT Pub. No.: WO2019/178542
PCT Pub. Date: Sep. 19, 2019

(65) Prior Publication Data

US 2021/0038654 A1 Feb. 11, 2021

Related U.S. Application Data

(60) Provisional application No. 62/644,203, filed on Mar. 16, 2018, provisional application No. 62/738,958, (Continued)

(51) Int. Cl.

| | |
|---|---|
| ***A61K 35/74*** | (2015.01) |
| ***A61K 9/00*** | (2006.01) |
| ***A61K 9/28*** | (2006.01) |
| ***A61K 9/48*** | (2006.01) |
| ***A61K 35/00*** | (2006.01) |
| ***A61K 35/741*** | (2015.01) |
| ***A61K 35/742*** | (2015.01) |
| ***A61K 35/744*** | (2015.01) |
| ***A61K 35/745*** | (2015.01) |
| ***A61K 35/747*** | (2015.01) |
| ***A61K 39/00*** | (2006.01) |
| ***A61K 39/395*** | (2006.01) |
| ***A61K 40/11*** | (2025.01) |
| ***A61K 40/31*** | (2025.01) |
| ***A61K 40/42*** | (2025.01) |
| ***A61P 35/00*** | (2006.01) |

(Continued)

(52) U.S. Cl.
CPC ............ *A61K 35/74* (2013.01); *A61K 9/0031* (2013.01); *A61K 9/0053* (2013.01); *A61K 9/0056* (2013.01); *A61K 9/2846* (2013.01); *A61K 9/4808* (2013.01); *A61K 9/4816* (2013.01); *A61K 9/4875* (2013.01); *A61K 9/4891* (2013.01); *A61K 35/741* (2013.01); *A61K 35/742* (2013.01); *A61K 35/744* (2013.01); *A61K 35/745* (2013.01); *A61K 35/747* (2013.01); *A61K 39/3955* (2013.01); *A61K 40/11* (2025.01); *A61K 40/31* (2025.01); *A61K 40/42* (2025.01); *A61P 35/00* (2018.01); *C07K 16/2818* (2013.01); *C07K 16/2827* (2013.01); *C12N 1/20* (2013.01); *A61K 2035/11* (2013.01); *A61K 2039/507* (2013.01)

(58) Field of Classification Search
None
See application file for complete search history.

(56) References Cited

U.S. PATENT DOCUMENTS

| | | | | |
|---|---|---|---|---|
| 2002/0151560 | A1* | 10/2002 | Jacobs | A61P 31/10 514/28 |
| 2020/0129569 | A1* | 4/2020 | Wargo | A61K 35/04 |
| 2022/0378855 | A1 | 12/2022 | Culler | |

FOREIGN PATENT DOCUMENTS

| | | | | |
|---|---|---|---|---|
| WO | WO-2016063263 A2 * | 4/2016 | | A61K 35/741 |
| WO | WO-2019143883 A2 * | 7/2019 | | A61K 45/06 |
| WO | WO-2019169160 A1 * | 9/2019 | | A61P 35/00 |

OTHER PUBLICATIONS

Lim ("The Principles of Engineering Immune Cells to Treat Cancer", Cell, vol. 168(4) (Feb. 2017), p. 724-740) (Year: 2017).*

(Continued)

*Primary Examiner* — Sin J Lee
(74) *Attorney, Agent, or Firm* — Gregory P. Einhorn; Greer, Burns & Crain, Ltd.

(57) ABSTRACT

In alternative embodiments, provided are compositions, including products of manufacture and kits, and methods, for or comprising administering to an individual in need thereof an inhibitor of an inhibitory immune checkpoint molecule and/or a stimulatory immune checkpoint molecule and a formulation, wherein the formulation comprises at least two different species or genera of non-pathogenic, live bacteria, and each of the non-pathogenic, live bacteria comprise non-pathogenic colony forming live bacteria, a plurality of non-pathogenic germinable bacterial spores, or a combination thereof, and optionally the non-pathogenic bacteria or non-pathogenic bacteria arising from germination of the germinable spores can individually or together metabolize urolithin A from ellagic acid, or can individually or together synthesize urolithin A.

21 Claims, 95 Drawing Sheets

Specification includes a Sequence Listing.

Related U.S. Application Data filed on Sep. 28, 2018, provisional application No. 62/742,024, filed on Oct. 5, 2018, provisional application No. 62/749,482, filed on Oct. 23, 2018, provisional application No. 62/784,028, filed on Dec. 21, 2018, provisional application No. 62/789,936, filed on Jan. 8, 2019, provisional application No. 62/797,062, filed on Jan. 25, 2019, provisional application No. 62/814,220, filed on Mar. 5, 2019.

(51) Int. Cl.

| | |
|---|---|
| ***C07K 16/28*** | (2006.01) |
| ***C12N 1/20*** | (2006.01) |

(56) References Cited

OTHER PUBLICATIONS

Ismail et al ("Ellagitannins in Cancer Chemoprevention and Therapy", Toxins (Basel), vol. 8(5), (May 2016), p. 1-22) (Year: 2016).*

Lawson, P., et al, Reclassification of Ruminococcus Obeum as Blautia Obeum comb. nov) International J. Systematic and Evolutionary Microbiol. (2015), pp. 789-793, vol. 65.

Valentino, V., et al., "Genomic features and prevalence of *Ruminococcus* species in humans are associated with age, lifestyle, and disease", Cell Reports, Dec. 24, 2024, pp. 1-15, vol. 43, No. 12.

Crost, E., et al., "Mechanistic Insights Into the Cross-Feeding of Ruminococcus gnavus and Ruminococcus bromii on Host and Dietary Carbohydrates", Front Microbiol, Nov. 5, 2018,, pp. 1-13, vol. 5, No. 9.

Crost, E., et al., "Ruminococcus gnavus: friend or foe for human health", FEMS Microbiol Reviews, Apr. 4, 2023, pp. 1-23, vol. 47, No. 2.

Ze, X., et al., "Unique Organization of Extracellular Amylases into Amylosomes in the Resistant Starch-Utilizing Human Colonic Firmicutes Bacterium Ruminococcus bromii", ASM Journals, mBio, Sep. 29, 2015, vol. 6, No. 5.

Henke, M., et al., "Ruminococcus gnavus, a member of the human gut microbiome associated with Crohn's disease, produces an inflammatory polysaccharide", Proc Natl Acad Sci USA, Jun. 25, 2019, pp. 12672-12677, vol. 116, No. 26.

* cited by examiner

Ellagitannin

Hexahydroxydiphenic Acid

Ellagic Acid

Luteic

Urolithin M5

Urolithin D

Urolithin E

Urolithin M6

Urolithin M7

Urolithin C

Isourolithin A

Urolithin A

Urolithin B

Table 2

D_0__Bacteria;D_1__Actinobacteria;D_2__Actinobacteria;D_3__Bifidobacteriales;D_4__Bifidobacteriaceae;D_5__Bifidobacterium
D_0__Bacteria;D_1__Actinobacteria;D_2__Actinobacteria;D_3__Glycomycetales;D_4__Glycomycetaceae;D_5__Glycomyces
D_0__Bacteria;D_1__Actinobacteria;D_2__Actinobacteria;D_3__Kineosporiales;D_4__Kineosporiaceae;D_5__Kineococcus
D_0__Bacteria;D_1__Actinobacteria;D_2__Actinobacteria;D_3__Micrococcales;D_4__Cellulomonadaceae;D_5__Cellulomonas
D_0__Bacteria;D_1__Actinobacteria;D_2__Actinobacteria;D_3__Micrococcales;D_4__Cellulomonadaceae;__
D_0__Bacteria;D_1__Actinobacteria;D_2__Actinobacteria;D_3__Micrococcales;D_4__Microbacteriaceae;D_5__Leucobacter
D_0__Bacteria;D_1__Actinobacteria;D_2__Actinobacteria;D_3__Micrococcales;D_4__Microbacteriaceae;__
D_0__Bacteria;D_1__Actinobacteria;D_2__Actinobacteria;D_3__Micrococcales;D_4__Micrococcaceae;D_5__Pseudarthrobacter
D_0__Bacteria;D_1__Actinobacteria;D_2__Actinobacteria;D_3__Micrococcales;D_4__Promicromonosporaceae;D_5__Promicromonospora
D_0__Bacteria;D_1__Actinobacteria;D_2__Actinobacteria;D_3__Micrococcales;D_4__Sanguibacteraceae;D_5__Sanguibacter
D_0__Bacteria;D_1__Actinobacteria;D_2__Actinobacteria;D_3__Micrococcales;__;__
D_0__Bacteria;D_1__Actinobacteria;D_2__Actinobacteria;D_3__Micromonosporales;D_4__Micromonosporaceae;D_5__Luedemannella
D_0__Bacteria;D_1__Actinobacteria;D_2__Actinobacteria;D_3__Propionibacteriales;D_4__Propionibacteriaceae;D_5__Propionibacterium
D_0__Bacteria;D_1__Actinobacteria;D_2__Actinobacteria;D_3__Pseudonocardiales;D_4__Pseudonocardiaceae;D_5__Saccharopolyspora
D_0__Bacteria;D_1__Actinobacteria;D_2__Actinobacteria;D_3__Pseudonocardiales;D_4__Pseudonocardiaceae;__
D_0__Bacteria;D_1__Actinobacteria;D_2__Actinobacteria;D_3__Streptomycetales;D_4__Streptomycetaceae;D_5__Streptomyces
D_0__Bacteria;D_1__Actinobacteria;D_2__Actinobacteria;D_3__Streptomycetales;D_4__Streptomycetaceae;__
D_0__Bacteria;D_1__Actinobacteria;D_2__Actinobacteria;D_3__Streptosporangiales;D_4__Nocardiopsaceae;D_5__Nocardiopsis
D_0__Bacteria;D_1__Actinobacteria;D_2__Actinobacteria;D_3__Streptosporangiales;D_4__Nocardiopsaceae;D_5__Thermobifida
D_0__Bacteria;D_1__Actinobacteria;D_2__Coriobacteriia;D_3__Coriobacteriales;D_4__Coriobacteriaceae;D_5__Adlercreutzia
D_0__Bacteria;D_1__Actinobacteria;D_2__Coriobacteriia;D_3__Coriobacteriales;D_4__Coriobacteriaceae;D_5__Collinsella
D_0__Bacteria;D_1__Actinobacteria;D_2__Coriobacteriia;D_3__Coriobacteriales;D_4__Coriobacteriaceae;D_5__Eggerthella
D_0__Bacteria;D_1__Actinobacteria;D_2__Coriobacteriia;D_3__Coriobacteriales;D_4__Coriobacteriaceae;D_5__Enterorhabdus
D_0__Bacteria;D_1__Actinobacteria;D_2__Coriobacteriia;D_3__Coriobacteriales;D_4__Coriobacteriaceae;D_5__Parvibacter
D_0__Bacteria;D_1__Actinobacteria;D_2__Coriobacteriia;D_3__Coriobacteriales;D_4__Coriobacteriaceae;__
D_0__Bacteria;D_1__Actinobacteria;__;__;__;__

FIG. 4

Figure 4:
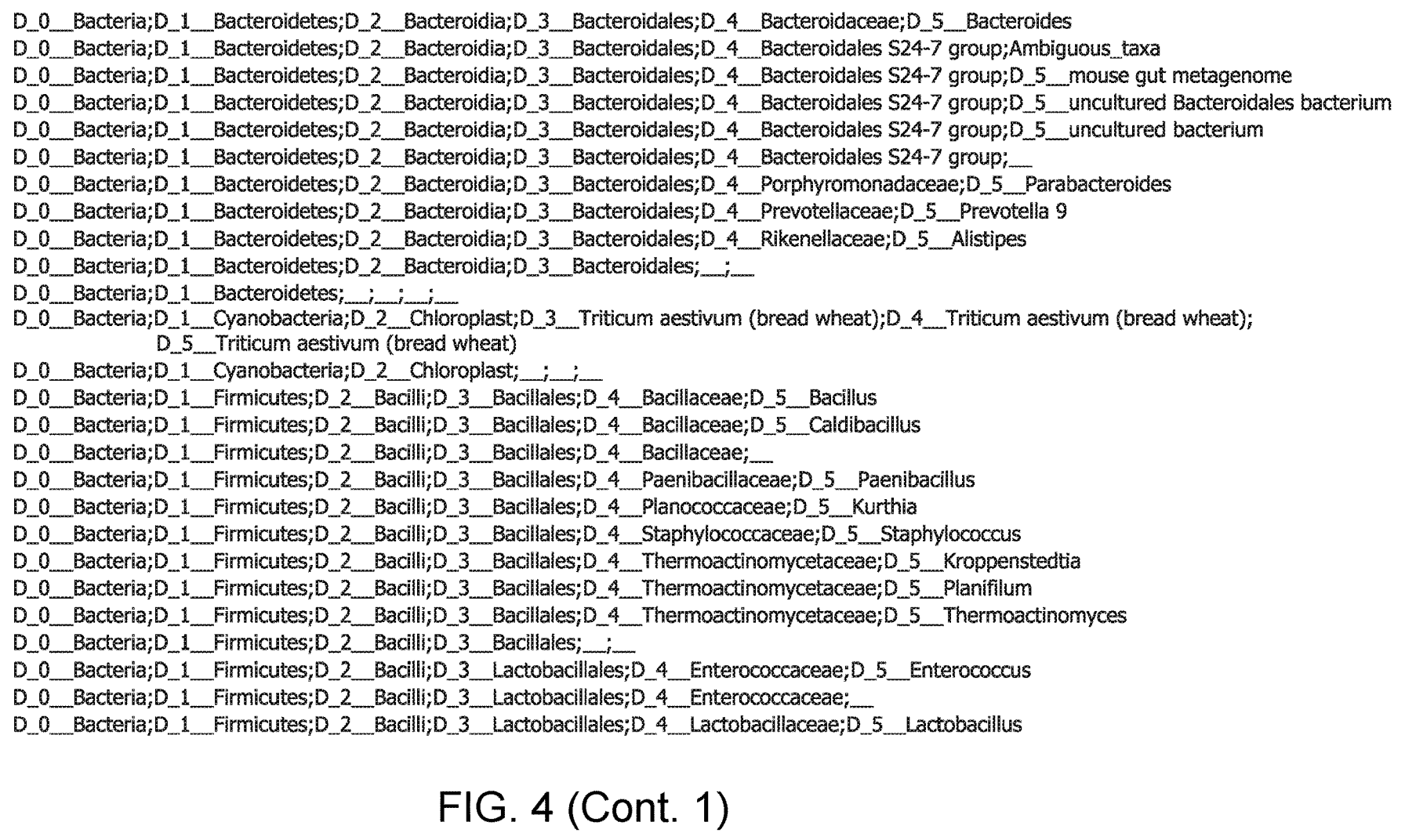

D_0__Bacteria;D_1__Bacteroidetes;D_2__Bacteroidia;D_3__Bacteroidales;D_4__Bacteroidaceae;D_5__Bacteroides
D_0__Bacteria;D_1__Bacteroidetes;D_2__Bacteroidia;D_3__Bacteroidales;D_4__Bacteroidales S24-7 group;Ambiguous_taxa
D_0__Bacteria;D_1__Bacteroidetes;D_2__Bacteroidia;D_3__Bacteroidales;D_4__Bacteroidales S24-7 group;D_5__mouse gut metagenome
D_0__Bacteria;D_1__Bacteroidetes;D_2__Bacteroidia;D_3__Bacteroidales;D_4__Bacteroidales S24-7 group;D_5__uncultured Bacteroidales bacterium
D_0__Bacteria;D_1__Bacteroidetes;D_2__Bacteroidia;D_3__Bacteroidales;D_4__Bacteroidales S24-7 group;D_5__uncultured bacterium
D_0__Bacteria;D_1__Bacteroidetes;D_2__Bacteroidia;D_3__Bacteroidales;D_4__Bacteroidales S24-7 group;__
D_0__Bacteria;D_1__Bacteroidetes;D_2__Bacteroidia;D_3__Bacteroidales;D_4__Porphyromonadaceae;D_5__Parabacteroides
D_0__Bacteria;D_1__Bacteroidetes;D_2__Bacteroidia;D_3__Bacteroidales;D_4__Prevotellaceae;D_5__Prevotella 9
D_0__Bacteria;D_1__Bacteroidetes;D_2__Bacteroidia;D_3__Bacteroidales;D_4__Rikenellaceae;D_5__Alistipes
D_0__Bacteria;D_1__Bacteroidetes;D_2__Bacteroidia;D_3__Bacteroidales;__;__
D_0__Bacteria;D_1__Bacteroidetes;__;__;__;__
D_0__Bacteria;D_1__Cyanobacteria;D_2__Chloroplast;D_3__Triticum aestivum (bread wheat);D_4__Triticum aestivum (bread wheat);
D_5__Triticum aestivum (bread wheat)
D_0__Bacteria;D_1__Cyanobacteria;D_2__Chloroplast;__;__;__
D_0__Bacteria;D_1__Firmicutes;D_2__Bacilli;D_3__Bacillales;D_4__Bacillaceae;D_5__Bacillus
D_0__Bacteria;D_1__Firmicutes;D_2__Bacilli;D_3__Bacillales;D_4__Bacillaceae;D_5__Caldibacillus
D_0__Bacteria;D_1__Firmicutes;D_2__Bacilli;D_3__Bacillales;D_4__Bacillaceae;__
D_0__Bacteria;D_1__Firmicutes;D_2__Bacilli;D_3__Bacillales;D_4__Paenibacillaceae;D_5__Paenibacillus
D_0__Bacteria;D_1__Firmicutes;D_2__Bacilli;D_3__Bacillales;D_4__Planococcaceae;D_5__Kurthia
D_0__Bacteria;D_1__Firmicutes;D_2__Bacilli;D_3__Bacillales;D_4__Staphylococcaceae;D_5__Staphylococcus
D_0__Bacteria;D_1__Firmicutes;D_2__Bacilli;D_3__Bacillales;D_4__Thermoactinomycetaceae;D_5__Kroppenstedtia
D_0__Bacteria;D_1__Firmicutes;D_2__Bacilli;D_3__Bacillales;D_4__Thermoactinomycetaceae;D_5__Planifilum
D_0__Bacteria;D_1__Firmicutes;D_2__Bacilli;D_3__Bacillales;D_4__Thermoactinomycetaceae;D_5__Thermoactinomyces
D_0__Bacteria;D_1__Firmicutes;D_2__Bacilli;D_3__Bacillales;__;__
D_0__Bacteria;D_1__Firmicutes;D_2__Bacilli;D_3__Lactobacillales;D_4__Enterococcaceae;D_5__Enterococcus
D_0__Bacteria;D_1__Firmicutes;D_2__Bacilli;D_3__Lactobacillales;D_4__Enterococcaceae;__
D_0__Bacteria;D_1__Firmicutes;D_2__Bacilli;D_3__Lactobacillales;D_4__Lactobacillaceae;D_5__Lactobacillus

FIG. 4 (Cont. 1)

Figure 4:
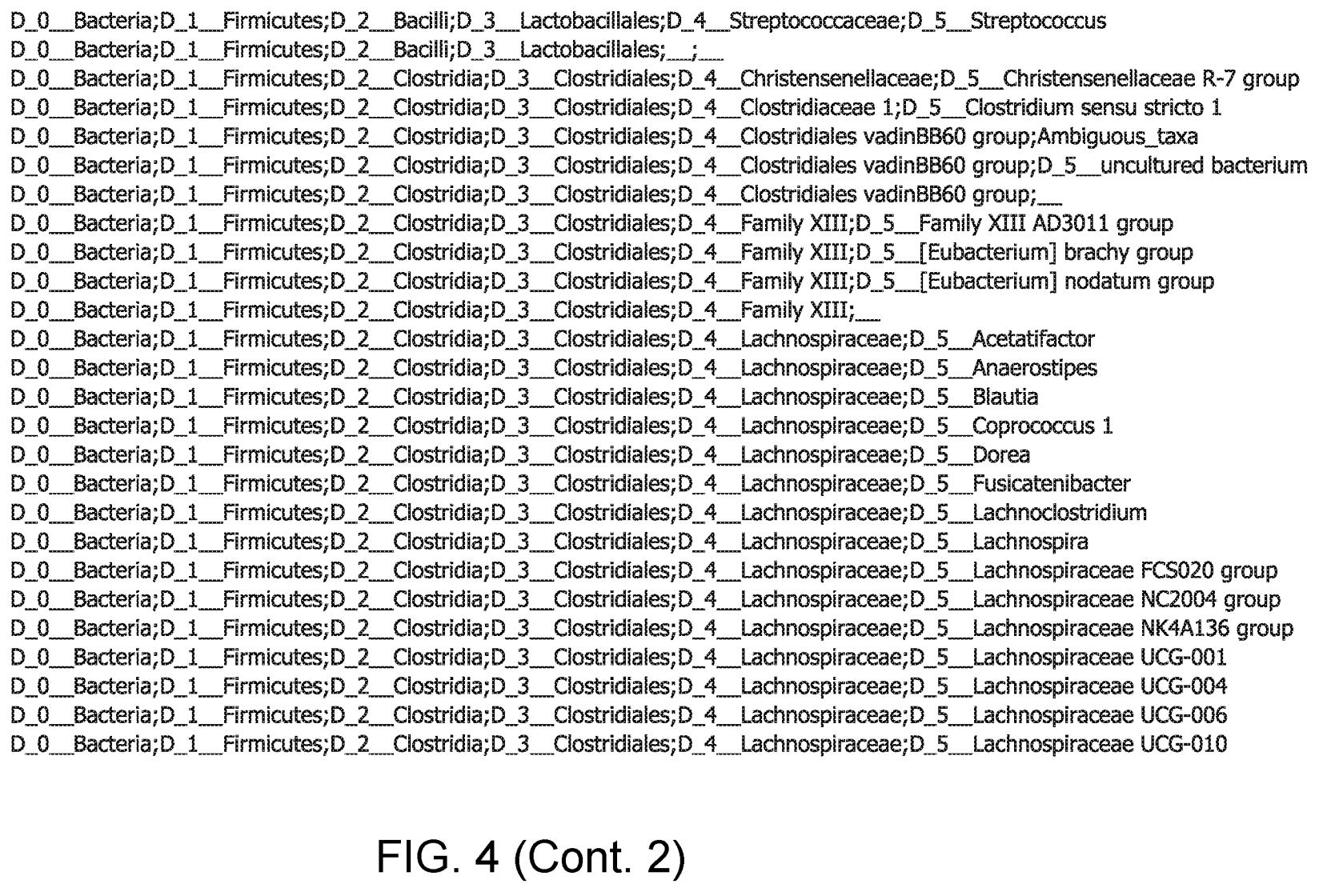

D_0__Bacteria;D_1__Firmicutes;D_2__Bacilli;D_3__Lactobacillales;D_4__Streptococcaceae;D_5__Streptococcus
D_0__Bacteria;D_1__Firmicutes;D_2__Bacilli;D_3__Lactobacillales;__;__
D_0__Bacteria;D_1__Firmicutes;D_2__Clostridia;D_3__Clostridiales;D_4__Christensenellaceae;D_5__Christensenellaceae R-7 group
D_0__Bacteria;D_1__Firmicutes;D_2__Clostridia;D_3__Clostridiales;D_4__Clostridiaceae 1;D_5__Clostridium sensu stricto 1
D_0__Bacteria;D_1__Firmicutes;D_2__Clostridia;D_3__Clostridiales;D_4__Clostridiales vadinBB60 group;Ambiguous_taxa
D_0__Bacteria;D_1__Firmicutes;D_2__Clostridia;D_3__Clostridiales;D_4__Clostridiales vadinBB60 group;D_5__uncultured bacterium
D_0__Bacteria;D_1__Firmicutes;D_2__Clostridia;D_3__Clostridiales;D_4__Clostridiales vadinBB60 group;__
D_0__Bacteria;D_1__Firmicutes;D_2__Clostridia;D_3__Clostridiales;D_4__Family XIII;D_5__Family XIII AD3011 group
D_0__Bacteria;D_1__Firmicutes;D_2__Clostridia;D_3__Clostridiales;D_4__Family XIII;D_5__[Eubacterium] brachy group
D_0__Bacteria;D_1__Firmicutes;D_2__Clostridia;D_3__Clostridiales;D_4__Family XIII;D_5__[Eubacterium] nodatum group
D_0__Bacteria;D_1__Firmicutes;D_2__Clostridia;D_3__Clostridiales;D_4__Family XIII;__
D_0__Bacteria;D_1__Firmicutes;D_2__Clostridia;D_3__Clostridiales;D_4__Lachnospiraceae;D_5__Acetatifactor
D_0__Bacteria;D_1__Firmicutes;D_2__Clostridia;D_3__Clostridiales;D_4__Lachnospiraceae;D_5__Anaerostipes
D_0__Bacteria;D_1__Firmicutes;D_2__Clostridia;D_3__Clostridiales;D_4__Lachnospiraceae;D_5__Blautia
D_0__Bacteria;D_1__Firmicutes;D_2__Clostridia;D_3__Clostridiales;D_4__Lachnospiraceae;D_5__Coprococcus 1
D_0__Bacteria;D_1__Firmicutes;D_2__Clostridia;D_3__Clostridiales;D_4__Lachnospiraceae;D_5__Dorea
D_0__Bacteria;D_1__Firmicutes;D_2__Clostridia;D_3__Clostridiales;D_4__Lachnospiraceae;D_5__Fusicatenibacter
D_0__Bacteria;D_1__Firmicutes;D_2__Clostridia;D_3__Clostridiales;D_4__Lachnospiraceae;D_5__Lachnoclostridium
D_0__Bacteria;D_1__Firmicutes;D_2__Clostridia;D_3__Clostridiales;D_4__Lachnospiraceae;D_5__Lachnospira
D_0__Bacteria;D_1__Firmicutes;D_2__Clostridia;D_3__Clostridiales;D_4__Lachnospiraceae;D_5__Lachnospiraceae FCS020 group
D_0__Bacteria;D_1__Firmicutes;D_2__Clostridia;D_3__Clostridiales;D_4__Lachnospiraceae;D_5__Lachnospiraceae NC2004 group
D_0__Bacteria;D_1__Firmicutes;D_2__Clostridia;D_3__Clostridiales;D_4__Lachnospiraceae;D_5__Lachnospiraceae NK4A136 group
D_0__Bacteria;D_1__Firmicutes;D_2__Clostridia;D_3__Clostridiales;D_4__Lachnospiraceae;D_5__Lachnospiraceae UCG-001
D_0__Bacteria;D_1__Firmicutes;D_2__Clostridia;D_3__Clostridiales;D_4__Lachnospiraceae;D_5__Lachnospiraceae UCG-004
D_0__Bacteria;D_1__Firmicutes;D_2__Clostridia;D_3__Clostridiales;D_4__Lachnospiraceae;D_5__Lachnospiraceae UCG-006
D_0__Bacteria;D_1__Firmicutes;D_2__Clostridia;D_3__Clostridiales;D_4__Lachnospiraceae;D_5__Lachnospiraceae UCG-010

FIG. 4 (Cont. 2)

Figure 4:
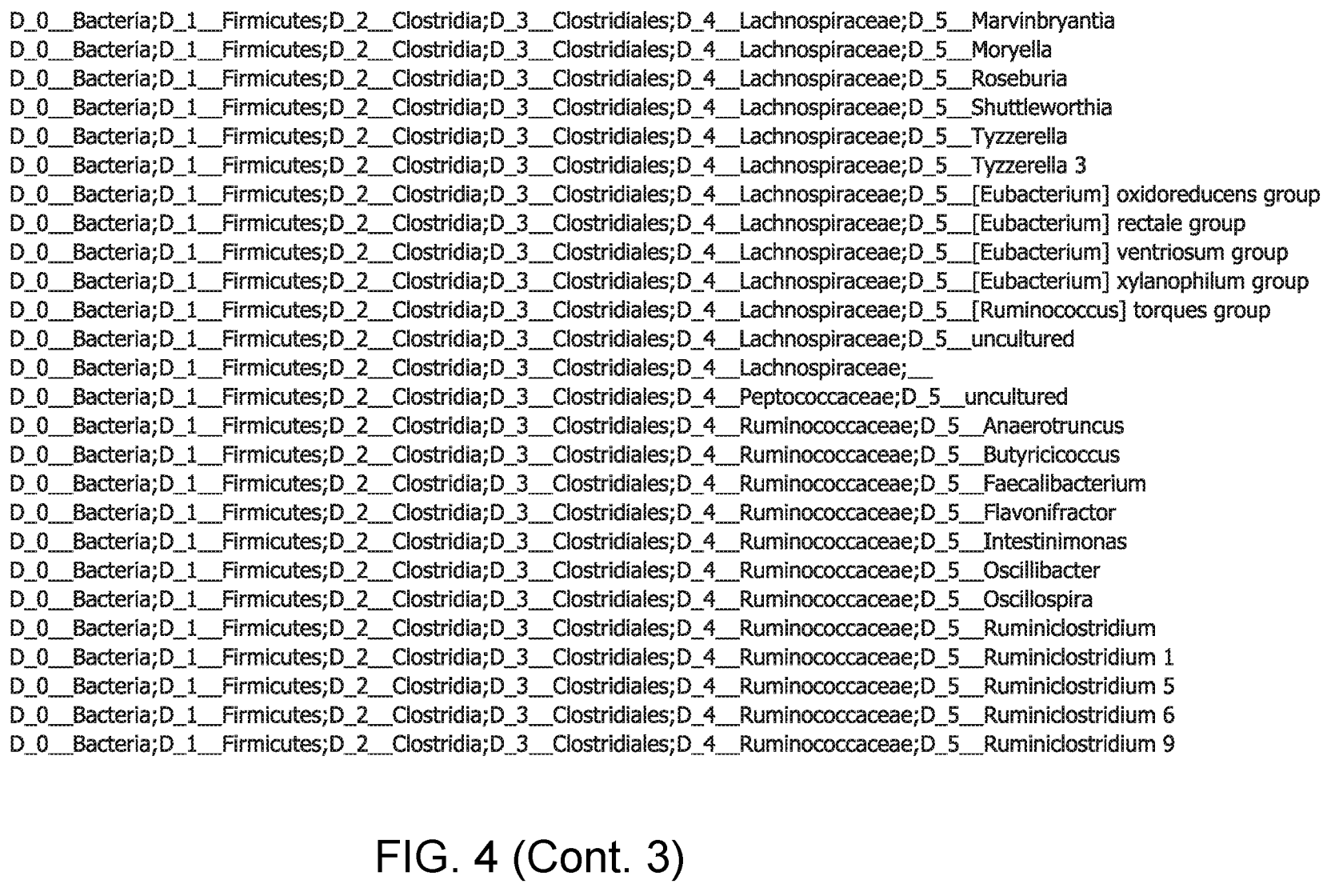

D_0__Bacteria;D_1__Firmicutes;D_2__Clostridia;D_3__Clostridiales;D_4__Lachnospiraceae;D_5__Marvinbryantia
D_0__Bacteria;D_1__Firmicutes;D_2__Clostridia;D_3__Clostridiales;D_4__Lachnospiraceae;D_5__Moryella
D_0__Bacteria;D_1__Firmicutes;D_2__Clostridia;D_3__Clostridiales;D_4__Lachnospiraceae;D_5__Roseburia
D_0__Bacteria;D_1__Firmicutes;D_2__Clostridia;D_3__Clostridiales;D_4__Lachnospiraceae;D_5__Shuttleworthia
D_0__Bacteria;D_1__Firmicutes;D_2__Clostridia;D_3__Clostridiales;D_4__Lachnospiraceae;D_5__Tyzzerella
D_0__Bacteria;D_1__Firmicutes;D_2__Clostridia;D_3__Clostridiales;D_4__Lachnospiraceae;D_5__Tyzzerella 3
D_0__Bacteria;D_1__Firmicutes;D_2__Clostridia;D_3__Clostridiales;D_4__Lachnospiraceae;D_5__[Eubacterium] oxidoreducens group
D_0__Bacteria;D_1__Firmicutes;D_2__Clostridia;D_3__Clostridiales;D_4__Lachnospiraceae;D_5__[Eubacterium] rectale group
D_0__Bacteria;D_1__Firmicutes;D_2__Clostridia;D_3__Clostridiales;D_4__Lachnospiraceae;D_5__[Eubacterium] ventriosum group
D_0__Bacteria;D_1__Firmicutes;D_2__Clostridia;D_3__Clostridiales;D_4__Lachnospiraceae;D_5__[Eubacterium] xylanophilum group
D_0__Bacteria;D_1__Firmicutes;D_2__Clostridia;D_3__Clostridiales;D_4__Lachnospiraceae;D_5__[Ruminococcus] torques group
D_0__Bacteria;D_1__Firmicutes;D_2__Clostridia;D_3__Clostridiales;D_4__Lachnospiraceae;D_5__uncultured
D_0__Bacteria;D_1__Firmicutes;D_2__Clostridia;D_3__Clostridiales;D_4__Lachnospiraceae;__
D_0__Bacteria;D_1__Firmicutes;D_2__Clostridia;D_3__Clostridiales;D_4__Peptococcaceae;D_5__uncultured
D_0__Bacteria;D_1__Firmicutes;D_2__Clostridia;D_3__Clostridiales;D_4__Ruminococcaceae;D_5__Anaerotruncus
D_0__Bacteria;D_1__Firmicutes;D_2__Clostridia;D_3__Clostridiales;D_4__Ruminococcaceae;D_5__Butyricicoccus
D_0__Bacteria;D_1__Firmicutes;D_2__Clostridia;D_3__Clostridiales;D_4__Ruminococcaceae;D_5__Faecalibacterium
D_0__Bacteria;D_1__Firmicutes;D_2__Clostridia;D_3__Clostridiales;D_4__Ruminococcaceae;D_5__Flavonifractor
D_0__Bacteria;D_1__Firmicutes;D_2__Clostridia;D_3__Clostridiales;D_4__Ruminococcaceae;D_5__Intestinimonas
D_0__Bacteria;D_1__Firmicutes;D_2__Clostridia;D_3__Clostridiales;D_4__Ruminococcaceae;D_5__Oscillibacter
D_0__Bacteria;D_1__Firmicutes;D_2__Clostridia;D_3__Clostridiales;D_4__Ruminococcaceae;D_5__Oscillospira
D_0__Bacteria;D_1__Firmicutes;D_2__Clostridia;D_3__Clostridiales;D_4__Ruminococcaceae;D_5__Ruminiclostridium
D_0__Bacteria;D_1__Firmicutes;D_2__Clostridia;D_3__Clostridiales;D_4__Ruminococcaceae;D_5__Ruminiclostridium 1
D_0__Bacteria;D_1__Firmicutes;D_2__Clostridia;D_3__Clostridiales;D_4__Ruminococcaceae;D_5__Ruminiclostridium 5
D_0__Bacteria;D_1__Firmicutes;D_2__Clostridia;D_3__Clostridiales;D_4__Ruminococcaceae;D_5__Ruminiclostridium 6
D_0__Bacteria;D_1__Firmicutes;D_2__Clostridia;D_3__Clostridiales;D_4__Ruminococcaceae;D_5__Ruminiclostridium 9

FIG. 4 (Cont. 3)

D_0__Bacteria;D_1__Firmicutes;D_2__Clostridia;D_3__Clostridiales;D_4__Ruminococcaceae;D_5__Ruminococcaceae NK4A214 group
D_0__Bacteria;D_1__Firmicutes;D_2__Clostridia;D_3__Clostridiales;D_4__Ruminococcaceae;D_5__Ruminococcaceae UCG-004
D_0__Bacteria;D_1__Firmicutes;D_2__Clostridia;D_3__Clostridiales;D_4__Ruminococcaceae;D_5__Ruminococcaceae UCG-005
D_0__Bacteria;D_1__Firmicutes;D_2__Clostridia;D_3__Clostridiales;D_4__Ruminococcaceae;D_5__Ruminococcaceae UCG-009
D_0__Bacteria;D_1__Firmicutes;D_2__Clostridia;D_3__Clostridiales;D_4__Ruminococcaceae;D_5__Ruminococcaceae UCG-013
D_0__Bacteria;D_1__Firmicutes;D_2__Clostridia;D_3__Clostridiales;D_4__Ruminococcaceae;D_5__Ruminococcaceae UCG-014
D_0__Bacteria;D_1__Firmicutes;D_2__Clostridia;D_3__Clostridiales;D_4__Ruminococcaceae;D_5__Ruminococcus 1
D_0__Bacteria;D_1__Firmicutes;D_2__Clostridia;D_3__Clostridiales;D_4__Ruminococcaceae;D_5__Subdoligranulum
D_0__Bacteria;D_1__Firmicutes;D_2__Clostridia;D_3__Clostridiales;D_4__Ruminococcaceae;D_5__[Eubacterium] coprostanoligenes group
D_0__Bacteria;D_1__Firmicutes;D_2__Clostridia;D_3__Clostridiales;D_4__Ruminococcaceae;D_5__uncultured
D_0__Bacteria;D_1__Firmicutes;D_2__Clostridia;D_3__Clostridiales;D_4__Ruminococcaceae;__
D_0__Bacteria;D_1__Firmicutes;D_2__Clostridia;D_3__Clostridiales;__;__
D_0__Bacteria;D_1__Firmicutes;D_2__Clostridia;__;__;__
D_0__Bacteria;D_1__Firmicutes;D_2__Erysipelotrichia;D_3__Erysipelotrichales;D_4__Erysipelotrichaceae;D_5__Candidatus Stoquefichus
D_0__Bacteria;D_1__Firmicutes;D_2__Erysipelotrichia;D_3__Erysipelotrichales;D_4__Erysipelotrichaceae;D_5__Erysipelatoclostridium
D_0__Bacteria;D_1__Firmicutes;D_2__Erysipelotrichia;D_3__Erysipelotrichales;D_4__Erysipelotrichaceae;D_5__Erysipelotrichaceae UCG-003
D_0__Bacteria;D_1__Firmicutes;D_2__Erysipelotrichia;D_3__Erysipelotrichales;D_4__Erysipelotrichaceae;D_5__Turicibacter
D_0__Bacteria;D_1__Firmicutes;D_2__Erysipelotrichia;D_3__Erysipelotrichales;D_4__Erysipelotrichaceae;D_5__uncultured bacterium
D_0__Bacteria;D_1__Firmicutes;D_2__Erysipelotrichia;D_3__Erysipelotrichales;D_4__Erysipelotrichaceae;__
D_0__Bacteria;D_1__Firmicutes;D_2__Negativicutes;D_3__Selenomonadales;D_4__Acidaminococcaceae;D_5__Acidaminococcus
D_0__Bacteria;D_1__Firmicutes;D_2__Negativicutes;D_3__Selenomonadales;D_4__Acidaminococcaceae;D_5__Phascolarctobacterium
D_0__Bacteria;D_1__Firmicutes;D_2__Negativicutes;D_3__Selenomonadales;D_4__Veillonellaceae;D_5__Dialister
D_0__Bacteria;D_1__Firmicutes;D_2__Negativicutes;D_3__Selenomonadales;D_4__Veillonellaceae;D_5__Sporomusa
D_0__Bacteria;D_1__Firmicutes;D_2__Negativicutes;D_3__Selenomonadales;D_4__Veillonellaceae;D_5__Veillonella
D_0__Bacteria;D_1__Firmicutes;__;__;__;__
D_0__Bacteria;D_1__Proteobacteria;D_2__Alphaproteobacteria;D_3__Rhizobiales;D_4__Aurantimonadaceae;D_5__Aureimonas

FIG. 4 (Cont. 4)

Figure 4:
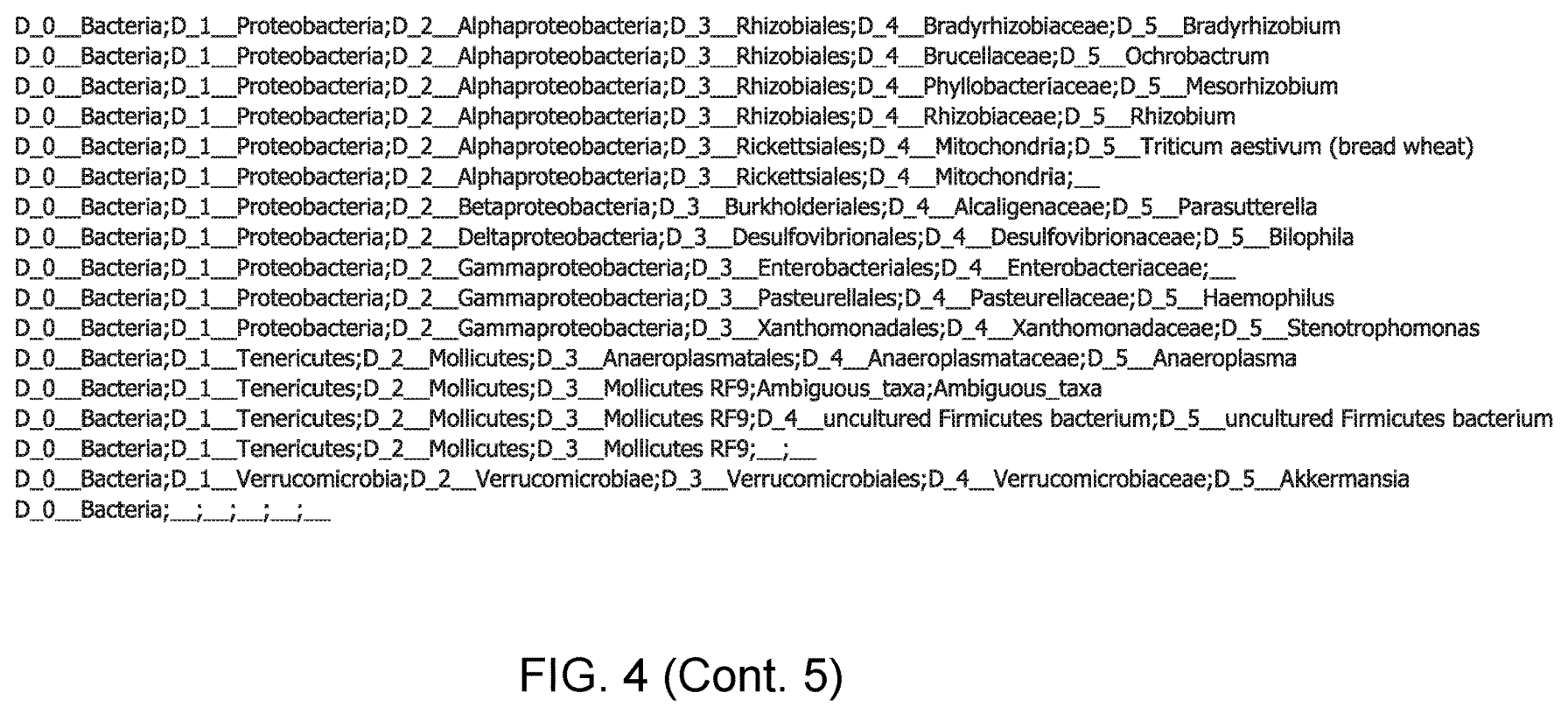

D_0__Bacteria;D_1__Proteobacteria;D_2__Alphaproteobacteria;D_3__Rhizobiales;D_4__Bradyrhizobiaceae;D_5__Bradyrhizobium
D_0__Bacteria;D_1__Proteobacteria;D_2__Alphaproteobacteria;D_3__Rhizobiales;D_4__Brucellaceae;D_5__Ochrobactrum
D_0__Bacteria;D_1__Proteobacteria;D_2__Alphaproteobacteria;D_3__Rhizobiales;D_4__Phyllobacteriaceae;D_5__Mesorhizobium
D_0__Bacteria;D_1__Proteobacteria;D_2__Alphaproteobacteria;D_3__Rhizobiales;D_4__Rhizobiaceae;D_5__Rhizobium
D_0__Bacteria;D_1__Proteobacteria;D_2__Alphaproteobacteria;D_3__Rickettsiales;D_4__Mitochondria;D_5__Triticum aestivum (bread wheat)
D_0__Bacteria;D_1__Proteobacteria;D_2__Alphaproteobacteria;D_3__Rickettsiales;D_4__Mitochondria;__
D_0__Bacteria;D_1__Proteobacteria;D_2__Betaproteobacteria;D_3__Burkholderiales;D_4__Alcaligenaceae;D_5__Parasutterella
D_0__Bacteria;D_1__Proteobacteria;D_2__Deltaproteobacteria;D_3__Desulfovibrionales;D_4__Desulfovibrionaceae;D_5__Bilophila
D_0__Bacteria;D_1__Proteobacteria;D_2__Gammaproteobacteria;D_3__Enterobacteriales;D_4__Enterobacteriaceae;__
D_0__Bacteria;D_1__Proteobacteria;D_2__Gammaproteobacteria;D_3__Pasteurellales;D_4__Pasteurellaceae;D_5__Haemophilus
D_0__Bacteria;D_1__Proteobacteria;D_2__Gammaproteobacteria;D_3__Xanthomonadales;D_4__Xanthomonadaceae;D_5__Stenotrophomonas
D_0__Bacteria;D_1__Tenericutes;D_2__Mollicutes;D_3__Anaeroplasmatales;D_4__Anaeroplasmataceae;D_5__Anaeroplasma
D_0__Bacteria;D_1__Tenericutes;D_2__Mollicutes;D_3__Mollicutes RF9;Ambiguous_taxa;Ambiguous_taxa
D_0__Bacteria;D_1__Tenericutes;D_2__Mollicutes;D_3__Mollicutes RF9;D_4__uncultured Firmicutes bacterium;D_5__uncultured Firmicutes bacterium
D_0__Bacteria;D_1__Tenericutes;D_2__Mollicutes;D_3__Mollicutes RF9;__;__
D_0__Bacteria;D_1__Verrucomicrobia;D_2__Verrucomicrobiae;D_3__Verrucomicrobiales;D_4__Verrucomicrobiaceae;D_5__Akkermansia
D_0__Bacteria;__;__;__;__;__

FIG. 4 (Cont. 5)

| Gate | Number | %Gated |
|---|---|---|
| All | 304,698 | 100.0 |
| SSC vs FSC | 291,105 | 95.5 |
| Single Cells | 260,626 | 89.5 |
| Live cells | 255,402 | 98.0 |
| CD45+ | 241,936 | 94.7 |
| CD3- | 234,743 | 97.0 |
| CD3+ | 7,230 | 3.0 |
| CD4+ | 4,345 | 60.1 |
| CD4+HLA-DR- | 4,049 | 93.2 |
| CD4+HLA-DR+ | 302 | 7.0 |
| CD8+ | 2,462 | 34.1 |
| CD8+HLA-DR- | 1,342 | 54.5 |
| CD8+HLA-DR+ | 1,135 | 46.1 |
| Foxp3+ | 3 | 0.0 |
| CD3+CD56+ | 89 | 0.0 |
| CD3+HLADR+ | 1,916 | 0.8 |
| CD3-CD56+ | 1,969 | 0.8 |
| CD3-HLA-DR+ | 27,115 | 11.2 |
| CD11b+ | 16,765 | 61.8 |
| CD14+CD15- | 7,823 | 46.7 |
| CD14+CD15+ | 330 | 2.0 |
| CD14-CD15- | 525 | 3.1 |
| CD14-CD15+ | 8,087 | 48.2 |
| CD3-HLA-DRlow | 9,815 | 4.1 |
| CD11b + | 8,535 | 87.0 |

Sample 1
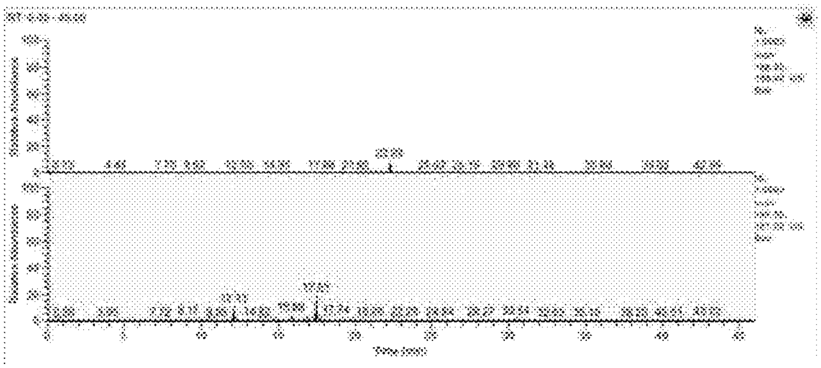
Sample 2
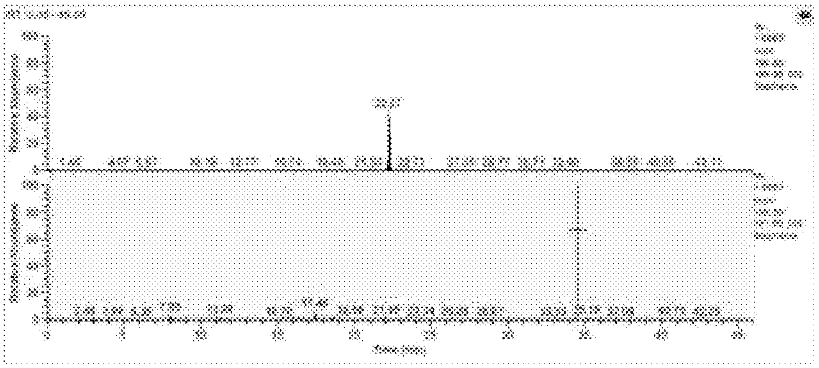
Sample 3
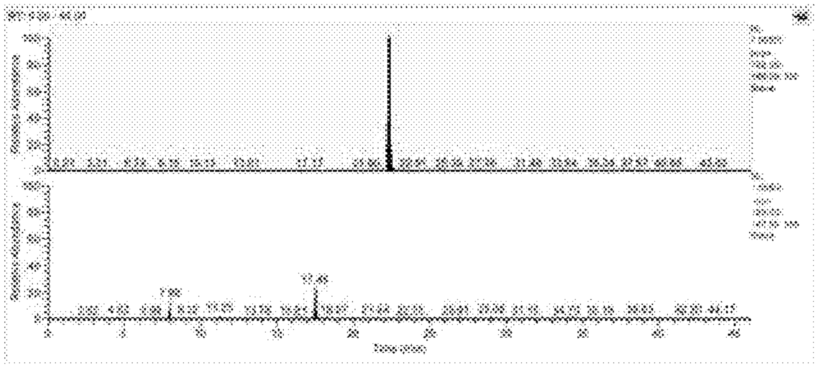
FIG. 12

| Animal | 597 | 945 | 394 | 964 | 329 | 361 |
|---|---|---|---|---|---|---|
| Detailed Timepoint | Timepoint 1 | Timepoint 1 | Timepoint 1 | Timepoint 1 | Timepoint 1 | Timepoint 1 |
| Description | Ellagic Acid | Ellagic Acid | Microbe Mix 4 + Ellagic Acid | Microbe Mix 4 + Ellagic Acid | Anti-CTLA4 + Vehicle | Anti-CTLA4 + Vehicle |
| Mus musculus | 8.693290698 | 3.509439196 | 4.413641733 | 5.503310852 | 1.700517275 | 26.71950476 |
| Lactobacillus murinus | 4.686022554 | 21.94937184 | 23.65087037 | 2.188680386 | 4.707415793 | 24.37406126 |
| Oscillibacter sp. 1-3 | 2.271940898 | 2.787730896 | 1.614883274 | 3.200952411 | 3.711156977 | 1.531988224 |
| Lachnospiraceae bacterium A2 | 4.725109563 | 1.655429005 | 2.413823648 | 2.88762412 | 4.537568792 | 3.310709949 |
| Lachnospiraceae bacterium A4 | 1.815812497 | 2.125584399 | 3.540746316 | 4.938362818 | 1.0585866 | 4.050679946 |
| Acetatifactor muris | 1.184914182 | 1.109205217 | 1.384219635 | 2.296901224 | 1.306684541 | 0.880071475 |
| Clostridium sp. ASF502 | 1.160442315 | 2.610740079 | 2.147490374 | 1.73312859 | 0.82398543 | 0.661966805 |
| Bacteroides thetaiotaomicron | 4.832038024 | 3.32711355 | 5.415839577 | 3.753642693 | 6.508703901 | 2.394218544 |
| Dorea sp. 5-2 | 3.232121772 | 1.308790607 | 1.709823953 | 1.905744604 | 0.718058527 | 0.766339871 |
| Anaerotruncus sp. G3(2012) | 0.713083 | 0.93918106 | 0.774031079 | 1.380592285 | 1.199847744 | 0.776389927 |
| Lachnospiraceae bacterium COE1 | 1.110274989 | 0.813530132 | 1.090182944 | 2.550787812 | 0.831947008 | 0.864304873 |
| Eubacterium plexicaudatum | 0.816000794 | 0.630137519 | 0.835561199 | 1.924383103 | 0.670516532 | 0.59322995 |
| Alistipes finegoldii | 6.957011768 | 3.109891841 | 4.116632572 | 1.501406703 | 8.143102164 | 0.587651707 |
| Lachnospiraceae bacterium 28-4 | 0.607582064 | 0.630514096 | 1.400449319 | 1.227370385 | 0.553670894 | 0.496094769 |
| Bacteroides cellulosilyticus | 2.746151289 | 5.62793141 | 1.527017073 | 1.032925497 | 6.92543565 | 1.702101568 |
| Lachnospiraceae bacterium 10-1 | 0.717093667 | 0.644823991 | 0.779916569 | 1.474540397 | 0.608112924 | 0.580506025 |
| Lachnospiraceae bacterium 3-1 | 0.939991584 | 0.662899649 | 0.737885849 | 1.429287464 | 0.711916739 | 0.616879854 |
| Bacteroides caecimuris | 2.582393716 | 1.503480506 | 2.165741337 | 0.990862937 | 4.170123003 | 0.853701602 |
| Lachnospiraceae bacterium M18-1 | 0.906410745 | 1.054225091 | 0.708577299 | 0.821521254 | 0.379881016 | 0.448426152 |
| Bacteroides ovatus | 2.884825199 | 1.525949553 | 2.325065706 | 0.776939978 | 4.182179107 | 0.907178968 |
| Adlercreutzia equolifaciens | 4.502211645 | 2.568061442 | 1.389213383 | 1.617939304 | 0.946972856 | 2.870443705 |
| Lachnospiraceae bacterium 3-2 | 0.845570966 | 1.477747798 | 0.742879598 | 1.054502499 | 0.232781381 | 1.193282874 |
| Eubacterium sp. 14-2 | 0.429345303 | 0.359567515 | 0.400926697 | 0.938557598 | 0.305118006 | 0.285781198 |
| Pseudoflavonifractor sp. An184 | 0.173954185 | 0.34808194 | 0.159205471 | 0.321807968 | 0.325059863 | 0.149874928 |
| Bacteroides caccae | 0.754073376 | 0.557207261 | 0.972948743 | 0.553613812 | 1.709312923 | 0.290898429 |

FIG. 20

| | | | | | | |
|---|---|---|---|---|---|---|
| Homo sapiens | 0.321873022 | 0.347517076 | 0.254324497 | 0.370922933 | 0.391027226 | 0.192472415 |
| Flavonifractor sp. An10 | 0.12086383 | 0.215338828 | 0.113786136 | 0.227356112 | 0.214810962 | 0.098702621 |
| Flavonifractor sp. An306 | 0.111890812 | 0.213267658 | 0.105998265 | 0.204771624 | 0.216175804 | 0.093032176 |
| Pseudoflavonifractor capillosus | 0.106044755 | 0.205798897 | 0.110992014 | 0.201833122 | 0.206849384 | 0.09593655 |
| Flavonifractor sp. An100 | 0.090409951 | 0.17171875 | 0.089352436 | 0.163884465 | 0.171590966 | 0.078971317 |
| Lachnoclostridium sp. YL32 | 0.150366024 | 0.142785145 | 0.126627204 | 0.268159314 | 0.130418233 | 0.099163632 |
| Bacteroides fragilis | 0.470879498 | 0.406702303 | 0.373044932 | 0.331714918 | 1.101806596 | 0.188461613 |
| Intestinimonas massiliensis | 0.088710516 | 0.15822477 | 0.087866201 | 0.168753983 | 0.180917386 | 0.072655455 |
| Muribaculum intestinale | 0.020325245 | 0.019644725 | 0.013613911 | 0.014608554 | 0.02979905 | 0 |
| Flavonifractor plautii | 0.101762178 | 0.157220566 | 0.080078331 | 0.193101572 | 0.166510721 | 0.083765839 |
| Acutalibacter muris | 0.103869478 | 0.175735563 | 0.087806751 | 0.160274305 | 0.141109495 | 0.08574819 |
| Ruminiclostridium sp. KB18 | 0.105229026 | 0.1756728 | 0.088639043 | 0.167410667 | 0.14118532 | 0.087223428 |
| Hungatella hathewayi | 0.138469978 | 0.123265945 | 0.133404435 | 0.245994612 | 0.131631426 | 0.084226851 |
| Faecalibacterium prausnitzii | 0.092585228 | 0.13431218 | 0.105463221 | 0.183530451 | 0.137621566 | 0.076481853 |
| Clostridium sp. C105KSO14 | 0.083272324 | 0.104248847 | 0.095832419 | 0.199398363 | 0.087729009 | 0.066846707 |
| [Clostridium] clostridioforme | 0.117872824 | 0.112094184 | 0.125557115 | 0.210228842 | 0.122911602 | 0.080769263 |
| Pseudoflavonifractor sp. Marseille-P3106 | 0.099382969 | 0.135316384 | 0.083764193 | 0.149947569 | 0.164008511 | 0.067907034 |
| Clostridium sp. SN20 | 0.070696503 | 0.114667455 | 0.071517618 | 0.119890889 | 0.122684129 | 0.054998705 |
| Flavonifractor sp. An82 | 0.05873248 | 0.106068965 | 0.056536371 | 0.109480196 | 0.111992866 | 0.05131061 |
| Intestinimonas butyriciproducens | 0.059888096 | 0.100106508 | 0.05671472 | 0.102847577 | 0.112675287 | 0.048406236 |
| Oscillibacter sp. PC13 | 0.073007735 | 0.084917935 | 0.057309214 | 0.09764223 | 0.117452234 | 0.044118827 |
| [Clostridium] lavalense | 0.097547579 | 0.104311609 | 0.069317991 | 0.132148641 | 0.085454272 | 0.066062987 |
| Bacteroides dorei | 0.230375432 | 0.205359558 | 0.204803154 | 0.166571095 | 0.566181946 | 0.110458421 |
| Oscillibacter valericigenes | 0.069268978 | 0.080085207 | 0.054396193 | 0.092772712 | 0.104486236 | 0.038402281 |
| Pseudoflavonifractor sp. An85 | 0.040990376 | 0.099102305 | 0.044587044 | 0.100748646 | 0.088108132 | 0.042090375 |

FIG. 20 (Cont. 1)

| 798 | 970 | 391 | 392 | 969 | 974 | 597 | 945 | 329 |
|---|---|---|---|---|---|---|---|---|
| Timepoint 1 | Timepoint 1 | Timepoint 1 | Timepoint 1 | Timepoint 1 | Timepoint 1 | Timepoint 4 | Timepoint 4 | Timepoint 4 |
| Anti-CTLA4 + Vehicle | Anti-CTLA4 + Vehicle | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Ellagic Acid | Ellagic Acid | Anti-CTLA4 + Vehicle |
| 15.13885746 | 2.615240085 | 3.253791587 | 8.478461332 | 1.680235721 | 3.914419053 | 29.52868762 | 1.771501869 | 0.769352733 |
| 27.64868113 | 8.20448585 | 11.22107924 | 21.88722445 | 6.779191252 | 9.126995172 | 6.416948229 | 9.247781471 | 8.999265574 |
| 2.563218223 | 4.608248447 | 5.646427302 | 1.875126431 | 4.34535799 | 5.602951046 | 3.765110839 | 6.489454977 | 7.788359567 |
| 1.446239267 | 2.757511796 | 2.146506351 | 1.710732685 | 4.961856952 | 2.022465308 | 1.750290014 | 1.632382549 | 2.477080962 |
| 1.674403949 | 4.848077902 | 4.207431533 | 1.373932393 | 1.808737848 | 5.600940797 | 2.523533924 | 4.543924803 | 1.99820806 |
| 1.501470814 | 2.255420627 | 2.342014416 | 1.17742177 | 1.451836899 | 2.374722818 | 1.282844483 | 2.166571214 | 1.937703893 |
| 1.239120967 | 1.694011942 | 1.509806207 | 1.255907798 | 1.487260207 | 1.261276725 | 1.366584047 | 2.390121569 | 1.652908014 |
| 2.74588379 | 3.323813424 | 0.725101855 | 8.230130228 | 2.381735801 | 0.495371788 | 1.843791798 | 0.448724383 | 0.15391542 |
| 1.495388044 | 2.163734414 | 2.043482359 | 1.288156032 | 1.157853081 | 2.017130416 | 1.130389031 | 2.108709386 | 2.021392598 |
| 1.145081351 | 1.467882726 | 1.812272176 | 0.670448007 | 1.338897312 | 1.786261029 | 1.475363072 | 2.467541286 | 1.888866785 |
| 1.27281951 | 1.436643171 | 1.953818828 | 0.670645043 | 0.79205925 | 2.200836264 | 1.672255643 | 1.379606067 | 1.221152077 |
| 1.061078305 | 1.440783353 | 2.183247616 | 0.718918876 | 0.832077214 | 2.171455699 | 0.952957509 | 1.376875343 | 1.245533237 |
| 0.130779543 | 2.352225611 | 0.09678911 | 1.196928339 | 10.99382389 | 0.030231055 | 0.422184328 | 0.226576292 | 0.066786429 |
| 1.252563887 | 3.047926747 | 1.736711352 | 2.450997134 | 0.638360627 | 1.201897057 | 0.634417531 | 0.970956905 | 0.94652748 |
| 0.457545919 | 1.208632054 | 0.298532057 | 2.75114872 | 2.090271633 | 0.261796297 | 2.167656623 | 0.320896976 | 0.122204954 |
| 0.770565235 | 1.164294468 | 1.490953113 | 0.647263432 | 0.671634823 | 1.439183777 | 0.884875532 | 1.0302948 | 1.027374209 |
| 0.893741317 | 1.124247616 | 1.262415022 | 0.643913819 | 0.849344224 | 1.286868743 | 0.808679501 | 1.09324906 | 1.191760065 |
| 0.739117317 | 1.446278503 | 0.401556048 | 3.018329607 | 1.863873709 | 0.524906987 | 0.776223289 | 0.231963937 | 0.155934718 |
| 0.491061979 | 0.706164505 | 0.913187442 | 0.423364798 | 1.00548839 | 0.81067164 | 0.893750277 | 1.17052117 | 1.778029733 |
| 0.680114453 | 1.506574609 | 0.380476211 | 2.846908242 | 1.781244025 | 0.562715135 | 0.586113559 | 0.25668806 | 0.167452199 |
| 0.884556335 | 1.50883289 | 1.017324805 | 2.204899104 | 0.983923154 | 0.753766125 | 0.376859735 | 0.394995542 | 0.684317829 |
| 0.669773745 | 1.086082665 | 1.096225744 | 0.572455411 | 0.713801899 | 1.113832679 | 0.529949097 | 1.143582946 | 0.563159918 |
| 0.513081604 | 0.564419727 | 0.672031139 | 0.306588097 | 0.388470676 | 0.712092113 | 0.415147923 | 0.514556973 | 0.666368509 |
| 0.238505391 | 0.42929924 | 0.587414892 | 0.164656461 | 0.545578237 | 0.564648067 | 0.382247973 | 0.711169104 | 0.989531059 |
| 0.399090504 | 0.587905851 | 0.199367753 | 1.558095423 | 0.647179401 | 0.211926654 | 0.231504079 | 0.061478193 | 0.023782849 |

FIG. 20 (Cont. 2)

| | | | | | | | | |
|---|---|---|---|---|---|---|---|---|
| 0.350306693 | 0.359066698 | 0.302094846 | 0.345010128 | 0.345488419 | 0.341510408 | 0.330457493 | 0.276319752 | 0.235061304 |
| 0.159551043 | 0.291167712 | 0.368748696 | 0.109552045 | 0.369573305 | 0.356046056 | 0.229158611 | 0.489537637 | 0.594795595 |
| 0.153224963 | 0.250142272 | 0.352716144 | 0.102721462 | 0.332519635 | 0.349319453 | 0.217241095 | 0.441344048 | 0.60855674 |
| 0.148845369 | 0.264068339 | 0.341062854 | 0.100225672 | 0.317253523 | 0.337103324 | 0.223516808 | 0.429535511 | 0.592851085 |
| 0.117519106 | 0.215891675 | 0.291109579 | 0.085973398 | 0.250779239 | 0.272311446 | 0.201329944 | 0.337207517 | 0.477451915 |
| 0.172933136 | 0.204374441 | 0.26550203 | 0.115857199 | 0.204536258 | 0.267595093 | 0.153152753 | 0.240672732 | 0.294593216 |
| 0.147446332 | 0.297415623 | 0.085581169 | 0.725026994 | 0.520529956 | 0.084739735 | 0.206464618 | 0.049448246 | 0.026176092 |
| 0.116241724 | 0.201965608 | 0.270994664 | 0.08735265 | 0.271825723 | 0.275404137 | 0.18339028 | 0.319789926 | 0.473936839 |
| 0 | 0.012947478 | 0 | 0.022527789 | 0.035052772 | 0 | 0.227130097 | 0.01210375 | 0 |
| 0.112044613 | 0.20249254 | 0.262755714 | 0.079405529 | 0.221951483 | 0.260791172 | 0.160823069 | 0.381637135 | 0.454416954 |
| 0.113261167 | 0.172306849 | 0.181405357 | 0.083280571 | 0.207648767 | 0.185716097 | 0.143517315 | 0.377799361 | 0.32383565 |
| 0.106874259 | 0.160036855 | 0.181924931 | 0.075793201 | 0.19920053 | 0.179453398 | 0.130331979 | 0.373444963 | 0.3161324 |
| 0.144648258 | 0.188491197 | 0.226830921 | 0.109617724 | 0.148288787 | 0.226462302 | 0.136988038 | 0.24613418 | 0.250467804 |
| 0.114903515 | 0.192029171 | 0.214806507 | 0.090045476 | 0.200830891 | 0.217725449 | 0.147954688 | 0.277500605 | 0.324882694 |
| 0.105292739 | 0.153036184 | 0.217478599 | 0.087221293 | 0.154513804 | 0.217338863 | 0.09933376 | 0.2179413 | 0.226610166 |
| 0.130475405 | 0.155143913 | 0.197586359 | 0.086892899 | 0.123611043 | 0.204581513 | 0.136037173 | 0.197054951 | 0.184429264 |
| 0.093613822 | 0.176070651 | 0.21064992 | 0.085776361 | 0.207055908 | 0.215560566 | 0.172106674 | 0.250414775 | 0.318450854 |
| 0.082117388 | 0.151831767 | 0.197586359 | 0.062657465 | 0.185194243 | 0.189504644 | 0.131409627 | 0.237868205 | 0.31740381 |
| 0.081326628 | 0.134894659 | 0.164630557 | 0.055761203 | 0.174596893 | 0.171644353 | 0.119175156 | 0.232111543 | 0.301399 |
| 0.074878892 | 0.129851164 | 0.168935594 | 0.056023918 | 0.163851329 | 0.175046313 | 0.114040482 | 0.209822931 | 0.284795879 |
| 0.075487169 | 0.131657789 | 0.163220287 | 0.060030317 | 0.116496739 | 0.158732368 | 0.122281317 | 0.20561614 | 0.256450911 |
| 0.086253671 | 0.129625336 | 0.137390064 | 0.067911759 | 0.095969005 | 0.140098904 | 0.104468434 | 0.165024296 | 0.160272471 |
| 0.062287559 | 0.109300806 | 0.030432159 | 0.241237807 | 0.243961363 | 0.038658638 | 0.076005857 | 0.026347797 | 0.013237624 |
| 0.070134332 | 0.11682841 | 0.149266028 | 0.05188616 | 0.126723551 | 0.151928448 | 0.110617365 | 0.174102108 | 0.241792299 |
| 0.07019516 | 0.104182036 | 0.153571065 | 0.040261033 | 0.154143267 | 0.161593107 | 0.090395623 | 0.203623449 | 0.274400231 |

FIG. 20 (Cont. 3)

| 361 | 798 | 970 | 391 | 392 | 329 | 361 | 798 | 970 |
|---|---|---|---|---|---|---|---|---|
| Timepoint 4 | Timepoint 4 | Timepoint 4 | Timepoint 4 | Timepoint 4 | Timepoint 5 | Timepoint 5 | Timepoint 5 | Timepoint 5 |
| Anti-CTLA4 + Vehicle | Anti-CTLA4 + Vehicle | Anti-CTLA4 + Vehicle | Anti-CTLA4 + Microbe mix 4 + Ellagic Acid | Anti-CTLA4 + Microbe mix 4 + Ellagic Acid | Anti-CTLA4 + Vehicle | Anti-CTLA4 + Vehicle | Anti-CTLA4 + Vehicle | Anti-CTLA4 + Vehicle |
| 1.012287144 | 18.72409474 | 1.589068656 | 48.77835302 | 2.751861002 | 5.336810452 | 1.590591829 | 1.725212013 | 1.500690805 |
| 8.265590763 | 7.070638157 | 2.978288205 | 9.567677718 | 6.356714948 | 14.19856327 | 1.082645506 | 0.465697757 | 0.604778478 |
| 4.747713455 | 2.231659618 | 6.902757985 | 2.467092878 | 4.522436984 | 6.513184396 | 4.881078414 | 7.040124526 | 7.304371694 |
| 5.479482788 | 0.820528258 | 1.708860759 | 2.598219357 | 2.067851895 | 2.018823424 | 8.896009194 | 2.412512986 | 1.794167783 |
| 6.410628417 | 3.668955602 | 4.268002347 | 2.113641709 | 5.589384618 | 3.113337594 | 3.423367717 | 3.43056376 | 4.123238573 |
| 3.189123298 | 1.076618039 | 2.590493755 | 0.9151429 | 2.265739799 | 1.918660497 | 3.739877768 | 3.233828312 | 2.733260641 |
| 1.785562045 | 1.895598927 | 2.792187107 | 0.772535301 | 1.333381776 | 1.647427939 | 2.076131051 | 4.600112711 | 1.990070152 |
| 0.418196639 | 5.936064067 | 1.303881298 | 0.754965004 | 3.58911011 | 0.231383567 | 0.171137156 | 0.237219834 | 0.568376287 |
| 1.533462462 | 0.745410465 | 1.387207645 | 0.562667859 | 1.467083273 | 1.925938523 | 1.717227078 | 1.699071151 | 1.583620855 |
| 1.607948129 | 0.910416404 | 1.959761925 | 0.740183642 | 1.297534273 | 1.700247669 | 1.922248143 | 2.026086543 | 2.49518194 |
| 2.142809067 | 0.984268168 | 2.013077374 | 0.771745102 | 1.582295855 | 1.43333869 | 2.283494321 | 2.108073792 | 2.205889121 |
| 1.730221288 | 0.8055469 | 1.756224327 | 0.562528412 | 1.331363335 | 1.584015438 | 1.86010162 | 1.750164653 | 1.666634588 |
| 0.158169866 | 0.213748104 | 0.534747255 | 0.318961326 | 2.482520306 | 0.115223396 | 0.055900641 | 0.030045017 | 0.30268213 |
| 2.167039344 | 0.629428029 | 1.361388214 | 0.43851372 | 1.070177138 | 1.127085136 | 3.589508168 | 1.442330543 | 1.499602923 |
| 0.350441604 | 4.003257918 | 0.658311677 | 0.695793076 | 3.450645094 | 0.157090058 | 0.162002555 | 0.196480829 | 0.608544222 |
| 1.667102911 | 0.667901281 | 1.923966804 | 0.552348796 | 1.464015243 | 1.280428092 | 1.775860292 | 1.791922134 | 2.151327676 |
| 1.479318262 | 0.66297783 | 1.374968564 | 0.482300017 | 1.267984305 | 1.23841731 | 1.663824791 | 1.632361029 | 1.428806937 |
| 0.330100137 | 3.438327096 | 0.58361975 | 0.284146107 | 1.467567698 | 0.215314263 | 0.130070485 | 0.180015481 | 0.3421806 |
| 1.046987294 | 0.484678573 | 1.660826557 | 0.361539084 | 0.652521436 | 1.204333091 | 1.151584424 | 0.939034078 | 1.564206353 |
| 0.372129198 | 3.659390041 | 0.600134127 | 0.255234136 | 1.244570395 | 0.240535144 | 0.147637027 | 0.195547227 | 0.303937378 |
| 0.243723685 | 0.794433968 | 0.167155671 | 0.667299445 | 1.53974713 | 0.644069238 | 0.187376449 | 0.154298984 | 0.508375433 |
| 0.654965337 | 0.311162096 | 0.542459552 | 0.282844603 | 0.874630625 | 0.756410247 | 0.925015068 | 0.580530829 | 0.608293172 |
| 0.659975919 | 0.362365985 | 0.648755135 | 0.25184093 | 0.611587463 | 0.698762519 | 0.733500723 | 0.881744852 | 0.643607482 |
| 0.576815214 | 0.229573481 | 0.65059938 | 0.249144959 | 0.43606388 | 0.661291496 | 0.678536965 | 0.679747282 | 0.708378278 |
| 0.0482362 | 1.556021486 | 0.297007293 | 0.13256743 | 0.651310372 | 0.047127017 | 0.024046644 | 0.057883337 | 0.135817832 |

FIG. 20 (Cont. 4)

| | | | | | | | | |
|---|---|---|---|---|---|---|---|---|
| 0.31147872 | 0.480739812 | 0.43004443 | 0.290514178 | 0.457782299 | 0.268061934 | 0.325020065 | 0.358333503 | 0.29481591 |
| 0.326286112 | 0.152556643 | 0.393494844 | 0.169846209 | 0.262881687 | 0.38746479 | 0.36062159 | 0.457040719 | 0.482433641 |
| 0.326660036 | 0.134199204 | 0.411937296 | 0.154367613 | 0.260459559 | 0.395535472 | 0.372879133 | 0.434973757 | 0.447119331 |
| 0.310730872 | 0.13947433 | 0.387459133 | 0.155483188 | 0.251901371 | 0.386672134 | 0.360699664 | 0.417065569 | 0.445529351 |
| 0.288220645 | 0.124281967 | 0.317126331 | 0.125455642 | 0.238498926 | 0.331330315 | 0.343289269 | 0.330240564 | 0.354230981 |
| 0.297867885 | 0.131807814 | 0.299606002 | 0.10142431 | 0.214762066 | 0.265467786 | 0.339385593 | 0.336775779 | 0.308539954 |
| 0.056088605 | 0.852179014 | 0.147623439 | 0.078369105 | 0.484425713 | 0.037182784 | 0.021392145 | 0.042691083 | 0.103432434 |
| 0.266607836 | 0.112043675 | 0.311593595 | 0.13544933 | 0.202893636 | 0.30481236 | 0.28941854 | 0.341019426 | 0.355988328 |
| 0 | 0.037910572 | 0 | 0 | 0.016308999 | 0 | 0 | 0 | 0 |
| 0.247911634 | 0.104166154 | 0.320144186 | 0.118390338 | 0.192962909 | 0.289319533 | 0.27278888 | 0.327015393 | 0.361093003 |
| 0.236544344 | 0.11323937 | 0.234135301 | 0.125316196 | 0.145246976 | 0.244714604 | 0.234454781 | 0.315302928 | 0.256572688 |
| 0.230486774 | 0.106909219 | 0.229357029 | 0.120714451 | 0.140402719 | 0.23923807 | 0.231878355 | 0.302062752 | 0.249543299 |
| 0.246864647 | 0.121468567 | 0.26020622 | 0.09937909 | 0.186019474 | 0.218917246 | 0.304096361 | 0.281862995 | 0.295150642 |
| 0.217324648 | 0.110355635 | 0.250398189 | 0.112765983 | 0.165431381 | 0.256676508 | 0.245853515 | 0.286785625 | 0.264606275 |
| 0.209621813 | 0.101493423 | 0.282672479 | 0.087758523 | 0.17972194 | 0.198524362 | 0.239217266 | 0.255212895 | 0.297326405 |
| 0.210519231 | 0.095303942 | 0.24788331 | 0.089385402 | 0.169306787 | 0.175609391 | 0.246556177 | 0.263869934 | 0.249292249 |
| 0.198179738 | 0.103673809 | 0.22432727 | 0.103190636 | 0.171405965 | 0.217403993 | 0.196432977 | 0.248423061 | 0.268120969 |
| 0.179184397 | 0.087285751 | 0.219716657 | 0.093382877 | 0.153159263 | 0.222015811 | 0.196979492 | 0.235776995 | 0.258581084 |
| 0.158020297 | 0.076313489 | 0.194148713 | 0.086178126 | 0.128211339 | 0.204793553 | 0.175509274 | 0.216341094 | 0.23046353 |
| 0.159366423 | 0.072937408 | 0.18962193 | 0.07971709 | 0.129422403 | 0.19693905 | 0.178866435 | 0.215746984 | 0.227116202 |
| 0.149644398 | 0.068857977 | 0.222986001 | 0.073488466 | 0.123609295 | 0.197443467 | 0.143030689 | 0.209890752 | 0.24485704 |
| 0.171780701 | 0.075680474 | 0.155419566 | 0.073627913 | 0.118603562 | 0.128842671 | 0.211657313 | 0.187314553 | 0.165441684 |
| 0.025950328 | 0.772489444 | 0.062033699 | 0.026308964 | 1.070257876 | 0.016429602 | 0 | 0.024698022 | 0.048870988 |
| 0.128405513 | 0.070616353 | 0.191382346 | 0.073116608 | 0.111094964 | 0.195858155 | 0.121794692 | 0.197923669 | 0.211551127 |
| 0.148223487 | 0.060488111 | 0.177299019 | 0.071117871 | 0.101083499 | 0.151613524 | 0.164813201 | 0.179675989 | 0.206279085 |

FIG. 20 (Cont. 5)

| 391 | 392 | 969 | 974 | 597 | 945 | 394 | 964 | 329 |
|---|---|---|---|---|---|---|---|---|
| Timepoint 5 | Timepoint 5 | Timepoint 5 | Timepoint 5 | Timepoint 7 | Timepoint 7 | Timepoint 7 | Timepoint 7 | Timepoint 7 |
| Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Ellagic Acid | Ellagic Acid | Microbe Mix 4 + Ellagic Acid | Microbe Mix 4 + Ellagic Acid | Anti-CTLA4 + Vehicle |
| 2.949793082 | 10.02918656 | 8.179716805 | 8.548532419 | 0.648109934 | 9.77722434 | 6.191374582 | 5.978400346 | 2.853606384 |
| 2.638791286 | 10.66860259 | 14.64330699 | 11.37657745 | 0.667047109 | 7.698018748 | 5.967349234 | 2.837752981 | 2.389139521 |
| 6.365581323 | 4.416017748 | 4.835979349 | 3.175592851 | 7.296501803 | 3.827746938 | 4.219261936 | 4.476721283 | 7.44707394 |
| 6.724213321 | 2.151179279 | 5.871731698 | 3.365536701 | 2.670905876 | 7.468422582 | 7.24272006 | 10.95201507 | 5.194795696 |
| 4.885297103 | 6.446521837 | 3.200340499 | 3.618253816 | 4.851992819 | 3.784268594 | 1.484101627 | 3.003514137 | 2.686755908 |
| 2.34816897 | 2.388837028 | 1.70567636 | 1.196646255 | 2.19008847 | 2.197181917 | 1.608137761 | 1.949897228 | 2.343464915 |
| 2.506051378 | 1.600977218 | 1.77246114 | 1.150184154 | 2.552527306 | 3.629869622 | 1.680190112 | 1.473987199 | 1.485887603 |
| 0.308190833 | 0.707877416 | 1.113333426 | 4.324576616 | 0.067171771 | 0.330854941 | 1.328857541 | 0.699941106 | 0.077939409 |
| 1.55469665 | 1.562647705 | 1.279430288 | 0.929665699 | 2.096676399 | 2.255343736 | 1.160794326 | 1.892251349 | 1.511244324 |
| 1.799172328 | 1.40526776 | 1.237906072 | 0.817535277 | 2.32128997 | 3.006235074 | 0.912987282 | 3.664764639 | 1.966771317 |
| 1.91270399 | 1.623354564 | 1.263166637 | 0.979093466 | 2.480090491 | 1.5955408 | 1.439367283 | 1.298709403 | 1.790493343 |
| 1.471382838 | 1.541082739 | 1.114094703 | 0.984318688 | 1.985600954 | 1.29615045 | 0.913340913 | 1.908086414 | 1.277832455 |
| 0.181150933 | 0.248883348 | 0.342090329 | 2.095525516 | 0.448547782 | 0.526761747 | 2.275970231 | 1.072650189 | 0.377425041 |
| 1.133754978 | 1.015178192 | 0.931111326 | 0.661131698 | 1.32483793 | 2.33435482 | 0.805394997 | 0.900024572 | 1.093346055 |
| 0.161864605 | 0.428862197 | 0.906958074 | 3.961000079 | 0.086278786 | 0.525045497 | 2.456587353 | 0.664916749 | 0.086716735 |
| 1.428437573 | 1.451647209 | 1.059559566 | 0.738168405 | 1.531363528 | 1.246760577 | 1.03605093 | 1.055255019 | 1.336429237 |
| 1.257671586 | 1.327131682 | 0.936509474 | 0.704133856 | 1.709355983 | 1.078631602 | 1.033487104 | 1.487170087 | 1.339273741 |
| 0.421566331 | 0.392009737 | 0.765083671 | 2.696355338 | 0.178586896 | 0.272629556 | 2.672921223 | 0.620453757 | 0.307043886 |
| 1.094323417 | 0.730550173 | 0.593035005 | 0.393586253 | 1.338679901 | 1.503117537 | 1.160175472 | 0.998233181 | 0.676666859 |
| 0.218786601 | 0.313578248 | 0.738923416 | 2.610139189 | 0.074984417 | 0.142766608 | 1.894490603 | 0.403443152 | 0.095087704 |
| 0.17833997 | 0.328053363 | 2.239400944 | 3.645015421 | 0.095619993 | 0.186117822 | 0.248337491 | 0.237603991 | 0.209355492 |
| 0.542281565 | 0.769618211 | 1.281368084 | 1.152867375 | 0.910767694 | 1.333463006 | 0.780198776 | 0.698771027 | 0.63562473 |
| 0.634652924 | 0.642813253 | 0.481611693 | 0.345500096 | 0.659659063 | 0.512968179 | 0.527087264 | 0.610937116 | 0.687313431 |
| 0.617552901 | 0.512389516 | 0.491369884 | 0.306028493 | 0.728783996 | 0.416476767 | 0.393326272 | 0.434411236 | 0.940149198 |
| 0.06488639 | 0.141870894 | 0.29669052 | 0.966030414 | 0.012313409 | 0.040745056 | 0.278926588 | 0.158350657 | 0.012515817 |

FIG. 20 (Cont. 6)

| | | | | | | | | |
|---|---|---|---|---|---|---|---|---|
| 0.344577184 | 0.348288982 | 0.342851606 | 0.324387378 | 0.35479603 | 0.264683952 | 0.36096902 | 0.364596537 | 0.275347984 |
| 0.394627938 | 0.299693955 | 0.254751062 | 0.167701355 | 0.405068709 | 0.22056996 | 0.214477307 | 0.268728085 | 0.501607957 |
| 0.388147107 | 0.300580186 | 0.258211414 | 0.168972354 | 0.391736259 | 0.21306931 | 0.211913481 | 0.27013218 | 0.538749052 |
| 0.393534786 | 0.269562083 | 0.257796171 | 0.169678465 | 0.385282334 | 0.205250836 | 0.205901751 | 0.269196117 | 0.511360543 |
| 0.298430546 | 0.266386421 | 0.265685772 | 0.153437913 | 0.384942653 | 0.222794729 | 0.203426332 | 0.228165356 | 0.478283025 |
| 0.273834622 | 0.232783476 | 0.192741567 | 0.136420639 | 0.294672625 | 0.248284226 | 0.180528714 | 0.272394332 | 0.288595246 |
| 0.058795971 | 0.097928582 | 0.192949188 | 0.695307469 | 0.031590264 | 0.046338761 | 0.337629363 | 0.138303308 | 0.033321332 |
| 0.310689467 | 0.225398213 | 0.210389359 | 0.135714528 | 0.320233564 | 0.161518233 | 0.15824995 | 0.215294489 | 0.409933658 |
| 0.487702038 | 0.167423902 | 0.011211538 | 0.040318936 | 0.270725166 | 0.343059388 | 2.39098877 | 0.40773344 | 0.51810608 |
| 0.306473023 | 0.21771754 | 0.190872977 | 0.122722086 | 0.306561434 | 0.172959903 | 0.18910427 | 0.231129555 | 0.40741424 |
| 0.337393613 | 0.159595524 | 0.169834042 | 0.113754477 | 0.382649812 | 0.172387819 | 0.160371737 | 0.212720316 | 0.334026038 |
| 0.325837433 | 0.162032661 | 0.163605409 | 0.112483477 | 0.391991019 | 0.170417309 | 0.170185002 | 0.21708861 | 0.335001296 |
| 0.236901694 | 0.191573711 | 0.163190167 | 0.112907144 | 0.258072077 | 0.205314401 | 0.186717259 | 0.207103938 | 0.245765143 |
| 0.268446943 | 0.184557711 | 0.187274212 | 0.130630529 | 0.260959359 | 0.165649947 | 0.147375791 | 0.207883991 | 0.286400914 |
| 0.219255095 | 0.189727395 | 0.193987294 | 0.120603753 | 0.226821493 | 0.19069449 | 0.171334303 | 0.17340567 | 0.210086936 |
| 0.208167408 | 0.175990807 | 0.144919512 | 0.097302091 | 0.250599111 | 0.190630925 | 0.146049675 | 0.226137219 | 0.212687626 |
| 0.223783868 | 0.17045186 | 0.160006644 | 0.115590365 | 0.24898563 | 0.125095586 | 0.152680259 | 0.16404504 | 0.280468092 |
| 0.213711252 | 0.16314045 | 0.155508187 | 0.107752534 | 0.231831777 | 0.128718781 | 0.126776776 | 0.159130709 | 0.285913285 |
| 0.201530413 | 0.147705251 | 0.141459161 | 0.094053981 | 0.211196201 | 0.113081833 | 0.100519661 | 0.136509187 | 0.258606047 |
| 0.188412587 | 0.142904831 | 0.126025994 | 0.087204704 | 0.19625027 | 0.104246321 | 0.102199409 | 0.135105093 | 0.253892297 |
| 0.173264621 | 0.133820958 | 0.118828463 | 0.079155039 | 0.237181741 | 0.110920629 | 0.122533202 | 0.143217639 | 0.218051547 |
| 0.193644101 | 0.135667273 | 0.14519634 | 0.114813643 | 0.171368691 | 0.127447484 | 0.099900806 | 0.174731759 | 0.168800993 |
| 0.039275396 | 0.033381387 | 0.078065525 | 0.310053326 | 0.017408613 | 0.027523571 | 0.184241841 | 0.052965565 | 0.018286097 |
| 0.165456391 | 0.12348159 | 0.120420225 | 0.079790539 | 0.185805102 | 0.099923913 | 0.108299547 | 0.126212494 | 0.207161161 |
| 0.18138518 | 0.12628799 | 0.105056265 | 0.066162598 | 0.172217891 | 0.077994047 | 0.0805395 | 0.1218442 | 0.223334198 |

FIG. 20 (Cont. 7)

| 361 | 798 | 970 | 391 | 392 | 969 | 974 | 392 | 974 |
|---|---|---|---|---|---|---|---|---|
| Timepoint 7 | Timepoint 7 | Timepoint 7 | Timepoint 7 | Timepoint 7 | Timepoint 7 | Timepoint 7 | Terminal | Terminal |
| Anti-CTLA4 + Vehicle | Anti-CTLA4 + Vehicle | Anti-CTLA4 + Vehicle | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid | Anti-CTLA4 + Microbe mix 4 + Ellagic Acid |
| 5.016039596 | 0.901148826 | 2.042136682 | 61.77425631 | 42.23826054 | 0.569950788 | 39.00612791 | 83.83507888 | 48.24682807 |
| 2.133176528 | 0.270474919 | 0.197897968 | 5.673196335 | 1.117378452 | 1.006829366 | 1.598340542 | 0.648099581 | 1.254907509 |
| 4.436025651 | 5.110201024 | 6.866352724 | 1.856123868 | 3.156322503 | 6.401922205 | 3.564581055 | 0.599218982 | 1.92426115 |
| 9.844601449 | 10.39765187 | 1.734053764 | 0.641004158 | 3.180127681 | 15.56320968 | 0.957455273 | 1.278814101 | 1.255002467 |
| 7.910348831 | 4.131622442 | 3.13202531 | 2.278681108 | 3.399013245 | 5.599684705 | 3.845100382 | 1.709957651 | 8.319441879 |
| 2.685360577 | 3.379633776 | 2.815968481 | 0.791491881 | 1.346030242 | 1.90767269 | 1.234383614 | 0.455673156 | 1.197220981 |
| 1.638073692 | 4.663453318 | 1.606108741 | 0.511742046 | 0.996460353 | 2.056646611 | 0.905421191 | 0.327964406 | 1.808745657 |
| 0.095609161 | 0.271940466 | 0.688293483 | 0.188284207 | 0.120307709 | 0.088790892 | 0.355507551 | 0 | 0 |
| 1.592737893 | 1.560645167 | 1.443277857 | 0.505970169 | 1.102423917 | 1.887281979 | 1.082506057 | 0.276702292 | 1.272427121 |
| 1.635904157 | 1.418649905 | 2.050744881 | 0.611912037 | 1.235610838 | 1.694711502 | 0.941190222 | 0.260031686 | 0.642860568 |
| 1.763532661 | 2.305631773 | 1.956145303 | 0.679778137 | 0.965635699 | 1.38923127 | 0.778680531 | 0.343116796 | 0.819196177 |
| 1.742286181 | 1.752387621 | 1.574213097 | 0.557358491 | 1.113105727 | 1.776730852 | 1.034555841 | 0.516788789 | 4.192789801 |
| 0.599390136 | 0.100634256 | 0.901142535 | 0.382619576 | 0.503326926 | 1.072110073 | 1.955890026 | 0.116724012 | 0.339377204 |
| 2.983933472 | 1.558691103 | 2.252539192 | 0.37307736 | 0.663126816 | 1.091055174 | 1.069409522 | 0.212520459 | 0.617649419 |
| 0.09171896 | 0.486398906 | 1.607739768 | 0.085135183 | 0.069706446 | 0.054172335 | 0.2668595 | 0 | 0 |
| 1.441244505 | 2.031167309 | 2.073488649 | 0.476226384 | 0.819203332 | 1.182432947 | 0.740869568 | 0.288758713 | 0.619216213 |
| 1.541791228 | 1.658918263 | 1.407214033 | 0.431401244 | 0.793505947 | 1.54588975 | 0.602651837 | 0.282626311 | 0.750589566 |
| 0.280992181 | 0.309800441 | 0.647155353 | 0.324668071 | 0.390282848 | 0.259981557 | 0.677992118 | 0 | 0.022789739 |
| 0.784773156 | 0.886411933 | 2.134289719 | 0.275281286 | 0.457181503 | 0.875507105 | 0.55751808 | 0.144260281 | 0.921702526 |
| 0.09366406 | 0.170329178 | 0.437749581 | 0.131217103 | 0.114509012 | 0.120137805 | 0.42598944 | 0 | 0.015810382 |
| 0.143413741 | 0.038022814 | 0.073849288 | 0.212814684 | 0.095464869 | 0.095258095 | 0.149413156 | 0.010180977 | 0.031905635 |
| 1.162571482 | 0.624486041 | 0.598586987 | 0.235669454 | 0.433254247 | 0.507561301 | 0.362267052 | 0.191027284 | 0.783349816 |
| 0.966265976 | 0.936321964 | 0.630029567 | 0.213652537 | 0.332234836 | 0.546288434 | 0.360999646 | 0.129792576 | 0.394262493 |
| 0.42096459 | 0.554546861 | 0.625045873 | 0.163800278 | 0.331807564 | 0.510604691 | 0.289884053 | 0.060877481 | 0.205345049 |
| 0.016458541 | 0.063588474 | 0.146701836 | 0.036865536 | 0.027589591 | 0.019021185 | 0.112869599 | 0 | 0 |

FIG. 20 (Cont. 8)

| | | | | | | | | |
|---|---|---|---|---|---|---|---|---|
| 0.333958758 | 0.334877586 | 0.406125776 | 0.348407241 | 0.276262148 | 0.292089317 | 0.38789683 | 0.092819553 | 0.169546166 |
| 0.2312425 | 0.312405859 | 0.389362441 | 0.098913211 | 0.195507658 | 0.26804654 | 0.180675852 | 0.031882534 | 0.098470666 |
| 0.255331819 | 0.312731536 | 0.404313523 | 0.101054392 | 0.183666107 | 0.287980741 | 0.178281861 | 0.031942072 | 0.094909769 |
| 0.244633768 | 0.304671025 | 0.391990207 | 0.101240581 | 0.179088188 | 0.294980538 | 0.167016025 | 0.031197849 | 0.092963146 |
| 0.223312476 | 0.297343288 | 0.324665028 | 0.089138259 | 0.18012585 | 0.271394268 | 0.154834839 | 0.032626758 | 0.112571817 |
| 0.278897457 | 0.341798227 | 0.316328666 | 0.082388887 | 0.141854448 | 0.26949215 | 0.133148104 | 0.052065875 | 0.155302579 |
| 0.031570474 | 0.076615562 | 0.22526298 | 0.04035659 | 0.045229839 | 0.042911793 | 0.082874309 | 0 | 0 |
| 0.18538302 | 0.237825779 | 0.312160486 | 0.082714718 | 0.154367426 | 0.23144978 | 0.143357768 | 0.025005909 | 0.079336781 |
| 0.530563511 | 0.385031876 | 0.599221275 | 0.379268163 | 0.644937218 | 0.388640853 | 0.743333969 | 0.012294572 | 0.021887646 |
| 0.191143509 | 0.231963589 | 0.328742596 | 0.078385811 | 0.136727179 | 0.244384185 | 0.125754899 | 0.027119504 | 0.083182549 |
| 0.19742768 | 0.22960243 | 0.256252498 | 0.08518173 | 0.165293393 | 0.289958945 | 0.11723511 | 0.03200161 | 0.118221774 |
| 0.199746838 | 0.22251895 | 0.259967615 | 0.083971498 | 0.165171315 | 0.294524029 | 0.109419436 | 0.034591508 | 0.123207029 |
| 0.240668755 | 0.269335049 | 0.263682733 | 0.077268673 | 0.139168735 | 0.188309732 | 0.12913465 | 0.039235462 | 0.11280921 |
| 0.177004127 | 0.226427077 | 0.248006749 | 0.0776876 | 0.130623287 | 0.212048171 | 0.144695587 | 0.028578182 | 0.087170754 |
| 0.221816245 | 0.260297506 | 0.274193797 | 0.07089168 | 0.138558346 | 0.220113153 | 0.108715321 | 0.045725091 | 0.103645836 |
| 0.254060023 | 0.249468739 | 0.215295592 | 0.066097299 | 0.123176539 | 0.204211443 | 0.115897292 | 0.037211174 | 0.156489544 |
| 0.143638175 | 0.180425172 | 0.247825524 | 0.073265598 | 0.134712894 | 0.171190665 | 0.127585597 | 0.019677269 | 0.065805373 |
| 0.14289006 | 0.176598464 | 0.220822962 | 0.060232327 | 0.12140641 | 0.172560191 | 0.112235895 | 0.019468886 | 0.061294904 |
| 0.121194711 | 0.155999381 | 0.198804095 | 0.054600093 | 0.100225905 | 0.156582395 | 0.087873524 | 0.016998064 | 0.053983195 |
| 0.122765753 | 0.15966325 | 0.200253897 | 0.052412365 | 0.1005311 | 0.147908735 | 0.09294315 | 0.016462224 | 0.049092897 |
| 0.131069835 | 0.152091255 | 0.207684132 | 0.05124868 | 0.11237265 | 0.156354141 | 0.12244556 | 0.018159053 | 0.058208793 |
| 0.181642443 | 0.175621433 | 0.148423476 | 0.072893218 | 0.097723309 | 0.252373083 | 0.082944721 | 0.022118322 | 0.076820414 |
| 0.016757787 | 0.029880884 | 0.098767759 | 0.02178418 | 0.023866217 | 0.020999388 | 0.04766857 | 0 | 0 |
| 0.113189875 | 0.146473323 | 0.189833445 | 0.048362742 | 0.098211621 | 0.146310955 | 0.101392528 | 0.014497474 | 0.050422299 |
| 0.103165127 | 0.10722922 | 0.171257857 | 0.041985749 | 0.072758391 | 0.110246788 | 0.069918597 | 0.012979258 | 0.033519908 |

FIG. 20 (Cont. 9)

| 329 | 798 |
|---|---|
| Terminal | Terminal |
| Anti-CTLA4 + Vehicle | Anti-CTLA4 + Vehicle |
| 86.43528576 | 68.76202419 |
| 0.334256378 | 0.171980069 |
| 0.670819165 | 0.862479669 |
| 1.054259722 | 3.453142828 |
| 0.927291886 | 3.642116076 |
| 0.381912561 | 1.067801265 |
| 0.261863954 | 1.484475518 |
| 0.014270908 | 0 |
| 0.231765311 | 0.527888537 |
| 0.277720518 | 0.352153278 |
| 0.299977368 | 0.760217149 |
| 0.309866099 | 0.710299687 |
| 0.106037171 | 0.074041706 |
| 0.195554684 | 0.435601923 |
| 0 | 0 |
| 0.227613774 | 0.562405931 |
| 0.26344961 | 0.603523353 |
| 0.028340005 | 0.012137985 |
| 0.135761021 | 0.316497949 |
| 0.012166309 | 0 |
| 0.027792233 | 0.010241425 |
| 0.112235646 | 0.296546136 |
| 0.122210866 | 0.288239203 |
| 0.052384323 | 0.092362477 |
| 0 | 0 |

FIG. 20 (Cont. 10)

| | |
|---|---|
| 0.090238267 | 0.123731581 |
| 0.029839171 | 0.053255407 |
| 0.032376221 | 0.054203688 |
| 0.030617584 | 0.053862307 |
| 0.029320229 | 0.05048643 |
| 0.04189016 | 0.116790171 |
| 0 | 0 |
| 0.026033596 | 0.042179497 |
| 0.045061473 | 0.014034545 |
| 0.023323565 | 0.042824327 |
| 0.030905886 | 0.05018298 |
| 0.029233739 | 0.049007113 |
| 0.033760067 | 0.090390054 |
| 0.024765071 | 0.051965747 |
| 0.030473434 | 0.08458658 |
| 0.033212295 | 0.080338286 |
| 0.020527043 | 0.034327738 |
| 0.018508935 | 0.032279453 |
| 0.016577317 | 0.028486333 |
| 0.015078151 | 0.028182883 |
| 0.023525376 | 0.024238038 |
| 0.022919943 | 0.056403697 |
| 0 | 0 |
| 0.021449607 | 0.024465625 |
| 0.011503217 | 0.020482849 |

FIG. 20 (Cont. 11)

| name | C1 | C10 | C11 | C2 | C3 | C4 | C5 | C6 | C7 | C8 | C9 |
|---|---|---|---|---|---|---|---|---|---|---|---|
| Bacteroides vulgatus | 2.688591 | 7.894047 | 1.470364 | 9.924293 | 1.634563 | 0.027734 | 20.06547 | 13.17783 | 0.662932 | 3.888451 | 0.029249 |
| Prevotella copri | 0.051444 | 0.106142 | 55.38343 | 0.020424 | 0.060288 | 0 | 0.05204 | 0.048547 | 0.01605 | 0.023413 | 0.023465 |
| Enterococcus faecalis | 0 | 0 | 0 | 0 | 0 | 0 | 0 | 0 | 0 | 39.45899 | 0.641885 |
| [Eubacterium] rectale | 0.104145 | 0.013636 | 7.088264 | 0.040518 | 9.061194 | 23.01955 | 0.020273 | 0.222581 | 0.086585 | 0.029361 | 0.087924 |
| Bacteroides thetaiotaomicron | 2.956329 | 1.786309 | 0.42863 | 1.743851 | 2.988953 | 0 | 11.59036 | 14.46855 | 0.79733 | 0.386839 | 0.810322 |
| Bacteroides dorei | 14.68217 | 1.086116 | 0.921916 | 1.330735 | 0.425901 | 0 | 2.518538 | 9.107573 | 4.35496 | 1.663378 | 0.218385 |
| Faecalibacterium prausnitzii | 2.026633 | 0.104929 | 2.411907 | 1.622184 | 9.016681 | 0.482063 | 0.020589 | 4.356411 | 0.243313 | 12.09938 | 1.909821 |
| Bacteroides ovatus | 3.940238 | 0.821099 | 0.116865 | 0.221662 | 1.34319 | 0.045002 | 10.39743 | 14.68651 | 0.492707 | 0.256301 | 1.184127 |
| Ruminococcus bromii | 3.701105 | 0 | 0 | 0.018547 | 3.396552 | 7.53609 | 4.672785 | 0.031753 | 9.185563 | 0.249453 | 0.012411 |
| Bacteroides cellulosilyticus | 4.584714 | 1.139544 | 0.082724 | 0.522463 | 0.540048 | 0.022152 | 6.704439 | 3.215038 | 2.916834 | 0.769871 | 0.02073 |
| Bacteroides caccae | 3.340878 | 1.147911 | 0.038013 | 0.824376 | 0.269147 | 0 | 8.335533 | 0.450359 | 0.130697 | 4.719723 | 0.042602 |
| Lactobacillus johnsonii | 0 | 0 | 0 | 0.090057 | 0 | 0 | 0 | 0 | 0 | 0 | 17.07011 |
| Akkermansia muciniphila | 0 | 0 | 0 | 8.137821 | 0 | 0 | 0 | 0 | 5.731283 | 0.013938 | 0 |
| Escherichia coli | 0.024025 | 2.031613 | 0.113161 | 0.045374 | 9.850456 | 0.017204 | 0 | 0 | 0.416915 | 0 | 0 |
| Fusicatenibacter saccharivorans | 0.396715 | 0.081014 | 1.005713 | 0.437066 | 0.158843 | 0.367896 | 0.185671 | 0.374227 | 0.184387 | 0.04624 | 9.107422 |
| Bacteroides caecimuris | 3.130554 | 0.760136 | 0.071322 | 0.289645 | 1.379479 | 0.016498 | 0.970335 | 2.230719 | 0.484077 | 0.416521 | 0.694976 |
| Bacteroides fragilis | 1.380869 | 0.468474 | 0.13639 | 0.4818 | 0.941328 | 0.011358 | 1.034216 | 1.904764 | 0.437023 | 0.539707 | 2.983581 |
| Methanobrevibacter smithii | 0 | 8.628336 | 0 | 0 | 0.265092 | 0.014259 | 0 | 0 | 1.100193 | 0 | 0 |
| Streptococcus salivarius | 0.028942 | 0 | 0 | 6.278973 | 0.563058 | 0.628063 | 0.011161 | 0 | 0.065554 | 1.384332 | 0.372592 |
| Prevotella denticola | 0.01875 | 0.021466 | 0.017094 | 0 | 0.025935 | 0 | 0.012973 | 0.010099 | 0 | 0 | 9.157562 |
| Alistipes finegoldii | 0.326716 | 3.324669 | 0.0195 | 0.632252 | 0.535044 | 0.329318 | 0.064427 | 0.694908 | 2.716968 | 0.326337 | 0.017227 |
| Dorea longicatena | 0.711582 | 0.036263 | 1.232194 | 0.053034 | 0.076634 | 0.187873 | 0.03043 | 0.530292 | 0.040057 | 0.257263 | 5.169125 |
| Gemmiger formicilis | 0.27424 | 0.167453 | 0.039745 | 0.212991 | 2.672989 | 0.02536 | 0 | 0.282356 | 3.917055 | 0.359007 | 0.038154 |
| Hungatella hathewayi | 0.167877 | 0.247236 | 0.036992 | 0.128141 | 0.095834 | 0.162613 | 0.170467 | 0.038051 | 6.546977 | 0.167127 | 0.052328 |
| Blautia obeum | 0.195122 | 0.050039 | 1.179028 | 0.174773 | 2.650559 | 2.667059 | 0.060242 | 0.09544 | 0.02498 | 0.573878 | 0.061693 |
| Ruminococcus faecis | 0.215977 | 0 | 0.040956 | 0.036682 | 0.058271 | 0.134201 | 0.016572 | 0.024762 | 0.016555 | 0.028838 | 7.08682 |
| Blautia wexlerae | 0.746484 | 0.0138 | 0.240106 | 0.174762 | 0.661939 | 1.293743 | 0.320648 | 0.492555 | 0.125391 | 0.408233 | 2.93066 |
| Lactobacillus fermentum | 0 | 0 | 0 | 3.665888 | 0 | 0.306738 | 0 | 0 | 0.010809 | 0.096972 | 3.202256 |
| Odoribacter splanchnicus | 0.42489 | 2.645636 | 0.052864 | 0.349752 | 0.932666 | 0 | 0.839277 | 0.732034 | 0.06193 | 0.071481 | 0.086442 |
| uncultured crAssphage | 0 | 5.771492 | 0 | 0.345999 | 0 | 0 | 0 | 0 | 0 | 0.025506 | 0 |
| Parabacteroides sp. CT06 | 1.742723 | 0.711954 | 0.147185 | 0.647418 | 0.569163 | 0 | 0.394969 | 0.52414 | 0.125284 | 0.982114 | 0.016146 |
| Lachnospira pectinoschiza | 0.046271 | 0 | 4.336572 | 0.0529 | 0.187978 | 0.131142 | 0.10767 | 0.550724 | 0.223508 | 0 | 0.032277 |
| Lactobacillus salivarius | 0 | 0 | 0 | 4.554659 | 0 | 0.011835 | 0 | 0 | 0.018836 | 0.791707 | 0 |

FIG. 21A

| | | | | | | | | | | | |
|---|---|---|---|---|---|---|---|---|---|---|---|
| Collinsella aerofaciens | 0 | 1.593395 | 0.631847 | 0.727443 | 0 | 0 | 0 | 0.084304 | 1.900071 | 0.339471 | 0 |
| Homo sapiens | 0.204251 | 0.207678 | 0.273568 | 0.137008 | 0.220548 | 0.356467 | 0.177687 | 0.201119 | 0.297125 | 0.07918 | 3.034421 |
| Ruminococcus callidus | 0 | 0 | 0 | 0.011135 | 0.010313 | 4.974179 | 0 | 0 | 0.032711 | 0 | 0 |
| Streptococcus parasanguinis | 0.031406 | 0 | 0 | 3.116372 | 0.202847 | 0.805605 | 0 | 0 | 0 | 0.27535 | 0.430813 |
| [Clostridium] leptum | 0.171046 | 0.137277 | 0 | 0.412394 | 0.086468 | 0.04255 | 2.439334 | 0.112583 | 0.133348 | 0.98036 | 0 |
| Roseburia hominis | 0.106148 | 0 | 0.048435 | 0.050426 | 0.223901 | 1.059356 | 0.072598 | 1.906813 | 0.023613 | 0 | 1.018798 |
| Bifidobacterium longum | 0.162397 | 0.196172 | 0.066499 | 0.123461 | 0.01013 | 0.02181 | 0.513254 | 0.012375 | 3.392141 | 0 | 0 |
| Parabacteroides distasonis | 0.793971 | 0.647823 | 0.097003 | 0.632706 | 0.491275 | 0 | 0.452963 | 0.4259 | 0.064725 | 0.763849 | 0 |
| Ruminococcus sp. 5_1_39BFAA | 0.349943 | 0.019699 | 0.203012 | 0.119976 | 0.446324 | 0.766171 | 0.119711 | 0.173248 | 0.080372 | 0.20028 | 1.739369 |
| Subdoligranulum sp. APC924/74 | 1.23116 | 0.033551 | 0.44459 | 0.218744 | 0.261311 | 0.075061 | 0.01416 | 0.317491 | 1.334173 | 0.037233 | 0.044565 |
| [Eubacterium] hallii | 0.422712 | 0.083675 | 0.361278 | 0.658233 | 0.047581 | 0.101897 | 0.030328 | 0.581936 | 0.712952 | 0.699887 | 0.064922 |
| Streptococcus thermophilus | 0 | 0 | 0 | 2.123079 | 0.022603 | 0.022829 | 0 | 0 | 0 | 1.529464 | 0.066675 |
| Roseburia intestinalis | 0.065746 | 0.013039 | 0.086142 | 0.081912 | 0.334704 | 1.594848 | 0.423844 | 0.619603 | 0.087234 | 0.025948 | 0.095795 |
| Roseburia inulinivorans | 0.112517 | 0.091924 | 0.143124 | 0.278686 | 0.216309 | 1.436528 | 0.019847 | 0.357347 | 0.030384 | 0.010146 | 0.636295 |
| [Eubacterium] eligens | 0.211847 | 0 | 0.05832 | 0.715278 | 0.822494 | 0.275888 | 0 | 1.11533 | 0 | 0.060793 | 0.033197 |
| Blautia hydrogenotrophica | 0.09388 | 2.054555 | 0 | 0.012609 | 0 | 0.020227 | 0.01029 | 0 | 0.05332 | 1.032695 | 0 |
| Ruthenibacterium lactatiforman | 0.491045 | 1.560169 | 0.013972 | 0.253571 | 0.082525 | 0.067582 | 0.083447 | 0.030176 | 0.61392 | 0.017288 | 0.020215 |

FIG. 21A (Cont.)

| name | H1 | H2 | H3 | H4 | H5 | H6 | H7 |
|---|---|---|---|---|---|---|---|
| Bacteroides vulgatus | 1.380534 | 5.881793 | 22.83735 | 7.678464 | 1.205789 | 32.08711 | 8.432489 |
| Bacteroides dorei | 12.48986 | 0.705845 | 2.178098 | 12.50058 | 6.894739 | 3.054785 | 1.000231 |
| Faecalibacterium prausnitzii | 7.764135 | 6.78107 | 0.167856 | 0.274366 | 3.165553 | 5.468682 | 8.084262 |
| Bacteroides cellulosilyticus | 0.844309 | 1.202254 | 0.272431 | 0.552796 | 2.113406 | 0.576544 | 0.218101 |
| [Eubacterium] rectale | 0.439673 | 10.95491 | 7.128677 | 2.161816 | 0.260976 | 1.192848 | 4.211515 |
| Bacteroides ovatus | 1.397551 | 0.687125 | 7.560379 | 8.350635 | 0.769993 | 4.297999 | 0.778899 |
| Ruminococcus bicirculans | 17.86951 | 2.353171 | 0.536657 | 1.510815 | 0.317427 | 0 | 1.796359 |
| [Eubacterium] eligens | 2.936309 | 0.613772 | 0.057603 | 0.048767 | 0.994562 | 0.502813 | 11.196 |
| Alistipes finegoldii | 0.33415 | 0.191458 | 0.160104 | 1.994053 | 3.179239 | 0.843275 | 0.186203 |
| Bacteroides fragilis | 0.450359 | 0.634685 | 4.512083 | 1.920592 | 0.516077 | 0.990315 | 0.184353 |
| Roseburia intestinalis | 4.105496 | 0.158622 | 0.10912 | 0.250383 | 0.067066 | 0.464407 | 7.309056 |
| Bacteroides thetaiotaomicron | 1.198136 | 0.82618 | 1.264536 | 1.771047 | 0.631005 | 4.595765 | 0.502226 |
| Escherichia coli | 0 | 0 | 0.327177 | 0.029338 | 0.020108 | 0.129598 | 0.013913 |
| Fusicatenibacter saccharivorans | 1.883388 | 1.380284 | 0.742754 | 1.153038 | 1.484171 | 0.658924 | 0.251751 |
| [Eubacterium] hallii | 1.229193 | 1.367582 | 1.779493 | 1.842486 | 0.995581 | 0.655564 | 1.242368 |
| Blautia wexlerae | 0.689569 | 1.205611 | 1.523443 | 1.111558 | 0.138223 | 0.440898 | 0.739106 |
| Bifidobacterium adolescentis | 0.128132 | 7.708298 | 1.078524 | 0 | 0 | 0 | 0.265977 |
| Subdoligranulum sp. APC924/74 | 0.318481 | 2.724799 | 0.013122 | 0.151857 | 1.025425 | 0.334108 | 1.853427 |
| Bacteroides caccae | 0.152577 | 0.624599 | 0.14232 | 5.495367 | 0.3403 | 0.249491 | 0.871701 |
| Dorea longicatena | 1.115025 | 0.470869 | 1.139232 | 0.912705 | 0.535382 | 0.927268 | 1.924453 |
| Ruminococcus bromii | 0.209989 | 7.144487 | 0 | 0 | 0.646565 | 0 | 0.094469 |
| uncultured crAssphage | 0 | 1.469923 | 5.476972 | 1.117183 | 0 | 0 | 0 |
| Anaeromassilibacillus sp. Marseille-P3876 | 0.07353 | 0.046664 | 0 | 0 | 7.501928 | 0.010156 | 0.033331 |
| Ruminococcus faecis | 0.539933 | 0.229548 | 0.808175 | 1.644494 | 0.21073 | 0.731484 | 2.586462 |
| Bacteroides caecimuris | 1.138786 | 0.245274 | 0.864003 | 1.354053 | 0.405519 | 1.129196 | 0.159431 |
| Bifidobacterium longum | 0 | 1.080581 | 0.121789 | 0.03047 | 0.206589 | 0.050136 | 1.115467 |
| Coprococcus comes | 0.752432 | 0.554535 | 1.477581 | 0.37171 | 0.186136 | 0.777051 | 1.399383 |
| Lachnospira pectinoschiza | 3.207718 | 0.12218 | 0.057917 | 0.258821 | 0.101625 | 0.389313 | 1.050674 |
| Roseburia inulinivorans | 0.351139 | 1.300905 | 0.134502 | 0.146382 | 0.110953 | 1.259322 | 1.987148 |
| Gemmiger formicilis | 0.485837 | 0.57358 | 0.030592 | 2.799784 | 0.555057 | 0.060916 | 0.73953 |
| Homo sapiens | 0.255674 | 0.166848 | 0.120964 | 2.430426 | 0.84603 | 0.222268 | 0.208233 |
| Lachnoclostridium sp. SNUG30099 | 0.049891 | 0.443166 | 1.019555 | 0.044513 | 0.40348 | 1.106494 | 1.654359 |
| Ruminococcus sp. 5_1_39BFAA | 0.534885 | 1.047745 | 0.548194 | 0.504719 | 0.065002 | 0.18008 | 0.470152 |
| Anaerostipes hadrus | 0.137414 | 0.755995 | 0.393417 | 0.49533 | 0.746036 | 0.241687 | 0.797346 |
| Roseburia hominis | 0.119741 | 2.038324 | 0.086266 | 0.075393 | 0.122294 | 1.762672 | 0.223117 |
| Clostridiales bacterium KLE1615 | 0.339076 | 0.465304 | 0.025031 | 0.306207 | 0.302658 | 0.144928 | 2.400142 |
| Methanobrevibacter smithii | 0 | 0 | 0 | 0 | 4.116725 | 0 | 0.015874 |
| Blautia obeum | 0.368278 | 0.878712 | 0.102544 | 1.529343 | 0.123811 | 0.281149 | 0.702948 |
| Blautia sp. Marseille-P2398 | 0.377204 | 0.554459 | 0.577719 | 0.333944 | 0.039516 | 0.150611 | 0.640129 |
| Streptococcus thermophilus | 0.068548 | 0.794857 | 0.04158 | 0.730438 | 0.671197 | 0 | 0.979153 |
| Odoribacter splanchnicus | 0.485284 | 0.431122 | 0.081962 | 0.193638 | 1.407433 | 0.270984 | 0.09858 |
| Butyricicoccus sp. GAM44 | 0.241935 | 0.260479 | 0.346232 | 0.444541 | 0.095954 | 0.76055 | 0.601177 |
| Ruminococcus lactaris | 0.113166 | 0.838572 | 0.51837 | 0.37136 | 0.091405 | 0.092641 | 1.134122 |
| [Eubacterium] siraeum | 0.066122 | 2.40952 | 0 | 0 | 0.6248 | 0 | 0.017405 |
| Akkermansia muciniphila | 0 | 0 | 0 | 0 | 3.032797 | 0 | 0.041239 |
| Blautia sp. SG-772 | 0.316196 | 0.832456 | 0.107016 | 0.593145 | 0.235681 | 0.252611 | 0.214909 |
| Lachnoclostridium sp. SNUG30386 | 0.268899 | 0.256608 | 0.345487 | 0.591804 | 0.154738 | 0.384455 | 0.48516 |
| Parabacteroides sp. CT06 | 0.245166 | 0.14152 | 0.114139 | 0.487693 | 0.712994 | 0.330259 | 0.184966 |
| Collinsella aerofaciens | 0.283566 | 0.334996 | 0.182921 | 0.579822 | 0.122128 | 0.163138 | 0.327201 |
| Lachnoclostridium sp. SNUG30370 | 0.786832 | 0.046785 | 0.074817 | 0.042701 | 0.122179 | 0.286602 | 0.337792 |

FIG. 21B

| H8 | H9 |
|---|---|
| 3.3432 | 1.073673 |
| 4.444476 | 12.11902 |
| 7.672102 | 13.82434 |
| 25.35998 | 0.267412 |
| 0.313437 | 4.256221 |
| 1.709009 | 2.867141 |
| 1.323112 | 0 |
| 0.024436 | 0.196857 |
| 8.85339 | 0.121461 |
| 1.68765 | 1.949346 |
| 0.119109 | 0.090783 |
| 0.709187 | 0.886151 |
| 11.41863 | 0 |
| 0.336537 | 3.739429 |
| 0.24526 | 1.038902 |
| 0.092705 | 3.305845 |
| 0 | 0.059323 |
| 0.179358 | 2.636567 |
| 0.095324 | 1.187477 |
| 0.156335 | 1.897741 |
| 0.011107 | 0 |
| 0 | 0 |
| 0.017902 | 0 |
| 0.122654 | 0.035009 |
| 0.951326 | 0.584036 |
| 0 | 3.260671 |
| 0.179064 | 0.039904 |
| 0.423321 | 0.116382 |
| 0.306623 | 0.083079 |
| 0.153432 | 0.105571 |
| 0.251611 | 0.64937 |
| 0.302345 | 0.091259 |
| 0.0764 | 1.601269 |
| 0.043785 | 1.087937 |
| 0.085742 | 0.04068 |
| 0.151054 | 0.103878 |
| 0 | 0 |
| 0.072532 | 0.039666 |
| 0.034053 | 1.174511 |
| 0.034188 | 0.326565 |
| 0.432927 | 0.131931 |
| 0.254456 | 0.32067 |
| 0.033729 | 0.099404 |
| 0 | 0 |
| 0 | 0 |
| 0.162783 | 0.090089 |
| 0.058952 | 0.237258 |
| 0.062955 | 0.412486 |
| 0.026404 | 0.668033 |
| 0.278796 | 0.674629 |

FIG. 21B (Cont.)

| | | | | |
|---|---|---|---|---|
| | 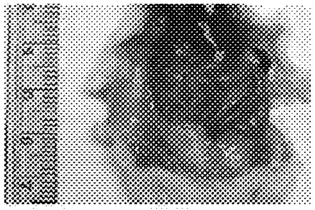 | 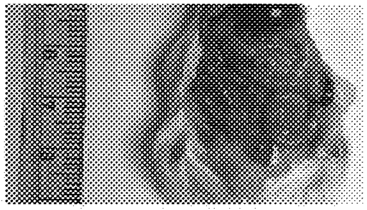 | 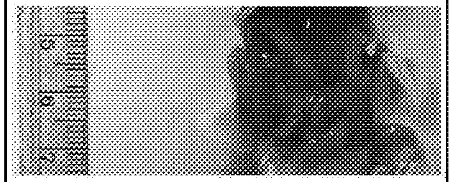 | 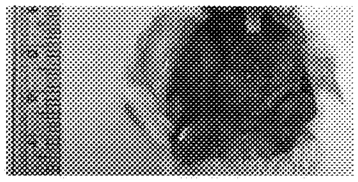 |
| Pre-treatment | Water | Water | Antibiotic | Antibiotic |
| Treatment | Vehicle | Vehicle | Vehicle | Vehicle |
| Tumor Volume ($m^3$) | 592.32 | 817.34 | 344.36 | 3989.98 |
FIG. 38A

| | | | | |
|---|---|---|---|---|
| | 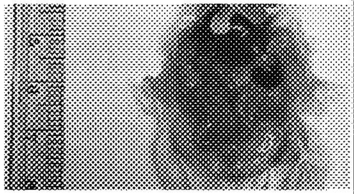 | 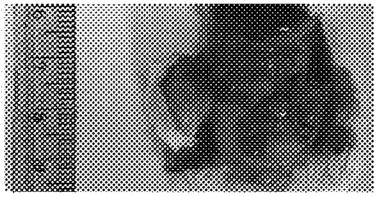 | 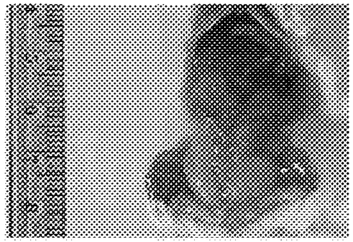 | 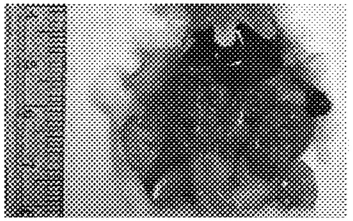 |
| Pre-treatment | Water | Water | Antibiotic | Antibiotic |
| Treatment | Anti-CTLA4 + Vehicle | Anti-CTLA4 + Vehicle | Anti-CTLA4 + Vehicle | Anti-CTLA4 + Vehicle |
| Tumor Volume ($m^3$) | 54.35 | 1316.90 | .5 | 2220.18 |
FIG. 38B

| | | | | |
|---|---|---|---|---|
| | 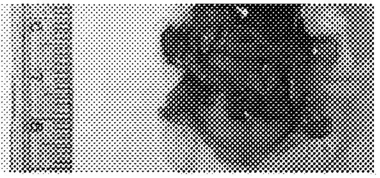 | 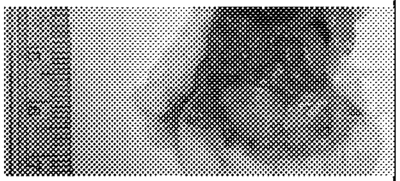 | 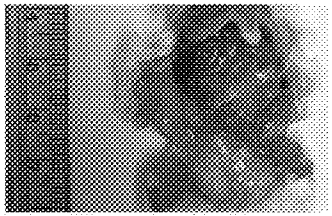 | 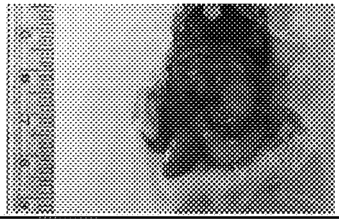 |
| Pre-treatment | Water | Water | Antibiotic | Antibiotic |
| Treatment | Anti-CTLA4 + Microbe Mix 4 + Ellagic Acid | Anti-CTLA4 + Microbe Mix 4 + Ellagic Acid | Anti-CTLA4 + Microbe Mix 4 + Ellagic Acid | Anti-CTLA4 + Microbe Mix 4 + Ellagic Acid |
| Tumor Volume ($m^3$) | .5 | 7.81 | 41.12 | 1893.88 |
FIG. 38C

| | | | | |
|---|---|---|---|---|
| | 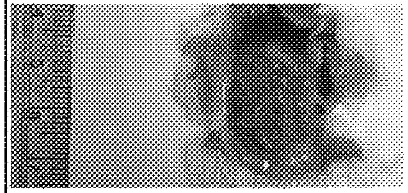 | 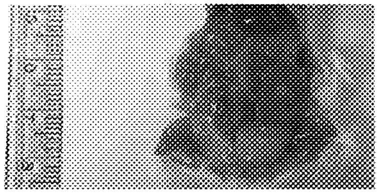 | 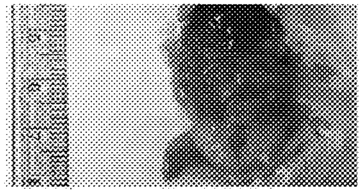 | 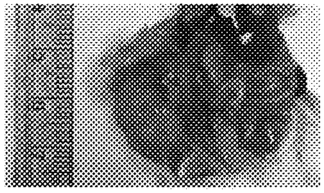 |
| Pre-treatment | Water | Water | Antibiotic | Antibiotic |
| Treatment | Anti-CTLA4 + Microbe Mix 2 | Anti-CTLA4 + Microbe Mix 2 | Anti-CTLA4 + Microbe Mix 2 | Anti-CTLA4 + Microbe Mix 2 |
| Tumor Volume ($m^3$) | .5 | 154.63 | .5 | 4717.21 |
FIG. 38D

| log10 Fold Change (Cancer / Healthy) | Metabolite | p value (Mann Whitney U) |
|---|---|---|
| -0.705733331 | 5alpha-pregnan-3beta,20alpha-diol monosulfate (2) | 4.38812E-07 |
| 0.165725175 | N-acetylneuraminate | 2.07479E-06 |
| -0.450387647 | X - 18899 | 3.28238E-06 |
| -0.218878755 | 1-(1-enyl-palmitoyl)-2-linoleoyl-GPC (P-16:0/18:2)* | 7.99802E-06 |
| 0.1826634 | orotidine | 8.91748E-06 |
| 0.160754145 | C-glycosyltryptophan | 9.93712E-06 |
| 0.140877734 | pseudouridine | 1.88061E-05 |
| 0.191129291 | N-acetylglucosamine/N-acetylgalactosamine | 2.0875E-05 |
| 0.523736128 | X - 12127 | 2.27214E-05 |
| 0.338206093 | N-stearoyl-sphinganine (d18:0/18:0)* | 2.5678E-05 |
| 0.320770308 | N4-acetylcytidine | 2.5678E-05 |
| 0.153985045 | 5,6-dihydrouridine | 2.5678E-05 |
| -0.231098187 | sphingomyelin (d18:2/14:0, d18:1/14:1)* | 2.84556E-05 |
| 0.251706578 | N6-succinyladenosine | 3.0924E-05 |
| 0.333952407 | X - 24337 | 3.48865E-05 |
| 0.169031735 | N2,N2-dimethylguanosine | 3.8596E-05 |
| 0.159774142 | ribitol | 4.26762E-05 |
| 0.239705973 | (N(1) + N(8))-acetylspermidine | 4.71618E-05 |
| -0.174309548 | guanidinoacetate | 5.75013E-05 |
| 0.353740567 | 5-(galactosylhydroxy)-L-lysine | 6.01426E-05 |
| 0.184897618 | 3-(3-amino-3-carboxypropyl)uridine* | 7.66797E-05 |
| 0.201855676 | N-stearoyl-sphingosine (d18:1/18:0)* | 8.49132E-05 |
| 0.212796529 | 3,4-dihydroxybutyrate | 8.49132E-05 |
| -0.273247279 | gamma-glutamylmethionine | 0.000102846 |
| 0.166199731 | N6-carbamoylthreonyladenosine | 0.000113093 |

FIG. 59

| | | |
|---|---|---|
| -0.177739256 | 1-(1-enyl-palmitoyl)-2-oleoyl-GPC (P-16:0/18:1)* | 0.000136525 |
| 0.239369094 | gulonate* | 0.00014988 |
| 0.309101355 | quinolinate | 0.000164451 |
| -1.076261428 | thymol sulfate | 0.000165343 |
| -0.45407372 | 5alpha-pregnan-3beta,20alpha-diol disulfate | 0.000180252 |
| 0.576609752 | lactose | 0.00018104 |
| -0.22315582 | sphingomyelin (d17:1/14:0, d16:1/15:0)* | 0.000197653 |
| -0.968327718 | X - 11843 | 0.000207189 |
| -0.546896792 | hydroxy-CMPF* | 0.000216512 |
| -0.699990169 | X - 12013 | 0.000229158 |
| -0.461604412 | X - 17367 | 0.000254576 |
| -0.402297258 | X - 17325 | 0.000256555 |
| 0.236201429 | X - 18887 | 0.000257016 |
| -0.481961965 | X - 18901 | 0.000258899 |
| -0.241125457 | 1-lignoceroyl-GPC (24:0) | 0.000283524 |
| -0.161690283 | 1-linoleoyl-2-arachidonoyl-GPC (18:2/20:4n6)* | 0.000283651 |
| -0.556838906 | 3-carboxy-4-methyl-5-propyl-2-furanpropanoate (CMPF) | 0.000283651 |
| -0.895899321 | X - 11850 | 0.000287624 |
| 0.270717955 | X - 24334 | 0.000314832 |
| -0.141939836 | 1-(1-enyl-palmitoyl)-2-palmitoyl-GPC (P-16:0/16:0)* | 0.000338687 |
| 0.267104048 | X - 25790 | 0.000369785 |
| 0.213527656 | N-acetyltaurine | 0.000369785 |
| 0.120469121 | N-acetylserine | 0.000369785 |
| 0.312054332 | cytidine | 0.000369785 |
| 0.501649148 | 2'-O-methyluridine | 0.000397134 |
| -0.511640403 | X - 21834 | 0.000406627 |
| 0.491004173 | 3-(methylthio)acetaminophen sulfate* | 0.000408108 |

FIG. 59 (Cont. 1)

| | | |
|---|---|---|
| -0.302103505 | glycosyl-N-tricosanoyl-sphingadienine (d18:2/23:0)* | 0.000439903 |
| 0.452563049 | 2-methoxyacetaminophen glucuronide* | 0.000454937 |
| -0.090380341 | 4-methylbenzenesulfonate | 0.000522615 |
| -0.609246575 | 3-phenylpropionate (hydrocinnamate) | 0.000541928 |
| 0.174186911 | 1-stearoyl-2-docosahexaenoyl-GPE (18:0/22:6)* | 0.000568818 |
| -0.209985215 | 1-(1-enyl-palmitoyl)-GPC (P-16:0)* | 0.000569048 |
| 0.148040863 | X - 12100 | 0.000569048 |
| 0.291217748 | X - 25420 | 0.000569048 |
| 0.397061503 | 3-(N-acetyl-L-cystein-S-yl) acetaminophen | 0.000579841 |
| 0.215898663 | X - 24728 | 0.000619022 |
| 0.100035004 | 2,3-dihydroxy-5-methylthio-4-pentenoate (DMTPA)* | 0.000619268 |
| -0.4799367 | beta-cryptoxanthin | 0.000619268 |
| 0.508569174 | glycoursodeoxycholic acid sulfate (1) | 0.000710847 |
| -0.346229252 | 1-stearoyl-2-oleoyl-GPI (18:0/18:1)* | 0.000729371 |
| 0.168924446 | X - 12026 | 0.000732202 |
| 1.193635909 | 4-acetamidophenylglucuronide | 0.000775109 |
| -0.190740979 | 4-hydroxychlorothalonil | 0.000795523 |
| 0.482176122 | X - 12117 | 0.000822029 |
| -0.451880216 | 5alpha-pregnan-3beta,20beta-diol monosulfate (1) | 0.000862552 |
| -0.496540016 | indolepropionate | 0.000930603 |
| -0.394418207 | pregnenolone sulfate | 0.00093615 |
| -0.188278055 | 1-(1-enyl-stearoyl)-2-linoleoyl-GPE (P-18:0/18:2)* | 0.00093754 |
| 0.261631708 | (S)-3-hydroxybutyrylcarnitine | 0.00093754 |
| 0.192607864 | 1-methyl-4-imidazoleacetate | 0.00093754 |
| -0.228316577 | isovalerylglycine | 0.001009545 |
| 0.509148307 | deoxycholic acid glucuronide | 0.001015477 |
| 0.181328897 | mannonate* | 0.001016963 |

FIG. 59 (Cont. 2)

| | | |
|---|---|---|
| -0.104463181 | lactosyl-N-nervonoyl-sphingosine (d18:1/24:1)* | 0.001016963 |
| -0.152894 | myristoyl dihydrosphingomyelin (d18:0/14:0)* | 0.001102517 |
| 0.264410267 | linoleoyl-arachidonoyl-glycerol (18:2/20:4) [2]* | 0.001102517 |
| 0.27509648 | 3-hydroxyadipate* | 0.001102517 |
| 0.087933284 | N-acetylthreonine | 0.001194623 |
| 0.113336172 | 1-methyladenosine | 0.001194623 |
| 0.377966263 | isoursodeoxycholate sulfate (1) | 0.00128712 |
| -0.112479564 | histidine | 0.001400287 |
| 0.75470649 | 2-hydroxyacetaminophen sulfate* | 0.001408322 |
| 0.171035614 | 2-methoxyacetaminophen sulfate* | 0.001468452 |
| -0.178564829 | 1-(1-enyl-palmitoyl)-2-palmitoleoyl-GPC (P-16:0/16:1)* | 0.001514811 |
| 0.189494075 | 1-palmitoyl-2-arachidonoyl-GPE (16:0/20:4)* | 0.001514811 |
| 0.188703438 | arachidonoyl ethanolamide | 0.001519937 |
| -0.117306437 | serine | 0.001637818 |
| 0.176466416 | 1-palmitoyl-2-docosahexaenoyl-GPE (16:0/22:6)* | 0.001637818 |
| 0.192646052 | oleoyl-arachidonoyl-glycerol (18:1/20:4) [2]* | 0.00176986 |
| 0.186373704 | glucuronate | 0.00176986 |
| 0.157761486 | X - 15461 | 0.00176986 |
| -0.727279468 | X - 11858 | 0.001775255 |
| -0.227806207 | xanthurenate | 0.001859838 |
| 0.113066378 | N-palmitoyl-heptadecasphingosine (d17:1/16:0)* | 0.001911517 |

FIG. 59 (Cont. 3)

```
                         SEQUENCE LISTING

<160> NUMBER OF SEQ ID NOS: 2

<210> SEQ ID NO 1
<211> LENGTH: 52
<212> TYPE: DNA
<213> ORGANISM: Artificial sequence
<220> FEATURE:
<223> OTHER INFORMATION: synthetic oligonucleotide

<400> SEQUENCE: 1

tcgtcggcag cgtcagatgt gtataagaga caggtgycag cmgccgcggt aa            52


<210> SEQ ID NO 2
<211> LENGTH: 54
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (42)..(42)
<223> OTHER INFORMATION: n is a, c, g, or t

<400> SEQUENCE: 2

gtctcgtggg ctcggagatg tgtataagag acagggacta cnvgggtwtc taat          54
```

COMPOSITIONS FOR MODULATING GUT MICROFLORA POPULATIONS, ENHANCING DRUG POTENCY AND TREATING CANCER, AND METHODS FOR MAKING AND USING SAME

RELATED APPLICATIONS

This application is a national phase application claiminq benefit of priority under 35 U.S.C. § 371 to Patent Convention Treaty (PCT) International Application serial number PCT/US2019/022583, filed Mar. 15, 2019, which claims the benefit of priority under 35 U.S.C. § 119(e) of U.S. Provisional Patent Application Ser. No. 62/644,203, Mar. 16, 2018; U.S. Ser. No. 62/738,958, Sep. 28, 2018; U.S. Ser. No. 62/742,024, Oct. 5, 2018; U.S. Ser. No. 62/749,482, Oct. 23, 2018; U.S. Ser. No. 62/784,028, filed Dec. 21, 2018; U.S. Ser. No. 62/789,936, Jan. 8, 2019; U.S. Ser. No. 62/797,062 Jan. 25, 2019; and, U.S. Ser. No. 62/814,220, filed Mar. 5, 2019. The aforementioned applications are expressly incorporated herein by reference in its entirety and for all purposes. All publications, patents, patent applications cited herein are hereby expressly incorporated by reference for all purposes.

REFERENCE TO SEQUENCE LISTING

This application includes an electronically submitted sequence listing in .txt format. The .txt file contains a sequence listing entitled "6411.130057_ST25.txt" created on 2024-05-28 and is 1,255 bytes in size. The sequence listing contained in this .txt file is part of the specification and is hereby incorporated by reference herein in its entirety.

TECHNICAL FIELD

This invention generally relates to microbiology, pharmacology and cancer therapies. In alternative embodiments, provided are compositions, including products of manufacture and kits, and methods, comprising non-pathogenic, live bacteria and/or bacterial spores for the control, amelioration, prevention, and treatment of a disease or condition, for example, a cancer. In alternative embodiment, these non-pathogenic, live bacteria and/or bacterial spores are administered to an individual in need thereof, thereby resulting in a modification or modulation of the individual's gut microfloral population(s). In alternative embodiments, by modulating or modifying the individual's gut microbial population(s) using compositions, products of manufacture and methods as provided herein, the pharmacodynamics of a drug administered to the individual is altered, for example, the pharmacodynamics of the drug is enhanced, e.g., the individual's ability to absorb a drug is modified (e.g., accelerated or slowed, or enhanced), or the dose efficacy of a drug is increased (e.g., resulting in needing a lower dose of drug for an intended effect). For example, in alternative embodiments, the modulating or modifying of the individual's gut microbial population(s) increases the dose efficacy of a cancer drug, thereby controlling, ameliorating, preventing and/or treating of that cancer. In alternative embodiments, the amount, identity, presence, and/or ratio of microbiota gut microbiota in a subject is manipulated to facilitate one or more co-treatments.

BACKGROUND

Checkpoint inhibitors are a class of cancer drugs which function by enabling the patient's own immune system to fight the tumor, a treatment approach known as immunotherapy. Examples include ipilimumab (YERVOY™) and nivolumab (OPDIVO™). Such therapy has been shown to be particularly effective against advanced melanoma, non-small-cell lung cancer, and renal cell carcinoma.

However, these drugs are effective in less than 50% of patients in which they have been used. Studies have shown that gut microbes influence and modulate the efficacy of immunotherapy. Intestinal microbiota can facilitate inflammatory responses and modify tumor-specific T-cell induction, which can influence the activity of immune checkpoint inhibitors (ICI). By metagenomic analysis of patient fecal samples, it was observed that response to two different immunotherapy treatments was highly correlated with the presence of a number of specific species. In mice, T-cell responses specific to certain *Bacteroides* species were associated with the effectiveness of CTLA-4 blockade, and germ-free mice not responding to the ICI could be restored by treatment with *B. fragilis*. The efficacy of another ICI, targeting the programmed cell death protein 1 (PD-1), was shown to be positively correlated with the presence of *Akkermansia muciniphila* in patient fecal samples and functional enrichment in anabolic pathways, and dosing of mice with *A. muciniphila* increased the rate of response to this ICI drug.

A combination of in vitro and/or in vivo data provide evidence that the gut microbiota metabolizes over 50 drugs (Spanogiannopoulos et al. (2016) Nat Rev Microbiol 5:273-87; Haiser et al. (2013) Pharmacol. Res 69:21-31). Recent human, animal and in vitro studies have suggested that the intestinal microbiota modulates the anticancer immune effects of chemotherapies including 5-fluorouracil, cyclophosphamide, irinotecan, cisplatin, oxaliplatin, gemcitabine and methotrexate (Alexander et al. (2017) Nat Rev Gastroenterol Hepatol 6: 356-365; Viaud et al. (2013) Science 342:971-976; Shen et al. (2017) Nat Neurosci 20:1213-1216; Viaud et al. (2014) Cell Death Differ 2: 199-214). The gut microbiome also modulates patient and animal tumor response to checkpoint blockade immunotherapy targeting cytotoxic T-lymphocyte-associated protein 4 (CTLA-4, e.g. Yervoy®/Ipilimumab), the programmed cell death protein 1 (PD-1, e.g. Keytruda®/Pembrolizumab, Opdivo®/Nivolumab) and its ligand (PD-L1, e.g. Tecentriq®/Atezolizumab, Bavencio®/Avelumab and Imfinzi®/Durvalumab) (Peled et al. (2017) J Clin Oncol 15:1650-1659; Iida et al. (2013) Science 342:967-970; Daillere et al. (2016) Immunity 45:931-943; Vetizou et al. (2015) Science 350:1079-1084; Sivan et al. (2015) Science 350:1084-1089; Gopalakrishnan et al. (2017) Science Nov 02 DOI: 10.1126/science.aan4236; Routy et al. (2017) Science Nov 02 DOI: 10.1126/science.aan3706). These studies also suggest that primary resistance to immune checkpoint inhibitors can be due to abnormal gut microbiome composition and that microbial diversity is correlated with patient response. Moreover, durable responses have been observed in about 20% of melanoma patients treated with ipilimumab and several combination-based drug therapies are under development to increase clinical benefit (Sharma et al. (2015) Science 6230:6-61). Thus, there is a need for means to manipulate a gut microbiota in conjunction with an immune checkpoint therapy to improve the efficacy of a cancer immunotherapy.

SUMMARY

In alternative embodiments, provided are methods for controlling, ameliorating or treating a cancer in an individual (for example, a patient) in need thereof, comprising:

(a) (i) providing or having provided: (1) an inhibitor of an inhibitory immune checkpoint molecule, a stimulatory immune checkpoint molecule (or any composition for use in checkpoint blockade immunotherapy) and, (2) a formulation comprising at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable bacterial spores, or a combination thereof, and (ii) administering or having administered to an individual in need thereof the inhibitor of the inhibitory immune checkpoint molecule and/or the stimulatory immune checkpoint molecule, and the formulation; or (b) administering or having administered to an individual in need thereof an inhibitor of an inhibitory immune checkpoint molecule and/or a stimulatory immune checkpoint molecule (or any composition for use in checkpoint blockade immunotherapy) and a formulation, wherein the formulation comprises at least two different species or genera (or types) of non-pathogenic, live bacteria, and each of the non-pathogenic, live bacteria comprise (or are in the form of) a plurality of non-pathogenic colony forming live bacteria, a plurality of non-pathogenic germinable bacterial spores, or a combination thereof, and optionally the non-pathogenic bacteria or non-pathogenic bacteria arising from germination of the germinable spores can individually or together metabolize urolithin A from ellagic acid, or can individually or together synthesize urolithin A, and optionally the different species or genera (or types) of non-pathogenic, live bacteria are present in approximately equal amounts, or each of the different species or genera (or types) of non-pathogenic, live bacteria or non-pathogenic germinable bacterial spores represent at least about 1%, 5%, 10%, 20%, 30%, 40%, or 50% or more of the total amount of non-pathogenic, live bacteria and non-pathogenic germinable bacterial spores in the formulation, and optionally only non-pathogenic, live bacteria are present in the formulation, or only non-pathogenic germinable bacterial spores are present in the formulation, or approximately equal amounts of non-pathogenic, live bacteria and non-pathogenic germinable bacterial spores are present in the formulation.

In alternative embodiments of the methods provided herein:

(a) the formulation comprises an inner core surrounded by an outer layer of polymeric material enveloping the inner core, wherein the non-pathogenic bacteria or the non-pathogenic germinable bacterial spores are substantially in the inner core, and optionally the polymeric material comprises a natural polymeric material;

(b) the formulation is formulated or manufactured as or in: a nano-suspension delivery system; an encochleated formulation; or, as a multilayer crystalline, spiral structure with no internal aqueous space;

(c) the formulation is formulated or manufactured as a delayed or gradual enteric release composition or formulation, and optionally the formulation comprises a gastro-resistant coating designed to dissolve at a pH of 7 in the terminal ileum, optionally an active ingredient is coated with an acrylic based resin or equivalent, optionally a poly(meth)acrylate, optionally a methacrylic acid copolymer B, NF, optionally EUDRAGIT S™ (Evonik Industries AG, Essen, Germany), which dissolves at pH 7 or greater, optionally comprises a multimatrix (MMX) formulation, and optionally manufactured as enteric coated to bypass the acid of the stomach and bile of the duodenum.

In alternative embodiments of the methods provided herein: the plurality of non-pathogenic colony forming live bacteria are substantially dormant colony forming live bacteria, or the plurality of non-pathogenic colony forming live bacteria or the plurality of non-pathogenic germinable bacterial spores are lyophilized, wherein optionally the dormant colony forming live bacteria comprise live vegetative bacterial cells that have been rendered dormant by lyophilization or freeze drying.

In alternative embodiments of the methods provided herein: the formulation comprises at least $1\times10^4$ colony forming units (CFUs), or between about $1\times10^1$ and $1\times10^{13}$ CFUs, $1\times10^2$ and $1\times10^{10}$ CFUs, $1\times10^2$ and $1\times10^8$ CFUs, $1\times10^3$ and $1\times10^7$ CFUs, or $1\times10^4$ and $1\times10^6$ CFUs, of non-pathogenic live bacteria and/or non-pathogenic germinable bacterial spores.

In alternative embodiments of the methods provided herein: the formulation comprises at least one (or any one, several, or all of) non-pathogenic bacteria or spore of the family or genus (or class): Clostridiaceae, *Faecalibacterium, Blautia* or *Clostridium*; Ruminococcaceae or *Ruminococcus*; Verrucomicrobiaceae or *Akkermansia*; Enterococcaceae or *Enterococcus; Eggerthella*; Eggerthellaceae or *Gordonibacter*; Bacteroidaceae or *Bacteroides*; Hyphomicrobiaceae or *Gemmiger; Bifidobacterium, Alistipes, Dorea, Roseburia, Monoglobus, Asacharobacter*, or a combination thereof.

In alternative embodiments of the methods provided herein, bacteria that are used to practice methods as provided herein comprise:

(a) bacteria of the genus *Faecalibacterium* comprise a bacteria of the species *Faecalibacterium prausnitzii;*

(b) bacteria from the genus *Clostridium* comprise *Clostridium* Cluster IV, *Clostridium* Cluster XIVa (also known as Lachnospiraceae), or of the species *C. coccoides, C. scindens*, or a combination thereof, or of the genus *Eubacterium*, or *Eubacterium hallii* or, *E. ramulus*, or, because *C. coccoides* is no longer in the genus *Clostridium* but is now in the genus *Blautia*, bacteria that are used to practice methods as provided herein can comprise *B. coccoides, B. hansenii, B hydrogenotrophica, B. luti, B. producta, B. schinkii*, or *B. wexlerae;*

(c) bacteria of the genus *Ruminococcus* comprise a bacteria of the species *Ruminococcus albus, R. bromii, R. callidus, R. flavefaciens, R. gauvreauii, R. gnavus R. lactaris, R. obeum* or *R. torques;*

(d) bacteria of the genus *Akkermansia* comprise a bacteria of the species *Akkermansia glycaniphila or A. muciniphila;*

(e) bacteria of the genus *Enterococcus* comprise a bacteria of the species *Enterococcus alcedinis, E. aquimarinus, E. asini, E. avium, E. bulliens, E. caccae, E. camelliae, E. canintestini, E. canis, E. casseliflavus, E. cecorum, E. lactis, E. lemanii*, or *E. hirae*, or any species of non-pathogenic *Enterococcus* found or capable of living in a human gut;

(f) bacteria of the genus *Eggerthella* comprise a bacteria of the species *Eggerthella lenta;*

(g) bacteria of the genus *Gordonibacter* comprise a bacteria of the species *Gordonibacter urolithinfaciens*, or any species of non-pathogenic *Gordonibacter* found or capable of living in a human gut;

(h) bacteria of the genus *Bacteroides* comprise a bacteria of the species *Bacteroides acidifaciens, B. caccae*, or *B. thetaiotamicron*, or any species of non-pathogenic *Bacteroides* found or capable of living in a human gut;

(i) bacteria of the genus *Gemmiger* comprise a bacteria of the species *Gemmiger formicilis;*

(j) bacteria of the genus *Bifidobacterium*, comprise a bacteria of the species *Bifidobacterium longum, B. bifidum*, or *B. brevis;*

(j) bacteria of the genus *Alistipes* comprise a bacteria of the species *Alistipes indistinctus;*

(k) bacteria of the genus *Dorea* comprise a bacteria of the species *Dorea formicigenerans, D. formicilis*, or *D. longicatena;*

(l) bacteria of the genus Anerostipes comprise a bacteria of the species *A. muciniphila;*

(m) bacteria of the genus *Eubacterium* comprise a bacteria of the species *E. hallii;*

(n) bacteria of the genus *Blautia* comprise a bacteria of the species *Blautia* sp. SG-772; and/or (o) bacteria of the genus *Coprococcus* comprise a bacteria of the species *C. comes.*

In alternative embodiments of the methods provided herein: the formulation comprises a combination of non-pathogenic bacteria and/or a spore thereof (or spore derived from) comprising (or a combination as described in Table 1 (Example 1) and/or Table 5 (see Example 22), below)):

(a) (i) *F. prausnitzii, C. coccoides, R. gnavus*, and *C. scindens;*

(ii) *F. prausnitzii, C. coccoides, R. gnavus, C. scindens, A. muciniphila*, and *E. hirae;*

(iii) *E. lenta* and *G. urolithinfaciens;*

(iv) *F. prausnitzii, C. coccoides, R. gnavus, C. scindens, E. lenta*, and *G. urolithinfaciens;*

(v) *F. prausnitzii, C. coccoides, R. gnavus, C. scindens, B. thetaiotamicron, B. caccae*, and *G. formicilis;*

(vi) *F. prausnitzii, C. coccoides, R. gnavus, C. scindens, A. indistinctus* and *D. formicigenerans*; and/or (vii) *F. prausnitzii, C. coccoides, R. gnavus, C. scindens, B. longum* and *B. breve;*

(viii) *Faecalibacterium prausnitzii, Clostridium coccoides, Ruminococcus gnavus, Clostridium scindens, Eggerthella lenta, Gordonibacter urolithinfaciens* and *Adlercreutzia equohfaciens;*

(ix) *Faecalibacterium prausnitzii, Clostridium coccoides, Ruminococcus gnavus, Clostridium scindens, Eggerthella lenta, Gordonibacter urolithinfaciens, Adlercreutzia equohfaciens*, and *Senegalimassilia anaerobia;*

(x) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia*, and *Ellagibacter isourolithinifaciens;*

(xi) *Faecalibacterium prausnitzii, Clostridium coccoides, Ruminococcus gnavus, Clostridium scindens, Eggerthella lenta, Gordonibacter urolithinfaciens, Adlercreutzia equohfaciens*, and *Ellagibacter isourolithinifaciens;*

(xii) *Eggerthella lenta, Gordonibacter urolithinfaciens, Adlercreutzia equohfaciens, Senegalimassilia anaerobia* and *Ellagibacter isourolithinifaciens;*

(xiii) *Eggerthella lenta, Gordonibacter urolithinfaciens, Adlercreutzia equohfaciens, Senegalimassilia anaerobia, Ellagibacter isourolithinifaciens* and *Collinsella aerofaciens;*

(xiv) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia*, and *Collinsella aerofaciens;*

(xv) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia, Collinsella aerofaciens* and *Ellagibacter isourolithinfaciens;*

(xvi) *Faecalibacterium prausnitzii, Clostridium coccoides, Ruminococcus gnavus, Clostridium scindens, Eggerthella lenta, Gordonibacter urolithinfaciens*, and *Ellagibacter isourolithinifaciens;*

(xvii) *Eggerthella lenta, Gordonibacter urolithinfaciens*, and *Ellagibacter isourolithinfaciens;*

(xviii) *Faecalibacterium prausnitzii, Clostridium coccoides, Ruminococcus gnavus, Clostridium scindens, Eggerthella lenta, Gordonibacter urolithinfaciens*, and *Paraeggerthella hongkongensis;*

(ixx) *Faecalibacterium prausnitzii, Clostridium coccoides, Ruminococcus gnavus, Clostridium scindens, Eggerthella lenta, Gordonibacter urolithinfaciens, Paraeggerthella hongkongensis; Slackia isoflavoniconvertens*, and *Slackia equohfaciens;*

(xx) *Faecalibacterium prausnitzii, Clostridium coccoides, Ruminococcus gnavus, Clostridium scindens*, and *Gordonibacter urolithinfaciens;*

(xxi) *Eubacterium hallii;*

(xxii) *Faecalibacterium prausnitzii, Clostridium coccoides, Ruminococcus gnavus, Clostridium scinden*, and *Eubacterium hallii;*

(xxiii) *Faecalibacterium prausnitzii, Clostridium coccoides, Ruminococcus gnavus, Clostridium scindens, Eggerthella lenta, Gordonibacter urolithinfaciens*, and *Eubacterium hallii;*

(xxiv) *Faecalibacterium prausnitzii, Clostridium coccoides, Ruminococcus gnavus, Clostridium scindens, Akkermansia muciniphila, Enterococcus hirae*, and *Eubacterium hallii;*

(xxv) *Blautia massiliensis;*

(xxvi) *Faecalibacterium prausnitzii, Clostridium coccoides, Ruminococcus gnavus, Clostridium scindens*, and *Blautia massiliensis;*

(xxvii) *Faecalibacterium prausnitzii, Clostridium coccoides, Ruminococcus gnavus, Clostridium scindens, Eggerthella lenta, Gordonibacter urolithinfaciens*, and *Blautia massiliensis;*

(xxviii) *Faecalibacterium prausnitzii, Clostridium coccoides, Ruminococcus gnavus, Clostridium scindens, Akkermansia muciniphila, Enterococcus hirae*, and *Blautia massiliensis;*

(xxviv) *Faecalibacterium prausnitzii, Clostridium coccoides, Ruminococcus gnavus, Clostridium scindens, Eggerthella lenta, Gordonibacter urolithinfaciens, Blautia massiliensis*, and *Eubacterium hallii;*

(xxx) *Faecalibacterium prausnitzii, Clostridium coccoides, Ruminococcus gnavus, Clostridium scindens, Akkermansia muciniphila, Enterococcus hirae, Blautia massiliensis*, and *Eubacterium hallii;*

(xxxi) *Faecalibacterium prausnitzii, Clostridium coccoides, Ruminococcus gnavus, Clostridium scindens, Gordonibacter urolithinfaciens*, and *Eubacterium hallii;*

(xxxii) *Faecalibacterium prausnitzii, Clostridium coccoides, Ruminococcus gnavus, Clostridium scindens, Gordonibacter urolithinfaciens, Eubacterium hallii* and *Blautia massiliensis;*

(xxxiii) *Akkermansia muciniphila*, and *Faecalibacterium prausnitzii;*

(xxxiv) *Eubacterium hallii, Dorea longicatena*, and *Blautia* sp. SG-772;

(xxxv) *Akkermansia muciniphila, Faecalibacterium prausnitzii, Eubacterium hallii, Dorea longicatena*, and *Blautia* sp. SG-772;

(xxxvi) *Akkermansia muciniphila, Faecalibacterium prausnitzii*, and *Ruminococcus gnavus;*

(xxxvii) *Dorea longicatena, Dorea formicigenerans, Blautia* sp. SG-772, *Eubacterium hallii, Ruminococcus faecis*, and *Coprococcus comes;*

(xxxviii) *Faecalibacterium prausnitzii*, and *Ruminococcus gnavus;*

(xxxix) *Ruminococcus gnavus, Eubacterium ramulus*, and *Gemmiger formililis;*

(xxxx) *Anaerostipes hadrus, Dorea formicigenerans, Dorea longicatena, Coprococcus comes*, and *Ruminococcus faecis;*

(xxxxi) *Anaerostipes hadrus, Dorea formicigenerans, Dorea longicatena, Coprococcus comes, Ruminococcus faecis* and *Ruminococcus gnavus;*

(xxxxii) *Anaerostipes hadrus, Dorea formicigenerans, Dorea longicatena, Coprococcus comes, Ruminococcus faecis* and *Akkermansia muciniphila;*

(xxxxiii) *Akkermansia muciniphila, Eubacterium ramulus*, and *Gemmiger formililis;*

(xxxxiv) *Akkermansia muciniphila, Ruminococcus gnavus, Ruminococcus torques*, and *Bifidobacterium bifidum;*

(xxxxv) *Akkermansia muciniphila, Ruminococcus gnavus*, and *Ruminococcus torques;*

(xxxxvi) *Akkermansia muciniphila, Ruminococcus torques, Dorea longicatena, Coprococcus comes*, and *Anaerostipes hadrus;*

(xxxxvii) *Akkermansia muciniphila, Roseburia inulinivorans, Dorea longicatena, Coprococcus comes*, and *Anaerostipes hadrus;*

(xxxxviii) *Dorea longicatena, Coprococcus comes, Anaerostipes hadrus, Eubacterium hallii, Faecalibacterium prausnitzii*, and *Collinsella aerofaciens;*

(xxxxix) *Dorea longicatena, Coprococcus comes, Anaerostipes hadrus, Eubacterium hallii, Faecalibacterium prausnitzii*, and *Blautia obeum;*

(xxxxx) *Akkermansia muciniphila, Ruminococcus gnavus, Dorea longicatena, Coprococcus comes*, and *Anaerostipes hadrus;*

(xxxxxi) *Akkermansia muciniphila, Gemmiger formicilis, Asacharobacter celatus, Collinsella aerofaciens, Alistipes putredinis*, and *Gordonibacter urolithinfaciens;*

(xxxxxii) *Akkermansia muciniphila, Monoglubus pectinilyticus, Bacteroides galacturonicus, Collinsella aerofaciens, Ruminococcus gnavus*, and *Dorea longicatena;*

(xxxxxiii) *Akkermansia muciniphila, Monoglubus pectinilyticus, Bacteroides galacturonicus, Collinsella aerofaciens, Ruminococcus torques*, and *Dorea longicatena*; and/or, (xxxxxiv) any combination of (i) to (xxxxxiii);

(b) any one of, or several of, or all of the following bacteria or a spore thereof (or a spore derived from): the genus Lachnospiraceae or the genus *Eubacterium*; or *Eubacterium hallii; Faecalibacterium prausnitzii* (ATCC-27768), *Clostridium coccoides* (ATCC-29236), *Ruminococcus gnavus* (ATCC-29149), *Clostridium scindens* (ATCC-35704), *Akkermansia muciniphila* (BAA-835), *Enterococcus hirae* (ATCC-9790), *Bacteroides thetaiotamicron* (ATCC-29148), *Bacteroides caccae* (ATCC-43185), *Bifidobacterium breve* (ATCC-15700), *Bifidobacterium longum* (ATCC BAA-999), *Gemmiger formicilis* (ATCC-27749), *Eggerthella lenta* (DSM-2243), *Gordonibacter urolithinfaciens* (DSM-27213), *Alistipes indistinctus* (DSM-22520) or *Alistipes putredinis, Faecalibacterium prausnitzii* (e.g., ATCC-27768), *Dorea longicatena* (e.g., DSM-13814), *Ruminococcus torques* (e.g., ATCC-27756), *Roseburia inulinivorans* (e.g., DSM-16841), *Coprococcus comes* (e.g., ATCC-27758), *Eubacterium hallii* (e.g., ATCC-27751), *Bacteroides galacturonicus* (e.g., ATCC-43244), *Collinsella aerofaciens* (e.g., ATCC-25986), *Anaerostipes hadrus* (e.g., ATCC-29173), *Blautia obeum* (e.g., ATCC-29174), *Fusicatenibacter saccharivorans* (e.g., DSM-26062), *Lachnoclostridium* sp. SNUG30099, *Monoglobus pectinyliticus, Asaccharobacter celatus* (e.g., DSM-18785), *Ruminococcus* bicirculans, *Blautia* hydrogenotrophica (e.g., DSM-10507), and *Dorea formicigenerans* (DSM-3992).

In alternative embodiments of the methods provided herein: the formulation comprises water, saline, a pharmaceutically acceptable preservative, a carrier, a buffer, a diluent, an adjuvant or a combination thereof.

In alternative embodiments of the methods provided herein: the formulation is administered orally or rectally, or is formulated as a liquid, a food, a gel, a candy, an ice, a lozenge, a tablet, pill or capsule, or a suppository or as an enema formulation, or for any form of intra-rectal or intra-colonic administration.

In alternative embodiments of the methods provided herein the formulation is administered to the subject in one, two, three, or four or more doses, and wherein the one, two, three, or four or more doses are administered on a daily basis (optionally once a day, bid or tid), every other day, every third day, or about once a week, and optionally the two, three, or four or more doses are administered at least a week apart (or dosages are separated by about a week).

In alternative embodiments of the methods provided herein: the formulation further comprises an antibiotic, or the method further comprises administration of an antibiotic, and optionally at least one dose of the antibiotic is administered before a first administration of the formulation, optionally at least one dose of the antibiotic is administered one day or two days, or more, before a first administration of the formulation.

In alternative embodiments of the methods provided herein: the inhibitor of the inhibitory immune checkpoint molecule comprises a protein or polypeptide that binds to an inhibitory immune checkpoint protein, and optionally inhibitor of the inhibitory immune checkpoint protein is an antibody or an antigen binding fragment thereof that specifically binds to the inhibitory immune checkpoint protein. The inhibitor may also be small molecule.

In alternative embodiments of the methods provided herein the inhibitor of the inhibitory immune checkpoint molecule targets a compound or protein comprising: a CTLA4 or CTLA-4 (cytotoxic T-lymphocyte-associated protein 4, also known as CD152, or cluster of differentiation 152); Programmed cell Death protein 1, also known as PD-1 or CD279; Programmed Death-Ligand 1 (PD-L1), also known as cluster of differentiation 274 (CD274) or B7 homolog 1 (B7-H1)); PD-L2; A2AR (adenosine $A_{2A}$ receptor, also known as ADORA2A); B7-H3; B7-H4; BTLA (B- and T-lymphocyte attenuator protein); KIR (Killer-cell Immunoglobulin-like Receptor); IDO (Indoleamine-pyrrole 2,3-dioxygenase); LAG3 (Lymphocyte-Activation Gene 3 protein); TIM-3; VISTA (V-domain Ig suppressor of T cell activation protein); or any combination thereof.

In alternative embodiments of the methods provided herein: the inhibitor of an inhibitory immune checkpoint molecule comprises: ipilimumab or YERVOY®; pembrolizumab or KEYTRUDA®; nivolumab or OPDIVO®; atezolizumab or TECENTRIP®; avelumab or BAVENCIO®; durvalumab or IMFINZI®; AMP-224 (MedImmune), AMP-514 (an anti-programmed cell death 1 (PD-1) monoclonal antibody (mAb) (MedImmune)), PDR001 (a humanized mAb that targets PD-1), STI-A1110 or STI-A1010 (Sorrento Therapeutics), BMS-936559 (Bristol-Myers Squibb), BMS-986016 (Bristol-Myers Squibb), TSR-042 (Tesaro), JNJ-61610588 (Janssen Research & Development), MSB-0020718C, AUR-012, enoblituzumab (also known as MGA271) (MacroGenics, Inc.), MBG453, LAG525 (Novartis), BMS-986015 (Bristol-Myers Squibb), or any combination thereof.

In alternative embodiments of the methods provided herein the activator of effector T cells or co-stimulatory checkpoint molecule comprises a protein or polypeptide that binds to an inhibitory immune checkpoint protein, and optionally inhibitor of the inhibitory immune checkpoint protein is an antibody or an antigen binding fragment thereof that specifically binds to the inhibitory immune checkpoint protein. The inhibitor may also be small molecule.

In alternative embodiments, the anticancer agent is an immune checkpoint inhibitor, a targeted antibody immunotherapy, a CAR-T cell therapy, an oncolytic virus, or a cytostatic drug, or any combination thereof.

In alternative embodiments, the anti-cancer agent comprises any one of or a combination of: Yervoy (ipilimumab, BMS); Keytruda (pembrolizumab, Merck); Opdivo (nivolumab, BMS); MEDI4736 (AZ/MedImmune); MPDL3280A (Roche/Genentech); Tremelimumab (AZ/MedImmune); CT-O11 (pidilizumab, CureTech); BMS-986015 (lirilumab, BMS); MEDIO680 (AZ/MedImmune); MSB-0010718C (Merck); PF-05082566 (Pfizer); MEDI6469 (AZ/MedImmune); BMS-986016 (BMS); BMS-663513 (urelumab, BMS); IMP321 (Prima Biomed); LAG525 (Novartis); ARGX-110 (arGEN-X); PF-05082466 (Pfizer); CDX-1127 (varlilumab; CellDex Therapeutics); TRX-518 (GITR Inc.); MK-4166 (Merck); JTX-2011 (Jounce Therapeutics); ARGX-115 (arGEN-X); NLG-9189 (indoximod, NewLink Genetics); INCB024360 (Incyte); IPH2201 (Innate Immotherapeutics/AZ); NLG-919 (NewLink Genetics); anti-VISTA (JnJ, Janssen Research & Development); Epacadostat (INCB24360, Incyte); F001287 (*Flexus*/BMS); CP 870893 (University of Pennsylvania); MGA271 (Macrogenix); Emactuzumab (Roche/Genentech); Galunisertib (Eli Lilly); Ulocuplumab (BMS); BKT140/BL8040 (Biokine Therapeutics); Bavituximab (Peregrine Pharmaceuticals); CC 90002 (Celgene); 852A (Pfizer); VTX-2337 (VentiRx Pharmaceuticals); IMO-2055 (Hybridon, Idera Pharmaceuticals); LY2157299 (Eli Lilly); EW-7197 (Ewha Women's University, Korea); Vemurafenib (Plexxikon); Dabrafenib (Genentech/GSK); BMS-777607 (BMS); BLZ945 (Memorial Sloan-Kettering Cancer Centre); Unituxin (dinutuximab, United Therapeutics Corporation); Blincyto (blinatumomab, Amgen); Cyramza (ramucirumab, Eli Lilly); Gazyva (obinutuzumab, Roche/Biogen); Kadcyla (ado-trastuzumab emtansine, Roche/Genentech); Perj eta (pertuzumab, Roche/Genentech); Adcetris (brentuximab vedotin, Takeda/Millennium); Arzerra (ofatumumab, GSK); Vectibix (panitumumab, Amgen); Avastin (bevacizumab, Roche/Genentech); Erbitux (cetuximab, BMS/Merck); Bexxar (tositumomab-I131, GSK); Zevalin (ibritumomab tiuxetan, Biogen); Campath (alemtuzumab, Bayer); Mylotarg (gemtuzumab ozogamicin, Pfizer); Herceptin (trastuzumab, Roche/Genentech); Rituxan (rituximab, Genentech/Biogen); volociximab (Abbvie); Enavatuzumab (Abbvie); ABT-414 (Abbvie); Elotuzumab (Abbvie/BMS); ALX-0141 (Ablynx); Ozaralizumab (Ablynx); Actimab-C (Actinium); Actimab-P (Actinium); Milatuzumab-dox (Actinium); Emab-SN-38 (Actinium); Naptumonmab estafenatox (Active Biotech); AFM13 (Affimed); AFM11 (Affimed); AGS-16C3F (Agensys); AGS-16M8F (Agensys); AGS-22ME (Agensys); AGS-15ME (Agensys); GS-67E (Agensys); ALXN6000 (samalizumab, Alexion); ALT-836 (Altor Bioscience); ALT-801 (Altor Bioscience); ALT-803 (Altor Bioscience); AMG780 (Amgen); AMG 228 (Amgen); AMG820 (Amgen); AMG172 (Amgen); AMG595 (Amgen); AMG110 (Amgen); AMG232 (adecatumumab, Amgen); AMG211 (Amgen/MedImmune); BAY20-10112 (Amgen/Bayer); Rilotumumab (Amgen); Denosumab (Amgen); AMP-514 (Amgen); MEDI575 (AZ/MedImmune); MEDI3617 (AZ/MedImmune); MEDI6383 (AZ/MedImmune); MEDI551 (AZ/MedImmune); Moxetumomab pasudotox (AZ/MedImmune); MEDI565 (AZ/MedImmune); MEDI0639 (AZ/MedImmune); MEDI0680 (AZ/MedImmune); MEDI562 (AZ/MedImmune); AV-380 (AVEO); AV203 (AVEO); AV299 (AVEO); BAY79-4620 (Bayer); Anetumab ravtansine (Bayer); vantictumab (Bayer); BAY94-9343 (Bayer); Sibrotuzumab (Boehringer Ingleheim); BI-836845 (Boehringer Ingleheim); B-701 (BioClin); BIIB015 (Biogen); Obinutuzumab (Biogen/Genentech); BI-505 (Bioinvent); BI-1206 (Bioinvent); TB-403 (Bioinvent); BT-062 (Biotest) BIL-010t (Biosceptre); MDX-1203 (BMS); MDX-1204 (BMS); Necitumumab (BMS); CAN-4 (Cantargia AB); CDX-011 (Celldex); CDX1401 (Celldex); CDX301 (Celldex); U3-1565 (Daiichi Sankyo); patritumab (Daiichi Sankyo); tigatuzumab (Daiichi Sankyo); nimotuzumab (Daiichi Sankyo); DS-8895 (Daiichi Sankyo); DS-8873 (Daiichi Sankyo); DS-5573 (Daiichi Sankyo); MORab-004 (Eisai); MORab-009 (Eisai); MORab-003 (Eisai); MORab-066 (Eisai); LY3012207 (Eli Lilly); LY2875358 (Eli Lilly); LY2812176 (Eli Lilly); LY3012217(Eli Lilly); LY2495655 (Eli Lilly); LY3012212 (Eli Lilly); LY3012211 (Eli Lilly); LY3009806 (Eli Lilly); cixutumumab (Eli Lilly); Flanvotumab (Eli Lilly); IMC-TR1 (Eli Lilly); Ramucirumab (Eli Lilly); Tabalumab (Eli Lilly); Zanolimumab (Emergent Biosolution); FG-3019 (FibroGen); FPA008 (Five Prime Therapeutics); FP-1039 (Five Prime Therapeutics); FPA144 (Five Prime Therapeutics); catumaxomab (Fresenius Biotech); IMAB362 (Ganymed); IMABO27 (Ganymed); HuMax-CD74 (Genmab); HuMax-TFADC (Genmab); GS-5745 (Gilead); GS-6624 (Gilead); OMP-21M18 (demcizumab, GSK); mapatumumab (GSK); IMGN289 (ImmunoGen); IMGN901 (ImmunoGen); IMGN853 (ImmunoGen); IMGN529 (ImmunoGen); IMMU-130 (Immunomedics); milatuzumab-dox (Immunomedics); IMMU-115 (Immunomedics); IMMU-132 (Immunomedics); IMMU-106 (Immunomedics); IMMU-102 (Immunomedics); Epratuzumab (Immunomedics); Clivatuzumab (Immunomedics); IPH41 (Innate Immunotherapeutics); Daratumumab (Janssen/Genmab); CNTO-95

(Intetumumab, Janssen); CNTO-328 (siltuximab, Janssen); KB004 (KaloBios); mogamulizumab (Kyowa Hakko Kirrin); KW-2871 (ecromeximab, Life Science); Sonepcizumab (Lpath); Margetuximab (Macrogenics); Enoblituzumab (Macrogenics); MGD006 (Macrogenics); MGF007 (Macrogenics); MK-0646 (dalotuzumab, Merck); MK-3475 (Merck); Sym004 (Symphogen/Merck Serono); DI17E6 (Merck Serono); MOR208 (Morphosys); MOR202 (Morphosys); Xmab5574 (Morphosys); BPC-1C (ensituximab, Precision Biologics); TAS266 (Novartis); LFA102 (Novartis); BHQ880 (Novartis/Morphosys); QGE031 (Novartis); HCD122 (lucatumumab, Novartis); LJM716 (Novartis); AT355 (Novartis); OMP-21M18 (Demcizumab, OncoMed); OMP52M51 (Oncomed/GSK); OMP-59R5 (Oncomed/GSK); vantictumab (Oncomed/Bayer); CMC-544 (inotuzumab ozogamicin, Pfizer); PF-03446962 (Pfizer); PF-04856884 (Pfizer); PSMA-ADC (Progenics); REGN1400 (Regeneron); REGN910 (nesvacumab, Regeneron/Sanofi); REGN421 (enoticumab, Regeneron/Sanofi); RG7221, RG7356, RG7155, RG7444, RG7116, RG7458, RG7598, RG7599, RG7600, RG7636, RG7450, RG7593, RG7596, DCDS3410A, RG7414 (parsatuzumab), RG7160 (imgatuzumab), RG7159 (obintuzumab), RG7686, RG3638 (onartuzumab), RG7597 (Roche/Genentech); SAR307746 (Sanofi); SAR566658 (Sanofi); SAR650984 (Sanofi); SAR153192 (Sanofi); SAR3419 (Sanofi); SAR256212 (Sanofi), SGN-LIV1A (lintuzumab, Seattle Genetics); SGN-CD33A (Seattle Genetics); SGN-75 (vorsetuzumab mafodotin, Seattle Genetics); SGN-19A (Seattle Genetics) SGN-CD70A (Seattle Genetics); SEA-CD40 (Seattle Genetics); ibritumomab tiuxetan (Spectrum); MLN0264 (Takeda); ganitumab (Takeda/Amgen); CEP-37250 (Teva); TB-403 (Thrombogenic); VB4-845 (Viventia); Xmab2512 (Xencor); Xmab5574 (Xencor); nimotuzumab (YM Biosciences); Carlumab (Janssen); NY-ESO TCR (Adaptimmune); MAGE-A-10 TCR (Adaptimmune); CTLO19 (Novartis); JCAR015 (Juno Therapeutics); KTE-C19 CAR (Kite Pharma); UCART19 (Cellectis); BPX-401 (Bellicum Pharmaceuticals); BPX-601 (Bellicum Pharmaceuticals); ATTCK20 (Unum Therapeutics); CAR-NKG2D (Celyad); Onyx-015 (Onyx Pharmaceuticals); H101 (Shanghai Sunwaybio); DNX-2401 (DNAtrix); VCN-01 (VCN Biosciences); Colo-Ad1 (PsiOxus Therapeutics); ProstAtak (Advantagene); Oncos-102 (Oncos Therapeutics); CG0070 (Cold Genesys); Pexa-vac (JX-594, Jennerex Biotherapeutics); GL-ONC1 (Genelux); T-VEC (Amgen); G207 (Medigene); HF10 (Takara Bio); SEPREHVIR (HSV1716, Virttu Biologics); OrienX010 (OrienGene Biotechnology); Reolysin (Oncolytics Biotech); SVV-001 (Neotropix); Cacatak (CVA21, Viralytics); Alimta (Eli Lilly), cisplatin, oxaliplatin, irinotecan, folinic acid, methotrexate, cyclophosphamide, 5-fluorouracil, Zykadia (Novartis), Tafinlar (GSK), Xalkori (Pfizer), Iressa (AZ), Gilotrif (Boehringer Ingelheim), Tarceva (Astellas Pharma), Halaven (Eisai Pharma), Veliparib (Abbvie), AZD9291 (AZ), Alectinib (Chugai), LDK378 (Novartis), Genetespib (Synta Pharma), Tergenpumatucel-L (NewLink Genetics), GV1001 (Kael-GemVax), Tivantinib (ArQule); Cytoxan (BMS); Oncovin (Eli Lilly); Adriamycin (Pfizer); Gemzar (Eli Lilly); Xeloda (Roche); Ixempra (BMS); Abraxane (Celgene); Trelstar (Debiopharm); Taxotere (Sanofi); Nexavar (Bayer); IMMU-132 (Immunomedics); E7449 (Eisai); Thermodox (Celsion); Cometriq (Exellxis); Lonsurf (Taiho Pharmaceuticals); Camptosar (Pfizer); UFT (Taiho Pharmaceuticals); and/or TS-1 (Taiho Pharmaceuticals).

In alternative embodiments of the methods provided herein the activator of effector T cells, or co-stimulatory checkpoint molecule, comprises a compound or protein comprising: a CD137 (tumor necrosis factor receptor superfamily member 9 (TNFRSF9), also known as 4-1BB); OX40 (tumor necrosis factor receptor superfamily, member 4 (TNFRSF4), also known as CD134 and OX40 receptor); GITR (glucocorticoid-induced TNF receptor); CD27 (member of tumor necrosis factor receptor superfamily); CD28 (cluster of differentiation 28); ICOS (inducible T-cell co-stimulator); or any combination thereof.

In alternative embodiments of the methods provided herein, the methods comprise use of an engineered (recombinantly engineered) cell comprising a multi-component chimeric antigen receptor (CAR) signaling polypeptide, for example, a CAR-T cells, wherein optionally the T cell, or the CAR-T cell, has been modified using CRISPR based or related technology, and wherein optionally the signaling polypeptide comprises: 1) an extracellular protein interaction domain and 2) an intracellular T cell receptor (TCR) signaling domain. In some embodiments, the extracellular protein interaction domain is a leucine zipper domain. In some embodiments, the leucine zipper domain is BZip (RR) or AZip (EE). In some embodiments, the protein interaction domain is a PSD95-Dlgl-zo-1 (PDZ) domain. In some embodiments, the extracellular protein interaction domain is streptavidin or streptavidin binding protein (SBP). In some embodiments, the extracellular protein interaction domain is FKBP-binding domain of mTOR (FRB) or FK506 binding protein (FKBP). In some embodiments, the extracellular protein interaction domain is PYL or ABI. In some embodiments, the protein interaction domain is a nucleotide tag or a zinc finger domain. In some embodiments, the nucleotide tag is a DNA tag. In some embodiments, the DNA tag is a dsDNA tag. In some embodiments, the protein interaction domain is a zinc finger domain. In some embodiments, the signaling polypeptide is present on the membrane of the cell. In some embodiments, the cell is a T cell, NK cell, or NKT cell. In some embodiments, the cell is a T cell. In some embodiments, the intracellular TCR signaling domain is a signaling domain derived from any one or a combination of the proteins: TCR FcRy, FcRp, CD3y, CD35, CD3s, CD3C, CD22, CD79a, CD79b, CD66d, CARD11, CD2, CD7, CD27, CD28, CD30, CD40, CD54 (ICAM), CD83, CD134 (OX40), CD137 (4-1BB), CD 150 (SLAMF1), CD 152 (CTLA4), CD223 (LAG3), CD270 (HVEM), CD273 (PD-L2), CD274 (PD-L1), CD278 (ICOS), DAPIO, LAT, NKD2C SLP76, TRIM, ZAP70, and/or 4 IBB. In some embodiments, the signaling polypeptide further comprises a secondary protein interaction domain that specifically binds with the protein interaction domain of the second recognition polypeptide. In some embodiments, the cell further comprises a second multi-component CAR signaling peptide according to any of the embodiments as provided herein.

In alternative embodiments of the methods provided herein, the methods comprise use of an engineered (recombinantly engineered) cell (e.g., immune cells or lymphocytes such as B cells or T cells) comprising a chimeric antigen receptor (CAR), for example, an engineered antigen receptor in a B cell, or an engineered T cell receptor (TCR) in a T cell, such as for example a CAR-T cell, wherein optionally the immune cell or lymphocyte, e.g., B cell or T cell, e.g., a CAR-T cell, has been modified using CRISPR based or related technology. In alternative embodiments, the CRISPR engineered (recombinantly engineered) cells, or the engineered (recombinantly engineered) lymphocyte, e.g., T cell (or CAR-T cell), is made by any method known in the art, for example as described in: U.S. Pat. No. 9,890,393 (also published as WO2014/191128), which describes use of RNA-guided endonucleases, in particular a Cas9/CRISPR system, to specifically target a selection of key genes in T-cells, and where these engineered T-cells express chimeric antigen receptors (CAR) to redirect their immune activity towards malignant or infected cells; or U.S. Pat. No. 9,993, 502, describing making and using cells with CARs; or U.S. Pat. App. Pub. No. 20180258149 A1; U.S. Pat. App. Pub. No. 20180187149 A1, describing making and using engineered cells having chimeric antigen receptor polypeptides directed to at least two targets; or U.S. Pat. App. Pub. No. 20180186878 A1, describing making and using immune cells encoding chimeric receptors to treat or prevent cancer; or U.S. Pat. App. Pub. No. 20180162939 A1, describing making and using cells with CARs for treating autoimmune diseases, asthma, and preventing or mediating organ rejection; or U.S. Pat. App. Pub. No. 20180112213 A1, describing making and using CRISPR/Cas-related compositions and methods which provide for efficient gene editing of eukaryotic cells using modified gRNAs; or U.S. Pat. App. Pub. No. 20180100026 A1, describing making and using cell with CARs having switches for regulating the activity of a chimeric antigen receptor effector cells (CAR-ECs); or U.S. Pat. App. Pub. No. 20170334968 A1, describing making and using cells with CARs to target cancer cells.

Alternative embodiments of the methods provided herein comprise use of adoptive cell transfer of tumor antigen-specific central memory T (Tcm) cells, which are administered to a subject in need thereof, optionally followed by vaccination of the subject with a recombinant oncolytic virus (OV) vaccine expressing the same antigen targeted by the adoptive cell transfer (ACT) T cells to induce cancer destruction and elimination. In alternative embodiments, the ACT T cells are genetically modified to express one or more recombinant T cell receptors (TCR) or chimeric antigen receptor s (CAR) specific for the tumor antigen. In some embodiments, the ACT T cells are autologous T cells derived from the subject to be treated. In alternative embodiments, the combination therapy does not comprise a step wherein the subject is immunodepleted. In alternative embodiments, the term "mammal" refers to humans as well as non-human mammals and the term "adoptive cell transfer" is meant to encompass infusion of a cell product produced by ex vivo culture of lymphocytes extracted from either peripheral blood or tumor tissue samples.

Alternative embodiments of the methods as provided herein for generating tumor antigen-specific central memory CD8+ T cells comprise a step of ex vivo cell culture comprising culturing lymphocytes from PBMCs or TTLs in the presence of a tumor antigen, an antigen presenting cell such as a dendritic cell, IL21, IL15, and rapamycin and preferably in the absence of IL2. In alternative embodiments, CD25+ cells (regulatory T cells and activated T and B cells) are removed from the PBMCs prior to culture. The tumor antigen may, for example be a tumor-associated antigen (TAA), a substance produced in tumor cells that triggers an immune response in a mammal. In some embodiments, the tumor antigen is a self-antigen. In other embodiments, the tumor antigen is a tumor-specific antigen that is unique to the tumor and not expressed in normal cells or expressed in very low amounts in normal cells (e.g. neo-antigen).

In alternative embodiments of the methods provided herein: the inhibitor of the inhibitory immune checkpoint molecule, or the stimulatory immune checkpoint molecule, is administered by: intravenous (IV) injection, intramuscular (IM) injection, intratumoral injection or subcutaneous injection; or, is administered orally or by suppository; or the formulation further comprises at least one immune checkpoint inhibitor.

In alternative embodiments of the methods provided herein: the cancer is advanced melanoma, non-small-cell lung cancer or renal cell carcinoma.

In some embodiments, the cancer is any one of: acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma *cutaneum*, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma *tuberosum*, tuberous carcinoma, verrucous carcinoma, carcinoma *villosum*, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma *mucosum*, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectaltic sarcoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and/or superficial spreading melanoma.

In alternative embodiments, methods as provided herein further comprise administering, or having administered, or delivering an ellagic acid and/or an ellagitannin, or a benzo-coumarin or a dibenzo-α-pyrone (optionally, an urolithin A, or any polycyclic aromatic compound containing a 1-benzopyran moiety with a ketone group at the C2 carbon atom, or a 1-benzopyran-2-one), wherein optionally the ellagic acid and/or the ellagitannin, or the benzo-coumarin or dibenzo-α-pyrone (or urolithin A) is delivered before administration of, simultaneously with, and/or after administration or delivery of the formulation.

In alternative embodiments, methods as provided herein further comprise administering, or having administered, or delivering, a genetically engineered cell, wherein optionally the genetically engineered cell is a lymphocyte, and optionally the genetically engineered cell expresses a chimeric antigen receptor (CAR), and optionally the lymphocyte is a B cell or a T cell (CAR-T cell), and optionally the lymphocyte is a tumor infiltrating lymphocyte (TIL), and optionally the genetically engineered cell is administered or delivered before administration of, simultaneously with, and/or after administration or delivery of the formulation.

In alternative embodiments, provided are formulations or pharmaceutical compositions comprising at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable non-pathogenic bacterial spores, or a combination thereof, and the formulation comprises at least one (or any one, several, or all of) non-pathogenic bacteria or spore of the family or genus (or class): *Anerostipes, Eubacterium, Coprococcus, Blautia*, Clostridiaceae, *Faecalibacterium* or *Clostridium*; Ruminococcaceae or *Ruminococcus*; Verrucomicrobiaceae or *Akkermansia*; Enterococcaceae or *Enterococcus; Eggerthella*; Eggerthellaceae or *Gordonibacter*; Bacteroidaceae or *Bacteroides*; Hyphomicrobiaceae or *Gemmiger; Bifidobacterium, Alistipes, Dorea, Adlercreutzia, Senegalimassilia, Ellagibacter, Paraeggerthella, Slackia, Roseburia, Monoglobus, Asacharobacter*, or a combination thereof.

In alternative embodiments, the formulations or pharmaceutical compositions provided herein comprise:

(a) bacteria of the genus *Faecalibacterium*, or comprise a bacterium of the species *Faecalibacterium prausnitzii;*

(b) bacteria from the genus *Clostridium* comprise *Clostridium* Cluster IV, *Clostridium* Cluster XIVa (also known as Lachnospiraceae), or of the species *C. coccoides* or *C. scindens*, or of the genus *Eubacterium*, or *Eubacterium* halii, *E. ramulus*, or a combination thereof;

(c) bacteria of the genus *Ruminococcus* comprise a bacteria of the species *Ruminococcus albus, R. bromii, R. callidus, R. flavefaciens, R. gauvreauii, R. gnavus R. lactaris, R. obeum* or *R. torques;*

(d) bacteria of the genus *Akkermansia* comprise a bacteria of the species *Akkermansia glycaniphila* or *A. muciniphila;*

(e) bacteria of the genus *Enterococcus* comprise a bacteria of the species *Enterococcus alcedinis, E. aquimarinus, E. asini, E. avium, E. bulliens, E. caccae, E. camelliae, E. canintestini, E. canis, E. casseliflavus, E. cecorum, E. lactis, E. lemanii*, or *E. hirae*, or any species of non-pathogenic *Enterococcus* found or capable of living in a human gut;

(f) bacteria of the genus *Eggerthella* comprise a bacteria of the species *Eggerthella lenta;*

(g) bacteria of the genus *Gordonibacter* comprise a bacteria of the species *Gordonibacter urolithinfaciens*, or any species of non-pathogenic *Gordonibacter* found or capable of living in a human gut;

(h) bacteria of the genus *Bacteroides* comprise a bacteria of the species *Bacteroides acidifaciens, B. caccae*, or *B. thetaiotamicron*, or any species of non-pathogenic *Bacteroides* found or capable of living in a human gut;

(i) bacteria of the genus *Gemmiger* comprise a bacteria of the species *Gemmiger formicilis;*

(j) bacteria of the genus *Bifidobacterium*, comprise a bacteria of the species *Bifidobacterium longum, B. bifidum*, or *B. brevis;*

(j) bacteria of the genus *Alistipes* comprise a bacteria of the species *Alistipes indistinctus;*

(k) bacteria of the genus *Dorea* comprise a bacteria of the species *Dorea formicigenerans, D. formicilis*, or *D. longicatena;*

(l) bacteria of the genus Anerostipes comprise a bacteria of the species A. *muciniphila;*

(m) bacteria of the genus *Eubacterium* comprise a bacteria of the species *E. hallii;*

(n) bacteria of the genus *Blautia* comprise a bacteria of the species *Blautia* sp.

SG-772; and/or (o) bacteria of the genus *Coprococcus* comprise a bacteria of the species *C. comes.*

In alternative embodiments of the formulations or pharmaceutical compositions provided herein: the formulation or pharmaceutical composition comprises a combination of non-pathogenic bacteria or spores comprising one of (or at least one of, or a combination of) the following mixes:

(a) (i) *F. prausnitzii, C. coccoides, R. gnavus*, and *C. scindens;*

(ii) *F. prausnitzii, C. coccoides, R. gnavus, C. scindens, A. muciniphila*, and *E. hirae;*

(iii) E. *lenta* and G. *urolithinfaciens;*

(iv) *F. prausnitzii, C. coccoides, R. gnavus, C. scindens, E. lenta*, and *G. urolithinfaciens;*

(v) *F. prausnitzii, C. coccoides, R. gnavus, C. scindens, B. thetaiotamicron, B. caccae*, and *G. formicilis;*

(vi) *F. prausnitzii, C. coccoides, R. gnavus, C. scindens, A. indistinctus* and D. *formicigenerans*; or (vii) *F. prausnitzii, C. coccoides, R. gnavus, C. scindens, B. longum* and *B. breve;*

(viii) *Faecalibacterium prausnitzii, Clostridium coccoides, Ruminococcus gnavus, Clostridium scindens, Eggerthella lenta, Gordonibacter urolithinfaciens* and *Adlercreutzia equohfaciens;*

(ix) *Faecalibacterium prausnitzii, Clostridium coccoides, Ruminococcus gnavus, Clostridium scindens, Eggerthella lenta, Gordonibacter urolithinfaciens, Adlercreutzia equohfaciens*, and *Senegalimassilia anaerobia;*

(x) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia*, and *Ellagibacter isourolithinifaciens;*

(xi) *Faecalibacterium prausnitzii, Clostridium coccoides, Ruminococcus gnavus, Clostridium scindens, Eggerthella lenta, Gordonibacter urolithinfaciens, Adlercreutzia equohfaciens*, and *Ellagibacter isourolithinifaciens;*

(xii) *Eggerthella lenta, Gordonibacter urolithinfaciens, Adlercreutzia equohfaciens, Senegalimassilia anaerobia* and *Ellagibacter isourolithinifaciens;*

(xiii) *Eggerthella lenta, Gordonibacter urolithinfaciens, Adlercreutzia equohfaciens, Senegalimassilia anaerobia, Ellagibacter isourolithinfaciens* and *Collinsella aerofaciens;*

(xiv) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia*, and *Collinsella aerofaciens;*

(xv) *Faecalibacterium prausnitzii, Clostridium coccoides, Ruminococcus gnavus, Clostridium scindens, Eggerthella lenta, Gordonibacter urolithinfaciens, Adlercreutzia equohfaciens, Senegalimassilia anaerobia, Collinsella aerofaciens* and *Ellagibacter isourolithinfaciens;*

(xvi) *Faecalibacterium prausnitzii, Clostridium coccoides, Ruminococcus gnavus, Clostridium scindens, Eggerthella lenta, Gordonibacter urolithinfaciens*, and *Ellagibacter isourolithinifaciens;*

(xvii) *Eggerthella lenta, Gordonibacter urolithinfaciens*, and *Ellagibacter isourolithinfaciens;*

(xviii) *Faecalibacterium prausnitzii, Clostridium coccoides, Ruminococcus gnavus, Clostridium scindens, Eggerthella lenta, Gordonibacter urolithinfaciens*, and *Paraeggerthella hongkongensis;*

(ixx) *Faecalibacterium prausnitzii, Clostridium coccoides, Ruminococcus gnavus, Clostridium scindens, Eggerthella lenta, Gordonibacter urolithinfaciens, Paraeggerthella hongkongensis; Slackia isoflavoniconvertens*, and *Slackia equohfaciens;*

(xx) *Faecalibacterium prausnitzii, Clostridium coccoides, Ruminococcus gnavus, Clostridium scindens*, and *Gordonibacter urolithinfaciens;*

(xxi) *Eubacterium hallii;*

(xxii) *Faecalibacterium prausnitzii, Clostridium coccoides, Ruminococcus gnavus, Clostridium scinden*, and *Eubacterium hallii;*

(xxiii) *Faecalibacterium prausnitzii, Clostridium coccoides, Ruminococcus gnavus, Clostridium scindens, Eggerthella lenta, Gordonibacter urolithinfaciens*, and *Eubacterium hallii;*

(xxiv) *Faecalibacterium prausnitzii, Clostridium coccoides, Ruminococcus gnavus, Clostridium scindens, Akkermansia muciniphila, Enterococcus hirae*, and *Eubacterium hallii;*

(xxv) *Blautia massiliensis;*

(xxvi) *Faecalibacterium prausnitzii, Clostridium coccoides, Ruminococcus gnavus, Clostridium scindens*, and *Blautia* massiliensis;

(xxvii) *Faecalibacterium prausnitzii, Clostridium coccoides, Ruminococcus gnavus, Clostridium scindens, Eggerthella lenta, Gordonibacter urolithinfaciens*, and *Blautia massiliensis;*

(xxviii) *Faecalibacterium prausnitzii, Clostridium coccoides, Ruminococcus gnavus, Clostridium scindens, Akkermansia muciniphila, Enterococcus hirae*, and *Blautia massiliensis;*

(xxviv) *Faecalibacterium prausnitzii, Clostridium coccoides, Ruminococcus gnavus, Clostridium scindens, Eggerthella lenta, Gordonibacter urolithinfaciens, Blautia massiliensis*, and *Eubacterium hallii;*

(xxx) *Faecalibacterium prausnitzii, Clostridium coccoides, Ruminococcus gnavus, Clostridium scindens, Akkermansia muciniphila, Enterococcus hirae, Blautia massiliensis*, and *Eubacterium hallii;*

(xxxi) *Faecalibacterium prausnitzii, Clostridium coccoides, Ruminococcus gnavus, Clostridium scindens, Gordonibacter urolithinfaciens*, and *Eubacterium hallii;*

(xxxii) *Faecalibacterium prausnitzii, Clostridium coccoides, Ruminococcus gnavus, Clostridium scindens, Gordonibacter urolithinfaciens, Eubacterium hallii* and *Blautia massiliensis;*

(xxxiii) *Akkermansia muciniphila*, and *Faecalibacterium prausnitzii;*

(xxxiv) *Eubacterium hallii, Dorea longicatena*, and *Blautia* sp. SG-772;

(xxxv) *Akkermansia muciniphila, Faecalibacterium prausnitzii, Eubacterium hallii, Dorea longicatena*, and *Blautia* sp. SG-772;

(xxxvi) *Akkermansia muciniphila, Faecalibacterium prausnitzii*, and *Ruminococcus gnavus;*

(xxxvii) *Dorea longicatena, Dorea formicigenerans, Blautia* sp. SG-772, *Eubacterium hallii, Ruminococcus faecis*, and *Coprococcus comes;*

(xxxviii) *Faecalibacterium prausnitzii*, and *Ruminococcus gnavus;*

(xxxix) *Ruminococcus gnavus, Eubacterium ramulus*, and *Gemmiger formililis;*

(xxxx) *Anaerostipes hadrus, Dorea formicigenerans, Dorea longicatena, Coprococcus comes*, and *Ruminococcus faecis;*

(xxxxi) *Anaerostipes hadrus, Dorea formicigenerans, Dorea longicatena, Coprococcus comes, Ruminococcus faecis* and *Ruminococcus gnavus;*

(xxxxii) *Anaerostipes hadrus, Dorea formicigenerans, Dorea longicatena, Coprococcus comes, Ruminococcus faecis* and *Akkermansia muciniphila;*

(xxxxiii) *Akkermansia muciniphila, Eubacterium ramulus*, and *Gemmiger formililis;*

(xxxxiv) *Akkermansia muciniphila, Ruminococcus gnavus, Ruminococcus torques*, and *Bifidobacterium bifidum;*

(xxxxv) *Akkermansia muciniphila, Ruminococcus gnavus*, and *Ruminococcus torques;*

(xxxxvi) *Akkermansia muciniphila, Ruminococcus torques, Dorea longicatena, Coprococcus comes*, and *Anaerostipes hadrus;*

(xxxxvii) *Akkermansia muciniphila, Roseburia inulinivorans, Dorea longicatena, Coprococcus comes*, and *Anaerostipes hadrus;*

(xxxxviii) *Dorea longicatena, Coprococcus comes, Anaerostipes hadrus, Eubacterium hallii, Faecalibacterium prausnitzii*, and *Collinsella aerofaciens;*

(xxxxix) *Dorea longicatena, Coprococcus comes, Anaerostipes hadrus, Eubacterium hallii, Faecalibacterium prausnitzii*, and *Blautia obeum;*

(xxxxx) *Akkermansia muciniphila, Ruminococcus gnavus, Dorea longicatena, Coprococcus comes*, and *Anaerostipes hadrus;*

(xxxxxi) *Akkermansia muciniphila, Gemmiger formicilis, Asacharobacter celatus, Collinsella aerofaciens, Alistipes putredinis*, and *Gordonibacter urolithinfaciens;*

(xxxxxii) *Akkermansia muciniphila, Monoglubus pectinilyticus, Bacteroides galacturonicus, Collinsella aerofaciens, Ruminococcus gnavus*, and *Dorea longicatena;*

(xxxxxiii) *Akkermansia muciniphila, Monoglubus pectinilyticus, Bacteroides galacturonicus, Collinsella aerofaciens, Ruminococcus torques*, and *Dorea longicatena*; and/or, (xxxxxiv) any combination of (i) to (xxxxxiii); or, (b) any one of, or several of, or all of the following bacteria or spore thereof (or spore derived from): *Faecalibacterium prausnitzii* (ATCC-27768), *Clostridium coccoides* (ATCC-29236), *Ruminococcus gnavus* (ATCC-29149), *Clostridium scindens* (ATCC-35704), *Akkermansia muciniphila* (BAA-835), *Enterococcus hirae* (ATCC-9790), *Bacteroides thetaiotamicron* (ATCC-29148), *Bacteroides caccae* (ATCC-43185), *Bifidobacterium breve* (ATCC-15700), *Bifidobacterium longum* (ATCC BAA-999) and *Gemmiger formicilis* (ATCC-27749). *Eggerthella lenta* (DSM-2243), *Gordonibacter urolithinfaciens* (DSM-27213), *Alistipes indistinctus* (DSM-22520) and *Dorea formicigenerans* (DSM-3992).

In alternative embodiments of the formulations or pharmaceutical compositions provided herein: the formulation or pharmaceutical composition comprises an inner core surrounded by an outer layer of polymeric material enveloping the inner core, wherein the non-pathogenic bacteria or the non-pathogenic germinable bacterial spores are substantially in the inner core, and optionally the polymeric material comprises a natural polymeric material.

In alternative embodiments of the formulations or pharmaceutical compositions provided herein: the plurality of non-pathogenic colony forming live bacteria are substantially dormant colony forming live bacteria, or the plurality of non-pathogenic colony forming live bacteria or the plurality of non-pathogenic germinable bacterial spores are lyophilized, wherein optionally the non-pathogenic dormant colony forming live bacteria comprise live vegetative bacterial cells that have been rendered dormant by lyophilization or freeze drying.

In alternative embodiments of the formulations or pharmaceutical compositions provided herein: the formulation comprises at least about $1\times10^4$ colony forming units (CFUs), or between about $1\times10^1$ and $1\times10^{13}$ CFUs, $1\times10^1$ and $1\times10^{12}$ CFUs, $1\times10^1$ and $1\times10^{11}$ CFUs, $1\times10^1$ and $1\times10^{10}$ CFUs, $1\times10^1$ and $1\times10^9$ CFUs, $1\times10^1$ and $1\times10^8$ CFUs, $1\times10^2$ and $1\times10^8$ CFUs, $1\times10^3$ and $1\times10^7$ CFUs, or $1\times10^4$ and $1\times10^6$ CFUs, of live non-pathogenic bacteria and/or non-pathogenic germinable bacterial spores, or any combination thereof.

In alternative embodiments of the formulations or pharmaceutical compositions provided herein: the formulation or pharmaceutical composition comprises water, saline, a pharmaceutically acceptable preservative, a carrier, a buffer, a diluent, an adjuvant or a combination thereof.

In alternative embodiments of the formulations or pharmaceutical compositions provided herein: the formulation or pharmaceutical composition is formulated for administration orally or rectally, or is formulated as a liquid, a food, a gel, a geltab, a candy, a lozenge, a tablet, pill or capsule, or a suppository.

In alternative embodiments of the formulations or pharmaceutical compositions provided herein: the formulation or pharmaceutical composition further comprises: a biofilm disrupting or dissolving agent, an antibiotic, a benzo-coumarin or a dibenzo-α-pyrone (optionally, an urolithin A, or any polycyclic aromatic compound containing a 1-benzopyran moiety with a ketone group at the C2 carbon atom, or a 1-benzopyran-2-one), an ellagic acid and/or an ellagitannin, an inhibitor of an inhibitory immune checkpoint molecule and/or a stimulatory immune checkpoint molecule (or any composition for use in checkpoint blockade immunotherapy).

In alternative embodiments of the formulations or pharmaceutical compositions provided herein: the inhibitor of an inhibitory immune checkpoint molecule comprises a protein or polypeptide that binds to an inhibitory immune checkpoint protein, and optionally the inhibitor of the inhibitory immune checkpoint molecule is an antibody or an antigen binding fragment thereof that binds to an inhibitory immune checkpoint protein.

In alternative embodiments of the formulations or pharmaceutical compositions provided herein: the inhibitor of an inhibitory immune checkpoint molecule targets a compound or protein comprising: CTLA4 or CTLA-4 (cytotoxic T-lymphocyte-associated protein 4, also known as CD152, or cluster of differentiation 152); Programmed cell Death protein 1, also known as PD-1 or CD279; Programmed Death-Ligand 1 (PD-L1), also known as cluster of differentiation 274 (CD274) or B7 homolog 1 (B7-H1)); PD-L2; A2AR (adenosine $A_{2A}$ receptor, also known as ADORA2A); B7-H3; B7-H4; BTLA (B- and T-lymphocyte attenuator protein); KIR (Killer-cell Immunoglobulin-like Receptor); IDO (Indoleamine-pyrrole 2,3-dioxygenase); LAG3 (Lymphocyte-Activation Gene 3 protein); TIM-3; VISTA (V-domain Ig suppressor of T cell activation protein) or any combination thereof.

In alternative embodiments of the formulations or pharmaceutical compositions provided herein: the inhibitor of an inhibitory immune checkpoint molecule comprises: ipilimumab or YERVOY®; pembrolizumab or KEYTRUDA®; nivolumab or OPDIVO®; atezolizumab or TECENTRIP®; avelumab or BAVENCIO®; durvalumab or IMFINZI®; AMP-224 (MedImmune), AMP-514 (an anti-programmed cell death 1 (PD-1) monoclonal antibody (mAb) (MedImmune)), PDR001 (a humanized mAb that targets PD-1), STI-A1110 or STI-A1010 (Sorrento Therapeutics), BMS-936559 (Bristol-Myers Squibb), BMS-986016 (Bristol-Myers Squibb), TSR-042 (Tesaro), JNJ-61610588 (Janssen Research & Development), MSB-0020718C, AUR-012, enoblituzumab (also known as MGA271) (MacroGenics, Inc.), MBG453, LAG525 (Novartis), BMS-986015 (Bristol-Myers Squibb), or any combination thereof.

In alternative embodiments of the formulations or pharmaceutical compositions provided herein: the stimulatory immune checkpoint molecule comprises a member of the tumor necrosis factor (TNF) receptor superfamily, optionally CD27, CD40, OX40, GITR (a glucocorticoid-Induced TNFR family Related gene protein) or CD137, or comprises a member of the B7-CD28 superfamily, optionally CD28 or Inducible T-cell co-stimulator (ICOS).

In alternative embodiments, provided are kits or products of manufacture comprising a formulation or pharmaceutical composition as provided herein, wherein optionally the product of manufacture is an implant.

In alternative embodiments, provided are Uses of a formulation or pharmaceutical composition as provided herein, or a kit or product of manufacture as provided herein, for controlling, ameliorating or treating a cancer in an individual in need thereof.

In alternative embodiments, provided are Uses of a formulation as provided herein in the manufacture of a medicament for controlling, ameliorating or treating a cancer in an individual in need thereof.

In alternative embodiments, provided are formulations or pharmaceutical compositions as provided herein, or kits or products of manufacture as provided herein, for use in controlling, ameliorating or treating a cancer in an individual in need thereof. In alternative embodiments of the Use, kit, formulation or pharmaceutical composition as provided herein, the cancer is advanced melanoma, non-small-cell lung cancer or renal cell carcinoma.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

Figures are described in detail herein.

FIG. 4, or Table 2, lists the microbe legend used to generate FIG. 2, where Table 2 indicates the bar color in order from top to bottom of the chart, and the taxonomic indicators are listed as kingdom, phylum, class, order, family, and genus; as discussed in detail in Example 4, below.

FIG. 12 graphically illustrates exemplary chromatograms from LCMS analysis of fecal samples producing urolithin A, as described in Example 17, below.

FIG. 19A-B graphically illustrate from the whole genome sequencing results differential abundance testing between healthy individuals and current or former cancer patients was performed for: FIG. 19A *Eubacterium hallii*, and FIG. 19B *Blautia massiliensis*. The Mann-Whitney non-parametric ranksum test was applied to assess statistical significance; as discussed in detail in Example 7, below.

FIG. 20 illustrates Table 17; as discussed in detail in Example 6, below.

FIG. 21 illustrates Table 18; as discussed in detail in Example 7, below.

FIG. 38A-D graphically illustrates images of the gastro-intestinal tract at day 21 for mice pre-treated with either water or antibiotics and treatments including vehicle, anti-CTLA-4, anti-CTLA-4 in combination with mix 4+ellagic acid and anti-CTLA-4 in combination with mix 2; as discussed in detail in Example 22, below.

FIG. 59 depicts in table form the results of a statistical analysis performed on metabolomics data on plasma obtained from a third party provider. A Mann Whitney U test is used to find significantly different metabolites between cancer and control cohorts. The top 100 metabolites ranked by p value are reported, as discussed in detail in Example 7, below.

Like reference symbols in the various drawings indicate like elements.

DETAILED DESCRIPTION

Figure 1:
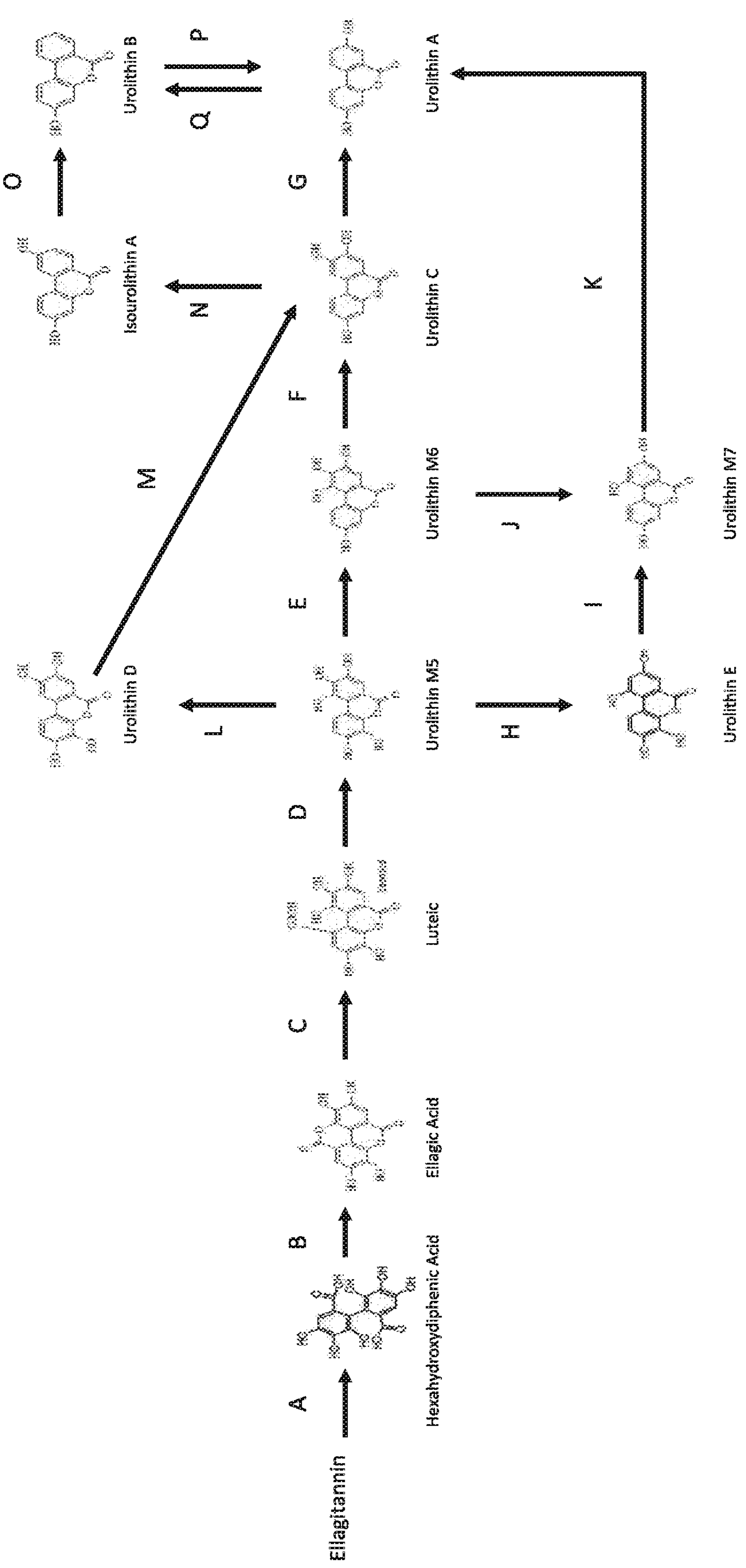
FIG. 1 illustrates currently known metabolic pathways that convert ellagitannin and derived metabolites to urolithin A; letters represent the following enzymes: A) Ellagitannin hydrolase; B) Hexahydroxydiphenic acid lactonase or a spontaneous condensation reaction; C) Ellagic acid lactonohydrolase; D) Luteic acid decarboxylase; E) Urolithin M5 dehydroxylase; F) Urolithin M6 dehydroxylase; G) Urolithin C dehydroxylase (urolithin A forming); H) Urolithin M5 dehydroxylase (urolithin E forming); I) Urolithin E dehydroxylase; J) Urolithin M6 dehyroxylase (urolithin M7 forming); K) Urolithin M7 dehydroxylase; L) Urolithin M5 dehydroxylase (urolithin D forming); M) Urolithin D dehydroxylase; N) Urolithin C dehydroxylase (isourolithin A forming); O) Isourolithin A dehydroxylase; P) Urolithin B hydroxylase; and Q) Urolithin A dehydroxylase.

In alternative embodiments, provided are compositions, including products of manufacture and kits, and methods, comprising novel combinations of non-pathogenic, live (optionally dormant) bacteria and/or bacterial spores. In alternative embodiments, the compositions, products of manufacture, kits and methods as provided herein are used as a co-therapy (or co-treatment) for the control, amelioration and/or treatment of a disease or condition, for example, a cancer. In alternative embodiments, the compositions, products of manufacture, kits and/or methods as provided herein are administered to an individual receiving a drug, e.g., a cancer, therapy, thereby resulting in a modification or modulation of the patient's gut microfloral population(s), thus resulting in an enhancement of the therapy, for example, lowering the dosage or amount of drug needed for effective therapy, or the frequency with which a drug must be administered to be effective. In alternative embodiments, by modulating or modifying the individual's gut microbial population(s) using compositions, products of manufacture and methods as provided herein, the pharmacodynamics of a drug administered to the patient is altered, for example, is the pharmacodynamics of the drug is enhanced, e.g., the individual's ability to absorb a drug is modified (e.g., accelerated or slowed, or enhanced), or the dose efficacy of a drug is increased (e.g., resulting in needing a lower dose of drug for an intended effect). For example, in alternative embodiments, by modulating or modifying of the patient's gut microbial population(s) using compositions, products of manufacture and methods as provided herein the dose efficacy of a cancer drug is increased, thereby enhancing the control or treatment of that cancer. In alternative embodiments, the amount, identity, presence, and/or ratio of gut microbiota in a subject is manipulated to facilitate one or more co-treatments.

Described here for the first time are novel combinations of specific microbes, e.g., bacteria, including bacteria found in a human gut, which can be administered as a co-therapy for cancer patients undergoing immune checkpoint inhibitor treatment. As described in the Examples, below, we demonstrated a correlation between these microbes and the metabolic functions associated with them and the efficacy of treatment in both human patients and mouse colon cancer models. We then demonstrated that administering these microbes to cancer mice improves the fraction of animals that show significant tumor size reduction.

In alternative embodiments, immune checkpoint inhibitors (or inhibitors of an inhibitory immune checkpoint molecule) and/or stimulatory immune checkpoint molecules (or more accurately, stimulatory immune molecules) are administered with, or formulated with, the combinations of non-pathogenic bacteria and/or non-pathogenic germination-competent bacterial spores as provided herein.

The immune checkpoint inhibitors (also described as an inhibitor of an inhibitory immune checkpoint molecule) can function by interfering with regulatory pathways that naturally exist to prevent T cell proliferation. In the tumor microenvironment these pathways are highly active, so T cells are often driven to an ineffective state. Checkpoint inhibitors target particular proteins in these regulatory pathways such as cytotoxic T lymphocyte-associated protein 4 (CTLA-4), programmed cell death protein 1 (PD-1), or programmed cell death ligand 1 (PD-L1). By binding to these molecules, the blockade is eliminated and T cells are able to respond to tumor antigens. Thus, in alternative embodiments, an inhibitor of an inhibitory immune checkpoint molecule is a molecule that can directly (or specifically) bind to CTLA-4, PD-1, PD-L1, or other component of the immune checkpoint blockade to prevent proper binding to its natural ligand. In alternative embodiments, a stimulatory immune checkpoint molecule—which can also be, or more accurately is, described as a stimulatory immune molecule, because it does not increase the function of the blockade to reducing immune activity, but rather is a molecule which enhances function of the immune system, either by enhancing the action of a checkpoint inhibitor or by an independent mechanism.

In alternative embodiments, provided are therapeutic compositions, including formulations and pharmaceutical compositions, comprising non-pathogenic (optionally dormant) live bacteria and/or germination-competent bacterial spores for the prevention or treatment of a cancer or the side effects of a cancer therapy, e.g., a drug therapy, as well as for gastrointestinal conditions, and other diseases and disorders and/or for general nutritional health.

In alternative embodiments, therapeutic compositions, formulations or pharmaceutical compositions as provided herein, or used to practice methods as provided herein, comprise a population of (e.g., a substantially purified population of) at least two types of colony forming live (optionally dormant) bacteria and/or germinable bacterial spores, wherein the live bacteria or bacteria arising from germination of the germinable spores can individually or together metabolize urolithin A from ellagic acid. In another embodiment, at least one of the types of live bacteria and/or bacteria arising from germination of the germinable spores can carry out the entire ellagic acid to urolithin A metabolic pathway. In yet another embodiment, at least one of the live bacteria and/or bacterial spores is or is derived from a *Gordonibacter* species.

In alternative embodiments, therapeutic compositions, formulations or pharmaceutical compositions as provided herein, or used to practice methods as provided herein, comprise colony forming (optionally dormant) live bacteria and/or germinable bacterial spores which can be used as an adjuvant to an antineoplastic treatment administered to a cancer patient. In some embodiments, the therapeutic composition can act as a probiotic composition. In alternative embodiments, therapeutic compositions (e.g., the formulations) as provided herein, comprise the bacteria and/or spores and an antineoplastic active agent.

In alternative embodiments, therapeutic compositions, formulations or pharmaceutical compositions as provided herein, or used to practice methods as provided herein, comprise colony forming (optionally dormant) live bacteria and/or germinable bacterial spores for use in combination (e.g., as a co-therapy) with (or supplementary to) a drug (which can be a protein, e.g., a therapeutic antibody) blocking an immune checkpoint for inducing immuno-stimulation in a cancer patient. The therapeutic composition and the drug (e.g., antibody) can be administered separately or together, or at different time points or at the same time.

In alternative embodiments, therapeutic compositions, formulations or pharmaceutical compositions as provided herein comprise colony forming (optionally dormant) live bacteria and/or germinable bacterial spores which can be used as an adjuvant to an antineoplastic and immune checkpoint treatment administered to a cancer patient. In alternative embodiments, the therapeutic composition comprises the anti-neoplastic and immune checkpoint active agents.

In alternative embodiments, therapeutic compositions as provided herein are manufactured as a formulation or pharmaceutical composition having a core comprising the at least two types of colony forming (optionally dormant) live bacteria (optionally as a purified population) and/or germinable bacterial spores, which optionally can individually or together (including the bacteria arising from germination of the germinable spores) metabolize urolithin A from ellagic acid or an ellagitannin. The formulation or pharmaceutical composition also comprises a layer of polymeric material (e.g., natural polymeric material) enveloping, or surrounding, the core.

In alternative embodiments, therapeutic compositions, formulations or pharmaceutical compositions as provided herein, or used to practice methods as provided herein, can comprise a pharmaceutically acceptable carrier, diluent, and/or adjuvant. In other embodiments a pharmaceutically acceptable preservative is present. In yet other embodiments, a pharmaceutically acceptable germinate is present. In still other embodiments the therapeutic composition contains ellagic acid.

In alternative embodiments, therapeutic compositions, formulations or pharmaceutical compositions as provided herein, or used to practice methods as provided herein, are in the form of a tablet, geltab or capsule, e.g., a polymer capsule such as a gelatin or a hydroxypropyl methylcellulose (HPMC, or hypromellose) capsule (e.g., VCAPS PLUS™ (Capsugel, Lonza)). In other embodiments, the therapeutic compositions, formulations or pharmaceutical compositions are in or are manufactured as a food or drink, e.g., an ice, candy, lolly or lozenge, or any liquid, e.g., in a beverage.

In alternative embodiments, in the preparation of bacteria (e.g., to prepare the purified population(s) of bacteria, or the bacteria induced to form germinable bacterial spores) used in therapeutic compositions, formulations or pharmaceutical compositions as provided herein, or used to practice methods as provided herein, the bacteria are fermented in a nutrient media, e.g., a nutrient media with or without fruits and/or fruit juices. In alternative embodiments, suitable fruits and/or juices are pomegranate, raspberry, blueberry, blackberry, cranberry, and strawberry fruits and/or juices.

In alternative embodiments, therapeutic compositions, formulations or pharmaceutical compositions as provided herein, or used to practice methods as provided herein, comprise at least one bacterial type that is not detectable, or not naturally found, in a healthy or normal subject's (e.g., human) gastrointestinal tract. In alternative embodiments, the gastrointestinal tract refers to the stomach, the small intestine, the large intestine and the rectum, or combinations thereof.

In alternative embodiments, provided are methods of ameliorating or treating cancer and/or at least one symptom resulting from a cancer therapy or of a condition of the gastrointestinal tract. In alternative embodiments, provided are methods comprising administration to a subject of a therapeutic composition, formulation or pharmaceutical composition as provided herein, e.g., a purified population of at least two types of colony forming live (optionally dormant) bacteria and/or germinable bacterial spores, wherein the live bacteria or the bacteria that germinate from the spores can individually or together metabolize urolithin A from ellagic acid, or synthesize urolithin A.

In alternative embodiments, by administration of a therapeutic composition, formulation or pharmaceutical composition as provided herein to a subject, or practicing a method as provided herein, the microbiome of the subject is modulated or altered.

In alternative embodiments, therapeutic compositions, formulations or pharmaceutical compositions as provided herein are delivered in conjunction with (e.g., together with), or further comprise, an ellagic acid and/or an ellagitannin. In alternative embodiments, methods as provided herein further comprise administration of an ellagic acid and/or an ellagitannin. In alternative embodiments, therapeutic compositions, formulations or pharmaceutical compositions as provided herein are delivered simultaneously with ellagic acid and/or ellagitannins, or, are delivered subsequent to delivery of ellagic acid and/or ellagitannins.

In alternative embodiments, the term "microbiome" encompasses the communities of microbes that can live sustainably and/or transiently in and on a subject's body, e.g., in the gut of a human, including bacteria, viruses and bacterial viruses, archaea, and eukaryotes. In alternative embodiments, the term "microbiome" encompasses the "genetic content" of those communities of microbes, which includes the genomic DNA, RNA (ribosomal-, messenger-, and transfer-RNA), the epigenome, plasmids, and all other types of genetic information.

In alternative embodiments, the term “subject” refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a gastrointestinal condition, diseases, and/or disorder or may be desirous of improved general nutritional health.

In alternative embodiments, the term “type” or “types” when used in conjunction with “bacteria” or “bacterial” refers to bacteria differentiated at the genus level, the species level, the sub-species level, the strain level, or by any other taxonomic method known in the art.

In alternative embodiments, the phrase “dormant live bacteria” refers to live vegetative bacterial cells that have been rendered dormant by lyophilization or freeze drying. Such dormant live vegetative bacterial cells are capable of resuming growth and reproduction immediately upon resuscitation.

In alternative embodiments, the term “spore” also includes “endospore”, and these terms can refer to any bacterial entity which is in a dormant, non-vegetative and non-reproductive stage, including spores that are resistant to environmental stress such as desiccation, temperature variation, nutrient deprivation, radiation, and chemical disinfectants. In alternative embodiments, “spore germination” refers to the dormant spore beginning active metabolism and developing into a fully functional vegetative bacterial cell capable of reproduction and colony formation. In alternative embodiments, “germinant” is a material, composition, and/or physical-chemical process capable of inducing vegetative growth of a dormant bacterial spore in a host organism or in vitro, either directly or indirectly.

In alternative embodiments, the term “colony forming” refers to a vegetative bacterium that is capable of forming a colony of viable bacteria or a spore that is capable of germinating and forming a colony of viable bacteria.

In alternative embodiments, the term “natural polymeric material” comprises a naturally occurring polymer that is not easily digestible by human enzymes so that it passes through most of the human digestive system essentially intact until it reaches the large or small intestine.

In alternative embodiments, bacteria used in formulations or pharmaceutical compositions as provided herein, or used to practice methods as provided herein, comprise a biosynthetic pathway capable of converting ellagitannin to urolithin A (as illustrated in FIG. 1), and include bacterial types currently known to be involved in the metabolic pathway capable of converting ellagic acid to urolithin A; for example, these bacteria include *Lactobacillus plantarum, L. paraplantarum*, and *Akkermansia muciniphila*, which are known to be capable of steps A and B as shown in FIG. 1, while steps C-E can be carried out by *Gordonibacter* and steps C-E and N by CEBAS 4A4 (see e.g., Selma et al. (2017) Front Microbiol 8: 1521). Populations of these bacterial types and/or additional bacteria and/or bacterial spores, non-naturally occurring microorganisms, engineered microorganisms and combinations thereof are formulated into compositions as provided herein and administered to mammals, e.g., humans, by the methods provided herein.

In alternative embodiments, therapeutic compositions, formulations or pharmaceutical compositions as provided herein comprise population(s) of non-pathogenic dormant live bacteria and/or bacterial spores. The dormant live bacteria can be capable of colony formation and, in the case of spores, germination and colony formation. In alternative embodiments, the compositions contain at least two types of dormant live bacteria and/or bacterial spores that are capable of metabolizing urolithin A from ellagic acid, individually or together. Thus, in alternative embodiments, compositions are useful for altering a subject’s gastrointestinal biome, e.g., by increasing the population of those bacterial types or microorganisms, or are capable of altering the microenvironment of the gastrointestinal biome, e.g., by changing the chemical microenvironment or disrupting or degrading intestinal mucin or biofilm, thereby providing treatment of cancer, gastrointestinal conditions, and symptoms resulting from cancer therapy, ultimately increasing the health of the subject to whom they are administered.

In alternative embodiments, the bacterial types that are capable of metabolizing urolithin A from ellagic acid, individually or together, are isolated from biological material associated with their mammalian (e.g., human) host, including feces as well as material isolated from the various segments of the gastrointestinal tract, such as the small and large intestine. If fecal matter is used, it can be obtained from a single mammalian donor or can be feces pooled from multiple donors, such as at least 2, 3, 4, 5, 6, 7, 8, 9, 10, 15, 20, 25, 30, 35, 40, 45, 50, 75, 100, 200, 300, 400, 500, or 1000 donors. If a single donor is used, in some cases multiple samples can be obtained from that donor and pooled, such as at least 2, 3, 4, 5, 6, 7, 8, 9, 10, 15, 20, 25, 30, 35, 40, 45, 50, 75, or 100 samples.

In alternative embodiments, the terms “purify,” purified,” and “purifying” are used interchangeably to describe a population’s known or unknown composition of bacterial type(s), amount of that bacterial type(s), and/or concentration of the bacterial type(s); a purified population does not have any undesired attributes or activities, or if any are present, they can be below an acceptable amount or level. In alternative embodiments, the terms various populations of bacterial types are purified, and the terms “purified,” “purify,” and “purifying” refer to a population of desired bacteria and/or bacterial spores that have undergone at least one process of purification; for example, a process comprising screening of individual colonies derived from fecal matter for a desired phenotype, such as their effectiveness in enhancing the pharmacodynamics of a drug (such as a cancer drug, e.g., a drug inhibitory to an ICI), e.g., the individual’s ability to absorb a drug is modified (e.g., accelerated or slowed, or enhanced), or the dose efficacy of a drug is increased (e.g., resulting in needing a lower dose of drug for an intended effect), and/or the ability to bioconvert ellagic acid to urolithin A, or a selection or enrichment of the desired bacterial types.

Enrichment can be accomplished by increasing the amount and/or concentration of the bacterial types, such as by augmenting with a cultured population of a single strain obtained from a culture collection or other pure source, or by a removal or reduction in unwanted bacterial types. In addition, enrichment can also occur by removal of material derived from the microbial environment found in the human or animal from which the bacterial type was isolated and/or cells from that human or animal host.

In alternative embodiments, purification can result in populations that are at least 75% free, 80% free, 90% free, 95% free, 96% free, 97% free, 98% free, 99% free or 100% free of anything other than the desired bacterial type(s). In alternative embodiments, the bacterial populations purified from a single fecal material donor are combined with at least one other purified population resulting from a different purification, either from the same donor purified at a different time, from one or more different fecal material donors, or combinations thereof.

In alternative embodiments, bacteria used to practice compositions and methods provided herein are derived from fecal material donors that are in good health, have microbial biomes associated with good health, and are typically free from antibiotic administration during the collection period and for a period of time prior to the collection period such that no antibiotic remains in the donor's system. In alternative embodiments, the donor subjects do not suffer from and have no family history of renal cancer, bladder cancer, breast cancer, prostate cancer, lymphoma, leukemia, autoimmune disease. In alternative embodiments, donor subjects are free from irritable bowel disease, irritable bowel syndrome, celiac disease, Crohn's disease, colorectal cancer, anal cancer, stomach cancer, sarcomas, any other type of cancer, or a family history of these diseases. In alternative embodiments, donor subjects do not have and have no family history of mental illness, such as anxiety disorder, depression, bipolar disorder, autism spectrum disorders, panic disorders, obsessive-compulsive disorder, attention-deficit disorders, eating disorders (e.g. bulimia, anorexia), mood disorder or schizophrenia. In yet other embodiments the donor subjects have no knowledge or history of food allergies or sensitivities.

In alternative embodiments, the health of fecal matter donors is screened prior to the collection of fecal matter, such as at 1, 2, 3, 4, 8, 16, 20, 24, 28, 32, 36, 40, 44, 48, or 52 weeks pre-collection. In alternative embodiments, fecal matter donors are also screened post-collection, such as at 1, 2, 3, 4, 8, 16, 20, 24, 28, 32, 36, 40, 44, 48, or 52 weeks post-collection. Pre- and post-screening can be conducted daily, weekly, bi-weekly, monthly, or yearly. In alternative embodiments, individuals who do not test positive for pathogenic bacteria and/or viruses (e.g. HIV, hepatitis, polio, adeno-associated virus, pox, coxsackievirus, etc.) pre- and post-collection are considered verified donors.

In alternative embodiments, a qualifying aspect of fecal matter donors is that their gut microbiota are demonstrably able to convert ellagitannins and/or ellagic acid to urolithin metabolites, including urolithin M-5, urolithin M-6, urolithin E, urolithin M-7, urolithin D, urolithin C, urolithin M-7, urolithin B, isourolithin A, and urolithin A, and also including adduct species, including metabolites having undergone sulfonation and glucuronidation. Urolithin metabolites can be detected directly or as extracts of feces, blood serum, or urine.

In alternative embodiments, to purify bacteria and/or bacterial spores, fecal matter is collected from donor subjects and placed in an anaerobic chamber within a short time after elimination, such as no more than 5 minutes, 10 minutes, 15 minutes, 20 minutes, 25 minutes, 30 minutes, 35 minutes, 40 minutes, 45 minutes, 50 minutes, 55 minutes, or 60 minutes after elimination. Bacteria from a sample of the collected fecal matter can be collected in several ways. For example, the sample can be mixed with anoxic nutrient broth, dilutions of the resulting mixture conducted, and bacteria present in the dilutions grown on solid anoxic media. Alternatively, bacteria can be isolated by streaking a sample of the collected material directly on anoxic solid media and growing colonies. In alternative embodiments, to increase the ease of isolating bacteria from fecal samples mixed with anoxic nutrient broth, the resulting mixture can be shaken, vortexed, blended, filtered, and centrifuged to remove large non-bacterial matter.

In alternative embodiments, purification of the isolated bacteria and/or bacterial spores by any means known in the art, for example, contamination by undesirable bacterial types, host cells, and/or elements from the host microbial environment can be eliminated by reiterative streaking to single colonies on solid media until at least two replicate streaks from serial single colonies show only a single colony morphology. Purification can also be accomplished by reiterative serial dilutions to obtain a single cell, for example, by conducting multiple 10-fold serial dilutions to achieve an ultimate dilution of $10^{-2}$, $10^{-3}$, $10^{-4}$, $10^{-5}$, $10^{-6}$, $10^{-7}$, $10^{-8}$, $10^{-9}$ or greater. Any methods known to those of skill in the art can also be applied. Confirmation of the presence of only a single bacterial type can be confirmed in multiple ways such as, gram staining, PCR, DNA sequencing, enzymatic analysis, metabolic profiling/analysis, antigen analysis, and flow cytometry using appropriate distinguishing reagents.

In alternative embodiments, purified population(s) of vegetative bacteria that are incorporated into therapeutic bacterial compositions as provided herein, or used to practice methods as provided herein, are fermented in media supplemented with ellagitannins or ellagic acid. Suitable media include Nutrient Broth (Thermo Scientific™ Oxoid™), Anaerobe Basal Broth (Thermo Scientific™ Oxoid™), or one of the following media available from Anaerobe Systems: Brain Heart Infusion Broth (BHI), *Campylobacter*-Thioglycollate Broth (CAMPY-THIO), Chopped Meat Broth (CM), Chopped Meat Carbohydrate Broth (CMC), Chopped Meat Glucose Broth (CMG), Cycloserine Cefoxitin Mannitol Broth with Taurocholate Lysozyme Cysteine (CCMB-TAL), Oral Treponeme Enrichment Broth (OTEB), MTGE-Anaerobic Enrichment Broth (MTGE), Thioglycollate Broth with Hemin, Vit. K, without indicator, (THIO), Thioglycollate Broth with Hemin, Vit. K, without indicator, (THIO), Lactobacilli-MRS Broth (LMRS), *Brucella* Broth (BRU-BROTH), Peptone Yeast Extract Broth (PY), PY Glucose (PYG), PY Arabinose, PY Adonitol, PY Arginine, PY Amygdalin, PYG Bile, PY Cellobiose, PY DL-Threonine, PY Dulcitol, PY Erythritol, PY Esculin, PYG Formate/Fumarate for FA/GLCf, PY Fructose, PY Galactose, PYG Gelatin, PY Glycerol, Indole-Nitrate Broth, PY Inositol, PY Inulin, PY Lactate for FA/GLCf, PY Lactose, PY Maltose, PY Mannitol, PY Mannose, PY Melezitose, PY Melibiose, PY Pyruvic Acid, PY Raffinose, PY Rhamnose, PY Ribose, PY Salicin, PY Sorbitol, PY Starch, PY Sucrose, PY Trehalose, PY Xylan, PY Xylose, Reinforced Clostridial Broth (RCB), Yeast Casitone Fatty Acids Broth with Carbohydrates (YCFAC Broth). In alternative embodiments, fermentation is conducted in stirred-tank fermentation vessels, performed in either batch or fed-batch mode, with nitrogen sparging to maintain anaerobic conditions. pH is controlled by the addition of concentrated base, such as NH40H or NaOH. In the case of fed-batch mode, the feed is a primary carbon source for growth of the microorganisms, such as glucose, along with an ellagic acid source. In alternative embodiments, the post-fermentation broth is collected, and/or the bacteria isolated by ultrafiltration or centrifugation and lyophilized or freeze dried prior to formulation.

In alternative embodiments, purified population(s) of vegetative bacteria to be incorporated into therapeutic bacterial compositions as provided herein, or used to practice methods as provided herein, are fermented with fruits (pomegranate, raspberry, blueberry, blackberry, cranberry, strawberry etc.) containing ellagitannins or ellagic acid. Here, the fermentation media consists of fruit juice supplemented with additional materials needed to support microbial growth, such as amino acids, inorganic phosphate, ammonium sulfate, or magnesium sulfate. Fermentation and bacteria isolation is conducted as described above.

In alternative embodiments, purified and isolated vegetative bacterial cells used in therapeutic bacterial compositions as provided herein, or used to practice methods as provided herein, have been made dormant; noting that bacterial spores are already in a dormancy state. Dormancy of the vegetative bacterial cells can be accomplished by, for example, incubating and maintaining the bacteria at temperatures of less than 4° C., freezing and/or lyophilization of the bacteria. Lyophilization can be accomplished according to normal bacterial freeze-drying procedures as used by those of skill in the art, such as those reported by the American Type Culture Collection (ATCC) on the ATCC website (see, e.g., (https://www.atcc.org). In alternative embodiments, the purified population of dormant live bacteria and/or bacterial spores has a reduced or undetectable level of one or more pathogenic activities, such as the ability to cause infection and/or inflammation, toxicity, an autoimmune response, an undesirable metabolic response (e.g. diarrhea), or a neurological response. Reduction of such pathogenic activities can be in the amount of at least 10%, 20%, 30%, 40%, 50%, 60%, 70%, 80%, 90%, 95%, 96%, 97%, 98%, 99%, 99.9% or 99.99%, or as compared to that seen for a purified population of each individual bacterial type.

In alternative embodiments, all of the types of dormant live bacteria or bacterial spores present in a purified population are obtained from fecal material treated as described herein or as otherwise known to those of skill in the art. In other embodiments, one or more of the types of dormant live bacteria or bacterial spores present in a purified population is generated in culture and combined with one or more types obtained from fecal material. In alternative embodiments, all of the types of dormant live bacteria or bacterial spores present in a purified population are generated in culture. In still other embodiments, one or all of the types of dormant live bacteria and/or bacterial spores present in a purified population are non-naturally occurring or engineered. In yet other embodiments, non-naturally occurring or engineered non-bacterial microorganisms are present, with or without dormant live bacteria and/or bacterial spores.

In alternative embodiments, bacterial compositions used in compositions as provided herein, or to practice methods as provided herein, comprise at least 2, 3, 4, 5, 6, 7, 8, 9, 10 or more bacterial types, or more than 20 bacterial types. In alternative embodiments, the bacterial compositions comprise at least about $10^2$, $10^3$, $10^4$, 105, $10^6$, $10^7$, $10^8$, $10^9$, $10^{10}$, $10^{11}$, $10^{12}$, $10^{13}$, $10^{14}$, $10^{15}$, or more (or between about $10^2$ to $10^{16}$) dormant live bacteria and/or bacterial spores. In some embodiments each bacterial type is equally represented in the total number of dormant live bacteria and/or bacterial spores.

In other embodiments, at least one bacterial type is represented in a higher amount than the other bacterial type(s) found in the composition. In alternative embodiments, a population of bacterial types used in compositions as provided herein, or to practice methods as provided herein, can increase those populations found in the subject's gastrointestinal tract by at least 10%, 20%, 30%, 40%, 50%, 60%, 70%, 80%, 90%, 100%, 200%, 300%, 400%, 500%, 600%, 700%, 800%, 900% or 1000% as compared to the subject's gastrointestinal population prior to treatment.

In alternative embodiments, the bacterial cells and/or spores used in compositions as provided herein, or to practice methods as provided herein, are mixed with pharmaceutically acceptable excipients, such as diluents, carriers, adjuvants, binders, fillers, salts, lubricants, glidants, disintegrants, coatings, coloring agents, etc. Examples of such excipients are acacia, alginate, alginic acid, aluminum acetate, benzyl alcohol, butyl paraben, butylated hydroxy toluene, citric acid, calcium carbonate, candelilla wax, croscarmellose sodium, confectioner sugar, colloidal silicone dioxide, cellulose, plain or anhydrous calcium phosphate, carnuba wax, corn starch, carboxymethylcellulose calcium, calcium stearate, calcium disodium EDTA, copolyvidone, calcium hydrogen phosphate dihydrate, cetylpyridine chloride, cysteine HCL, crossprovidone, calcium phosphate di or tri basic, dibasic calcium phosphate, disodium hydrogen phosphate, dimethicone, erythrosine sodium, ethyl cellulose, gelatin, glyceryl monooleate, glycerin, glycine, glyceryl monostearate, glyceryl behenate, hydroxy propyl cellulose, hydroxyl propyl methyl cellulose, hypromellose, HPMC phthalate, iron oxides or ferric oxide, iron oxide yellow, iron oxide red or ferric oxide, lactose hydrous or anhydrous or monohydrate or spray dried, magnesium stearate, microcrystalline cellulose, mannitol, methyl cellulose, magnesium carbonate, mineral oil, methacrylic acid copolymer, magnesium oxide, methyl paraben, providone or PVP, PEG, polysorbate 80, propylene glycol, polyethylene oxide, propylene paraben, polaxamer 407 or 188 or plain, potassium bicarbonate, potassium sorbate, potato starch, phosphoric acid, polyoxy140 stearate, sodium starch glycolate, starch pregelatinized, sodium crossmellose, sodium lauryl sulfate, starch, silicon dioxide, sodium benzoate, stearic acid, sucrose, sorbic acid, sodium carbonate, saccharin sodium, sodium alginate, silica gel, sorbiton monooleate, sodium stearyl fumarate, sodium chloride, sodium metabisulfite, sodium citrate dihydrate, sodium starch, sodium carboxy methyl cellulose, succinic acid, sodium propionate, titanium dioxide, talc, triacetin, and triethyl citrate.

In alternative embodiments, the bacterial cells and/or spores used in compositions as provided herein, or to practice methods as provided herein, are fabricated as microflora-triggered delivery systems.

In alternative embodiments, bacterial cells and/or spores used in compositions as provided herein, or to practice methods as provided herein, are encapsulated in at least one polymeric material, e.g., a natural polymeric material, such that there is a core of bacterial cells and/or spores surrounded by a layer of the polymeric material. Examples of suitable polymeric materials are those that have been demonstrated to remain intact through the GI tract until reaching the small or large intestine, where they are degraded by microbial enzymes in the intestines. Exemplary natural polymeric materials can include, but are not restricted to, chitosan, inulin, guar gum, xanthan gum, amylose, alginates, dextran, pectin, khava, and *albizia* gum (Dafe et al. (2017) Int J Biol Macromol; Kofla et al. (2016) Int J Nanomedicine 11:1089-1095).

In alternative embodiments, compositions provided herein are suitable for therapeutic administration to a mammal in need thereof. In alternative embodiments the compositions are produced by a process comprising, e.g.: (a) obtaining fecal material from a mammalian donor subject, (b) subjecting the fecal material to at least one purification treatment under conditions that produce a single bacterial type population of bacteria and/or bacterial spores, (c) optionally combining the purified population with another purified population obtained from the same or different fecal material, from cultured conditions, or from a genetic stock center such as ATCC or DSMZ, (d) treating the purified population(s) under conditions that cause vegetative bacterial cells to become dormant, and (e) placing the dormant bacteria and/or bacterial spores in a vehicle for administration.

In alternative embodiments, formulations and pharmaceutical compositions, and bacterial cells and/or spores used in compositions as provided herein or to practice methods as provided herein, are formulated for oral or gastric administration to a mammalian subject. In particular embodiments, the composition is formulated for oral administration as a solid, semi-solid, gel or liquid form, such as in the form of a pill, tablet, capsule, lozenge, food, extract or beverage. Examples of suitable foods are those that require little mastication, such as yogurt, puddings, gelatins, and ice cream. Examples of extracts include crude and processed pomegranate juice, strawberry, raspberry and blackberry. Examples of suitable beverages include cold beverages, such as juices (pomegranate, raspberry, blackberry, blueberry, cranberry, acai, cloudberry, etc., and combinations thereof) and teas (green, black, etc.) and oaked wine.

In alternative embodiments, formulations and pharmaceutical compositions further comprise, or methods as provided herein further comprise administration of, at least one antibiotic, e.g., a doxycycline, chlortetracycline, tetracycline hydrochloride, oxytetracycline, demeclocycline, methacycline, minocycline, penicillin, amoxycillin, erythromycin, clarithromycin, roxithromycin, azithromycin, spiramycin, oleandomycin, josamycin, kitsamysin, flurithromycin, nalidixic acid, oxolinic acid, norfloxacin, perfloxacin, amifloxacin, ofloxacin, ciprofloxacin, sparfloxacin, levofloxacin, rifabutin, rifampicin, rifapentin, sulfisoxazole, sulfamethoxazole, sulfadiazine, sulfadoxine, sulfasalazine, sulfaphenazole, dapsone, sulfacytidine, linezolid or any combination thereof.

Mucin Digesting or Degrading Agents

In alternative embodiments, formulations or pharmaceutical compositions provided herein comprise, or also comprise, bacteria that can degrade or digest the mucin layer of the inner wall of the large intestine. In alternative embodiments, these mucin-digesting or mucin-degrading bacteria comprise: bacteria of the genus *Faecalibacterium*, e.g., *F. prausnitzii*; bacteria of the genus *Akkermansia*, e.g., *A. muciniphila*; bacteria of the genus *Eubacterium*, e.g., *E. hallii*; bacteria of the genus *Blautia*; bacteria of the genus *Ruminococcus*, e.g., *R. torques, R. faecis* or *R. gnavus*; bacteria of the species *Gemmiger*, e.g., *G. formicilis*; bacteria of the genus *Dorea*, e.g., *D. formicigenerans, D. formicilis*, or *D. longicatena*; bacteria of the genus *Coprococcus*, e.g., *C. comes*; bacteria of the genus *Anaerostipes*, e.g., *A. hadrus*; or bacteria of the genus *Bifidobacterium*, or *B. longum, B. bifidum*, or *B. brevis*. In alternative embodiments, any formulation or pharmaceutical composition as provided herein can further comprise a mucin-digesting or mucin-degrading bacteria.

While the invention is not limited by any particular mechanism of action, mucin-digesting (e.g., fermenting) or mucin-degrading bacteria can contribute to the efficacy of formulations or pharmaceutical compositions as provided herein because they can either degrade, digest or change the composition of the thick mucin layer of the inner wall of the large intestine which that effectively acts as a semi-permeable barrier between processed feces in the intestinal lumen and the intestinal epithelium. The mucin layer itself consists of an inner layer attached to the intestinal wall that is mostly devoid of bacteria in healthy individuals, and an outer layer that consists of secreted mucin structures that is colonized by a variety of bacterial species that can utilize mucin as a carbon source (Tailford et al 2015 Frontiers in Genetics 6:81). These mucin-associating bacteria can provide nutrients and signaling factors to immune cells on the host side of the intestinal wall that help to maintain healthy and proper immuno responses throughout the body. Such bacteria include *Akkermansia muciniphila, Faecalibacterium prausnitzii, Ruminococcus gnavus*, and *Eubacterium hallii*. In particular, *A. muciniphila* has been shown to degrade mucin to ferment the released constituent sugars into short-chain fatty acid (SCFA) compounds like acetate and proprionate, which can be further utilized by *F. prausnitzii* and other bacteria to produce the SCFA butyrate (Belzer et al. 2017 mBio 8:e00770-17). These SCFA compounds can find their way to the host where they support epithelial cell health and provide modulatory stimuli to immune cells (McDermott and Huffnagle 2014 Immunology 142:24-31), where that modulatory stimuli is beneficial to the individual. Biofilm Dissolving or Disrupting agents In alternative embodiments, formulations or pharmaceutical compositions provided herein further comprise (e.g., are co-formulated with) biofilm dissolving agents, or formulations or pharmaceutical compositions provided herein are administered with biofilm dissolving or disrupting agents (they can be administered before, during and/or after administration of formulations or pharmaceutical compositions as provided herein).

In alternative embodiments, biofilm dissolving or disrupting components or agents that can be used include, e.g., enzymes such as a deoxyribonuclease (DNase), a N-acetylcysteine, an auranofin, alginate lyase, glycoside hydrolase dispersin B; Quorum-sensing inhibitors e.g., ribonucleic acid III inhibiting peptide, Salvadorapersica extracts, Competence-stimulating peptide, Patulin and penicillic acid; peptides—cathelicidin-derived peptides, small lytic peptide, PTP-7 (a small lytic peptide, see e.g., Kharidia (2011) J. Microbiol. 49(4):663-8, Epub 2011 September 2), Nitric oxide, neo-emulsions; ozone, lytic bacteriophages, lactoferrin, xylitol hydrogel, synthetic iron chelators, cranberry components, curcumin, silver nanoparticles, Acetyl-11-keto-β-boswellic acid (AKBA), barley coffee components, probiotics, sinefungin, S-adenosylmethionine, S-adenosyl-homocysteine, Delisea furanones, N-sulfonyl homoserine lactones and/or macrolide antibiotics or any combination thereof.

In alternative embodiments, biofilm disrupting agents comprise enzymes or degrading substances such as: N-acetylcysteine, deoxyribonuclease (DNase). Others would include Alginate, lyase and Glycoside hydrolase dispersin, Ribonucleic-acid-III inhibiting peptide (RIP), Salvadora *persica* extracts, Competence-stimulating peptide (CSP) Patulin (PAT) and penicillic acid (PA)/EDTA, Cathelicidin-derived peptides, Small lytic peptide, PTP-7, Nitric oxide, Chlorhexidine, Povidone-iodine (PI), Nanoemulsions, Lytic bacteriophages, Lactoferrin/xylitol hydrogel, Synthetic iron chelators, Cranberry components, Curcumin, Acetyl-11-keto-boswellic acid (AKBA), Barley coffee (BC) components, silver nanoparticles, azithromycin, clarithromycin, gentamicin, streptomycin and also Disodium EDTA.

Gradual or Delayed Release Formulations

In alternative embodiments, exemplary formulations contain or are coated by an enteric coating to protect the bacteria through the stomach and small intestine, although spores are typically resistant to the stomach and small intestines.

In alternative embodiments, compositions and formulations as provided herein, and compositions and formulations used to practice methods as provided herein, are formulated with a delayed release composition or formulation, coating or encapsulation. In alternative embodiments, compositions and formulations as provided herein, and compositions and formulations used to practice methods as provided herein, are designed or formulated for implantation of living bacteria or spores into the gut, including the intestine and/or the distal small bowel and/or the colon. In this embodiment the living bacteria pass the areas of danger, e.g., stomach acid and pancreatic enzymes and bile, and reach the intestine undamaged to be viable and implanted in the GI tract. In alternative embodiments, a formulation or pharmaceutical preparation is liquid, frozen or freeze-dried. In alternative embodiments, e.g., for an encapsulated formulation, all are in powdered form.

In alternative embodiments, compositions and formulations as provided herein, and compositions and formulations used to practice methods as provided herein, are formulated for delayed or gradual enteric release using cellulose acetate (CA) and polyethylene glycol (PEG), e.g., as described by Defang et al. (2005) Drug Develop. & Indust. Pharm. 31:677-685, who used CA and PEG with sodium carbonate in a wet granulation production process.

In alternative embodiments, compositions and formulations as provided herein, and compositions and formulations used to practice methods as provided herein, are formulated for delayed or gradual enteric release using a hydroxypropylmethylcellulose (HPMC), a microcrystalline cellulose (MCC) and magnesium stearate, as described e.g., in Huang et al. (2004) European J. of Pharm. & Biopharm. 58: 607-614).

In alternative embodiments, compositions and formulations as provided herein, and compositions and formulations used to practice methods as provided herein, are formulated for delayed or gradual enteric release using e.g., a poly (meth)acrylate, e.g. a methacrylic acid copolymer B, a methyl methacrylate and/or a methacrylic acid ester, a polyvinylpyrrolidone (PVP) or a PVP-K90 and a EUDRAGIT® RL PO™, as described e.g., in Kuksal et al. (2006) AAPS Pharm. 7(1), article 1, E1 to E9.

In alternative embodiments, compositions and formulations as provided herein, and compositions and formulations used to practice methods as provided herein, are formulated for delayed or gradual enteric release as described in U.S. Pat. App. Pub. 20100239667. In alternative embodiments, the composition comprises a solid inner layer sandwiched between two outer layers. The solid inner layer can comprise the non-pathogenic bacteria and/or spores, and one or more disintegrants and/or exploding agents, or one or more effervescent agents or a mixture. Each outer layer can comprise a substantially water soluble and/or crystalline polymer or a mixture of substantially water soluble and/or crystalline polymers, e.g., a polyglycol. These can be adjusted to achieve delivery of the living components to the intestine.

In alternative embodiments, compositions and formulations as provided herein, and compositions and formulations used to practice methods as provided herein, are formulated for delayed or gradual enteric release as described in U.S. Pat. App. Pub. 20120183612, which describes stable pharmaceutical formulations comprising active agents in a non-swellable diffusion matrix. In alternative embodiments, compositions and formulations as provided herein, and compositions and formulations used to practice methods as provided herein, are released from a matrix in a sustained, invariant and, if several active agents are present, independent manner and the matrix is determined with respect to its substantial release characteristics by ethylcellulose and at least one fatty alcohol to deliver bacteria distally.

In alternative embodiments, compositions and formulations as provided herein, and compositions and formulations used to practice methods as provided herein, are formulated for delayed or gradual enteric release as described in U.S. Pat. No. 6,284,274, which describes a bilayer tablet containing an active agent (e.g., an opiate analgesic), a polyalkylene oxide, a polyvinylpyrrolidone and a lubricant in the first layer and a second osmotic push layer containing polyethylene oxide or carboxy-methylcellulose.

In alternative embodiments, compositions and formulations as provided herein, and compositions and formulations used to practice methods as provided herein, are formulated for delayed or gradual enteric release as described in U.S. Pat. App. Pub. No. 20030092724, which describes sustained release dosage forms in which a nonopioid analgesic and opioid analgesic are combined in a sustained release layer and in an immediate release layer, sustained release formulations comprising microcrystalline cellulose, EUDRAGIT RSPO™, CAB-O-SIL™, sodium lauryl sulfate, povidone and magnesium stearate.

In alternative embodiments, compositions and formulations as provided herein, and compositions and formulations used to practice methods as provided herein, are formulated for delayed or gradual enteric release as described in U.S. Pat. App. Pub. 20080299197, describing a multi-layered tablet for a triple combination release of active agents to an environment of use, e.g., in the GI tract. In alternative embodiments, a multi-layered tablet is used, and it can comprise two external drug-containing layers in stacked arrangement with respect to and on opposite sides of an oral dosage form that provides a triple combination release of at least one active agent. In one embodiment the dosage form is an osmotic device, or a gastro-resistant coated core, or a matrix tablet, or a hard capsule. In these alternative embodiments, the external layers may contain biofilm dissolving agents and internal layers can comprise viable/living bacteria, for example, a formulation comprising at least two different species or genera (or types) of non-pathogenic bacteria as used to practice methods as provided herein.

In alternative embodiments, compositions and formulations as provided herein, and compositions and formulations used to practice methods as provided herein, are formulated as multiple layer tablet forms, e.g., where a first layer provides an immediate release of a formulation or pharmaceutical preparation as provided herein and a second layer provides a controlled-release of another (or the same) bacteria or drug, or another active agent, e.g., as described e.g., in U.S. Pat. No. 6,514,531 (disclosing a coated trilayer immediate/prolonged release tablet), U.S. Pat. No. 6,087,386 (disclosing a trilayer tablet), U.S. Pat. No. 5,213,807 (disclosing an oral trilayer tablet with a core comprising an active agent and an intermediate coating comprising a substantially impervious/impermeable material to the passage of the first active agent), and U.S. Pat. No. 6,926,907 (disclosing a trilayer tablet that separates a first active agent contained in a film coat from a core comprising a controlled-release second active agent formulated using excipients which control the drug release, the film coat can be an enteric coating configured to delay the release of the active agent until the dosage form reaches an environment where the pH is above four).

In alternative embodiments, compositions and formulations as provided herein, and compositions and formulations used to practice methods as provided herein, are formulated for delayed or gradual enteric release as described in U.S. Pat. App. Pub. 20120064133, which describes a release-retarding matrix material such as: an acrylic polymer, a cellulose, a wax, a fatty acid, shellac, zein, hydrogenated vegetable oil, hydrogenated castor oil, polyvinylpyrrolidine, a vinyl acetate copolymer, a vinyl alcohol copolymer, polyethylene oxide, an acrylic acid and methacrylic acid copolymer, a methyl methacrylate copolymer, an ethoxyethyl methacrylate polymer, a cyanoethyl methacrylate polymer, an aminoalkyl methacrylate copolymer, a poly(acrylic acid), a poly(methacrylic acid), a methacrylic acid alkylamide copolymer, a poly(methyl methacrylate), a poly(methacrylic acid anhydride), a methyl methacrylate polymer, a polymethacrylate, a poly(methyl methacrylate) copolymer, a polyacrylamide, an aminoalkyl methacrylate copolymer, a glycidyl methacrylate copolymer, a methyl cellulose, an ethylcellulose, a carboxymethylcellulose, a hydroxypropylmethylcellulose, a hydroxymethyl cellulose, a hydroxyethyl cellulose, a hydroxypropyl cellulose, a crosslinked sodium carboxymethylcellulose, a crosslinked hydroxypropylcellulose, a natural wax, a synthetic wax, a fatty alcohol, a fatty acid, a fatty acid ester, a fatty acid glyceride, a hydrogenated fat, a hydrocarbon wax, stearic acid, stearyl alcohol, beeswax, glycowax, castor wax, carnauba wax, a polylactic acid, polyglycolic acid, a co-polymer of lactic and glycolic acid, carboxymethyl starch, potassium methacrylate/divinylbenzene copolymer, crosslinked polyvinylpyrrolidone, polyvinylalcohols, polyvinylalcohol copolymers, polyethylene glycols, non-crosslinked polyvinylpyrrolidone, polyvinylacetates, polyvinylacetate copolymers or any combination. In alternative embodiments, spherical pellets are prepared using an extrusion/spheronization technique, of which many are well known in the pharmaceutical art. The pellets can comprise one or more formulations or pharmaceutical preparations as provided herein.

In alternative embodiments, compositions and formulations as provided herein, and compositions and formulations used to practice methods as provided herein, are formulated for delayed or gradual enteric release as described in U.S. Pat. App. Pub. 20110218216, which describes an extended release pharmaceutical composition for oral administration, and uses a hydrophilic polymer, a hydrophobic material and a hydrophobic polymer or a mixture thereof, with a microenvironment pH modifier. The hydrophobic polymer can be ethylcellulose, cellulose acetate, cellulose propionate, cellulose butyrate, methacrylic acid-acrylic acid copolymers or a mixture thereof. The hydrophilic polymer can be polyvinylpyrrolidone, hydroxypropylcellulose, methylcellulose, hydroxypropylmethyl cellulose, polyethylene oxide, acrylic acid copolymers or a mixture thereof. The hydrophobic material can be a hydrogenated vegetable oil, hydrogenated castor oil, carnauba wax, candellia wax, beeswax, paraffin wax, stearic acid, glyceryl behenate, cetyl alcohol, cetostearyl alcohol or and a mixture thereof. The microenvironment pH modifier can be an inorganic acid, an amino acid, an organic acid or a mixture thereof. Alternatively, the microenvironment pH modifier can be lauric acid, myristic acid, acetic acid, benzoic acid, palmitic acid, stearic acid, oxalic acid, malonic acid, succinic acid, adipic acid, sebacic acid, fumaric acid, maleic acid; glycolic acid, lactic acid, malic acid, tartaric acid, citric acid, sodium dihydrogen citrate, gluconic acid, a salicylic acid, tosylic acid, mesylic acid or malic acid or a mixture thereof.

In alternative embodiments, compositions and formulations as provided herein, and compositions and formulations used to practice methods as provided herein, are powders that can be included into a tablet or a suppository. In alternative embodiments, compositions and formulations as provided herein, and compositions and formulations used to practice methods as provided herein, are 'powders for reconstitution' as a liquid to be drunk placed down a naso-duodenal tube or used as an enema for patients to take home self-administer enemas. In alternative embodiments, compositions and formulations as provided herein, and compositions and formulations used to practice methods as provided herein, are micro-encapsulated, formed into tablets and/or placed into capsules, especially enteric-coated capsules.

In alternative embodiments, bacterial spores comprise the largest or only component of the compositions, and the compositions may be formulated, co-formulated or co-administered with a germinant.

In alternative embodiments containing dormant live bacteria with or without bacterial spores, the compositions are co-formulated or co-administered with prebiotic substance, such as substrates in the ellagic acid to urolithin A metabolic pathway, to enhance efficacy or engraftment.

In alternative embodiments, composition as provided herein are formulated to be effective in a given mammalian subject in a single administration or over multiple administrations. In some embodiments, a substrate or prebiotic required by the bacterial type is administered for a period of time in advance of the administration of the bacterial composition; such administration pre-loads the gastrointestinal tract with the substrates needed by the bacterial types of the composition and increases the potential for the bacterial composition to have adequate resources to perform the required metabolic reactions. In other embodiments, the composition is administered simultaneously with the substrates required by the bacterial types of the composition. In still other embodiments the composition is administered alone. Efficacy can be measured by an increase in the population of those bacterial types originally found in the subject's intestinal tract before treatment.

Products of Manufacture and Kits

Provided are products of manufacture, e.g., implants or pharmaceuticals, and kits, containing components for practicing methods as provided herein, e.g., including a formulation comprising at least two different species or genera (or types) of non-pathogenic bacteria, wherein each of the non-pathogenic bacteria comprise (or are in the form of) a plurality of non-pathogenic colony forming live bacteria, a plurality of non-pathogenic germinable bacterial spores, or a combination thereof, and optionally including instructions for practicing methods as provided herein.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

The following Examples describe methods and compositions for practicing embodiments as provided herein, including methods for making and using compositions comprising non-pathogenic bacteria and non-pathogenic germinable bacterial spores used to practice methods as provide herein.

Example 1: Exemplary Bacterial Strains and Culture Conditions

Anaerobe Basal Broth Supplemented with Rumen Fluid (ABB+RF)

34.5 grams of anaerobic basal broth dry powder (Fisher Scientific/Oxoid) is combined with 600 ml distilled water and is brought to a gentle boil while stirring on a heated stirplate until the solution clarifies. 150 ml of rumen fluid (Bar Diamond Inc., Parma Idaho) that has been centrifuge-clarified is then added, along with 1 ml 2.5 mg/ml resazurin (ACROS Organics™) solution followed by distilled water to one liter final volume. The medium is kept at 55° C. in a water bath while it is dispensed in 50 ml volumes into 100 ml serum bottles. Nitrogen is bubbled through a metal canula into each bottle for 15 minutes to displace oxygen from the medium, then the bottles are quickly sealed by insertion of a butyl-rubber bung that is secured by a crimped collar. The medium bottles are then sterilized by autoclaving and then stored in the dark until use. L-cysteine is added to 1 mM final concentration to each ABB+RF bottle one hour prior to use to fully reduce the medium prior to inoculation with microorganisms.

Preparation of Centrifuge-Clarified Rumen Fluid

Rumen fluid is the liquid obtained from the rumen of fistulated cows and is obtained in 1 liter volumes from Bar Diamond Inc., Parma Idaho. The rumen fluid is aliquoted in 50 ml volumes into 50 ml conical tubes and centrifuged at 4000 g for 30 minutes at 4° C. to pellet large fibrous material. After centrifugation the supernatant is decanted into fresh 50 ml conical tubes that are then subjected to centrifugation at 34,000 g for 90 minutes at 4° C. The supernatant from this centrifugation is then decanted into fresh 50 ml conical tubes and stored at −20° C. until use.

Microorganisms in Mouse Study

The following obligate anaerobic microbes were obtained from the American Type Culture Collection (ATCC): *Faecalibacterium prausnitzii* (ATCC-27768), *Clostridium coccoides* (ATCC-29236), *Ruminococcus gnavus* (ATCC-29149), *Clostridium scindens* (ATCC-35704), *Akkermansia muciniphila* (BAA-835), *Enterococcus hirae* (ATCC-9790), *Bacteroides thetaiotamicron* (ATCC-29148), *Bacteroides caccae* (ATCC-43185), *Bifidobacterium breve* (ATCC-15700), *Bifidobacterium longum* (ATCC BAA-999) and *Gemmiger formicilis* (ATCC-27749). *Eggerthella lenta* (DSM-2243), *Gordonibacter urolithinfaciens* (DSM-27213), *Gordonibacter* species CEBAS 4A4*; Alistipes indistinctus* (DSM-22520) and *Dorea formicigenerans* (DSM-3992) were obtained from the Leibnitz Institute-German Collection of Microorganisms and Cell Cultures (DSMZ).

Culture of Individual Microbes for Mouse study 0.5 ml starter cultures of *C. coccoides, R. gnavus, C. scindens, A. muciniphila, E. hirae, B. thetaiotamicron, B. caccae, B. breve, B. lonum, G. formicilis, E. lenta, G. urolithinfaciens, A. indistinctus* and *D. formicigenerans* are each inoculated into four 50 ml anaerobic bottles of fully reduced ABB+RF anaerobic medium and cultured at 37° C. *F. prausnitzii* is inoculated into fifteen 7 ml tubes of YCFAC (Anaerobe Systems) and cultured at 37° C. Cultures are harvested after 48 hours when they achieve 0.1 to $1.0\times10^9$ cells/ml as measured by optical absorbance at 600 nm by spectrophotometer (1 $OD_{600}=1.0\times10^9$ cells/ml). Bacterial starter cultures may be modified in order to achieve $1.0\times10^{10}$ cells/ml, $1.0\times10^{11}$ cells/ml or $1.0\times10^{12}$ cell/ml.

To harvest cultures, they are first brought into the anaerobic chamber where they are opened and decanted into 50 ml conical tubes that are tightly capped and sealed by wrapping the caps in parafilm. These are brought out of the anaerobic chamber and then centrifuged at 4000 g for 15 minutes at 4° C. The centrifuged tubes are brought back into the anaerobic chamber where the supernatant is decanted and discarded. The cell pellets are each combined with anoxic Phosphate Buffered Saline with 2.5 mM L-Cysteine and 15% glycerol (PBS-C-G) followed by tight capping and parafilm seal. The capped and sealed tubes are brought out of the anaerobic chamber and are centrifuged at 4000 g for 15 minutes. The culture tubes are again brought into the anaerobic chamber where the supernatant is decanted and discarded. Pelleted cells are resuspended in volumes of PBS-C-G to attain effective cell densities of each microbial strain at $1\times10^9$ cells/ml, $1.0\times10^{10}$ cells/ml, $1.0\times10^{11}$ cells/ml or $1.0\times10^{12}$ cell/ml.

Assembly of Microbe Mixes

The PBS-C-G suspended microbe cultures are mixed together to form 20 ml of the following microbe mixes to attain $1\times10^9$, $1.0\times10^{10}$ cells/ml, $1.0\times10^{11}$ cells/ml or $1.0\times10^{12}$ total microbial cells/ml (see Table 1):

TABLE 1

| Microbe Mix | Strains |
|---|---|
| 1 | *Faecalibacterium prausnitzii*<br>*Clostridium coccoides*<br>*Ruminococcus gnavus*<br>*Clostridium scindens* |
| 2 | *Faecalibacterium prausnitzii*<br>*Clostridium coccoides*<br>*Ruminococcus gnavus*<br>*Clostridium scindens*<br>*Akkermansia muciniphila*<br>*Enterococcus hirae* |
| 3 | *Eggerthella lenta*<br>*Gordonibacter urolithinfaciensans* |
| 4 | *Faecalibacterium prausnitzii*<br>*Clostridium coccoides*<br>*Ruminococcus gnavus*<br>*Clostridium scindens*<br>*Eggerthella lenta*<br>*Gordonibacter urolithinfaciensans* |
| 5 | *Faecal/bacterium prausnitzii*<br>*Clostridium coccoides*<br>*Ruminococcus gnavus*<br>*Clostridium scindens*<br>*Bacteroides thetaiotamicron*<br>*Bacteroides caccae*<br>*Gemmiger formicilis* |
| 6 | *Faecal/bacterium prausnitzii*<br>*Clostridium coccoides*<br>*Ruminococcus gnavus*<br>*Clostridium scindens*<br>*Alistipes indistinctus*<br>*Dorea formicigenerans* |
| 7 | *Faecal/bacterium prausnitzii*<br>*Clostridium coccoides*<br>*Ruminococcus gnavus*<br>*Clostridium scindens*<br>*Bifidobacterium longum*<br>*Bifidobacterium breve* |

Microbe Mix 1 consists of 5 ml each of *F. prausnitzii, C. coccoides, R. gnavus*, and *C. scindens* cultures.

Microbe Mix 2 consists of 3.3 ml each of *F. prausnitzii, C. coccoides, R. gnavus, C. scindens, A. muciniphila*, and *E. hirae* cultures.

Microbe Mix 3 consists of 10 ml each of *E. lenta* and *G. urolithinfaciens* cultures.

Microbe Mix 4 consists of 3.3 ml each of *F. prausnitzii, C. coccoides, R. gnavus, C. scindens, E. lenta*, and *G. urolithinfaciens* cultures.

Microbe Mix 5 consists of 2.9 ml each of *F. prausnitzii, C. coccoides, R. gnavus, C. scindens, B. thetaiotamicron, B. caccae*, and *G. formicilis* cultures.

Microbe Mix 6 consists of 3.3 ml each of *F. prausnitzii, C. coccoides, R. gnavus, C. scindens, A. indistinctus* and *D. formicigenerans* cultures.

Microbe Mix 7 consists of 3.3 ml each of *F. prausnitzii, C. coccoides, R. gnavus, C. scindens, B. longum* and *B. breve* cultures.

After assembly, 20 ml of PBS-C-G is added to each microbe mix to double the volume to 40 ml and to reduce the total cell density of each microbe mix to attain a gavage dosage of $1\times10^8$/0.2 ml. Microbe mixes are aliquoted into eight 5.0 ml volumes into 15 ml conical tubes and stored at −20° C., or −80° C., until required.

Example 2—Therapeutic Effect of Microbes on Efficacy of Cancer Immunotherapy

Animals and Tumor Model

BALB/c mice are obtained from Jackson laboratory or Taconic farms. 6-8-week-old female mice are used. For tumor growth experiments, mice are injected subcutaneously with $1\times10^6$ CT-26 colon cancer tumor cells (Griswold and Corbett (1975) Cancer 36:2441-2444). Tumor size is measured twice a week until endpoint, and tumor volume determined as length×width×0.5.

Tumor Cell Preparation

Cryo vials containing CT-26 tumor cells are thawed and cultured according to manufacturer's protocol (ATCC CRL-2638). On the day of injection cells are washed in serum free media, counted, and resuspended in cold serum free media at a concentration of 250,000 viable cells/100 μl.

Flow Cytometry

A whole-blood flow cytometry-based assay is utilized to assess T cell activation in response to CTLA4 and microbial treatment. Whole blood via cardiac puncture is collected into an EDTA tube at the end of the experiment. 100 μL of whole mouse blood is transferred to a 15 mL conical tube. 1 mL of RBC Lysis Buffer is added to the tube and allowed to incubate at room temperature for 10 minutes. Lysis is quenched by adding 10 mL of cold DPBS. Samples are centrifuged at 1500 rpm for 5 minutes at 4° C. The pellet is aspirated and resuspend in another 10 mL of cold DPBS. Samples are recentrifuged at 1500 rpm for 5 minutes at 4° C. Samples are resuspended in 500 μL of FACS buffer and transferred to a 96-well plate. Samples are stained with Fixable Viability ef780 (eBioscience), CD45-PEcy7 (BioLegend), CD3-BV605 (BioLegend), CD8-AF700 (BioLegend), and CD4-AF488 (BioLegend). Stained samples are run on a BD LSRFortessa™ flow cytometer and analyses are performed with FlowJo™ (Tree Star).

Tumor Challenge and Treatment

Mice are divided into immunotherapy treatment and non-treatment groups. The treatment group is injected intraperitoneally once the tumor reached a size of 40 to 60 $mm^3$ (day 0) with 100 g anti-PD1 mAb (BioXCell), or with 100 g anti-PD-L1 mAb, or with 100 g anti-CTLA-4 mAb (BioXCell) in 100 μl PBS twice a week for three weeks starting from day 1. Tumor size is routinely monitored by means of a caliper. Stool is collected on day 0 and 48 hours after each subsequent administration of treatment until the end of the study.

To test whether manipulation of the microbial community is effective as a combination therapy, microbial cocktails as provided herein, e.g., mixes 1-7 (Table 1, see Example 1) or as described in Table 5, in the presence or absence of ellagic acid and/or ellagitannin is administered. In some groups, ellagic acid is administered separately via oral gavage (0.2 mL of a 5.5 mg/mL suspension) prior to administration of the microbe cocktails. In other groups, urolithin A is administered alone via oral gavage (0.2 mL of a 5.5 mg/mL suspension), without microbe cocktails. Each mouse treated by combination therapy is given 200 l of the suspension by oral gavage twice a week for the duration of the study starting from day 1. Tumor growth and tumor-specific T cell responses are compared among the different treatment groups.

GI Tract Removal and Analysis

After mice are euthanized at the termination of the study, the intact digestive tract of each mouse from stomach to rectum are removed and kept in a 5 ml Eppendorf tube on ice prior to dissection. Forceps are sterilized by soaking in 100% ethanol and then used to remove the intestine length and stretch it on a work surface covered with cellophane. With the use of ethanol-sterilized dissection scissors, 3 cm lengths of the jejunum nearest to the stomach and the ilium nearest to the cecum/large intestine are excised and then each placed with forceps in a 1.5 ml Eppendorf tube and placed on ice. A 2 cm segment of the cecum/ascending colon is then excised, as are 2 cm segments of the transcending colon and the descending colon, and all are placed in 1.5 ml Eppendorf tubes on ice. Dissection instruments are sterilized by dipping in 100% ethanol between each intestine fragment removal. To each tube containing dissected intestinal segments is added 0.5 ml ice cold PBS buffer. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice and then stored at −80° C. for later analysis.

Example 3—Fecal Sample Processing

After harvesting, mouse fecal samples are transferred into the anaerobic chamber for manipulation. Approximately 50 mg of mouse fecal matter is resuspended in 600 μL phosphate-buffered saline (PBS) in a 1.5 mL tube and mixed for 10 seconds using a micro-blender with pestle attachment, until all large particles are broken up. The material is then allowed to stand for 15 minutes or more to allow most particulate matter to settle. From the top of the fecal resuspension, 50 μL is removed and transferred to a cryostorage vial containing 50 μL of dimethylsulfoxide (DMSO). Vials are frozen in liquid nitrogen for permanent storage. The remainder of each sample is removed from the anaerobic chamber, mixed well with a pipette, and aliquoted in 4 equal parts for subsequent analysis. 3 of these aliquots are placed in 1.5 mL microcentrifuge tubes to be used for DNA extraction, RNA extraction, and LCMS metabolomics analysis, respectively. The fourth is placed in a headspace GCMS autosampler vial and capped immediately with a crimp-top cap. All samples are frozen and stored at −80 deg. C. until processed.

DNA Sequencing Analysis

Sample tubes containing approximately 10 mg fecal matter resuspended in 130 μL PBS are thawed and total genomic DNA is extracted using the QIAmp PowerSoil DNA™ kit (Qiagen). 16S RNA sequencing is used to monitor the overall species composition of fecal samples, to determine how species abundance varies with immunotherapy treatment, microbial supplementation, nutrient addition, and time course. Amplicons specific for the v4 region of 16S RNA are generated using primers homologous to the conserved regions surrounding v4.

16S Primers that Target the Variable 4 Region:

```
515FB FORWARD primer:
                                          (SEQ ID NO: 1)
TCGTCGGCAGCGTCAGATGTGTATAAGAGACAGGTGYCAGCMGCCGCGG

TAA

806RB REVERSE primer:
                                          (SEQ ID NO: 2)
GTCTCGTGGGCTCGGAGATGTGTATAAGAGACAGGGACTACNVGGGTWT

CTAAT
```

The 515FB FOR and 806RB REV primer sequences are used to amplify the v4 region of the 16S rRNA gene (see, for example, Caporaso et al. (2011) Proc Natl Acad Sci USA 108, 4516-4522; Caporaso et al. (2012) ISME J doi:10.1038/ismej.2012.8; April (2015) Aquat Microb Ecol 75, 129-137).

A second round of PCR is then used to add barcodes, using the Illumina NEXTERA® XT Index Kit v2 Set A. The amplicons are purified and quantities normalized using magnetic beads, using the Illumina NEXTERA XT® DNA library preparation kit protocol. Finally, sequencing is performed on MISEQ® (Illumina) with 2×250 bp paired-end reads. Published computational workflows such as QIIVIE™ (see, e.g., Kuczynski et al. (2011) Curr. Protoc. Bioinformatics) are used to identify the microbial species represented by the 16S RNA amplicons, and to determine the relative proportions of species in each sample.

As opposed to 16S RNA sequencing which only sequences a specific region of each genome, whole metagenome sequencing is used to get entire sequences. The DNA isolated from the fecal samples is fragmented and then library preparation performed using the Illumina NEXTERA® XT DNA kit (Illumina), following the manufacturer's instructions. Sequencing is performed on MISEQ® (Illumina) with 2×250 bp paired-end reads. Multiple genomes can be multiplexed in the same run by ligating unique barcodes onto each library, as described in the NEXTERA® XT protocol. The barcodes are deconvoluted in the BASESPACE® software platform (Illumina), thus binning sequencing reads into the appropriate samples. Metaphlan2 and HuMann2® (huttenhower.sph.harvard.edu/metaphlan2) are used to assemble the raw sequence reads into contigs. Open reading frames are compared to the NCBI protein database (www.ncbi.nlm.nih.gov) to match to known gene functions. Hits are counted per gene family and normalized for length and alignment quality. Gene family abundances are then combined into structured pathways from MetaCyc57® (metacyc.org) and KEGG® (http://www.genome.jp/kegg/), and sum-normalized to relative abundances. From this data, gene functions differentially present across samples are determined.

Transcriptome Analysis

For analysis, samples are thawed and brought to room temperature. 10 μl of mutanolysin and 10 μl of Proteinase K are added to each and incubated for 10 minutes at room temperature. RNA is extracted by binding to an RNeasy™ column (Qiagen) followed by washing and elution using the reagents provided in the RNeasy™ kit (Qiagen). Sequencing libraries are prepared from RNA by fragmentation, ribodepletion, cDNA synthesis, PCR amplification, and barcoding as described in the TRUSEQ® mRNA sample preparation kit (Illumina). DNA concentration is measured using the QUBIT® fluorometer (ThermoFisher Scientific) and quality and size distribution are determined using a Bioanalyzer 2100® (Agilent), following the manufacturer's instructions. Sample libraries are normalized to 40 nM and sequenced on an Illumina MISEQ® instrument using 2×75 cycles. Reads are then mapped to the DNA metagenomic reference sequence created from the whole genome sequencing data to determine relative abundance of each transcript.

Proteomics Analysis

Proteomics is conducted on raw fecal material to measure the various proteins present in the samples, including both microbial and mammalian (human or any non-human, including e.g., rat, mouse, pig, monkey, dog, etc.). Although it is not as sensitive as RNA sequencing (hundreds of proteins detected as opposed to thousands of genes), it may be a more accurate reflection of actual microbial metabolism due to the potential for post-translational regulation. Furthermore, analysis of the mammalian proteins can provide information on immune system interactions with the gut. For example, it was shown recently that immunoglobulin A binds to the surface of commensal bacteria and helps them colonize the gut (see, e.g., Donaldson, G. P., et al, Gut microbiota utilize immunoglobulin A for mucosal colonization, Science, 2018, 360(6390): p. 795-800).

Proteomics also can be performed on mammalian blood plasma to look for biomarkers that may be related to immune system function. Plasma is isolated from whole blood by centrifugation at 1500×g for 10 minutes, taking the supernatant. A second centrifugation is performed to remove any residual blood cells. Proteomics can be conducted (e.g., at the University of California San Diego Biomolecular & Proteomics Mass Spectrometry Facility (http://massspec.ucsd.edu/bioms/)), applying the method known as isobaric tag for relative and absolute quantitation (iTRAQ) (see e.t., Wiese, S., et al, Protein labeling by iTRAQ: a new tool for quantitative mass spectrometry in proteome research, Proteomics, 2007, vol 7(3): p. 340-50).

Metabolomics Analysis Using LCMS

This protocol also can be used for urolithin analysis, e.g., as shown in FIG. 12 and discussed in Example 17.

To extract metabolites from the fecal matter suspension or whole blood, 0.5 mL of a solution containing 40% DMSO, 40% methanol, and 20% 0.1M hydrochloric acid is added to the sample aliquot, and vortexed for 30 seconds. The material is then pelleted by centrifugation at 14,000 rpm for 5 minutes, and the supernatant removed and passed through a 0.45 um pore filter. Untargeted metabolomics analysis is performed on this supernatant using HPLC equipped with a triple quadrupole mass spectrometer in negative ionization mode (ThermoFinnegan). A C18 POROSHELL® 120 (3×150 mm, 2.7 um particle size) is used for the separation, with mobile phases of 0.1% formic acid (A) and 0.1% formic acid in acetonitrile (B) at a flow of 0.3 mL/min ramping from 0 to 90% B over 30 minutes. Optimal mass spectrometer conditions for urolithin detection are: gas temperature 300° C., drying gas 11 L/min, nebulizer pressure 45 psi, sheath gas temperature 400° C., and sheath gas flow 12 L/min. Spectra are analyzed using XCMS software for feature alignment and clustering Smith C A, Want E J, O'Maille G, Abagyan R, Siuzdak G. Anal Chem. 2006; 78(3):779-87). In particular, features are identified that show differences based on mouse treatment. Next, MS2 based molecular network analysis is used to identify known compounds and group compounds with related structure (Garg et al., Int. J. Mass Spectrom. 2015; 377:719-717).

Headspace GCMS Analysis

GCMS in the headspace of capped samples is used to determine the relative amounts of volatile organic acids present in the samples. Primarily, the compounds of interest are acetate, propionate, and butyrate. Analysis is carried out as described previously (Renom et al., Clinical Chemistry and Laboratory Medicine 2005; 39(1):15-19). Peaks are quantified by comparison to authentic standards prepared in PBS solution.

Figure 2:
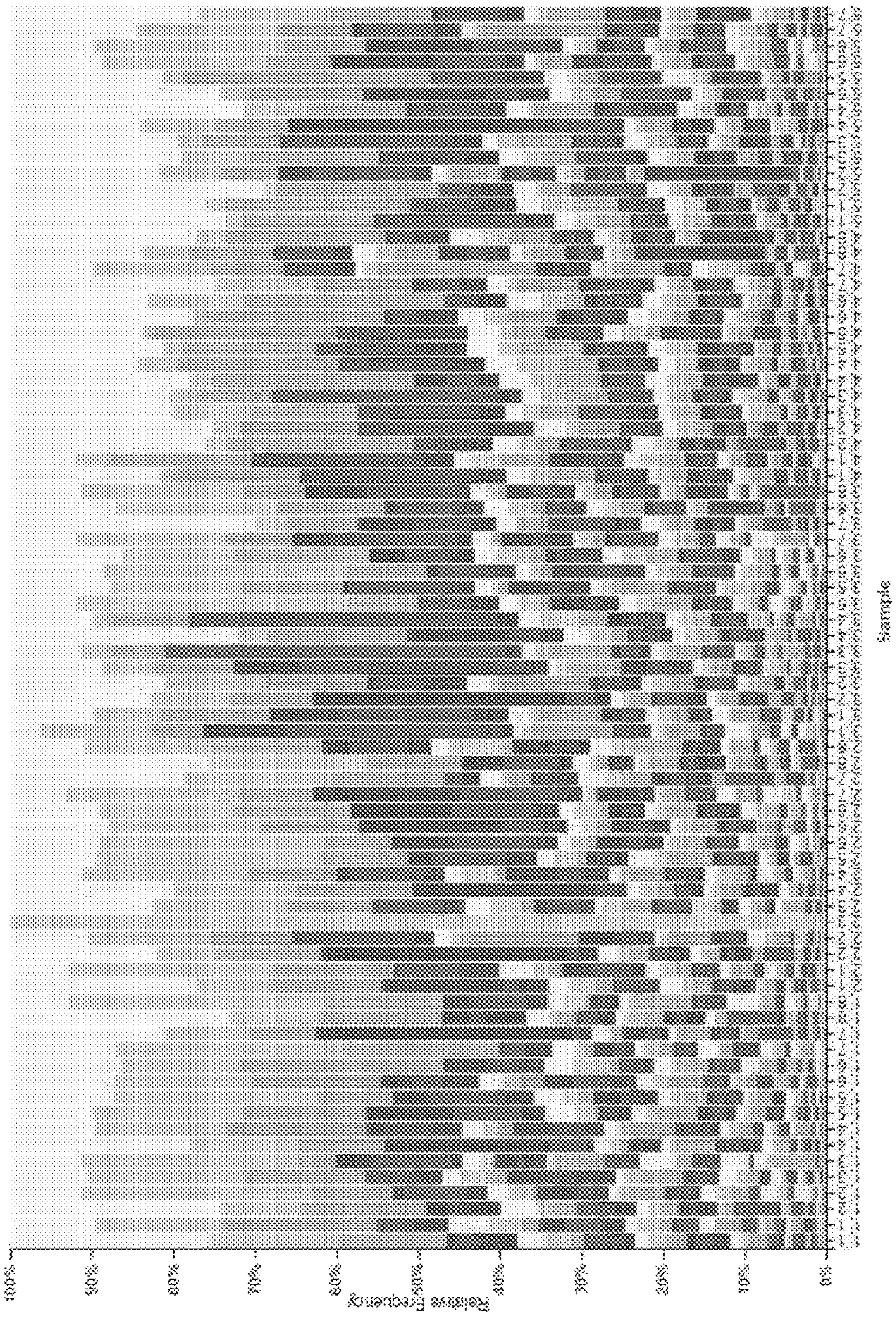
FIG. 2 illustrates a bar graph showing relative abundance of genera in each fecal sample from non-tumor mice: labels on each bar indicate timepoint:treatment. Timepoints 1-7 refer to days 0, 3, 7, 10, 14, 17, and 21, respectively; treatments are as follows: 1) Vehicle only; 2) ellagic acid (EA); 3) urolithin A (UA); 4) microbe mix 1; 5) microbe mix 2; 6) microbe mix 3+EA; 7) microbe mix 4+EA; 8) microbe mix 5; as discussed in detail in Example 4, below. Microbe Mix 3 consists of 10 ml each of *E. lenta* and *G. urolithinfaciens* cultures. Microbe Mix 4 consists of 3.3 ml each of *F. prausnitzii, C. coccoides, R. gnavus, C. scindens, E. lenta*, and *G. urolithinfaciens* cultures. Combined microbial concentration in each mix is $1\times10^9$ cells/mL. 0.2 mL of the mixture was given in each dose. Ellagic acid was supplemented as 1.35 mg per dose.

Example 4—Differences in Microbiomes Between Non-Tumor, CT26-Vehicle Treatment, and CT26-Anti-CTLA4 Treatment The 16S RNA sequencing results are used to determine the distribution of organisms in each sample at both the phylum and genus level, and the distribution is compared across all mouse fecal samples, see FIG. 2 and FIG. 4. The microbe legend is given Table 2, listed in FIG. 4, indicating the bar color in order from top to bottom of the chart. The taxonomic indicators are listed as kingdom, phylum, class, order, family, and genus. Cases where not complete taxonomic information is given indicate it is unknown beyond the last level given.

In FIG. 2, the bar graph illustrates the relative abundance of genera in each fecal sample from non-tumor mice. Labels on each column indicate timepoint:treatment. Timepoints 1-7 refer to days 0, 3, 7, 10, 14, 17, and 21, respectively. Treatments are as follows: 1) Vehicle only; 2) ellagic acid (EA); 3) urolithin A (UA); 4) microbe mix 1; 5) microbe mix 2; 6) microbe mix 3+EA; 7) microbe mix 4+EA; 8) microbe mix 5. Consecutive columns with the same label are replicate mice. The microbe legend is given in Table 2 (FIG. 4), indicating the taxonomy of each genus identified in the samples. Each line in the table corresponds to a bar color or shade in the graph, in a consistent order across all columns in the graph. Relative abundance (percent) is indicated by the length of the bar. For example, the first line in the table indicates the genus represented by the top set of bars (yellow), extending downward from 100%. The second line in the table indicates the next set of bars, and so on moving downward in the graph. Taxonomic indicators are listed in each line of the table as kingdom (1), phylum (2), class (3), order (4), family (5), and genus (6). Cases where incomplete taxonomic information is given indicate it cannot be uniquely identified beyond the last level given.

Specifically, a comparison is made across all mice that did not receive microbial treatment, including those without tumors, those with subcutaneous CT26 tumor graft that receive vehicle treatment, and those with tumor graft that receive anti-CTLA4 treatment. Principal Components Analysis (PCA) is used to reduce the dimensionality of the dataset, and the samples are viewed in the first 3 components. As a more quantitative measure, similarity scores are calculated to determine within-group and between-group variability, showing the significant differences in composition among the mouse treatments. Calculations are all performed by the QIIME platform (referenced above).

The genes identified from whole genome sequencing are classified into gene ontology (GO) categories using tools available publicly from the Panther Classification System website (http://www.pantherdb.org/). This establishes a GO composition of the DNA corresponding to each sample, analogous to the species composition above. The same approach is also applied using the RNAseq transcriptomics data. Both the DNA and RNA datasets are visualized on PCA plots generated using the R programming environment. As a more quantitative measure, GO enrichment analysis is performed to identify which GO terms are over- or under-represented in samples from mice with the cancer graft, with and without anti-CTLA4 treatment. This is also conducted using Panther tools.

Specific genes differentially present or expressed among the cultures are identified using commercial expression analysis software such as SPOTFIRE® (TIBCO Software) or free tools such as BioConductor®. This approach is used to identify genes and transcripts overrepresented in samples from mice with the cancer graft, both with and without anti-CTLA4, compared to the control.

Tools available from the XCMS website are used to classify the LCMS metabolomics samples according to patterns in the spectral signatures obtained. Specific peaks are also identified that correlate with cancer and/or treatment type, thus representing biomarkers of the condition.

Example 5—Differences in Microbiomes Based on Anti-CTLA4 Treatment Efficacy

The tumor size is measured over time in all animals. Although there is significant heterogeneity, the animals receiving anti-CTLA4 on average had less tumor growth than those receiving the vehicle only, see FIG. 3. Based on this data, the mice receiving the treatment are classified based on treatment efficacy as determined by reduction in tumor growth.

Figure 3:
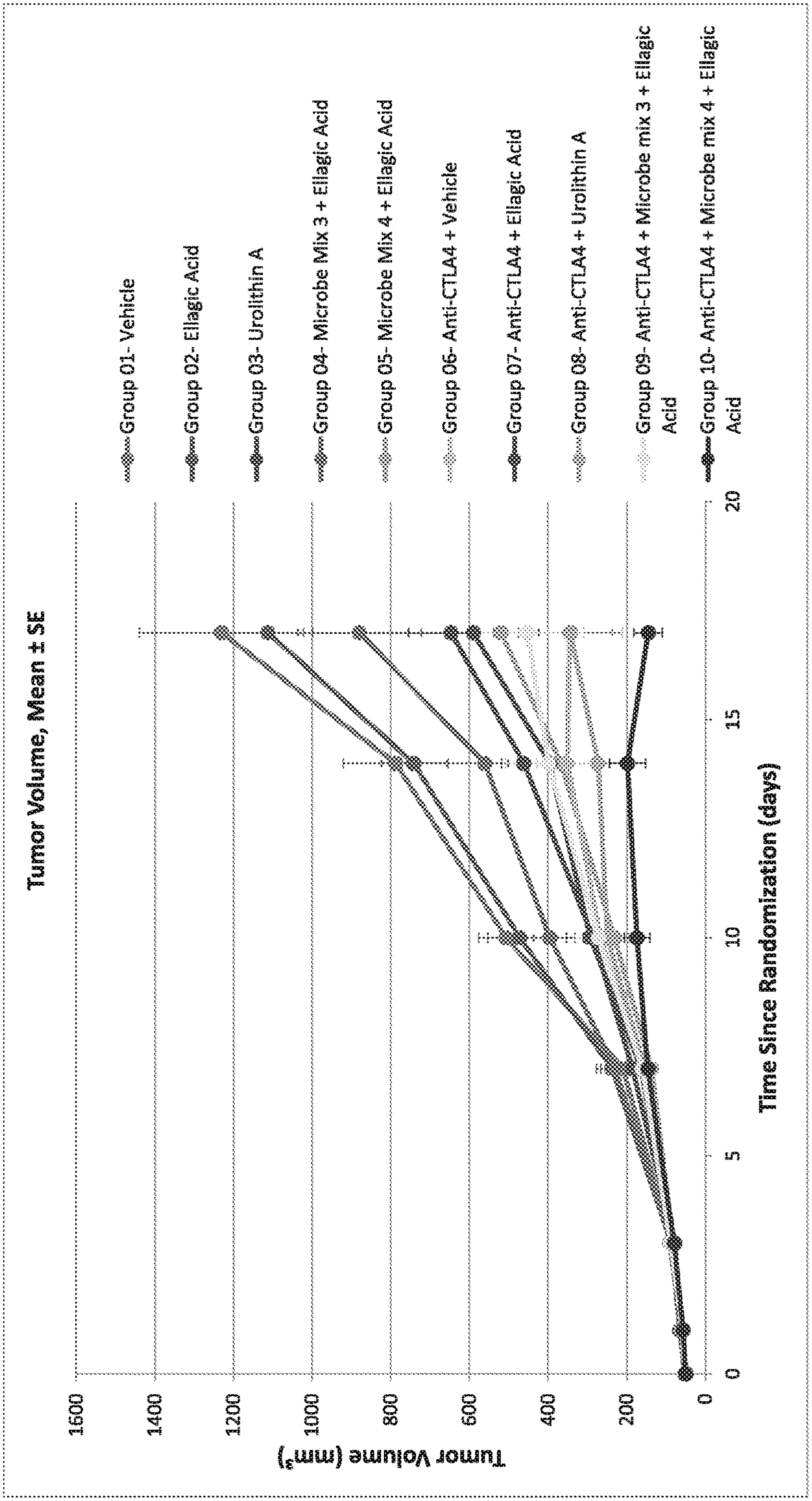
FIG. 3 graphically illustrates data showing the efficacy of anti-CTLA-4 treatment in mice with CT26 cancer tumor graft, and supplemented with nutrients and/or microbial mixtures, including microbial mix 3 and ellagic acid, and microbial mix 4 (defined in the FIG. 2 legend) with ellagic acid, with or without addition of CTLA4; datapoints refer to tumor volume ($mm^3$) at each day measurements were taken; as discussed in detail in Example 5, below.
Figure 5:
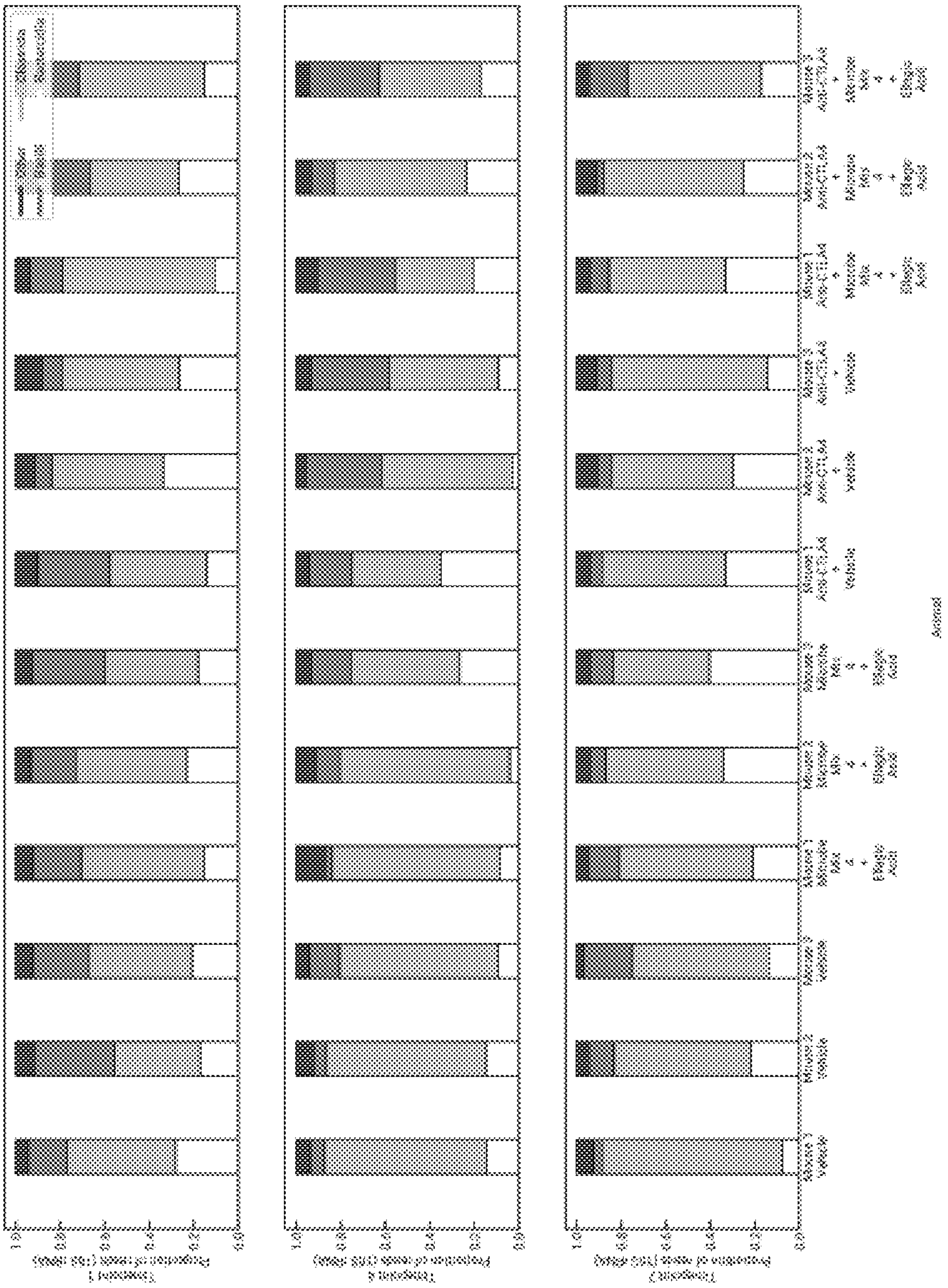
FIG. 5, lists the 16S rRNA analysis of fecal samples from mice (syngeneic mice with CT26 tumor) treated with vehicle, microbe mix 4 and ellagic acid and the anti-CTLA4 checkpoint inhibitor; taxonomic indicators are listed as class, discussed in detail in Example 6, below.

FIG. 3 illustrate data showing the efficacy of anti-CTLA-4 treatment in mice with CT26 cancer tumor graft, and supplemented with nutrients and/or microbial mixtures. Datapoints refer to tumor volume ($mm^3$) at each day measurements were taken, averaged over either 4 mice (no CTLA-4) or 8 mice (with CTLA-4) with standard error shown.

The 16S RNA sequencing results are used to determine the distribution of organisms in each sample at both the phylum and genus level, and the distribution is compared across all fecal samples from mice receiving anti-CTLA4 treatment. Principal Components Analysis (PCA) is used to reduce the dimensionality of the dataset, and used to determine differences that are correlated with treatment efficacy. As a more quantitative measure, regression analysis is used to identify particular species associated with the treatment efficacy or lack of efficacy.

The genes identified from whole genome sequencing are classified into gene ontology (GO) categories using tools available publicly from the Panther Classification System website (http://www.pantherdb.org/). This establishes a GO composition of the DNA corresponding to each sample, analogous to the species composition above. The same approach is also applied using the RNAseq transcriptomics data. Both the DNA and RNA datasets for samples from mice receiving anti-CTLA4 are visualized on PCA plots generated using the R programming environment. As a more quantitative measure, GO enrichment analysis is performed to identify which GO terms are over- or under-represented in samples from mice that responded well to the anti-CTLA4 treatment. This is also conducted using Panther tools.

Specific genes differentially present or expressed among the samples are identified using commercial expression analysis software such as SPOTFIRE® (TIBCO Software) or free tools such as BioConductor (an open source, open development software).

Tools available from the XCMS website are used to classify the LCMS metabolomics samples according to patterns in the spectral signatures obtained, to determine whether samples from mice responding well to anti-CTLA4 treatment have significantly different metabolite profiles. Finally, organic acid data from the headspace GCMS analysis are used to identify which of these molecules are correlated with treatment efficacy.

Example 6—Efficacy of Microbial Cocktails

Mice with and without tumors are given microbial cocktails by oral gavage, as described in the example above. The 16S RNA sequencing results are used to determine the distribution of organisms in each sample at both the phylum and genus level, and the distribution is compared across all fecal samples from mice without tumors to determine how these microbes colonize the gut. PCA is used to classify all samples of mice without tumors, showing that samples with the same microbial treatment type cluster together. In addition, the genera represented by each microbial treatment have increased representation in those samples compared to those of different treatment type.

Figure 6:
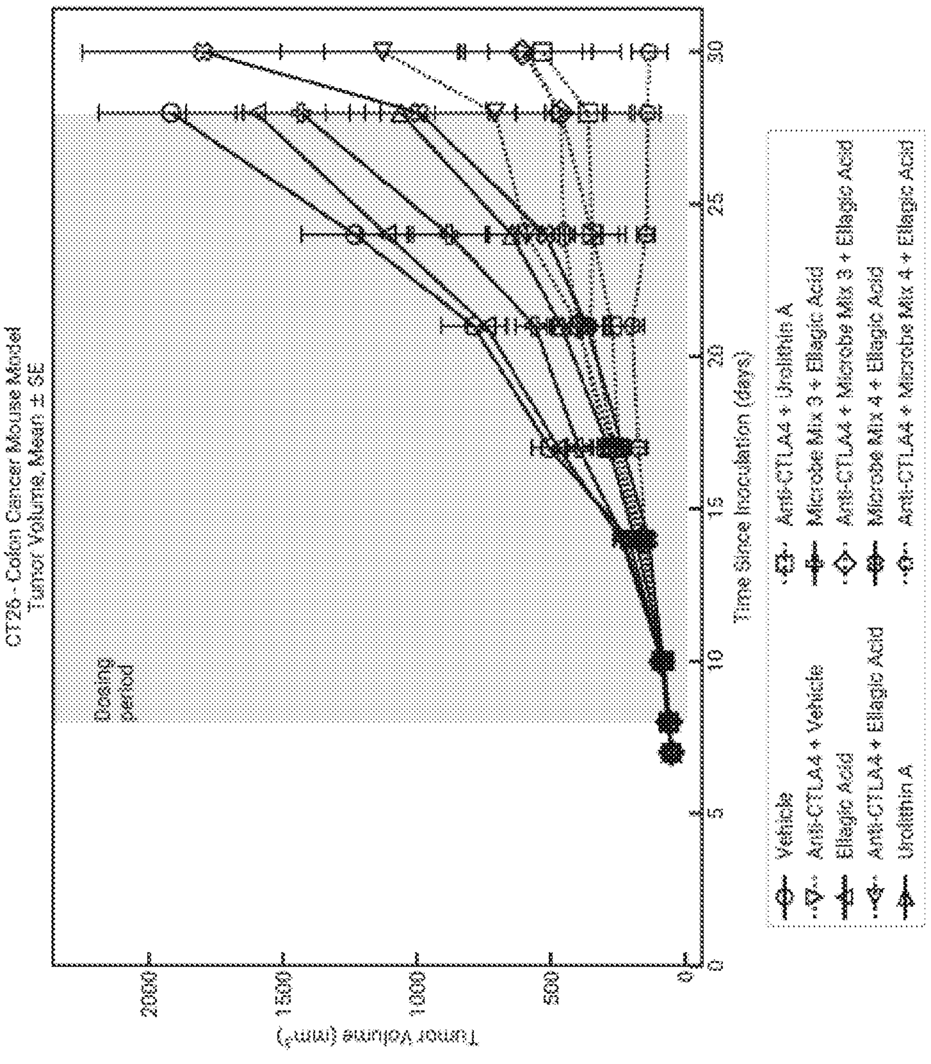
FIG. 6 graphically illustrates data from studies where mice inoculated with CT-26 colon cancer cells were treated with mix 4 and anti-CTLA4 therapy, the data showing that the anti-CTLA4 therapy with mix 4 (or “microbe mix 4”) had minimal tumor growth in contrast to the other groups, tumor volume is shown as a function of time since tumor inoculation, as described in Example 6, below.

Tumor size is measured in all animals receiving the different microbial treatments, with and without anti-CTLA4 therapy. On average, the animals receiving Microbe Mix 4 (equal amounts of *F. prausnitzii, C. coccoides, R. gnavus, C. scindens, E. lenta*, and *G. urolithinfaciens*) in conjunction with ellagic acid and anti-CTLA4 have a reduction in tumor size compared to those with other microbes or not receiving any CTLA4 treatment, as illustrated in FIG. 3. Termination of dosing of both the microbial and anti-CTLA4 treatments were performed at day 28 and mice were evaluated. Mice treated with mix 4 and the anti-CTLA4 therapy had minimal tumor growth in contrast to the other groups, as shown in FIG. 6.

Specific genes differentially present or expressed among the cultures are identified using commercial expression analysis software such as SPOTFIRE® (TIBCO Software) or free tools such as BioConductor™. This approach is used to identify genes overrepresented in samples from mice receiving microbial cocktail 4 (equal amounts of *F. prausnitzii, C. coccoides, R. gnavus, C. scindens, E. lenta*, and *G. urolithinfaciens*) in conjunction with ellagic acid and anti-CTLA4. Similarly, LCMS peaks from the metabolomics analysis are identified that have significantly higher or lower concentration in the samples from mice receiving microbial cocktail 4, ellagic acid, and anti-CTLA4. These represent candidate metabolites either produced or degraded by these microbes that are important for stimulating immune function and thus contribute to anti-CTLA4 function.

Whole genome sequencing was performed on fecal samples obtained from mice receiving ellagic acid only, microbe mix 4 in conjunction with ellagic acid, anti-CTLA4 and vehicle, or anti-CTLA4 in conjunction with microbe mix 4 and ellagic acid. A taxonomic classification was assigned to each read by using the centrifuge software package together with a proprietary in-house genome database. The classified read percentages are reported in Table 17 (illustrated as FIG. 20), with percentages normalized to the total number of classified reads.

Figure 7:
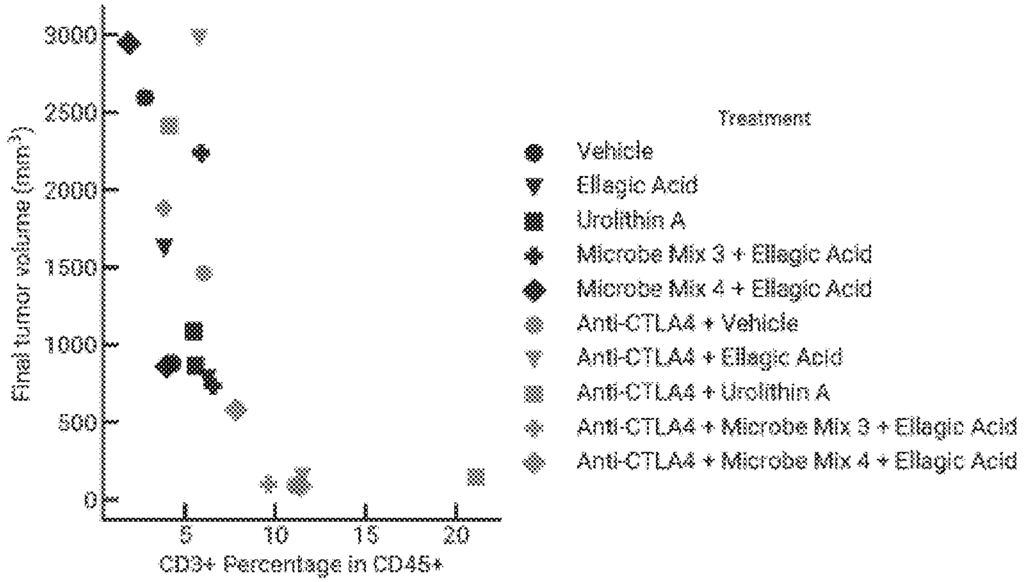
FIG. 7 illustrates a plot summarizing data from a FACS analysis of whole blood obtained from the animals at the end of a study (as described in Example 6) that indicated that CD4 and CD8 T-lymphocyte activity are increased by treatment with a microbial cocktail 4 in conjunction with anti-CTLA4.

FACS analysis of whole blood obtained from the animals at the end of the study indicated that CD4 and CD8 T-lymphocyte activity are increased by treatment with the microbial cocktail 4 in conjunction with anti-CTLA4 as shown in the "population table" of FIG. 7.

Figure 8:
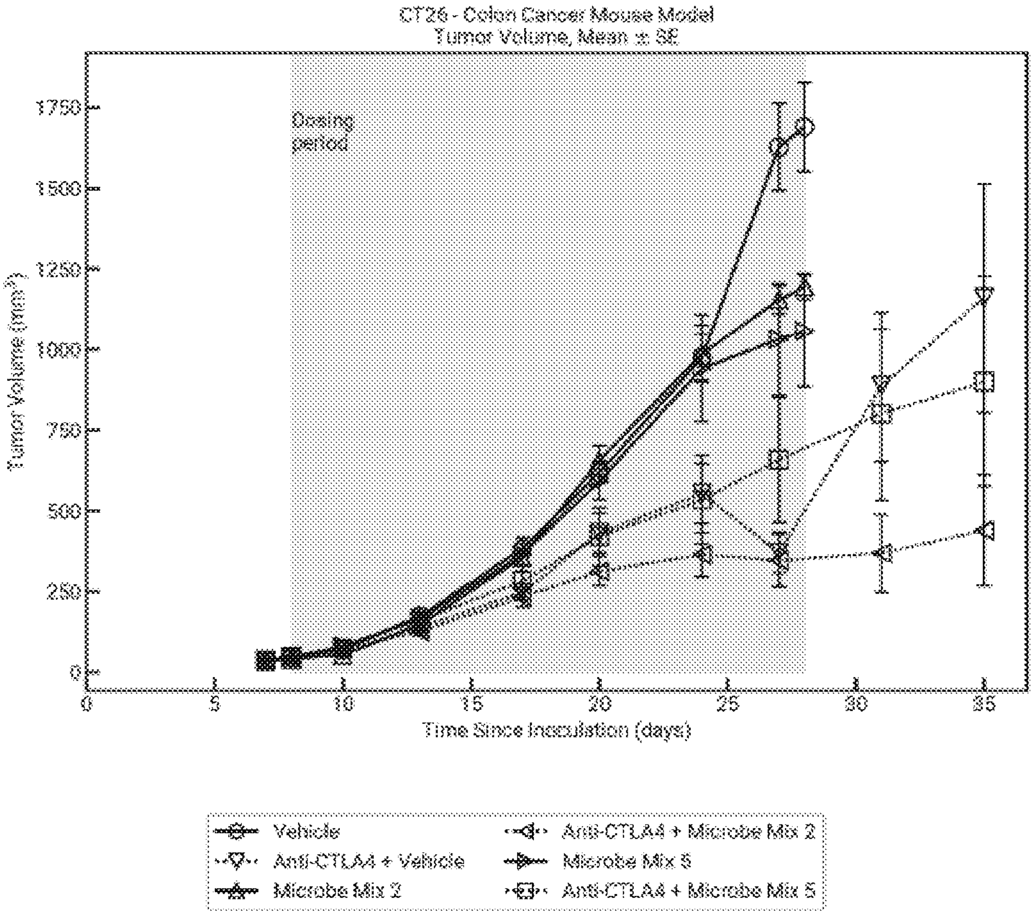
FIG. 8 graphically illustrates data from studies where mice inoculated with CT-26 colon cancer cells were treated with microbial mix 2, mix5 and anti-CTLA4 therapy, the data showing that the anti-CTLA4 therapy with microbial mix 2 (or “mix D”) had minimal tumor growth in contrast to the other groups, tumor volume is shown as a function of time since tumor inoculation, as described in Example 6, below.

FIG. 8 graphically illustrates data showing the efficacy of anti-CTLA-4 treatment in mice with CT26 cancer tumor graft, and supplemented with nutrients and/or microbial mixtures. Datapoints refer to tumor volume ($mm^3$) at each day measurements were taken, averaged over either 8 mice (no CTLA-4) or 8 mice (with CTLA-4) with standard error shown.

Tumor size is measured in all animals receiving the different microbial treatments, with and without anti-CTLA4 therapy. On average, the animals receiving Microbe Mix 2 (*F. prausnitzii, C. coccoides, R. gnavus, C. scindens, A. muciniphila*, and *E. hirae*) in conjunction with anti-CTLA4 have a reduction in tumor size compared to those with other microbes or not receiving any CTLA4 treatment, as illustrated in FIG. 8.

Whole Genome Sequencing and corresponding computer analyses is used to assign a phylogenetic identification to each isolated strain. Resulting sequence information is compared to in-house and publicly available genomic DNA databases to assign identities to each strain.

Specific genes differentially present or expressed among the cultures are identified using commercial expression analysis software such as SPOTFIRE® (TIBCO Software) or free tools such as BioConductor™. This approach is used to identify genes overrepresented in samples from mice receiving microbial cocktail 4 (equal amounts of *F. prausnitzii, C. coccoides, R. gnavus, C. scindens, E. lenta*, and *G. urolithinfaciens*) in conjunction with ellagic acid and anti-CTLA4. Similarly, LCMS peaks from the metabolomics analysis are identified that have significantly higher or lower concentration in the samples from mice receiving microbial cocktail 2 and anti-CTLA4. These represent candidate metabolites either produced or degraded by these microbes that are important for stimulating immune function and thus contribute to anti-CTLA4 function.

Specific genes differentially present or expressed among the cultures are identified using commercial expression analysis software such as SPOTFIRE® (TIBCO Software) or free tools such as BioConductor™. This approach is used to identify genes overrepresented in samples from mice receiving microbial cocktail 2 (equal amounts of *F. prausnitzii, C. coccoides, R. gnavus, C. scindens, A. muciniphila*, and *E. hirae*) in conjunction with anti-CTLA4. Similarly, LCMS peaks from the metabolomics analysis are identified that have significantly higher or lower concentration in the samples from mice receiving microbial cocktail 2 and anti-CTLA4. These represent candidate metabolites either produced or degraded by these microbes that are important for stimulating immune function and thus contribute to anti-CTLA4 function.

Stool Meta-Transcriptomics Analysis:

For performing meta-transcriptomics analysis, stool samples are thawed by adding the appropriate volume of 60° C. PM1 containing 1% beta-mercaptoethanol and vortexing at room temperature until the sample is completely homogeneous. The remainder of the total RNA isolation is performed using the RNeasy® PowerMicrobiome® Kit (Qiagen) according to Qiagen's specifications.

To remove contaminating DNA, the Lucigen Baseline-ZERO™ DNase kit (Lucigen) is used in accordance with the manufacturer's specifications. To ensure the cleanliness of the prep, the RNeasy® MinElute® Cleanup Kit (Qiagen) is used in accordance with Qiagen's specifications. To deplete gram-positive and gram-negative ribosomal RNA, Illumina's Ribo-Zero® rRNA Removal Kit is used in accordance with the manufacture's specifications (Illumina, San Diego, CA). The rRNA-depleted samples are assessed using the Fragment Analyzer™ Automated CE System with the High Sensitivity RNA Analysis Kit (Fragment Analyzer™). The depleted-RNA concentration is determined using the Invitrogen™ Qubit™ RNA HS Assay Kit (Invitrogen). Sequencing libraries are prepared by brief fragmentation, random priming, cDNA synthesis, adaptor ligation, and PCR enrichment according to the NEBNext® Ultra™ II Directional RNA Library Prep Kit™ for Illumina®-used in conjunction with the NEBNext® Multiplex Oligos for Illumina® (New England Biolabs). The quality of the double-stranded cDNA fragments is assessed using the Fragment Analyzer™ Automated CE System with the High Sensitivity NGS Fragment Analysis Kit™ (Fragment Analyzer™). Sample libraries are denatured, then normalized to 1.6 picomolar and analyzed on Illumina's MiniSeq™ or NexSeq NGS™ sequencing platform with the MiniSeq™/NexSeq High Output Reagent Kit-1×150™ cycles (Illumina).

Metabolomics

Mouse and human fecal samples, either raw or resuspended in PBS, were kept frozen at −80 deg. C. until processing, then immediately placed in a lyophilizer and freeze-dried overnight. The resulting material was weighed, and lyophilized fecal samples were extracted and processed at a constant per-mass basis using an established procedure (Evans, A. et al. High resolution mass spectrometry improves data quantity and quality as compared to unit mass resolution mass spectrometry in high-throughput profling metabolomics. J. Postgenomics Drug Biomark. Dev. 4, S24-S36 (2014)) by Metabolon, Inc. Recovery standards were added before the first step in the extraction process for quality-control purposes. Samples are prepared using the automated MicroLab STAR® system from Hamilton Company. Several recovery standards are added prior to the first step in the extraction process for QC purposes. Samples are extracted with methanol under vigorous shaking for 2 min (Glen Mills GenoGrinder 2000) to precipitate protein and dissociate small molecules bound to protein or trapped in the precipitated protein matrix, followed by centrifugation to recover chemically diverse metabolites. The resulting extract is divided into five fractions: two for analysis by two separate reverse phase (RP)/UPLC-MS/MS methods using positive ion mode electrospray ionization (ESI), one for analysis by RP/UPLC-MS/MS using negative ion mode ESI, one for analysis by HILIC/UPLC-MS/MS using negative ion mode ESI, and one reserved for backup. Samples are placed briefly on a TurboVap® (Zymark) to remove the organic solvent. The sample extracts are stored overnight under nitrogen before preparation for analysis.

All analytical methods utilize a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. The sample extract is dried then reconstituted in solvents compatible to each of the four methods. Each reconstitution solvent contains a series of standards at fixed concentrations to ensure injection and chromatographic consistency. One aliquot is analyzed using acidic positive ion conditions, chromatographically optimized for more hydrophilic compounds. In this method, the extract is gradient-eluted from a C18 column (Waters UPLC BEH C18-2.1×100 mm, 1.7 μm) using water and methanol, containing 0.05% perfluoropentanoic acid (PFPA) and 0.1% formic acid (FA). A second aliquot is also analyzed using acidic positive ion conditions, but is chromatographically optimized for more hydrophobic compounds. In this method, the extract is gradient eluted from the aforementioned C18 column using methanol, acetonitrile, water, 0.05% PFPA and 0.01% FA, and is operated at an overall higher organic content. A third aliquot is analyzed using basic negative ion optimized conditions using a separate dedicated C18 column. The basic extracts are gradient-eluted from the column using methanol and water, however with 6.5 mM Ammonium Bicarbonate at pH 8. The fourth aliquot is analyzed via negative ionization following elution from a HILIC column (Waters UPLC BEH Amide 2.1×150 mm, 1.7 μm) using a gradient consisting of water and acetonitrile with 10 mM Ammonium Formate, pH 10.8. The MS analysis alternates between MS and data-dependent $MS^n$ scans using dynamic exclusion. The scan range varies slightly between methods, but covers approximately 70-1000 m/z.

Three types of controls were analyzed in concert with the experimental samples: a pooled sample generated from a small portion of each experimental sample of interest served as a technical replicate throughout the platform run; extracted water samples served as process blanks; and a cocktail of standards spiked into every analyzed sample allowed for instrument performance monitoring. Instrument variability was determined by calculation of the median relative s.d. (RSD) for the standards that were added to each sample before injection into the mass spectrometers (median RSDs were determined to be 3%). Overall process variability was determined by calculating the median RSD for all endogenous metabolites (i.e., noninstrument standards) present in 90% or more of the pooled technical-replicate samples (median RSD=8%, n=797 metabolites).

Compounds are identified by comparison to library entries of purified standards maintained by Metabolon, that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library +/−10 ppm, and the MS/MS forward and reverse scores. MS/MS scores are based on a comparison of the ions present in the experimental spectrum to ions present in the library entry spectrum. While there may be similarities between these molecules based on one of these factors, the use of all three data points can be utilized to distinguish and differentiate biochemicals. Peaks are quantified as area-under-the-curve detector ion counts.

Metabolomics Performed on Fecal Samples

Metabolomics was performed on fecal samples taken from mice in the control group, treated with vehicle and no checkpoint inhibitor, the group treated with microbe cocktail #4 and ellagic acid only, the group treated with anti-CTLA-4 only, and the group treated with anti-CTLA-4, microbe mix 4, and ellagic acid. In the tables and figures that follow, these are referred to as the Control, Microbe, Drug, and Combo, respectively. Samples were processed from timepoint 1 (T1), prior to any treatment; timepoint 4 (T4), 10 days from start and 48 hours after the $3^{rd}$ treatment dose; and timepoint 7 (T7), 20 days from start and 48 hours after the $6^{th}$ treatment dose.

Figure 15:
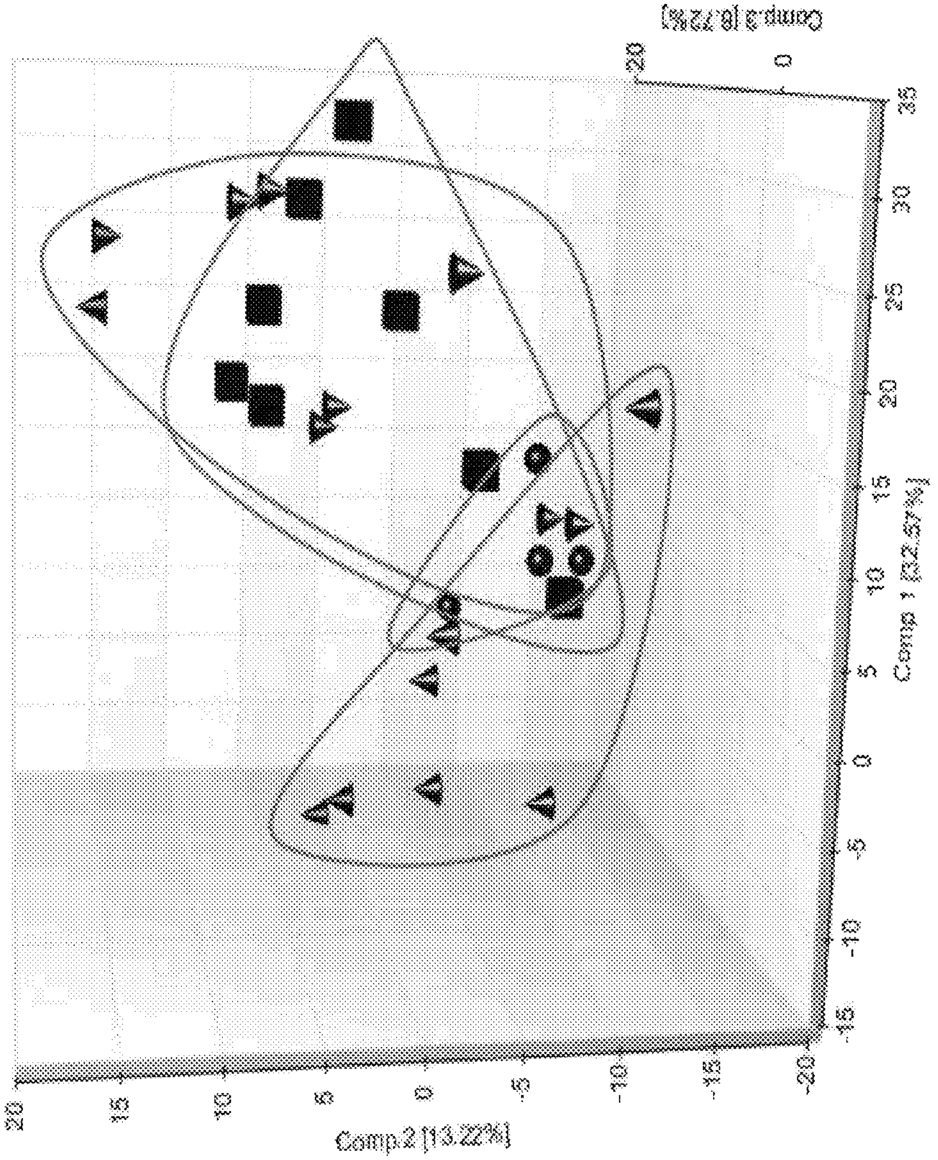
FIG. 15 graphically illustrates a principal component analysis on metabolome profile from all samples at timepoint T7. Downward cones, Control; circles, Microbe; squares, Drug; and upward cones, Combo; as described in detail in Example 6, below FIG. 16 graphically illustrates data of concentrations of pterin and biopterin in mouse samples over time; in order from lightest to darkest lines and symbols, groups are indicated as follows: Control, Microbe, Drug, Combo; as described in detail in Example 6, below.

Principal components analysis (PCA) was applied on all samples to give a global view of the data. The Control group segregated by timepoint, indicating a gradual shift in the metabolome over time as the cancer progressed. A similar pattern was exhibited by the drug group, while the Microbe and Combo groups shifted in a different direction. There was little distinction among treatment groups at T1 and T4, while significant differences were observed at T7 (FIG. 15). At T7, the microbe and combo groups had changes with $p<0.05$ in 25% and 40% of all the metabolites detected, respectively, whereas the drug group only had such change in 9% of the metabolites.

Next, individual metabolic pathways and classes of metabolites were considered. The levels of amino acids (unmodified, gamma-glutamyl and acetylated) along with peptides (dipeptides and polypeptides) were lower in the Microbe and Combo groups relative to the Controls at T7 (Table 6). Declines in dipeptides and amino acids in the fecal samples highlight the possibility that proteolysis of both human and microbial-derived peptides, and microbial amino acid excretion, may have lessened following treatment with microbe mix 4. More evidence to support this notion came from the levels of gamma-glutamyl amino acids and N-acetylated amino acids, both of which were decreased in the fecal samples of Microbe and Combo groups. N-acetyl amino acids can be derived from proteins that have undergone post-translational acetylation reactions or from free amino acids reacting with acetyl groups. Gamma-glutamyl AAs are generated by gamma-glutamyl transpeptidase, which plays an important role in amino acid uptake. Decreased fecal levels of proteolysis markers may reflect diminished gut motility and increased transit time.

TABLE 6

Amino acids, acylated amino acids, and gamma-glutamyl amino acids in mouse fecal samples at T7. Ratio of the mean peak areas for the specified metabolites in each group relative to the control group. Up or down arrows indicate whether the increase or decrease in the treatment relative to the control is significant based on Welch's two sample t-test with $p < 0.05$.

| Compound | Microbe T7 | Drug T7 | ComboT7 |
|---|---|---|---|
| Glycine | 0.59↓ | 0.79 | 0.71↓ |
| Serine | 0.59↓ | 0.81 | 0.60↓ |
| Threonine | 0.46↓ | 0.84 | 0.57↓ |
| Alanine | 0.59↓ | 0.97 | 0.65↓ |
| Aspartate | 0.49↓ | 0.81 | 0.62 |
| Asparagine | 0.30↓ | 0.59↓ | 0.42↓ |
| Glutamate | 0.51↓ | 0.97 | 0.57↓ |
| glutamine | 0.91 | 0.71 | 0.62↓ |
| histidine | 0.77 | 0.84 | 0.62↓ |
| lysine | 0.50↓ | 1.05 | 0.56↓ |
| Phenylalanine | 0.74 | 0.98 | 0.66↓ |
| tyrosine | 0.60↓ | 0.97 | 0.57↓ |
| tryptophan | 0.79 | 0.91 | 0.67↓ |
| Leucine | 0.74 | 0.97 | 0.66↓ |
| isoleucine | 0.61↓ | 0.92 | 0.65↓ |
| valine | 0.60 | 0.97 | 0.64↓ |
| Arginine | 0.95 | 1.39 | 0.86↓ |
| proline | 1.14 | 1.12 | 1.03 |
| N-acetylserine | 0.79 | 1.42 | 0.53 |
| N-acetylthreonine | 0.59 | 1 | 0.42↓ |
| N-acetylalanine | 0.47↓ | 1.05 | 0.52↓ |
| N-acetylaspartate | 0.27↓ | 1.04 | 0.65↓ |
| N-acetylasparagine | 0.27↓ | 0.93 | 0.36↓ |
| N-acetylglutamate | 0.36↓ | 1.18 | 0.76↓ |
| N-acetylglutamine | 0.86 | 0.94 | 0.64↓ |
| N-acetylhistidine | 0.88 | 0.88 | 0.67 |
| N2-acetyllysine | 0.37↓ | 1.04 | 0.61↓ |
| N6-acetyllysine | 0.41↓ | 1.05 | 0.56↓ |
| N-acetylphenylalanine | 0.71 | 0.95 | 0.53↓ |
| N-acetyltyrosine | 0.38↓ | 0.96 | 0.36↓ |
| N-acetyltryptophan | 1.17 | 0.97 | 1.01 |
| N-acetylleucine | 0.78 | 1.12 | 0.58 |
| N-acetylisoleucine | 0.79 | 0.99 | 0.55↓ |

TABLE 6-continued

Amino acids, acylated amino acids, and gamma-glutamyl amino acids in mouse fecal samples at T7. Ratio of the mean peak areas for the specified metabolites in each group relative to the control group. Up or down arrows indicate whether the increase or decrease in the treatment relative to the control is significant based on Welch's two sample t-test with $p < 0.05$.

| Compound | Microbe T7 | Drug T7 | ComboT7 |
|---|---|---|---|
| N-acetylvaline | 0.99 | 1.3 | 0.8 |
| N-acetylarginine | 0.59 | 1.2 | 0.51↓ |
| N-acetylcitrulline | 0.4 ↓ | 1.23 | 0.35↓ |
| N-acetylproline | 0.85 | 0.97 | 0.66↓ |
| Gamma-glutamylglutamate | 0.48 ↓ | 0.91 | 0.55↓ |
| Gamma-glutamylglutamine | 0.77 | 0.69 | 0.56↓ |
| Gamma-glutamylisoleucine | 1.07 | 0.79 | 1.65 |
| Gamma-glutamylleucine | 0.57 | 0.83 | 0.50↓ |
| Gamma-glutamyl-alpha-lysine | 0.36 ↓ | 0.69 | 0.36↓ |
| Gamma-glutamyl-epsilon-lysine | 0.48 | 0.72 | 0.24↓ |
| Gamma-glutamylmethionine | 0.33 ↓ | 0.86 | 0.41↓ |
| Gamma-glutamylphenylalanine | 0.61 | 0.93 | 0.53↓ |
| Gamma-glutamylthreonine | 0.39 ↓ | 0.82 | 0.58↓ |
| Gamma-glutamyltyrosine | 0.53 | 0.98 | 0.48↓ |
| Gamma-glutamylvaline | 0.30 | 0.89 | 0.55 |
| Gamma-glutamylserine | 0.47 ↓ | 0.74 | 0.42↓ |
| Gamma-glutamylcitrulline | 0.25 ↓ | 0.83 | 0.51 |

Cysteine is an important amino acid for redox balance because it contains a highly reactive thiol group which imparts the ability to participate in numerous reactions. Cysteine can be synthesized from methionine and serves as a precursor to antioxidants such as glutathione and taurine. Cysteine levels, as were upstream and downstream metabolites, were lower in the Microbe and Combo groups relative to Control (Table 7). This was consistent with the overall pattern of amino acid detection. Changes in cysteine metabolites may be signals of changes in redox status, as they are precursors for glutathione synthesis.

TABLE 7

Methionine and derivatives in mouse fecal samples at time T7. Ratio of the mean peak areas for the specified metabolites in each group relative to the control group. Up or down arrows indicate whether the increase or decrease in the treament relative to the control is significant based on Welch's two-sample t-test with $p < 0.05$.

| Compound | Microbe T7 | Drug T7 | Combo T7 |
|---|---|---|---|
| Methionine | 0.43↓ | 0.95 | 0.5 ↓ |
| N-acetylmethionine | 0.56↓ | 0.99 | 0.58 ↓ |
| N-formylmethionine | 0.64 | 1.09 | 0.57 ↓ |
| Methionine sulfoxide | 0.52↓ | 0.93 | 0.6 ↓ |
| N-acetylmethionine sulfoxide | 0.76 | 0.88 | 0.64 ↓ |
| cysteine | 0.59↓ | 1 | 0.72 ↓ |
| N-acetylcysteine | 0.44↓ | 1.16 | 0.49 ↓ |
| Cysteine sulfate | 0.87 | 0.72 | 1.33 |
| cystine | 0.39↓ | 0.68 | 0.32 ↓ |
| taurine | 1.19 | 1.75 | 1.85 |
| 3-sulfo-L-alanine | 0.3 ↓ | 1.04 | 0.54 ↓ |

Carboxyethyl amino acids were elevated only following Microbe monotherapy. Interestingly, this increase was not sustained during the combination treatment (Table 8). The Drug potentially had an opposing effect on the production of these analytes. Indeed, although never reaching significance, these levels tended to be lower in the Drug T7 group relative to Control.

TABLE 8

Carboxyethyl amino acids in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$.

| Compound | Microbe T7 | Drug T7 | Combo T7 |
|---|---|---|---|
| 1-carboxyethylisoleucine | 1.56 | 0.64 | 0.89 |
| 1-carboxyethylleucine | 2.43↑ | 0.67 | 0.82 |
| 1-carboxyethylphenylalanine | 2.77↑ | 0.69 | 0.92 |
| 1-carboxyethyltyrosine | 2.52↑ | 0.8 | 1 |
| 1-carboxyethylvaline | 3.26↑ | 0.84 | 1.19 |

Figure 16:
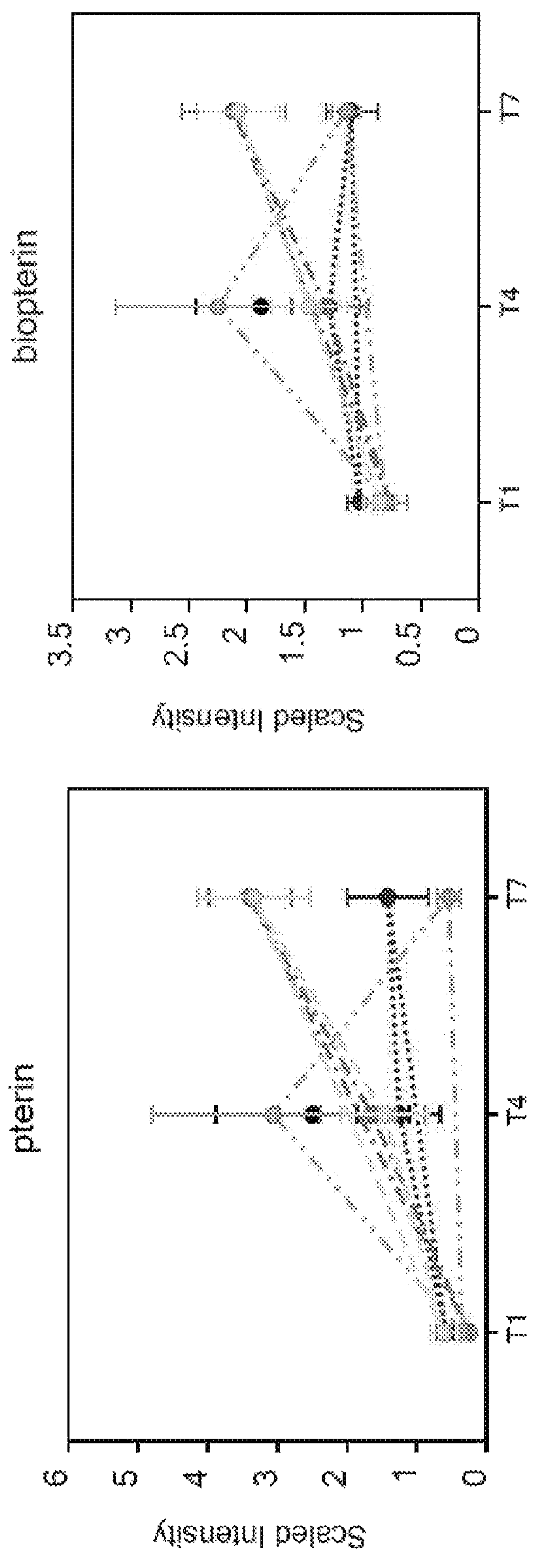

Pterins make up a group of small metabolites that serve as cofactors for various cell processes. Pterins are excreted by human urine and elevated levels have been detected when the cellular immune system is activated by diseases such as cancer (Koslinski, P., et al., Metabolic profiling of pteridines for determination of potential biomarkers in cancer diseases. Electrophoresis, 2011. 32(15): p. 2044-54). In humans, 5,6,7,8-tetrahydrobiopterin (BH4) is the most important unconjugated pterin and a cofactor for the hydroxylation of aromatic amino acids (phenylalanine, tyrosine, and tryptophan), the biosynthesis of the neurotransmitters serotonin and dopamine and the vasodilator nitric oxide (NO) (Thony, B., G. Auerbach, and N. Blau, Tetrahydrobiopterin biosynthesis, regeneration and functions. Biochem J, 2000. 347 Pt 1: p. 1-16), and for the biosynthesis of thymidine. Pterins may be host or bacterial-derived. BH4 is absorbed in the small intestine but in the colon it is decomposed by enteric bacteria (Sawabe, K., et al., Tetrahydrobiopterin in intestinal lumen: its absorption and secretion in the small intestine and the elimination in the large intestine. J Inherit Metab Dis, 2009. 32(1): p. 79-85). Pterin and biopterin are BH4 degradation products. BH4 was not detected in these samples, but the degradation products increased over time in the Drug and Control group; however, levels were stationary in the Combo group and decreased after an initial rise in the Microbe group (see FIG. 16).

The polyamines, putrescine, spermidine and spermine, are organic polycations present in all eukaryotes and are essential for cell proliferation. Polyamines have been proposed to regulate cellular activities at transcriptional, translational and post-translational levels. The main sources for polyamines in mammals are cellular synthesis, food intake and microbial synthesis in the gut. The rate limiting enzyme in polyamine biosynthesis is ODC (ornithine decarboxylase) that converts ornithine to putrescine. Spermidine is then synthesized from putrescine by spermidine synthase, and spermine from spermidine. Over the course of the study, spermidine, diacetylspermadine and N1, N12-diacetylspermine increased in the feces receiving Control, Drug or Combo treatments. Conversely, these levels remained low in the Microbe group (Table 9). Since no differences in putrescine were observed, altered spermidine synthase activity could explain these findings. Polyamines stimulate mucosal growth and impacts intestinal enzyme activity (Wang, J. Y., et al., Stimulation of proximal small intestinal mucosal growth by luminal polyamines. Am J Physiol, 1991. 261(3 Pt 1): p. G504-11). Potential bacterial sources of polyamines include species of *Bacteroides, Fusobacterium*, and *Clostridium* (Matsumoto, M. and Y. Benno, The relationship between microbiota and polyamine concentration in the human intestine: a pilot study. Microbiol Immunol, 2007. 51(1): p. 25-35).

TABLE 9

Polyamines in mouse fecal samples at time T7. Ratio of the mean peak areas for the specified metabolites in each group relative to the control group.
Up or own arrows indicate whether the increase or decrease in the treatment relative to the control is significant based on Welch's two-sample t-test with $p < 0.05$.

| Compound | Microbe T7 | Drug T7 | Combo T7 |
|---|---|---|---|
| spermidine | 0.23↓ | 1.46 | 0.75 |
| diacetylspermidine | 0.27↓ | 0.91 | 0.79↓ |
| N1,N12-diacetylspermine | 0.25↓ | 1.18 | 0.87 |

Nucleotides are the building blocks for DNA and RNA biosynthesis, and they are composed of a nitrogenous base, a five-carbon sugar, and at least one phosphate group. Nucleotides carry energy, participate in cell signaling, and are incorporated into important cofactors. Nucleotides can be synthesized de novo or recycled through salvage pathways. In energy-preserving salvage reactions, nucleosides and free bases generated by DNA and RNA breakdown are converted back to nucleotide monophosphates, allowing them to re-enter the pathways of nucleotide biosynthesis (inter-conversion). Thus, nucleotide levels may reflect epithelial cell turnover. Nucleotides tended to decline in response to the Microbe treatment. 5'-AMP, 5'-GMIP and 5'-CMIP were notable exceptions although the biological meaning of these changes remains unknown (Table 10). These nucleic monophosphates may serve as signaling molecules or reflect the degradation of nucleotides.

TABLE 10

Nucleotide synthesis, degradation, and salvage intermediates in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$

| Compound | Microbe T7 | Drug T7 | Combo T7 |
|---|---|---|---|
| Inosine | 0.51 | 1.59 | 0.88 |
| Hypoxanthine | 0.44 | 1.17 | 0.54↓ |
| Xanthine | 0.23↓ | 1.29 | 0.61 |
| Xanthosine | 0.65 | 1.31 | 0.40 |
| 2'-deoxyinosine | 0.48 | 1.16 | 0.68 |
| Urate | 0.33↓ | 1.15 | 0.91 |
| Allantoin | 1.1 | 1.07 | 0.61 |
| 1-methylhypoxanthine | 0.66 | 0.96 | 0.75 |
| AMP | 3.41↑ | 0.99 | 4.50↑ |
| 3' -AMP | 0.02↓ | 0.11 | 0.20↓ |
| Adenosine-2',3'-cyclic monophosphate | 0 ↓ | 0.01↓ | 0.04↓ |
| Adenosine | 0.07↓ | 0.65 | 0.96 |
| Adenine | 0.23↓ | 0.51↓ | 0.92 |
| 1-methyladenine | 0.27↓ | 1.24 | 0.37↓ |
| Ni-methyladenosine | 1.24 | 1.05 | 0.08 |
| 2'-deoxyadenosine 5'-monophosphate | 1.62 | 1.09 | 3.61↑ |

TABLE 10-continued

Nucleotide synthesis, degradation, and salvage intermediates in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$

| Compound | Microbe T7 | Drug T7 | Combo T7 |
|---|---|---|---|
| 2'-deoxyadenosine | 0.28↓ | 0.76↓ | 0.84 |
| 3'-GMP | 0.15 | 0.98 | 0.56 |
| Guanosine-2',3'-cyclic monophosphate | 0.13↓ | 0.68 | 0.43↓ |
| Guanosine | 0.41 | 1.73 | 0.96 |
| Guanine | 0.62 | 0.83 | 0.67 |
| 7-methylguanine | 0.53↓ | 1.18 | 0.53 |
| 8-hydroxyguanine | 0.53 | 1.12 | 0.94 |
| dGMP | 1.22 | 1 | 1.9 |
| 2'-deoxyguanosine | 0.64 | 0.92 | 0.88 |
| N-carbamoylaspartate | 0.14↓ | 0.89 | 0.25↓ |
| orotate | 0.14↓ | 0.97 | 0.29↓ |
| UMP | 1.25 | 0.84 | 1.66↑ |
| 3' -UMP | 0.29 | 0.98 | 0.89 |
| Uridine-2',3'-cyclic monophosphate | 0.13↓ | 0.59 | 0.45 |
| Uridine | 0.82 | 1.12 | 1 |
| Uracil | 0.24↓ | 1.26 | 0.55 |
| Pseudouridine | 0.14↓ | 1.16 | 0.29↓ |
| 5,6-dihydrouridine | 0.24↓ | 1.3 | 0.49 |
| 2'-O-methyluridine | 0.11↓ | 1.41 | 0.46 |
| 5-methyluridine | 0.29 | 2.28 | 0.50 |
| 2'-deoxyuridine | 0.44 | 1.29 | 0.71 |
| 3-ureidopropionate | 0.09↓ | 1.37 | 0.37 |
| Beta-alanine | 0.21↓ | 1.16 | 0.28↓ |
| 5'-CMP | 2.84↑ | 1 | 3.32↑ |
| 3'-CMP | 0.44↓ | 1.14 | 0.83 |
| Cytidine 2',3'-cyclic monophosphate | 0.07↓ | 0.4 | 0.29↓ |
| Cytidine | 0.81 | 0.87 | 1.15 |
| Cytosine | 0.56 | 0.43 | 1.39 |
| 5-methylcytidine | 0.45 | 0.93 | 0.47↓ |
| 5-methylcytosine | 0.72 | 1.15 | 0.99 |
| 2'-deoxycytidine 5'-monophosphate | 1.74 | 0.87 | 2.51↑ |
| 2'-deoxycytidine | 1.2 | 0.86 | 1.47 |
| 2'-O-methylcytidine | 0.66 | 1.17 | 0.92 |
| 5-methyl-2'-deoxycytidine | 1.06 | 0.89 | 1.11 |
| Thymidine 5'-monophosphate | 1.69 | 0.81 | 2.26↑ |
| Thymidine | 0.66 | 1.21 | 0.8 |
| thymine | 0.17↓ | 1.56 | 0.54 |
| 3-aminoisobutyrate | 0.8 | 1.31 | 0.86 |

Most dietary triacylglycerol (TAG) digestion is completed in the lumen of the small intestine. The products of TAG digestion, primarily 2-monoacylglycerols (MAG), fatty acids (FA), cholesterol, and lysophospholipids combine with bile salts, forming micelles. The lipid contents of micelles then diffuse into the enterocytes in the distal duodenum and the jejunum, whereas the bile salts are absorbed in the ileum. Within the enterocytes, TAG, cholesterol ester, and phospholipids are reformed from MAG, FA, cholesterol, and lysophospholipids. These reformed lipids are then incorporated into the lipoprotein chylomicrons, from which tissues like skeletal muscle, adipose tissue, and liver can release and take up free FA. Phospholipids were consistently elevated only in the Microbe monotherapy group (Table 11). Microbe treatment may have impacted membrane stability and potentially reflect cellular turnover. This would be consistent with changes in nucleotide levels. Interestingly, these elevations were not observed in the Combo treatment groups, suggesting that the Drug treatment may have negated this influence of Microbe exposure. In addition to dietary sources, these phospholipids could be the result of the shedding of intestinal epithelial cells.

TABLE 11

Phospholipids and related species in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$.

| Compound | Microbe T7 | Drug T7 | ComboT7 |
|---|---|---|---|
| 1,2-dipalmitoyl-GPC | 1.13 | 0.72 | 0.74↓ |
| 1-palmitoy1-2-oleoyl-GPC | 1.43 | 0.82 | 0.82 |
| 1-palmitoly-2-linoleoyl-GPC | 1.71↑ | 0.84 | 0.77 |
| 1-stearoy1-2-arachidonoyl-GPC | 0.78 | 0.88 | 0.94 |
| 1-oleoy1-2-linoleoyl-GPC | 1.95↑ | 0.82 | 0.66 |
| 1,2-dilinoleoyl-GPC | 2.21↑ | 0.80 | 0.62 |
| 1-linoleoy1-2-linolenoyl-GPC | 1.98↑ | 0.74 | 0.61 |
| 1-palmitoy1-2-linoleoyl-GPE | 1.61 | 1.03 | 1.06 |
| 1-stearoy1-2-arachidonoyl-GPE | 1.27 | 0/.81 | 1.07 |
| 1-oleoy1-2-linoleoyl-GPE | 1.61 | 0.79 | 0.77 |
| 1,2-dilinoleoyl-GPE | 2.11↑ | 0.77 | 0.6 |
| 1-palmitoy1-2-oleoyl-GPI | 3.20↑ | 0.94 | 1.19 |
| 1-palmitoy1-2-linoleoyl-GPI | 3.03↑ | 0.81 | 1.01 |
| 1-oleoyl-GPA | 0.9 | 0.85 | 0.67 |
| 1-linoleoyl-GPA | 1.54↑ | 0.83 | 1.3 |
| 1-palmitoyl-GPC | 2.71↑ | 0.88 | 1.44 |
| 2-palmitoyl-GPC | 3.89↑ | 1.01 | 2.17↑ |
| 1-stearoyl-GPC | 1.26 | 0.85 | 1.27 |
| 1-oleoyl-GPC | 2.93↑ | 1.01 | 1.66 |
| 1-linoleoyl-GPA | 3.78↑ | 0.87 | 1.54 |
| 1-lignoceroyl-GPC | 1.07 | 0.95 | 1 |
| 1-palmitoyl-GPE | 1.92↑ | 1.22 | 1.28 |
| 1-stearoyl-GPE | 0.75 | 0.86 | 1.32 |
| 2-stearoyl-GPE | 0.63 | 0.72 | 1.58 |
| 1-oleoyl-GPE | 1.78↑ | 1.16 | 1.24 |
| 1-linoleoyl-GPE | 3.22↑ | 0.89 | 1.28 |
| 1-palmitoyl-GPS | 3.41↑ | 1.83↑ | 2.48↑ |
| 1-linoleoyl-GPG | 1.11 | 1.18 | 1.27 |
| 1-palmitoyl-GPI | 3.13↑ | 0.67 | 1.33 |
| 1-stearoyl-GPI | 1.38 | 0.93 | 1.87 |
| 1-oleoyl-GPI | 2.90↑ | 0.84 | 2.92 |
| 1-linoleoyl-GPI | 3.28↑ | 0.93 | 2.68 |

Nicotinamide adenine dinucleotide ($NAD^+$) is a coenzyme that plays an essential role in energy metabolism and redox status. $NAD^+$ can be synthesized from the amino acid tryptophan through intermediates including kynurenine and quinolinate or salvaged from nicotinic acid and nicotinamide. Prokaryotic and eukaryotic $NAD^+$ synthetic pathways are similar. Metabolites involved in $NAD^+$ metabolism were lower in the Combo group at T7, and to a lesser extent the Microbe group (Table 12). Declines in $NAD^+$ metabolites in the feces may reflect retention within the colon or decreased production. Increasing $NAD^+$ levels in aged mice decreases colon degradation and increases motility (Zhu, X., et al., Nicotinamide adenine dinucleotide replenishment rescues colon degeneration in aged mice. Signal Transduct Target Ther, 2017. 2: p. 17017).

TABLE 12

Nicotinamide and related metabolites in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$.

| Compound | Microbe T7 | Drug T7 | Combo T7 |
|---|---|---|---|
| N1-methy1-4-pyridone-3-carboxamide | 0.65 | 0.89 | 0.45 |
| N'-methylnicotinate | 0.51 | 1.04 | 0.53↓ |
| 1-methylnicotinamide | 1.01 | 1.03 | 0.87 |
| Nicotinamide | 1.33 | 0.94 | 1 |
| Nicotinate ribonucleoside | 0.71 | 0.47 | 0.44↓ |

TABLE 12-continued

Nicotinamide and related metabolites in mouse fecal samples at time T7. Ratio of the mean peak areas for the specified metabolites in each group relative to the control group.
Up or down arrows indicate whether the increase or decrease in the treatment relative to the control is significant based on Welch's two-sample t-test with $p < 0.05$.

| Compound | Microbe T7 | Drug T7 | Combo T7 |
|---|---|---|---|
| Nicotinate | 0.37↓ | 1.25 | 0.52↓ |
| quinolinate | 0.68 | 1.05 | 0.65↓ |

Metabolomics data was used to determine metabolic signatures that could differentiate response to checkpoint inhibitor treatment. Of the mice receiving anti-CTLA4, responders to the treatment (R) were defined as those mice with tumor size less than 400 $mm^3$ at the end of the study (21 days from first treatment). Those with tumor size greater than 400 $mm^3$ were considered non-responders (NR). Of the 16 mice given anti-CTLA4 in the metabolomics study (Microbe and Combo groups), there were 12 responders and 4 non-responders.

High level views of the responder data demonstrate relatively low numbers of metabolites were significantly different between R and NR during the study (9% at T1, 6% at T4 and 4% at T7). However, there were clear differences in specific metabolites, though each only at a specific timepoint. Guanosine 3'-monophosphate (3'-GMP) and guanosine-2',3'-cyclic monophosphate were present in R but not detected in any NR at T1. At T4, multiple primary and secondary bile acids were elevated in the feces of R compared to NR (Table 13). Bile acids are necessary for the efficient absorption of dietary lipids. They are synthesized and conjugated in the liver and secreted into the intestine via the bile duct. Most of the bile acid pool is reabsorbed into enterohepatic circulation; however, a small percentage is excreted in the feces. Interestingly, the differences observed here seemed to be unique to taurine-conjugated bile acids. Taurine levels were not different between these groups at any timepoint; however, cysteine, a precursor to taurine was lower in R versus NR at T1. Secondary bile acids are generated by the gut microbiota, and thus differences in these metabolites may reflect differences in microbial population or metabolism. At T7, diacylglycerols (DAGs) and monoacylglycerols (MAGs) were lower in R versus NR at T7 (Table 14). The bulk of DAGs and MAGs in the colon are derived from dietary sources. Assuming the dietary intake was identical between mice included in the study, changes in these metabolites likely reflect differences in digestion and absorption of these metabolites between R and NR.

TABLE 13

Primary and secondary bile acids in mouse fecal samples at each timepoint. Ratio of the mean peak areas for the specified metabolites in responders (R) relative to non-responders (NR). Up or down arrows indicate the increase or decrease in the treatment relative to the control is significant based on Welch's two-sample t-test with $p < 0.05$.

| Compound | R/NR T1 | R/NR T4 | R/NR T7 |
|---|---|---|---|
| Taurocholate | 0.9 | 4.81 ↑ | 0.85 |
| Tauro-beta-muricholate | 0.56 | 5.34 ↑ | 1.5 |
| Taurodeoxycholate | 0.49 | 15.26 ↑ | 1.31 |
| Taurolithocholate | 0.87 | 5.95 ↑ | 1.41 |
| Taurohyodeoxycholic acid | 0.54 | 7.20 ↑ | 1.13 |

TABLE 14

Monoacylglycerols and diacylglycerols in mouse fecal samples at each timepoint. Ratio of the mean peak areas for the specified metabolites in responders (R) relative to non-responders (NR). Up or down arrows indicate the increase or decrease in the treatment relative to the control is significant based on Welch's two-sample t-test with $p < 0.05$.

| Compound | R/NR T1 | R/NR T4 | R/NR T7 |
|---|---|---|---|
| 1-myristoylglycerol | 0.91 | 0.71 | 0.73 |
| 1-palmitoylglycerol | 0.96 | 1.11 | 0.61 ↓ |
| 1-oleoylglycerol | 0.88 | 1.46 | 0.47 ↓ |
| 1-linoleoylglycerol | 0.94 | 2.03 | 0.41 ↓ |
| 1-linolenoylglycerol | 1.04 | 2.24 | 0.44 ↓ |
| 2-palmitoylglycerol | 0.91 | 1.05 | 0.63 ↓ |
| 2-oleoylglycerol | 0.99 | 1.2 | 0.47 ↓ |
| 2-linoleoylglycerol | 0.98 | 1.47 | 0.41 ↓ |
| 1-heptadecenoylglycerol | 0.93 | 1.69 | 0.52 ↓ |
| Palmitoyl-linoleoyl-glycerol | 0.89 | 1.36 | 0.63 ↓ |
| Oleoyl-oleoyl-glycerol | 0.82 | 1.09 | 0.63 ↓ |
| Oleoyl-linoleoyl-glycerol | 0.84 | 1.33 | 0.66 ↓ |
| Linoleoyl-lineoyl-glycerol | 0.84 | 1.54 | 0.63 ↓ |
| Linoleoyl-linolenoyl-glycerol | 0.91 | 1.61 | 0.60 ↓ |

Metabolomics Performed on Fecal Samples

In a separate experiment, metabolomics was performed on fecal samples taken from mice treated with anti-CTLA-4 only and the group treated with anti-CTLA-4 in combination with microbe mix 2. In the tables and figures that follow, these are referred to as the Drug (D) and Drug+Microbe (D+M) groups. Samples were processed from timepoint 2 (T2), 48 hours after the first treatment dose; timepoint 4 (T4), 10 days from start and 48 hours after the $3^{rd}$ treatment dose; and timepoint 6 (T6), 17 days from start and 48 hours after the$_5$th treatment dose. All mice in the study were classified as responders or non-responders to CTLA-4 treatment. responders to the treatment (R) were defined as those mice with tumor size less than 400 $mm^3$ at the end of the study (21 days from first treatment). Those with tumor size greater than 400 $mm^3$ were considered non-responders (NR). Of the 16 mice given anti-CTLA4 in the study, there were 8 responders and 8 non-responders.

As in the above example, instrument variability was determined by calculation of the median relative s.d. (RSD) for the standards that were added to each sample before injection into the mass spectrometers (median RSDs were determined to be 3%). Overall process variability was determined by calculating the median RSD for all endogenous metabolites (i.e., noninstrument standards) present in 90% or more of the pooled technical-replicate samples (median RSD=10%, n=802 metabolites).

Several metabolites were differentially present in the R and NR groups, as summarized in Table 19. Proline is consistently elevated in NR samples but only significantly at the mid-time-point. Correlation analysis shows that, although proline is the sentinel signal, the top correlating metabolites to its abundance across the samples are primarily other amino acids. Hence, amino acids generally increase in NR samples at the mid-point. The increase observed in the NR samples in the feces reflects a difference in the potential availability for the tumor for anabolic processes such as protein synthesis. Also elevated in responder samples were particular sugars, mannose and myo-inositol, and trace amines. Mannose (an epimer of glucose) and myo-inositol are both monosaccharides that can be made from glucose and they are abundant in the diet. Mannose is most prominently known for its role in posttranslational modification of proteins through N-linked glycosylation while inositol is most known for its role as a second messenger in the form of inositol phosphates. However, the increase in abundance in the feces of NR animals most plausibly indicates differences in either the use or potential use of these sugars as carbon sources by microbes within the lumen of the intestine. Trace amines such as tyramine, tryptamine and phenethylamine are best known for having neuroactive activity. They are present in the diet and can be produced by the microbiota. All three were detected in this study but only phenethylamine was identified as significant for differences between R and NR groups. These amines act through trace amine-associated receptors (TAARs). TAAR1 may regulate immune responses through leukocyte differentiation and activation. So, the elevation in phenylethylamine in NR samples could reflect the potential to modulate the immune response.

Steroids were more abundant in the responder group, particularly at the last timepoint. Steroids include progestogens, androgens, estrogens, glucocorticoids, and mineralocorticoids, and they have vital roles in coordinating changes in metabolism, inflammation, and immune function. Since the steroids detected in this data all change in a similar manner and are from 3 of these 5 classes of steroids, a general change in steroid metabolism—perhaps at the earliest steps (cholesterol conversion to pregnenolone) is most likely.

TABLE 19

Select metabolites with different abundance in responders and non-responders to the anti-CTLA-4 treatment. Ratio of the mean peak areas for the specified metabolites in responders (R) relative to non-responders (NR) are shown. Up or down arrows indicate the increase or decrease in the treatment relative to the control is significant based on Welch's two-sample t-test with $p < 0.05$.

| Compound | R/NR T2 | R/NR T4 | R/NR T6 |
|---|---|---|---|
| Phenethylamine | 0.79 | 0.49 ↓ | 0.77 |
| Proline | 1.08 | 0.58 ↓ | 0.66 |
| Mannose | 1.02 | 0.82 | 0.47 ↓ |
| Myo-inositol | 1.1 | 0.62 ↓ | 0.64 |
| 5alpha-pregnan-3beta,20alpha-diol disulfate | 0.94 | 0.77 | 2.88 ↑ |
| 5alpha-pregnan-diol disulfate | 0.72 | 0.88 | 2.67 ↑ |
| pregnanolone/allopregnanolone sulfate | 1.28 | 1.37 | 3.93 ↑ |
| 5alpha-androstan-3beta,17beta-diol disulfate | 0.85 | 0.87 | 2.27 ↑ |

Several metabolites were differentially abundant in the R and NR groups, but only when comparing just those mice treated with D+M. These are listed in Table 20, and include several fatty acids and ceramides as well as serotonin. Serotonin is a key neurotransmitter in the brain-gut axis and significant amounts of peripheral serotonin is synthesized from tryptophan in the gastrointestinal tract by enterochromaffin cells. Various studies have shown that the production of serotonin in the gut is highly influenced by the presence of microbes and their metabolic products. Serotonin trends higher for the non-responder group. The metabolite that serotonin is derived from—tryptophan—does not correlate with the pattern of serotonin change, indicating that the serotonin change is not simply due to changes in tryptophan levels. Tryptophan can also be metabolized into the anti-inflammatory metabolite kynurenine which naturally then has an immunosuppressive role. However, the steady state pools in these fecal samples for kynurenine are unchanged between the R/NR groups.

Certain bile acids also changed between microbe R and NR groups; in particular, minor secondary bile acids that are the products of bacterial metabolism of primary bile acids. Bile acids such as lithocholate (LCA) are reduced with responders and slightly elevated with non-responders. Thus, since these bile acids are by-products of microbial activity, their changes represent the clearest indication of differential microbe activity between the R and NR groups. How this precisely impacts response is not clear but LCA is known to be biologically potent. For example, it is the most powerful known endogenous agonist for a GPCR that regulates vast aspects of metabolism—TGR5. And, bile acids such as LCA also act on receptors involved in the innate immune response—G protein-coupled bile acid receptor 1 (GPBAR1 or Takeda G-protein receptor 5) and the Farnesoid-X-Receptor (FXR). GPBAR1 and FXR are reported to modulate the liver and intestinal innate immune system and therefore contribute to tolerance.

TABLE 20

Select metabolites with different abundance in responders and non-responders to anti-CTLA-4 and microbe mix 2 combination treatment. Ratio of the mean peak areas for the specified metabolites in responders (R) relative to non-responders (NR) are shown, just for the D + M group. Up or down arrows indicate the increase or decrease in the treatment relative to the control is significant based on Welch's two-sample t-test with $p < 0.05$.

| Compound | R/NR T2 | R/NR T4 | R/NR T6 |
|---|---|---|---|
| Serotonin | 0.88 | 0.8 | 0.6 ↓ |
| Stearate (18:0) | 1.09 | 1.41 ↑ | 1.03 |
| Arachidate (20:0) | 1.05 | 1.44 ↑ | 1.04 |
| Behenate (22:0) | 0.93 | 1.53 ↑ | 1.1 |
| Nervonate (24:1n9) | 1.01 | 1.75 ↑ | 1.18 |
| 1-palmitoyl-2-arachidonoyl-GPC (16:0/20:4n6) | 0.68 | 2.73 ↑ | 1.22 |
| 1-stearoyl-GPS (18:0) | 0.73 | 2.77 ↑ | 1.09 |
| 1-stearoyl-GPG (18:0) | 2.56 ↑ | 2.23 ↑ | 1.46 |
| 1-stearoyl-GPI (16:0) | 0.66 | 1.8 ↑ | 1.11 |
| 1-palmitoyl-galactosylglycerol (16:0) | 1.33 | 3.18 ↑ | 1.04 |
| Sphingadienine | 1.25 | 0.65 | 0.65 |
| Ceramide (d18:1/14:0, d16:1/16:0) | 1.13 | 1.25 | 0.84 |
| Glycosyl-N-palmitoyl-sphingosine (d18:1/16:0) | 0.64 | 0.51 | 0.4 |
| Eicosanoylsphingosine (d20:1) | 1.25 | 0.94 | 0.7 |
| Pregnenediol disulfate | 1.11 | 1.39 | 1.15 |
| 5alpha-pregnan-3beta, 20alpha-diol disulfate | 1.52 | 2.03 ↑ | 2.69 ↑ |
| 5alpha-pregnan-diol disulfate | 1.01 | 1.71 | 2.64 ↑ |
| Pregnanolone/allopregnanolone sulfate | 2.54 | 4.19 | 3.3 ↑ |
| 5alpha-androstan-3beta, 17beta-diol disulfate | 1.41 | 1.22 | 2.03 ↑ |
| 6-oxolithocholate | 0.97 | 0.41 | 0.51 |
| Isohyodeoxycholate | 1.39 | 0.61 | 0.48 |
| nicotinamide | 1.28 | 2.38 ↑ | 1.81 |

The strongest signal in the data is from microbe treatment (G8 D+M) independent of R/NR. Despite not correlating with response, the changes induced solely by the microbe could provide insights into how the microbe treatment works. Compounds with increased concentration as a result of microbe treatment include those derived from aromatic catabolism, histamine side products, acylglycines, creatine, and NAD+ catabolites. Table 21 indicates the ratio of these metabolites in the D+M treatment group relative to the D group.

Many metabolites that typically arise from microbial catabolism of aromatic amino acids (e.g., p-cresol sulfate, p-cresol glucuronide, and 4-hydroxyphenyl acetate) and benzoate metabolites (e.g., benzoate, hippurate, catechol sulfate, etc.) are increased by microbe treatment. Benzoate metabolites are simple carboxylic acids produced from the microbial degradation of dietary aromatic compounds in the intestine, such as polyphenols, purines and aromatic organic acids. There is precedent for several aromatic amino acid metabolites having biological activity. For example, tryptophan metabolites such as kynurenate, indole, indoxyl sulphate, and indolepropionate, are ligands for the aryl hydrocarbon receptor (AhR). The AhR mediates tumor-promoting effects of dioxin and AhR signaling is also important for the immune response at barrier sites. These examples illustrate the potential for these types of metabolites to have important biological functions, particularly given that many are at fairly high levels in the blood.

While histamine itself is not elevated, many side-products and metabolites of it such as 1-methylhistamine and 1-ribosyl-imidazoleacetate are. This may be important since histamine is involved in inflammatory responses and gut physiology. Histamine may also have specific microbe-induced influences in specific tumors. For example, it was shown that administration of histidine decarboxylase (HDC) from *Lactobacillus reuteri* resulted in luminal histamine production of Hdc−/− mice and an associated decrease in the number and size of colon tumors. If the microbe treatment has the potential to alter histamine, it may have similar effects as those described in colon tumors.

Several acylglycines are recognized in biology to have important biological properties. Consequently, they are sometimes described as having "endocannabinoid-like" properties. N-arachidonoyl glycine (NAGly) is probably the best studied acylglycine and has been described to influence things such as inflammation, analgesia and, vasorelaxation. In these data, two acylglycines (3,4-methylene heptanoylglycine and picolinoylglycine) increased in the microbe treated group. However, these acylglycines are probably distantly related to versions like NAGly and there are many missing values, likely contributing to the large fold changes. 3,4-methylene heptanoylglycine is glycine conjugated to a short (C7) unsaturated acyl chain, in contrast to long fatty acyl chains that comprise most canonical acylglycines such as the C20-bearing NAGly. Picolinoylglycine is a pyridine-like ring structure conjugated to glycine. Hence, these molecules are highly unique; given the biosynthetic capacity of the microbiome, these unconventional acylglycines may be synthesized by microbes for some biological function. For example, a recent study revealed that one commensal bacteria effector gene family (Cbeg12) encoded enzymes for the production of the acylglycine N-acyl-3-hydroxypalmitoyl-glycine (commendamide).

Creatine is a key metabolite for cellular energy homeostasis in highly dynamic tissues such as brain, skeletal muscle and the gut. Creatine facilitates channeling of high energy phosphates (via phosphocreatine) to maintain ATP generation. In addition to creatine, several of its metabolites are also elevated by microbe treatment. Relevant to the effects in the gut, creatine supplementation is reported to maintain intestinal homeostasis and protect against colitis through rapidly replenishing ATP within colonic epithelial. Notably, gut microbiota express specific enzymes that can mediate creatine and creatinine breakdown.

Catabolites of NAD+ and/or nicotinamide (NAM) are increased with microbe treatment. NAD+ has numerous critical cellular functions—a coenzyme for energy metabolism and redox status, holistic regulation of metabolism as a substrate for sirtuins, and in DNA repair through Poly(ADP-ribose) polymerases (PARPs). In this study, the methylated metabolites of NAM increased: Ni-methyl-2-pyridone-5-carboxamide (2py) and N1-methyl-4-pyridone-3-carboxamide (4py) are increased by microbe treatment, suggesting an upregulation of NAD+/NAM catabolism. 2py and 4py are produced through methylation of NAM by Nicotinamide N-methyltransferase (NNMT) followed by aldehyde oxidase (Aox) oxidation. These reactions have generally been regarded as clearance pathways as 2py and 4py are excreted in the urine. However, recent studies suggest that the products of this pathway may possess biological activity. For example, pharmacological doses of N1-methylnicotinamide (MNAM) is reported to inhibit cyclooxygenase 2 (COX2) and endothelial nitric oxide synthase (eNOS). This may have relevance in an immunotherapy context as inhibition may help combat COX-2 immune evasion.

TABLE 21

Select metabolites with different abundance in mice treated with microbe mix 2. Ratio of the mean peak areas for the specified metabolites in the D + M group compared to the D group is shown. Up or down arrows indicate the increase or decrease in the treatment relative to the control is significant based on Welch's two-sample t-test with $p < 0.05$.

| Compound | D + M/D T2 | D + M/D T4 | D + M/D T6 |
|---|---|---|---|
| Phenol sulfate | 1 | 55.66 ↑ | 22.17 |
| N-formylphenylalanine | 1.25 | 0.64 ↓ | 0.61 ↓ |
| 4-hydroxyphenylacetate sulfate | 0.96 | 46.99 ↑ | 8.24 ↑ |
| Kynurenate | 0.57 | 3.03 | 1.86 |
| N-formylanthranilic acid | 1.1 | 5.59 ↑ | 1.74 |
| Xanthurenate | 1.04 | 5.43 | 3.04 |
| Serotonin | 1.07 | 0.81 | 0.92 |
| 5-hydroxyindoleacetate | 0.74 | 1.65 | 2.02 |
| Tryptamine | 1.78 ↑ | 1.21 | 1.06 |
| Indole-3-carboxylate | 0.93 | 0.51 ↓ | 0.7 |
| Indoleacetylglycine | 1 | 71.3 ↑ | 5.71 ↑ |
| 3-indoxyl sulfate | 1 | 44.11 | 47.76 |
| Hippurate | 1.31 | 96.34 ↑ | 11.88 |
| Benzoate | 1.47 | 2.76 | 2.32 ↑ |
| 4-hydroxybenzoate | 0.93 | 1.83 ↑ | 0.97 |
| Catechol sulfate | 1 | 4.01 | 4.29 ↑ |
| Imidazole lactate | 0.7 | 2.42 | 1.41 |
| Histamine | 1.25 | 1.09 | 0.82 |
| 1-methylhistamine | 0.61 | 8.99 ↑ | 3.94 |
| 1-methyl-4-imidazoleacetate | 1.06 | 8.52 | 3.13 |
| 1-methyl-5-imidazoleacetate | 1.07 | 0.6 | 0.92 |
| 1-ribosyl-imidazoleacetate | 1 | 27.27 ↑ | 5.14 |
| 3,4-methylene heptanoyl-glycine | 1 | 16.15 ↑ | 4.83 |
| picolinoylglycine | 1 | 24.6 ↑ | 5.78 |
| Guanidinoacetate | 0.5 | 37.6 ↑ | 9.04 |
| Creatine | 0.47 | 16.4 ↑ | 2.92 |
| Creatinine | 0.41 | 15.91 ↑ | 4.88 |
| 4-guanidinobutanoate | 1.66 | 4.95 ↑ | 3.71 |
| Nicotinate | 1.93 | 0.91 | 0.69 |
| Nicotinate ribonucleoside | 1.28 | 1.37 | 0.5 |
| Nicotinic acid mononucleotide | 1.39 | 1.22 | 0.59 |
| Nicotinamide | 1.43 | 0.78 | 1.16 |
| Nicotinamide ribonucleotide | 0.76 | 0.82 | 0.89 |
| Nicotinamide riboside | 2.06 | 1.2 | 1.03 |
| 1-methylnicotinamide | 1.05 | 2.48 | 12.05 |
| Trigonelline (N'1-methylnicotinate) | 0.8 | 10.26 ↑ | 2.28 |
| N1-methy1-2-pyridone-5-carboxamide | 0.64 | 4.65 ↑ | 3.11 |
| N1-methy1-4-pyridone-3-carboxamide | 0.8 | 9.25 ↑ | 3.67 |

Example 7—Patient Data Collection from Clinical Trials

Eligible patients were selected from those undergoing immunotherapy treatment as follows: melanoma patients receiving Nivolumab and Ipilimumab; head/neck and non-small cell lung cancer patients receiving PD-1 monotherapy and selected by their PD-L1 and TMB status. Each patient provided stool samples using the BIOCOLLECTIVE™ (BioCollective®) kit (see e.g., https://www.thebiocollective-.com/) and cheek swabs of the oral biome. Urine, Blood and plasma samples were also taken by healthcare personnel within 1-2 days of the stool samples. Samples were kept on ice or at 4 deg. C. until processed. Whole blood is collected into an EDTA tube. Plasma is isolated from the blood by centrifugation at 1000×g for 10 minutes, followed by centrifugation at 2000×g for 10 minutes. Three timepoints were taken for each patient, corresponding to 1 week prior to Cycle 1 start, on treatment at Cycle 2 Day 1 (approximately 2-3 weeks on treatment), and at the time of initial on-treatment scan (8-12 weeks on treatment). Urine, oral and fecal samples are processed using the same procedures as the mouse fecal samples described above.

Figure 11:
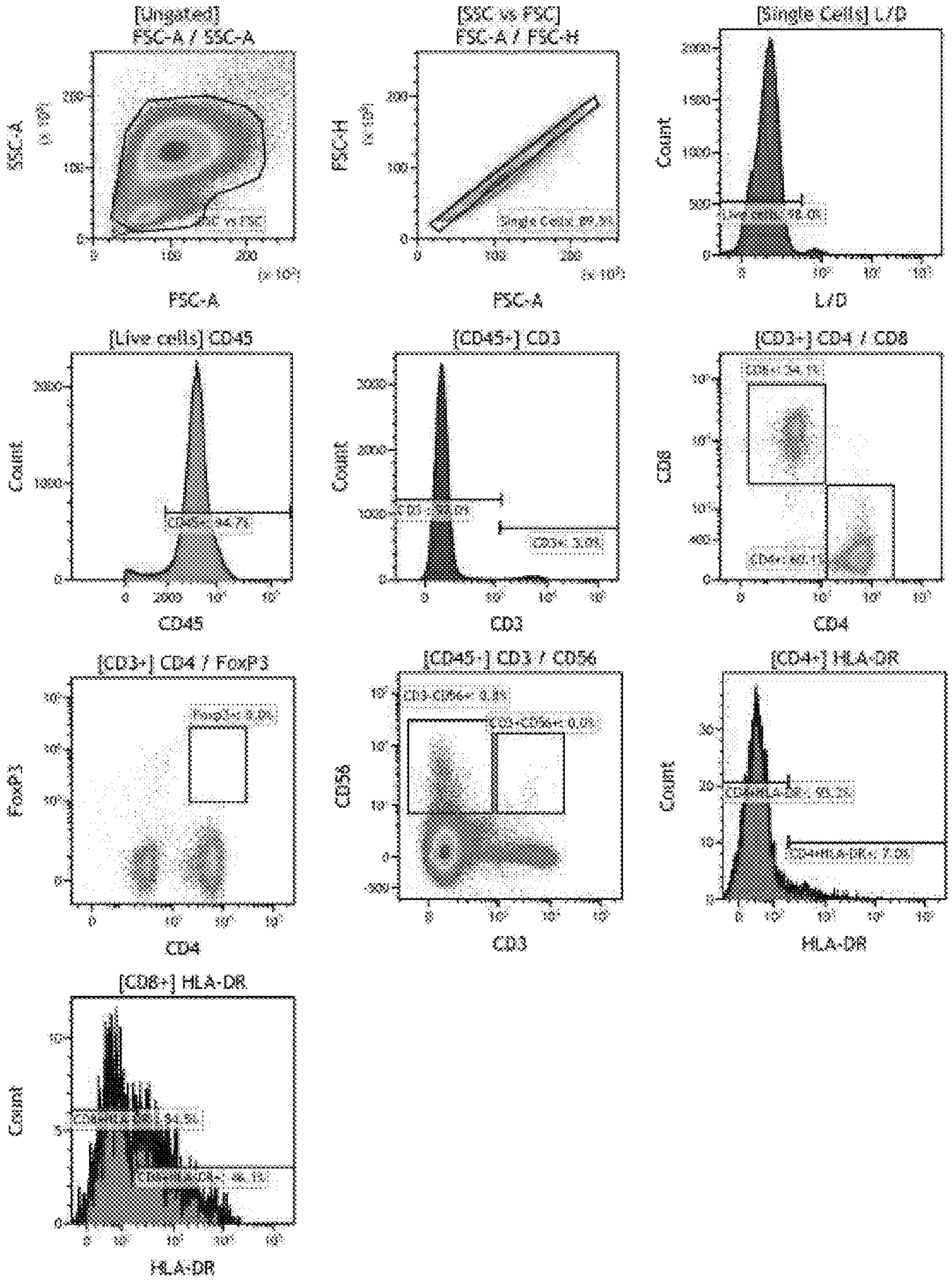
FIG. 11 graphically illustrates exemplary flow cytometry analysis of peripheral blood samples from a patient undergoing immunotherapy are shown, as described in Example 7, below.
Figure 11:
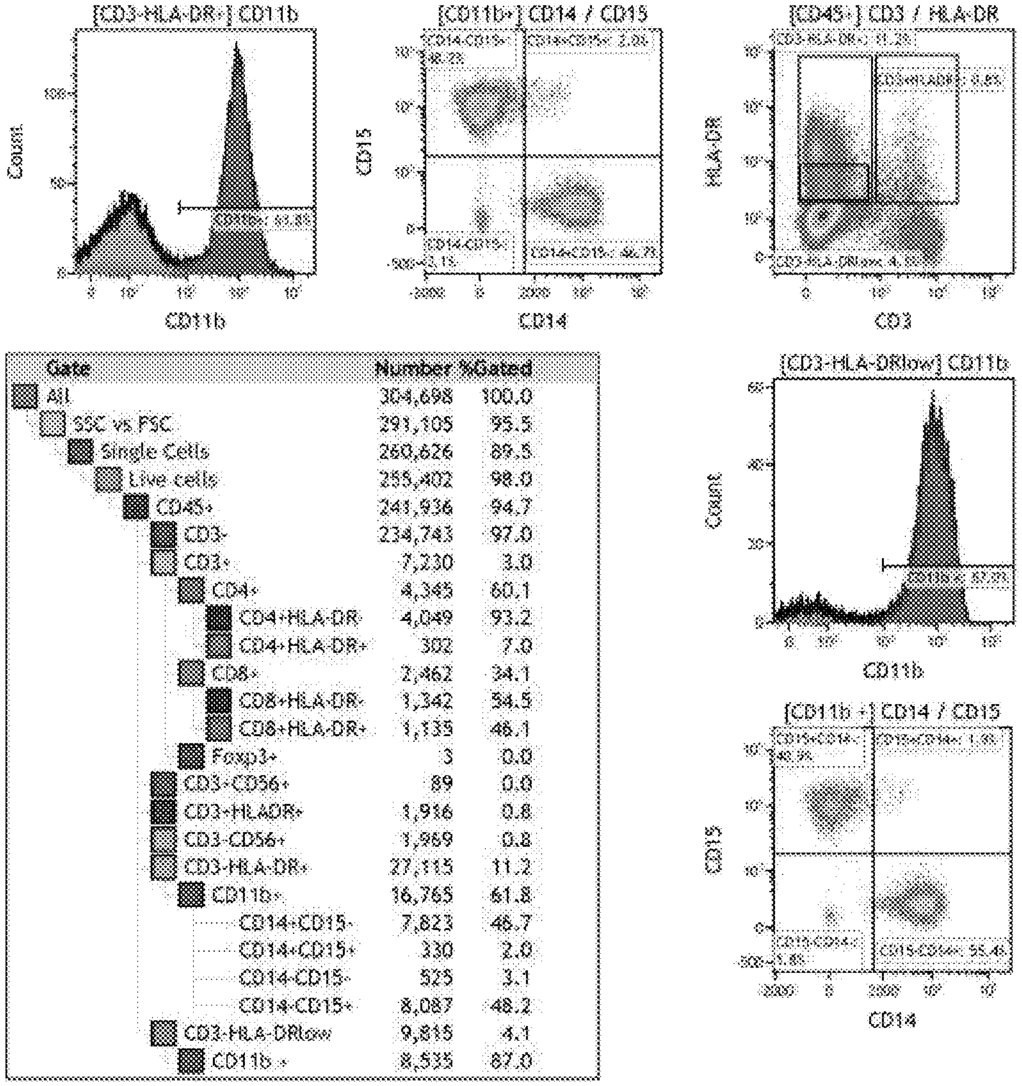
Figure 13:
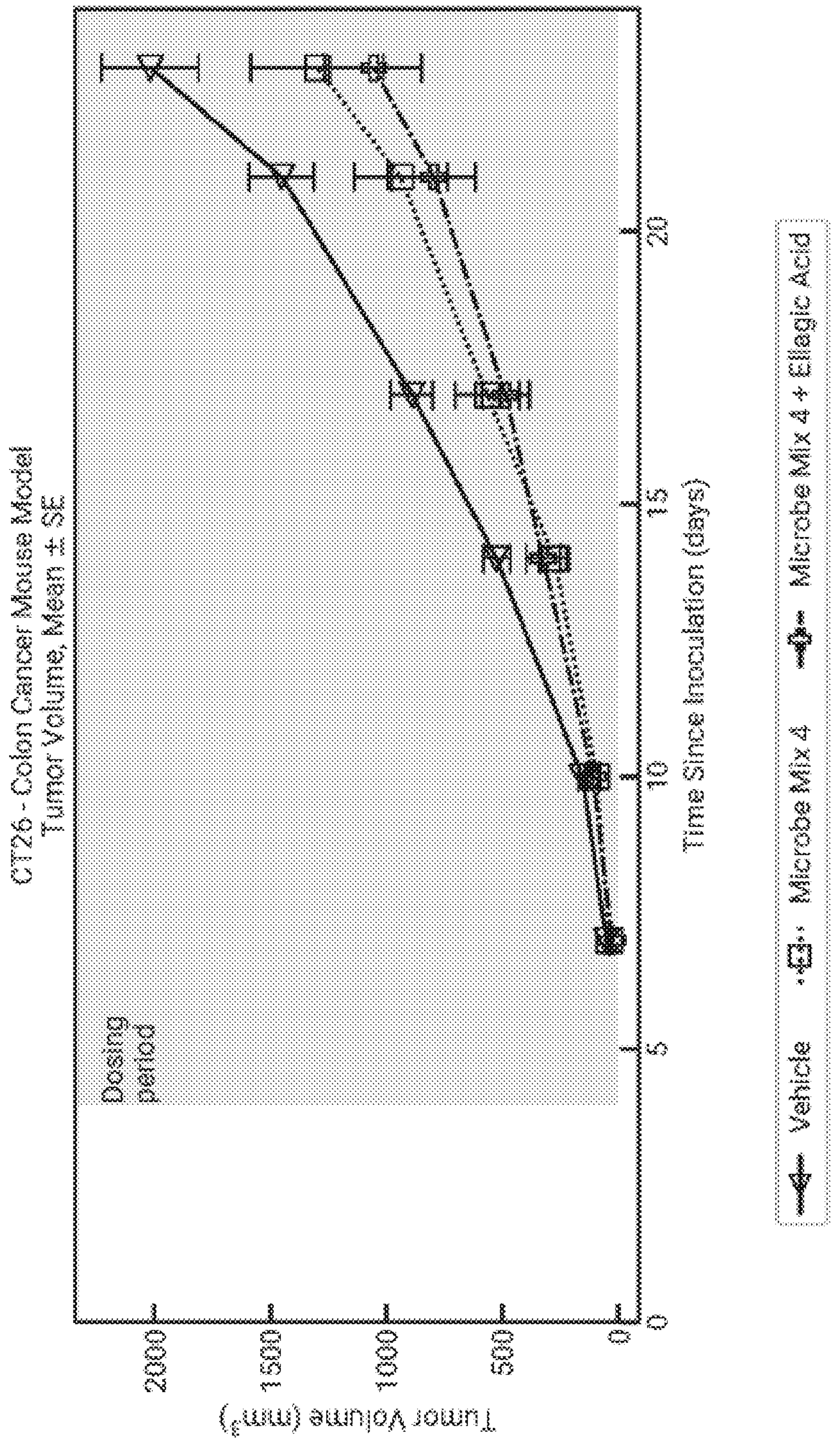
FIG. 13 graphically illustrates data from studies where mice inoculated with CT-26 colon cancer cells were treated with microbial mix 4 and prebiotic (ellagic acid) therapy, the data showing that the prebiotic therapy (ellagic acid) with microbial mix 4 had minimal tumor growth in contrast to the other groups, tumor volume is shown as a function of time since tumor inoculation, as described in Example 18, below FIG. 14 graphically illustrates flow cytometry data from a immune-phenotyping of mice subjected to cancer receiving the different microbial treatments, where measurements were conducted on both peripheral blood and on the tumor itself, with stains for various cell surface markers, where final tumor volume is a function of CD3+ proportion in CD45 cells (left image) or CD4 to CD8 ratio in CD3+ cells (right image), as discussed in detail in Example 18, below.
Figure 14:
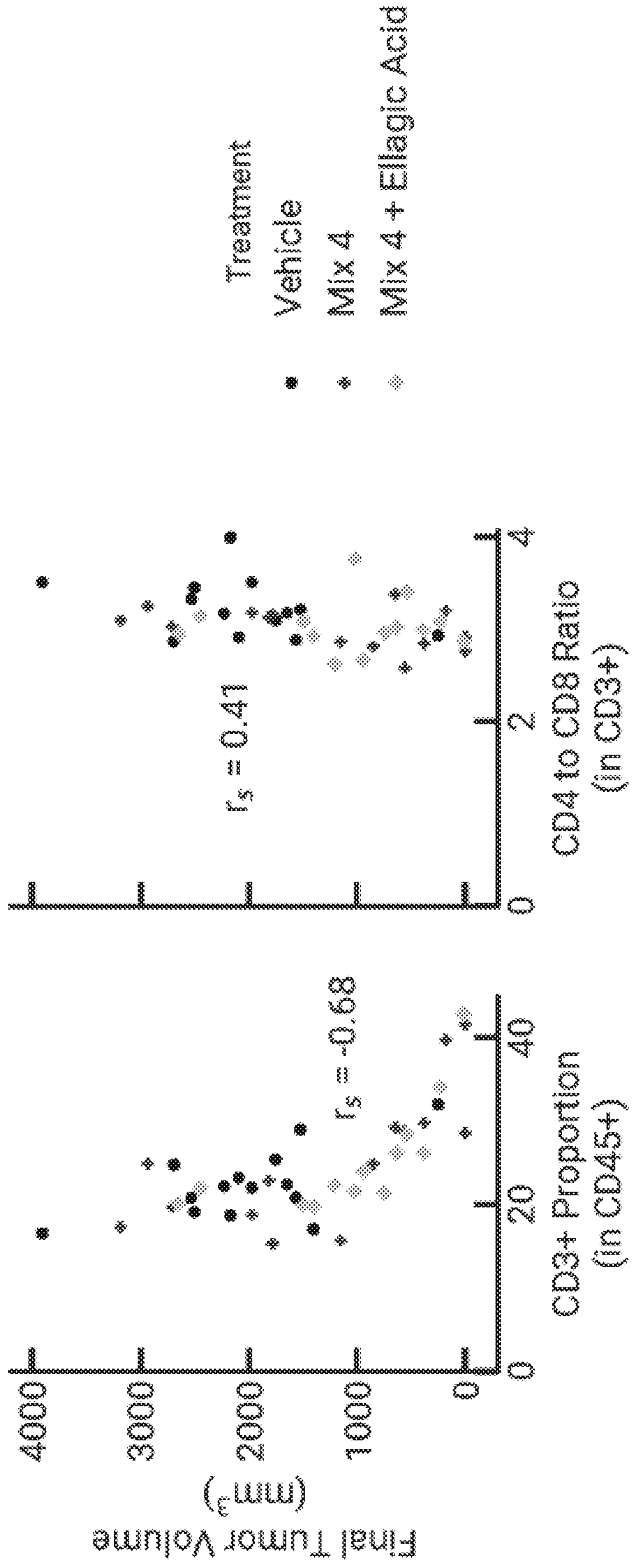

Flow cytometry analysis of peripheral blood can provide a non-invasive immune profile of the patients on study (Showe et al. Cancer Res. 2009 Dec. 15; 69(24): 9202-9210). The peripheral blood immuno-profile evaluation was performed on blood samples collected prior to and after the dosing with the immunotherapy. Phenotypic markers of lymphocyte subpopulations and regulatory T cells (Tregs) was evaluated using flow cytometry with populations gated to include CD3, CD4, CD8, CD25, CD45 and FoxP3-expressing cells using antibodies to each cell type (BD Biosciences). Peripheral blood cells are stained with Live/Dead violet dye (Invitrogen, Carlsbad, CA) to gate on live cells. Data is acquired on an LSR II™ flow cytometer (BD Biosciences) and analyzed with FLOWJO™ software (Tree-Star, Ashland, OR). Exemplary flow cytometry analysis of peripheral blood samples from a patient undergoing immunotherapy are shown in FIG. 11.

Figure 22:
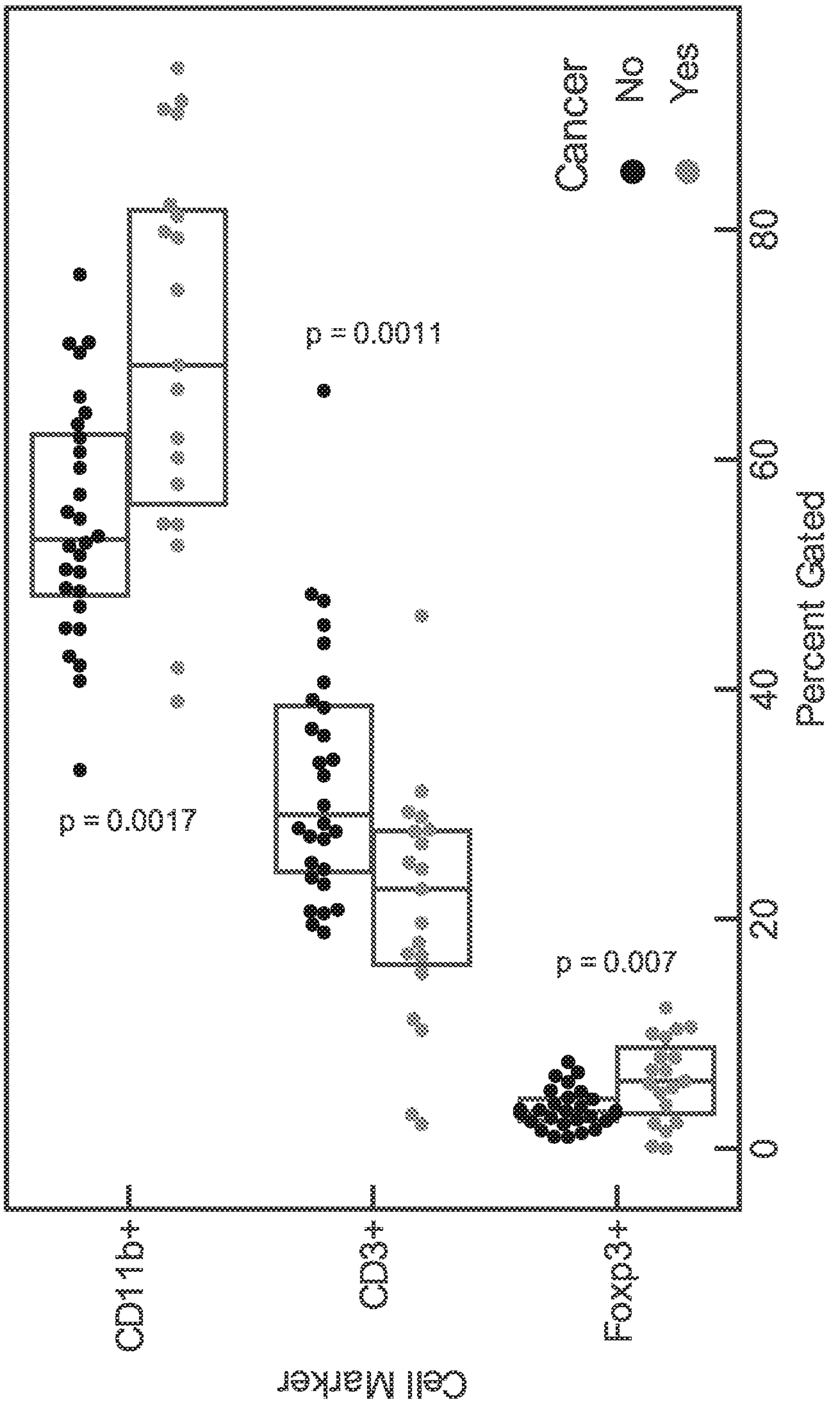
FIG. 22 graphically illustrates flow cytometry data from immune-phenotyping blood samples obtained from human subjects with and without cancer. The resulting gated percentages are plotted for different cell markers. P values are computed using the Mann-Whitney U test; as discussed in detail in Example 7, below.
Figure 23A:
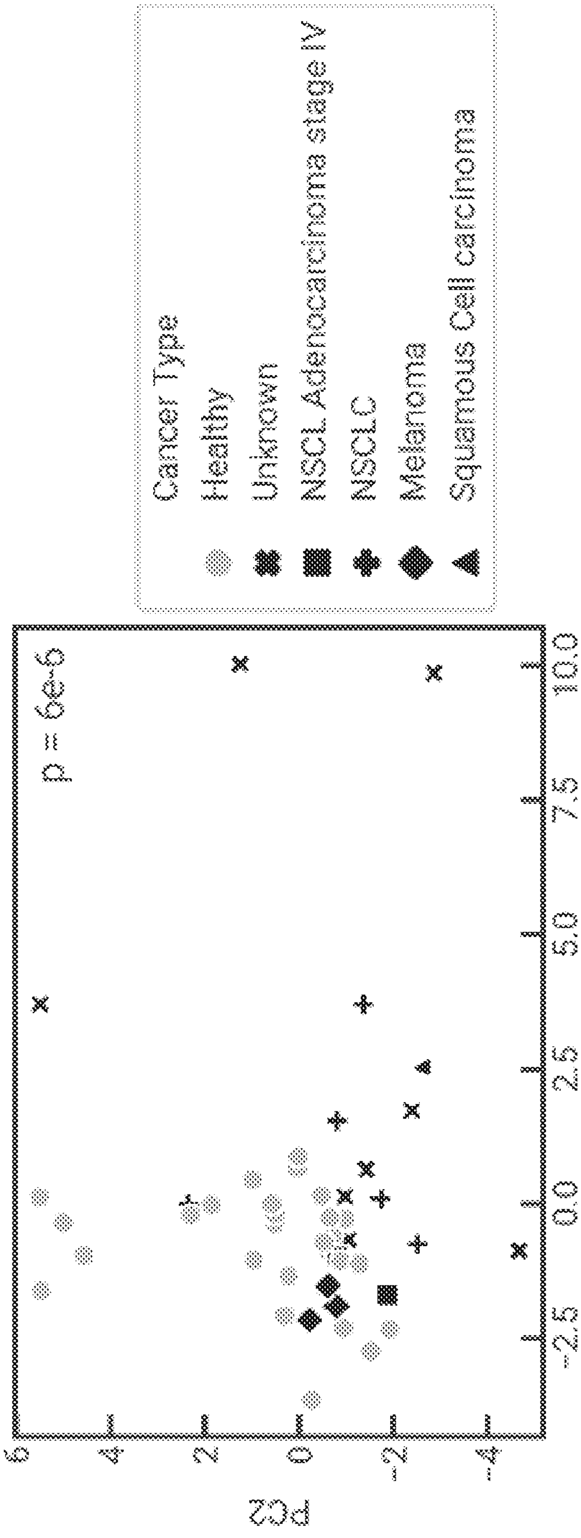
FIG. 23A graphically illustrates principal component analysis of flow cytometry data from immune-phenotyping blood samples obtained from human subjects with and without cancer. The first two principal components are plotted. The P value is computed using permutational multivariate analysis of variance (PERMANOVA); as discussed in detail in Example 7, below.
Figure 43:
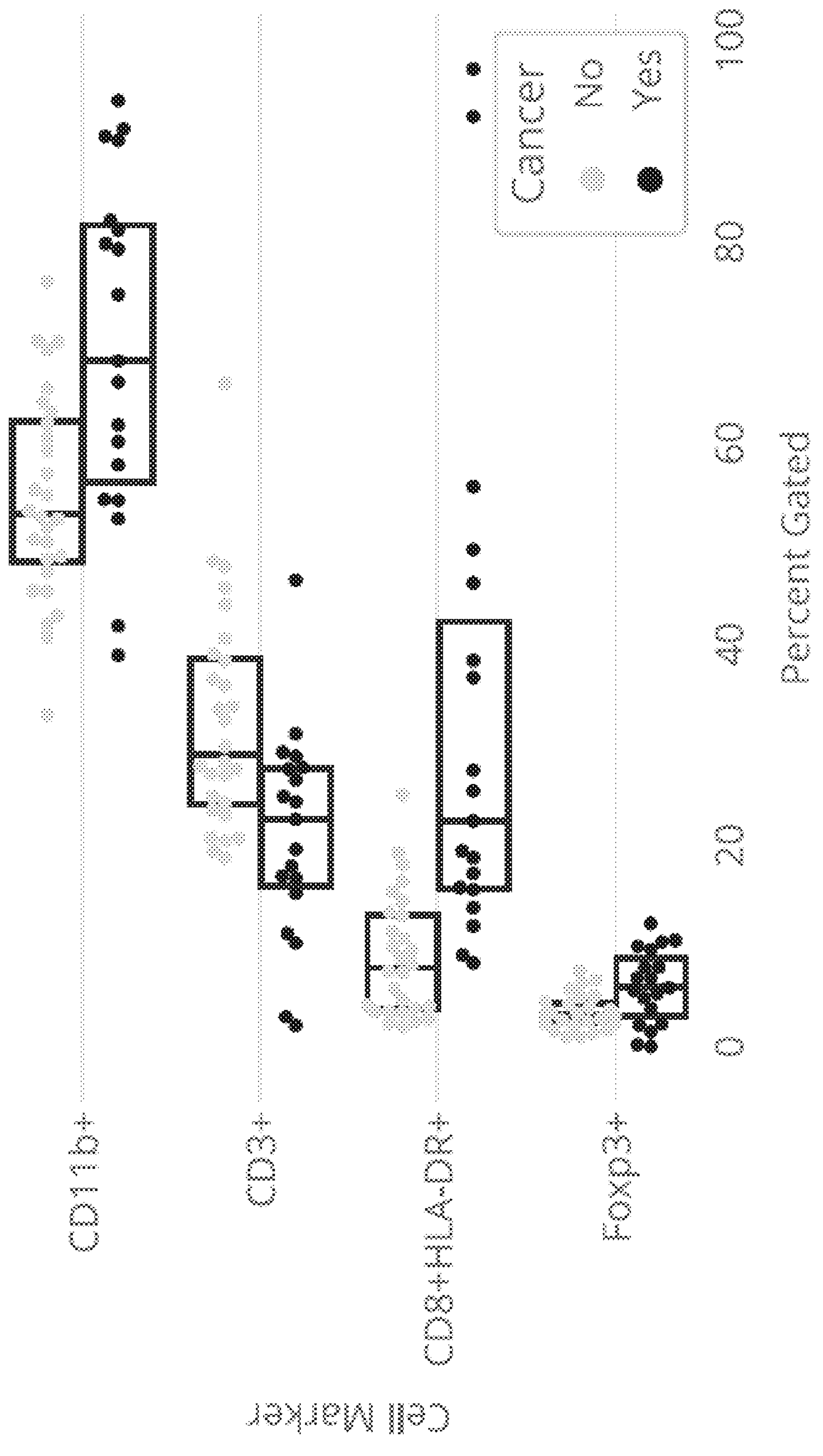
FIG. 43 graphically illustrates flow cytometry data from immune-phenotyping 47 blood samples obtained from human subjects with and without cancer; as discussed in detail in Example 7, below.
Figure 44:
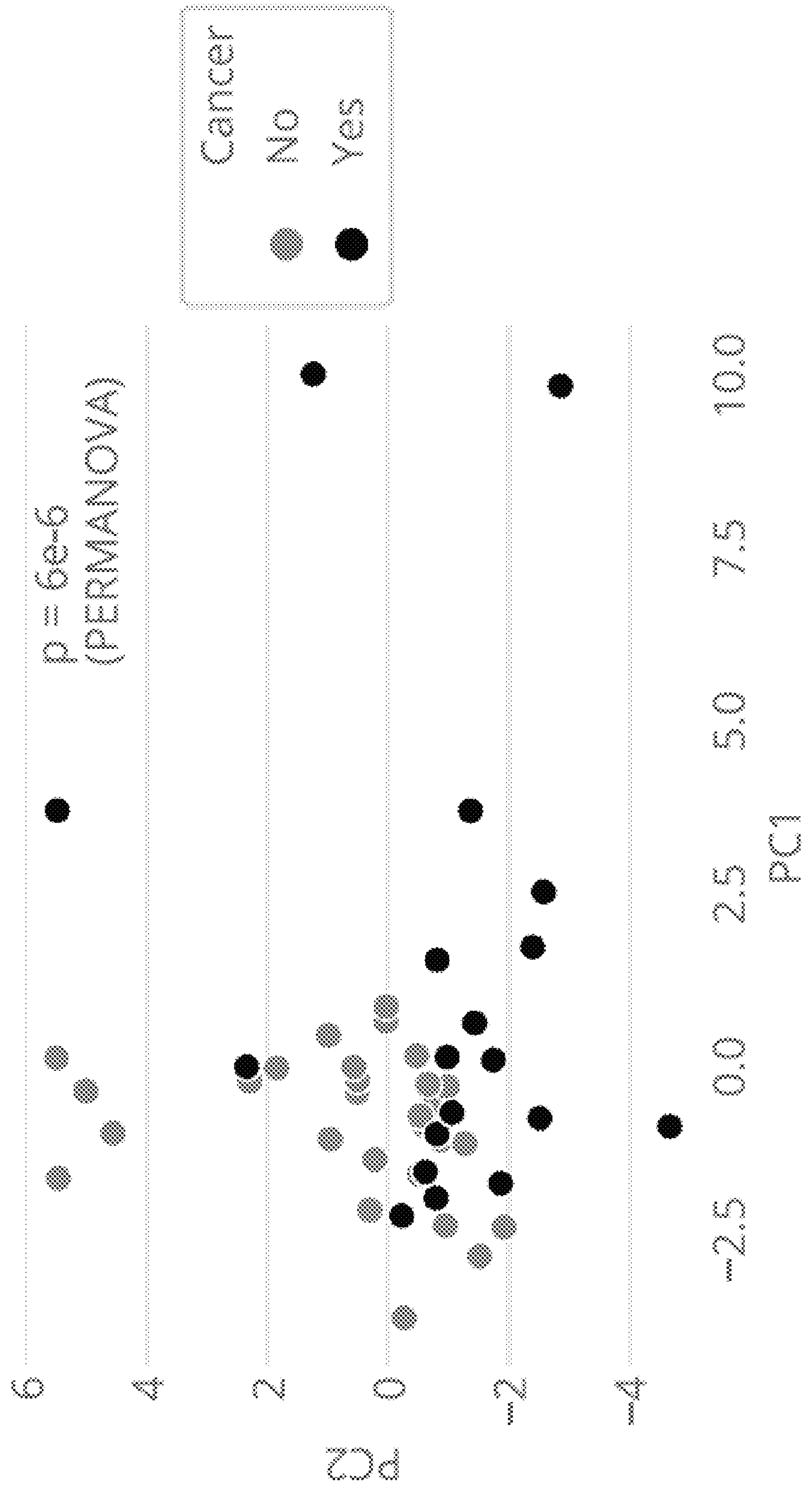
FIG. 44 graphically illustrates principal component analysis of flow cytometry data from immune-phenotyping blood samples obtained from human subjects with and without cancer. The first two principal components are plotted. The P value is computed using permutational multivariate analysis of variance (PERMANOVA); as discussed in detail in Example 7, below.

Flow cytometry was performed on blood samples obtained from human subjects with (19) and without cancer (28). The resulting gated percentages are plotted for different cell markers. For CD3, Foxp3, CD8+HLA-DR+ and CD11b, statistically differences are observed between the cancer and non-cancer populations as shown in FIG. 22 and FIG. 43. CD3 (general T cells) is depleted and Foxp3 (T regulatory cells) and CD11b+(leukocytes) are enriched in the cancer population. P values are computed using the Mann-Whitney U test. Principal component analysis was also conducted on the same data set where the gated percentages are mean and standard deviation scaled. The first two principal components are plotted as shown in FIG. 23 and FIG. 44. A statistically significant difference is observed between the cancer and control populations in the scaled data. The P value is computed using permutational multivariate analysis of variance (PERMANOVA).

Figure 50:
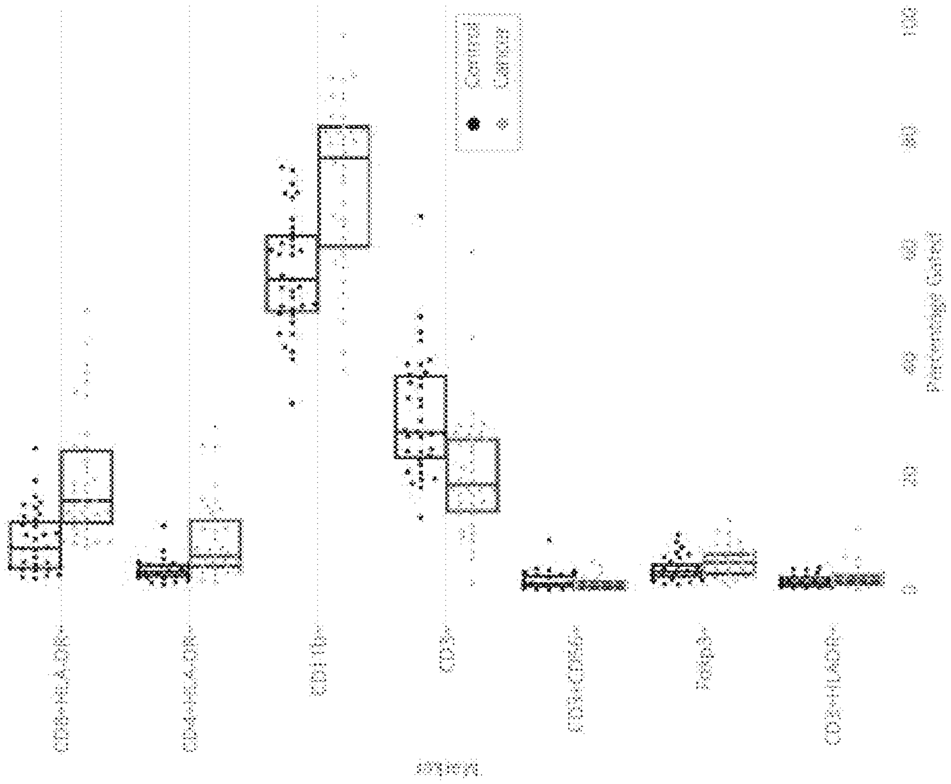
FIG. 50 graphically illustrates flow cytometry data from immune-phenotyping 73 blood samples obtained from human subjects with and without cancer. Statistical analysis was performed to find significantly different differences in immune markers between cancer and control sample cohorts, using a Mann Whitney U test and filtering for a false discovery rate of 0.05. Markers passing the FDR filter are plotted. The box denotes the 25th, 50th, and 75th percentiles of the data, and each point is a single sample; as discussed in detail in Example 7, below.
Figure 51:
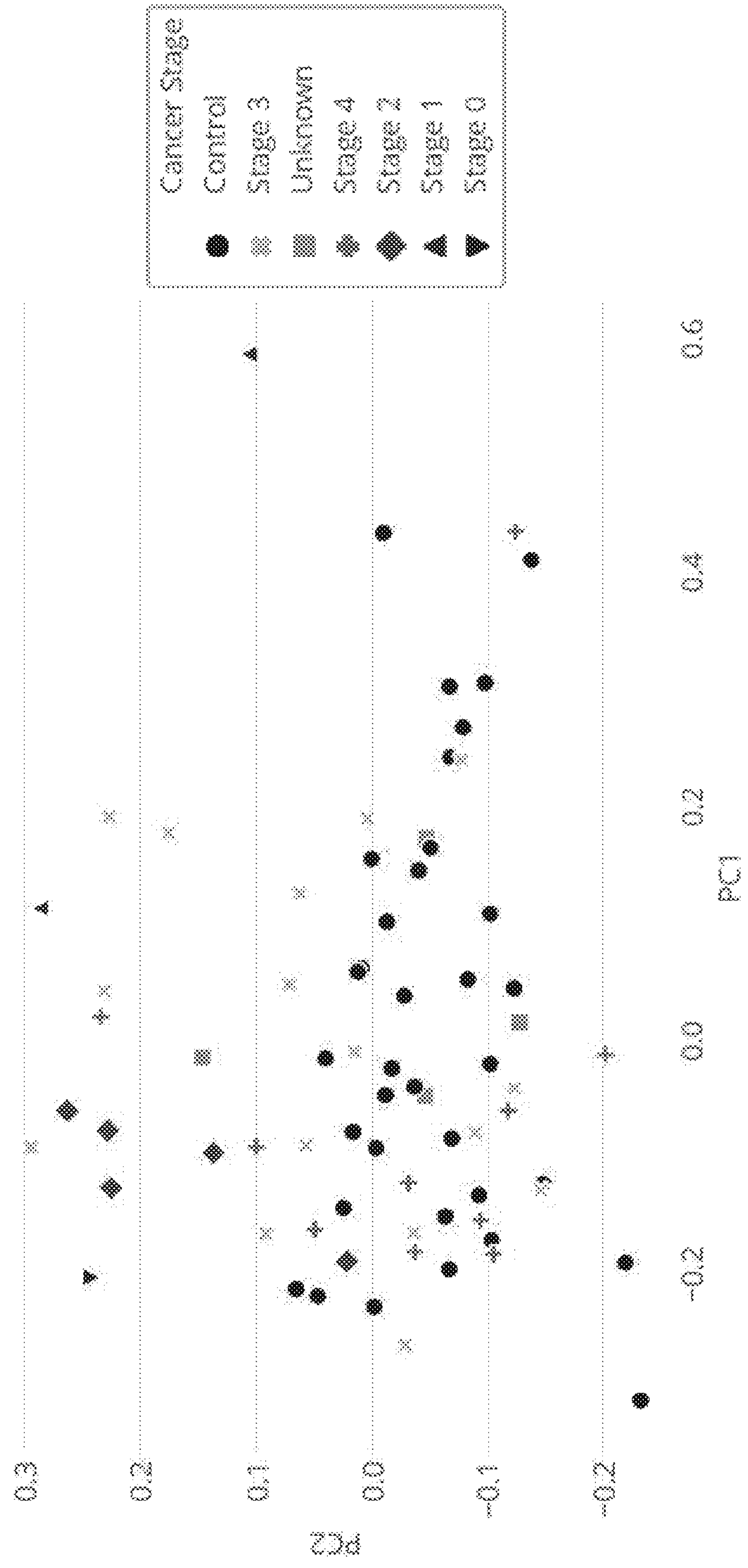
FIG. 51 graphically illustrates principal component analysis of flow cytometry data from immune-phenotyping 73 blood samples obtained from human subjects with and without cancer. Principal component analysis is performed on the immune marker percentages and the first two components are plotted by stage of cancer. The P value is computed using permutational multivariate analysis of variance (PERMANOVA); as discussed in detail in Example 7, below.

Flow cytometry was performed on 73 blood samples obtained from human subjects with and without cancer. The resulting gated percentages are plotted for different cell markers. For CD8+HLA-DR+, CD4+HLA-DR+, CD11b+, CD3+, CD3+CD56+, Foxp3+, and CD3+HLA-DR+, statistically differences are observed between the cancer and non-cancer populations as shown in FIG. 50. CD8+HLA-DR+(activated cytotoxic T cells) and CD4+HLA-DR+(activated T helper cells) are enriched in the cancer population. P values are computed using the Mann-Whitney U test. Principal component analysis was also conducted on the same data set where the gated percentages are mean and standard deviation scaled. The first two principal components are plotted as shown in FIG. 51. A statistically significant difference is observed between the cancer and control populations in the scaled data. The P value is computed using permutational multivariate analysis of variance (PERMANOVA).

Whole genome sequencing was performed on fecal sample obtained from 20 humans, 11 with cancer on in remission, and 9 healthy individuals. A taxonomic classification was assigned to each read by using the centrifuge software package together with a proprietary in-house genome database. The classified read percentages are reported in Table 18, with percentages normalized to the total number of classified reads.

Figure 18:
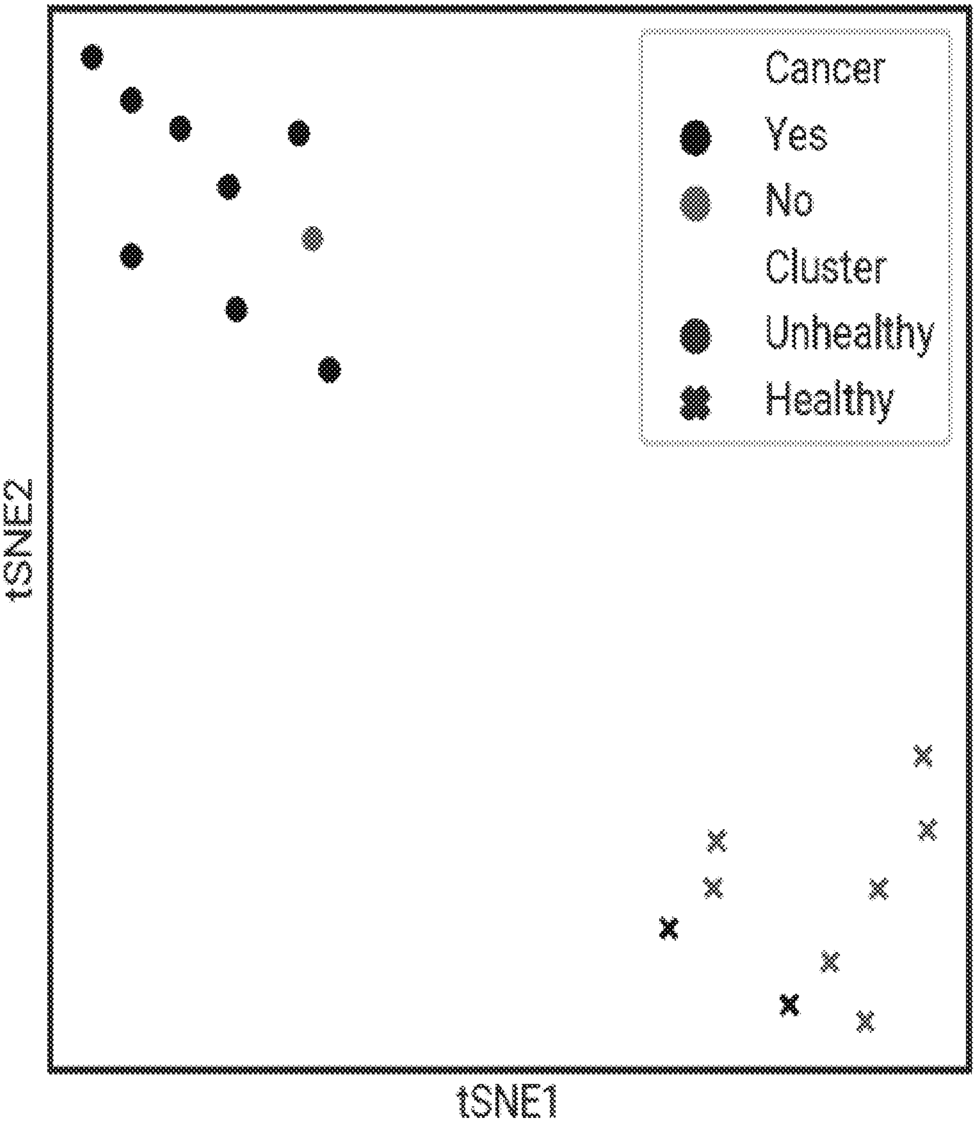
FIG. 18 graphically illustrates results from unsupervised clustering using t-SNE on the whole genome sequences from fecal samples obtained from 20 humans, 11 with cancer on in remission, and 9 healthy individuals. In the first cluster, deemed here as the "unhealthy" cluster, all but one of the humans have had cancer, while in the other "healthy" cluster, only two members have had cancer; as discussed in detail in Example 7, below.

Unsupervised clustering was performed on the whole genome sequencing results from humans using t-SNE (Laurens van der Maaten, Geoffrey Hinton; Journal of Machine Learning Research 9 (2008) 2579-2605). The classified read percentages across the cohort of 20 individuals were filtered to only the species level and to only organisms that appeared at 0.01% or greater in at least 5 samples. The remaining categories were normalized by mean and variance and inputted to principal component analysis. The top ten principal components were used as the input to t-SNE, which generated two distinct clusters as shown in FIG. 18. These clusters were visually apparent, and were further verified using k-means clustering. In the first cluster, deemed here as the "unhealthy" cluster, all but one of the humans have had cancer, while in the other "healthy" cluster, only two members have had cancer. Notably, both of the cancer patients in the healthy cluster are in remission and were elite responders to therapy.

Figure 19B:
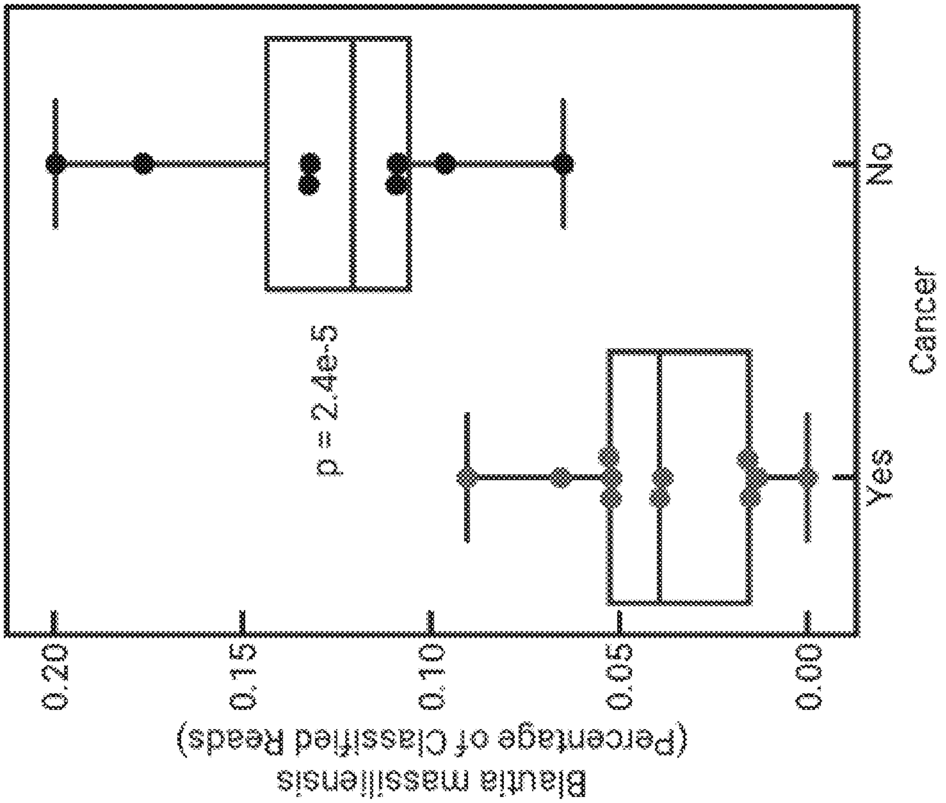
Figure 19A:
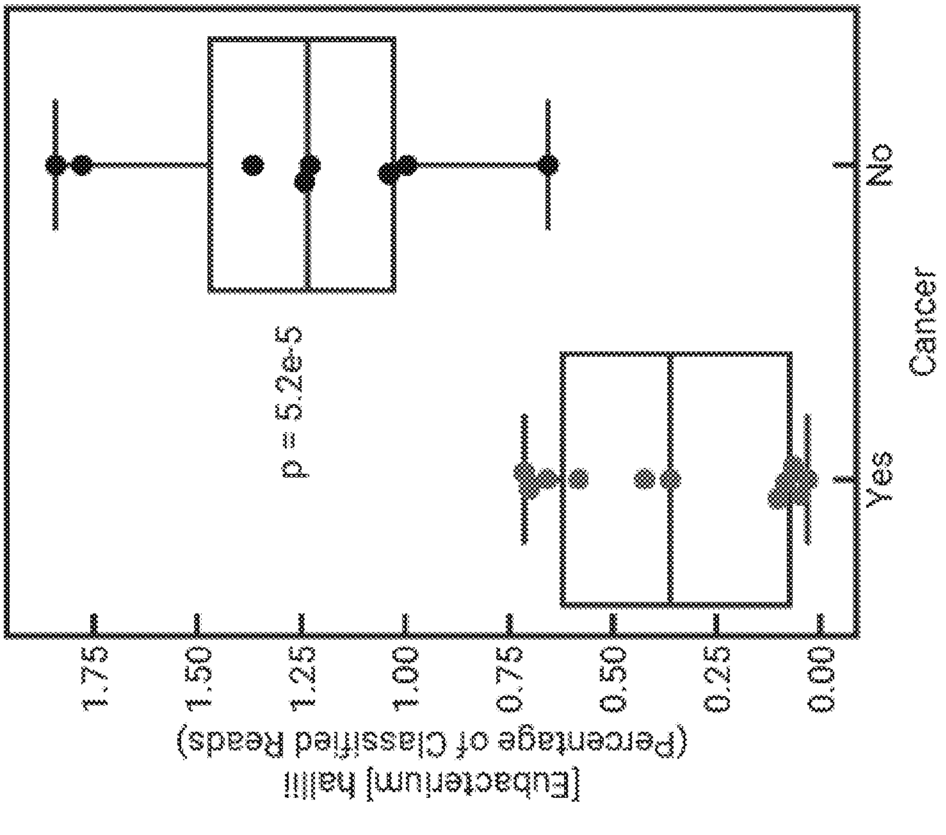

From the whole genome sequencing results, differential abundance testing between healthy individuals and current or former cancer patients was performed for *Eubacterium hallii* and *Blautia massiliensis*. The classified reads percentages were plotted for both healthy individuals and current or former cancer patients, and the Mann-Whitney non-parametric ranksum test was applied to assess statistical significance. As shown in FIG. 19, both *Eubacterium hallii* and *Blautia massiliensis* occur at a lower level in the cancer group, with strong statistical significance (p=5.2e-5, 2.4e-5 respectively).

Figure 52:
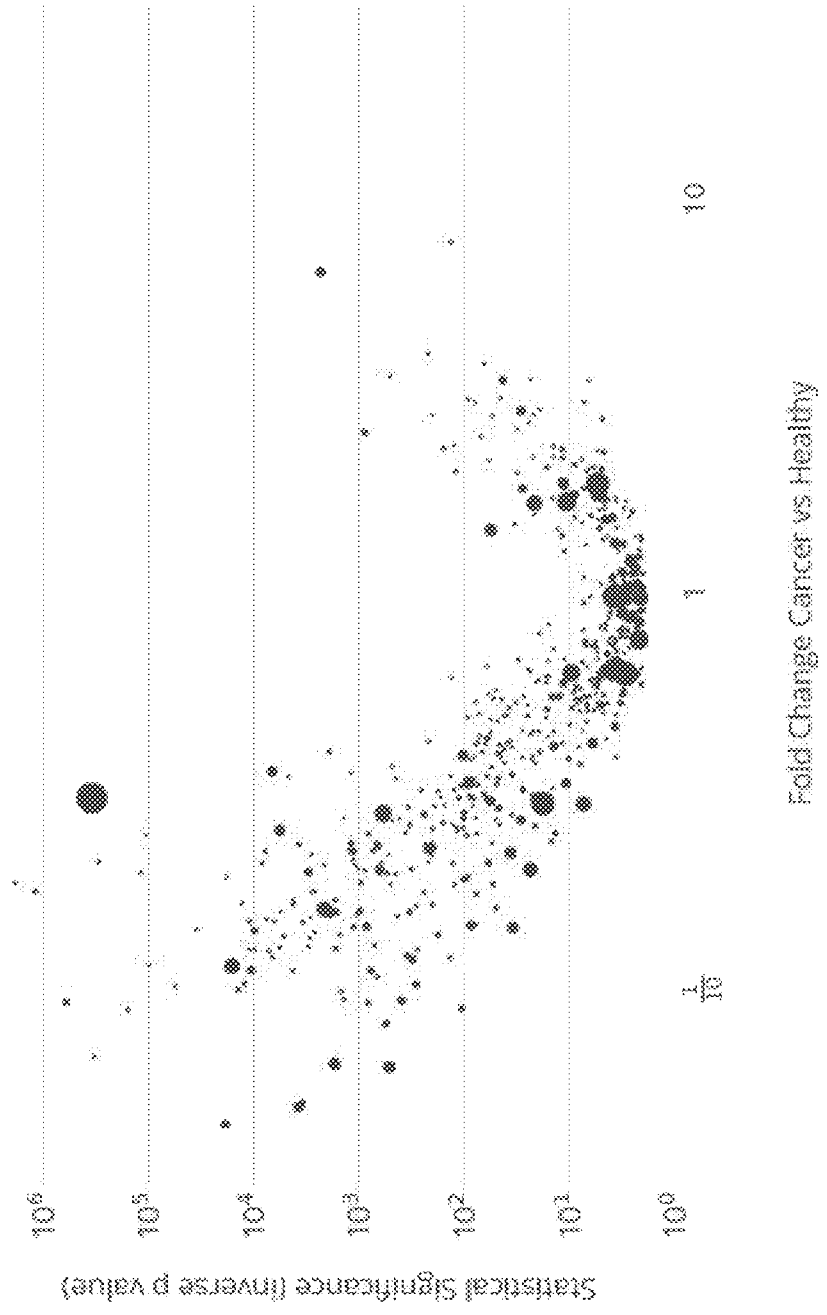
FIG. 52 graphically illustrates a volano plot of the whole genome sequencing data performed on performed on fecal samples from subjects with and without cancer where the reads are classified and abundance of each species or strain is estimated computationally. The fold change difference and statistical significance (inverse p value, Mann Whitney U test) was calculated for abundances between cancer and control sample cohorts. Each point is a microbial species or strain, and the area of each point corresponds to the average abundance of that organism in control samples; as discussed in detail in Example 7, below.
Figure 53:
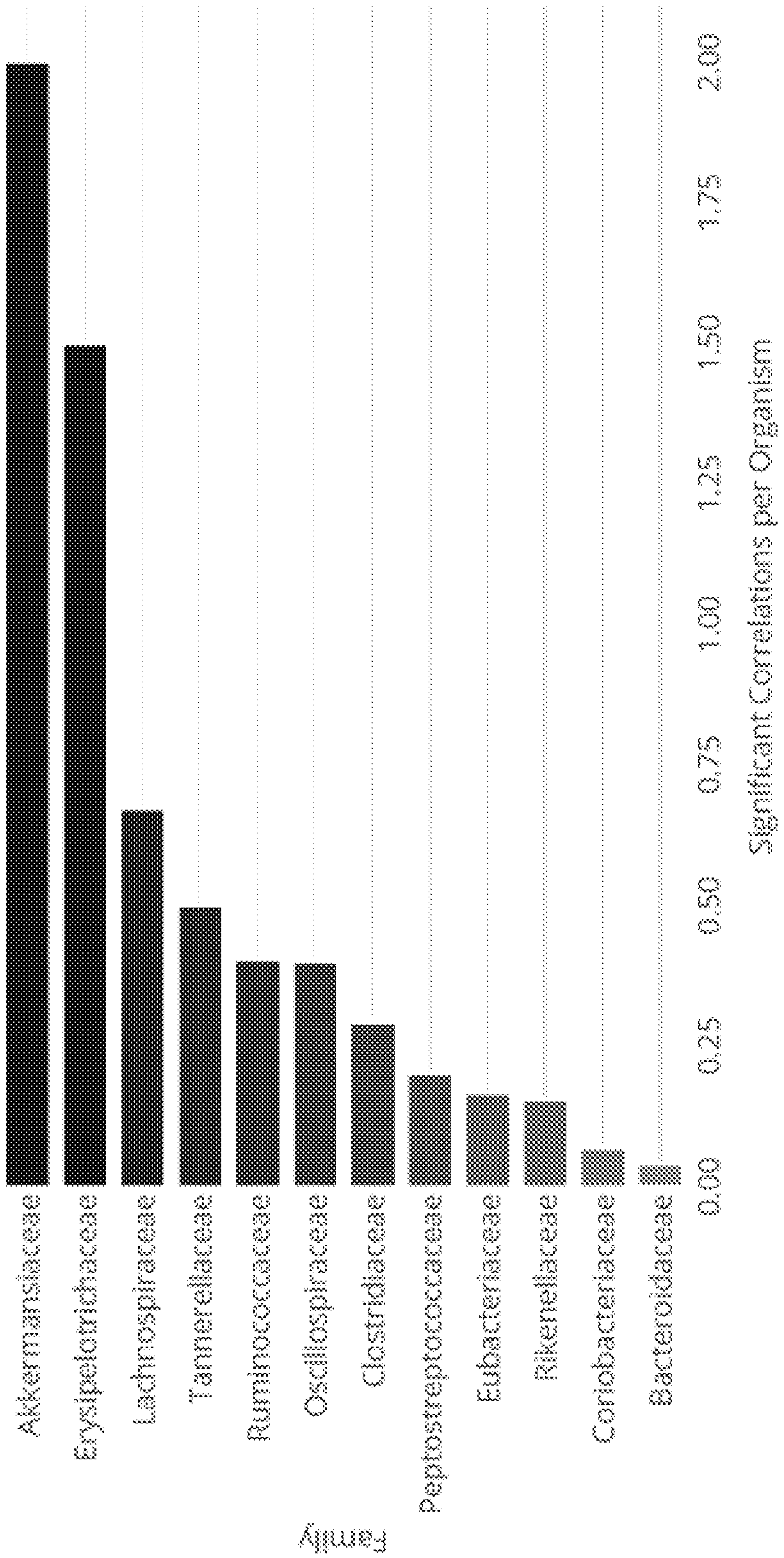
FIG. 53 graphically the results of a statistical analysis performed to find significantly significant correlations between immune markers and organisms, using a Spearman correlation and p value and filtering for a false discovery rate of 0.15. The ratio of the number of statistically significant correlations discovered to the total number of organisms considered for each family is plotted. A higher value indicates bacterial families that contain species that are more likely to be significantly correlated to the immune system; as discussed in detail in Example 7, below.
Figure 54:
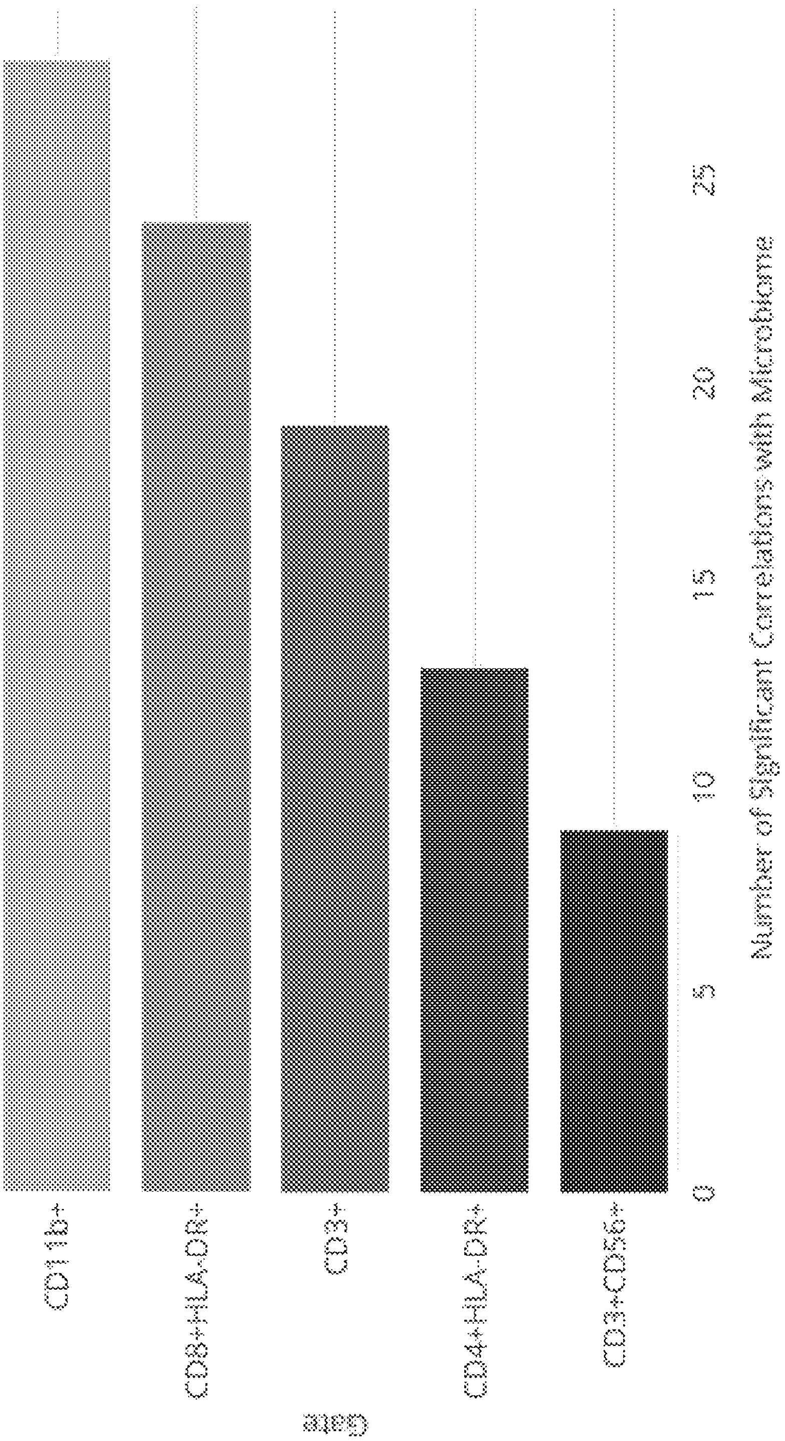
FIG. 54 graphically illustrates the results of a statistical analysis performed to find significantly significant correlations between immune markers and organisms, using a Spearman correlation and p value and filtering for a false discovery rate of 0.15. The number of statistically significant correlations for each immune marker is plotted, as discussed in detail in Example 7, below.
Figure 55:
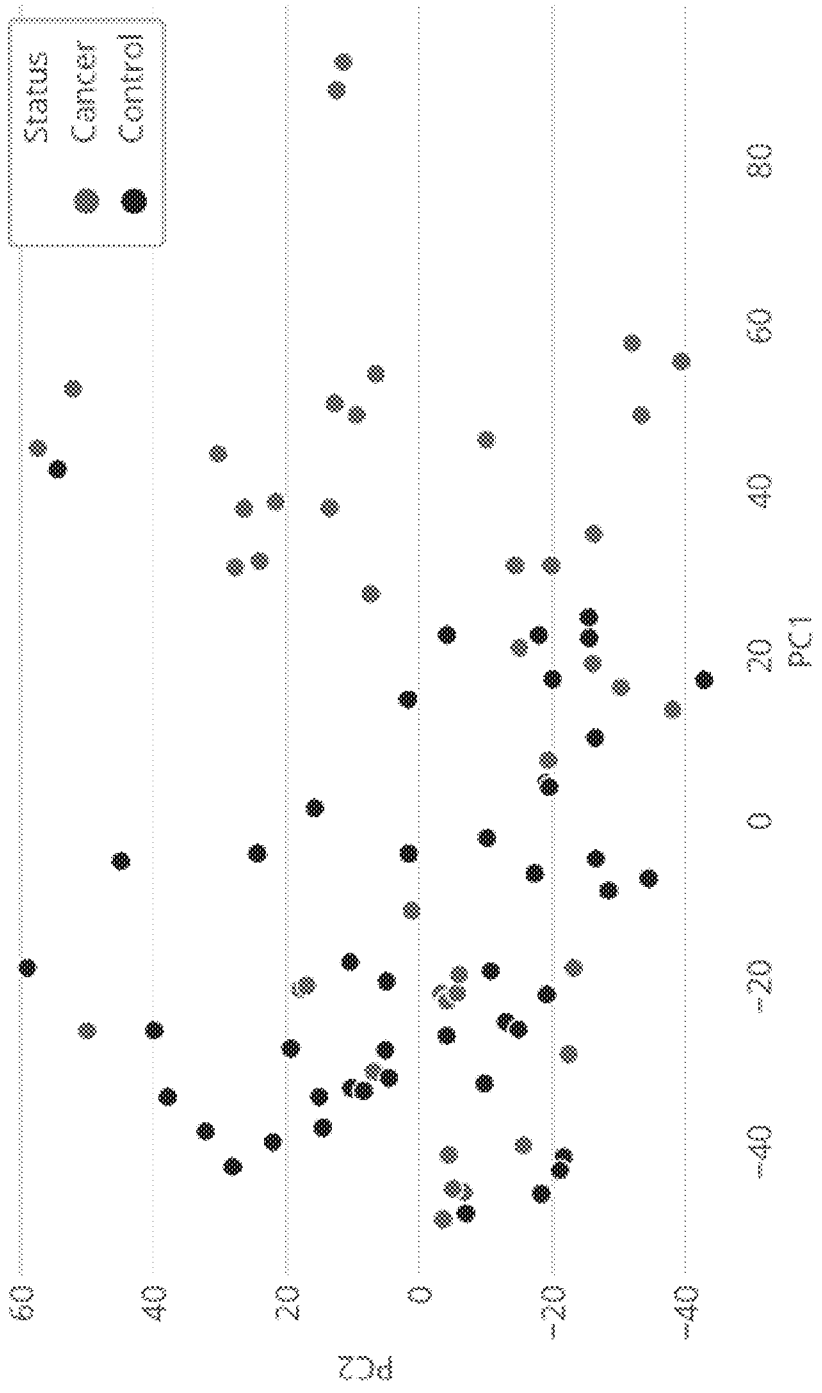
FIG. 55 graphically illustrates the results of a principal component analysis performed on centered-log-ratio transformed abundances from whole genome sequencing data, and the first two principal coordinates are plotted for cancer and control sample cohorts; as discussed in detail in Example 7, below.
Figure 56:
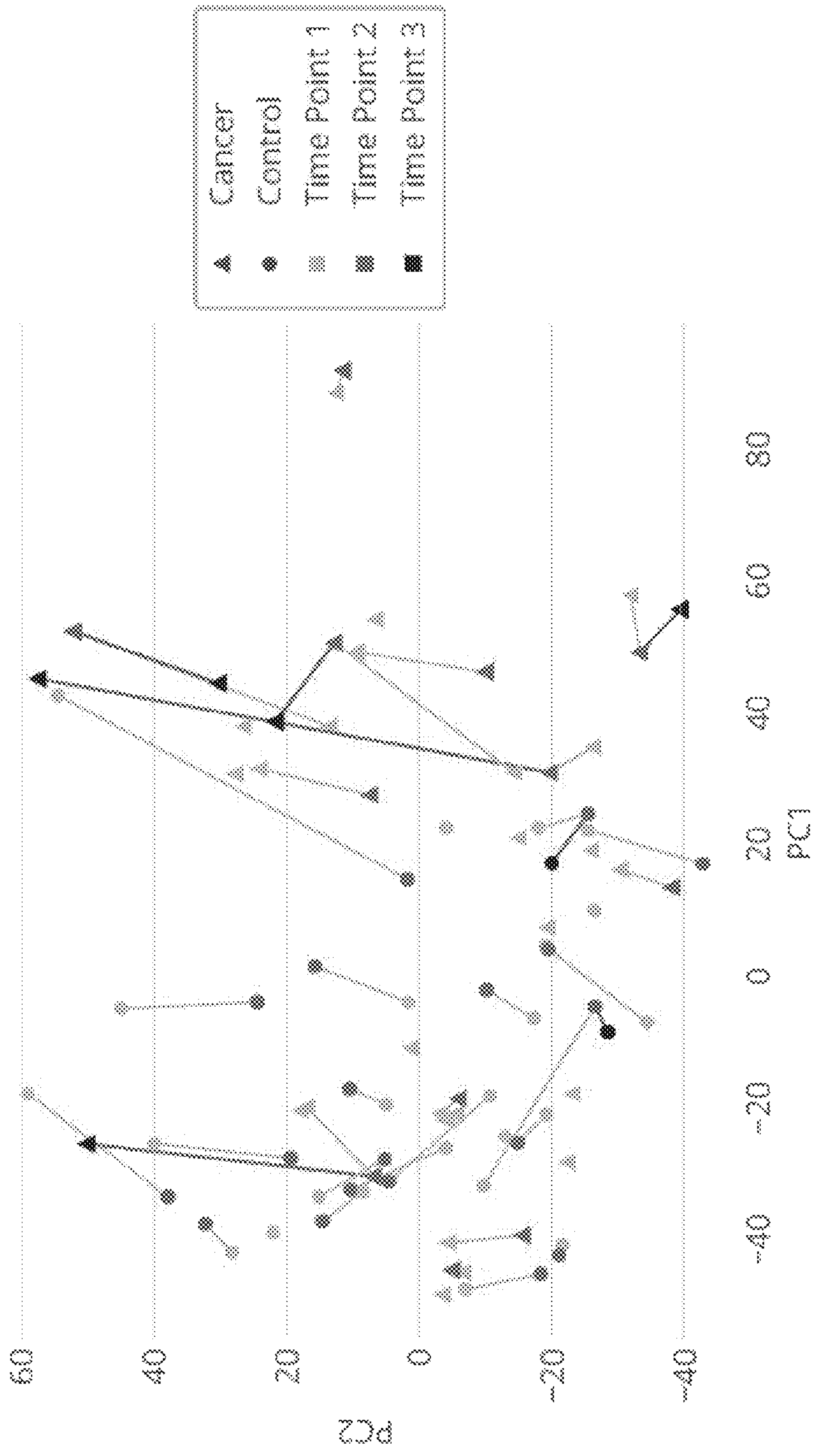
FIG. 56 graphically illustrates the results of a principal component analysis performed on centered-log-ratio transformed abundances from whole genome sequencing data, and the first two principal coordinates are plotted for cancer and control sample cohorts. Points corresponding to longitudinal samples from the same subject are connected, with darker points corresponding to later samples; as discussed in detail in Example 7, below.

Whole genome seuqencing was performed on fecal samples from subjects with and without cancer and the reads are classified and abundance of each species or strain was estimated computationally. The fold change difference and statistical significance (inverse p value, Mann Whitney U test) was calculated for abundances between cancer and control sample cohorts. The results are displayed on a volcano plot as shown in FIG. 52. Each point is a microbial species or strain, and the area of each point corresponds to the average abundance of that organism in control samples. Immune flow cytometry was performed on 73 blood samples from human subjects in addition to whole genome sequencing. Statistical analysis was performed to find significantly significant correlations between immune markers and organisms, using a Spearman correlation and p value and filtering for a false discovery rate of 0.15. The ratio of the number of statistically significant correlations discovered to the total number of organisms considered for each family was plotted as shown in FIG. 53. A higher value indicates bacterial families that contain species that are more likely to be significantly correlated to the immune system. Further statistical analysis was performed to find significantly significant correlations between immune markers and organisms, using a Spearman correlation and p value and filtering for a false discovery rate of 0.15. The number of statistically significant correlations for each immune marker was plotted as shown in FIG. 54. PCA (principal component analysis) was performed on centered-log-ratio transformed abundances from the whole genome sequencing data, and the first two principal coordinates were plotted for cancer and control sample cohorts as shown in FIG. 55. For the same PCA analysis, points corresponding to longitudinal samples from the same subject were connected, with darker points corresponding to later samples as shown in FIG. 56.

Figure 60:
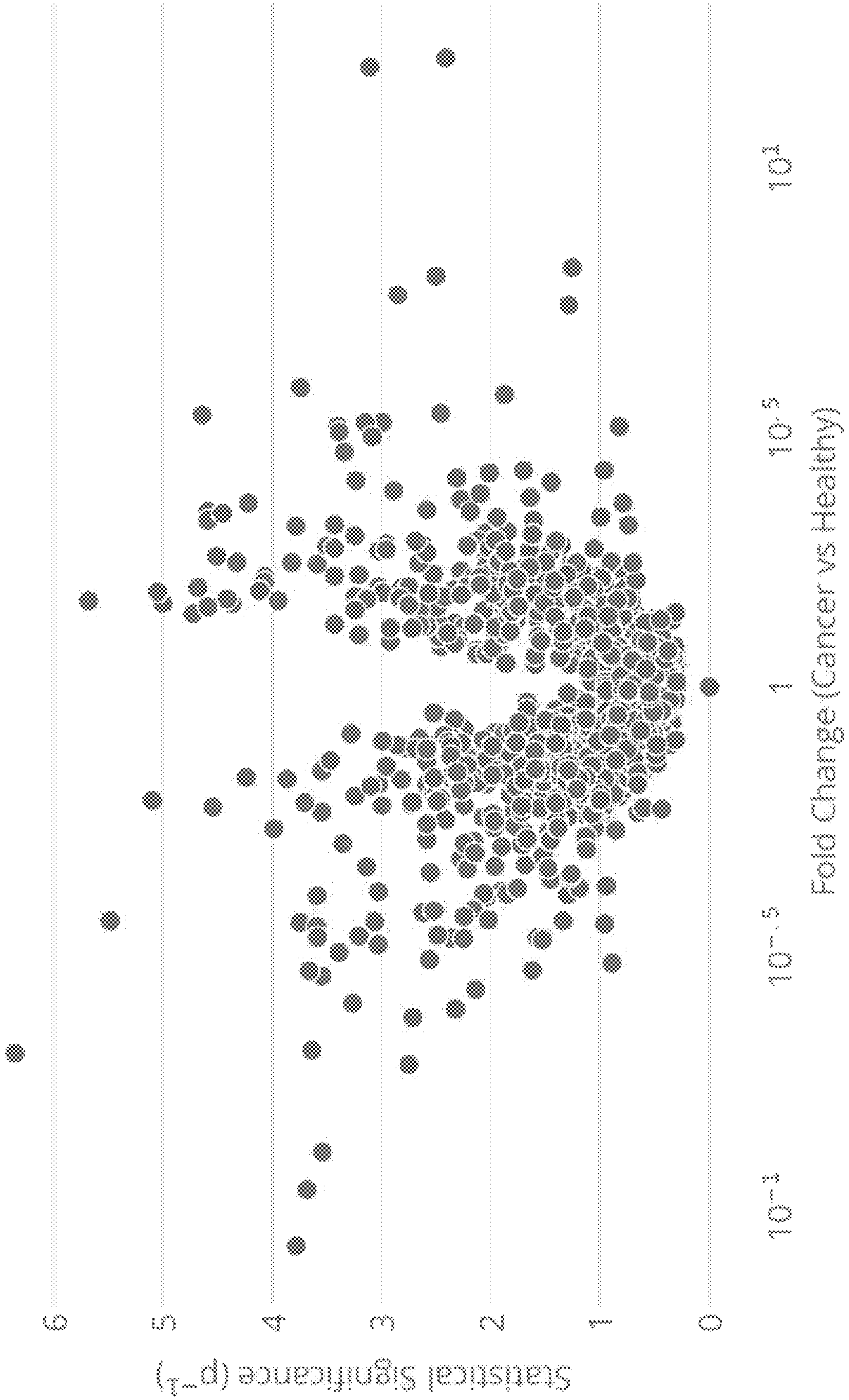
FIG. 60 graphically illustrates the results of a statistical analysis performed on metabolomics data on plasma obtained from a third party provider (as "a volcano plot"). A Mann Whitney U test is used to find significantly different metabolites between cancer and control cohorts. Metabolites enriched in cancer samples appear on the right side of the plot and those enriched in control samples occur on the left, with higher points on the y-axis corresponding to increased statistical significance, as discussed in detail in Example 7, below.

FIG. 60 illustrates metabolomics data on plasma from a third party provider was processed using a Mann Whitney U test to find significantly different metabolites between cancer and control cohorts. Metabolites enriched in cancer samples appear on the right and those enriched in control samples occur on the left, with higher points on the y-axis corresponding to increased statistical significance.

Figure 61:
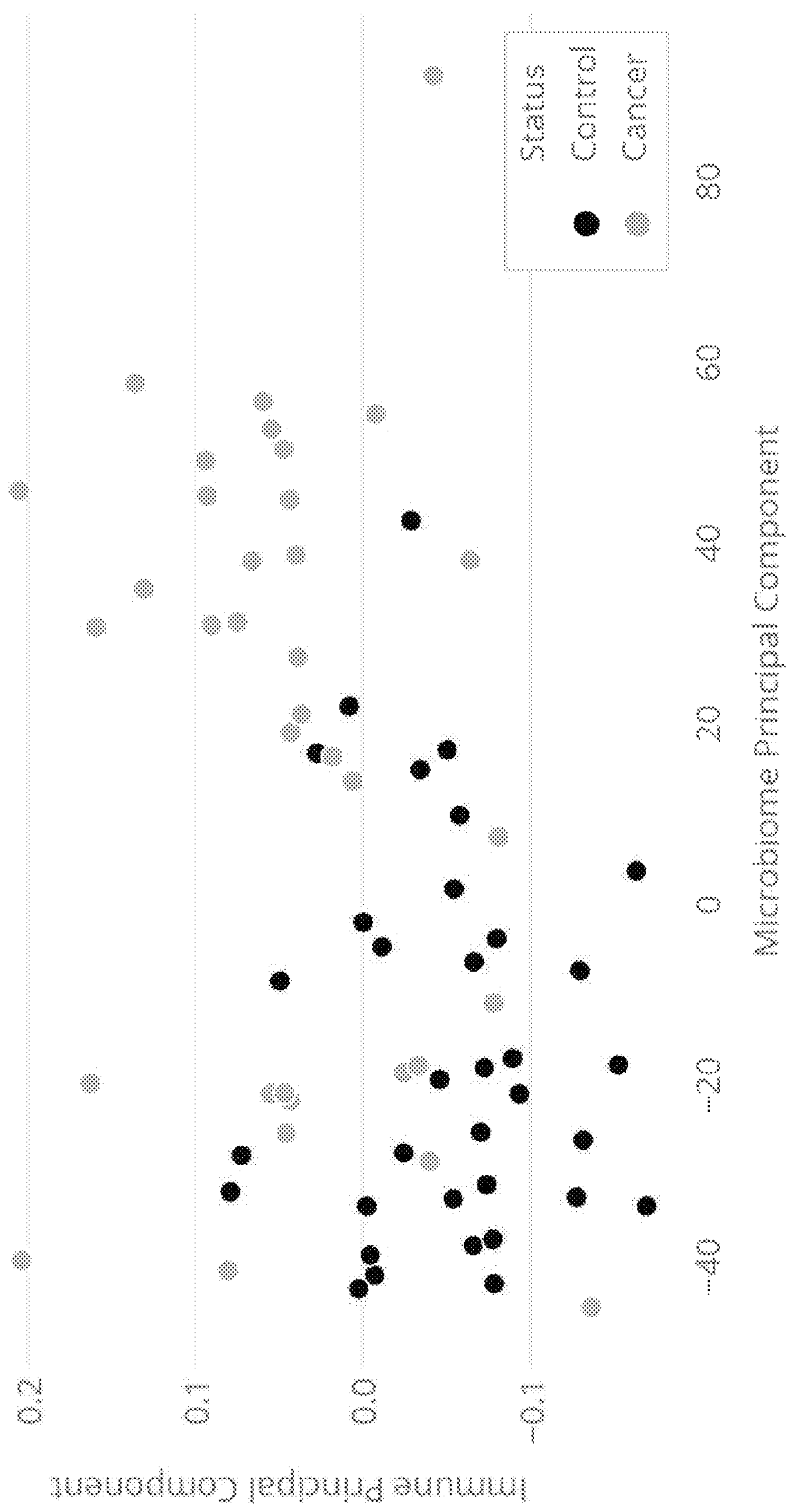
FIG. 61 graphically illustrates the results of a principal component analysis comparing immune flow cytometry data to whole genome sequencing data. The primary principal component for the whole genome sequencing data and the second principal component for immune flow cytometry data are plotted against each other, revealing a strong correlation and suggesting that the microbiome may play a role in affecting the immune system and vice versa, as discussed in detail in Example 7, below.

FIG. 61 illustrates the primary principal components for the microbiome sequencing data and immune flow cytometry data are plotted against each, revealing a strong correlation and suggesting that the microbiome may play a role in affecting the immune system and vice versa.

Figure 62:
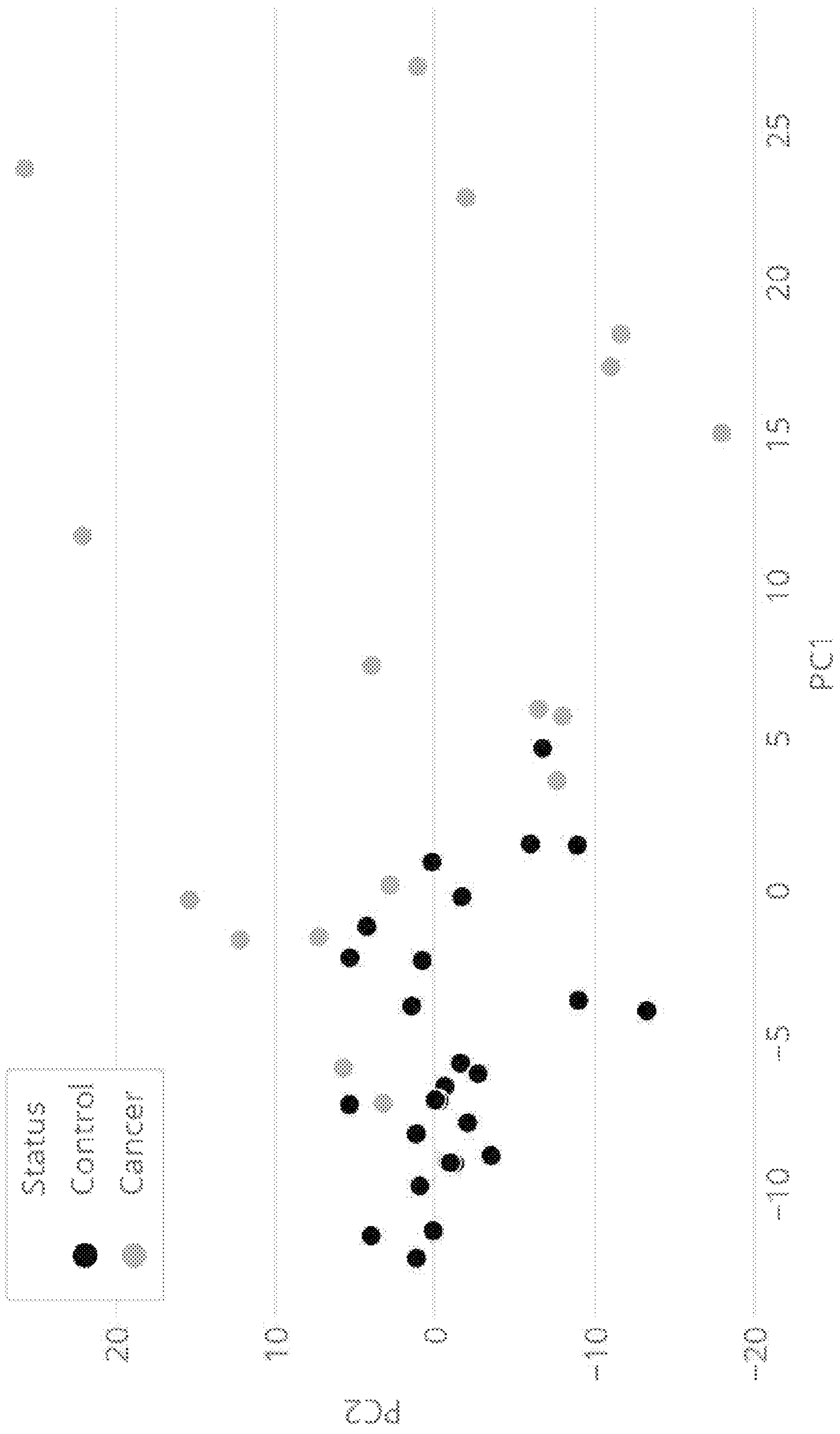
FIG. 62 graphically illustrates the results of a principal component analysis performed on the plasma metabolomics of cancer and control samples, showing clear separation between cancer and control samples, as discussed in detail in Example 7, below.

FIG. 62 illustrates metabolomics data on plasma from a third party provider was processed using a log transform and PCA to show clear separation between samples from a cancer and control cohort.

Figure 63:
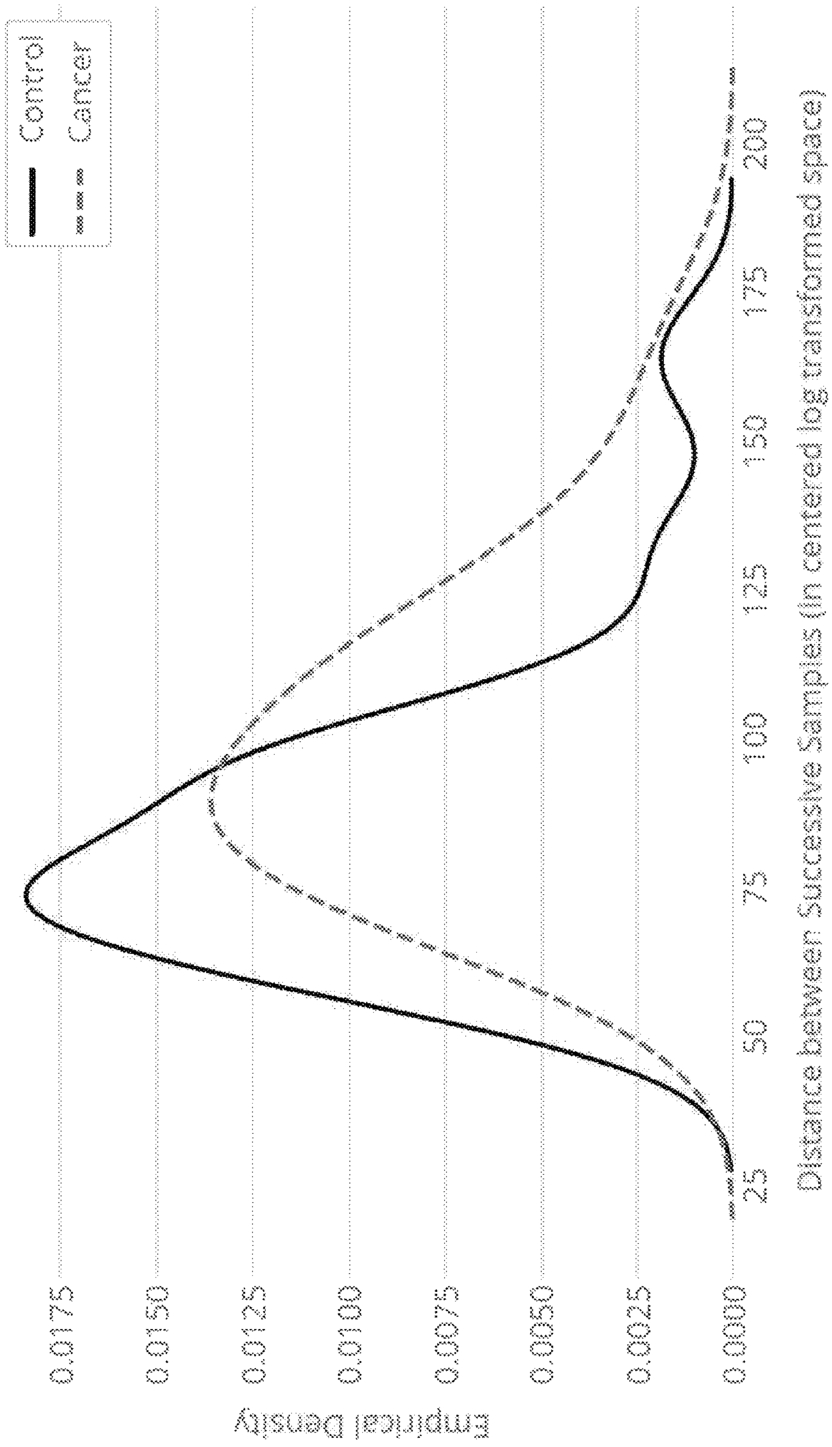
FIG. 63 graphically illustrates the distribution of Euclidean distances in a centered-log-transformed space between successive longitudinal fecal whole genome sequencing samples for both cancer and control cohorts. The plot shows a higher average distance between longitudinal cancer samples than control, as discussed in detail in Example 7, below.

The empirical distribution between successive longitudinal samples is plotted in FIG. 63 for both cancer and control cohorts, demonstrating the increased variability of the cancer microbiome. In FIG. 63, centered log transformed estimated species abundances were generated for both cancer and control sample cohorts. Distances between successive longitudinal samples in the transformed space were computed for both cancer and control cohorts, and the empirical densities of the distances are displayed, revealing that cancer microbiomes are less stable and move around more over time than control.

Table 34 shows the organism level weights for the first principal component, which separates cancer and control sample cohorts. Only weights with magnitude greater than 0.014 and corresponding to organisms with minimum abundance 0.001 are reported. The organisms driving separation towards the control side of the principal component are also some of the organisms most strongly missing from the cancer microbiome, while organisms driving separation towards the cancer side of the principal component tend to be pathogenic or otherwise negative for health.

Figure 58:
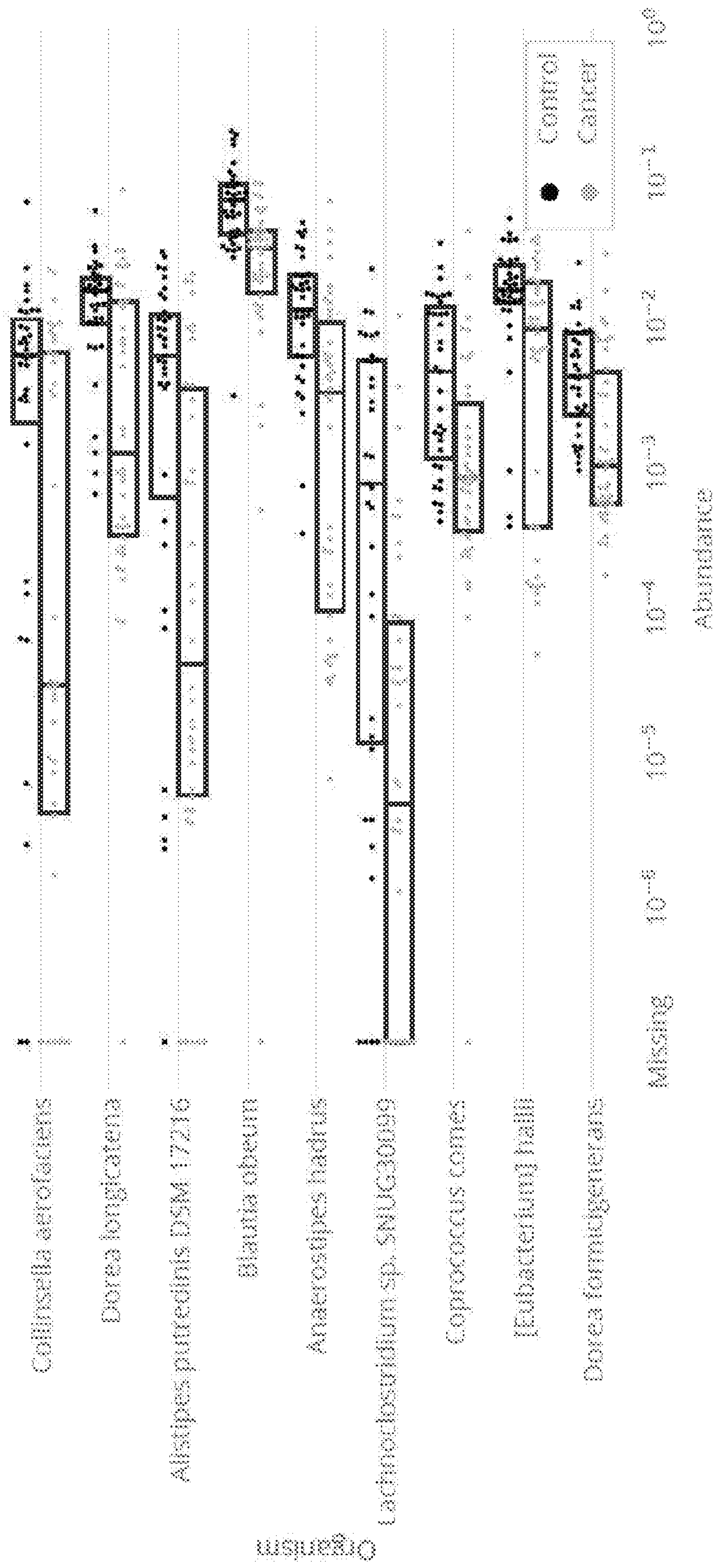
FIG. 58 graphically illustrates the results of a statistical analysis to find differentially abundant organisms between cancer and control sample cohorts. Whole genome sequencing is performed on fecal samples from subject with and without cancer and the reads are classified and abundance of each species or strain is estimated computationally. The fold change difference and statistical significance (inverse p value, Mann Whitney U test) is calculated for abundances between cancer and control sample cohorts. Some statistically significant differential organisms' abundances are displayed, as discussed in detail in Example 7, below.

The whole genome sequencing was also used to determine statistically significant differentially abundant organisms between cancer and control sample cohorts; FIG. 58 illustrates some manually curated hits.

The primary principal component from whole genome sequencing data was plotted against the second principal component from immune flow cytometry analysis in FIG. 61, revealing a strong correlation and suggesting that the microbiome may play a role in affecting the immune system and vice versa.

TABLE 26

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 5.43E−07 | 9.37E−05 | 2.59E−04 | −7.35E−01 | *Ruminococcus* sp. OF02-6:2293228 |
| 8.47E−07 | 1.78E−04 | 5.35E−04 | −7.56E−01 | *Blautia obeum* ATCC 29174:411459 |
| 1.67E−06 | 3.86E−04 | 1.37E−03 | −1.04E+00 | *Ruminococcus* sp. AM16-34:2293184 |
| 2.91E−06 | 3.12E−02 | 7.12E−02 | −5.20E−01 | *Blautia obeum*:40520 |
| 3.06E−06 | 1.05E−04 | 3.23E−04 | −1.18E+00 | *Ruminococcus faecis* JCM 15917:1298596 |
| 3.40E−06 | 2.11E−04 | 3.73E−04 | −6.81E−01 | *Blautia* sp. OM07-19:2292985 |
| 6.46E−06 | 5.51E−05 | 2.34E−04 | −1.06E+00 | *Lachnospiraceae bacterium* AM23-7LB:2292904 |
| 7.30E−06 | 3.18E−05 | 9.97E−05 | −9.48E−01 | *Ruminococcus* sp. AF25-17:2293164 |
| 8.48E−06 | 6.76E−05 | 2.70E−04 | −7.10E−01 | *Ruminococcus* sp. AF46-10NS:2292072 |
| 9.21E−06 | 2.72E−05 | 8.87E−05 | −1.01E+00 | *Ruminococcus* sp. AM49-10BH:2293222 |
| 9.40E−06 | 4.04E−05 | 1.26E−04 | −6.15E−01 | *Lachnospiraceae bacterium* Choco86:2109690 |
| 9.43E−06 | 3.55E−18 | 2.74E−05 | −2.46E−01 | *Clostridium* sp. AM54-37XD:2293038 |
| 1.02E−05 | 4.19E−05 | 1.63E−04 | −9.45E−01 | *Ruminococcus* sp. OM08-13AT:2293235 |
| 1.04E−05 | 7.91E−06 | 7.72E−05 | −8.98E−01 | *Ruminococcus* sp. AM27-27:2293193 |
| 1.69E−05 | 9.77E−06 | 6.64E−05 | −4.51E−01 | *Tidjanibacter massiliensis*:1871003 |
| 1.79E−05 | 6.69E−05 | 2.44E−04 | −9.99E−01 | *Blautia* sp. AM16-16B:2292969 |
| 2.85E−05 | 1.09E−04 | 3.52E−04 | −8.54E−01 | *Blautia* sp. AM22-22LB:2292970 |
| 3.27E−05 | 5.18E−07 | 2.05E−05 | −3.33E−01 | *Clostridioides difficile* P51:1151426 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 4.07E−05 | 6.77E−04 | 4.30E−05 | 1.02E+00 | *Anaerostipes* sp. AF04-45:2292912 |
| 5.00E−05 | 2.11E−05 | 5.38E−05 | −7.92E−01 | *Ruminococcus* sp. AM57-5:2293227 |
| 5.38E−05 | 4.70E−04 | 3.21E−03 | −1.35E+00 | *Lachnoclostridium* sp. SNUG30099:2126738 |
| 5.50E−05 | 2.21E−06 | 1.61E−04 | −7.21E−01 | *Clostridium* sp. AF15-31:2292995 |
| 6.22E−05 | 7.78E−03 | 1.52E−02 | −9.47E−01 | *Anaerostipes hadrus*:649756 |
| 6.58E−05 | 8.77E−07 | 1.57E−05 | −4.48E−01 | *Collinsella* sp. TF06-26:2018038 |
| 7.09E−05 | 3.45E−04 | 1.03E−03 | −1.01E+00 | *Blautia* sp. AF22-5LB:2292964 |
| 7.73E−05 | 9.61E−05 | 2.30E−04 | −7.87E−01 | *Ruminococcus* sp. OM04-4AA:2293231 |
| 8.13E−05 | 4.69E−04 | 8.47E−04 | −9.91E−01 | *Dora longicatena* DSM 13814:411462 |
| 8.50E−05 | 2.79E−05 | 7.45E−05 | −6.15E−01 | *Clostridium* sp. AF32-12BH:2292006 |
| 8.60E−05 | 3.93E−07 | 1.72E−06 | −1.92E−01 | *Lachnoanaerobaculum saburreum* DSM 3986:887325 |
| 9.05E−05 | 6.58E−05 | 3.03E−04 | −9.05E−01 | *Dorea* sp. AM10-31:2293098 |
| 9.07E−05 | 4.12E−04 | 8.39E−04 | −8.33E−01 | *Lachnospiraceae bacterium* 5_1_63FAA:658089 |
| 9.48E−05 | 1.35E−03 | 3.53E−03 | −9.58E−01 | *Gemmiger formicilis*:745368 |
| 1.01E−04 | 1.00E−03 | 2.63E−03 | −8.57E−01 | *Blautia* sp. SF-50:1520805 |
| 1.02E−04 | 6.37E−05 | 2.32E−04 | −9.04E−01 | *Blautia* sp. AM46-5:2292978 |
| 1.21E−04 | 1.10E−04 | 4.20E−04 | −6.85E−01 | *Dorea* sp. AM58-8:2292346 |
| 1.22E−04 | 1.58E−05 | 3.61E−05 | −6.27E−01 | *Faecalibacterium prausmtzn* A2-165:411483 |
| 1.29E−04 | 2.76E−04 | 5.36E−04 | −6.55E−01 | [*Eubacterium*] *hallii* DSM 3353:411469 |
| 1.32E−04 | 6.47E−04 | 1.63E−04 | −8.26E−01 | *Ruminococcus* sp. OM06-36AC:2292375 |
| 1.39E−04 | 9.34E−05 | 5.94E−05 | −5.36E−01 | *Coprococcus* sp. TF11-13:2293096 |
| 1.40E−04 | 1.18E−04 | 3.26E−04 | −9.09E−01 | *Dorea* sp. AF36-15AT:2292041 |
| 1.43E−04 | 8.95E−04 | 5.72E−05 | 5.72E−01 | *Blautia* sp. N6H1-15:1912897 |
| 1.49E−04 | 1.53E−04 | 5.53E−04 | −9.23E−01 | *Blautia* sp. AF25-12LB:2292965 |
| 1.49E−04 | 3.36E−03 | 5.38E−03 | −4.53E−01 | *Dorea formicigenerans*:39486 |
| 1.50E−04 | 2.34E−05 | 9.10E−05 | −7.82E−01 | *Ruminococcus* sp. AM49-8:2293223 |
| 1.56E−04 | 2.70E−04 | 5.20E−04 | −8.33E−01 | *Anaerostipes hadms* DSM 3319:649757 |
| 1.63E−04 | 5.79E−06 | 3.62E−05 | −6.15E−01 | *Collinsella aerofaciens* ATCC 25986:411903 |
| 1.75E−04 | 1.18E−04 | 2.59E−04 | −8.99E−01 | *Lachnospiraceae bacterium* AM25-27:2292905 |
| 1.77E−04 | 3.31E−03 | 7.23E−03 | −6.01E−01 | *Coprococcus comes*:410072 |
| 1.80E−04 | 2.54E−05 | 1.56E−04 | −8.08E−01 | *Collinsella* sp. AF23-3LB:2292223 |
| 1.92E−04 | 1.56E−04 | 4.92E−04 | −8.72E−01 | *Blautia* sp. AF19-34:2292963 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 2.08E−04 | 1.76E−05 | 6.94E−05 | −7.11E−01 | *Raoultibacter massiliensis*:1852371 |
| 2.14E−04 | 8.24E−05 | 2.09E−04 | −4.65E−01 | *Ruminococcus* sp. AF20-12LB:2293160 |
| 2.26E−04 | 3.19E−05 | 8.82E−05 | −6.79E−01 | *Massilimaliae massiliensis*:1852384 |
| 2.30E−04 | 1.13E−52 | 1.01E−05 | −4.46E−01 | *Collinsella* sp. AF19-7AC:2292220 |
| 2.36E−04 | 2.81E−04 | 5.09E−04 | −9.60E−01 | *Lachnospiraceae bacterium* AM21-21:2292903 |
| 2.37E−04 | 2.21E−04 | 4.61E−04 | −7.90E−01 | *Ruminococcaceae bacterium* AF10-16:2292180 |
| 2.38E−04 | 5.80E−05 | 2.02E−04 | −7.78E−01 | *Gordonibacter faecihominis*:1432309 |
| 2.42E−04 | 5.64E−04 | 3.49E−05 | 1.05E+00 | *Anaerostipes caccae*:105841 |
| 2.64E−04 | 1.06E−03 | 5.20E−03 | −1.30E+00 | *Monoglobus pectinilyticus*:1981510 |
| 2.68E−04 | 4.74E−04 | 6.87E−04 | −6.38E−01 | *Ruminococcaceae bacterium* TF06-43:2292270 |
| 2.84E−04 | 7.60E−07 | 1.82E−06 | −2.24E−01 | *Asaccharobacter celatus* DSM 18785:1121021 |
| 2.87E−04 | 2.04E−04 | 1.63E−03 | −1.30E+00 | *Clostridium sporogenes*:1509 |
| 2.91E−04 | 2.60E−04 | 4.15E−04 | −8.36E−01 | *Lachnospiraceae bacterium* AM10-38:2292902 |
| 3.09E−04 | 6.10E−05 | 8.84E−05 | −5.88E−01 | *Clostridiaceae bacterium* AF42-6:2291990 |
| 3.16E−04 | 5.41E−06 | 3.45E−05 | −4.10E−01 | *Ruminococcus* sp. AF17-6LB:2293155 |
| 3.26E−04 | 3.25E−05 | 1.02E−04 | −7.15E−01 | *Collinsella* sp. TF11-5AC:2292336 |
| 3.27E−04 | 1.42E−04 | 2.92E−04 | −8.97E−01 | *Clostridium* sp. AF46-9NS:2293020 |
| 3.29E−04 | 2.07E−03 | 3.74E−03 | −7.08E−01 | *Blautia* sp. KLE 1732:1226324 |
| 3.37E−04 | 1.46E−04 | 3.12E−04 | −8.75E−01 | *Lachnospiraceae bacterium* TF10-8AT:2292907 |
| 3.44E−04 | 5.02E−05 | 1.31E−04 | −8.24E−01 | *Ruminococcus* sp. AF12-5:2293146 |
| 3.48E−04 | 8.41E−05 | 1.74E−04 | −7.60E−01 | *Christensenella minuta*:626937 |
| 3.55E−04 | 1.25E−04 | 3.57E−04 | −6.63E−01 | *Eubacterium ventriosum* ATCC 27560:411463 |
| 3.58E−04 | 1.14E−06 | 3.05E−06 | −2.88E−01 | *Enterorhabdus caecimuris* B7:1235794 |
| 3.64E−04 | 6.73E−06 | 1.21E−05 | −3.51E−01 | *Roseburia* sp. AF22-2LB:2293130 |
| 3.65E−04 | 6.81E−05 | 7.53E−05 | −8.90E−01 | *Adlercreutzia equolifaciens*:446660 |
| 3.68E−04 | 4.92E−05 | 9.35E−05 | −7.93E−01 | *Collinsella* sp. AM23-17:2292030 |
| 3.78E−04 | 1.53E−04 | 3.78E−04 | −8.61E−01 | *Blautia hydrogenotrophica*:53443 |
| 3.78E−04 | 4.92E−05 | 2.48E−04 | −7.55E−01 | *Clostridium* sp. OM08-29:2293049 |
| 4.02E−04 | 5.58E−05 | 7.90E−05 | −3.87E−01 | *Dorea* sp. *Marseille*-P4042:2080749 |
| 4.18E−04 | 2.43E−06 | 2.92E−05 | −5.16E−01 | *Parabacteroides distasonis* CL09T03C24:999417 |
| 4.18E−04 | 1.46E−05 | 8.14E−05 | −6.84E−01 | *Collinsella* sp. TM06-3:2292342 |
| 4.36E−04 | 1.65E−02 | 4.80E−03 | 8.16E−01 | *Bacteroides caccae*:47678 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 4.60E−04 | 1.01E−05 | 4.88E−05 | −6.26E−01 | *Collinsella* sp. TF09-1AT:2292334 |
| 4.69E−04 | 4.79E−04 | 3.46E−04 | −6.90E−01 | *Ruminococcus* sp. AF17-22AC:2292248 |
| 4.71E−04 | 9.05E−03 | 1.48E−02 | −8.03E−01 | *Dorea longicatena*:88431 |
| 4.72E−04 | 6.20E−06 | 4.23E−05 | −5.54E−01 | Alistipes sp. CHKCI003:1780376 |
| 4.90E−04 | 0.00E+00 | 1.21E−05 | −1.77E−01 | *Brochothrix thermosphacta*:2756 |
| 5.04E−04 | 1.63E−05 | 5.37E−05 | −6.50E−01 | *Collinsella* sp. OM06-18AC:2292327 |
| 5.20E−04 | 3.49E−04 | 6.46E−04 | −4.03E−01 | *Ruminococcus* sp. AF31-8BH:2293174 |
| 5.30E−04 | 1.58E−03 | 3.65E−03 | −8.13E−01 | *Ruminococcus* sp. AM26-12LB:2293190 |
| 5.52E−04 | 2.20E−05 | 9.78E−05 | −7.55E−01 | *Collinsella* sp. AM18-10:2292028 |
| 5.76E−04 | 4.38E−05 | 5.22E−05 | −5.26E−01 | *Roseburia* sp. AF12-17LB:2293127 |
| 5.84E−04 | 3.12E−03 | 7.90E−03 | −1.20E+00 | *Alistipes putredinis* DSM 17216:445970 |
| 5.93E−04 | 5.01E−05 | 3.01E−04 | −7.77E−01 | *Dorea* sp. AM13-35:2293099 |
| 5.93E−04 | 3.15E−04 | 7.67E−04 | −7.79E−01 | *Ruminococcus* sp. OM08-9BH:2293236 |
| 5.96E−04 | 1.14E−03 | 2.42E−03 | −8.11E−01 | *Ruminococcus* sp. AF17-12:2293151 |
| 5.99E−04 | 3.35E−04 | 7.01E−04 | −9.02E−01 | *Gordonibacter urolithinfaciens*:1335613 |
| 6.13E−04 | 1.91E−06 | 3.72E−06 | −1.32E−01 | *Leuconostoc gelidum* subsp. *gasicomitatum* KG16-1:1165892 |
| 6.31E−04 | 4.69E−04 | 3.62E−05 | 6.36E−01 | *Clostridia bacterium* UC5.1-2H11:1697795 |
| 6.35E−04 | 1.72E−05 | 2.97E−05 | −5.04E−01 | *Roseburia* sp. AF25-15LB:2293133 |
| 6.52E−04 | 2.18E−04 | 5.93E−04 | −8.67E−01 | *Blautia* sp. TF11-31AT:2292987 |
| 6.79E−04 | 1.70E−04 | 4.57E−04 | −1.01E+00 | *Collinsella* sp. AM34-10:2292316 |
| 6.90E−04 | 8.99E−07 | 8.75E−05 | −4.66E−01 | *Alistipes* sp. AF17-16:2292190 |
| 7.15E−04 | 4.04E−04 | 7.67E−04 | −1.03E+00 | *Ruminococcus* sp. AM36-5:2293211 |
| 7.19E−04 | 2.44E−05 | 1.34E−04 | −5.72E−01 | *Dorea* sp. OM02-2LB:2292347 |
| 7.33E−04 | 1.55E−05 | 4.71E−05 | −6.08E−01 | *Collinsella* sp. TM09-10AT:2292343 |
| 7.47E−04 | 5.43E−04 | 9.49E−07 | 7.81E−01 | *Coprococcus* sp. AM25-15LB:2302944 |
| 7.91E−04 | 1.86E−06 | 1.46E−05 | −5.33E−01 | *Ruminococcus* sp. TF10-12AC:2293239 |
| 8.05E−04 | 1.82E−05 | 9.46E−05 | −7.05E−01 | *Collinsella* sp. AF20-14LB:2292221 |
| 8.05E−04 | 2.21E−05 | 1.14E−04 | −6.51E−01 | *Collinsella* sp. AM44-11:2292323 |
| 8.41E−04 | 8.09E−05 | 1.82E−04 | −4.57E−01 | *Subdoligranulum variabile* DSM 15176:411471 |
| 8.41E−04 | 4.97E−04 | 1.21E−03 | −6.35E−01 | *Coprococcus catus*:116085 |
| 8.45E−04 | 1.10E−05 | 9.81E−05 | −7.91E−01 | *Ruminococcus* sp. AF17-1AC:2293152 |
| 8.58E−04 | 4.36E−04 | 7.00E−05 | −6.08E−01 | *Ruminococcus champanellensis* 18P13 = JCM 17042:213810 |
| 8.70E−04 | 6.26E−05 | 2.87E−03 | −6.55E−01 | *Bifidobacterium animalis*:28025 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 8.83E−04 | 4.26E−05 | 2.16E−04 | −6.76E−01 | *Dorea* sp. OM07-5:2293100 |
| 8.94E−04 | 9.03E−04 | 9.72E−04 | −8.47E−01 | *Ruminococcus lactaris* ATCC 29176:471875 |
| 9.19E−04 | 6.87E−05 | 1.34E−04 | −6.90E−01 | *Ruminococcus* sp. AM27-11LB:2293191 |
| 9.42E−04 | 6.27E−06 | 2.66E−06 | 3.64E−01 | *Plantactinospora* sp. BB1:2071627 |
| 9.59E−04 | 2.40E−04 | 3.24E−04 | −8.16E−01 | *Lachnospiraceae bacterium* OM02-26:2292908 |
| 9.62E−04 | 3.17E−05 | 1.20E−04 | −7.00E−01 | *Collinsella* sp. AM24-1:2292031 |
| 9.80E−04 | 2.16E−05 | 5.96E−05 | −6.47E−01 | *Collinsella* sp. AM41-2BH:2292320 |
| 1.01E−03 | 6.38E−04 | 1.59E−03 | −8.07E−01 | *Blautia* sp. SG-772:2109334 |
| 1.04E−03 | 3.79E−04 | 7.50E−04 | −7.35E−01 | *Ruminococcus* sp. AM41-10BH:2293213 |
| 1.08E−03 | 5.59E−05 | 4.02E−05 | −4.46E−01 | *Coprococcus* sp. AF38-1:2302943 |
| 1.12E−03 | 3.76E−06 | 6.68E−05 | −5.28E−01 | *Clostridium* sp. OM05-9:2293045 |
| 1.13E−03 | 3.75E−04 | 3.15E−04 | −7.03E−01 | *Blautia* sp. *Marseille*-P3087:1917876 |
| 1.13E−03 | 4.31E−03 | 1.34E−03 | 4.08E−01 | *Flavonifractor plautii*:292800 |
| 1.17E−03 | 1.32E−03 | 3.09E−03 | −8.46E−01 | *Ruminococcus* sp. AM23-1:2293188 |
| 1.21E−03 | 5.92E−04 | 1.14E−03 | −1.04E+00 | *Blautia hydrogenotrophica* DSM 10507:476272 |
| 1.22E−03 | 5.25E−04 | 1.05E−03 | −6.12E−01 | *Ruminococcus* sp. OF03-6AA:2293229 |
| 1.25E−03 | 1.02E−05 | 2.94E−05 | −4.18E−01 | *Clostridium* sp. AM29-11AC:2293028 |
| 1.26E−03 | 2.40E−05 | 4.03E−05 | −6.05E−01 | *Ruminococcus* sp. AF31-14BH:2293173 |
| 1.29E−03 | 5.58E−04 | 2.08E−03 | −9.58E−01 | *Erysipelotrichaceae bacterium* GAM147:2109692 |
| 1.35E−03 | 1.44E−06 | 5.13E−06 | −1.97E−01 | *Clostridium* sp. chh4-2:2067550 |
| 1.36E−03 | 4.38E−04 | 1.03E−03 | −6.53E−01 | *Blautia* sp. BCRC 81119:2212480 |
| 1.40E−03 | 2.25E−04 | 7.21E−04 | −8.94E−01 | *Ruminococcus* sp. AF37-20:2293178 |
| 1.40E−03 | 2.23E−05 | 4.12E−05 | −5.64E−01 | *Ruminococcus* sp. AF25-3LB:2293168 |
| 1.40E−03 | 3.50E−05 | 8.30E−05 | −7.30E−01 | *Collinsella* sp. AM33-4BH:2292315 |
| 1.41E−03 | 4.24E−05 | 5.31E−05 | −3.87E−01 | *Roseburia* sp. AF42-8:2293137 |
| 1.42E−03 | 4.21E−05 | 2.79E−05 | −3.76E−01 | *Coprococcus eutactus* ATCC 27759:411474 |
| 1.43E−03 | 3.93E−06 | 1.53E−17 | 5.73E−02 | [*Clostridium*] *bolteae* WAL-14578:742732 |
| 1.45E−03 | 4.32E−06 | 3.95E−06 | −2.20E−01 | *Campylobacter jejuni*:197 |
| 1.46E−03 | 4.59E−05 | 9.68E−05 | −7.31E−01 | *Blautia* sp. TF12-31AT:2292989 |
| 1.49E−03 | 1.48E−03 | 3.16E−03 | −6.41E−01 | *Blautia massiliensis*:1737424 |
| 1.49E−03 | 1.88E−04 | 4.78E−04 | −9.73E−01 | *Collinsella* sp. AF28-5AC:2292227 |
| 1.54E−03 | 3.47E−05 | 9.81E−05 | −5.55E−01 | *Lachnotalea* sp. AF33-28:2292046 |
| 1.56E−03 | 1.79E−05 | 4.76E−05 | −5.12E−01 | *Christensenella* sp. *Marseille*-P3954:2086585 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 1.57E−03 | 6.08E−03 | 5.49E−03 | −7.04E−01 | *Ruminococcus lactaris*:46228 |
| 1.59E−03 | 9.42E−06 | 2.16E−05 | −4.76E−01 | *Ruminococcus* sp. AF24-16:2293162 |
| 1.64E−03 | 8.80E−05 | 1.82E−04 | −6.84E−01 | *Ruminococcus* sp. AF14-10:2292247 |
| 1.69E−03 | 1.83E−04 | 4.54E−05 | 4.81E−01 | *Flavonifractor plautii* ATCC 29863:411475 |
| 1.69E−03 | 1.29E−02 | 1.78E−02 | −5.59E−01 | [*Eubacterium*] *hallii*:39488 |
| 1.69E−03 | 3.82E−06 | 3.54E−06 | −1.46E−01 | *Leuconostoc gelidum* subsp. *gasicomitatum* LMG 18811:762550 |
| 1.73E−03 | 3.07E−04 | 1.35E−05 | −3.25E−01 | *Pseudoflavonifractor* sp. An44:1965635 |
| 1.80E−03 | 9.78E−04 | 1.86E−03 | −1.09E+00 | *Collinsella* sp. TF05-9AC:2292330 |
| 1.86E−03 | 6.63E−05 | 4.48E−04 | −7.12E−01 | *Clostridium* sp. *Marseille*-P3244:1871020 |
| 1.89E−03 | 4.03E−05 | 7.56E−05 | −5.10E−01 | *Butyricicoccus* sp. OF10-2:2292298 |
| 1.90E−03 | 3.28E−05 | 8.59E−05 | −5.54E−01 | *Collinsella* sp. AM20-15AC:2292029 |
| 1.92E−03 | 3.63E−06 | 9.38E−06 | −3.71E−01 | *Eubacterium sulci* ATCC 35585:888727 |
| 1.92E−03 | 3.59E−05 | 1.04E−04 | −6.64E−01 | *Collinsella* sp. AF04-24:2292208 |
| 1.93E−03 | 3.48E−03 | 7.74E−03 | −1.20E+00 | *Collinsella aerofaciens*:74426 |
| 1.94E−03 | 2.13E−06 | 9.26E−06 | −2.13E−01 | *Collinsella* sp. AM29-10AC:2292313 |
| 1.97E−03 | 1.07E−04 | 7.29E−05 | −2.62E−01 | *Alistipes inops*:1501391 |
| 1.98E−03 | 4.10E−04 | 1.96E−04 | 5.52E−01 | *Clostridiales bacterium* VE202-03:1232439 |
| 2.00E−03 | 2.98E−06 | 2.10E−05 | −4.41E−01 | *Collinsella* sp. TM04-9:2292339 |
| 2.00E−03 | 3.58E−05 | 1.02E−04 | −7.39E−01 | *Collinsella* sp. AM42-18AC:2292321 |
| 2.01E−03 | 5.54E−04 | 2.45E−05 | 5.79E−01 | [*Clostridium*] *clostridioforme* 90A7:999407 |
| 2.03E−03 | 3.18E−05 | 6.93E−05 | −5.21E−01 | *Clostridiaceae bacterium* AF29-16BH:2292179 |
| 2.05E−03 | 1.30E−04 | 2.27E−04 | −4.40E−01 | *Dora longicatena* AGR2136:1280698 |
| 2.07E−03 | 2.83E−05 | 1.31E−04 | −5.77E−01 | *Collinsella* sp. OF02-10:2292324 |
| 2.08E−03 | 1.03E−05 | 2.27E−05 | −4.85E−01 | *Collinsella* sp. AF18-8LB:2292218 |
| 2.20E−03 | 2.42E−03 | 3.85E−04 | −7.14E−01 | *Ruminococcus callidus* ATCC 27760:411473 |
| 2.22E−03 | 1.42E−05 | 4.30E−06 | −1.99E−01 | *Campylobacter coli*:195 |
| 2.23E−03 | 2.39E−05 | 4.31E−05 | −6.19E−01 | *Collinsella* sp. AF29-7AC:2292010 |
| 2.23E−03 | 1.52E−04 | 2.59E−04 | −4.71E−01 | *Blautia* sp. AF19-10LB:2292961 |
| 2.27E−03 | 3.89E−05 | 7.59E−05 | −4.90E−01 | *Ruminococcus* sp. AM33-14:2293205 |
| 2.27E−03 | 3.07E−05 | 8.70E−06 | 3.36E−01 | [*Clostridium*] *bolteae* 90B8:997897 |
| 2.32E−03 | 2.17E−04 | 3.85E−04 | −8.20E−01 | *Lachnospiraceae bacterium* AM26-1LB:2292906 |
| 2.35E−03 | 1.71E−05 | 3.41E−05 | −5.63E−01 | *Collinsella* sp. TF12-2AT:2292337 |
| 2.39E−03 | 2.53E−05 | 1.17E−04 | −5.73E−01 | *Collinsella* sp. AF14-35:2292213 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 2.52E−03 | 2.04E−03 | 3.07E−03 | −1.03E+00 | *Asaccharobacter celatus*:394340 |
| 2.53E−03 | 3.93E−04 | 1.43E−05 | 7.50E−01 | *Lachnospiraceae bacterium* 6_1_63FAA:658083 |
| 2.55E−03 | 1.74E−03 | 1.84E−05 | 7.26E−01 | *Lactobacillus fermentum*:1613 |
| 2.62E−03 | 1.41E−05 | 8.33E−05 | −6.33E−01 | *Ruminococcus* sp. AF17-6:2293154 |
| 2.64E−03 | 3.89E−04 | 1.35E−05 | 7.17E−01 | *Coprococcus* sp. HPP0074:1078090 |
| 2.70E−03 | 1.18E−05 | 1.47E−05 | −3.52E−01 | *Collinsella* sp. AF05-8-2:2292209 |
| 2.71E−03 | 4.81E−06 | 2.00E−05 | −3.00E−01 | *Christensenella timonensis*:1816678 |
| 2.74E−03 | 2.36E−06 | 1.04E−05 | −3.59E−01 | *Lachnospiraceae bacterium* VE202-12:1232455 |
| 2.74E−03 | 1.71E−04 | 3.08E−04 | −6.08E−01 | *Blautia* sp. TM10-2:2292990 |
| 2.87E−03 | 7.81E−04 | 1.82E−03 | −9.21E−01 | *Ruminococcus* sp. AF16-50:2293149 |
| 2.93E−03 | 1.11E−03 | 8.28E−04 | −5.44E−01 | *Eubacterium ramulus*:39490 |
| 3.01E−03 | 6.41E−04 | 1.60E−03 | −8.10E−01 | *Romboutsia timonensis*:1776391 |
| 3.04E−03 | 5.39E−04 | 8.81E−04 | −5.87E−01 | *Clostridiales bacterium* KLE1615:1715004 |
| 3.10E−03 | 5.21E−05 | 7.89E−05 | −7.08E−01 | *Collinsella* sp. AM36-4AA:2292317 |
| 3.13E−03 | 5.26E−04 | 8.04E−04 | −7.01E−01 | *Clostridium* sp. SS2/1:411484 |
| 3.21E−03 | 1.59E−04 | 2.41E−05 | 6.28E−01 | *Lachnospiraceae bacterium* AM25-17:2302974 |
| 3.21E−03 | 2.76E−06 | 2.17E−06 | −1.15E−01 | *Lactococcus lactis* subsp. *lactis bv. diacetylactis*:44688 |
| 3.24E−03 | 3.42E−03 | 2.29E−03 | −9.29E−01 | *Ruminococcus* sp. AF19-15:2293157 |
| 3.35E−03 | 2.23E−05 | 8.63E−05 | −5.78E−01 | *Collinsella* sp. TM05-38:2292341 |
| 3.49E−03 | 1.96E−04 | 6.06E−04 | −7.95E−01 | *Ruminococcus* sp. AM43-6:2293216 |
| 3.49E−03 | 6.23E−04 | 2.40E−03 | −9.94E−01 | *Ruminococcus* sp. OM07-17:2293233 |
| 3.53E−03 | 5.53E−07 | 3.13E−06 | −2.76E−01 | *Ruminococcus* sp. AM29-10LB:2293197 |
| 3.62E−03 | 1.83E−04 | 4.74E−04 | −9.04E−01 | *Ruminococcus* sp. AF21-11:2293161 |
| 3.62E−03 | 1.40E−05 | 3.63E−05 | −4.37E−01 | [*Ruminococcus*] *gnavus* CC55_001C:1073375 |
| 3.64E−03 | 1.02E−06 | 7.33E−06 | −3.05E−01 | *Clostridium* sp. KNHs214:1540257 |
| 3.65E−03 | 1.83E−05 | 4.77E−06 | 4.06E−01 | *Bacteroides* sp. OM05-10AA:2292282 |
| 3.69E−03 | 2.19E−05 | 4.96E−05 | −4.27E−01 | *Lachnoclostridium* sp. An298:1965627 |
| 3.71E−03 | 1.96E−05 | 4.83E−05 | −5.76E−01 | *Collinsella* sp. OM07-12:2292328 |
| 3.76E−03 | 2.60E−05 | 5.42E−05 | −4.56E−01 | *Clostridium* sp. AM45-5:2292306 |
| 3.80E−03 | 1.55E−06 | 2.60E−06 | −1.38E−01 | *Collinsella* sp. AM10-32:2292021 |
| 3.83E−03 | 3.94E−05 | 6.79E−05 | −3.81E−01 | *Ruminococcus* sp. OM07-7:2293234 |
| 3.86E−03 | 3.17E−06 | 1.43E−05 | −2.84E−01 | *Clostridiales bacterium Marseille*-P2846:1852363 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 3.89E−03 | 1.28E−04 | 3.16E−04 | −5.00E−01 | *Dorea formicigenerans* ATCC 27755:411461 |
| 4.11E−03 | 2.01E−04 | 5.38E−04 | −7.59E−01 | *Ruminococcus* sp. AM54-1NS:2293226 |
| 4.15E−03 | 1.91E−03 | 1.73E−03 | −5.62E−01 | *Lachnospira pectinoschiza*:28052 |
| 4.22E−03 | 2.37E−06 | 1.16E−05 | −2.41E−01 | *Clostridioides difficile* 050-P50-2011:997828 |
| 4.24E−03 | 4.28E−05 | 6.65E−05 | −6.09E−01 | *Collinsella* sp. AM13-34:2292024 |
| 4.32E−03 | 2.67E−04 | 3.10E−04 | −6.39E−01 | *Lachnoclostridium* sp. SNUG30370:2126739 |
| 4.35E−03 | 2.48E−05 | 6.11E−05 | −5.32E−01 | *Collinsella* sp. AF31-11:2292011 |
| 4.47E−03 | 3.45E−06 | 9.51E−92 | 1.60E−01 | *Prevotella* sp. P4-98:2024219 |
| 4.49E−03 | 6.84E−04 | 1.87E−05 | 8.13E−01 | *Lachnospiraceae bacterium* 6_1_37FAA:658656 |
| 4.51E−03 | 2.72E−03 | 2.93E−04 | 6.08E−01 | [*Clostridium*] *clostridioforme*: 1531 |
| 4.53E−03 | 2.77E−05 | 1.39E−04 | −6.83E−01 | *Collinsella* sp. TF10-11AT:2292335 |
| 4.60E−03 | 3.73E−04 | 2.10E−04 | −3.77E−01 | *Collinsella* sp. MS5:1499681 |
| 4.64E−03 | 1.27E−05 | 2.54E−05 | −5.10E−01 | *Collinsella* sp. AF38-3AC:2292015 |
| 4.66E−03 | 5.10E−03 | 7.10E−03 | −6.48E−01 | *Subdoligranulum* sp. APC924/74:2086273 |
| 4.70E−03 | 8.12E−06 | 2.68E−05 | −4.27E−01 | *Ruminococcus bromii* L2-63:657321 |
| 4.73E−03 | 2.02E−05 | 4.53E−05 | −5.41E−01 | *Collinsella* sp. TF08-11AT:2292333 |
| 4.79E−03 | 4.71E−05 | 1.06E−04 | −6.65E−01 | *Collinsella* sp. AF23-4AC:2292224 |
| 4.84E−03 | 2.49E−04 | 2.21E−05 | 4.51E−01 | *Streptococcus intermedius*:1338 |
| 4.85E−03 | 1.91E−06 | 5.45E−06 | −3.68E−01 | *Ruminococcus* sp. AF25-13:2293163 |
| 4.86E−03 | 3.83E−04 | 1.64E−05 | 7.73E−01 | *Lachnospiraceae bacterium* 9_1_43BFAA:658088 |
| 4.87E−03 | 2.42E−05 | 6.25E−05 | −5.59E−01 | *Collinsella* sp. TF07-1:2292332 |
| 4.90E−03 | 7.45E−05 | 2.09E−04 | −7.89E−01 | *Blautia* sp. AM28-36:2292974 |
| 4.92E−03 | 5.18E−05 | 1.46E−04 | −6.35E−01 | *Collinsella* sp. AF23-6:2292225 |
| 4.94E−03 | 1.95E−04 | 5.50E−04 | −7.92E−01 | *Ruminococcus* sp. AF25-19:2293165 |
| 4.95E−03 | 1.15E−03 | 2.93E−05 | 7.72E−01 | [*Clostridium*] *scindens* ATCC 35704:411468 |
| 4.96E−03 | 3.37E−04 | 7.71E−04 | −5.98E−01 | *Clostridium* sp. AM49-4BH:2293035 |
| 4.96E−03 | 3.37E−04 | 1.31E−04 | 4.53E−01 | *Flavonifractor plautii* 1_3_50AFAA:742738 |
| 4.98E−03 | 1.09E−06 | 1.73E−05 | −2.21E−01 | *Olsenella* sp. GAM18:2109685 |
| 5.01E−03 | 2.26E−05 | 7.60E−05 | −6.70E−01 | *Collinsella* sp. AM12-1:2292023 |
| 5.06E−03 | 4.14E−05 | 7.78E−05 | −6.50E−01 | *Collinsella* sp. AF33-16:2292012 |
| 5.09E−03 | 1.03E−05 | 7.02E−06 | −3.03E−01 | *Faecalibacterium* sp. An77:1965655 |
| 5.11E−03 | 5.53E−05 | 4.51E−05 | −3.54E−01 | *Lachnoclostridium edouardi*:1926283 |
| 5.12E−03 | 4.50E−04 | 8.20E−04 | −6.45E−01 | *Butyricicoccus* sp. GAM44:2109686 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 5.20E−03 | 5.10E−05 | 7.85E−05 | −4.05E−01 | *Butyricicoccus* sp. AM29-23AC:2292295 |
| 5.20E−03 | 4.04E−04 | 2.79E−04 | −5.42E−01 | *Ruminococcus* sp. AF45-4BH:2292071 |
| 5.22E−03 | 7.70E−06 | 2.17E−06 | −1.28E−01 | *Ruminococcus flavefaciens*:1265 |
| 5.31E−03 | 3.34E−06 | 3.11E−06 | −1.17E−01 | *Collinsella* sp. AM10-48:2292022 |
| 5.46E−03 | 1.41E−03 | 5.18E−05 | 7.25E−01 | *Lachnospiraceae bacterium* 5_1_57FAA:658085 |
| 5.61E−03 | 6.83E−04 | 1.59E−03 | −8.67E−01 | *Ruminococcus* sp. AF34-12:2293177 |
| 5.63E−03 | 2.64E−04 | 4.61E−04 | −5.02E−01 | *Oscillibacter* sp. ER4:1519439 |
| 5.67E−03 | 2.86E−04 | 3.66E−05 | −3.65E−01 | *Ruminococcus* sp. AM22-13:2292074 |
| 5.96E−03 | 2.59E−05 | 7.49E−05 | −5.99E−01 | *Collinsella* sp. AF11-11:2292212 |
| 5.98E−03 | 6.28E−05 | 1.05E−04 | −5.17E−01 | *Butyricicoccus* sp. AF24-19AC:2292199 |
| 6.00E−03 | 5.93E−05 | 7.07E−05 | −2.96E−01 | *Clostridium* sp. AF20-7:2293002 |
| 6.07E−03 | 4.56E−05 | 4.73E−05 | −3.93E−01 | *Roseburia* sp. AF02-12:2293126 |
| 6.10E−03 | 1.85E−05 | 8.16E−06 | −8.51E−02 | *Peptococcus niger*:2741 |
| 6.29E−03 | 2.65E−04 | 5.40E−04 | −5.83E−01 | *Clostridium* sp. AF36-18BH:2293014 |
| 6.38E−03 | 1.08E−03 | 5.59E−04 | 3.69E−01 | *Oscillospiraceae bacterium* VE202-24:1232459 |
| 6.48E−03 | 5.08E−05 | 1.39E−04 | −5.39E−01 | *Adlercreutzia equolifaciens* DSM 19450:1384484 |
| 6.56E−03 | 1.78E−05 | 4.64E−05 | −5.52E−01 | *Collinsella* sp. AF02-46-1:2292207 |
| 6.81E−03 | 2.41E−07 | 4.05E−05 | −1.64E−01 | *Odoribacter* sp. AF15-53:2292236 |
| 6.87E−03 | 4.36E−05 | 8.10E−06 | −1.72E−01 | *Clostridium* sp. OM07-9AC:2293048 |
| 6.87E−03 | 6.15E−04 | 2.37E−06 | 7.52E−01 | *Anaerostipes* sp. BG01:2025494 |
| 6.96E−03 | 6.26E−05 | 5.91E−06 | 5.05E−01 | [*Ruminococcus*] *gnavus* AGR2154:1384063 |
| 7.01E−03 | 9.19E−07 | 1.35E−05 | −2.51E−01 | *Prevotella timonensis*:386414 |
| 7.08E−03 | 3.49E−05 | 4.40E−05 | −5.18E−01 | *Collinsella* sp. OM08-14AT:2292329 |
| 7.10E−03 | 1.18E−06 | 2.49E−06 | −1.65E−01 | *Enterorhabdus mucosicola* DSM 19490:1121866 |
| 7.10E−03 | 1.83E−06 | 2.34E−05 | −1.31E−01 | *Clostridium* sp. AF15-6B:2292998 |
| 7.30E−03 | 2.77E−04 | 6.29E−04 | −9.24E−01 | *Collinsella* sp. AF25-2LB:2292226 |
| 7.33E−03 | 4.37E−05 | 6.69E−05 | −5.25E−01 | *Catabacter hongkongensis*:270498 |
| 7.35E−03 | 5.23E−06 | 6.11E−06 | −2.42E−01 | *Romboutsia* sp. MT17:1720299 |
| 7.40E−03 | 1.73E−04 | 2.01E−04 | −4.64E−01 | *Ruminococcaceae bacterium*:1898205 |
| 7.45E−03 | 1.15E−03 | 2.11E−04 | 8.92E−01 | *Paraprevotella clara*:454154 |

TABLE 26-continued

Whole genome sequencing was performed on fecal samples from subject with and without cancer and the reads are classified and abundance of each species or strain was estimated computationally. The fold change difference and statistical significance (inverse p value, Mann Whitney U test) was calculated for abundances between cancer and control sample cohorts. P values are filtered for a false discovery rate of 0.05, and hits passing the threshold are included in Table 26.

| p value (Mann Whitney U) | Mean Abundance in Cancer Samples | Mean Abundance in Control Samples | log10 Fold Change (Cancer vs Healthy) | Organism (name:NCBI Taxonomic ID) |
|---|---|---|---|---|
| 7.54E−03 | 1.39E−06 | 1.14E−04 | −2.15E−01 | *Clostridiales bacterium* VE202-08:1232449 |
| 7.68E−03 | 2.17E−04 | 6.29E−04 | −6.86E−01 | *Clostridium* sp. AM34-9AC:2293030 |
| 7.71E−03 | 1.08E−05 | 0.00E+00 | 1.39E−01 | *Lactobacillus johnsonii* F19785:633699 |
| 7.74E−03 | 6.81E−06 | 2.93E−06 | −1.33E−01 | *Lactococcus lactis* subsp. *cremons* UC509.9:1111678 |
| 7.79E−03 | 3.10E−05 | 1.19E−04 | −5.87E−01 | *Collinsella* sp. AF37-9:2292014 |
| 7.79E−03 | 1.61E−05 | 4.56E−05 | −5.04E−01 | *Collinsella* sp. AM43-1:2292322 |
| 7.92E−03 | 4.16E−05 | 2.09E−05 | −2.39E−01 | *Christensenella massiliensis*:1805714 |
| 8.01E−03 | 4.41E−05 | 1.14E−04 | 3.78E−01 | *Bacteroides* sp. KFT8:2025659 |
| 8.02E−03 | 1.17E−04 | 2.01E−04 | −5.00E−01 | *Massilioclostridium coli*:1870991 |
| 8.06E−03 | 1.92E−04 | 4.38E−04 | −7.40E−01 | *Ruminococcus* sp. AM47-2BH:2293221 |
| 8.18E−03 | 2.10E−05 | 5.25E−06 | 4.24E−01 | *Streptococcus gordonii* str. *Challis* substr. CH1:467705 |
| 8.18E−03 | 1.05E−05 | 4.14E−05 | −4.72E−01 | *Alistipes indistinctus*:626932 |
| 8.28E−03 | 5.31E−04 | 3.20E−04 | 3.10E−01 | *Clostridium* sp. ATCC BAA-442:649724 |
| 8.37E−03 | 3.12E−05 | 5.89E−05 | −4.10E−01 | *Ruminococcus* sp. AM41-2AC:2293214 |
| 8.38E−03 | 2.39E−05 | 1.16E−05 | −2.47E−01 | *Eubacteriaceae bacterium* CHKCI005:1780381 |
| 8.40E−03 | 8.35E−07 | 1.85E−05 | −3.29E−01 | *Hungatella hathewayi* WAL-18680:742737 |
| 8.40E−03 | 6.02E−04 | 9.60E−05 | 5.45E−01 | *Streptococcus gordonii*:1302 |
| 8.43E−03 | 6.12E−05 | 1.10E−04 | −5.93E−01 | *Blautia* sp. AM46-3MH:2292977 |
| 8.44E−03 | 4.99E−05 | 5.92E−05 | −5.43E−01 | *Collinsella* sp. TM10-22:2292344 |
| 8.52E−03 | 5.84E−05 | 1.51E−04 | −6.03E−01 | *Collinsella* sp. AF15-51:2292214 |
| 8.56E−03 | 2.56E−05 | 1.51E−05 | −3.12E−01 | *Clostridioides difficile* Y358:1151389 |
| 8.69E−03 | 4.81E−04 | 9.51E−05 | 6.41E−01 | *Anaerostipes caccae* DSM 14662:411490 |
| 8.80E−03 | 2.47E−05 | 2.21E−05 | −2.39E−01 | *Roseburia* sp. OM04-10AA:2293141 |
| 8.88E−03 | 2.52E−04 | 6.23E−04 | −5.19E−01 | *Anaeromassilibacillus* sp. *Marseille*-P3876:2086583 |
| 8.95E−03 | 5.36E−05 | 1.08E−05 | 5.03E−01 | *Bacteroides* sp. AF36-11BH:2292933 |

Figure 42:
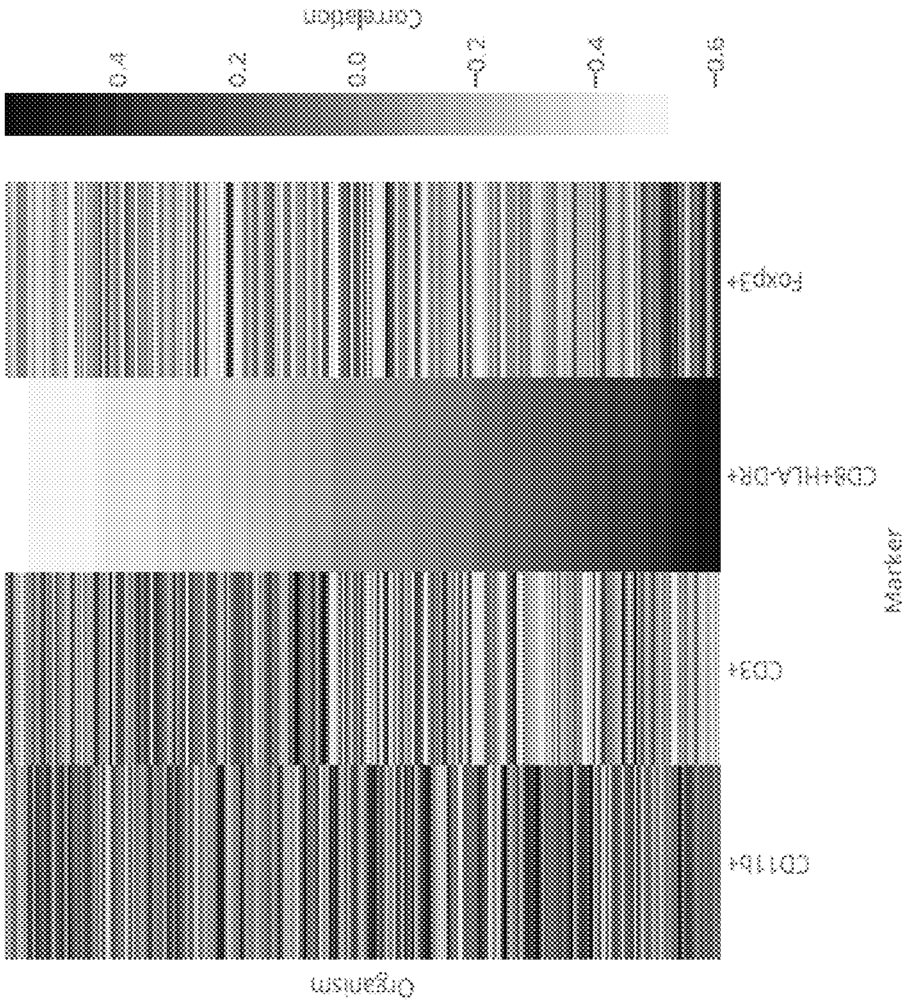
FIG. 42 graphically illustrates a heatmap of the Spearman correlations calculated between each flow gate (CD11b+, CD3+, CD8-HLADR+ and FoxP3+) for humans and each organism in the gut whose mean abundance is greater than or equal to 0.0005; as discussed in detail in Example 7, below.

Spearman correlations were calculated from the peripheral blood flow cytometry analyses and microbiome whole genome sequencing results. Spearman correlations were calculated between each flow gate for humans and each organism in the gut whose mean abundance is greater than or equal to 0.0005. Results are reported after filtering for a false discovery rate of 0.15 as illustrated in Table 24. Flow cytometry gated percentages for CD11b+, CD3+, CD8-HLADR+ and FoxP3+ populations were plotted with respect to whether an organism is present in the microbiome above a certain threshold abundance or not, revealing relationships between the presence or absence of microbes and the immune cell population as reported in FIG. 41A-D. Spearman correlations were calculated between each flow gate (CD11b+, CD3+, CD8-HLADR+ and FoxP3+) for humans and each organism in the gut whose mean abundance is greater than or equal to 0.0005. Results are plotted in a heat map fashion as reported in FIG. 42.

TABLE 24

| Mean Abundance | Organism | p (p value over all samples, Spearman) | p_c (p–value for Cancer Samples only) | p_h (p–value for Healthy Samples Only) | rho (Spearman) | rho _c (cancer only) | rho _h (healthy only) | Immune Gate |
|---|---|---|---|---|---|---|---|---|
| 0.0006 | *Bacteroides massiliensis* B84634 = Timone 84634 = DSM 17679 = JCM 13223:1121098 | 0.0007 | 0.0153 | 0.0114 | −0.5244 | −0.6783 | −0.4884 | CD14+CD15+ |
| 0.0009 | *Clostridiales* bacterium KLE1615:1715004 | 0.0015 | 0.0625 | 0.0150 | −0.4959 | −0.5524 | −0.4716 | CD14+CD15+ |
| 0.0020 | *Lachnospiraceae* bacterium 8_1_57FAA:665951 | 0.0005 | 0.0676 | 0.0041 | 0.5385 | 0.5439 | 0.5432 | CD14+CD15− |
| 0.0020 | *Lachnospiraceae* bacterium 8_1_57FAA:665951 | 0.0006 | 0.0190 | 0.0157 | −0.5338 | −0.6620 | −0.4687 | CD14−CD15+ |
| 0.0006 | *Bacteroides massiliensis* B84634 = Timone 84634 = DSM 17679 = JCM 13223:1121098 | 0.0009 | 0.0051 | 0.0071 | −0.5180 | −0.7483 | −0.5148 | CD15+CD14+ |
| 0.0044 | *Clostridium* sp. AF15-41:2292996 | 0.0020 | 0.1268 | 0.0804 | −0.4850 | −0.4660 | −0.3492 | CD15+CD14+ |
| 0.0020 | *Lachnospiraceae* bacterium 8_1_57FAA:665951 | 0.0015 | 0.0490 | 0.0235 | −0.4973 | −0.5779 | −0.4427 | CD15+CD14− |
| 0.0020 | *Lachnospiraceae* bacterium 8_1_57FAA:665951 | 0.0016 | 0.0525 | 0.0170 | 0.4943 | 0.5709 | 0.4639 | CD15-CD14+ |
| 0.0015 | *Clostridium sporogenes*:1509 | 0.0019 | 0.7379 | 0.0224 | 0.4867 | 0.1082 | 0.4458 | CD3+ |
| 0.0012 | *Eubacterium* sp. OM08-24:2292352 | 0.0003 | 0.6366 | 0.0055 | 0.5502 | 0.1523 | 0.5284 | CD3+ |
| 0.0028 | *Lachnoclostridium* sp. SNUG30099:2126738 | 0.0002 | 0.5291 | 0.0092 | 0.5621 | 0.2019 | 0.5005 | CD3+ |
| 0.0015 | *Clostridium sporogenes*:1509 | 0.0019 | 0.2760 | 0.0244 | 0.4886 | 0.3424 | 0.4402 | CD3+CD56+ |
| 0.0028 | *Lachnoclostridium* sp. SNUG30099:2126738 | 0.0009 | 0.5764 | 0.0182 | 0.5167 | 0.1796 | 0.4595 | CD3+CD56+ |
| 0.0012 | *Eubacterium* sp. OM08-24:2292352 | 0.0004 | 0.6366 | 0.0055 | −0.5475 | −0.1523 | −0.5284 | CD3− |
| 0.0028 | *Lachnoclostridium* sp. SNUG30099:2126738 | 0.0003 | 0.5291 | 0.0092 | −0.5553 | −0.2019 | −0.5005 | CD3− |
| 0.0082 | *Coprococcus* comes:410072 | 0.0014 | 0.7456 | 0.0245 | −0.4993 | −0.1049 | −0.4400 | CD4+HLA−DR+ |
| 0.0057 | *Ruminococcus* sp. AM42-11:2292372 | 0.0008 | 0.2170 | 0.0055 | −0.5196 | −0.3846 | −0.5289 | CD4+HLA−DR+ |
| 0.0075 | *Subdoligranulum* sp. APC924/74: 2086273 | 0.0007 | 0.7292 | 0.0022 | −0.5247 | −0.1119 | −0.5726 | CD4+HLA−DR+ |
| 0.0082 | *Coprococcus* comes:410072 | 0.0015 | 0.7456 | 0.0260 | 0.4966 | 0.1049 | 0.4360 | CD4+HLA−DR− |
| 0.0022 | *Ruminococcus* sp. AF26−25AA:2293169 | 0.0020 | 0.7908 | 0.0015 | 0.4853 | 0.0858 | 0.5900 | CD4+HLA−DR− |
| 0.0057 | *Ruminococcus* sp. AM42-11:2292372 | 0.0007 | 0.2170 | 0.0042 | 0.5266 | 0.3846 | 0.5430 | CD4+HLA−DR− |
| 0.0075 | *Subdoligranulum* sp. APC924/74: 2086273 | 0.0006 | 0.7292 | 0.0017 | 0.5303 | 0.1119 | 0.5837 | CD4+HLA−DR− |
| 0.0011 | *Blautia* hydrogenotrophic a DSM 10507:476272 | 0.0016 | 0.9562 | 0.0242 | −0.4937 | −0.0178 | −0.4408 | CD8+HLA−DR+ |

TABLE 24-continued

| Mean Abundance | Organism | p (p value over all samples, Spearman) | p_c (p-value for Cancer Samples only) | p_h (p-value for Healthy Samples Only) | rho (Spearman) | rho _c (cancer only) | rho _h (healthy only) | Immune Gate |
|---|---|---|---|---|---|---|---|---|
| 0.0005 | *Blautia* sp. AF19-34: 2292963 | 0.0017 | 0.9175 | 0.2140 | −0.4916 | −0.0336 | −0.2521 | CD8+HLA-DR+ |
| 0.0011 | *Blautia* sp. AF22-SLB:2292964 | 0.0005 | 0.4694 | 0.1908 | −0.5345 | −0.2314 | −0.2650 | CD8+HLA-DR+ |
| 0.0006 | *Blautia* sp. AF25-12LB:2292965 | 0.0017 | 0.4979 | 0.1627 | −0.4915 | −0.2171 | −0.2821 | CD8+HLA-DR+ |
| 0.0005 | *Clostridiales* bacterium CCNA10:2109688 | 0.0001 | 0.0368 | 0.0056 | 0.5933 | 0.6060 | 0.5276 | CD8+HLA-DR+ |
| 0.0006 | *Clostridium* sp. Marseille-P3244: 1871020 | 0.0014 | 0.9287 | 0.0092 | −0.4993 | −0.0290 | −0.5005 | CD8+HLA-DR+ |
| 0.0082 | *Coprococcus* comes:410072 | 0.0008 | 0.7456 | 0.0397 | −0.5216 | 0.1049 | −0.4058 | CD8+HLA-DR+ |
| 0.0010 | *Dorealongicatena* DSM 13814:411462 | 0.0003 | 0.9656 | 0.0208 | −0.5553 | 0.0140 | −0.4509 | CD8+HLA-DR+ |
| 0.0011 | *Blautia* hydrogenotrophic a DSM 10507:476272 | 0.0017 | 0.9562 | 0.0252 | 0.4928 | 0.0178 | 0.4380 | CD8+HLA-DR− |
| 0.0005 | *Blautia* sp. AF19-34: 2292963 | 0.0015 | 0.9175 | 0.1917 | 0.4962 | 0.0336 | 0.2645 | CD8+HLA-DR− |
| 0.0011 | *Blautia* sp. AF22-SLB:2292964 | 0.0005 | 0.4694 | 0.1781 | 0.5373 | 0.2314 | 0.2725 | CD8+HLA-DR− |
| 0.0006 | *Blautia* sp. AF25-12LB:2292965 | 0.0016 | 0.4979 | 0.1483 | 0.4957 | 0.2171 | 0.2916 | CD8+HLA-DR− |
| 0.0005 | *Clostridiales* bacterium CCNA10:2109688 | 0.0001 | 0.0368 | 0.0045 | −0.5990 | −0.6060 | −0.5392 | CD8+HLA-DR− |
| 0.0006 | *Clostridium* sp. Marseille-P3244: 1871020 | 0.0013 | 0.9287 | 0.0081 | 0.5019 | 0.0290 | 0.5080 | CD8+HLA-DR− |
| 0.0082 | *Coprococcus* comes:410072 | 0.0007 | 0.7456 | 0.0362 | 0.5240 | −0.1049 | 0.4126 | CD8+HLA-DR− |
| 0.0010 | *Dorealongicatena* DSM 13814:411462 | 0.0003 | 0.9656 | 0.0221 | 0.5540 | −0.0140 | 0.4468 | CD8+HLA-DR− |
| 0.0005 | *Blautia* sp. AF19-34: 2292963 | 0.0016 | 0.2321 | 0.0244 | −0.4947 | 0.3732 | −0.4403 | Foxp3+ |
| 0.0022 | *Collinsella* sp. TF05-9AC:2292330 | 0.0015 | 0.7477 | 0.0047 | −0.4984 | 0.1040 | −0.5369 | Foxp3+ |

TABLE 25

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD11b+ | *Alistipes putredinis* DSM 17216:445970 | 3.89E−04 | −4.04E−01 | 7.90E−03 | 3.12E−03 |
| CD11b+ | *Lachnospiraceae* bacterium AM23-7LB:2292904 | 3.16E−06 | −5.15E−01 | 2.34E−04 | 5.51E−05 |
| CD11b+ | *Blautia obeum*:40520 | 7.60E−06 | −4.97E−01 | 7.12E−02 | 3.12E−02 |
| CD11b+ | *Dorea formicigenerans* ATCC 27755:411461 | 1.03E−05 | −4.91E−01 | 3.16E−04 | 1.28E−04 |
| CD11b+ | *Sellimonas intestinalis*:1653434 | 1.12E−05 | 4.89E−01 | 6.83E−04 | 2.34E−03 |
| CD11b+ | *Drancourtella massiliensis*:1632013 | 1.73E−05 | 4.80E−01 | 1.40E−04 | 5.99E−04 |
| CD11b+ | *Ruminococcus* sp. DSM 100440:1671366 | 7.27E−05 | 4.47E−01 | 8.68E−04 | 2.26E−03 |
| CD11b+ | *Blautia obeum* ATCC 29174:411459 | 8.67E−05 | −4.43E−01 | 5.35E−04 | 1.78E−04 |
| CD11b+ | *Clostridium* sp. ATCC BAA-442:649724 | 1.01E−04 | 4.39E−01 | 3.20E−04 | 5.31E−04 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD11b+ | *Dorea formicigenerans*:39486 | 1.03E−04 | −4.39E−01 | 5.38E−03 | 3.36E−03 |
| CD11b+ | *Blautia* sp. OM07-19:2292985 | 1.15E−04 | −4.36E−01 | 3.73E−04 | 2.11E−04 |
| CD11b+ | *Ruminococcus* sp. AM16-34:2293184 | 2.10E−04 | −4.21E−01 | 1.37E−03 | 3.86E−04 |
| CD11b+ | *Ruminococcus lactaris*:46228 | 2.24E−04 | −4.19E−01 | 5.49E−03 | 6.08E−03 |
| CD11b+ | *Lachnospiraceae* bacterium OM02-26:2292908 | 2.86E−04 | −4.13E−01 | 3.24E−04 | 2.40E−04 |
| CD11b+ | *Lachnospiraceae* bacterium 3_1_46FAA:665950 | 3.65E−04 | 4.06E−01 | 4.77E−04 | 1.06E−03 |
| CD11b+ | *Lachnospiraceae* bacterium AM21-21:2292903 | 4.35E−04 | −4.01E−01 | 5.09E−04 | 2.81E−04 |
| CD11b+ | *Ruminococcaceae* bacterium TF06-43:2292270 | 4.64E−04 | −3.99E−01 | 6.87E−04 | 4.74E−04 |
| CD11b+ | *Anaerostipes hadrus*:649756 | 4.69E−04 | −3.99E−01 | 1.52E−02 | 7.78E−03 |
| CD11b+ | *Clostridiales* bacterium VE202-03:1232439 | 4.83E−04 | 3.98E−01 | 1.96E−04 | 4.10E−04 |
| CD11b+ | *Ruminococcus* sp. OF03-6AA:2293229 | 5.23E−04 | −3.96E−01 | 1.05E−03 | 5.25E−04 |
| CD11b+ | *Lachnospiraceae* bacterium TF10-8AT:2292907 | 5.35E−04 | −3.95E−01 | 3.12E−04 | 1.46E−04 |
| CD11b+ | *Eubacterium ventriosum*:39496 | 5.68E−04 | −3.94E−01 | 1.13E−03 | 4.74E−04 |
| CD11b+ | *Clostridium* sp. L2-50:411489 | 6.60E−04 | −3.89E−01 | 3.67E−03 | 3.38E−05 |
| CD11b+ | *Flavonifractor plautii*:292800 | 7.66E−04 | 3.85E−01 | 1.34E−03 | 4.31E−03 |
| CD11b+ | *Lachnospiraceae* bacterium AM10-38:2292902 | 7.75E−04 | −3.85E−01 | 4.15E−04 | 2.60E−04 |
| CD11b+ | *Ruminococcus lactaris* ATCC 29176:471875 | 7.93E−04 | −3.84E−01 | 9.72E−04 | 9.03E−04 |
| CD11b+ | *Ruminococcus* sp. AF46-10NS:2292072 | 8.86E−04 | −3.81E−01 | 2.70E−04 | 6.76E−05 |
| CD11b+ | *Blautia* sp. TM10-2:2292990 | 1.04E−03 | −3.76E−01 | 3.08E−04 | 1.71E−04 |
| CD11b+ | *Oscillibacter* sp. ER4:1519439 | 1.06E−03 | −3.75E−01 | 4.61E−04 | 2.64E−04 |
| CD11b+ | *Tyzzerella nexilis* DSM 1787:500632 | 1.39E−03 | 3.67E−01 | 1.26E−04 | 3.79E−04 |
| CD11b+ | [*Clostridium*] *bolteae*:208479 | 1.40E−03 | 3.67E−01 | 3.59E−04 | 7.79E−04 |
| CD11b+ | *Blautia* sp. AF26-2:2292966 | 1.47E−03 | −3.66E−01 | 2.86E−04 | 1.84E−04 |
| CD11b+ | *Blautia* sp. OM06-15AC:2292984 | 1.55E−03 | −3.64E−01 | 3.50E−04 | 1.90E−04 |
| CD11b+ | *Butyricicoccus* sp. AF24-19AC:2292199 | 1.82E−03 | −3.59E−01 | 1.05E−04 | 6.28E−05 |
| CD11b+ | *Gemmiger formicilis*:745368 | 1.93E−03 | −3.57E−01 | 3.53E−03 | 1.35E−03 |
| CD11b+ | *Anaerostipes hadrus* DSM 3319:649757 | 2.02E−03 | −3.56E−01 | 5.20E−04 | 2.70E−04 |
| CD11b+ | *Ruminococcus* sp. AF17-12:2293151 | 2.03E−03 | −3.55E−01 | 2.42E−03 | 1.14E−03 |
| CD11b+ | *Ruminococcus* sp. AF12-5:2293146 | 2.14E−03 | −3.54E−01 | 1.31E−04 | 5.02E−05 |
| CD11b+ | [*Eubacterium*] *hallii*.39488 | 2.14E−03 | −3.54E−01 | 1.78E−02 | 1.29E−02 |
| CD11b+ | *Lachnospiraceae* bacterium AM25-27:2292905 | 2.20E−03 | −3.53E−01 | 2.59E−04 | 1.18E−04 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD11b+ | *Ruminococcus faecis* JCM 15917:1298596 | 2.36E−03 | −3.51E−01 | 3.23E−04 | 1.05E−04 |
| CD11b+ | *Roseburia hominis* A2-183:585394 | 2.47E−03 | −3.49E−01 | 1.00E−03 | 8.82E−04 |
| CD14+CD15− | *Mordavella* sp. Marseille-P3756:2086584 | 1.59E−04 | 4.28E−01 | 2.02E−04 | 1.22E−04 |
| CD14+CD15− | *Dorea longicatena* AGR2136:1280698 | 4.28E−04 | 4.02E−01 | 2.27E−04 | 1.30E−04 |
| CD14+CD15− | *Angelakisella massiliensis*:1871018 | 6.30E−04 | 3.91E−01 | 1.18E−04 | 9.54E−05 |
| CD14+CD15- | *Parabacteroides* sp. 2_1_7:457388 | 9.80E−04 | −3.78E−01 | 1.60E−04 | 9.28E−05 |
| CD14+CD15- | *Lachnoclostridium* sp. SNUG30370:2126739 | 1.67E−03 | 3.62E−01 | 3.10E−04 | 2.67E−04 |
| CD14+CD15- | *Lachnospiraceae* bacterium 8_1_57FAA:665951 | 2.68E−03 | 3.46E−01 | 1.89E−03 | 2.97E−03 |
| CD14−CD15+ | *Angelakisella massiliensis*:1871018 | 3.36E−04 | −4.08E−01 | 1.18E−04 | 9.54E−05 |
| CD14−CD15+ | *Ruminococcus* sp. DSM 100440:1671366 | 6.95E−04 | −3.88E−01 | 8.68E−04 | 2.26E−03 |
| CD14−CD15+ | *Mordavella* sp. Marseille-P3756:2086584 | 8.27E−04 | −3.83E−01 | 2.02E−04 | 1.22E−04 |
| CD14−CD15+ | *Lachnospiraceae* bacterium 8_1_57FAA:665951 | 1.43E−03 | −3.66E−01 | 1.89E−03 | 2.97E−03 |
| CD14−CD15+ | *Lachnoclostridium* sp. SNUG30370:2126739 | 1.88E−03 | −3.58E−01 | 3.10E−04 | 2.67E−04 |
| CD15+CD14− | *Lachnoclostridium* sp. SNUG30370:2126739 | 6.40E−04 | −3.90E−01 | 3.10E−04 | 2.67E−04 |
| CD15+CD14− | *Angelakisella massiliensis*:1871018 | 1.14E−03 | −3.73E−01 | 1.18E−04 | 9.54E−05 |
| CD15+CD14− | *Erysipelotrichaceae* bacterium GAM147:2109692 | 2.24E−03 | −3.52E−01 | 2.08E−03 | 5.58E−04 |
| CD15−CD14+ | *Lachnoclostridium* sp. SNUG30370:2126739 | 6.51E−04 | 3.90E−01 | 3.10E−04 | 2.67E−04 |
| CD15−CD14+ | *Angelakisella massiliensis*:1871018 | 1.54E−03 | 3.64E−01 | 1.18E−04 | 9.54E−05 |
| CD15−CD14+ | *Erysipelotrichaceae* bacterium GAM147:2109692 | 1.70E−03 | 3.61E−01 | 2.08E−03 | 5.58E−04 |
| CD3+ | *Blautia obeum*:40520 | 2.07E−05 | 4.76E−01 | 7.12E−02 | 3.12E−02 |
| CD3+ | *Blautia obeum* ATCC 29174:411459 | 4.39E−05 | 4.59E−01 | 5.35E−04 | 1.78E−04 |
| CD3+ | *Ruminococcaceae* bacterium TF06-43:2292270 | 6.13E−05 | 4.51E−01 | 6.87E−04 | 4.74E−04 |
| CD3+ | *Blautia* sp. OM07-19:2292985 | 6.69E−05 | 4.49E−01 | 3.73E−04 | 2.11E−04 |
| CD3+ | *Blautia* sp. AM46-5:2292978 | 7.61E−05 | 4.46E−01 | 2.32E−04 | 6.37E−05 |
| CD3+ | *Ruminococcaceae* bacterium AF10-16:2292180 | 9.35E−05 | 4.41E−01 | 4.61E−04 | 2.21E−04 |
| CD3+ | *Bacteroides finegoldii* CL09T03C10:997888 | 1.06E−04 | −4.38E−01 | 1.05E−04 | 5.69E−05 |
| CD3+ | *Lachnoclostridium* sp. SNUG30099:2126738 | 1.98E−04 | 4.22E−01 | 3.21E−03 | 4.70E−04 |
| CD3+ | *Ruminococcus* sp. AM16-34:2293184 | 2.03E−04 | 4.22E−01 | 1.37E−03 | 3.86E−04 |
| CD3+ | *Flavonifractor plautii*:292800 | 2.12E−04 | −4.21E−01 | 1.34E−03 | 4.31E−03 |
| CD3+ | *Dorea* sp. AM58-8:2292346 | 5.21E−04 | 3.96E−01 | 4.20E−04 | 1.10E−04 |
| CD3+ | *Clostridiales* bacterium VE202-03:1232439 | 6.55E−04 | −3.90E−01 | 1.96E−04 | 4.10E−04 |
| CD3+ | *Eubacterium* sp. AF22-8LB:2292232 | 7.08E−04 | 3.87E−01 | 2.43E−04 | 3.38E−05 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD3+ | *Oscillospiraceae* bacterium VE202-24:1232459 | 7.13E−04 | −3.87E−01 | 5.59E−04 | 1.08E−03 |
| CD3+ | *Clostridium* sp. L2-50:411489 | 7.47E−04 | 3.86E−01 | 3.67E−03 | 3.38E−05 |
| CD3+ | *Ruminococcus* sp. AF46-10NS:2292072 | 8.19E−04 | 3.83E−01 | 2.70E−04 | 6.76E−05 |
| CD3+ | *Clostridium* sp. ATCC BAA-442:649724 | 8.89E−04 | −3.81E−01 | 3.20E−04 | 5.31E−04 |
| CD3+ | *Clostridium sporogenes*:1509 | 9.15E−04 | 3.80E−01 | 1.63E−03 | 2.04E−04 |
| CD3+ | *Lachnospiraceae* bacterium AM23-7LB:2292904 | 1.06E−03 | 3.76E−01 | 2.34E−04 | 5.51E−05 |
| CD3+ | *Eubacterium ventriosum* ATCC 27560:411463 | 1.23E−03 | 3.71E−01 | 3.57E−04 | 1.25E−04 |
| CD3+ | *Coprococcus eutactus*:33043 | 1.55E−03 | 3.64E−01 | 3.22E−03 | 6.87E−03 |
| CD3+ | *Roseburia* sp. AM16-25:2292065 | 1.75E−03 | 3.60E−01 | 1.45E−04 | 3.21E−05 |
| CD3+ | *Collinsella* sp. AF23-3LB:2292223 | 1.77E−03 | 3.60E−01 | 1.56E−04 | 2.54E−05 |
| CD3+ | *Ruminococcus* sp. OM04-4AA:2293231 | 1.78E−03 | 3.60E−01 | 2.30E−04 | 9.61E−05 |
| CD3+ | *Coprococcus catus*:116085 | 1.79E−03 | 3.59E−01 | 1.21E−03 | 4.97E−04 |
| CD3+ | *Lachnospiraceae* bacterium Choco86:2109690 | 1.88E−03 | 3.58E−01 | 1.26E−04 | 4.04E−05 |
| CD3+ | *Ruminococcus lactaris*:46228 | 1.91E−03 | 3.57E−01 | 5.49E−03 | 6.08E−03 |
| CD3+ | *Bacteroides finegoldii*:338188 | 2.12E−03 | −3.54E−01 | 1.23E−04 | 6.06E−04 |
| CD3+ | *Dorea* sp. AF36-15AT:2292041 | 2.23E−03 | 3.52E−01 | 3.26E−04 | 1.18E−04 |
| CD3+ | *Ruminococcus* sp. OM06-36AC:2292375 | 2.43E−03 | 3.50E−01 | 1.63E−04 | 6.47E−04 |
| CD3+ | *Mediterraneibacter* sp. KCTC 15684:2316025 | 2.56E−03 | 3.48E−01 | 1.29E−04 | 6.01E−05 |
| CD3+ | *Anaerostipes hadrus*:649756 | 2.70E−03 | 3.46E−01 | 1.52E−02 | 7.78E−03 |
| CD3+ | *Lachnospiraceae* bacterium TF10-8AT:2292907 | 2.76E−03 | 3.45E−01 | 3.12E−04 | 1.46E−04 |
| CD3+CD56+ | *Lachnoclostridium* sp. SNUG30099:2126738 | 3.68E−06 | 5.12E−01 | 3.21E−03 | 4.70E−04 |
| CD3+CD56+ | *Clostridiaceae* bacterium TF01-6:2305245 | 7.71E−06 | 4.97E−01 | 1.06E−04 | 1.02E−04 |
| CD3+CD56+ | *Clostridium sporogenes*:1509 | 2.34E−05 | 4.73E−01 | 1.63E−03 | 2.04E−04 |
| CD3+CD56+ | *Dorea formicigenerans*:39486 | 2.99E−05 | 4.68E−01 | 5.38E−03 | 3.36E−03 |
| CD3+CD56+ | *Erysipelotrichaceae* bacterium GAM147:2109692 | 2.30E−04 | 4.18E−01 | 2.08E−03 | 5.58E−04 |
| CD3+CD56+ | *Dorea* sp. AM58-8:2292346 | 3.22E−04 | 4.09E−01 | 4.20E−04 | 1.10E−04 |
| CD3+CD56+ | *Dorea* sp. AGR2135:1280669 | 6.22E−04 | 3.91E−01 | 1.26E−04 | 1.08E−04 |
| CD3+CD56+ | *Dorea* sp. AF36-15AT:2292041 | 6.87E−04 | 3.88E−01 | 3.26E−04 | 1.18E−04 |
| CD3+CD56+ | *Clostridium* sp. AM34-11AC:2305242 | 7.45E−04 | 3.86E−01 | 1.33E−04 | 1.48E−04 |
| CD3+CD56+ | *Lachnoclostridium* sp. SNUG30370:2126739 | 1.26E−03 | 3.70E−01 | 3.10E−04 | 2.67E−04 |
| CD3+CD56+ | *Subdoligranulum variabile* DSM 15176:411471 | 2.13E−03 | 3.54E−01 | 1.82E−04 | 8.09E−05 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD3+HLADR+ | *Blautia hansenii* DSM 20583:537007 | 2.11E−03 | 3.54E−01 | 1.22E−04 | 8.69E−04 |
| CD3−CD56+ | *Roseburia* sp. OF03-24:2292367 | 4.81E−04 | 3.98E−01 | 1.26E−04 | 6.70E−05 |
| CD3−CD56+ | *Roseburia faecis*:301302 | 8.22E−04 | 3.83E−01 | 1.60E−02 | 1.83E−02 |
| CD3−CD56+ | *Roseburia intestinalis* L1-82:536231 | 1.68E−03 | 3.61E−01 | 5.17E−04 | 2.56E−04 |
| CD3−CD56+ | *Butyricicoccus* sp. GAM44:2109686 | 1.79E−03 | 3.59E−01 | 8.20E−04 | 4.50E−04 |
| CD3−CD56+ | *Roseburia* sp. TF10-5:2293144 | 2.23E−03 | 3.52E−01 | 2.34E−03 | 2.67E−03 |
| CD3−HLA-DR+ | *Tyzzerella nexilis*:29361 | 6.47E−04 | −3.90E−01 | 2.04E−04 | 3.99E−03 |
| CD3−HLA-DR+ | *Parabacteroides* sp. OF01-14:2293123 | 1.06E−03 | 3.76E−01 | 1.13E−04 | 4.22E−05 |
| CD3−HLA-DRlow | *Dorea* sp. OM07-5:2293100 | 7.95E−05 | −4.45E−01 | 2.16E−04 | 4.26E−05 |
| CD3−HLA-DRlow | *Roseburia inulinivorans* DSM 16841:622312 | 1.52E−03 | −3.65E−01 | 2.97E−04 | 2.22E−04 |
| CD3−HLA-DRlow | *Ruminococcaceae* bacterium AF10-16:2292180 | 2.62E−03 | −3.47E−01 | 4.61E−04 | 2.21E−04 |
| CD3−HLA-DRlow | *Dorea formicigenerans*:39486 | 2.78E−03 | −3.45E−01 | 5.38E−03 | 3.36E−03 |
| CD4+ | *Neglecta timonensis*:1776382 | 3.07E−05 | 4.67E−01 | 8.07E−04 | 2.25E−03 |
| CD4+ | *Parabacteroides merdae*:46503 | 4.04E−04 | −4.03E−01 | 4.54E−03 | 1.07E−02 |
| CD4+ | *Alckermansia muciniphila*:239935 | 1.89E−03 | 3.58E−01 | 7.54E−03 | 2.63E−03 |
| CD4+ | *Clostridium* sp. AM09-51:2293022 | 2.54E−03 | 3.48E−01 | 1.05E−03 | 4.22E−04 |
| CD4+HLA-DR+ | *Ruminococcus* sp. AF14-10:2292247 | 7.78E−05 | −4.46E−01 | 1.82E−04 | 8.80E−05 |
| CD4+HLA-DR+ | *Clostridiales* bacterium VE202-031232439 | 1.69E−04 | 4.26E−01 | 1.96E−04 | 4.10E−04 |
| CD4+HLA-DR+ | *Subdoligranulum* sp. APC924/74:2086273 | 1.77E−04 | −4.25E−01 | 7.10E−03 | 5.10E−03 |
| CD4+HLA-DR+ | *Ruminococcus* sp. AM42-11:2292372 | 1.88E−04 | −4.24E−01 | 5.88E−03 | 3.65E−03 |
| CD4+HLA-DR+ | *Ruminococcus* sp. AF46-10NS:2292072 | 2.05E−04 | −4.21E−01 | 2.70E−04 | 6.76E−05 |
| CD4+HLA-DR+ | *Flavonifractor plautii*:292800 | 2.17E−04 | 4.20E−01 | 1.34E−03 | 4.31E−03 |
| CD4+HLA-DR+ | *Ruminococcus* sp. OF02-6:2293228 | 3.98E−04 | −4.04E−01 | 2.59E−04 | 9.37E−05 |
| CD4+HLA-DR+ | *Ruminococcus* sp. OM06-36AC:2292375 | 8.55E−04 | −3.82E−01 | 1.63E−04 | 6.47E−04 |
| CD4+HLA-DR+ | *Flavonifractor plautii* 1_3_50AFAA742738 | 9.96E−04 | 3.77E−01 | 1.31E−04 | 3.37E−04 |
| CD4+HLA-DR+ | *Blautia obeum*:40520 | 1.02E−03 | −3.77E−01 | 7.12E−02 | 3.12E−02 |
| CD4+HLA-DR+ | *Lachnospiraceae* bacterium Choco86:2109690 | 1.04E−03 | −3.76E−01 | 1.26E−04 | 4.04E−05 |
| CD4+HLA-DR+ | *Coprococcus catus*:116085 | 1.10E−03 | −3.75E−01 | 1.21E−03 | 4.97E−04 |
| CD4+HLA-DR+ | *Clostridium* sp. AT4:1720194 | 1.13E−03 | 3.74E−01 | 1.03E−03 | 1.64E−03 |
| CD4+HLA-DR+ | *Blautia* sp. OM07-19:2292985 | 1.31E−03 | −3.69E−01 | 3.73E−04 | 2.11E−04 |
| CD4+HLA-DR+ | *Alistipes putredinis* DSM 17216:445970 | 1.43E−03 | −3.66E−01 | 7.90E−03 | 3.12E−03 |
| CD4+HLA-DR+ | *Anaerostipes hadrus*:649756 | 1.46E−03 | −3.66E−01 | 1.52E−02 | 7.78E−03 |
| CD4+HLA-DR+ | *Blautia hydrogenotrophica*:53443 | 1.80E−03 | −3.59E−01 | 3.78E−04 | 1.53E−04 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD4+HLA-DR+ | *Clostridium* sp. ATCC BAA-442:649724 | 2.39E−03 | 3.50E−01 | 3.20E−04 | 5.31E−04 |
| CD4+HLA-DR+ | *Blautia* sp. AM46-5:2292978 | 2.84E−03 | −3.45E−01 | 2.32E−04 | 6.37E−05 |
| CD45+ | *Roseburia inulinivorans*:360807 | 2.42E−03 | 3.50E−01 | 7.03E−03 | 6.33E−03 |
| CD8+ | *Neglecta timonensis*:1776382 | 3.74E−05 | −4.63E−01 | 8.07E−04 | 2.25E−03 |
| CD8+ | *Clostridium* sp. CL-2:1499684 | 8.26E−04 | −3.83E−01 | 1.06E−04 | 4.41E−05 |
| CD8+ | *Parabacteroides merdae*:46503 | 1.11E−03 | 3.74E−01 | 4.54E−03 | 1.07E−02 |
| CD8+ | *Negativibacillus massiliensis*:1871035 | 1.48E−03 | −3.65E−01 | 1.39E−04 | 1.48E−04 |
| CD8+ | *Akkermansia muciniphila*:239935 | 1.69E−03 | −3.61E−01 | 7.54E−03 | 2.63E−03 |
| CD8+HLA-DR+ | *Blautia hydrogenotrophica*:53443 | 4.44E−06 | −5.08E−01 | 3.78E−04 | 1.53E−04 |
| CD8+HLA-DR+ | *Blautia* sp. AM16-16B:2292969 | 6.00E−06 | −5.02E−01 | 2.44E−04 | 6.69E−05 |
| CD8+HLA-DR+ | *Ruminococcus* sp. OF02-6:2293228 | 3.94E−05 | −4.62E−01 | 2.59E−04 | 9.37E−05 |
| CD8+HLA-DR+ | *Blautia* sp. OM07-19:2292985 | 4.70E−05 | −4.58E−01 | 3.73E−04 | 2.11E−04 |
| CD8+HLA-DR+ | *Blautia* sp. AF22-5LB:2292964 | 4.70E−05 | −4.58E−01 | 1.03E−03 | 3.45E−04 |
| CD8+HLA-DR+ | *Ruminococcus* sp. AM42-11:2292372 | 5.37E−05 | −4.54E−01 | 5.88E−03 | 3.65E−03 |
| CD8+HLA-DR+ | *Ruminococcus* sp. AF46-10NS:2292072 | 9.44E−05 | −4.41E−01 | 2.70E−04 | 6.76E−05 |
| CD8+HLA-DR+ | *Blautia* sp. AF25-12LB:2292965 | 1.12E−04 | −4.37E−01 | 5.53E−04 | 1.53E−04 |
| CD8+HLA-DR+ | *Blautia* sp. AF19-34:2292963 | 1.28E−04 | −4.34E−01 | 4.92E−04 | 1.56E−04 |
| CD8+HLA-DR+ | *Romboutsia timonensis*:1776391 | 2.03E−04 | −4.22E−01 | 1.60E−03 | 6.41E−04 |
| CD8+HLA-DR+ | *Blautia hydrogenotrophica* DSM 10507:476272 | 2.57E−04 | −4.15E−01 | 1.14E−03 | 5.92E−04 |
| CD8+HLA-DR+ | *Ruminococcus* sp. OF03-6AA:2293229 | 3.80E−04 | −4.05E−01 | 1.05E−03 | 5.25E−04 |
| CD8+HLA-DR+ | *Ruminococcus* sp. OM08-9BH:2293236 | 4.61E−04 | −4.00E−01 | 7.67E−04 | 3.15E−04 |
| CD8+HLA-DR+ | *Dorea longicatena* DSM 13814:411462 | 5.14E−04 | −3.97E−01 | 8.47E−04 | 4.69E−04 |
| CD8+HLA-DR+ | *Ruminococcus* sp. AF31-8BH:2293174 | 6.40E−04 | −3.90E−01 | 6.46E−04 | 3.49E−04 |
| CD8+HLA-DR+ | *Blautia obeum*:40520 | 7.12E−04 | −3.87E−01 | 7.12E−02 | 3.12E−02 |
| CD8+HLA-DR+ | *Dorea* sp. AM10-31:2293098 | 7.57E−04 | −3.86E−01 | 3.03E−04 | 6.58E−05 |
| CD8+HLA-DR+ | *Blautia* sp. AM22-22LB:2292970 | 8.36E−04 | −3.83E−01 | 3.52E−04 | 1.09E−04 |
| CD8+HLA-DR+ | *Ruminococcus faecis* JCM 15917:1298596 | 8.95E−04 | −3.81E−01 | 3.23E−04 | 1.05E−04 |
| CD8+HLA-DR+ | *Ruminococcus* sp. AF17-12:2293151 | 9.03E−04 | −3.80E−01 | 2.42E−03 | 1.14E−03 |
| CD8+HLA-DR+ | *Clostridiales* bacterium CCNA10:2109688 | 9.44E−04 | 3.79E−01 | 7.44E−04 | 8.83E−04 |
| CD8+HLA-DR+ | *Collinsella* sp. AF23-3LB:2292223 | 9.72E−04 | −3.78E−01 | 1.56E−04 | 2.54E−05 |
| CD8+HLA-DR+ | *Lachnospiraceae* bacterium Choco86:2109690 | 1.01E−03 | −3.77E−01 | 1.26E−04 | 4.04E−05 |
| CD8+HLA-DR+ | *Blautia* sp. TF11-31AT:2292987 | 1.19E−03 | −3.72E−01 | 5.93E−04 | 2.18E−04 |
| CD8+HLA-DR+ | *Ruminococcus* sp. OM06-36AC:2292375 | 1.26E−03 | −3.70E−01 | 1.63E−04 | 6.47E−04 |

TABLE 25-continued

Immune flow cytometry was performed on 73 blood from human subjects in addition to whole genome seugencing. Statistical analysis was performed to find significantly significant correlations between immune markers and organisms, using a Spearman correlation and p value and filtering for a false discovery rate of 0.15. Markers passing the FDR filter are included in a table that includes for each significant correlation, the immune marker and organism involved, the correlation and p value, as well as the mean abundance of the organism in the control and cancer sample cohorts.

| Marker | Organism | P value | Correlation | Mean Abundance in Control | Mean Abundance in Cancer |
|---|---|---|---|---|---|
| CD8+HLA-DR+ | *Ruminococcus* sp. AM16-34:2293184 | 1.32E−03 | −3.69E−01 | 1.37E−03 | 3.86E−04 |
| CD8+HLA-DR+ | *Roseburia hominis*:301301 | 1.40E−03 | −3.67E−01 | 4.21E−04 | 3.92E−04 |
| CD8+HLA-DR+ | *Blautia obeum* ATCC 29174:411459 | 1.66E−03 | −3.62E−01 | 5.35E−04 | 1.78E−04 |
| CD8+HLA-DR+ | *Clostridium* sp. Marseille-P3244:1871020 | 1.71E−03 | −3.61E−01 | 4.48E−04 | 6.63E−05 |
| CD8+HLA-DR+ | *Coprococcus catus*:116085 | 1.82E−03 | −3.59E−01 | 1.21E−03 | 4.97E−04 |
| CD8+HLA-DR+ | *Blautia* sp. SG-772:2109334 | 2.36E−03 | −3.51E−01 | 1.59E−03 | 6.38E−04 |
| CD8+HLA-DR+ | *Clostridiales* bacterium VE202-031232439 | 2.58E−03 | 3.48E−01 | 1.96E−04 | 4.10E−04 |
| CD8+HLA-DR+ | *Subdoligranulum* sp. APC924/74:2086273 | 2.59E−03 | −3.48E−01 | 7.10E−03 | 5.10E−03 |
| CD8+HLA-DR+ | *Ruminococcaceae* bacterium TF06-43:2292270 | 2.60E−03 | −3.47E−01 | 6.87E−04 | 4.74E−04 |
| CD8+HLA-DR+ | *Ruminococcus* sp. AF14-10:2292247 | 2.65E−03 | −3.47E−01 | 1.82E−04 | 8.80E−05 |
| CD8+HLA-DR+ | *Ruminococcaceae* bacterium AF10-16:2292180 | 2.67E−03 | −3.47E−01 | 4.61E−04 | 2.21E−04 |
| CD8+HLA-DR+ | *Roseburia hominis* A2-183:585394 | 2.72E−03 | −3.46E−01 | 1.00E−03 | 8.82E−04 |
| CD8+HLA-DR+ | *Ruminococcaceae* bacterium:1898205 | 2.86E−03 | −3.44E−01 | 2.01E−04 | 1.73E−04 |

Metabolomics was performed on fecal samples taken from eight cancer patients and two healthy individuals. A total of 856 metabolites could be identified in one or more of these samples.

Here we look at all metabolites that were significantly increased in the cancer patients relative to the healthy controls, based on Welch's two-sample t-test with $p<0.05$, see Tables 15 and 16:

TABLE 15

List of metabolites increased in the cancer population relative to the control group, given as the ratio of the mean peak areas for the specified metabolites. Significance was evaluated based on Welch's two-sample t-test with $p < 0.05$.

| Compound | Ratio cancer/ control | P value |
|---|---|---|
| tyramine | 566 | 0.00415 |
| Taurine | 278 | 0.00390 |
| creatinine | 274 | 0.0230 |
| Indolelactate | 97.6 | 0.0537 |
| OAHSA (18:1/OH-18:0) | 92.5 | 0.00853 |
| Arachidonic acid (20:4n6) | 86.5 | 0.00836 |
| LAHSA (18:2/OH-18:0)* | 73.9 | 0.00797 |
| Alpha-hydroxyisovalerate | 55.0 | 0.0182 |
| docosahexaenoate (DHA; 22:6n3) | 47.2 | 0.0176 |
| docosahexaenoate (DHA; 22:6n3) | 41.0 | 0.0359 |
| sulfate | 30.7 | 0.0113 |
| 2-hydroxypalmitate | 30.4 | 0.0429 |
| stachydrine | 25.4 | 9.56E−5 |
| Cholate sulfate | 25.2 | 0.0317 |
| Palmitoylcarnitine (C16) | 24.6 | 0.0139 |
| phenethylamine | 21.5 | 0.0223 |
| N-propionylmethionine | 20.6 | 0.00669 |

TABLE 15-continued

List of metabolites increased in the cancer population relative to the control group, given as the ratio of the mean peak areas for the specified metabolites. Significance was evaluated based on Welch's two-sample t-test with $p < 0.05$.

| Compound | Ratio cancer/ control | P value |
|---|---|---|
| dihydroferulate | 20.0 | 0.0120 |
| Beta-alanine | 19.6 | 0.0145 |
| tryptamine | 19.5 | 0.0289 |
| 3-ureidopropionate | 18.7 | 0.00232 |
| Stearoylcarnitine (C18) | 17.7 | 0.00365 |
| 2-hydroxybutyrate | 17.5 | 0.00802 |
| 3-methylhistidine | 15.5 | 0.0331 |
| Nervonate (24:1n9) | 14.8 | 0.0278 |
| 1-palmitoyl-2-oleoyl-GPE (16:0/18:1) | 14.5 | 0.0281 |
| 5,6-dihydrothymine | 11.8 | 0.0294 |
| octadecadienedioate (C18:2-DC) | 11.2 | 0.0299 |
| agmatine | 10.8 | 0.0428 |
| caffeine | 10.0 | 0.0268 |
| N-methylhydantoin | 9.8 | 0.0405 |
| gentisate | 9.6 | 0.0121 |
| ceramide (d18:2/24:1, d18:1/24:2) | 8.9 | 0.0292 |
| homostachydrine | 8.3 | 0.00739 |
| N-acetylvaline | 8.3 | 0.00242 |
| xanthurenate | 7.9 | 0.0141 |
| N-acetylalanine | 7.4 | 0.0304 |
| Margaroylcarnitine (C17) | 7.3 | 0.0256 |
| S-methylcysteine | 6.5 | 0.0449 |
| Hydatoin-5-propionate | 6.3 | 0.0238 |
| N-acetylphenylalanine | 6.3 | 0.0079 |
| N-acetylleucine | 6.0 | 0.00918 |
| Adrenate (22:4n6) | 4.9 | 0.0212 |
| diaminopimelate | 4.3 | 0.0268 |

TABLE 15-continued

List of metabolites increased in the cancer population relative to the control group, given as the ratio of the mean peak areas for the specified metabolites. Significance was evaluated based on Welch's two-sample t-test with $p < 0.05$.

| Compound | Ratio cancer/ control | P value |
|---|---|---|
| pristanate | 4.0 | 0.0331 |
| 2-aminoheptanoate | 3.9 | 0.0296 |
| sarcosine | 3.8 | 0.0380 |
| 2-hydroxyheptanoate | 3.6 | 0.0163 |
| Gamma-glutamylglutamate | 3.6 | 0.0466 |
| lysine | 3.2 | 0.0109 |
| 4-oxovalerate | 3.2 | 0.00970 |
| 3-methy1-2-oxovalerate | 3.2 | 0.0122 |
| Eicosenoylcarnitine (C20:1) | 3.1 | 0.0414 |
| 1-methylguanidine | 3.0 | 0.00760 |

TABLE 16

List of metabolites decreased in the cancer population relative to the control group, given as the ratio of the mean peak areas for the specified metabolites. Significance was evaluated based on Welch's two-sample t-test with $p < 0.05$.

| Compound | Ratio cancer/ control | P value |
|---|---|---|
| L-urobilin | 0.07 | 0.00466 |
| Linolenate (18:3n3 or 18:3n6) | 0.11 | 0.0192 |
| Linoleoyl-linolenoyl-glycerol (18:2/18:3) | 0.12 | 0.000537 |
| Heptadecatrienoate (17:3) | 0.13 | 0.00224 |
| Heptadecatrienoate (17:3) | 0.13 | 0.00224 |
| Azelate (C9-DC) | 0.13 | 0.0151 |
| Undecanedioate (C11-DC) | 0.14 | 0.0203 |
| Linoleoyl-linolenoyl-glycerol (18:3/18:3) | 0.15 | 0.0348 |
| Suberate (C8-DC) | 0.29 | 0.00177 |
| Octadecanedioate (C18-DC) | 0.35 | 0.00999 |
| N-acetylglutamate | 0.43 | 0.0178 |
| Oleoyl-linolenoyl-glycerol (18:1/18:3) | 0.59 | 0.0214 |
| pyridoxamine | 0.60 | 0.0446 |
| 2-oxo-1-pyrrolindinepropionate | 0.75 | 0.0314 |

In a separate study, metabolomics was performed on a total of 55 samples obtained from 22 healthy subjects and 18 cancer patients. In some cases two or more samples were from the same individual, spaced 6 weeks apart; in such a case they are referred to as timepoints T1 and T2. In general, T1 samples were prior to immunotherapy treatment while T2 samples were during treatment. Approximately 1 gram of raw fecal material stored at −80 deg. C. was processed for metabolite extraction by methanol as described above.

Metabolomics was also performed on plasma extracted from blood obtained from some of the same subjects as the fecal samples. There were a total of 44 plasma samples obtained from 18 healthy subjects and 10 cancer patients. To obtain plasma, 1 mL whole blood was centrifuged at 2800×g for 10 minutes, creating two phases with the plasma on top. 0.5 mL of plasma was removed using a pipette, and transferred to a clean tube which was then stored at −80 deg. C. until processing. 0.1 mL of the plasma was used for metabolite extraction, with methanol under vigorous shaking for 2 min (Glen Mills GenoGrinder 2000) to precipitate protein and dissociate small molecules bound to protein or trapped in the precipitated protein matrix, followed by centrifugation to recover chemically diverse metabolites. The resulting extract was divided into five fractions: two for analysis by two separate reverse phase (RP)/UPLC-MS/MS methods using positive ion mode electrospray ionization (ESI), one for analysis by RP/UPLC-MS/MS using negative ion mode ESI, one for analysis by HILIC/UPLC-MS/MS using negative ion mode ESI, and one reserved for backup. Samples are placed briefly on a TurboVap® (Zymark) to remove the organic solvent. The sample extracts are stored overnight under nitrogen before preparation for analysis.

Three types of controls were analyzed in concert with the experimental samples: a pooled sample generated from a small portion of each experimental sample of interest served as a technical replicate throughout the platform run; extracted water samples served as process blanks; and a cocktail of standards spiked into every analyzed sample allowed for instrument performance monitoring. Instrument variability was determined by calculation of the median relative s.d. (RSD) for the standards that were added to each sample before injection into the mass spectrometers (median RSDs were determined to be 3% for plasma and 4% for fecal extracts). Overall process variability was determined by calculating the median RSD for all endogenous metabolites (i.e., noninstrument standards) present in 90% or more of the pooled technical-replicate samples (median RSD of 7% for plasma and 10% for fecal).

Compounds are identified by comparison to library entries of purified standards maintained by Metabolon, that contains the retention time/index (RI), mass to charge ratio (m/z), and chromatographic data (including MS/MS spectral data) on all molecules present in the library. Furthermore, biochemical identifications are based on three criteria: retention index within a narrow RI window of the proposed identification, accurate mass match to the library +/−10 ppm, and the MS/MS forward and reverse scores. MS/MS scores are based on a comparison of the ions present in the experimental spectrum to ions present in the library entry spectrum. While there may be similarities between these molecules based on one of these factors, the use of all three data points can be utilized to distinguish and differentiate biochemicals. Peaks are quantified as area-under-the-curve detector ion counts.

A total of 992 known compounds were identified in at least one of the plasma samples, and 1049 were identified in at least one of the fecal samples. 734 of these compounds were common between the two sample types.

Figure 57:
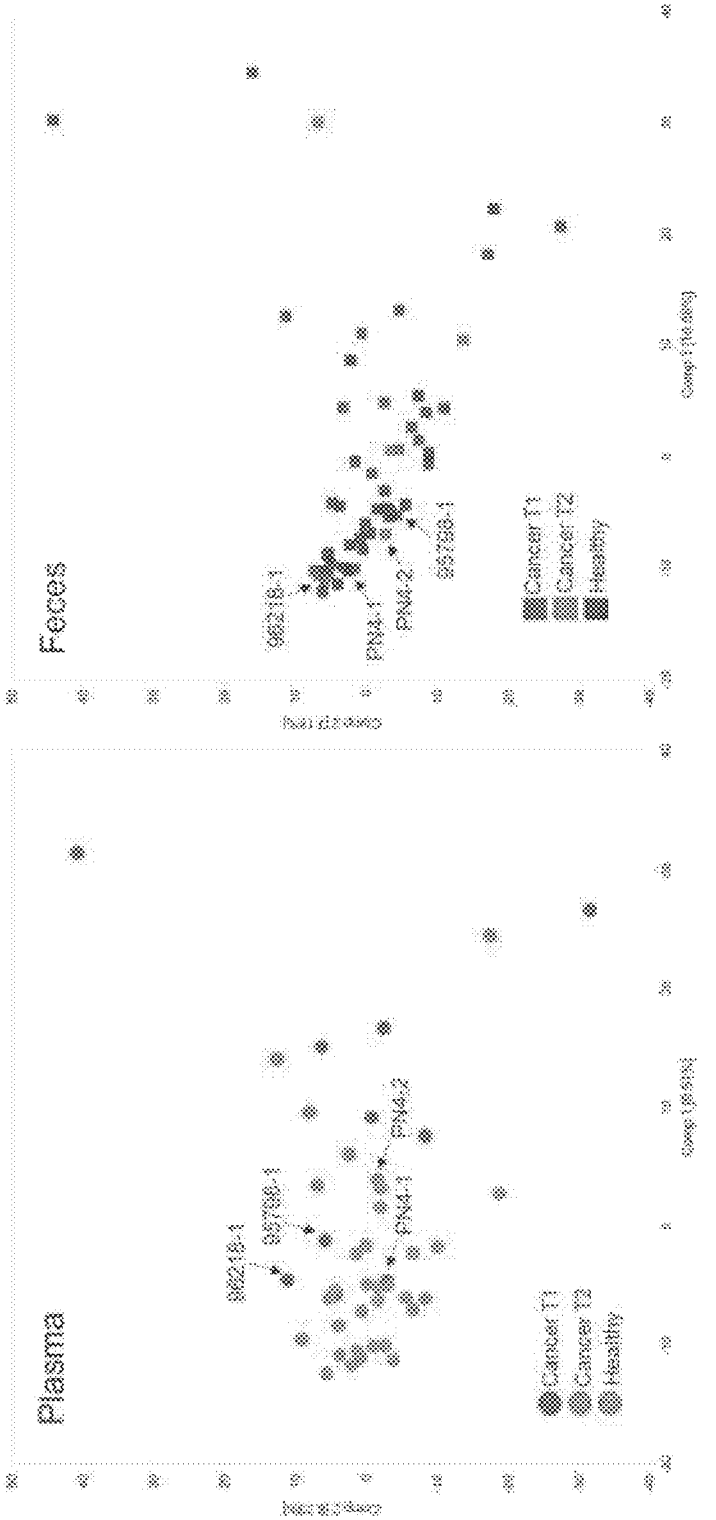
FIG. 57 graphically illustrates the results of a principal component analysis performed on untargeted metabolomics data from plasma and fecal samples for cancer and control sample cohorts. The first two principal coordinates are plotted; as discussed in detail in Example 7, below.

The overall metabolic profiles were represented as two principal components. Principal components analysis is an unsupervised statistical method that compresses the number of dimensions of the data to provide a high-level view of the data over an entire set of samples. Each principal component is a linear combination of every metabolite and the principal components are uncorrelated. Principal components analysis exhibited a reasonable ability to separate the cancer and healthy groups, especially in plasma. When considering two principal components, there was a notable separation of healthy controls from cancer samples collected at T1 or T2 in plasma (FIG. 57, left panel). Interestingly, four samples from three cancer group subjects whose fecal whole metagenomic sequencing data clustered with healthy rather than cancer subjects also clustered on PCAs with healthy subject on the basis of metabolic profiles in plasma. Points corresponding to these samples are indicated in the plots by arrows. In fecal samples, there was much greater overlap of healthy and cancer groups on PCA, though samples from these same cancer patients (labeled 95798, 96218, and PN4) were centered among the greatest concentration of healthy samples (FIG. 57, right panel).

FIG. 59 is a table of the top 100 differential metabolites, ranked by p value (Mann Whitney U test). Metabolomics data on plasma from a third party provider was processed using a Mann Whitney U test to find significantly different metabolites between cancer and control cohorts. The top 100 metabolites ranked by p value are reported.

FIG. 60 is a volcano plot showing the fold change difference between cancer and control in each metabolite plotted against its statistical significance.

FIG. 61 graphically illustrates the results of a principal component analysis comparing immune flow cytometry data to whole genome sequencing data.

FIG. 62 illustrates the results of a principal component analysis performed on log transformed metabolomics data from plasma and shows a clear separation between control and cancer sample cohorts.

Examination of the results demonstrated potential differences between the plasma metabolic phenotype in healthy versus cancer T1 and cancer T2 groups (Table 27). Specifically, compounds connected to pathways of protein degradation (i.e., modified amino acids), chromatin packing in the nucleus (i.e., polyamines), nucleotide metabolism (i.e., pentose phosphate and nucleotide pathways), and extracellular matrix metabolism (i.e., aminosugars) were prioritized for their connection to activities prominent in cancer including proliferation and DNA synthesis, cell division, and invasion. Potential markers of protein post-translational modification and proteolysis (e.g., N-acetyl amino acids) were elevated in plasma from both cancer T1 and T2 relative to the healthy group, respectively. Elevated proteinase expression and activity are associated with metastatic cancers (extracellular matrix invasion, autophagy, etc.) and signs of proteinase activity can be registered in the metabolome by the appearance of post-translationally modified amino acids. Likewise, polyamines and nucleic acids are required for the synthesis and packaging of DNA in proliferating cells, and these metabolites tended to be higher at both cancer T1 and T2 with respect to the healthy control group. Glycosaminoglycan degradation and oxidation products (e.g., N-acetylneuraminate, the isobar N-acetylglucosamine/N-acetylgalactosamine, erythronate) were moderately elevated in cancer T1 and T2 compared to healthy controls. Reductions in various progestin steroids were noticeable in cancer T1 and T2 compared to the healthy group. Together, these biomarker patterns could reflect a persistent cancer phenotype related to protein degradation, nucleic acid synthesis, turnover, and packaging, extracellular matrix glycan turnover, and altered hormonal regulatory cues.

TABLE 27

Compounds in plasma possibly representative of a cancer phenotype with statistically-significant elevations in either cancer T1, cancer T2 or both relative to the healthy control group. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| N-acetylserine | 1.41 ↑ | 1.31 | 0.93 |
| N-acetylalanine | 1.24 ↑ | 1.21 | 0.98 |
| Hydroxyasparagine | 1.4 ↑ | 1.32 | 0.94 |
| 5-galactosylhydroxy-L-lysine | 2.3 ↑ | 1.73 ↑ | 0.75 |
| C-glycosyltryptophan | 1.44 ↑ | 1.41 ↑ | 0.98 |
| N-acetylputrescine | 1.65 | 1.22 ↑ | 0.74 |
| N-acetyl-isoputreanine | 1.2 | 1.19 ↑ | 0.98 |
| (N(1)+N(8))-acetylspermidine | 1.9 ↑ | 1.89 ↑ | 1 |
| Acisoga | 1.43 ↑ | 1.35 ↑ | 0.94 |

TABLE 27-continued

Compounds in plasma possibly representative of a cancer phenotype with statistically-significant elevations in either cancer T1, cancer T2 or both relative to the healthy control group. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| 5-methylthioadenosine | 2.01 ↑ | 1.95 ↑ | 0.97 |
| Ribitol | 1.82 ↑ | 1.29 | 0.71 |
| Ribonate | 1.37 ↑ | 1.11 | 0.81 |
| Arabitol/xylitol | 1.48 ↑ | 1.08 | 0.73 |
| Glucuronate | 2.2 ↑ | 1.07 | 0.48 |
| N-acetylneuraminate | 1.47 ↑ | 1.5 ↑ | 1.02 |
| Erythronate | 1.2 ↑ | 1.26 | 1.05 |
| N-acetylglucosamine/N-acetylgalactosamine | 1.52 ↑ | 1.57 ↑ | 1.03 |
| 5-alpha-pregnan-3beta,20beta-diol monosulfate (1) | 0.18 ↓ | 0.24 ↓ | 1.3 |
| 5-alpha-pregnan-3beta,20beta-diol monosulfate (2) | 0.11 ↓ | 0.14 ↓ | 1.24 |
| 5-alpha-pregnan-3beta,20beta-diol disulfate | 0.24 ↓ | 0.38 ↓ | 1.19 |
| 5-alpha-pregnan-diol disulfate | 0.25 ↓ | 0.3 | 1.21 |
| Pregnanediol-3-glucuronide | 0.25 ↓ | 0.23 ↓ | 0.92 |
| Adenine | 1.55 ↑ | 1.5 | 0.97 |
| N1-methyladenosine | 1.29 ↑ | 1.41 ↑ | 1.1 |
| N6-carbamoylthreonyladenosine | 1.5 ↑ | 1.31 | 0.87 |
| N6-succinyladenosine | 1.88 ↑ | 1.82 ↑ | 0.97 |
| 7-methylguanine | 1.29 ↑ | 1.02 | 0.8 ↓ |
| N2,N2-dimethylguanosine | 1.55 ↑ | 1.45 ↑ | 0.94 |
| Orotidine | 1.62 ↑ | 1.54 ↑ | 0.95 |
| Pseudouridine | 1.45 ↑ | 1.38 ↑ | 0.95 |
| | 1.46 ↑ | 1.43 ↑ | 0.98 |
| 2'-O-methyluridine | 2.81 ↑ | 0.46 | 0.16 |
| Cytidine | 2.41 ↑ | 2.25 ↑ | 0.93 |
| N4-acetylcytidine | 2.38 ↑ | 2.1 ↑ | 0.88 |
| 2'-O-methylcytidine | 1.92 ↑ | 1.58 | 0.82 |

The tricarboxylic acid (TCA) cycle and glycolysis pathways connected to energy production from glucose were enriched with connected metabolites that differed significantly between the plasma cancer T1 and cancer T2 groups (Table 28). In cancer the TCA cycle has been noted to serve as both a source of energy production and as a central metabolic node in the utilization and production of key metabolite classes including free fatty acid synthesis from citrate, heme from fumarate, nucleotides and proteins from oxaloacetate and alpha-ketoglutarate [3]. Mutations affecting dysregulation of oncogenes and tumor suppressors have direct impact on TCA cycle metabolism and transport of substrates into the mitochondria and direct mutations of TCA cycle enzymes also occur with some cancers [4]. Although carbon from glucose is presented as the canonical substrate for citrate production, carbons from both fatty acids and amino acids readily enter the cycle at specific points. Glutamine, via glutaminolysis to glutamate, is noted as a highly utilized fuel and carbon source for many cancers [5; 6]. The shifting profile of glutamate, pyruvate, and TCA cycle metabolites in the cancer T2 group relative to the cancer T1 group suggest that anticancer treatment has a disruptive effect on energy or mitochondrial carbon repurposing.

TABLE 28

The tricarboxylic acid (TCA) cycle profile in plasma shifted in cancer T2 compared to cancer T1 as a possible sign of response to anticancer treatment. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| Glutamate | 1.29 ↑ | 1.31 | 1.01 |
| Pyruvate | 0.93 | 0.68 | 0.73 ↓ |
| Lactate | 1.12 | 0.81 | 0.72 ↓ |
| Citrate | 1 | 1.1 | 1.09 ↑ |
| Isocitric lactone | 1.37 | 2.01 | 1.47 ↑ |
| Alpha-ketoglutarate | 1.11 | 1.21 | 1.09 ↑ |
| Succinate | 1.08 | 0.93 | 0.86 ↓ |
| Fumarate | 0.91 | 0.85 | 0.93 ↓ |
| Malate | 0.97 | 0.91 | 0.94 ↓ |

Plasma metabolites connected to glutathione metabolism and oxidative stress differed in the cancer T2 group with respect to the cancer T1 group (Table 29). Oxidized forms of glutathione and cysteine were reduced in the cancer T2 group relative to the cancer T1 group and may suggest a relative decrease in oxidative stress in the cancer T2 plasma samples. Oxidized ascorbic acid derivatives showed significant reductions in the cancer T2 group compared to the healthy control group. Tumors operate with a high level of incidental oxidative stress through the production of free radicals, reactive oxygen and nitrogen species, and hydrogen peroxide and thus depend on antioxidants such as glutathione and ascorbate to neutralize oxidative species and repair oxidative damage [7; 8]. The decreasing level of oxidative intermediates of glutathione, cysteine, and ascorbate in the cancer T2 group may be a sign of overall reduced metabolic activity and oxidative species production in response to anticancer treatment.

TABLE 29

Most oxidized forms of cysteine, glutathione, and ascorbate in plasma decreased during anticancer treatment in the cancer T2 group. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/ All Healthy | Cancer T2/ All Healthy | Cancer T2/ Cancer T1 |
|---|---|---|---|
| Glycine | 0.79 ↓ | 0.72 ↓ | 0.9 |
| Glutamate | 1.29 ↑ | 1.31 | 1.01 |
| Methionine | 0.79 | 0.8 | 1.02 |
| cysteine | 1.04 | 0.97 | 0.93 ↓ |
| Cystine | 1.25 | 1.63 ↑ | 1.31 |
| Cysteine sulfinic acid | 1.04 | 0.81 | 0.78 ↓ |
| Cysteine-glutathione disulfide | 1.03 | 0.66 | 0.64 |
| Cysteinylglycine | 1.21 | 0.62 | 0.51 ↓ |
| Cysteinylglycine disulfide | 1.14 | 0.89 | 0.78 ↓ |
| Cys-Gly, oxidized | 1.15 | 0.56 | 0.49 ↓ |
| Ascorbic acid 3-sulfate | 1.55 | 0.5 ↓ | 0.32 |
| Threonate | 0.79 | 0.46 ↓ | 0.58 |
| Oxalate | 0.76 | 0.56 ↓ | 0.74 |
| Gulonate | 2.17 ↑ | 1.28 | 0.59 |

Some statistically significant differences in fecal primary and secondary acids were observed for the cancer T2 group with respect to the cancer T1 group (Table 30). Most bile acids in the cancer T1 and cancer T2 groups showed large fold-change differences with respect to the healthy control group but the combination of low statistical power and large within-group variation prevented many of these differences from reaching statistical significance. Primary bile acids produced in the liver serve as emulsifiers to aid nutrient absorption from the digestive tract and are transformed into secondary bile acids by members of the gut microbiota. The significantly altered levels of some primary and secondary bile acids in the cancer T2 group relative to the baseline cancer T1 could reflect altered liver synthesis of primary bile acids, modified systemic transport, or changes in gut microflora composition and bile acid metabolism secondary to the anticancer treatment.

TABLE 30

Altered levels of primary and secondary bile acids in feces among the sample groups. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| Cholate | 1.07 | 3.28 | 3.07 |
| Glycocholate | 4.5 | 1.52 | 0.34 |
| Taurocholate | 15.98 | 11.5 | 0.72 |
| Chenodeoxycholate | 1.83 | 4.47 | 2.45 |
| Chenodeoxycholic acid (1) | 3.44 ↑ | 2.72 | 0.79 |
| Chenodeoxycholic acid (1) | 1.55 | 5.62 | 3.63 |
| Glycochenodeoxycholate | 3.41 | 1.29 | 0.38 |
| Taurochenodeoxycholate | 8.62 | 3.54 | 0.41 ↓ |
| Cholate sulfate | 2 | 5.74 | 2.86 ↑ |
| Glycochenodeoxycholate 3-sulfate | 17.41 | 1.29 | 0.07 |
| Glycocholate sulfate | 2.85 | 1 | 0.35 ↓ |
| Deoxycholate | 1.27 | 1.56 | 1.23 |
| Deoxycholic acid 3-sulfate | 3.83 | 6.56 | 1.71 |
| Deoxycholic acid (12 or 24)-sulfate | 8.23 ↑ | 4.25 | 0.52 |
| Deoxycholic acid glucuronide | 0.48 | 0.33 | 0.69 ↓ |
| Taurodeoxycholate | 15.78 ↑ | 16.4 | 1.04 |
| Lithocholate | 1.17 | 1.03 | 0.88 ↓ |
| Lithocholate sulfate (1) | 3.58 ↑ | 1.74 | 0.48 |
| Lithocholate sulfate (2) | 4.33 | 6.12 | 1.41 |
| Glycolithocholate sulfate | 2.23 | 1.86 | 0.83 |
| Taurolithocholate 3-sulfate | 2.5 | 2.54 ↑ | 1.01 |
| Ursodeoxycholate | 1.48 ↑ | 2.72 | 1.84 |
| Isoursodeoxycholate | 2.13 | 2.1 | 0.98 |
| Isoursodeoxycholate sulfate (1) | 3.89 ↑ | 5.62 | 1.45 |
| Glycoursodeoxycholate | 2.59 | 1.12 | 0.43 |
| Tauroursodeoxycholate | 2.84 | 1.26 | 0.44 ↓ |
| Taurochenodeoxycholic acid 3-sulfate | 10.04 | 1.13 | 0.11 |
| Ursodeoxycholate sulfate (1) | 2.76 | 11.72 | 4.24 |

Several fecal metabolites with metabolic origins possibly connected to the microbiome were altered in either the cancer T1 or cancer T2 groups compared to the healthy control group (Table 31). These included polyamine compounds such as cadaverine and putrescine, derivatives of the aromatic amino acids—phenylalanine, tyrosine, and tryptophan, benzoates, and compounds related to the microbial-aided breakdown of complex polymers such as lignin present in plant foodstuffs. Many differential changes were apparent between cancer T1 and the healthy group relative to the cancer T2 and healthy group comparison, and other compounds differed in the baseline cancer T1 to cancer T2 treatment groups. The differential pattern of microbiome-associated metabolites in the cancer T1 and cancer T2 groups could reflect compositional changes in the microflora both driven by cancer (i.e., cancer T1 differences) as well as anticancer treatment (i.e., cancer T2 distinctions). A healthy microflora maintains an intestinal barrier that keeps out genotoxic and inflammatory bacteria and their toxins [9]. An increasing number of publications point to likely contributions of dysbiosis and toxins to carcinogenesis and the role of a healthy microflora supported by lifestyle, diet, prebiotics, and probiotics to prevent and serve as anticancer adjuvants are being explored [10].

TABLE 31

Microbiome-associated compounds displayed differential patterns in the fecal metabolome of the cancer T1 and cancer T2 groups. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| Cadaverine | 1.85 | 3.91 ↑ | 2.11 |
| N-acetyl-cadaverine | 5.06 | 5.56 ↑ | 1.1 |
| Phenethylamine | 0.73 | 1.42 ↑ | 1.95 |
| Tyramine | 2.26 ↑ | 12.82 | 5.69 |
| Phenol sulfate | 6.03 ↑ | 2.12 | 0.35 |
| p-cresol glucuronide | 2.56 | 1 | 0.39 ↓ |
| Vanillic alcohol sulfate | 1 | 35.29 | 35.29 ↑ |
| Tryptamine | 4.79 ↑ | 12.5 | 2.61 |
| Skatol | 1.41 | 0.13 ↓ | 0.09 |
| Indole | 2.63 | 0.89 ↓ | 0.34 |
| Indole-3-carboxylate | 0.83 | 0.26 ↓ | 0.31 |
| 2-aminophenol | 2.82 ↑ | 0.95 | 0.34 |
| Agmatine | 2.67 | 1.92 | 0.72 ↓ |
| Putrescine | 2.18 | 4.89 ↑ | 2.24 |
| N-acetylputrescine | 2.39 | 2.67 | 1.12 |
| Spermidine | 1.16 | 2.37 | 2.04 |
| N('1)-acetylspermidine | 1.46 | 1.42 ↑ | 0.97 |
| Acisoga | 2.26 ↑ | 1.46 | 0.64 |
| Alpha-CEHC sulfate | 4.5 ↑ | 6.95 | 1.54 |
| Delta-CEHC | 0.78 | 0.56 | 0.73 |
| Gamma-CEHC sulfate | 1.53 ↑ | 3.58 | 2.34 |
| 3-hydroxyhippurate | 0.49 | 0.15 ↓ | 0.31 |
| 2-(4-hydroxyphenyl)propionate | 1.52 | 0.23 ↓ | 0.15 |
| 4-hydroxycyclohexylcarboxylic acid | 0.5 ↓ | 0.94 | 1.89 |
| Caffeate | 0.54 | 0.57 | 1.05 |
| Coumaroylquinate (1) | 0.35 | 0.42 | 1.2 ↑ |
| Coumaroylquinate (3) | 0.54 | 0.58 | 1.08 ↑ |
| Genistein sulfate | 15.6 | 2.23 | 0.14 ↓ |
| Enterolactone | 1.1 ↑ | 0.47 | 0.43 |

Heme degradation markers, including bilirubin and L-urobilinogen, showed changes across the cancer T1 and cancer T2 compared to the healthy group in feces and in the cancer T1 group of plasma compared to the healthy controls (Tables 32 and 33). Urobilinogen and urobilin are downstream products connected to the microbiome. An interesting recent metabolomic publication found increasing fecal levels of urobilinogen with increasing radiation dose and cross-omic analysis showed that the increase was positively correlated to microbes of the Lachnospiraceae, Ruminococcaceae, and Rikenellacea taxa [11I]. This work shows how cross-omic integration can lead to a greater understanding and provide needed specificity to changes in distinct metabolites.

TABLE 32

Heme degradation markers with altered levels in feces. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| Protoporphyrin IX | 1.32 | 0.86 | 0.65 ↓ |
| Bilirubin (Z,Z) | 4.39 ↑ | 2.95 | 0.67 |
| Bilirubin (E,E) | 3.54 | 1.81 | 0.51 |
| Biliverdin | 1.8 | 0.86 | 0.48 |
| Urobilinogen | 3.74 | 5.02 ↑ | 1.34 |
| D-urobilin | 0.99 | 0.73 | 0.74 |
| L-urobilin | 0.37 ↓ | 0.7 | 1.9 |

TABLE 33

Heme degradation markers with altered levels in plasma. Values given are ratios of the mean peak areas for the specified metabolites between the two groups indicated. Up or down arrows indicate whether the increase or decrease in the treatment relative to the control is significant based on Welch's two-sample t-test with $p < 0.05$.

| Compound | Cancer T1/All Healthy | Cancer T2/All Healthy | Cancer T2/ Cancer T1 |
|---|---|---|---|
| Heme | 1.15 | 1.98 | 1.72 |
| Bilirubin (Z,Z) | 0.68 ↓ | 0.71 | 1.05 |
| Bilirubin (E,Z) or (Z,E) | 0.66 ↓ | 0.66 | 1 |
| Biliverdin | 0.77 | 0.87 | 1.12 |
| Urobilinogen | 1.72 ↑ | 1.3 | 0.75 |

REFERENCES EXAMPLE 7

[1] A. M. Evans, B. R. Bridgewater, Q. Liu, M. W. Mitchell, R. J. Robinson, H. Dai, S. J. Stewart, C. D. DeHaven, and L. A. D. Miller, High resolution mass spectrometry improves data quantity and quality as compared to unit mass resolution mass spectrometry in high-throughput profiling metabolomics. Metabolomics 4 (2014).

[2] C. D. DeHaven, A. M. Evans, H. Dai, and K. A. Lawton, Organization of GC/MS and LC/MS metabolomics data into chemical libraries. Journal of cheminformatics 2 (2010) 9.

[3] W. X. Zong, J. D. Rabinowitz, and E. White, Mitochondria and Cancer. Mol Cell 61 (2016) 667-676.

[4] N. M. Anderson, P. Mucka, J. G. Kern, and H. Feng, The emerging role and targetability of the TCA cycle in cancer metabolism. Protein Cell 9 (2018) 216-237.

[5] T. Li, and A. Le, Glutamine Metabolism in Cancer. Adv Exp Med Biol 1063 (2018) 13-32.

[6] D. Xiao, L. Zeng, K. Yao, X. Kong, G. Wu, and Y. Yin, The glutamine-alpha-ketoglutarate (AKG) metabolism and its nutritional implications. Amino Acids 48 (2016) 2067-80.

[7] L. Andrisic, D. Dudzik, C. Barbas, L. Milkovic, T. Grune, and N. Zarkovic, Short overview on metabolomics approach to study pathophysiology of oxidative stress in cancer. Redox Biol 14 (2018) 47-58.

[8] J. M. Estrela, A. Ortega, and E. Obrador, Glutathione in cancer biology and therapy. Crit Rev Clin Lab Sci 43 (2006) 143-81.

[9] R. F. Schwabe, and C. Jobin, The microbiome and cancer. Nat Rev Cancer 13 (2013) 800-12.

[10]A. P. Bhatt, M. R. Redinbo, and S. J. Bultman, The role of the microbiome in cancer development and therapy. CA Cancer J Clin 67 (2017) 326-344.

[11]M. Goudarzi, T. D. Mak, J. P. Jacobs, B. H. Moon, S. J. Strawn, J. Braun, D. J. Brenner, A. J. Fornace, Jr., and H. H. Li, An Integrated Multi-Omic Approach to Assess Radiation Injury on the Host-Microbiome Axis. Radiat Res 186 (2016) 219-34.

Figure 24A:
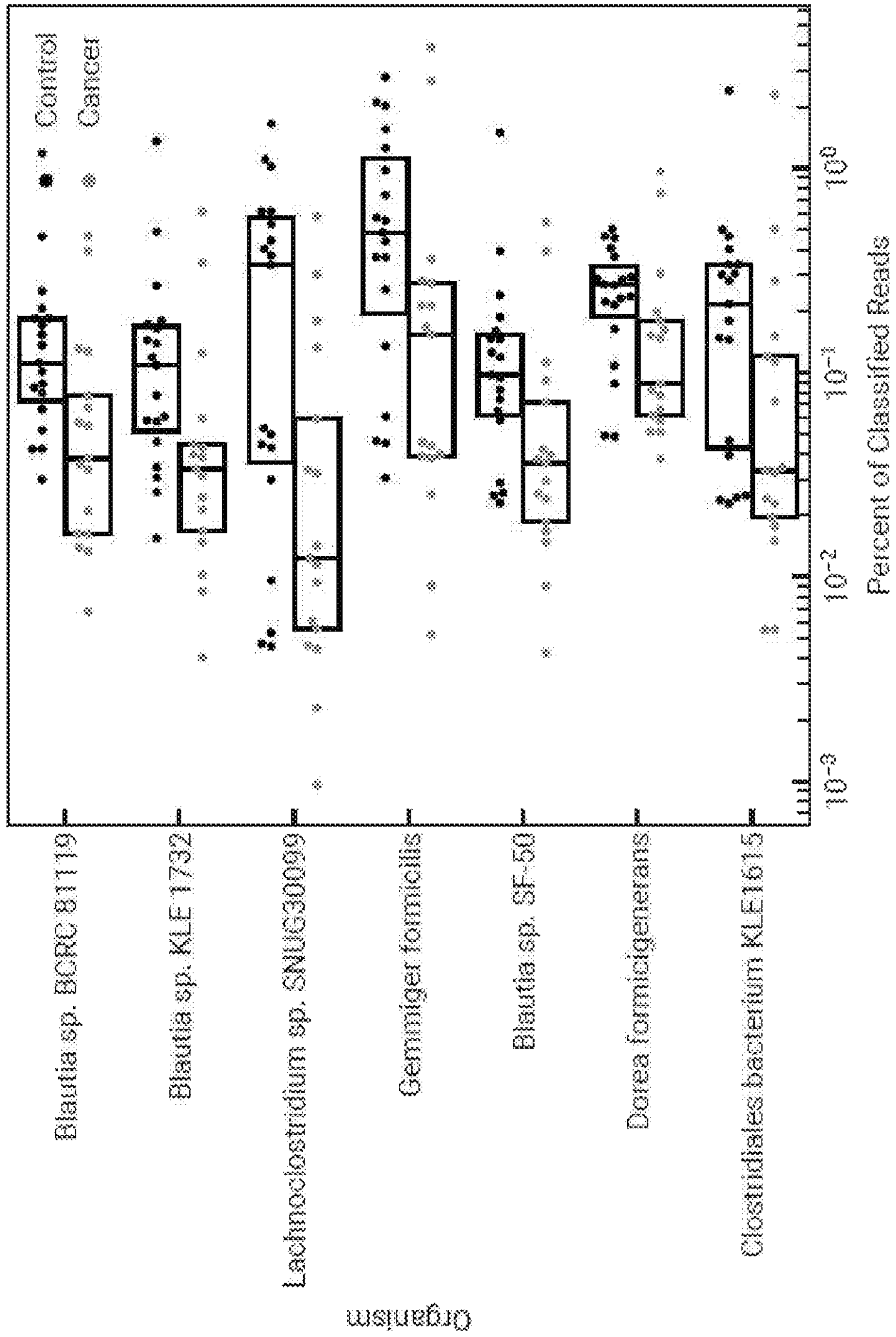
FIG. 24A-C graphically illustrate boxplots of the organisms that are statistically significantly depleted in the cancer population ($p<0.01$, Mann-Whitney U) in comparison to human subjects without cancer; as discussed in detail in Example 7, below.
Figure 24B:
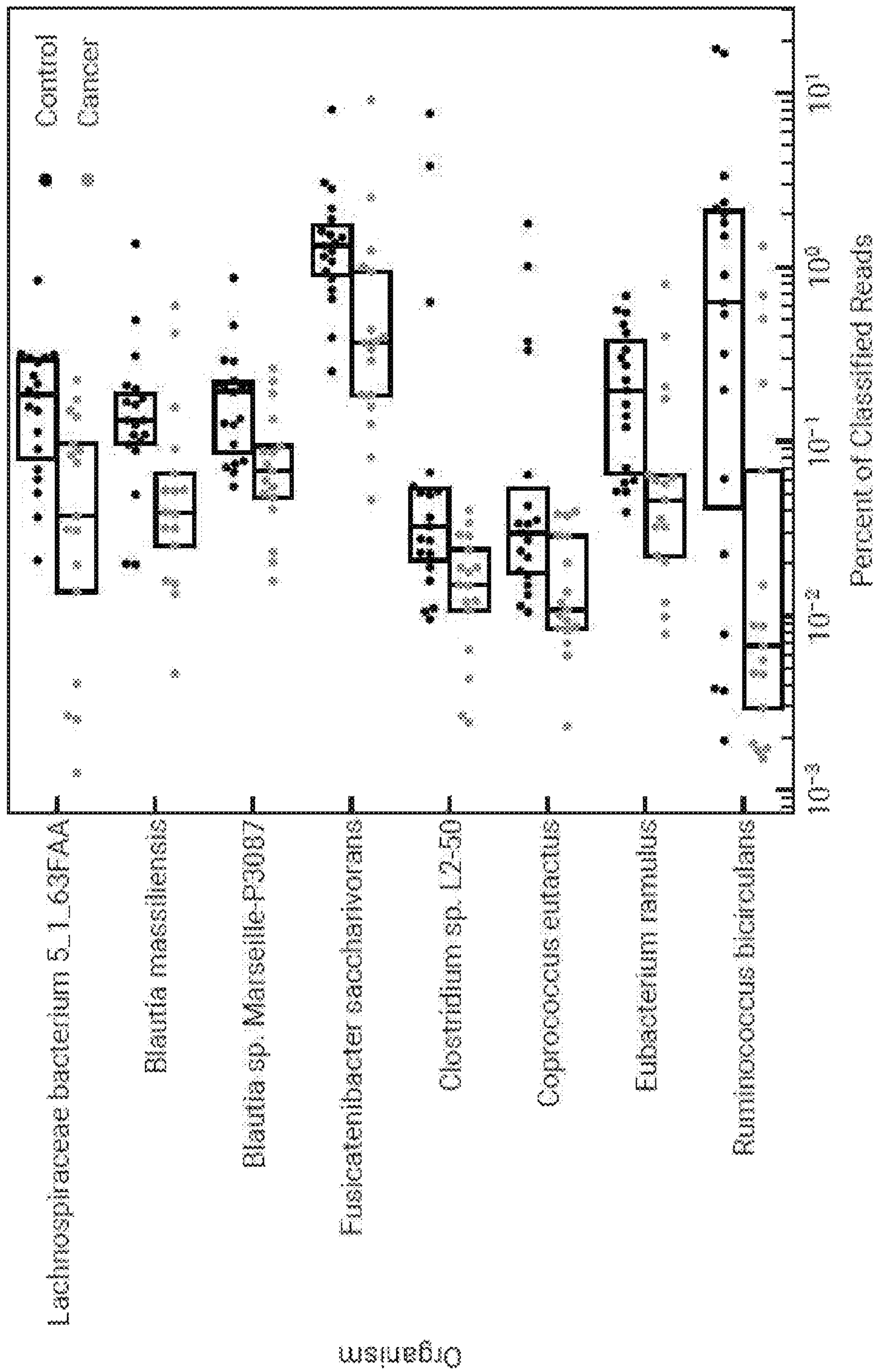
Figure 24C:
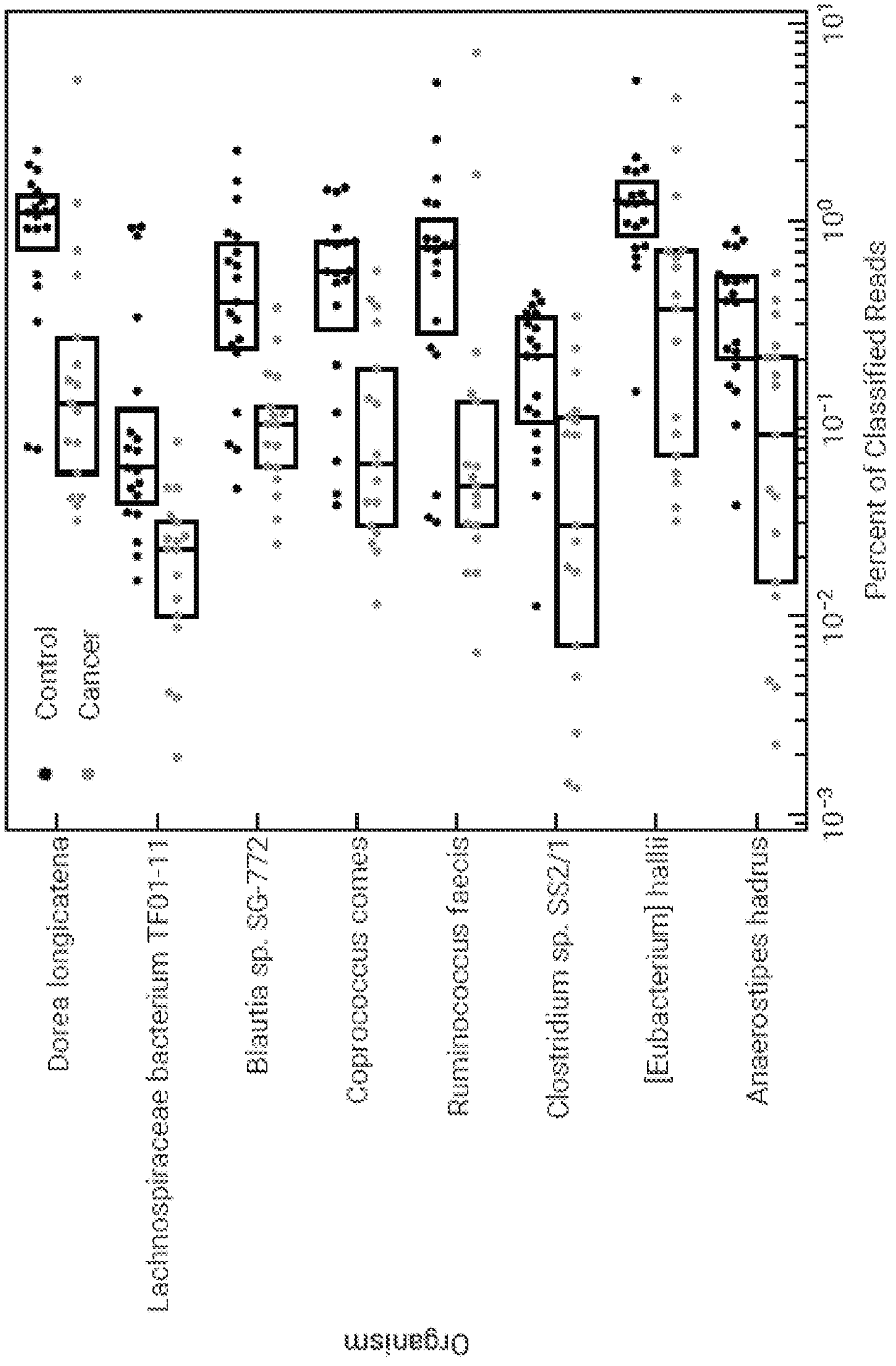
Figure 25:
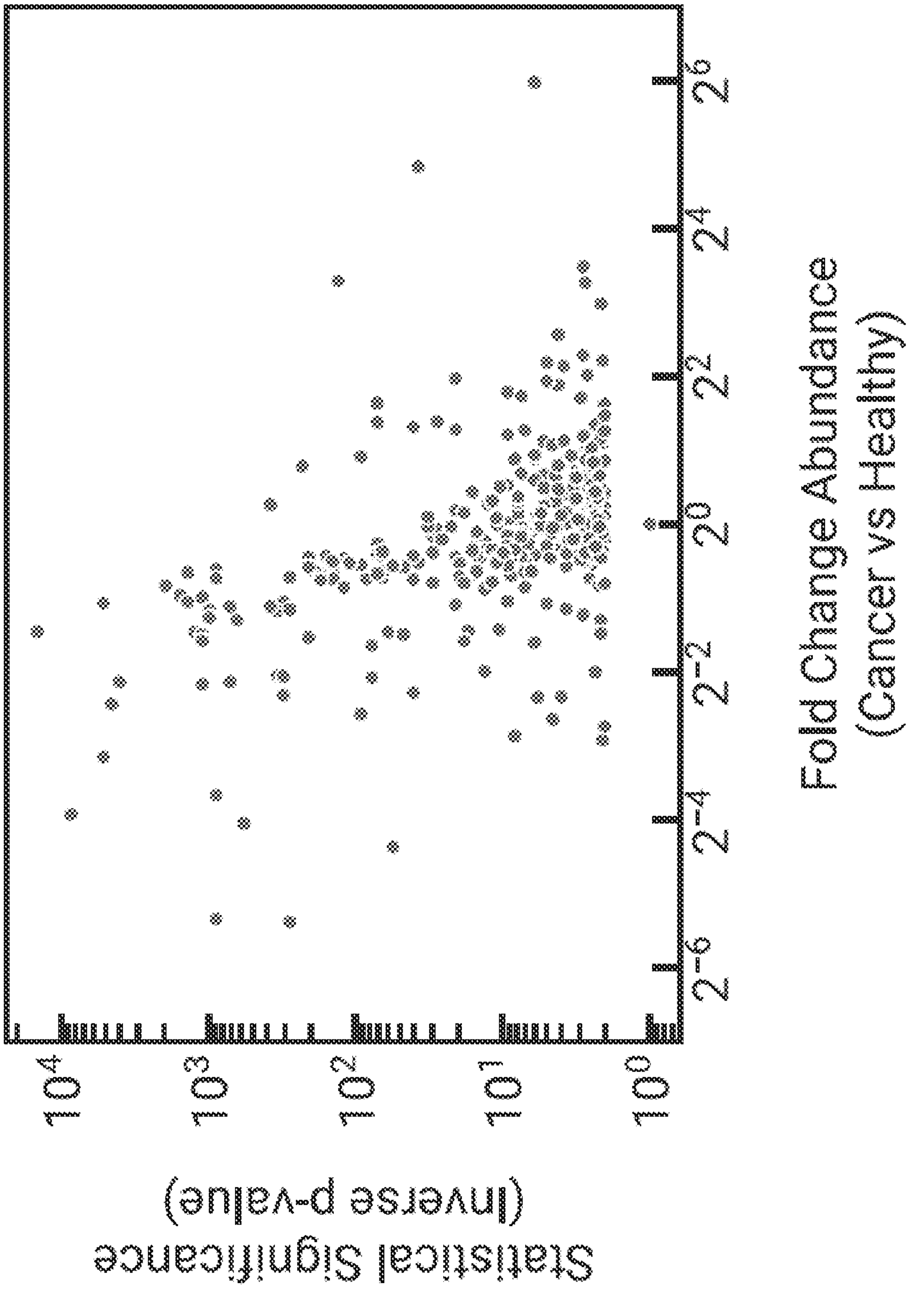
FIG. 25 graphically illustrates the fold change for each microbial species within human subjects with and without cancer is plotted against the inverse p-value (Mann-Whitney U). Organisms statistically significantly enriched in healthy samples appear at the top left of the plot; as discussed in detail in Example 7, below.
Figure 26:
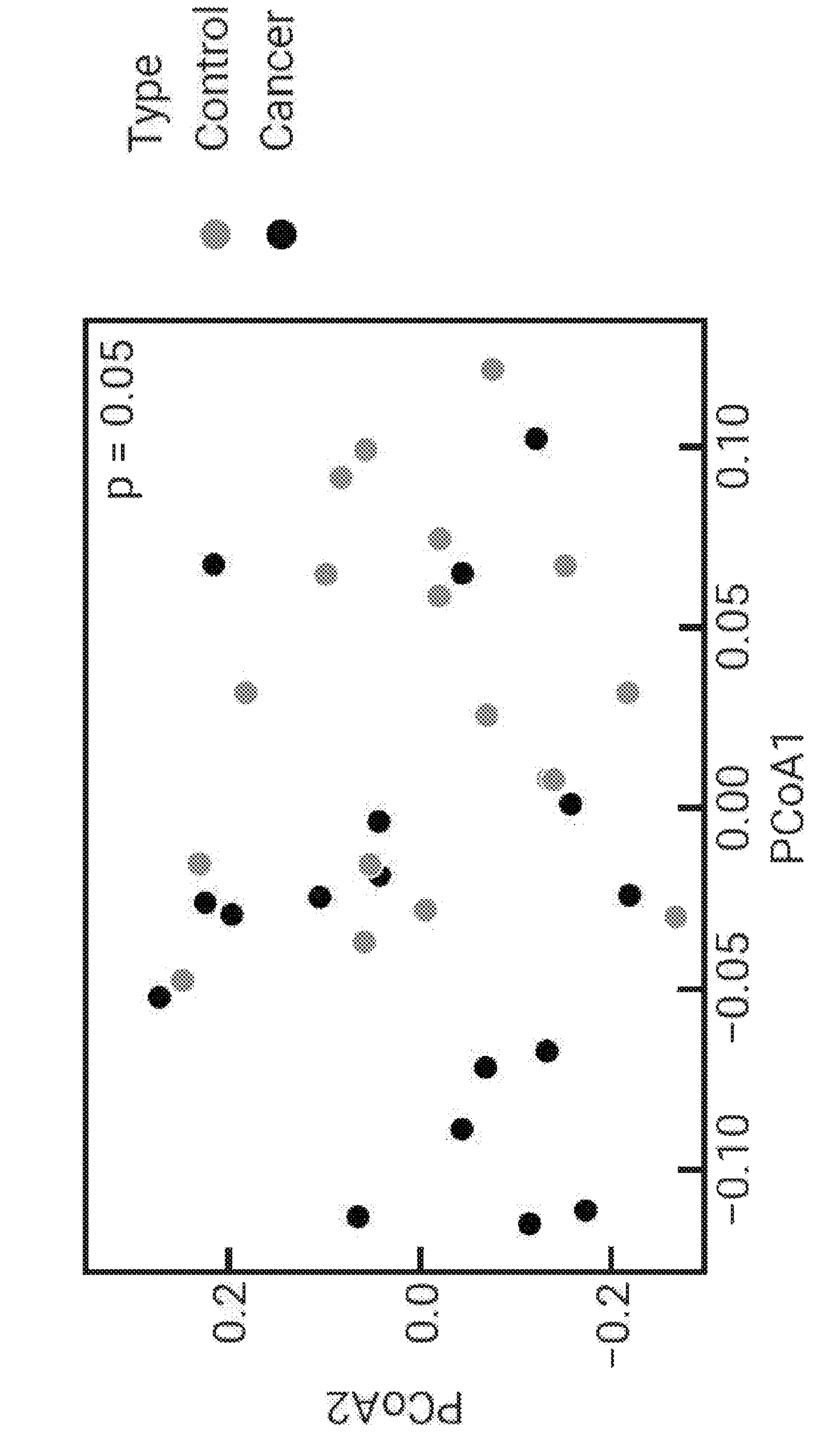
FIG. 26 graphically illustrates the distance between the whole genome sequences from samples as calculated using the generalized Unifrac metric and principal coordinates analysis (PCoA) which was performed on the resulting distance matrix. A statistically significant difference ($p=0.05$, PERMANOVA) was observed between the cancer and healthy populations; as discussed in detail in Example 7, below.
Figure 27:
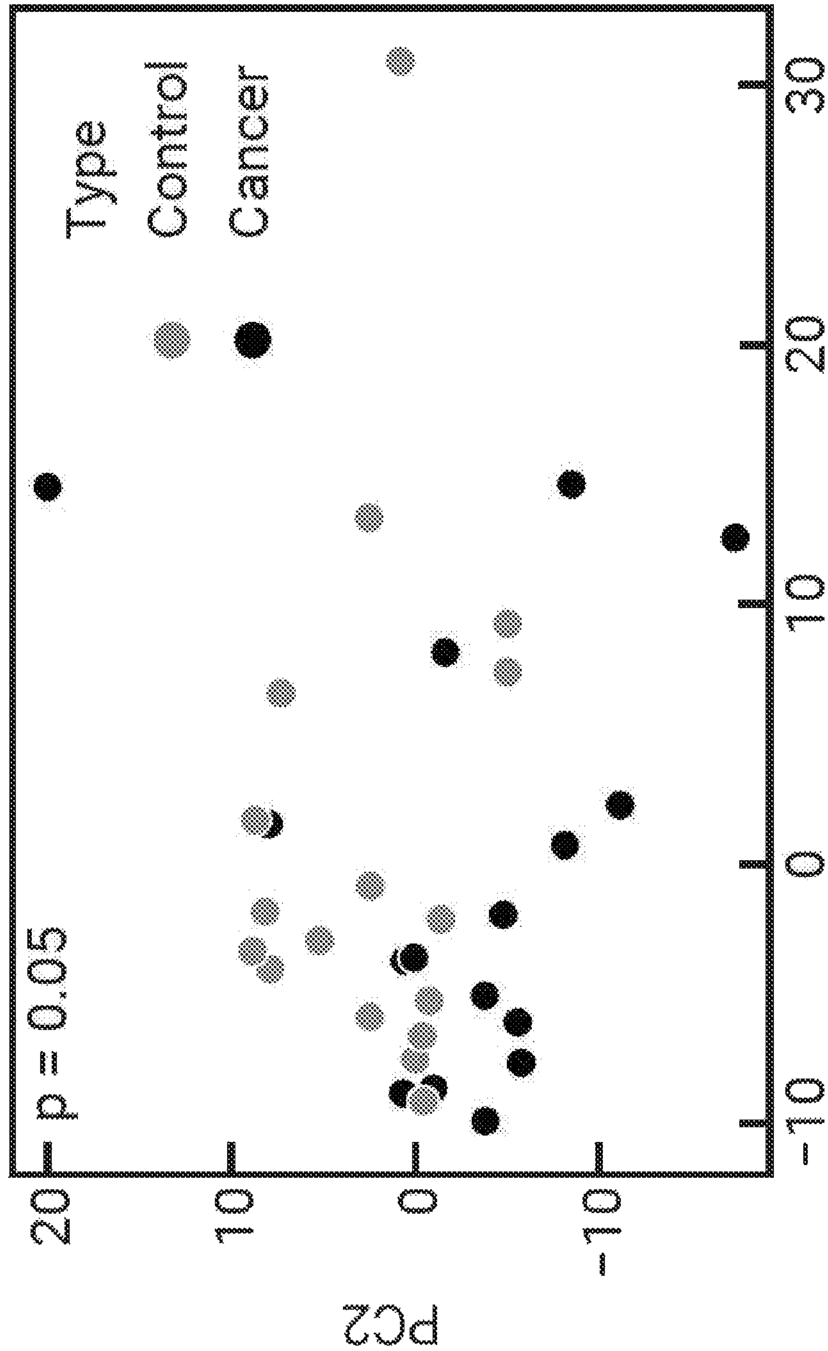
FIG. 27 graphically illustrates the distance between the whole genome sequences from samples as calculated using a Euclidean distance metric on scaled species-level read percentages, where PCA was performed on the data. A statistically significant difference ($p=0.05$, PERMANOVA) is observed between the cancer and healthy populations; as discussed in detail in Example 7, below.
Figure 34:
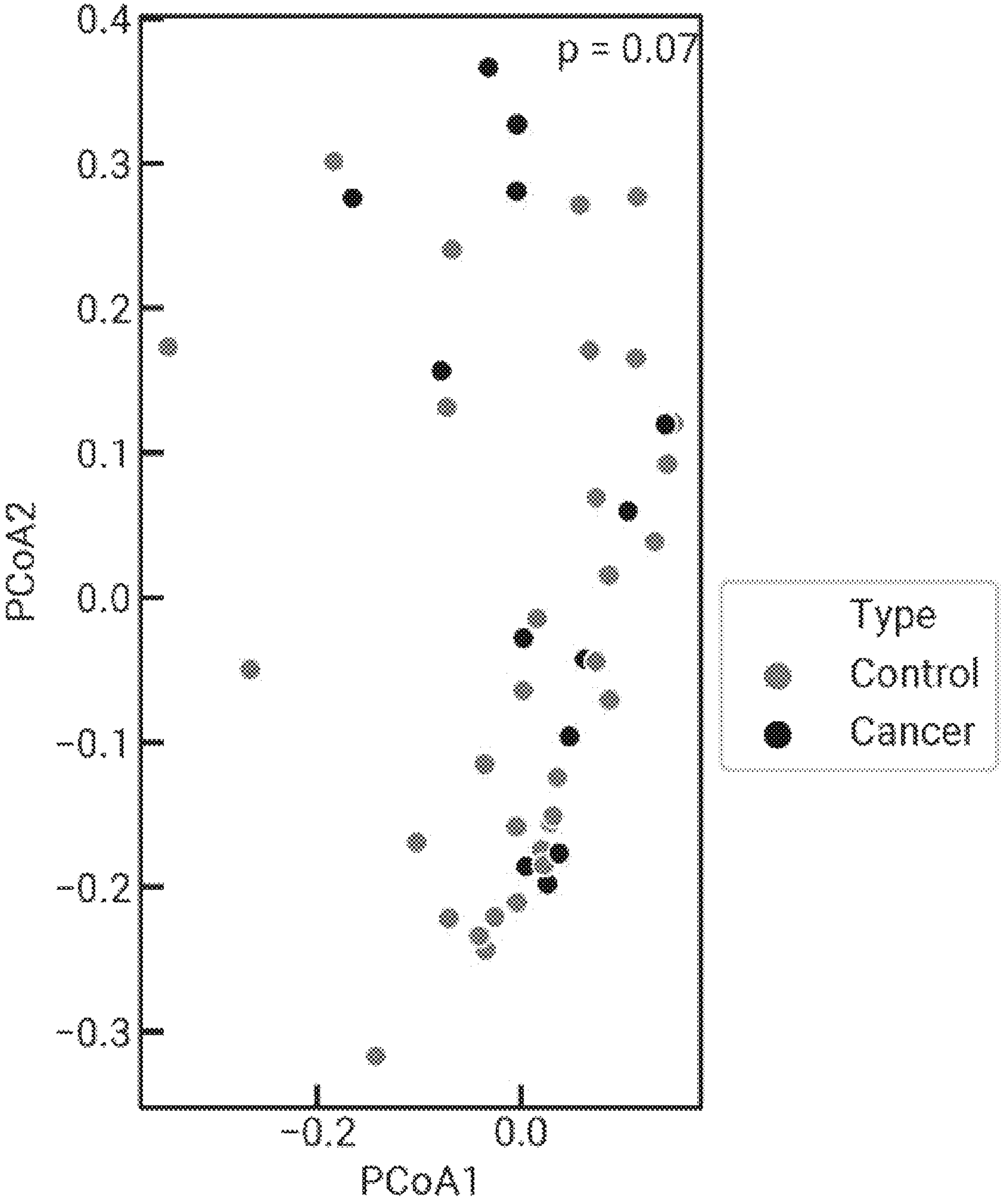
FIG. 34 graphically illustrates the distance between the whole genome sequences from samples as calculated using the generalized Unifrac metric and principal coordinates analysis (PCoA) which was performed on the resulting distance matrix. A statistically significant difference ($p=0.05$, PERMANOVA) was observed between the cancer and healthy populations; as discussed in detail in Example 7, below.
Figure 35:
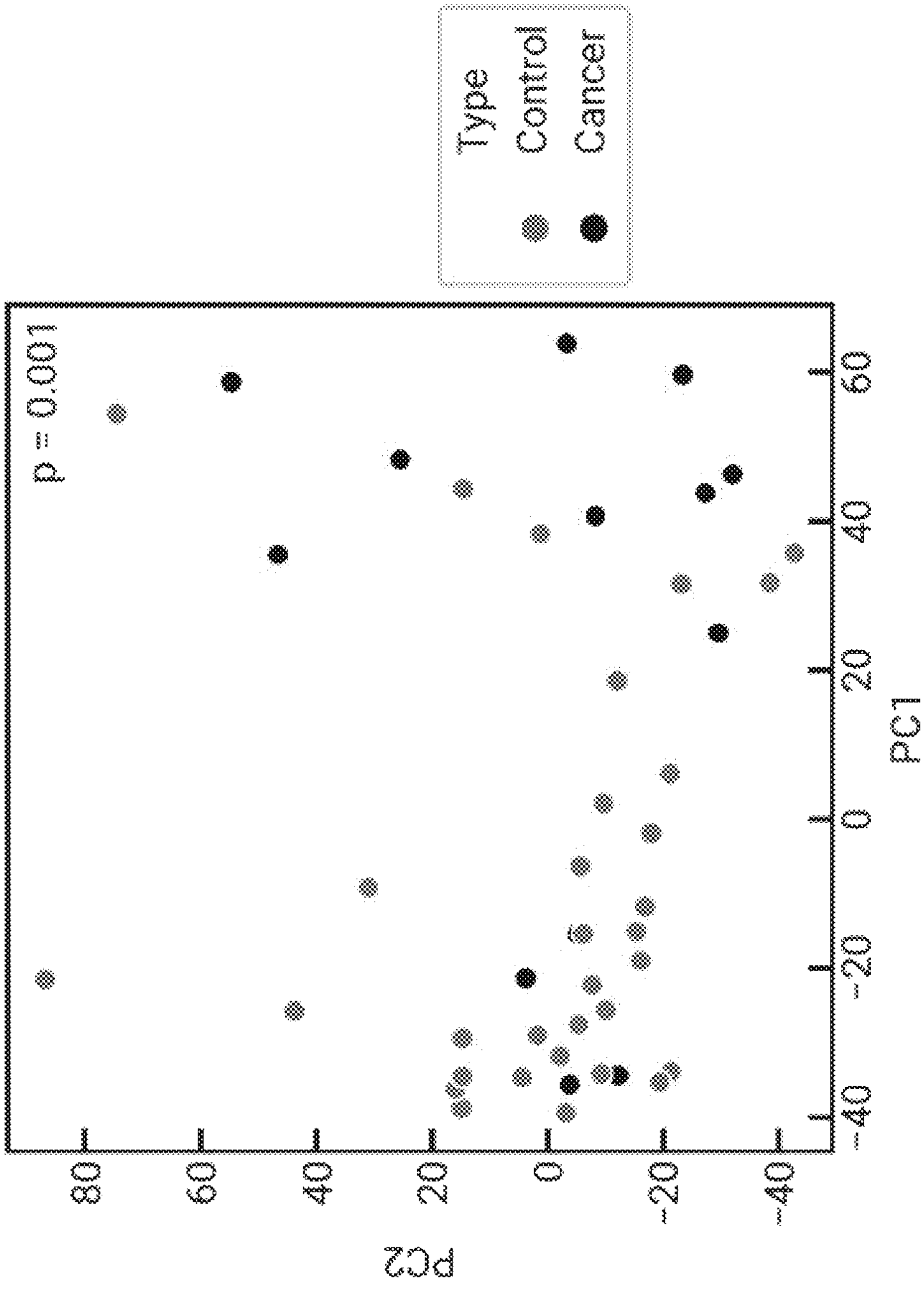
FIG. 35 graphically illustrates the distance between the whole genome sequences from samples as calculated using a Euclidean distance metric on scaled species-level read percentages, where PCA was performed on the data. A statistically significant difference ($p=0.05$, PERMANOVA) is observed between the cancer and healthy populations; as discussed in detail in Example 7, below.

Whole genome sequencing (WGS) is performed on fecal samples obtained from an additional set of human subjects with (19) and without cancer (28). Sequencing reads are aligned to a database of known reference genomes and the percentage of uniquely aligned reads is compared for each organism between the control and cancer populations. The organisms displayed all show a statistically significant depletion in the cancer population ($p<0.01$, Mann-Whitney U) as shown in FIG. 24. All organisms displayed are present in healthy samples at a minimum average read abundance of 0.18 percent. The fold change for each species is plotted against the inverse p-value (Mann-Whitney U) as shown in FIG. 25. Organisms statistically significantly enriched in healthy samples appear at the top left of the plot. From the WGS data, sequencing reads were aligned to a database of known reference genomes. The distance between the samples was calculated using the generalized Unifrac metric and principal coordinates analysis (PCoA) was performed on the resulting distance matrix as shown in FIG. 26 and FIG. 34. A statistically significant difference ($p=0.05$, PERMANOVA) is observed between the cancer and healthy populations. The distance between samples was also calculated using a Euclidean distance metric on scaled species-level read percentages, and PCA was performed on the data as shown in FIG. 27 and FIG. 35. A statistically significant different ($p=0.5$, PERMANOVA) was observed between the cancer and healthy populations.

Figure 36:
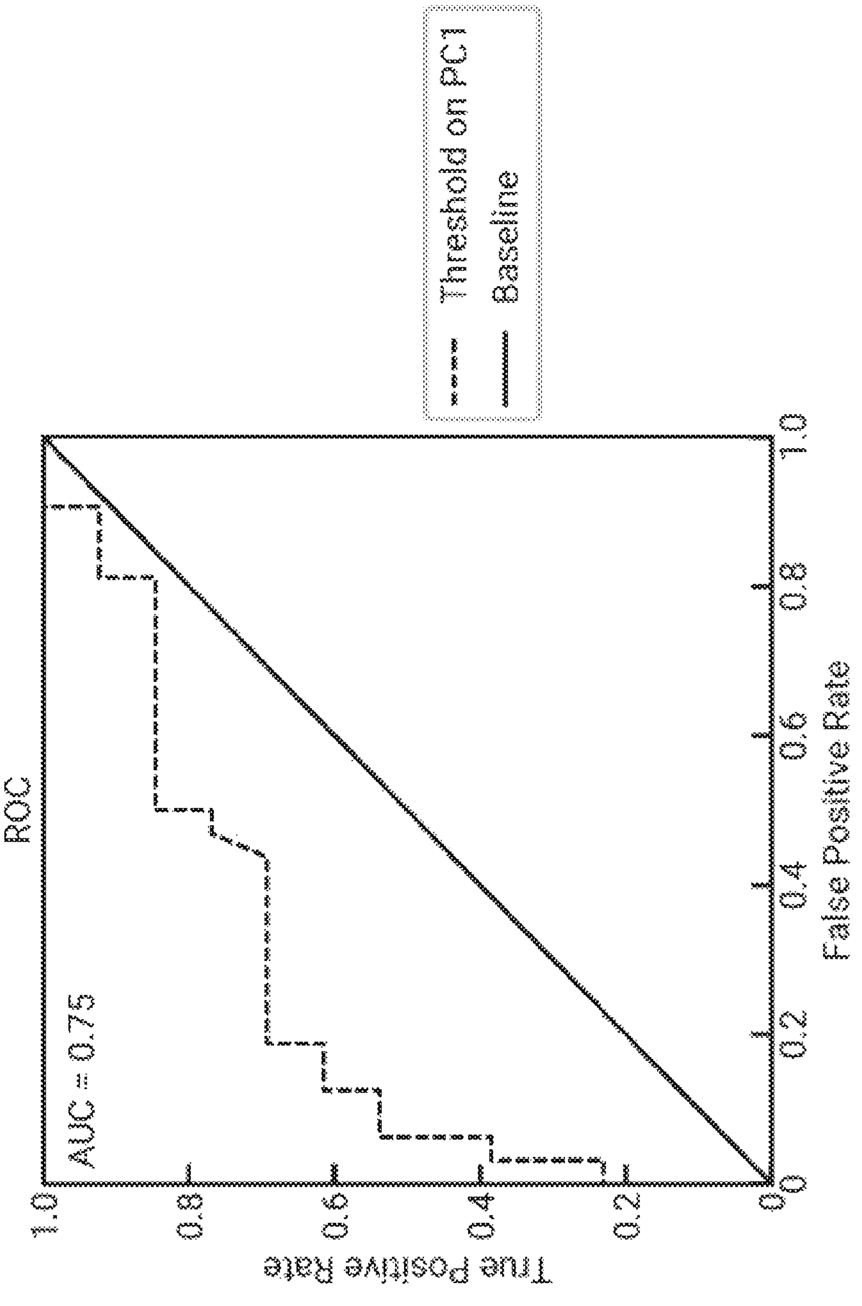
FIG. 36 graphically illustrates a receiver operating characteristic curve wherein any samples above the shown threshold in the first principal component are marked as cancer.

To determine if the patient sequencing data alone could be diagnostic of patients with cancer, we used a receiver operating characteristic (ROC) curve to illustrate the diagnostic ability of a binary classifier system as its discrimination threshold is varied. A basic classifier as illustrated in FIG. 36 was determined by inspection of the PCA plot in FIG. 35, wherein any samples above a certain threshold in the first principal component are marked as cancer. The threshold is varied across the range of the first principal component, and the results for each threshold are collated into a receiver operating characteristic, which demonstrates the ability of just the first principal component to distinguish cancer vs healthy control samples.

TABLE 19

Lists microbial species statistically significantly enriched in the healthy population, along with their average read percentages in healthy samples as well as the associated NCBI taxonomic ID's.

| Fold Change Cancer vs Healthy | p value Mann-Whitney-U | NCBI Tax ID | Percentage of Classified Reads In Control Samples | Species Name |
|---|---|---|---|---|
| 0.365409536 | 6.89045E−05 | 28051 | 0.015497591 | *Lachnospira multipara* |
| 0.065807259 | 0.000116595 | 36834 | 0.021762173 | *Clostridium celatum* |
| 0.476620076 | 0.000194063 | 88431 | 1.107516493 | *Dorea longicatena* |
| 0.112949906 | 0.000194063 | 1703332 | 0.209666708 | *Lachnospiraceae* bacterium TF01-11 |
| 0.184986545 | 0.000219857 | 2109334 | 0.592048367 | *Blautia* sp. SG-772 |
| 0.227853266 | 0.000248824 | 410072 | 0.624881754 | *Coprococcus comes* |
| 0.562253724 | 0.000511744 | 592978 | 1.0133648 | *Ruminococcus faecis* |
| 0.512690256 | 0.000645485 | 42322 | 0.010955176 | *Eubacterium ruminantium* |
| 0.634865773 | 0.000723834 | 831 | 0.012145534 | *Butyrivibrio fibrisolvens* |
| 0.480809188 | 0.000723834 | 140626 | 0.01194996 | *Lachnobacterium bovis* |
| 0.362799705 | 0.000810866 | 411484 | 0.212274371 | *Clostridium* sp. SS2/1 |
| 0.504677863 | 0.000907438 | 39488 | 1.388484326 | [*Eubacterium*] *hallii* |
| 0.352959262 | 0.000907438 | 649756 | 0.410941368 | *Anaerostipes hadrus* |
| 0.335272214 | 0.000907438 | 658089 | 0.206387473 | *Lachnospiraceae* bacterium 5_1_63FAA |
| 0.223425272 | 0.000907438 | 457397 | 0.03371062 | *Clostridium* sp. 1_1_41A1FAA |
| 0.44575276 | 0.001014481 | 1737424 | 0.224787105 | *Blautia massiliensis* |
| 0.417180861 | 0.001014481 | 1917876 | 0.215613527 | *Blautia* sp. Marseille-P3087 |
| 0.602052162 | 0.001133 | 1150298 | 1.738517722 | *Fusicatenibacter saccharivorans* |
| 0.024662601 | 0.001133 | 411489 | 0.697153152 | *Clostridium* sp. L2-50 |
| 0.078937095 | 0.001133 | 33043 | 0.215593885 | *Coprococcus eutactus* |
| 0.653885611 | 0.001133 | 655607 | 0.02281469 | *Tepidibacter mesophilus* |
| 0.461852488 | 0.001408902 | 39490 | 0.260172588 | *Eubacterium ramulus* |

TABLE 19-continued

Lists microbial species statistically significantly enriched in the healthy population, along with their average read percentages in healthy samples as well as the associated NCBI taxonomic ID's.

| Fold Change Cancer vs Healthy | p value Mann-Whitney-U | NCBI Tax ID | Percentage of Classified Reads In Control Samples | Species Name |
|---|---|---|---|---|
| 0.227682525 | 0.001408902 | 1776391 | 0.069449626 | *Romboutsia timonensis* |
| 0.406785423 | 0.001568724 | 43997 | 0.010933518 | *Catonella morbi* |
| 0.060470303 | 0.001744912 | 1160721 | 2.786142614 | *Ruminococcus bicirculans* |
| 0.462970555 | 0.002644242 | 2212480 | 0.199499508 | *Blautia* sp. BCRC 81119 |
| 0.443607295 | 0.002926449 | 1226324 | 0.195300791 | *Blautia* sp. KLE 1732 |
| 0.242143043 | 0.002926449 | 1264 | 0.038832875 | *Ruminococcus albus* |
| 0.201016823 | 0.003235526 | 2126738 | 0.407929696 | *Lachnoclostridium* sp. SNUG30099 |
| 0.239882255 | 0.003235526 | 1712675 | 0.027538954 | *Turicibacter* sp. H121 |
| 0.483336745 | 0.003235526 | 729 | 0.023050433 | *Haemophilus parainfluenzae* |
| 0.608564369 | 0.003573663 | 745368 | 0.821432218 | *Gemmiger formicilis* |
| 0.449711985 | 0.003573663 | 1520805 | 0.197958438 | *Blautia* sp. SF-50 |
| 0.024001006 | 0.003573663 | 28025 | 0.082480921 | *Bifidobacterium animalis* |
| 0.739384992 | 0.004786459 | 39486 | 0.27361996 | *Dorea formicigenerans* |
| 0.344508633 | 0.004786459 | 261299 | 0.04348204 | *Intestinibacter bartlettii* |
| 0.669003485 | 0.004786459 | 1898203 | 0.017746608 | *Lachnospiraceae* bacterium |
| 0.641157443 | 0.005265604 | 1715004 | 0.343706393 | *Clostridiales* bacterium KLE1615 |
| 0.592253944 | 0.005786952 | 1870993 | 0.078219633 | *Tyzzerella* sp. Marseille-P3062 |
| 0.623775728 | 0.005786952 | 397287 | 0.011208448 | *Lachnospiraceae* bacterium 28-4 |
| 0.742157802 | 0.006353603 | 1235790 | 0.012323192 | *Eubacterium* sp. 14-2 |
| 0.646191195 | 0.006968824 | 39496 | 0.141254074 | *Eubacterium ventriosum* |
| 0.599503299 | 0.006968824 | 290052 | 0.031977146 | *Acetivibrio ethanolgignens* |
| 0.705770831 | 0.006968824 | 1261637 | 0.012244286 | *Anaerostipes* sp. 992a |
| 0.552534289 | 0.008358888 | 1870991 | 0.041252394 | *Massilioclostridium coli* |
| 0.718290687 | 0.008358888 | 97253 | 0.016085333 | *Eubacterium plexicaudatum* |
| 0.727402964 | 0.008358888 | 397291 | 0.010254489 | *Lachnospiraceae* bacterium A4 |
| 0.695322632 | 0.009141122 | 2126739 | 0.148804869 | *Lachnoclostridium* sp. SNUG30370 |

TABLE 22

Figure 37:
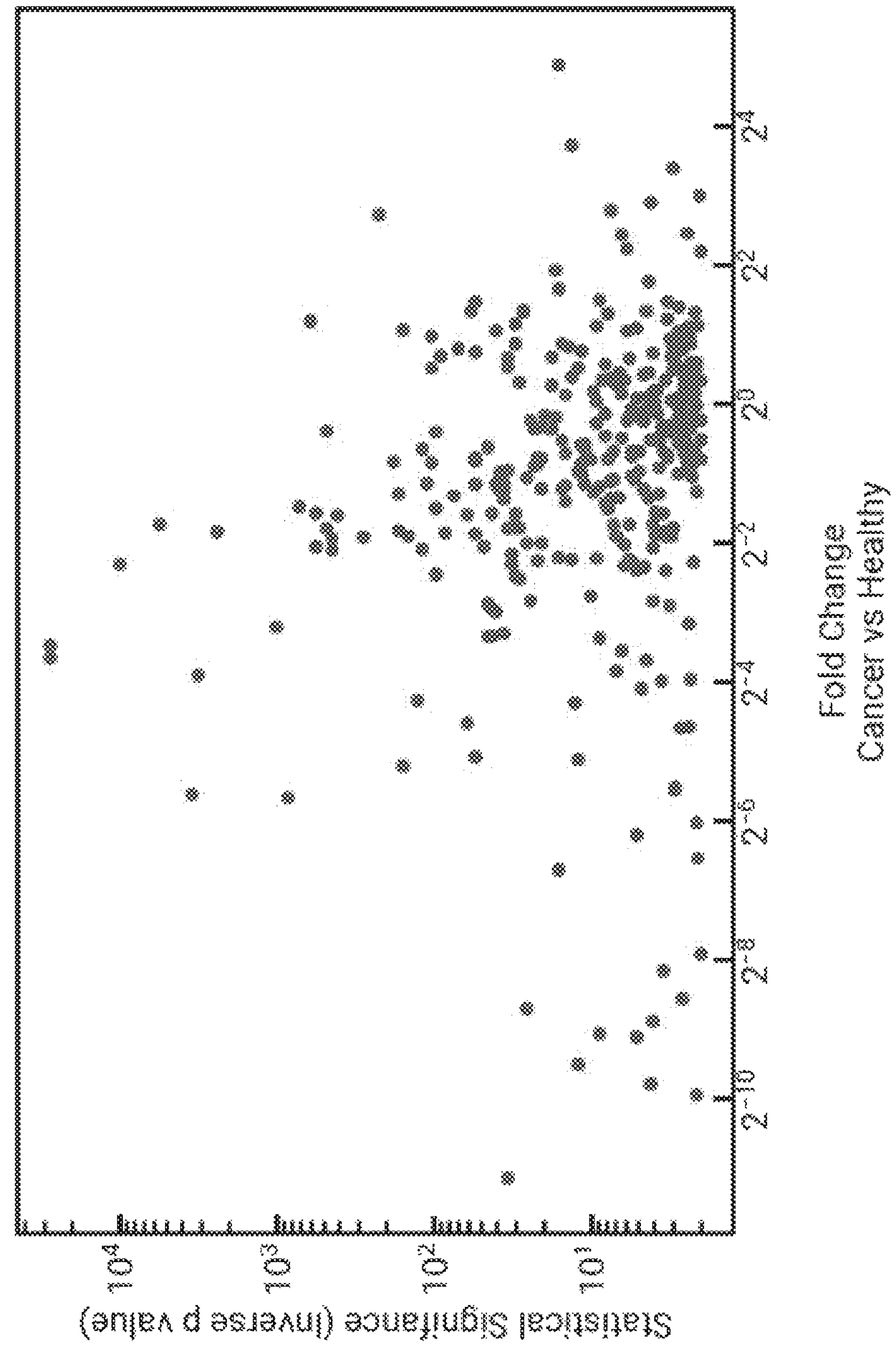
FIG. 37 graphically illustrates the fold change for each microbial species within human subjects with and without cancer is plotted against the inverse p-value (Mann-Whitney U). Organisms statistically significantly enriched in healthy samples appear at the top left of the plot; as discussed in detail in Example 7, below.

Lists microbial species statistically significantly enriched in the healthy population, along with their average read percentages in healthy samples as well as the associated NCBI taxonomic ID's. The Mann-Whitney U test is used to statistically compare both the abundances and the centered log ratio transformed abundances for each organism present in control samples at a minimum abundance of 0.0002. The reported organisms are significant (FDR = 0.10) in both tests. The fold change of each organism was plotted on the x-axis with the y-axis being the inverse p-value computed using the Mann-Whitney U test on the log ratio transformed abundances as illustrated in FIG. 37.

| Fold Change (cancer vs. healthy) | Mean Abundance in healthy control samples | Species Name | p-value computed using abundance (Mann-Whitney-U) | NCBI Taxonomic ID | p-value computed using centered log ratio transformed abundance (Mann-Whitney-U) |
|---|---|---|---|---|---|
| 0.300866775 | 0.015927018 | *Dorea longicatena* | 0.000238521 | 88431 | 0.000179548 |
| 0.240698227 | 0.007904504 | *Coprococcus comes* | 0.000453266 | 410072 | 0.001765005 |
| 0.45145998 | 0.007751434 | *Collinsella aerofaciens* | 0.009494766 | 74426 | 0.008979864 |
| 0.636721645 | 0.00558429 | *Dorea formicigenerans* | 0.000495635 | 39486 | 0.00839009 |
| 1.966036338 | 0.004924097 | *Bacteroides caccae* | 0.012505315 | 47678 | 0.009605642 |

TABLE 22-continued

Lists microbial species statistically significantly enriched in the healthy population, along with their average read percentages in healthy samples as well as the associated NCBI taxonomic ID's. The Mann-Whitney U test is used to statistically compare both the abundances and the centered log ratio transformed abundances for each organism present in control samples at a minimum abundance of 0.0002. The reported organisms are significant (FDR = 0.10) in both tests. The fold change of each organism was plotted on the x-axis with the y-axis being the inverse p-value computed using the Mann-Whitney U test on the log ratio transformed abundances as illustrated in FIG. 37.

| Fold Change (cancer vs. healthy) | Mean Abundance in healthy control samples | Species Name | p-value computed using abundance (Mann-Whitney-U) | NCBI Taxonomic ID | p-value computed using centered log ratio transformed abundance (Mann-Whitney-U) |
|---|---|---|---|---|---|
| 0.020318105 | 0.003065262 | *Lachnoclostridium* sp. SNUG30099 | 0.000170387 | 2126738 | 0.000287391 |
| 0.26100244 | 0.002439867 | *Ruminococcus* sp. AF19-15 | 0.005488725 | 2293157 | 0.002239881 |
| 0.20242531 | 0.001627527 | *Ruminococcus* sp. AM16-34 | 6.6998E−05 | 2293184 | 0.000100124 |
| 0.282386423 | 0.001601046 | *Ruminococcus* sp. AF34-12 | 0.007961206 | 2293177 | 0.005923016 |
| 0.234296244 | 0.001571365 | *Blautia* sp. SG-772 | 0.001383551 | 2109334 | 0.002239881 |
| 0.027016407 | 0.001558972 | *Clostridium sporogenes* | 0.00484825 | 1509 | 0.006357452 |
| 0.358466753 | 0.00116327 | *Coprococcus catus* | 0.001765005 | 116085 | 0.001383551 |
| 0.089653897 | 0.000996704 | *Blautia* sp. AF22-5LB | 4.92772E−05 | 2292964 | 3.60692E−05 |
| 0.560789735 | 0.000949247 | *Ruminococcus* sp. AF31-8BH | 0.001077407 | 2293174 | 0.005515113 |
| 0.052099554 | 0.0008824 | *Eubacterium* sp. AM49-13BH | 0.005509831 | 2292351 | 0.007834598 |
| 0.235312977 | 0.000706669 | *Ruminococcus* sp. AF37-20 | 0.010366074 | 2293178 | 0.00839009 |
| 0.407533547 | 0.000660071 | *Collinsella* sp. AM34-10 | 0.011571753 | 2292316 | 0.005923016 |
| 0.289312091 | 0.000575356 | *Blautia* sp. TF11-31AT | 0.002713323 | 2292987 | 0.002070064 |
| 0.066825763 | 0.000556696 | *Blautia* sp. AF25-12LB | 0.000414111 | 2292965 | 0.000315182 |
| 0.266995412 | 0.000504981 | *Collinsella* sp. AF28-5AC | 0.007149916 | 2292227 | 0.006819856 |
| 0.079330413 | 0.000486663 | *Blautia* sp. AF19-34 | 6.02323E−05 | 2292963 | 3.60692E−05 |
| 0.763198908 | 0.000448662 | *Clostridium* sp. ATCC BAA-442 | 0.010970216 | 649724 | 0.002070064 |
| 0.019720485 | 0.000373046 | *Blautia hydrogenotrophica* | 0.00041918 | 53443 | 0.001172816 |
| 0.336328012 | 0.000361407 | *Blautia* sp. AM22-22LB | 0.002239881 | 2292970 | 0.001765005 |
| 2.278815584 | 0.000344902 | *Bacteroides* sp. 3_1_40A | 0.010260883 | 469593 | 0.001628352 |
| 1.427576554 | 0.000323651 | *Lachnospiraceae* bacterium OM02-26 | 0.014074346 | 2292908 | 0.009605642 |
| 0.264401982 | 0.000317499 | *Ruminococcus* sp. AF17-22AC | 0.002811946 | 2292248 | 0.00355135 |
| 0.556781967 | 0.000311206 | *Lachnoclostridium* sp. SNUG30370 | 0.005088659 | 2126739 | 0.009605642 |
| 0.328791864 | 0.000311181 | *Ruminococcus* sp. OM04-4AA | 0.000703414 | 2293231 | 0.002422223 |
| 0.279120894 | 0.000283624 | *Dorea* sp. AF36-15AT | 0.001071585 | 2292041 | 0.000414275 |
| 0.353289184 | 0.000272142 | *Dorea* sp. AM10-31 | 0.011694284 | 2293098 | 0.010269206 |
| 0.107899648 | 0.000244589 | *Blautia* sp. AM16-16B | 0.000637421 | 2292969 | 0.000991861 |
| 0.182250913 | 0.000204297 | *Blautia* sp. OF03-15BH | 0.003547574 | 2292287 | 0.010269206 |

TABLE 34 depicts the organism level weights for the first principal component microbiome PCA weights for the first component, which strongly separates cancer and control samples. Only weights with sufficient magnitude (>= 0.014) and corresponding to organisms with abundance greater than or equal to 0.001 are reported, as discussed in this Example 7:

| Organism | Weight on 1st Principal Component | Mean Abundance Across All Samples | NCBI Taxonomic ID |
|---|---|---|---|
| *Collinsella* sp. 4_8_47FAA | −0.08926 | 0.001105 | 742722 |
| *Collinsella* sp. TF05-9AC | −0.08514 | 0.001403 | 2292330 |
| *Collinsella aerofaciens* | −0.07566 | 0.005519 | 74426 |

TABLE 34-continued depicts the organism level weights for the first principal component microbiome PCA weights for the first component, which strongly separates cancer and control samples. Only weights with sufficient magnitude (>= 0.014) and corresponding to organisms with abundance greater than or equal to 0.001 are reported, as discussed in this Example 7:

| Organism | Weight on 1st Principal Component | Mean Abundance Across All Samples | NCBI Taxonomic ID |
|---|---|---|---|
| *Asaccharobacter celatus* | −0.06735 | 0.00253 | 394340 |
| *Ruminococcus* sp. AF34-12 | −0.06511 | 0.00112 | 2293177 |
| *Ruminococcus* sp. AM28-13 | −0.06371 | 0.004699 | 2293194 |
| *Ruminococcus* sp. OM07-17 | −0.06073 | 0.001477 | 2293233 |

TABLE 34-continued depicts the organism level weights for the first principal component microbiome PCA weights for the first component, which strongly separates cancer and control samples. Only weights with sufficient magnitude (>= 0.014) and corresponding to organisms with abundance greater than or equal to 0.001 are reported, as discussed in this Example 7:

| Organism | Weight on 1st Principal Component | Mean Abundance Across All Samples | NCBI Taxonomic ID |
|---|---|---|---|
| *Ruminococcus* sp. AF16-50 | −0.05948 | 0.001278 | 2293149 |
| *Ruminococcus bicirculans* | −0.0593 | 0.002567 | 1160721 |
| *Lachnoclostridium* sp. SNUG30099 | −0.05902 | 0.001785 | 2126738 |
| *Ruminococcus* sp. AF19-15 | −0.0585 | 0.002877 | 2293157 |
| *Alistipes putredinis* DSM 17216 | −0.0545 | 0.005412 | 445970 |
| *Ruminococcus* sp. AF26-25AA | −0.05364 | 0.00128 | 2293169 |
| *Ruminococcus* sp. AF37-3AC | −0.05189 | 0.004319 | 2293179 |
| *Ruminococcus* sp. AM31-32 | −0.04992 | 0.008284 | 2293203 |
| *Ruminococcus* sp. AF16-40 | −0.04909 | 0.009569 | 2293148 |
| *Ruminococcus callidus* ATCC 27760 | −0.04881 | 0.001444 | 411473 |
| *Gemmiger formicilis* | −0.04559 | 0.002397 | 745368 |
| *Erysipelotrichaceae* bacterium GAM147 | −0.04475 | 0.001286 | 2109692 |
| *Ruminococcus* sp. AF43-11 | −0.04475 | 0.001062 | 2293181 |
| *Akkermansia muciniphila* | −0.04387 | 0.004982 | 239935 |
| *Ruminococcus* sp. AM23-1 | −0.04066 | 0.002168 | 2293188 |
| *Ruminococcus* sp. AF17-12 | −0.0389 | 0.001753 | 2293151 |
| *Bacteroides* sp. AF14-46 | −0.03857 | 0.001891 | 2292914 |
| *Clostridium disporicum* | −0.0381 | 0.001937 | 84024 |
| *Blautia* sp. SG-772 | −0.03746 | 0.001094 | 2109334 |
| *Subdoligranulum* sp. APC924/74 | −0.03599 | 0.006058 | 2086273 |
| *Clostridium* sp. L2-50 | −0.03508 | 0.001775 | 411489 |
| *Coprococcus eutactus* | −0.03428 | 0.005119 | 33043 |
| *Romboutsia timonensis* | −0.03335 | 0.0011 | 1776391 |
| *Blautia* sp. AM42-2 | −0.03164 | 0.001356 | 2292976 |
| [*Eubacterium*] *siraeum* | −0.03157 | 0.001665 | 39492 |
| *Blautia* sp. SF-50 | −0.03121 | 0.001784 | 1520805 |
| *Alistipes* sp. HGB5 | −0.0309 | 0.001096 | 908612 |
| *Bifidobacterium adolescentis* ATCC 15703 | −0.0308 | 0.001409 | 367928 |
| *Clostridium* sp. AF15-41 | −0.0299 | 0.001581 | 2292996 |
| *Bacteroides* sp. AM25-34 | −0.02934 | 0.002631 | 2292944 |
| *Anaerostipes hadrus* | −0.02835 | 0.011336 | 649756 |
| *Ruminococcaceae* bacterium KLE1738 | −0.02772 | 0.003377 | 2283482 |
| *Monoglobus pectinilyticus* | −0.02695 | 0.003048 | 1981510 |
| *Ruminococcus* sp. AM26-12LB | −0.02691 | 0.002569 | 2293190 |
| *Faecalibacteriurn prausnitzii* | −0.02685 | 0.035873 | 853 |
| *Blautia massiliensis* | −0.02639 | 0.002288 | 1737424 |
| *Faecalibacterium* cf. *prausnitzii* KLE1255 | −0.02604 | 0.00125 | 748224 |

TABLE 34-continued depicts the organism level weights for the first principal component microbiome PCA weights for the first component, which strongly separates cancer and control samples. Only weights with sufficient magnitude (>= 0.014) and corresponding to organisms with abundance greater than or equal to 0.001 are reported, as discussed in this Example 7:

| Organism | Weight on 1st Principal Component | Mean Abundance Across All Samples | NCBI Taxonomic ID |
|---|---|---|---|
| *Dorea longicatena* | −0.02478 | 0.011832 | 88431 |
| *Neglecta timonensis* | −0.02463 | 0.001558 | 1776382 |
| *Methanobrevibacter smithii* ATCC 35061 | −0.0237 | 0.001652 | 420247 |
| [*Eubacterium*] *eligens* | −0.02359 | 0.003742 | 39485 |
| *Faecalibacterium* sp. AF27-11BH | −0.02241 | 0.001309 | 2302956 |
| *Blautia* sp. KLE 1732 | −0.02118 | 0.002869 | 1226324 |
| [*Eubacterium*] *rectale* ATCC 33656 | −0.02067 | 0.001009 | 515619 |
| *Roseburia* sp. TF10-5 | −0.0205 | 0.002512 | 2293144 |
| *Ruminococcus lactaris* | −0.02047 | 0.005798 | 46228 |
| *Methanobrevibacter smithii* | −0.02028 | 0.002282 | 2173 |
| *Alistipes* sp. AF14-19 | −0.02021 | 0.001215 | 2292910 |
| *Bifidobacterium bifidum* | −0.01858 | 0.004235 | 1681 |
| *Bifidobacterium pseudocatenulatum* DSM 20438 = JCM 1200 = LMG 10505 | −0.01857 | 0.001782 | 547043 |
| *Roseburia faecis* | −0.01843 | 0.017213 | 301302 |
| *Coprococcus comes* | −0.01693 | 0.00519 | 410072 |
| *Eubacterium* sp. AM28-29 | −0.01663 | 0.001441 | 2292349 |
| *Ruminococcus bromii* | −0.0155 | 0.046732 | 40518 |
| *Fusicatenibacter saccharivorans* | −0.01498 | 0.006614 | 1150298 |
| *Ruminococcus* sp. TF12-19AC | −0.01487 | 0.006625 | 2293242 |
| *Alistipes* sp. AM16-43 | −0.01427 | 0.001135 | 2292911 |
| *Bacteroides eggerthii* | 0.015134 | 0.00237 | 28111 |
| *Lachnospiraceae bacterium* 8_1_57FAA | 0.016944 | 0.002452 | 665951 |
| *Bacteroides vulgatus* | 0.017505 | 0.032287 | 821 |
| *Bifidobacterium longum* | 0.017965 | 0.019597 | 216816 |
| *Bacteroides xylanisolvens* | 0.018092 | 0.004668 | 371601 |
| *Bacteroides caccae* | 0.018374 | 0.010902 | 47678 |
| *Bacteroides fragilis* | 0.020763 | 0.004021 | 817 |
| *Bacteroides coprocola* DSM 17136 | 0.021108 | 0.001144 | 470145 |
| *Clostridium* sp. AT4 | 0.021895 | 0.001351 | 1720194 |
| *Streptococcus thermophilus* | 0.023361 | 0.006659 | 1308 |
| *Bacteroides thetaiotaomicron* | 0.024738 | 0.011241 | 818 |
| *Hungatella hathewayi* | 0.025951 | 0.001426 | 154046 |
| *Eggerthella lenta* | 0.027089 | 0.006395 | 84112 |
| *Bacteroides ovatus* | 0.027165 | 0.013099 | 28116 |
| *Streptococcus salivarius* | 0.028117 | 0.006978 | 1304 |
| *Flavonifractor plautii* | 0.028121 | 0.002887 | 292800 |
| *Eubacterium* sp. 3_1_31 | 0.02868 | 0.001124 | 457402 |
| *Sellimonas intestinalis* | 0.028958 | 0.001543 | 1653434 |

TABLE 34-continued depicts the organism level weights for the first principal component microbiome PCA weights for the first component, which strongly separates cancer and control samples. Only weights with sufficient magnitude (>= 0.014) and corresponding to organisms with abundance greater than or equal to 0.001 are reported, as discussed in this Example 7:

| Organism | Weight on 1st Principal Component | Mean Abundance Across All Samples | NCBI Taxonomic ID |
|---|---|---|---|
| [*Ruminococcus*] *gnavus* | 0.032793 | 0.016176 | 33038 |
| *Collinsella* sp. AF08-23 | 0.039069 | 0.002849 | 2292211 |
| *Escherichia coli* | 0.042781 | 0.005618 | 562 |
| [*Clostridium*] *clostridioforme* | 0.044191 | 0.001555 | 1531 |
| *Klebsiella pneumoniae* | 0.046508 | 0.001149 | 573 |
| *Enterococcus faecalis* | 0.048447 | 0.002972 | 1351 |
| *Streptococcus anginosus* | 0.048788 | 0.003081 | 1328 |
| *Ruminococcus* sp. DSM 100440 | 0.048917 | 0.001592 | 1671366 |
| *Clostridiales* bacterium VE202-18 | 0.053718 | 0.001422 | 1232446 |
| *Tyzzerella nexilis* | 0.056217 | 0.002176 | 29361 |
| *Blautia producta* | 0.057323 | 0.003505 | 33035 |

Example 8—Microbiome Signatures Related to Treatment Efficacy

The tumor size and cancer progression is tracked in patients over time, and are classified based on radiographic assessment using the Response Criteria in Solid Tumors version 1.1 (Schwartz et al. Eur. J. Cancer 2016, 62:132-137) criteria. This is based on measurements of lesions in cancer tissue over a period of time, given a strict set of guidelines for lesion selection and measurement techniques. Responders to the checkpoint inhibitor treatment are defined as patients that were cured or had stable disease lasting at least 6 months, while non-responders are defined as those whose cancer progressed or was stable for less than 6 months.

The 16S RNA sequencing results are used to determine the distribution of organisms in each patient fecal sample at both the phylum and genus level, and the distribution is compared across all samples from both responders and non-responders. Principal Components Analysis (PCA) is used to reduce the dimensionality of the dataset, and used to determine differences that are correlated with treatment efficacy. As a more quantitative measure, regression analysis is used to identify particular species associated with the treatment efficacy or lack of efficacy.

The genes identified from whole genome sequencing are classified into gene ontology (GO) categories using tools available publicly from the Panther Classification System website (see e.g., http://www.pantherdb.org/). This establishes a GO composition of the DNA corresponding to each sample, analogous to the species composition above. The same approach is also applied using the RNAseq transcriptomics data. Both the DNA and RNA datasets are visualized on PCA plots generated using the R programming environment. As a more quantitative measure, GO enrichment analysis is performed to identify which GO terms are over- or under-represented in samples from responders. This is also conducted using Panther tools.

Specific genes differentially present or expressed among the samples are identified using commercial expression analysis software such as SPOTFIRE® (TIBCO Software) or free tools such as BioConductor (an open source, open development software).

Tools available from the XCMS website are used to classify the LCMS metabolomics samples according to patterns in the spectral signatures obtained, to determine whether samples from responders have significantly different metabolite profiles than those from non-responders. Finally, organic acid data from the headspace GCMS analysis are used to identify which of these molecules are correlated with treatment efficacy.

Prior patient medical history is also collected and analyzed when available. This includes but is not limited to prior cancer history, diabetes, autoimmune disease, neurodegenerative disease, heart disease, metabolic syndrome, digestive disease, psychological disorders, HIV, and allergies. In addition, lifestyle and dietary habits are collected, including diet regimen, exercise routine, alcohol, nicotine, and caffeine intake, medical as well as recreational drug use, recent courses of antibiotics, vitamins, and probiotics. This data is assembled and used as input to the machine learning algorithms described in example 10, with the goal of determining correlations between patient history and treatment efficacy. In addition, relationships between this data and the results of sample analysis described above are elucidated.

Example 9—Exemplary Methods: Single Isolates of Fecal Samples

Bacteria used to practice methods as provided herein, including clonal *Blautia*, Clostridiaceae, *Faecalibacterium* or *Clostridium*; Ruminococcaceae or *Ruminococcus*; Verrucomicrobiaceae or *Akkermansia*; Enterococcaceae or *Enterococcus; Eggerthella*; Eggerthellaceae or *Gordonibacter*; Bacteroidaceae or *Bacteroides*; Hyphomicrobiaceae or *Gemmiger; Bifidobacterium, Alistipes, Adlercreutzia, Senegalimassilia, Ellagibacter, Paraeggerthella, Dorea, Roseburia, Monoglobus, Asacharobacter*, and/or *Slackia* species (and also including specific species of bacteria as used in methods as provided herein) can be isolated directly from fecal matter samples and cultured in ABB+RF broth and solid agar plates, or on Yeast Casitone Fatty Acids with Carbohydrates (YCFAC) broth and on Yeast Casitone Fatty Acids with Carbohydrates and Sheep's Blood (YCFAC+B) Agar, both obtained as pre-reduced anaerobically sterilized (PRAS) media from Anaerobe Systems (Morgan Hill, CA).

Serial dilutions of bacteria from fecal samples are performed using reduced and anoxic Nutrient Broth prepared as follows: Two grams of Nutrient Broth dehydrated powder (Remel™) is mixed in 250 ml Reagent Grade Water (NERL™) and Resazurin color indicator (ACROS Organics™) added to a final concentration of 0.025%, 10 ml volumes of the resulting liquid volume are aliquoted into 18 mm×150 mm Anaerobic Tubes (Bellco Glass, Inc). Nitrogen gas is bubbled into each 10 ml volume via a metal cannula for 15 minutes to displace oxygen, followed by quick insertion of a butyl rubber stopper held fast with a crimped metal collar. The filled, bubbled and sealed anaerobic tubes of nutrient broth are autoclaved for 20 minutes, allowed to cool to room temperature, and stored in the dark until needed.

Immediately prior to use, L-cysteine is added via syringe injection through the butyl-rubber stopper to 0.5 mM final concentration to reduce the medium. Full reduction is indicated by change of the resazurin color from pink to colorless, at which time the reduced nutrient broth tubes are ready for use in fecal matter dilutions.

Anoxic ellagic acid (EA) solution in DMSO is prepared as follows: 18 mm×150 mm Anaerobic Tubes (Bellco Glass, Inc) are fitted with butyl rubber stoppers and metal collars and sterilized by autoclaving. EA (Millipore-Sigma) is dissolved in 10 ml DMSO (Fisher Scientific) to a final concentration of 3.5 mM and injected into an autoclaved stoppered anaerobic tube. As a control, 10 ml DMSO without EA is injected into another autoclaved stoppered anaerobic tube. Oxygen is displaced from the liquid in both tubes by sparging nitrogen via inserted 20 gauge needles for 30 minutes.noxic sterile 50 mM L-cysteine solution is prepared as follows: A 100 ml anaerobic serum bottle is fitted with a butyl-rubber stopper, held tight with a crimped metal collar, and autoclaved for 20 minutes to sterilize the interior. L-cysteine (Fisher Scientific) is dissolved into 50 ml reagent grade water to a final concentration of 50 mM and filled into a 50 ml syringe that is then fitted with a sterile 0.45 micron PVDF filter disk (Fisher Scientific) and a sterile 1.5 inch 20 gauge needle. The needle of the filled and filtered syringe is inserted through the stopper of the bottle and a second needle is inserted through the stopper to serve as a vent. The L-cysteine solution is injected into the bottle, and the syringe and filter then removed, leaving the two needles inserted through the stopper. A second 0.45 micron filter is fitted to a hose connected to a source of 100% nitrogen gas, and then fitted to one of the needles. Nitrogen gas is bubbled into the L-cysteine solution through the sterile filter for 20 minutes, allowed to vent out of the second needle to displace oxygen in the solution, and then both needles are removed simultaneously. The now sterile and anoxic 50 mM solution of L-cysteine is ready for use.

Sequencing Methods

16S RNA sequence analysis is used to confirm the identity of plated colonies. First, total genomic DNA is extracted from the cell pellet using the QIAmp® PowerFecal DNA™ kit (Qiagen). Amplicons specific for the v4 region of 16S RNA are generated using primers homologous to the conserved regions surrounding v4.

Example 10—in Silico Modeling to Discover Microbe-Microbe Interactions

Genome scale metabolic modeling is used as a tool to explore the diversity of metabolic reactions present in the gut microbiome, interpret the omics data described here in the framework of cellular metabolism, and evaluate interspecies interactions. A set of 773 different organism-specific metabolic models have been created, and are leveraged here (Magnusdottir et al. Nature Biotechnology 2017, 35(1):85-89). Models are combined according to the microbe mixes administered here, enabling multispecies simulations that predict how these organisms interact when supplied with a nutrient mix mimicking the typical Western human diet or variations thereof. Simulations are performed using the COBRA™ Package v2.0™ (Schellenberger et al., Nature Protocols 2011, 6:1290-1307) or updated versions thereof. Commensal relationships among the organisms result when one or more species consume a compound that another species produces, and can be detected by an increased maximum predicted growth rate of each species when growing together than when each is grown separately. In the cases where commensalism is not predicted in the microbe mixes provided, simulations are used to identify a suitable microbial partner that can be included in the live biotherapeutic product, thus improving the ability of the active microbes to colonize the gut. Similarly, simulations are used to identify prebiotic compounds to be supplemented that can be utilized by the active species as a carbon or energy source, also improving colonization likelihood.

The consortia of gut microbe metabolic models are used as a framework for interpreting genomic, transcriptomic, and metabolomic data obtained from the mouse and human studies. Enriched genes or pathways at the genomic or transcriptomic level are mapped to the source organism model to determine the metabolic functions these represent and how they connect with the rest of metabolism in that organism, as well as in the gut ecosystem as a whole. Enrichments also in metabolic intermediates or end products of these pathways provide further evidence for these pathways' contribution to checkpoint inhibitor function.

Machine learning (or artificial intelligence) techniques are used to identify correlations among species abundance, pathway enrichment, and metabolite production and the efficacy of checkpoint inhibitors in shrinking tumor size. This data-driven approach uncovers relationships that do not necessarily have a rational basis. Machine learning techniques employed include supervised and unsupervised learning algorithms. Supervised learning techniques include but are not limited to linear regression, support vector machines, decision tree, random forest, Bayesian networks, k-nearest neighbor classification, information fuzzy networks, learning vector quantization, artificial neural networks, and hidden Markov models. Unsupervised learning techniques include but are not limited to hierarchical clustering, k-means clustering, expectation maximization, fuzzy clustering, association rule learning, logic learning machines, and self-organizing maps. Algorithms are run on the cloud via Amazon™ Web Services (AWS). Input independent data to the machine learning algorithms include fecal microbial composition obtained from 16S sequencing data, differentially expressed genes, gene functions, or functional families, relative concentrations of known metabolites, peak intensities associated with particular mass spectrum features, cancer type and treatment regimen, and patient metadata including medical history and antibiotic use. Dependent data include tumor size over a time course, immunological profile from blood, and any other indications of checkpoint inhibitor therapy efficacy. The machine learning techniques identify relationships between the independent and dependent variables, thus indicating predictors of treatment efficacy and cancer survival.

Example 11—in Silico Modeling of Microbe-Microbe Interactions

Genome scale metabolic modeling is used as a tool to explore the diversity of metabolic reactions present in the gut microbiome, interpret the -omics data described here in the framework of cellular metabolism, and evaluate interspecies interactions. A set of 773 different organism-specific metabolic models have been created, and are leveraged here (Magnusdottir et al. Nature Biotechnology 2017, 35(1):85-89). Models are combined according to the microbe mixes administered here, enabling multispecies simulations that predict how these organisms interact when supplied with a nutrient mix mimicking the typical Western human diet or variations thereof. Simulations are performed using the COBRA package v2.0 (Schellenberger et al., Nature Protocols 2011, 6:1290-1307) or updated versions thereof. Commensal relationships among the organisms result when one or more species consume a compound that another species produces, and can be detected by an increased maximum predicted growth rate of each species when growing together than when each is grown separately. In the cases where commensalism is not predicted in the microbe mixes provided, simulations are used to identify a suitable microbial partner that can be included in the live biotherapeutic product, thus improving the ability of the active microbes to colonize the gut. Similarly, simulations are used to identify prebiotic compounds to be supplemented that can be utilized by the active species as a carbon or energy source, also improving colonization likelihood.

The consortia of gut microbe metabolic models are used as a framework for interpreting genomic, transcriptomic, and metabolomic data obtained from the mouse and human studies. Enriched genes or pathways at the genomic or transcriptomic level are mapped to the source organism model to determine the metabolic functions these represent and how they connect with the rest of metabolism in that organism, as well as in the gut ecosystem as a whole. Enrichments also in metabolic intermediates or end products of these pathways provide further evidence for these pathways' contribution to checkpoint inhibitor function.

Metabolic models are downloaded from the Thiele lab website (https://wwwen.uni.lu/lcsb/research/mol_systems-_physiology/in_silico_models) for the following organisms: *Clostridium scindens* ATCC 35704*, Blautia producta* DSM 2950*, Ruminococcus gnavus* ATCC 29149, *Faecalibacterium prausnitzii* L2-6*, Gordonibacter pamelaeae* 7-10-1-bT DSM 19378, and *Eggerthella lenta* DSM 2243. The models are then used for simulations in the COBRA v2.0™ package (Schellenberger et al., Nature Protocols 2011, 6:1290-1307). Cell metabolism is simulated by defining nutrient uptake rates (mmol/gDCW-hr) and optimizing for growth of each organism ($hr^{-1}$). Oxygen uptake rate is set to zero, to simulate anaerobic conditions. Values for each nutrient uptake rate are obtained from (Magnusdottir et al. Nature Biotechnology 2017, 35(1):85-89, Supplemental Table 12), as estimated for a typical Western diet. To simulate the gut ecosystem comprising of multiple bacterial species, each organism model is treated as a separate compartment, with the extracellular space in the gut considered an additional compartment. Nutrients can enter and exit the extracellular space freely, to simulate food uptake and waste excretion. Nutrients can enter and exit each microbial species based on the specific transporters present in the respective model. The objective function to be maximized is defined to be the total biomass of all species; i.e., the sum of all individual growth rates. The minimum growth rate of each species is set at 0.001 $hr^{-1}$.

Simulations indicate that with the defined objective function, all species will grow at above the lower bound of 0.001 $hr^{-1}$. Furthermore, the total biomass produced is greater than the sum of all growth rates for each model run individually, thus indicating favorable interactions in the community. Various metabolites are predicted to be secreted by one species and taken up by another, including organic acids, amino acids, vitamin precursors, and monosaccharides.

Example 12: In Silico Simulation of Gut Microbial Metabolism

To simulate a typical gut environment, models were downloaded for the following organisms: *Bifidobacterium longum* E18, *Lactobacillus casei* ATCC 334, *Bacteroides* dorei DSM 17855, and *Streptococcus thermophilus* LMG 18311. The models are then used for simulations in the COBRA package v2.0 (Schellenberger et al., Nature Protocols 2011, 6:1290-1307). Cell metabolism is simulated by defining nutrient uptake rates (mmol/gDCW-hr) and optimizing for growth of each organism ($hr^{-1}$). Oxygen uptake rate is set to zero, to simulate anaerobic conditions. Values for each nutrient uptake rate are obtained from Magnusdottir et al. Nature Biotechnology 2017, 35(1):85-89, Supplemental Table 12, as estimated for a typical Western diet. To simulate the gut ecosystem comprising of multiple bacterial species, each organism model is treated as a separate compartment, with the extracellular space in the gut considered an additional compartment. Nutrients can enter and exit the extracellular space freely, to simulate food uptake and waste excretion. Nutrients can enter and exit each microbial species based on the specific transporters present in the respective model. The objective function to be maximized is defined to be the total biomass of all species; i.e., the sum of all individual growth rates. The minimum growth rate of each species is set at 0.001 $hr^{-1}$, and simulations indicate all species grow at a rate above this bound.

Next, microbes from our candidate live biotherapeutic formulations are evaluated in the presence of these four typical gut organisms. Models for *Clostridium scindens* ATCC 35704*, Blautia producta* DSM 2950*, Ruminococcus gnavus* ATCC 29149, and *Faecalibacterium prausnitzii* L2-6 are each run in conjunction with those listed above. Nutrient uptake is defined as above, oxygen uptake is set to zero, minimum growth rates set at 0.001 $hr^{-1}$, and the objective function is the sum of individual growth rates. Each species separately is predicted to grow at a rate greater than the lower bound in the presence of these other organisms. Finally, simulations are performed using all eight organisms together.

Example 13: Fermentation Medium Preparation for Isolated Anaerobic Microorganisms Individual microbial strains isolated as described herein are cultured in a bioreactor (fermenter) to produce a large volume of material at high cell density. Volume of the vessel can range from less than 1 L for laboratory-scale processing, up to 10,000 L or more for commercial production. Fermentations are maintained in strict anaerobic conditions, using a nitrogen purge and maintaining a positive pressure in the headspace. Temperature is maintained at the determined optimal growth temperature by means known to the fermentation industry, such as internal cooling coils or water jacketed vessel. pH is maintained at the optimal value by addition of base such as ammonium hydroxide, potassium hydroxide, sodium hydroxide, or gaseous ammonia, using a feedback controller linked to a pH sensor. One or more nutrients may be fed into the vessel, either continuously or as a bolus, to prevent depletion as the nutrients are consumed by the growing cells. Cell growth is monitored by aseptic sampling of the vessel, and determining optical density (OD) or dry cell weight. Alternatively, cell growth is monitored by measurement of carbon dioxide concentration in the off-gas using an on-line mass spectrometer, as this is a byproduct of biomass production. All data is stored in a laboratory information management system (LIMS), which is connected to the online instruments for automated data transfer. When the cells reach the desired density, the culture is transferred to a centrifuge or filtration device to remove the broth from the cells. Anaerobic conditions are maintained during this process to ensure cell viability. Cell paste is then rapidly frozen and lyophilized. In between fermentation runs, the bioreactor is sterilized by steam.

The fermentation process is operated under Good Manufacturing Process (GMP) conditions. This requires following established written procedures and thorough documentation of everything added and removed from the bioreactor in batch records. Manufacturers' certificates of analysis are also provided for all reagent additions. All online measurements are logged electronically. Offline measurements are entered into the LIMS. Batch records will also track the time, temperature, and pressure of the sterilization process between runs. Sterility of the broth will be tested by plate counts or qPCR, and the contents considered sterile of the organism count is less than 1000 cfu/L. Microbial purity of the fermentation broth, post-centrifugation cell paste, and the final lyophilized product is monitored by 16S sequencing or whole genome sequencing of DNA extracted from the broth. Viable cell count of the lyophilized product is measured by resuspending in growth medium and immediately plating dilution series on agar plates. Results of these tests are all recorded in the LIMS.

For each microbe produced by fermentation, growth media is developed. Media contains all components that are certified by the manufacturer to be made without animal products. Media is prepared from the powdered components as described below:

1) Weigh required amount of powdered anaerobic growth medium as specified by the manufacturer to formulate 1 L of growth medium. 2) In a fume hood, place 800 mis of purified water in a 2 L beaker, include a stir bar and then set on a heated stir plate. With constant stirring, heat the volume of water just to boiling.
3) Add preweighed powdered anaerobic growth medium as well as any additional supplements and allow to stir in the heating volume of water until dissolved.
4) While heating, add the oxygen indicator dye resazurin (ACROS Organics) to final concentration of 0.0025 mg/ml.
5) Add purified water to bring the final volume to 1 L
6) Continue to heat the solution to a gentle boil until all medium ingredients are fully solubilized, and the color imbued by the resazurin turns from red to colorless. Carefully remove the beaker from the stir plate and allow to cool for 10 minutes prior to further manipulations.
7) Pour entire contents into a plastic 2 L beaker to make it safer to handle. Use a 1 L cylinder to divide into two 900 ml volumes into two 2 L plastic beakers.
8) Insert a funnel into the neck of a 1 L anaerobic bottle (Chemglass Life Sciences). Carefully add hot 900 ml volume to the side of the funnel so that a spiral flow is established. Do not pour directly into the hole of the funnel as the hot liquid could bump. It is advisable to use a face shield while doing this operation.
9) When all liquid is transferred, insert a blue rubber bung into the top of the bottle and crimp with an aluminum collar to seal the bottle. Then quickly insert a 20-gauge needle through bung to relieve pressure.
10) At this point the red color of the resazurin will probably return due to oxygenation during transfer and manipulation. To remove oxygen, place the filled, stoppered and needled bottles back onto a heated stir plate and bring to a gentle boil until the resazurin oxygen indicator returns to colorless.
11) Remove the bottle from the heat and as quickly and carefully as possible bring into the anaerobic chamber. Place the bottles onto two thicknesses of cardboard on the floor of the airlock to protect the floor from heat damage, then close the door and cycle/purge the airlock. The needles in the bungs allow for venting of the bottle contents during this step without boil-over. Once cycle/purge is completed, open the interior door of the anaerobic chamber and carefully lift and place the hot bottles in the chamber.
12) Allow the bottles to cool in the anaerobic chamber for about a half-hour, then remove the needle and decrimp/debung the bottles so that they are open to the interior atmosphere of the anaerobic chamber. Keep multiple bottles well-separated from each other so that they can cool as quickly as possible. Allow the bottles to cool to ambient temperature (4-5 hours).
13) Once cooled, reinsert new bungs into the necks of the bottles and crimp to seal. Remove the bottles from the anaerobic chamber and then autoclave for 20 minutes with conditions appropriate for liquid media. Once done, bring the bottles back into the chamber and allow to cool overnight before using.

Example 14: Laboratory-Scale Fermentation of Isolated Anaerobic Microorganisms A laboratory-scale fermentation is performed using a Sartorius Biostat A™ bioreactor with 2 L vessel, using the growth media described in Example 12. While still in the anaerobic chamber, 1 L media is transferred to a sterile feed bottle, which has two ports with tubing leading blocked by pinch clamps and covered in foil to maintain sterility.

The fermentation vessel is sterilized by autoclaving, then flushed with a continuous purge of sterile nitrogen gas with oxygen catalytically removed. Two inlet ports are fitted with tubing leading to a connector blocked with a pinch clamp, and the sampling port fitted with tubing leading to a syringe. The vessel is also fitted with a dissolved oxygen probe, a pH probe, and a thermowell containing a temperature probe. Once anaerobic conditions are ensured, the media is removed from the anaerobic chamber and connected to one of the inlet ports. The other feed bottle port is connected to sterile nitrogen purge. The pinch clamp is removed and media transferred into the fermentation vessel by peristaltic pump or just by the nitrogen pressure. Once the transfer is complete, both lines are sealed again by the pinch clamps, the feed bottle removed, and returned to the anaerobic chamber.

A 50 mL seed culture of *Clostridium scindens*, grown to mid-exponential phase in a sealed culture bottle using the same media composition as above, is transferred into the feed bottle in the anaerobic chamber. Repeating the above transfer procedure, this time with the culture, the fermenter is inoculated.

5 M ammonium hydroxide is prepared in another feed bottle. One port is connected to sterile nitrogen, and the bottle is purged for 5 minutes to remove all oxygen. The outlet tubing is then blocked by a pinch clamp, and attached to the other inlet port in the fermentation vessel. This tubing is then threaded into a peristaltic pump head, and the pinch clamp removed. Using the software built into the Biostat A™ unit, this pump is controlled to maintain pH at 7.0.

During growth of the culture, temperature is maintained at 37° C. using a temperature controller and heating blanket on the vessel. Nitrogen purge is set at 0.5 L/min to maintain anaerobic conditions and positive pressure in the vessel, and agitation is set at 500 rpm to keep the culture well mixed. Periodic samples are taken using the syringe attached to the sample port. For each sample, optical density is measured at 600 nm wavelength using a spectrophotometer.

Example 15: Fecal Matter Collection from Patients and Processing

Fecal matter donations are acquired from healthy volunteers as well as individuals exhibiting disease symptoms.

Donors can be cancer patients participating in clinical trials testing various cancer treatment regimens. Donors can be healthy volunteers that do not exhibit disease symptoms.

Fecal matter donors are provided with a specimen collection kit that includes the following items:

1. One fecal matter collection kit with two fecal matter collection containers (one is for back-up)
2. One Ziploc bag
3. One Thermosafe shipping container
4. Eight to ten polar gel packs for transport of specimen
5. One roll of packing tape
6. Specimen collection instructions
7. Body site-specific, pre-printed clinic label
8. Fecal matter box label Fecal Matter Specimens are Collected by the Fecal Matter Donor Using the Above Kit as Follows:

1. At least 12 hours prior to sampling, place all polar gel packs into a freezer to allow them to freeze completely.
2. A form is provided for the Fecal matter Donor to log time and date of collection. This is included with the packaged fecal matter sample.
3. To collect sample, first raise the toilet seat. Place the fecal matter collection frame on the back of the toilet bowl. All four corners of the collection frame should be supported by the toilet bowl. Place collection bowl in frame.
4. Deposit fecal matter directly into the collection chamber. Do not urinate into the collection container.
5. After collecting the fecal matter specimen, remove the container from the frame. Place the container on a flat surface and firmly press the lid closed.
6. Place the closed container into the provided ZIPLOC™ bag and seal the bag.
7. Discard the collection frame in trash
8. Place two of the frozen polar gel packs in the bottom of the styrofoam box that is part of the THERMO-SAFE™ shipping container.
9. Place the sealed ZIPLOC™ bag containing the fecal matter specimen in the Styrofoam container.
10. Place four of the frozen polar gel packs around the specimen container so that the container is completely surrounded.
11. Place one frozen polar gel pack on top of the specimen container.
12. Place the styrofoam lid on the styrofoam container and close the cardboard box.
13. Use packing tape provided to seal the cardboard box closed.
14. Stool packages are shipped by overnight courier to the lab.

Preparation of Fecal Matter for Samples for Analysis

Upon receipt of the fecal matter specimen package at Persephone Biome, the time and date that it is received is logged. The box is then quickly un-packed in the laboratory and intactness and temperature of the packed materials is assessed to insure proper refrigeration during transit. The ZIPLOC™ bag containing the fecal matter specimen along with a freshly frozen ice block is then promptly brought into an anaerobic chamber (Coy Lab Products Type A Vinyl Anaerobic Chamber) for further processing. Once in the anaerobic chamber, the bag containing the fecal matter specimen is unsealed and the fecal matter collection container is placed on the frozen ice block. The fecal matter container is opened and the fecal matter material within is inspected for consistency and rated on the Bristol Fecal matter Scale, a standard for typing the consistency, color and moisture of fecal matter samples. Using a sterile wooden tongue depressor, 30 grams of fecal matter is placed and weighed in a specimen cup. Any remaining fecal matter that is not used in the study is resealed in the fecal matter collection container for later safe disposal outside of the anaerobic chamber. The specimen cup containing the weighed fecal matter sample is kept on ice for further processing. For fecal matter judged to be "3" or "4" on the Bristol Fecal matter Scale (moderate moisture and homogeneity), 10 ml of ice-cold reduced Phosphate Buffered Saline (PBS; Fisher Scientific) is added and a sterile wooden tongue depressor is used to gently mix the material until thoroughly homogenized. More or less PBS may be added depending on the dryness (Low Bristol Scale) or wetness (High Bristol Scale) to best accommodate complete homogenization.

Homogenized fecal matter is then aliquoted into nine 3-gram portions each into tared 50 ml conical tubes (Fisher Scientific) which are then placed on ice. Four aliquots are immediately removed from the anaerobic chamber and flash frozen on dry ice, to be used later for genomic DNA and metabolomic analyses. Two aliquots are combined with equal volume to weight of ice cold RNA later (Thermo Fisher Scientific), vortexed and then brought out of the anaerobic chamber and flash frozen on dry ice, to be used later for transcriptomic analyses such as RNAseq. Two aliquots are combined with a 1/10 weight to volume amount of reduced cryopreservation buffer I (CBP-1; PBS plus 5 mM L-cysteine plus 15% glycerol), vortexed thoroughly, and then brought out of the anaerobic chamber and frozen on dry ice, to be used for fecal matter transfer (FMT) in mice for in vivo mouse model testing. All dry-ice frozen aliquots are then stored at −80° C. until required for analyses.

The ninth fecal aliquot remaining on ice in the anaerobic chamber is prepared for cryopreservation as a live stock for bacterial discovery efforts. The 3-gram fecal aliquot is suspended in 10 ml ice cold reduced PBS, shaken gently by hand for 2 minutes to homogenize, then placed upright on ice for 15 minutes to allow solids to settle to the bottom of the tube. One ml is removed from the top of the suspension and then combined with ice-cold 4 ml of anaerobe basal broth (ABB; Oxoid), and then with 5 ml reduced ice-cold cryopreservation buffer 2 (CPB-2; PBS plus 2% trehalose plus 10% DMSO). This suspension is rocked back and forth gently by hand 10 times to homogenize, and is then placed on ice. One ml of this suspension is added to each of eight appropriately labeled 2 ml cryotubes (ThermoFisher), sealed tightly and placed on ice, then taken out of the anaerobic chamber. The eight cryotubes are then immediately placed in a designated freezer box and then stored in the gas phase of a liquid nitrogen dewar until required for further experimentation.

Example 16: Isolation and Characterization of Pure Microbial Strains from Fecal Matter Individual bacterial strains can be isolated and cultured from fecal matter material for further study and for assembly of therapeutic biologicals. The majority of live bacteria that inhabit fecal matter tend to be obligate anaerobes so care must be taken to perform all culture and isolation work in the anaerobic chamber to prevent their exposure to oxygen, and to use anaerobic growth media that includes reductant compounds. Suitable reductant compounds include but are not limited to L-cysteine, Sodium thioglycolate, and dithiothreitol. Additional reductants that are not part of the original formulation of chosen anaerobic growth media can be added to improve anaerobic bacterial growth. Particular growth media that favor growth of target bacteria can be used to improve the ability to find and isolate them as pure living cultures. Different anaerobic growth media are used to enable growth of different subsets of microbes to improve overall ability to isolate and purify an inclusive number of unique bacterial species by this method.

To begin a microbial isolation and characterization campaign, one cryotube containing cryogenically preserved fecal matter is removed from storage in the liquid nitrogen dewar, brought into the anaerobic chamber, and then allowed to thaw gently on ice. The entire 1 ml contents are added to 9 ml ABB to establish a 1/10 dilution. Successive 10-fold serial dilutions are then performed in ABB to establish 1/100, 1/1000, 1/10000, 1/100000, 1/1000000 dilutions of the fecal matter. From each of the 1/10000, 1/100000, and 1,1000000 dilutions, four 0.1 ml volumes are removed and then added to and spread over anaerobic growth medium solid medium. The plating's are incubated at 37° C. for 2, 3, 4, 5, 6, 7, 8, 9, 10, 11, 12 days to allow for a wide variety of bacterial colonies to grow. Platings are made from several liquid dilutions of fecal matter to ensure that there will be ones that have numerous yet non-overlapping colonies for efficient colony picking.

Colonies are manually picked from plates using sterile pipette tips. Colonies may also be picked by an automated colony picking machine that is enclosed in an anaerobic chamber. Colonies are picked in multiples of 96 to accommodate subsequent 96-well-based genomic DNA isolation steps and large-scale cryogenic storage steps. The individual colonies picked are then struck on anaerobic growth medium solid medium to isolate single purified colonies from each picked colony, and then incubated at 37° C. for 2, 3, 4, 5, 6, 7, 8, 9, 10, 11, 12 days to allow for visible colony growth to arise. After visible colonies are evident, single colonies are picked from the first streaks to be struck once again on the same anaerobic growth medium solid medium used in previous steps, and then incubated at 37° C. for 2, 3, 4, 5, 6, 7, 8, 9, 10, 11, 12 days to allow for visible colony growth to arise. Single colonies from this secondary streak are each inoculated into 1 ml anaerobic growth medium in an individual well of a 2 ml 96-well deep well block. Once representative secondary colonies of all originally picked colonies are so inoculated, the 66-well deep well block is covered with an adhesive gas-permeable seal and then incubated at 37° C. in an incubator within the anaerobic chamber for 2, 3, 4, 5, 6, 7, 8, 9, 10, 11, 12 days to allow for liquid growth from each isolated colony.

After turbid growth is apparent in all wells, the gas-permeable seal is removed from the 96-well deep well block and 0.2 ml is removed from each well and placed in a 96-well PCR plate. The 96-well PCR plate is then centrifuged at 4000 rpm for 10 minutes at 4° C. to pellet cell growth. After centrifugation, supernatant is carefully removed by pipette and discarded, then the plate is resealed with an aluminum impermeable adhesive seal suitable for deep freeze storage and stored at −20° C. in preparation for subsequent genomic DNA isolation steps. Remaining cultures in the 96-well deep well culture plate are each combined with equal volumes CPB-2, mixed thoroughly by pipette, then the plate is resealed with an aluminum impermeable adhesive seal suitable for deep freeze storage and stored at −80° C. to preserve each culture for long-term storage and for later analyses.

The 96-well PCR plate containing representative cell pellets from each originally picked colony is removed from −20° C. storage and allowed to thaw at ambient laboratory temperature. Genomic DNA is then isolated from each cell pellet using a Quick-DNA Fungal/Bacterial 96 Kit (Zymo Research) following directions provided in the kit. Isolated genomic DNA corresponding to each originally picked colony is then subjected to next generation sequencing of 16S RNA genes or by Whole Genome Sequencing and corresponding computer analyses to assign a phylogenetic identification to each isolated strain. Resulting sequence information is compared to in-house and publicly available genomic DNA databases to assign identities to each strain.

Isolated and Purified Strains from plating screens of bacterial colony growth from fecal matter obtained from four healthy donors. Fecal matter was diluted and plated on either YCFACB solid medium or on Anaerobe Basal Broth (ABB) plus 15% Rumen Fluid. Colonies were picked and then purified cultures from each were subjected to 16S RNA sequencing. Sequence data was compared by BLASTn to the 16S ribosomal RNA sequences (Bacteria and Archaea) database at the National Center for Biotechnology Information. Listed are the closest genome/species matches as well as percent identity and E values from this analysis for each strain. Exemplary strains isolated from human fecal material are listed in Table 3:

TABLE 3

| | | | Closest 16S RNA Sequence Strain Identification by BLASTn | | |
|---|---|---|---|---|---|
| Strain # | Donor # | Screening Medium | Strain | % identity | E Value |
| 1 | 1 | YCFACB | [*Eubacterium*] *eligens* strain ATCC 27750 | 0.96 | 0 |
| 2 | 1 | YCFACB | [*Eubacterium*] *eligens* strain ATCC 27750 | 0.96 | 0 |
| 3 | 1 | YCFACB | [*Eubacterium*] *eligens* strain ATCC 27750 | 0.99 | 0 |
| 4 | 1 | YCFACB | *Falcatimonas natans* strain WN011 | 1.00 | 3E−15 |
| 5 | 1 | YCFACB | *Dorea longicatena* strain 111-35 | 0.99 | 0 |
| 6 | 1 | YCFACB | *Faecalibacterium prausnitzii* strain ATCC 27768 | 1.00 | 1E−28 |
| 7 | 1 | YCFACB | [*Eubacterium*] *rectale* strain ATCC 33656 | 0.99 | 0 |
| 8 | 1 | YCFACB | *Faecalibacterium prausnitzii* strain ATCC 27768 | 0.99 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 9 | 1 | YCFACB | *Blautia faecis* strain M25 | 1.00 | 0 |
| 10 | 1 | YCFACB | *Bifidobacterium bifidum* strain NBRC 100015 | 1.00 | 0 |
| 11 | 1 | YCFACB | *Dorea longicatena* strain 111-35 | 0.99 | 0 |
| 12 | 1 | YCFACB | *Gemmiger formicilis* strain X2-56 | 0.97 | 0 |
| 13 | 1 | YCFACB | *Dorea longicatena strain* 111-35 | 0.99 | 0 |
| 14 | 1 | YCFACB | *Bariatricus massiliensis* strain AT12 | 1.00 | 2E−37 |
| 15 | 1 | YCFACB | *Bacteroides vulgatus* strain ATCC 8482 | 0.98 | 0 |
| 16 | 1 | YCFACB | *Blautia obeum* strain ATCC 29174 | 0.98 | 0 |
| 17 | 1 | YCFACB | [*Eubacterium*] *rectale* strain ATCC 33656 | 0.92 | 0 |
| 18 | 1 | YCFACB | *Gemmiger formicilis* strain X2-56 | 0.98 | 0 |
| 19 | 1 | YCFACB | *Dorea longicatena* strain 111-35 | 0.96 | 0 |
| 20 | 1 | YCFACB | *Coprococcus catus* strain VPI-C6-61 | 0.99 | 0 |
| 21 | 1 | YCFACB | [*Clostridium*] *spiroforme* strain JCM 1432 | 0.94 | 0 |
| 22 | 1 | YCFACB | *Dorea longicatena* strain 111-35 | 0.99 | 0 |
| 23 | 1 | YCFACB | [*Eubacterium*] *eligens* strain ATCC 27750 | 1.00 | 2E−117 |
| 24 | 1 | YCFACB | [*Eubacterium*] *eligens* strain ATCC 27750 | 0.99 | 0 |
| 25 | 1 | YCFACB | [*Clostridium*] *hathewayi* strain 1313 | 0.94 | 0 |
| 26 | 1 | YCFACB | [*Eubacterium*] *rectale* strain ATCC 33656 | 1.00 | 0 |
| 27 | 1 | YCFACB | *Blautia luti strain* DSM 14534 | 0.97 | 0 |
| 28 | 1 | YCFACB | [*Eubacterium*] *eligens* strain ATCC 27750 | 0.99 | 0 |
| 29 | 1 | YCFACB | [*Eubacterium*] *eligens* strain ATCC 27750 | 0.99 | 0 |
| 30 | 1 | YCFACB | [*Eubacterium*] *eligens* strain ATCC 27750 | 1.00 | 2E−151 |
| 31 | 1 | YCFACB | *Gemmiger formicilis* strain X2-56 | 0.96 | 0 |
| 32 | 1 | YCFACB | [*Eubacterium*] *eligens* strain ATCC 27750 | 0.99 | 0 |
| 33 | 1 | YCFACB | [*Eubacterium*] *eligens* strain ATCC 27750 | 0.99 | 0 |
| 34 | 1 | YCFACB | [*Eubacterium*] *eligens* strain ATCC 27750 | 0.99 | 0 |
| 35 | 1 | YCFACB | *Faecalibacterium prausnitzii* strain ATCC 27768 | 0.99 | 0 |
| 36 | 1 | YCFACB | [*Eubacterium*] *eligens* strain ATCC 27750 | 1.00 | 0 |
| 37 | 1 | YCFACB | [*Eubacterium*] *eligens* strain ATCC 27750 | 0.99 | 0 |
| 38 | 1 | YCFACB | [*Eubacterium*] *eligens* strain ATCC 27750 | 0.99 | 0 |
| 39 | 1 | YCFACB | [*Eubacterium*] *eligens* strain ATCC 27750 | 0.99 | 0 |
| 40 | 1 | YCFACB | *Faecalibacterium prausnitzii* strain ATCC 27768 | 0.99 | 0 |
| 41 | 1 | YCFACB | [*Eubacterium*] *eligens* strain ATCC 27750 | 1.00 | 0 |
| 42 | 1 | YCFACB | *Alteromonas lipolytica* strain JW12 | 1.00 | 1E−09 |
| 43 | 1 | YCFACB | [*Eubacterium*] *eligens* strain ATCC 27750 | 0.99 | 0 |
| 44 | 1 | YCFACB | [*Eubacterium*] *eligens* strain ATCC 27750 | 0.99 | 0 |
| 45 | 1 | YCFACB | [*Eubacterium*] *rectale* strain ATCC 33656 | 1.00 | 0 |
| 46 | 1 | YCFACB | [*Eubacterium*] *eligens* strain ATCC 27750 | 1.00 | 6E−37 |
| 47 | 1 | YCFACB | *Bacteroides vulgatus* strain ATCC 8482 | 0.96 | 0 |
| 48 | 1 | YCFACB | [*Eubacterium*] *eligens* strain ATCC 27750 | 1.00 | 1E−93 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 49 | 1 | YCFACB | [*Clostridium*] *spiroforme* strain JCM 1432 | 0.95 | 0 |
| 50 | 1 | YCFACB | *Maivinbiyantia formatexigens* strain 1-52 | 0.96 | 0 |
| 51 | 2 | ABB + Rumen Fluid | *Alistipes onderdonkii* strain JCM 16771 | 1.00 | 0 |
| 52 | 2 | ABB + Rumen Fluid | [*Clostridium*] *methylpentosum* strain R2 | 0.90 | 0 |
| 53 | 2 | ABB + Rumen Fluid | *Ruminococcus faecis* strain Eg2 | 1.00 | 5E−33 |
| 54 | 2 | ABB + Rumen Fluid | *Alistipes onderdonkii* strain JCM 16771 | 1.00 | 0 |
| 55 | 2 | ABB + Rumen Fluid | *Bacteroides dorei* strain 175 | 0.99 | 0 |
| 56 | 2 | ABB + Rumen Fluid | *Alistipes onderdonkii* strain JCM 16771 | 1.00 | 8E−126 |
| 57 | 2 | ABB + Rumen Fluid | [*Ruminococcus*] *torques* strain VPI B2-51 | 0.99 | 0 |
| 58 | 2 | ABB + Rumen Fluid | *Cloacibacillus eviyensis* strain 158 | 1.00 | 0 |
| 59 | 2 | ABB + Rumen Fluid | *Bacteroides uniformis* strain JCM 5828 | 0.99 | 0 |
| 60 | 2 | ABB + Rumen Fluid | *Collinsella aerofaciens* strain JCM 10188 | 0.99 | 0 |
| 61 | 2 | ABB + Rumen Fluid | *Alistipes onderdonkii* strain JCM 16771 | 1.00 | 0 |
| 62 | 2 | ABB + Rumen Fluid | *Phascolarctobacterium faecium* strain ACM 3679 | 0.84 | 0 |
| 63 | 2 | ABB + Rumen Fluid | *Alistipes onderdonkii* strain JCM 16771 | 1.00 | 0 |
| 64 | 2 | ABB + Rumen Fluid | [*Ruminococcus*] *torques* strain VPI B2-51 | 0.98 | 0 |
| 65 | 2 | ABB + Rumen Fluid | *Bacteroides uniformis* strain JCM 5828 | 0.99 | 0 |
| 66 | 2 | ABB + Rumen Fluid | *Alistipes onderdonkii* strain JCM 16771 | 1.00 | 0 |
| 67 | 2 | ABB + Rumen Fluid | *Alistipes onderdonkii* strain JCM 16771 | 1.00 | 0 |
| 68 | 2 | ABB + Rumen Fluid | *Alistipes shahii* strain JCM 16773 | 1.00 | 0 |
| 69 | 2 | ABB + Rumen Fluid | *Alistipes onderdonkii* strain JCM 16771 | 1.00 | 0 |
| 70 | 2 | ABB + Rumen Fluid | *Cloacibacillus eviyensis* strain 158 | 0.99 | 0 |
| 71 | 2 | ABB + Rumen Fluid | *Bacteroides dorei* strain 175 | 0.99 | 0 |
| 72 | 2 | ABB + Rumen Fluid | *Bacteroides dorei* strain 175 | 0.99 | 0 |
| 73 | 2 | ABB + Rumen Fluid | *Bacteroides dorei* strain 175 | 0.99 | 0 |
| 74 | 2 | ABB + Rumen Fluid | *Subdoligranulum variabile* strain BI 114 | 1.00 | 2E−172 |
| 75 | 2 | ABB + Rumen Fluid | *Parabacteroides merdae* strain JCM 9497 | 0.83 | 0 |
| 76 | 2 | ABB + Rumen Fluid | *Alistipes onderdonkii* strain JCM 16771 | 1.00 | 0 |
| 77 | 2 | ABB + Rumen Fluid | *Alistipes onderdonkii* strain JCM 16771 | 1.00 | 0 |
| 78 | 2 | ABB + Rumen Fluid | *Bacteroides dorei* strain 175 | 0.99 | 0 |
| 79 | 2 | ABB + Rumen Fluid | *Odoribacter splanchnicus* strain DSM 220712 | 0.99 | 0 |
| 80 | 2 | ABB + Rumen Fluid | *Odoribacter splanchnicus* strain DSM 220712 | 0.99 | 0 |
| 81 | 2 | ABB + Rumen Fluid | *Bacteroides ovatus* strain JCM 5824 | 1.00 | 4E−29 |
| 82 | 2 | ABB + Rumen Fluid | *Bacteroides uniformis* strain JCM 5828 | 0.99 | 0 |
| 83 | 2 | ABB + Rumen Fluid | [*Ruminococcus*] *torques* strain VPI B2-51 | 0.99 | 0 |
| 84 | 2 | ABB + Rumen Fluid | [Ruminococcus] *torques* strain VPI B2-51 | 0.98 | 0 |
| 85 | 2 | ABB + Rumen Fluid | *Phascolarctobacterium faecium* strain ACM 3679 | 0.92 | 0 |

TABLE 3-continued

| Strain # | Donor # | Screening Medium | Closest 16S RNA Sequence Strain Identification by BLASTn: Strain | % identity | E Value |
|---|---|---|---|---|---|
| 86 | 2 | ABB + Rumen Fluid | *Pseudoflavonifractor phocaeensis* strain Marseille-P3064 | 0.96 | 0 |
| 87 | 2 | ABB + Rumen Fluid | *Collinsella aerofaciens* strain JCM 10188 | 0.99 | 6E−147 |
| 88 | 2 | ABB + Rumen Fluid | [*Clostridium*] *hylemonae* strain TN-272 | 0.97 | 3E−169 |
| 89 | 2 | ABB + Rumen Fluid | *Bacteroides dorei* strain 175 | 0.99 | 0 |
| 90 | 2 | ABB + Rumen Fluid | *Alistipes onderdonkii* strain JCM 16771 | 1.00 | 0 |
| 91 | 2 | ABB + Rumen Fluid | *Bacteroides dorei* strain 175 | 0.99 | 0 |
| 92 | 2 | ABB + Rumen Fluid | *Cloacibacillus eviyensis* strain 158 | 1.00 | 0 |
| 93 | 2 | ABB + Rumen Fluid | *Alistipes shahii* strain JCM 16773 | 1.00 | 1E−163 |
| 94 | 2 | ABB + Rumen Fluid | *Alistipes shahii* strain JCM 16773 | 0.99 | 0 |
| 95 | 2 | ABB + Rumen Fluid | *Subdoligranulum variabile* strain BI 114 | 1.00 | 3E−144 |
| 96 | 2 | ABB + Rumen Fluid | *Cloacibacillus eviyensis* strain 158 | 1.00 | 8E−111 |
| 97 | 2 | ABB + Rumen Fluid | *Bacteroides cellulosilyticus* strain JCM 15632 | 1.00 | 0 |
| 98 | 2 | ABB + Rumen Fluid | *Alistipes shahii* strain WAL 8301 | 1.00 | 3E−179 |
| 99 | 2 | ABB + Rumen Fluid | *Alistipes onderdonkii* strain JCM 16771 | 1.00 | 0 |
| 100 | 2 | ABB + Rumen Fluid | *Cloacibacillus eviyensis* strain 158 | 1.00 | 9E−175 |
| 101 | 2 | ABB + Rumen Fluid | *Alistipes onderdonkii* strain JCM 16771 | 1.00 | 0 |
| 102 | 2 | ABB + Rumen Fluid | *Flintibacter butyricus* strain BL S21 | 0.98 | 7E−176 |
| 103 | 2 | ABB + Rumen Fluid | *Cloacibacillus eviyensis* strain 158 | 1.00 | 2E−101 |
| 104 | 2 | ABB + Rumen Fluid | *Bacteroides sartorii* strain A-C2-0 | 0.99 | 0 |
| 105 | 2 | ABB + Rumen Fluid | *Alistipes onderdonkii* strain JCM 16771 | 1.00 | 0 |
| 106 | 2 | ABB + Rumen Fluid | *Alistipes onderdonkii* strain JCM 16771 | 1.00 | 0 |
| 107 | 2 | ABB + Rumen Fluid | *Coprococcus eutactus* strain ATCC 27759 | 0.97 | 0 |
| 108 | 2 | ABB + Rumen Fluid | *Ruminococcus bromii* strain ATCC 27255 | 0.92 | 0 |
| 109 | 2 | ABB + Rumen Fluid | *Alistipes onderdonkii* strain JCM 16771 | 1.00 | 1E−98 |
| 110 | 2 | ABB + Rumen Fluid | *Cloacibacillus eviyensis* strain 158 | 1.00 | 2E−131 |
| 111 | 2 | ABB + Rumen Fluid | *Bacteroides stercorirosoris* strain JCM 17103 | 0.99 | 6E−127 |
| 112 | 2 | ABB + Rumen Fluid | *Ruminococcus faecis* strain Eg2 | 1.00 | 0 |
| 113 | 2 | ABB + Rumen Fluid | *Alistipes onderdonkii* strain JCM 16771 | 1.00 | 0 |
| 114 | 2 | ABB + Rumen Fluid | *Ruminococcus bromii* strain ATCC 27255 | 0.92 | 0 |
| 115 | 2 | ABB + Rumen Fluid | *Ruminococcus bromii* strain ATCC 27255 | 0.92 | 0 |
| 116 | 2 | ABB + Rumen Fluid | *Phocea massiliensis* strain Marseille-P2769 | 0.95 | 3E−70 |
| 117 | 2 | ABB + Rumen Fluid | *Caldicoprobacter guelmensis* strain D2C22 | 1.00 | 3E−10 |
| 118 | 2 | ABB + Rumen Fluid | *Alistipes onderdonkii* strain JCM 16771 | 1.00 | 0 |
| 119 | 2 | ABB + Rumen Fluid | *Alistipes onderdonkii* strain JCM 16771 | 1.00 | 0 |
| 120 | 2 | ABB + Rumen Fluid | *Alistipes onderdonkii* strain JCM 16771 | 1.00 | 0 |
| 121 | 2 | ABB + Rumen Fluid | *Alistipes onderdonkii* strain JCM 16771 | 1.00 | 8E−111 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 122 | 2 | ABB + Rumen Fluid | *Alistipes onderdonkii* strain JCM 16771 | 0.80 | 0 |
| 123 | 2 | ABB + Rumen Fluid | *Alistipes onderdonkii* strain JCM 16771 | 1.00 | 8E−126 |
| 124 | 2 | ABB + Rumen Fluid | *Alistipes onderdonkii* strain JCM 16771 | 1.00 | 0 |
| 125 | 2 | ABB + Rumen Fluid | *Odoribacter splanchnicus* strain DSM 220712 | 0.99 | 0 |
| 126 | 2 | ABB + Rumen Fluid | *Alistipes onderdonkii* strain JCM 16771 | 1.00 | 9E−150 |
| 127 | 2 | ABB + Rumen Fluid | *Pseudoflavonifractor phocaeensis* strain Marseille-P3064 | 0.94 | 0 |
| 128 | 2 | ABB + Rumen Fluid | [*Ruminococcus*] *torques* strain VPI B2-51 | 0.99 | 0 |
| 129 | 2 | ABB + Rumen Fluid | *Ruminococcus bromii* strain ATCC 27255 | 0.94 | 0 |
| 130 | 2 | ABB + Rumen Fluid | *Faecalicatena orotica* strain ATCC 13619 | 1.00 | 3E−57 |
| 131 | 2 | ABB + Rumen Fluid | *Bariatricus massiliensis* strain AT12 | 0.99 | 2E−108 |
| 132 | 2 | ABB + Rumen Fluid | *Ruminococcus faecis* strain Eg2 | 0.95 | 0 |
| 133 | 2 | ABB + Rumen Fluid | *Alistipes onderdonkii* strain JCM 16771 | 1.00 | 0 |
| 134 | 2 | ABB + Rumen Fluid | *Alistipes onderdonkii* strain JCM 16771 | 1.00 | 0 |
| 135 | 2 | ABB + Rumen Fluid | *Bacteroides oleiciplenus* strain JCM 16102 | 1.00 | 9E−48 |
| 136 | 2 | ABB + Rumen Fluid | [*Ruminococcus*] *torques* strain VPI B2-51 | 0.99 | 0 |
| 137 | 2 | ABB + Rumen Fluid | *Odoribacter splanchnicus* strain DSM 220712 | 0.99 | 0 |
| 138 | 2 | ABB + Rumen Fluid | *Faecalibacterium prausnitzii* strain ATCC 27768 | 0.95 | 5E−59 |
| 139 | 2 | ABB + Rumen Fluid | *Cloacibacillus eviyensis* strain 158 | 1.00 | 4E−36 |
| 140 | 2 | ABB + Rumen Fluid | *Alistipes onderdonkii* strain JCM 16771 | 0.94 | 0 |
| 141 | 2 | ABB + Rumen Fluid | *Alistipes onderdonkii* strain JCM 16771 | 1.00 | 4E−41 |
| 142 | 2 | ABB + Rumen Fluid | [*Ruminococcus*] *torques* strain VPI B2-51 | 0.99 | 0 |
| 143 | 2 | ABB + Rumen Fluid | *Alistipes onderdonkii* strain JCM 16771 | 1.00 | 4E−41 |
| 144 | 2 | ABB + Rumen Fluid | [*Ruminococcus*] *torques* strain VPI B2-51 | 0.92 | 0 |
| 145 | 2 | ABB + Rumen Fluid | *Bacteroides uniformis* strain JCM 5828 | 0.99 | 0 |
| 146 | 2 | ABB + Rumen Fluid | *Bacteroides dorei* strain 175 | 0.99 | 0 |
| 147 | 2 | ABB + Rumen Fluid | *Alistipes onderdonkii* strain JCM 16771 | 0.97 | 0 |
| 148 | 2 | ABB + Rumen Fluid | *Alistipes onderdonkii* strain JCM 16771 | 1.00 | 4E−41 |
| 149 | 2 | ABB + Rumen Fluid | *Eubacterium ramulus* strain ATCC 29099 | 0.89 | 1E−39 |
| 150 | 2 | ABB + Rumen Fluid | *Alistipes onderdonkii* strain JCM 16771 | 1.00 | 0 |
| 151 | 2 | ABB + Rumen Fluid | *Alistipes onderdonkii* strain JCM 16771 | 1.00 | 0 |
| 152 | 2 | ABB + Rumen Fluid | *Alistipes onderdonkii* strain JCM 16771 | 1.00 | 0 |
| 153 | 2 | ABB + Rumen Fluid | [*Clostridium*] *leptum* strain DSM 753 | 1.00 | 0 |
| 154 | 2 | ABB + Rumen Fluid | *Parabacteroides distasonis* strain JCM 5825 | 0.99 | 0 |
| 155 | 2 | ABB + Rumen Fluid | *Bacteroides stercorirosoris* strain JCM 17103 | 0.99 | 0 |
| 156 | 2 | ABB + Rumen Fluid | *Pseudoflavonifractor phocaeensis* strain Marseille-P3064 | 0.97 | 0 |
| 157 | 2 | ABB + Rumen Fluid | *Alistipes onderdonkii* strain JCM 16771 | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 158 | 2 | ABB + Rumen Fluid | *Alistipes onderdonkii* strain JCM 16771 | 1.00 | 0 |
| 159 | 2 | ABB + Rumen Fluid | *Alistipes onderdonkii* strain JCM 16771 | 1.00 | 0 |
| 160 | 2 | ABB + Rumen Fluid | *Bacteroides uniformis* strain JCM 5828 | 0.99 | 0 |
| 161 | 2 | ABB + Rumen Fluid | [*Ruminococcus*] *torques* strain VPI B2-51 | 0.97 | 0 |
| 162 | 2 | ABB + Rumen Fluid | *Blautia wexlerae* strain DSM 19850 | 0.99 | 0 |
| 163 | 2 | ABB + Rumen Fluid | *Alistipes onderdonkii* strain JCM 16771 | 1.00 | 0 |
| 164 | 2 | ABB + Rumen Fluid | *Phascolarctobacterium faecium* strain ACM 3679 | 0.94 | 3E−71 |
| 165 | 2 | ABB + Rumen Fluid | *Alistipes onderdonkii* strain JCM 16771 | 1.00 | 0 |
| 166 | 2 | ABB + Rumen Fluid | *Parabacteroides merdae* strain JCM 9497 | 1.00 | 0 |
| 167 | 2 | ABB + Rumen Fluid | *Alistipes onderdonkii* strain JCM 16771 | 1.00 | 0 |
| 168 | 2 | ABB + Rumen Fluid | *Alistipes onderdonkii* strain JCM 16771 | 1.00 | 0 |
| 169 | 2 | ABB + Rumen Fluid | *Butyrivibrio hungatei* strain JK 615 | 0.94 | 4E−35 |
| 170 | 2 | ABB + Rumen Fluid | *Bacteroides dorei* strain 175 | 0.98 | 3E−175 |
| 171 | 2 | ABB + Rumen Fluid | [*Eubacterium*] *contortum* strain DSM 3982 | 0.95 | 2E−32 |
| 172 | 2 | ABB + Rumen Fluid | *Bacteroides dorei* strain 175 | 0.99 | 0 |
| 173 | 2 | ABB + Rumen Fluid | *Alistipes finegoldii* strain DSM 17242 | 1.00 | 4E−31 |
| 174 | 2 | ABB + Rumen Fluid | *Bariatricus massiliensis* strain AT12 | 0.99 | 2E−108 |
| 175 | 2 | ABB + Rumen Fluid | *Alistipes onderdonkii* strain JCM 16771 | 1.00 | 0 |
| 176 | 2 | ABB + Rumen Fluid | *Bacteroides dorei* strain 175 | 0.99 | 0 |
| 177 | 2 | ABB + Rumen Fluid | *Ruminococcus albus* strain 7 | 0.94 | 0 |
| 178 | 2 | ABB + Rumen Fluid | *Ruminococcus bromii* strain ATCC 27255 | 0.91 | 0 |
| 179 | 2 | ABB + Rumen Fluid | *Ruminococcus bromii* strain ATCC 27255 | 0.92 | 0 |
| 180 | 2 | ABB + Rumen Fluid | *Extibacter muris* strain 40cc-B-5824-ARE | 0.96 | 0 |
| 181 | 2 | ABB + Rumen Fluid | [*Ruminococcus*] *torques* strain VPI B2-51 | 0.99 | 0 |
| 182 | 3 | ABB + Rumen Fluid | *Desulfotomaculum guttoideum* | 0.90 | 0 |
| 183 | 3 | ABB + Rumen Fluid | *Blautia wexlerae* DSM 19850 | 0.91 | 0 |
| 184 | 3 | ABB + Rumen Fluid | *Eggerthella* sp. Marseille-P3135 | 0.94 | 2.88E−90 |
| 185 | 3 | ABB + Rumen Fluid | *Dorea formicigenerans* | 0.96 | 2.7E−95 |
| 186 | 3 | ABB + Rumen Fluid | *Bacteroides uniformis* | 0.99 | 2.2E−111 |
| 187 | 3 | ABB + Rumen Fluid | *Eubacterium contortum* | 0.98 | 0 |
| 188 | 3 | ABB + Rumen Fluid | *Bacteroides xylanisolvens* XB1A | 0.97 | 6.9E−153 |
| 189 | 3 | ABB + Rumen Fluid | *Parabacteroides merdae* | 1.00 | 0 |
| 190 | 3 | ABB + Rumen Fluid | *Bacteroides uniformis* | 1.00 | 0 |
| 191 | 3 | ABB + Rumen Fluid | *Bacteroides dorei* | 1.00 | 1.6E−107 |
| 192 | 3 | ABB + Rumen Fluid | *Bacteroides dorei* | 1.00 | 1.1E−160 |
| 193 | 3 | ABB + Rumen Fluid | *Bacteroides vulgatus* | 1.00 | 1.4E−159 |
| 194 | 3 | ABB + Rumen Fluid | *Bacteroides uniformis* | 1.00 | 1.4E−164 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 195 | 3 | ABB + Rumen Fluid | *Ruminococcus faecis* JCM 15917 | 0.90 | 0 |
| 196 | 3 | ABB + Rumen Fluid | *Bacteroides dorei* | 1.00 | 0 |
| 197 | 3 | ABB + Rumen Fluid | *Bacteroides caccae* | 0.99 | 8.2E−157 |
| 198 | 3 | ABB + Rumen Fluid | *Bacteroides dorei* | 1.00 | 0 |
| 199 | 3 | ABB + Rumen Fluid | *Bacteroides vulgatus* | 1.00 | 0 |
| 200 | 3 | ABB + Rumen Fluid | *Bacteroides caccae* | 0.99 | 0 |
| 201 | 3 | ABB + Rumen Fluid | *Blautia wexlerae* DSM 19850 | 0.99 | 0 |
| 202 | 3 | ABB + Rumen Fluid | *Bacteroides dorei* | 1.00 | 0 |
| 203 | 3 | ABB + Rumen Fluid | *Collinsella aerofaciens* | 0.94 | 0 |
| 204 | 3 | ABB + Rumen Fluid | *Collinsella aerofaciens* | 0.94 | 9.1E−178 |
| 205 | 3 | ABB + Rumen Fluid | *Bacteroides caccae* | 1.00 | 0 |
| 206 | 3 | ABB + Rumen Fluid | *Parabacteroides distasonis* | 0.99 | 0 |
| 207 | 3 | ABB + Rumen Fluid | *Bacteroides xylanisolvens* XB1A | 0.96 | 6.9E−148 |
| 208 | 3 | ABB + Rumen Fluid | *Bacteroides uniformis* | 1.00 | 0 |
| 209 | 3 | ABB + Rumen Fluid | *Bacteroides dorei* | 1.00 | 0 |
| 210 | 3 | ABB + Rumen Fluid | *Ruminococcus faecis* JCM 15917 | 0.97 | 0 |
| 211 | 3 | ABB + Rumen Fluid | *Collinsella aerofaciens* | 0.91 | 0 |
| 212 | 3 | ABB + Rumen Fluid | *Parabacteroides merdae* | 1.00 | 0 |
| 213 | 3 | ABB + Rumen Fluid | *Blautia wexlerae* DSM 19850 | 0.99 | 9.9E−105 |
| 214 | 3 | ABB + Rumen Fluid | *Bacteroides uniformis* | 1.00 | 0 |
| 215 | 3 | ABB + Rumen Fluid | *Clostridium xylanolyticum* | 0.95 | 0 |
| 216 | 3 | ABB + Rumen Fluid | *Bacteroides uniformis* | 1.00 | 0 |
| 217 | 3 | ABB + Rumen Fluid | *Bacteroides dorei* | 1.00 | 0 |
| 218 | 3 | ABB + Rumen Fluid | *Anaerostipes hadrus* | 0.99 | 8.5E−162 |
| 219 | 3 | ABB + Rumen Fluid | *Bacteroides uniformis* | 1.00 | 0 |
| 220 | 3 | ABB + Rumen Fluid | *Bacteroides uniformis* | 1.00 | 0 |
| 221 | 3 | ABB + Rumen Fluid | *Bacteroides dorei* | 1.00 | 0 |
| 222 | 3 | ABB + Rumen Fluid | *Bacteroides dorei* | 1.00 | 0 |
| 223 | 3 | ABB + Rumen Fluid | *Blautia wexlerae* DSM 19850 | 1.00 | 2.6E−100 |
| 224 | 3 | ABB + Rumen Fluid | *Anaerostipes hadrus* | 1.00 | 0 |
| 225 | 3 | ABB + Rumen Fluid | *Ruminococcus faecis* JCM 15917 | 0.94 | 0 |
| 226 | 3 | ABB + Rumen Fluid | *Bacteroides uniformis* | 1.00 | 0 |
| 227 | 3 | ABB + Rumen Fluid | *Roseburia inulinivorans* | 0.93 | 3.7E−115 |
| 228 | 3 | ABB + Rumen Fluid | *Roseburia inulinivorans* | 0.94 | 9.9E−85 |
| 229 | 3 | ABB + Rumen Fluid | *Bacteroides dorei* | 1.00 | 0 |
| 230 | 3 | ABB + Rumen Fluid | *Bacteroides vulgatus* | 0.99 | 7.3E−137 |
| 231 | 3 | ABB + Rumen Fluid | *Ruminococcus faecis* JCM 15917 | 0.96 | 4.1E−109 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 232 | 3 | ABB + Rumen Fluid | *Bacteroides vulgatus* | 0.99 | 0 |
| 233 | 3 | ABB + Rumen Fluid | *Bacteroides dorei* | 1.00 | 2.3E−116 |
| 234 | 3 | ABB + Rumen Fluid | *Bacteroides uniformis* | 0.99 | 8.8E−157 |
| 235 | 3 | ABB + Rumen Fluid | *Bacteroides uniformis* | 0.94 | 2.83E−85 |
| 236 | 3 | ABB + Rumen Fluid | *Bacteroides dorei* | 0.97 | 8.9E−147 |
| 237 | 3 | ABB + Rumen Fluid | *Bacteroides dorei* | 0.98 | 1.5E−169 |
| 238 | 3 | ABB + Rumen Fluid | *Bacteroides dorei* | 1.00 | 0 |
| 239 | 3 | ABB + Rumen Fluid | *Blautia schinkii* | 0.96 | 1.3E−134 |
| 240 | 3 | ABB + Rumen Fluid | *Bacteroides dorei* | 1.00 | 0 |
| 241 | 3 | ABB + Rumen Fluid | *Blautia hydrogenotrophica* | 1.00 | 0 |
| 242 | 3 | ABB + Rumen Fluid | *Eubacterium contortum* | 0.98 | 0 |
| 243 | 3 | ABB + Rumen Fluid | *Anaerostipes hadrus* | 0.99 | 1.7E−148 |
| 244 | 3 | ABB + Rumen Fluid | *Eubacterium contortum* | 0.97 | 0 |
| 245 | 3 | ABB + Rumen Fluid | *Bacteroides dorei* | 1.00 | 0 |
| 246 | 3 | ABB + Rumen Fluid | *Bacteroides dorei* | 1.00 | 0 |
| 247 | 3 | ABB + Rumen Fluid | *Blautia wexlerae* DSM 19850 | 0.99 | 0 |
| 248 | 3 | ABB + Rumen Fluid | *Bacteroides dorei* | 1.00 | 0 |
| 249 | 3 | ABB + Rumen Fluid | *Bacteroides uniformis* | 1.00 | 0 |
| 250 | 3 | ABB + Rumen Fluid | *Bacteroides dorei* | 1.00 | 0 |
| 251 | 3 | ABB + Rumen Fluid | *Ruminococcus faecis* JCM 15917 | 0.97 | 4.1E−114 |
| 252 | 3 | ABB + Rumen Fluid | *Bacteroides vulgatus* | 1.00 | 0 |
| 253 | 3 | ABB + Rumen Fluid | *Bacteroides dorei* | 1.00 | 0 |
| 254 | 3 | ABB + Rumen Fluid | *Bacteroides dorei* | 0.99 | 0 |
| 255 | 3 | ABB + Rumen Fluid | *Bacteroides caccae* | 0.99 | 0 |
| 256 | 3 | ABB + Rumen Fluid | *Ruminococcaceae bacterium* GD1 | 0.96 | 8.2E−137 |
| 257 | 3 | ABB + Rumen Fluid | *Bacteroides vulgatus* | 0.99 | 0 |
| 258 | 3 | ABB + Rumen Fluid | *Bacteroides uniformis* | 1.00 | 0 |
| 259 | 3 | ABB + Rumen Fluid | *Collinsella aerofaciens* | 0.97 | 0 |
| 260 | 3 | ABB + Rumen Fluid | *Anaerostipes hadrus* | 0.99 | 1.1E−160 |
| 261 | 3 | ABB + Rumen Fluid | *Parabacteroides distasonis* | 0.98 | 2.7E−136 |
| 262 | 3 | ABB + Rumen Fluid | *Bacteroides uniformis* | 1.00 | 0 |
| 263 | 3 | ABB + Rumen Fluid | *Bacteroides uniformis* | 1.00 | 0 |
| 264 | 3 | ABB + Rumen Fluid | *Bacteroides dorei* | 1.00 | 0 |
| 265 | 3 | ABB + Rumen Fluid | *Dorea longicatena* | 0.90 | 5.03E−74 |
| 266 | 3 | ABB + Rumen Fluid | *Bacteroides dorei* | 1.00 | 3.7E−155 |
| 267 | 3 | ABB + Rumen Fluid | *Ruminococcus faecis* JCM 15917 | 0.94 | 9.8E−147 |
| 268 | 3 | ABB + Rumen Fluid | *Bacteroides caccae* | 0.99 | 4E−119 |

TABLE 3-continued

| Strain # | Donor # | Screening Medium | Closest 16S RNA Sequence Strain Identification by BLASTn: Strain | % identity | E Value |
|---|---|---|---|---|---|
| 269 | 3 | ABB + Rumen Fluid | *Bacteroides dorei* | 1.00 | 2.4E−126 |
| 270 | 3 | ABB + Rumen Fluid | *Bacteroides caccae* | 0.99 | 0 |
| 271 | 3 | ABB + Rumen Fluid | *Bacteroides vulgatus* | 1.00 | 0 |
| 272 | 3 | ABB + Rumen Fluid | *Bacteroides dorei* | 1.00 | 0 |
| 273 | 3 | ABB + Rumen Fluid | *Bacteroides dorei* | 1.00 | 0 |
| 274 | 3 | ABB + Rumen Fluid | *Bacteroides uniformis* | 1.00 | 0 |
| 275 | 3 | ABB + Rumen Fluid | *Bacteroides dorei* | 1.00 | 5.9E−148 |
| 276 | 3 | ABB + Rumen Fluid | *Bacteroides ovatus* | 0.90 | 0 |
| 277 | 3 | ABB + Rumen Fluid | *Bacteroides dorei* | 1.00 | 0 |
| 278 | 3 | ABB + Rumen Fluid | *Blautia wexlerae* DSM 19850 | 0.96 | 0 |
| 279 | 3 | ABB + Rumen Fluid | *Bacteroides dorei* | 1.00 | 0 |
| 280 | 3 | ABB + Rumen Fluid | *Bacteroides vulgatus* | 1.00 | 0 |
| 281 | 3 | ABB + Rumen Fluid | *Bacteroides caccae* | 0.98 | 0 |
| 282 | 3 | ABB + Rumen Fluid | *Bacteroides dorei* | 1.00 | 0 |
| 283 | 3 | ABB + Rumen Fluid | *Bacteroides dorei* | 1.00 | 0 |
| 284 | 3 | ABB + Rumen Fluid | *Ruminococcus faecis* JCM 15917 | 0.94 | 1.5E−139 |
| 285 | 3 | ABB + Rumen Fluid | *Bacteroides vulgatus* | 0.98 | 4.3E−170 |
| 286 | 3 | ABB + Rumen Fluid | *Bacteroides uniformis* | 1.00 | 0 |
| 287 | 3 | ABB + Rumen Fluid | *Hespellia porcina* | 0.97 | 0 |
| 288 | 3 | ABB + Rumen Fluid | *Dorea formicigenerans* | 0.97 | 0 |
| 289 | 3 | ABB + Rumen Fluid | [*Ruminococcus*] *obeum* | 0.99 | 0 |
| 290 | 3 | ABB + Rumen Fluid | *Hespellia porcina* | 0.97 | 0 |
| 291 | 3 | ABB + Rumen Fluid | *Ruminococcus faecis* JCM 15917 | 0.94 | 1.1E−99 |
| 292 | 3 | ABB + Rumen Fluid | *Bacteroides salyersiae* | 1.00 | 0 |
| 293 | 3 | ABB + Rumen Fluid | *Bacteroides dorei* | 0.99 | 0 |
| 294 | 3 | ABB + Rumen Fluid | *Bacteroides dorei* | 0.98 | 0 |
| 295 | 3 | ABB + Rumen Fluid | *Bacteroides dorei* | 0.99 | 0 |
| 296 | 3 | ABB + Rumen Fluid | *Collinsella aerofaciens* | 0.91 | 1.3E−135 |
| 297 | 3 | ABB + Rumen Fluid | *Ruminococcus faecis* JCM 15917 | 0.91 | 7.6E−133 |
| 298 | 3 | ABB + Rumen Fluid | *Eggerthella lenta* | 1.00 | 0 |
| 299 | 3 | ABB + Rumen Fluid | *Bacteroides dorei* | 1.00 | 0 |
| 300 | 3 | ABB + Rumen Fluid | *Blautia hydrogenotrophica* | 0.97 | 4.9E−144 |
| 301 | 3 | ABB + Rumen Fluid | *Blautia hydrogenotrophica* | 1.00 | 0 |
| 302 | 3 | ABB + Rumen Fluid | *Bacteroides salyersiae* | 0.98 | 0 |
| 303 | 3 | ABB + Rumen Fluid | *Bacteroides dorei* | 1.00 | 0 |
| 304 | 3 | ABB + Rumen Fluid | *Ruminococcus faecis* JCM 15917 | 0.99 | 6.7E−122 |
| 305 | 3 | ABB + Rumen Fluid | *Bacteroides dorei* | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 306 | 3 | ABB + Rumen Fluid | *Ruminococcus faecis* JCM 15917 | 0.97 | 2.6E−121 |
| 307 | 3 | ABB + Rumen Fluid | *Bacteroides xylanisolvens* XB1A | 0.96 | 0 |
| 308 | 3 | ABB + Rumen Fluid | *Bacteroides uniformis* | 1.00 | 0 |
| 309 | 3 | ABB + Rumen Fluid | *Bacteroides uniformis* | 0.99 | 0 |
| 310 | 3 | ABB + Rumen Fluid | *Clostridium mayombei* | 0.91 | 3.03E−74 |
| 311 | 3 | ABB + Rumen Fluid | *Ruminococcus faecis* JCM 15917 | 0.96 | 5.9E−174 |
| 312 | 3 | ABB + Rumen Fluid | *Bacteroides dorei* | 1.00 | 0 |
| 313 | 3 | ABB + Rumen Fluid | *Ruminococcus faecis* JCM 15917 | 0.98 | 8.7E−116 |
| 314 | 3 | ABB + Rumen Fluid | *Bacteroides caccae* | 1.00 | 0 |
| 315 | 3 | ABB + Rumen Fluid | *Bacteroides uniformis* | 1.00 | 5.6E−102 |
| 316 | 3 | ABB + Rumen Fluid | *Catenibacterium mitsuokai* | 0.96 | 1.6E−169 |
| 317 | 3 | ABB + Rumen Fluid | *Bacteroides vulgatus* | 1.00 | 6.1E−129 |
| 318 | 3 | ABB + Rumen Fluid | *Bacteroides uniformis* | 0.99 | 0 |
| 319 | 3 | ABB + Rumen Fluid | *Ruminococcus faecis* JCM 15917 | 0.96 | 4.7E−180 |
| 320 | 3 | ABB + Rumen Fluid | *Bacteroides dorei* | 0.99 | 4.3E−134 |
| 321 | 3 | ABB + Rumen Fluid | *Bacteroides dorei* | 1.00 | 0 |
| 322 | 3 | ABB + Rumen Fluid | *Flavonifractor plautii* | 0.99 | 7.5E−158 |
| 323 | 3 | ABB + Rumen Fluid | *Bacteroides dorei* | 1.00 | 0 |
| 324 | 3 | ABB + Rumen Fluid | *Bacteroides dorei* | 0.99 | 4.3E−150 |
| 325 | 3 | ABB + Rumen Fluid | *Butyrivibrio crossotus* | 0.94 | 9.5E−123 |
| 326 | 3 | ABB + Rumen Fluid | *Bacteroides dorei* | 1.00 | 1E−109 |
| 327 | 3 | ABB + Rumen Fluid | *Bacteroides dorei* | 0.95 | 1.1E−176 |
| 328 | 3 | ABB + Rumen Fluid | *Roseburia hominis* | 0.94 | 1.3E−160 |
| 329 | 3 | ABB + Rumen Fluid | *Bacteroides vulgatus* | 1.00 | 0 |
| 330 | 3 | ABB + Rumen Fluid | *Ruminococcus faecis* JCM 15917 | 0.91 | 0 |
| 331 | 3 | ABB + Rumen Fluid | *Blautia hydrogenotrophica* | 0.99 | 5.3E−174 |
| 332 | 3 | ABB + Rumen Fluid | *Ruminococcus faecis* JCM 15917 | 0.95 | 1.5E−103 |
| 333 | 3 | ABB + Rumen Fluid | *Bacteroides caccae* | 0.97 | 5.7E−164 |
| 334 | 3 | ABB + Rumen Fluid | *Bacteroides dorei* | 0.99 | 0 |
| 335 | 3 | ABB + Rumen Fluid | *Bacteroides dorei* | 1.00 | 2.9E−115 |
| 336 | 3 | ABB + Rumen Fluid | *Bacteroides dorei* | 1.00 | 0 |
| 337 | 3 | ABB + Rumen Fluid | *Ruminococcus faecis* JCM 15917 | 0.96 | 6E−179 |
| 338 | 3 | ABB + Rumen Fluid | *Ruminococcus faecis* JCM 15917 | 0.94 | 0 |
| 339 | 3 | ABB + Rumen Fluid | *Blautia wexlerae* DSM 19850 | 1.00 | 0 |
| 340 | 3 | ABB + Rumen Fluid | *Bacteroides dorei* | 0.98 | 0 |
| 341 | 3 | ABB + Rumen Fluid | *Bacteroides uniformis* | 1.00 | 0 |
| 342 | 3 | ABB + Rumen Fluid | *Bacteroides dorei* | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 343 | 3 | ABB + Rumen Fluid | *Bacteroides ovatus* | 0.91 | 8E−134 |
| 344 | 3 | ABB + Rumen Fluid | *Bacteroides vulgatus* | 0.99 | 0 |
| 345 | 3 | ABB + Rumen Fluid | *Ruminococcus faecis* JCM 15917 | 0.97 | 5.3E−154 |
| 346 | 3 | ABB + Rumen Fluid | *Blautia* sp. M25 | 1.00 | 2.4E−152 |
| 347 | 3 | ABB + Rumen Fluid | *Bacteroides dorei* | 1.00 | 0 |
| 348 | 3 | ABB + Rumen Fluid | *Anaerostipes hadrus* | 1.00 | 1.3E−149 |
| 349 | 3 | ABB + Rumen Fluid | *Bacteroides uniformis* | 1.00 | 0 |
| 350 | 3 | ABB + Rumen Fluid | *Bacteroides dorei* | 0.99 | 0 |
| 351 | 3 | ABB + Rumen Fluid | *Bacteroides caccae* | 1.00 | 0 |
| 352 | 3 | ABB + Rumen Fluid | *Anaerostipes hadrus* | 1.00 | 0 |
| 353 | 3 | ABB + Rumen Fluid | *Bacteroides dorei* | 1.00 | 0 |
| 354 | 3 | ABB + Rumen Fluid | *Bacteroides dorei* | 0.99 | 0 |
| 355 | 3 | ABB + Rumen Fluid | *Butyrivibrio crossotus* | 0.91 | 3.67E−70 |
| 356 | 3 | ABB + Rumen Fluid | [*Ruminococcus*] *obeum* | 0.98 | 0 |
| 357 | 3 | ABB + Rumen Fluid | *Bacteroides dorei* | 1.00 | 0 |
| 358 | 3 | ABB + Rumen Fluid | *Ruminococcus faecis* JCM 15917 | 0.98 | 5.3E−164 |
| 359 | 3 | ABB + Rumen Fluid | *Bacteroides dorei* | 1.00 | 0 |
| 360 | 3 | ABB + Rumen Fluid | *Collinsella aerofaciens* | 0.99 | 3.7E−150 |
| 361 | 3 | ABB + Rumen Fluid | *Collinsella aerofaciens* | 0.95 | 5.8E−118 |
| 362 | 3 | ABB + Rumen Fluid | *Catenibacterium mitsuokai* | 0.97 | 0 |
| 363 | 3 | ABB + Rumen Fluid | *Dorea longicatena* | 1.00 | 0 |
| 364 | 3 | ABB + Rumen Fluid | *Bacteroides vulgatus* | 1.00 | 0 |
| 365 | 3 | ABB + Rumen Fluid | *Dorea formicigenerans* | 0.98 | 0 |
| 366 | 3 | ABB + Rumen Fluid | *Bacteroides dorei* | 1.00 | 0 |
| 367 | 3 | ABB + Rumen Fluid | *Bacteroides uniformis* | 0.99 | 1.6E−174 |
| 368 | 3 | ABB + Rumen Fluid | *Bacteroides dorei* | 1.00 | 0 |
| 369 | 3 | ABB + Rumen Fluid | *Ruminococcus faecis* JCM 15917 | 0.93 | 0 |
| 370 | 3 | ABB + Rumen Fluid | *Bacteroides vulgatus* | 0.99 | 0 |
| 371 | 3 | ABB + Rumen Fluid | *Blautia hydrogenotrophica* | 1.00 | 0 |
| 372 | 3 | ABB + Rumen Fluid | *Bacteroides dorei* | 1.00 | 0 |
| 373 | 3 | ABB + Rumen Fluid | *Blautia wexlerae* DSM 19850 | 0.99 | 0 |
| 374 | 3 | ABB + Rumen Fluid | *Bacteroides xylanisolvens* XB1A | 0.96 | 0 |
| 375 | 3 | ABB + Rumen Fluid | *Bacteroides uniformis* | 1.00 | 0 |
| 376 | 3 | ABB + Rumen Fluid | [*Ruminococcus*] *obeum* | 0.93 | 0 |
| 377 | 3 | ABB + Rumen Fluid | *Ruminococcus faecis* JCM 15917 | 0.91 | 0 |
| 378 | 3 | ABB + Rumen Fluid | *Collinsella* sp. Marseille-P3296T | 0.92 | 1.1E−96 |
| 379 | 3 | ABB + Rumen Fluid | *Bacteroides dorei* | 1.00 | 0 |

TABLE 3-continued

| Strain # | Donor # | Screening Medium | Closest 16S RNA Sequence Strain Identification by BLASTn: Strain | % identity | E Value |
|---|---|---|---|---|---|
| 380 | 3 | ABB + Rumen Fluid | *Blautia wexlerae* DSM 19850 | 0.99 | 0 |
| 381 | 3 | ABB + Rumen Fluid | *Flavonifractor plautii* | 1.00 | 0 |
| 382 | 3 | ABB + Rumen Fluid | *Ruminococcus faecis* JCM 15917 | 0.90 | 0 |
| 383 | 3 | ABB + Rumen Fluid | *Bacteroides dorei* | 1.00 | 0 |
| 384 | 3 | ABB + Rumen Fluid | *Bacteroides xylanisolvens* XB1A | 0.98 | 0 |
| 385 | 3 | ABB + Rumen Fluid | *Bacteroides vulgatus* | 1.00 | 0 |
| 386 | 4 | ABB + Rumen Fluid | *Bacteroides vulgatus* | 1.00 | 0 |
| 387 | 4 | ABB + Rumen Fluid | *Bacteroides vulgatus* | 0.98 | 3.4E−125 |
| 388 | 4 | ABB + Rumen Fluid | *Bacteroides uniformis* | 0.91 | 4.8E−99 |
| 389 | 4 | ABB + Rumen Fluid | *Bacteroides vulgatus* | 1.00 | 0 |
| 390 | 4 | ABB + Rumen Fluid | *Bacteroides vulgatus* | 1.00 | 0 |
| 391 | 4 | ABB + Rumen Fluid | *Blautia luti* | 0.99 | 0 |
| 392 | 4 | ABB + Rumen Fluid | *Blautia obeum* | 1.00 | 1.5E−123 |
| 393 | 4 | ABB + Rumen Fluid | *Bacteroides vulgatus* | 1.00 | 0 |
| 394 | 4 | ABB + Rumen Fluid | *Bacteroides vulgatus* | 1.00 | 0 |
| 395 | 4 | ABB + Rumen Fluid | *Bacteroides vulgatus* | 1.00 | 0 |
| 396 | 4 | ABB + Rumen Fluid | *Bacteroides stercoris* ATCC 43183 | 1.00 | 0 |
| 397 | 4 | ABB + Rumen Fluid | *Bacteroides stercoris* ATCC 43183 | 1.00 | 0 |
| 398 | 4 | ABB + Rumen Fluid | *Bacteroides stercoris* ATCC 43183 | 1.00 | 0 |
| 399 | 4 | ABB + Rumen Fluid | *Bacteroides stercoris* ATCC 43183 | 1.00 | 0 |
| 400 | 4 | ABB + Rumen Fluid | *Bacteroides vulgatus* | 1.00 | 0 |
| 401 | 4 | ABB + Rumen Fluid | *Bacteroides stercoris* ATCC 43183 | 0.99 | 3.5E−140 |
| 402 | 4 | ABB + Rumen Fluid | *Bacteroides vulgatus* | 1.00 | 0 |
| 403 | 4 | ABB + Rumen Fluid | *Bacteroides vulgatus* | 1.00 | 0 |
| 404 | 4 | ABB + Rumen Fluid | *Bacteroides stercoris* ATCC 43183 | 1.00 | 0 |
| 405 | 4 | ABB + Rumen Fluid | *Bacteroides stercoris* ATCC 43183 | 1.00 | 0 |
| 406 | 4 | ABB + Rumen Fluid | *Flavonifractor plautii* | 0.99 | 0 |
| 407 | 4 | ABB + Rumen Fluid | *Bacteroides vulgatus* | 1.00 | 0 |
| 408 | 4 | ABB + Rumen Fluid | *Bacteroides vulgatus* | 1.00 | 0 |
| 409 | 4 | ABB + Rumen Fluid | *Bacteroides stercoris* ATCC 43183 | 1.00 | 0 |
| 410 | 4 | ABB + Rumen Fluid | *Blautia luti* | 1.00 | 0 |
| 411 | 4 | ABB + Rumen Fluid | *Bacteroides stercoris* ATCC 43183 | 1.00 | 0 |
| 412 | 4 | ABB + Rumen Fluid | *Bacteroides vulgatus* | 1.00 | 0 |
| 413 | 4 | ABB + Rumen Fluid | *Bacteroides stercoris* ATCC 43183 | 0.99 | 0 |
| 414 | 4 | ABB + Rumen Fluid | *Bacteroides vulgatus* | 1.00 | 0 |
| 415 | 4 | ABB + Rumen Fluid | *Bacteroides vulgatus* | 1.00 | 0 |
| 416 | 4 | ABB + Rumen Fluid | *Bacteroides stercoris* ATCC 43183 | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 417 | 4 | ABB + Rumen Fluid | *Blautia hydrogenotrophica* | 1.00 | 0 |
| 418 | 4 | ABB + Rumen Fluid | *Faecalibacterium prausnitzii* | 0.99 | 0 |
| 419 | 4 | ABB + Rumen Fluid | *Coprococcus comes* ATCC 27758 | 0.99 | 0 |
| 420 | 4 | ABB + Rumen Fluid | *Bacteroides vulgatus* | 0.99 | 0 |
| 421 | 4 | ABB + Rumen Fluid | *Blautia wexlerae* DSM 19850 | 1.00 | 1.5E−123 |
| 422 | 4 | ABB + Rumen Fluid | *Bacteroides vulgatus* | 1.00 | 0 |
| 423 | 4 | ABB + Rumen Fluid | *Bacteroides vulgatus* | 1.00 | 0 |
| 424 | 4 | ABB + Rumen Fluid | *Bacteroides vulgatus* | 1.00 | 0 |
| 425 | 4 | ABB + Rumen Fluid | *Bacteroides vulgatus* | 1.00 | 0 |
| 426 | 4 | ABB + Rumen Fluid | *Bacteroides vulgatus* | 0.99 | 1E−145 |
| 427 | 4 | ABB + Rumen Fluid | *Bifidobacterium longum* subsp. *suillum* | 1.00 | 0 |
| 428 | 4 | ABB + Rumen Fluid | *Parabacteroides distasonis* | 0.98 | 1.6E−97 |
| 429 | 4 | ABB + Rumen Fluid | *Bacteroides vulgatus* | 1.00 | 0 |
| 430 | 4 | ABB + Rumen Fluid | *Blautia luti* DSM 14534 | 0.99 | 1.6E−179 |
| 431 | 4 | ABB + Rumen Fluid | *Bacteroides vulgatus* | 1.00 | 0 |
| 432 | 4 | ABB + Rumen Fluid | *Eggerthella lenta* | 0.99 | 1.7E−148 |
| 433 | 4 | ABB + Rumen Fluid | *Bacteroides vulgatus* | 1.00 | 0 |
| 434 | 4 | ABB + Rumen Fluid | [*Ruminococcus*] *torques* | 0.99 | 6.6E−163 |
| 435 | 4 | ABB + Rumen Fluid | *Agathobaculum butyriciproducens* | 1.00 | 0 |
| 436 | 4 | ABB + Rumen Fluid | *Bacteroides vulgatus* | 1.00 | 0 |
| 437 | 4 | ABB + Rumen Fluid | *Bacteroides vulgatus* | 1.00 | 0 |
| 438 | 4 | ABB + Rumen Fluid | *Bacteroides stercoris* ATCC 43183 | 1.00 | 0 |
| 439 | 4 | ABB + Rumen Fluid | *Bacteroides vulgatus* | 1.00 | 0 |
| 440 | 4 | ABB + Rumen Fluid | *Blautia hydrogenotrophica* | 1.00 | 0 |
| 441 | 4 | ABB + Rumen Fluid | *Bacteroides vulgatus* | 1.00 | 0 |
| 442 | 4 | ABB + Rumen Fluid | *Bacteroides vulgatus* | 1.00 | 0 |
| 443 | 4 | ABB + Rumen Fluid | *Blautia obeum* | 0.99 | 0 |
| 444 | 4 | ABB + Rumen Fluid | *Bacteroides stercoris* ATCC 43183 | 1.00 | 0 |
| 445 | 4 | ABB + Rumen Fluid | *Blautia luti* DSM 14534 | 0.99 | 0 |
| 446 | 4 | ABB + Rumen Fluid | *Bacteroides vulgatus* | 1.00 | 0 |
| 447 | 4 | ABB + Rumen Fluid | *Bacteroides vulgatus* | 1.00 | 0 |
| 448 | 4 | ABB + Rumen Fluid | *Bacteroides vulgatus* | 1.00 | 0 |
| 449 | 4 | ABB + Rumen Fluid | *Bacteroides uniformis* | 1.00 | 0 |
| 450 | 4 | ABB + Rumen Fluid | *Blautia luti* DSM 14534 | 0.97 | 0 |
| 451 | 4 | ABB + Rumen Fluid | *Coprococcus comes* ATCC 27758 | 1.00 | 0 |
| 452 | 4 | ABB + Rumen Fluid | *Bacteroides vulgatus* | 1.00 | 0 |
| 453 | 4 | ABB + Rumen Fluid | *Bacteroides vulgatus* | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 454 | 4 | ABB + Rumen Fluid | *Blautia wexlerae* DSM 19850 | 0.97 | 0 |
| 455 | 4 | ABB + Rumen Fluid | *Blautia wexlerae* DSM 19850 | 1.00 | 0 |
| 456 | 4 | ABB + Rumen Fluid | *Bacteroides vulgatus* | 1.00 | 0 |
| 457 | 4 | ABB + Rumen Fluid | *Bacteroides vulgatus* | 1.00 | 0 |
| 458 | 4 | ABB + Rumen Fluid | *Bacteroides vulgatus* | 1.00 | 0 |
| 459 | 4 | ABB + Rumen Fluid | *Bacteroides vulgatus* | 1.00 | 0 |
| 460 | 4 | ABB + Rumen Fluid | *Bacteroides vulgatus* | 0.99 | 0 |
| 461 | 4 | ABB + Rumen Fluid | *Bacteroides vulgatus* | 1.00 | 0 |
| 462 | 4 | ABB + Rumen Fluid | *Bacteroides vulgatus* | 1.00 | 0 |
| 463 | 4 | ABB + Rumen Fluid | *Agathobaculum butyriciproducens* | 1.00 | 0 |
| 464 | 4 | ABB + Rumen Fluid | *Bacteroides stercoris* ATCC 43183 | 1.00 | 0 |
| 465 | 4 | ABB + Rumen Fluid | *Bacteroides vulgatus* | 1.00 | 0 |
| 466 | 4 | ABB + Rumen Fluid | *Bacteroides vulgatus* | 0.99 | 0 |
| 467 | 4 | ABB + Rumen Fluid | *Bacteroides vulgatus* | 1.00 | 0 |
| 468 | 4 | ABB + Rumen Fluid | *Bacteroides vulgatus* | 1.00 | 0 |
| 469 | 4 | ABB + Rumen Fluid | *Bacteroides vulgatus* | 1.00 | 0 |
| 470 | 4 | ABB + Rumen Fluid | *Alistipes onderdonkii* | 0.94 | 6.26E−92 |
| 471 | 4 | ABB + Rumen Fluid | [*Ruminococcus*] *torques* | 0.99 | 5.1E−118 |
| 472 | 4 | ABB + Rumen Fluid | *Blautia luti* DSM 14534 | 0.99 | 0 |
| 473 | 4 | ABB + Rumen Fluid | *Bacteroides vulgatus* | 1.00 | 0 |
| 474 | 4 | ABB + Rumen Fluid | *Coprococcus catus* | 0.97 | 0 |
| 475 | 4 | ABB + Rumen Fluid | *Bacteroides vulgatus* | 1.00 | 0 |
| 476 | 4 | ABB + Rumen Fluid | *Bacteroides vulgatus* | 1.00 | 0 |
| 477 | 4 | ABB + Rumen Fluid | *Bacteroides vulgatus* | 1.00 | 0 |
| 478 | 4 | ABB + Rumen Fluid | *Bacteroides vulgatus* | 1.00 | 0 |
| 479 | 4 | ABB + Rumen Fluid | *Sutterella wadsworthensis* | 1.00 | 0 |
| 480 | 4 | ABB + Rumen Fluid | *Bacteroides vulgatus* | 1.00 | 0 |
| 481 | 4 | ABB + Rumen Fluid | *Coprococcus comes* ATCC 27758 | 0.99 | 0 |
| 482 | 4 | ABB + Rumen Fluid | *Bacteroides vulgatus* | 1.00 | 0 |
| 483 | 4 | ABB + Rumen Fluid | *Blautia luti* DSM 14534 | 0.98 | 0 |
| 484 | 4 | ABB + Rumen Fluid | *Bacteroides vulgatus* | 1.00 | 0 |
| 485 | 4 | ABB + Rumen Fluid | *Blautia wexlerae* DSM 19850 | 0.99 | 3.6E−104 |
| 486 | 4 | ABB + Rumen Fluid | *Bacteroides vulgatus* | 1.00 | 0 |
| 487 | 4 | ABB + Rumen Fluid | *Bacteroides stercoris* ATCC 43183 | 1.00 | 0 |
| 488 | 4 | ABB + Rumen Fluid | [*Eubacterium*] *rectale* | 0.93 | 0 |
| 489 | 4 | ABB + Rumen Fluid | *Anaerostipes hadrus* | 1.00 | 0 |
| 490 | 4 | ABB + Rumen Fluid | *Bacteroides thetaiotaomicron* | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 491 | 4 | ABB + Rumen Fluid | *Bacteroides vulgatus* | 1.00 | 0 |
| 492 | 4 | ABB + Rumen Fluid | *Anaerostipes hadrus* | 1.00 | 1.8E−163 |
| 493 | 4 | ABB + Rumen Fluid | *Flavonifractor plautii* | 0.99 | 0 |
| 494 | 4 | ABB + Rumen Fluid | *Parabacteroides merdae* | 1.00 | 0 |
| 495 | 4 | ABB + Rumen Fluid | *Parabacteroides merdae* | 1.00 | 0 |
| 496 | 4 | ABB + Rumen Fluid | *Gordonibacter pamelaeae* | 1.00 | 0 |
| 497 | 4 | ABB + Rumen Fluid | *Bacteroides stercoris* ATCC 43183 | 1.00 | 0 |
| 498 | 4 | ABB + Rumen Fluid | *Coprococcus catus* | 0.97 | 0 |
| 499 | 4 | ABB + Rumen Fluid | *Bacteroides vulgatus* | 1.00 | 0 |
| 500 | 4 | ABB + Rumen Fluid | *Bacteroides vulgatus* | 1.00 | 0 |
| 501 | 4 | ABB + Rumen Fluid | *Bacteroides vulgatus* | 1.00 | 0 |
| 502 | 4 | ABB + Rumen Fluid | *Bacteroides vulgatus* | 1.00 | 0 |
| 503 | 4 | ABB + Rumen Fluid | *Faecalibacterium prausnitzii* | 0.98 | 0 |
| 504 | 4 | ABB + Rumen Fluid | *Bacteroides vulgatus* | 1.00 | 0 |
| 505 | 4 | ABB + Rumen Fluid | *Gordonibacter pamelaeae* | 0.97 | 3.8E−104 |
| 506 | 4 | ABB + Rumen Fluid | *Bacteroides vulgatus* | 1.00 | 0 |
| 507 | 4 | ABB + Rumen Fluid | *Bacteroides stercoris* ATCC 43183 | 1.00 | 0 |
| 508 | 4 | ABB + Rumen Fluid | *Blautia luti* DSM 14534 | 0.99 | 3.7E−140 |
| 509 | 4 | ABB + Rumen Fluid | *Blautia obeum* | 0.94 | 2.05E−81 |
| 510 | 4 | ABB + Rumen Fluid | *Bacteroides stercoris* ATCC 43183 | 0.99 | 0 |
| 511 | 4 | ABB + Rumen Fluid | *Bacteroides stercoris* ATCC 43183 | 1.00 | 0 |
| 512 | 4 | ABB + Rumen Fluid | *Bacteroides vulgatus* | 1.00 | 0 |
| 513 | 4 | ABB + Rumen Fluid | *Bacteroides vulgatus* | 1.00 | 0 |
| 514 | 4 | ABB + Rumen Fluid | *Bacteroides uniformis* | 0.95 | 0 |
| 515 | 4 | ABB + Rumen Fluid | *Bacteroides uniformis* | 1.00 | 0 |
| 516 | 4 | ABB + Rumen Fluid | *Bacteroides uniformis* | 0.93 | 0 |
| 517 | 4 | ABB + Rumen Fluid | *Dorea longicatena* | 1.00 | 0 |
| 518 | 4 | ABB + Rumen Fluid | *Faecalicatena contorta* | 0.98 | 0 |
| 519 | 4 | ABB + Rumen Fluid | *Bacteroides vulgatus* | 1.00 | 0 |
| 520 | 4 | ABB + Rumen Fluid | *Bacteroides uniformis* | 1.00 | 0 |
| 521 | 4 | ABB + Rumen Fluid | *Bacteroides stercoris* ATCC 43183 | 1.00 | 0 |
| 522 | 4 | ABB + Rumen Fluid | *Bacteroides vulgatus* | 1.00 | 0 |
| 523 | 4 | ABB + Rumen Fluid | *Bacteroides uniformis* | 1.00 | 0 |
| 524 | 4 | ABB + Rumen Fluid | *Blautia luti* DSM 14534 | 0.98 | 0 |
| 525 | 4 | ABB + Rumen Fluid | *Bacteroides vulgatus* | 1.00 | 0 |
| 526 | 4 | ABB + Rumen Fluid | *Dorea longicatena* | 1.00 | 0 |
| 527 | 4 | ABB + Rumen Fluid | *Bacteroides vulgatus* | 1.00 | 0 |

TABLE 3-continued

| | | | Closest 16S RNA Sequence Strain Identification by BLASTn | | |
|---|---|---|---|---|---|
| Strain # | Donor # | Screening Medium | Strain | % identity | E Value |
| 528 | 4 | ABB + Rumen Fluid | *Faecalibacterium prausnitzii* | 1.00 | 0 |
| 529 | 4 | ABB + Rumen Fluid | *Bacteroides vulgatus* | 1.00 | 0 |
| 530 | 4 | ABB + Rumen Fluid | *Bacteroides uniformis* | 1.00 | 0 |
| 531 | 4 | ABB + Rumen Fluid | *Collinsella aerofaciens* | 1.00 | 0 |
| 532 | 4 | ABB + Rumen Fluid | *Bacteroides vulgatus* | 1.00 | 0 |
| 533 | 4 | ABB + Rumen Fluid | *Bacteroides vulgatus* | 1.00 | 0 |
| 534 | 4 | ABB + Rumen Fluid | *Eggerthella timonensis* | 0.98 | 0 |
| 535 | 4 | ABB + Rumen Fluid | *Bacteroides uniformis* | 1.00 | 0 |
| 536 | 4 | ABB + Rumen Fluid | *Bacteroides stercoris* ATCC 43183 | 1.00 | 0 |
| 537 | 4 | ABB + Rumen Fluid | *Bacteroides vulgatus* | 1.00 | 0 |
| 538 | 4 | ABB + Rumen Fluid | *Bacteroides vulgatus* | 1.00 | 0 |
| 539 | 4 | ABB + Rumen Fluid | *Bacteroides vulgatus* | 1.00 | 0 |
| 540 | 4 | ABB + Rumen Fluid | *Blautia wexlerae* DSM 19850 | 0.99 | 0 |
| 541 | 4 | ABB + Rumen Fluid | *Blautia luti* | 1.00 | 0 |
| 542 | 4 | ABB + Rumen Fluid | *Bacteroides vulgatus* | 1.00 | 0 |
| 543 | 4 | ABB + Rumen Fluid | *Bacteroides vulgatus* | 1.00 | 0 |
| 544 | 4 | ABB + Rumen Fluid | *Bacteroides vulgatus* | 1.00 | 0 |
| 545 | 4 | ABB + Rumen Fluid | *Bacteroides vulgatus* | 1.00 | 0 |
| 546 | 4 | ABB + Rumen Fluid | *Bacteroides vulgatus* | 1.00 | 0 |
| 547 | 4 | ABB + Rumen Fluid | *Bacteroides uniformis* | 1.00 | 0 |
| 548 | 4 | ABB + Rumen Fluid | *Bifidobacterium longum* subsp. *suillum* | 1.00 | 0 |
| 549 | 4 | ABB + Rumen Fluid | *Bacteroides vulgatus* | 1.00 | 0 |
| 550 | 4 | ABB + Rumen Fluid | *Bacteroides stercoris* ATCC 43183 | 1.00 | 0 |
| 551 | 4 | ABB + Rumen Fluid | *Bacteroides vulgatus* | 1.00 | 0 |
| 552 | 4 | ABB + Rumen Fluid | *Bacteroides uniformis* | 1.00 | 0 |
| 553 | 4 | ABB + Rumen Fluid | *Faecalicatena contorta* | 0.98 | 0 |
| 554 | 4 | ABB + Rumen Fluid | *Faecalicatena contorta* | 0.98 | 0 |

Preparation of Anaerobic Growth Media

1) Weigh required amount of powdered anaerobic growth medium as specified by the manufacturer to formulate 1 L of growth medium. Lesser or greater amounts of anaerobic growth media can be made by scaling these specifications.
2) In a fume hood, place 800 mls of purified water in a 2 L beaker, include a stir bar and then set on a heated stir plate. With constant stirring, heat the volume of water just to boiling.
3) Add pre-weighed powdered anaerobic growth medium as well as any additional supplements and allow to stir in the heating volume of water until dissolved.
4) While heating, add the oxygen indicator dye resazurin (ACROS Organics) to final concentration of 0.0025 mg/ml.
5) Add purified water to bring the final volume to 1 L
6) Continue to heat the solution to a gentle boil until all medium ingredients are fully solubilized, and the color imbued by the resazurin turns from red to colorless. Carefully remove the beaker from the stir plate and allow to cool for 10 minutes prior to further manipulations.
7) To make anaerobic growth medium solid medium in plates, proceed as follows:
    a. Transfer 500 ml of growth medium prepared as per step 6 into a 1 L bottle with a sealable cap. Include a stir bar, then add 7.5 grams agar (Fisher Scientific) and swirl to mix.
    b. Place the bottle with cap loosely affixed on the stir plate and heat until any red color that has returned is reduced to colorless.
    c. Immediately transfer the bottle to an autoclave and sterilize for 20 minutes on a setting appropriate for liquid media.
    d. Immediately after autoclaving, bring the bottles into the anaerobic chamber and allow to cool to 55° C.
    e. Pour 25 ml by hand into Petri dishes until all volume is used up. Store plates upright in anaerobic chamber and allow to cool until solidified and until any residual red color in the plate medium turns colorless.
    f. Invert the cooled plates and store in anaerobic chamber for 24 to 48 hours to dry sufficiently for further use. Plates are stored for up to a month within the anaerobic chamber in a sealed box to prevent desiccation.
8) To make tubes of individual 10 ml liquid anaerobic growth media, proceed as follows:
    a. After brief 10 minutes cooling, bring the thoroughly solubilized and colorless growth medium solution prepared as per step 6 into the anaerobic chamber. Allow to cool for an additional 30 minutes prior to further handling.
    b. Using a pipette, transfer 10 ml aliquots of anaerobic growth medium solution to 16×125 mm Hungate Anaerobic Tubes (Chemglass Life Sciences).
    c. Allow the transferred volumes in the Hungate tubes to further cool for 2 hours.
    d. Insert butyl rubber stoppers and screw caps to each filled Hungate tube to seal.
    e. Bring out filled and sealed Hungate tubes from the anaerobic chamber and autoclave the tubes for 20 minutes at a setting appropriate for liquid media.
    f. Once cooled, autoclaved Hungate media tubes can be stored in ambient air for extended periods prior to use.
9) To make 900 ml anaerobic growth medium volumes in anaerobic bottles, proceed as follows:
    a. Such volumes of anaerobic growth medium are suitable for medium to large scale cultures, such as those required for producing Microbe Mixes.
    b. In a fume hood, set a 2 L beaker on a stir plate and add 1500 ml purified water. Bring to a near boil while stirring.
    c. Add all powdered anaerobic growth medium and supplemental ingredients to the heated stirring water. Also add resazurin to a final concentration of 0.0025 mg/ml. Once powdered ingredients are fully solubilized, additional purified water to bring volume up to 1800 ml.
    d. Continue to stir and bring to a gentle boil until there is no residual cloudiness and the red color of the resazurin turns colorless.
    e. Carefully remove the beaker and set aside in the hood to cool for 10 minutes.
    f. Pour entire contents into a plastic 2 L beaker to make it safer to handle.

Use a 1 L cylinder to divide into two 900 ml volumes into two 2 L plastic beakers.
    g. Insert a funnel into the neck of a 1 L anaerobic bottle (Chemglass Life Sciences). Carefully add hot 900 ml volume to the side of the funnel so that a spiral flow is established. Do not pour directly into the hole of the funnel as the hot liquid could bump. It is advisable to use a face shield while doing this operation.
    h. When all liquid is transferred, insert a blue rubber bung into the top of the bottle and crimp with an aluminum collar to seal the bottle. Then quickly insert a 20-gauge needle through bung to relieve pressure.
    i. At this point the red color of the resazurin will probably return due to oxygenation during transfer and manipulation. To remove oxygen, place the filled, stoppered and needled bottles back onto a heated stir plate and bring to a gentle boil until the resazurin oxygen indicator returns to colorless.
    j. Remove the bottle from the heat and as quickly and carefully as possible bring into the anaerobic chamber. Place the bottles onto two thicknesses of cardboard on the floor of the airlock to protect the floor from heat damage, then close the door and cycle/purge the airlock. The needles in the bungs allow for venting of the bottle contents during this step without boil-over. Once cycle/purge is completed, open the interior door of the anaerobic chamber and carefully lift and place the hot bottles onto 96-well eppy racks set up as trivets to prevent heat damage to the floor of the chamber.
    k. Allow the bottles to cool in the anaerobic chamber for about a half-hour, then remove the needle and decrimp/debung the bottles so that they are open to the interior atmosphere of the anaerobic chamber. Keep multiple bottles well-separated from each other so that they can cool as quickly as possible. Allow the bottles to cool to ambient temperature (4-5 hours).
    l. Once cooled, reinsert new bungs into the necks of the bottles and crimp to seal. Remove the bottles from the anaerobic chamber and then autoclave for 20 minutes with conditions appropriate for liquid media. Once done, bring the bottles back into the chamber and allow to cool overnight.
    m. Bottles can then be removed and stored in a cool dark place for up to a week in ambient laboratory conditions. Discard any bottles that have turned red, signifying oxygenation due to leaks.

Preparation of Pure Concentrated Cryopreserved Bacterial Cultures for Later Assembly of Microbe Mixes 1) Microbe mixes can include a number of different anaerobic microbes, each cultured separately to a specified cell density and then mixed and combined as a cocktail. Individual cultures are grown, prepared and verified as follows:
2) A week prior to full scale inoculations, set up starter cultures by inoculating each microbe from frozen stocks into 10 ml Hungate tubes containing the appropriate anaerobic growth medium. Growth in one 10 ml Hungate tube can be enough to inoculate two 900 ml anaerobic growth bottles, so set up as many starter cultures as necessary for volume of cultures required.
3) Once the starter cultures are grown to visible turbidity, take 1.0 ml samples from each starter culture for preparation of purified genomic DNA. Perform next generation sequencing of 16S rRNA regions or Whole Genome Sequencing followed by appropriate sequence data analyses to verify identity and purity of the contents of the starter cultures. Discard all starter cultures that fail to contain pure growth of the originally inoculated organism.
4) On the day of inoculation, add 3 ml of starter culture per 900 ml anaerobic bottle, either in the anaerobic chamber or on the bench top by anaerobic needle/syringe transfer.
5) Once all requisite 900 ml anaerobic bottle cultures are inoculated, place them securely in an incubated shaker in ambient lab conditions and shake at 115 rpm at 37° C. until desired turbidity and cell density is reached. This may take as little as 18 hours or as long as five days depending on the growth rate of the particular microbe in question.

a. At least one day prior to harvest make up liter quantities of Vehicle Buffer (1×PBS+5 mM L-Cysteine+15% glycerol) for later use to wash and cryogenically store harvested cell mass.
b. Assemble all ingredients in an appropriately sized beaker and mix thoroughly by stirring on a stir plate.
c. Filter sterilize the Vehicle Buffer and then aseptically transfer the volumes to pre-sterilized 1 L bottles with plastic screw caps that include inserted butyl rubber bungs in their center. Tighten the cap thoroughly to seal.
d. Carefully insert a sterilized 6-inch metal pipetting needle with a luer-lock head (Cadence Science) through the center of the butyl rubber bung into the Vehicle Buffer Volume. Also insert a 1.5 inch 20-gauge needle through the butyl rubber bung to serve as a vent.
e. Attach a sterile 0.2-micron SCFA membrane filter to the luer-lock of the pipetting needle, then attach to this a tube delivering an anoxic nitrogen stream.
f. Bubble nitrogen into the Vehicle Buffer volume inside the bottle for 30 minutes to drive out dissolved oxygen.
g. Quickly remove both needles and store the Vehicle Buffer bottle at 4° C. until use.

6) On the day of harvest, remove bottles from shaker and bring to lab. If not visibly dense enough, keep them in the shaker for a few extra hours while other more-ready bottles are being processed.
7) Perform OD determination for each bottle by removing one ml using gassing station delivering an anoxic nitrogen stream and anaerobic syringe/needle technique and place in Eppendorf centrifuge tube.

a. Spin 2 minutes to pellet cells, remove medium, and resuspend in equal volume PBS. For more dense cells, it is good to dilute the washed cells 1/5 to be in range of the spectrophotometer.
b. Blank the spectrophotometer using PBS. Read OD of each bottle and adjust reading to account for dilutions. Try to read in the range of 0.1 to 0.6 OD. If too high, dilute further.
c. Correlate optical density with previously determined viable colony-forming units per ml to achieve desired cell density.

8) Also remove 1 ml for 16S/WGS sequence determination from each bottle. Spin down the cells to pellet in an Eppendorf tube, remove volume and quick freeze the cell pellet for later individual genomic DNA preparation and sequence analysis.
9) Once requisite samples have been taken, bring bottles into the anaerobic chamber. Decrimp and remove butyl rubber stopper. Pour contents of one 900 ml culture bottle into two 450 ml centrifuge tubes. Cap and tightly seal the centrifuge bottles, then bring them out of anaerobic chamber.
10) Place in an F12-6×500 LEX™ rotor prechilled at 4° C. in the Sorvall Lynx 6000™ floor centrifuge or similar rotor and instrument. Spin at 6000 g for 15 minutes to pellet cells.
11) Bring back centrifuged bottles into chamber and carefully pour supernatant in the 4 L waste beaker to not disturb the pellet. Add 100 ml ice-cold Vehicle Buffer to each pellet and cap tightly, then remove from chamber and place on ice.
12) Swirl gently by hand outside chamber to resuspend the pellets. Gentle vortexing can be used to assist the resuspension. Do not shake violently.
13) Once resuspended, centrifuge bottles again as per step 10 to pellet cells, then bring into chamber.
14) Decant supernatant into 4 L waste beaker and then add 50 ml ice cold Vehicle Buffer to each pellet. Bring out of chamber and resuspend pellet as per step 12.
15) Bring bottles back into chamber. Combine multiple resuspended pellets for each microbe into one centrifuge bottle and add additional cold Vehicle buffer to at least 200 ml.
16) Remove from anaerobic chamber and centrifuge as per step 10 to pellet cells. Return to anaerobic chamber.
17) Decant supernatant and add final required volume of cold Vehicle Buffer to achieve desired final cell concentration. Remove from chamber and gently resuspend as per step 12. Always keep cells on ice.
18) Bring back into chamber and take out five 0.3 ml aliquots per resuspended microbe and place in a cryotube. Store the cryotubes in the vapor space of a liquid nitrogen Dewar for later analyses.
19) Set up a flow of argon gas through a tube introduced into the anaerobic chamber from an external argon tank. Attach a sterile 0.2-micron SCFA membrane filter and an 18 gauge needle at the end of the tube. Carefully unscrew the cap of the centrifuge bottle with the pure concentrated bacterial culture and introduce the argon needle into the gap between the centrifuge bottle and the cap. Introduce argon at 5-10 psi flow for one minute to add a sterilized argon gas blanket to the bottle over the resuspended cells. The argon is heavier than air and will serve as a barrier against oxygenation during storage.

20) Remove argon needle and seal tightly. Wrap cap securely with parafilm and remove from anaerobic chamber.
21) Store the bottles upright in a −80° C. freezer to allow gentle freezing and storage until required.
22) Verify purity of each pure concentrated cryopreserved bacterial cultures by NGS sequencing before further use.

Assembling Microbe Mixes by Combining Individual Pure Concentrated Cryopreserved Bacterial Cultures 1) To assemble a microbe mix, remove the requisite individual pure concentrated cryopreserved bacterial cultures from −80° C. storage and bring into anaerobic chamber. Allow to thaw gently on ice.
2) When all constituent bacterial cultures have been thawed, remove 0.5 ml from each to perform dilution plating on appropriate anaerobic growth solid medium to gauge the viability of the culture by counting number of colony-forming units per ml.
3) Within the anaerobic chamber, place a sterile 1 L bottle with a stir bar and a plastic screw top lid in a 2 L beaker. Pack ice around the bottle to continuously chill internal contents. Place on a stir plate.
4) Carefully move required volumes of each thawed pure concentrated cryopreserved bacterial culture to the chilled bottle to fully assemble the desired microbe mix at the desired cell density for each component microbe. Stir continuously during this process and keep the volume on ice.
5) Once all required microbe components have been added to the microbe mix, continue to stir on ice for an additional 10 minutes to insure homogeneity of the microbe mix.
6) Use a pipette to transfer volumes into appropriately sized conical tubes and place each aliquoted volume on ice.
7) Introduce a sterile argon gas stream into each aliquoted tube at 5-10 psi for 10 seconds to introduce an argon gas barrier above the aliquoted liquid to serve as a barrier against oxygenation.
8) Place microbe mix aliquots upright in a −80° C. freezer and allow to freeze slowly. Store in this condition until required.

Isolation and Characterization of Pure Microbial Strains from Endospores Purified from Fecal Matter Individual spore-forming bacterial strains can be preferentially isolated and cultured from endospores purified from fecal matter using a protocol adapted from Kearney et al 2018 ISME J. 12:2403-2416. Purified endospores are spread on solid anaerobic medium plates and allowed to germinate and form colonies that can be further characterized. Vegetative cells in the fecal matter are rendered non-viable during the endospore purification process, and thus any resulting colonies are restricted to spore-forming bacteria. Endospores are purified from fecal matter as follows:

Fecal samples are collected and processed in a biosafety cabinet within 30 minutes of defecation. Samples (5 g) are suspended in 20 mL of 1% sodium hexametaphosphate solution (a flocculant) in order to bring biomass into suspension. The suspension is bump vortexed with glass beads to homogenize, and centrifuged at 50×g for 5 min at room temperature to sediment particulate matter and beads. Quadruplicate 1 mL aliquots of of the supernatant liquid are transferred into cryovials and stored at −80° C. until processing.

The frozen supernatant liquid samples are thawed at 4° C., centrifuged at 4° C. and 10,000×g for 5 minutes, washed and then resuspended in 1 mL Tris-EDTA pH 7.6. The samples are heated at 65° C. for 30 minutes with shaking at 100 rpm and then cooled on ice for 5 minutes. Lysozyme (10 mg/mL) is added to a final concentration of 2 mg/mL and the samples are incubated at 37° C. for 30 minutes with shaking at 100 rpm. At 30 minutes, 50 uL Proteinase K (>600 mAU/ml) (Qiagen) is added and the samples incubated for an additional 30 minutes at 37° C. 200 µL 6% SDS, 0.3 N NaOH solution is added to each sample and incubated for 1 hour at room temperature with shaking at 100 rpm. Samples are then centrifuged at 10,000 rpm for 30 minutes. At this step, a pellet containing resistant endospores is visible, and the pellet is washed three times at 10,000×g with 1 mL chilled sterile ddH2O. The pellet containing endospores is stored at −20° C. until required.

To germinate and resuscitate spore-forming bacterial colonies from the purified endospores, the endospore pellet is brought into the anaerobic chamber, thawed and then suspended in 1.0 ml reduced ABB. Successive 10-fold serial dilutions of the suspended spores are then performed in ABB to establish 1/10, 1/100, 1/1000, 1/10000, 1/100000, 1/1000000 dilutions of the endospore preparation. From each 10-fold serial dilution, four 0.1 ml volumes are removed and then added to and spread over Reinforced Clostridial Medium Agar (Oxoid), with 0.1% intestinal bile salts (taurocholate, cholate, glycocholate) to stimulate endospore germination. The plating's are incubated at 37° C. for 2, 3, 4, 5, 6, 7, 8, 9, 10, 11, 12 days to allow for the endospores to germinate and grow as single colonies. These colonies are then manually picked, individually cultivated, and the subjected to identification by NGS 16S RNA sequencing and/or whole genome sequencing analyses as described in Example 16.

Example 17—Discovery of Novel Clonal Strains from Gut Microbiota Able to Convert Ellagitannin and EA to Urolithin Metabolites Determining Human Individuals with Gut Microbiota Able to Convert EA to Urolithin A Individuals who have gut microbiomes that are capable of converting dietary-derived ellagitannin and ellagic acid (EA) to urolithin A are identified as follows (Garcia-Villalba (2013) J Agric Food Chem 61:8797-8806). Candidate individuals consume walnuts (rich in ellagitannins and EA) for five consecutive days, at a daily dose of 0.6 g/Kg body mass. After this dietary course, one gram of freshly-obtained fecal samples from each individual is placed in a 50 ml conical tube with 10 ml of 40% methanol, 40% DMSO, and 20% water, to which 6 N hydrochloric acid is added to 0.1% (v/v). Each suspension is vortexed for 5 minutes and centrifuged for 15 minutes at 4200 rpm in a swinging bucket centrifuge. The supernatant is transferred to a 15 ml conical tube and again centrifuged for 15 minutes at 4200 rpm in a swinging bucket centrifuge. The resulting supernatant is passed via a 10 ml syringe through a 0.45 micron PVDF filter disc (ThermoFisher) and collected in a fresh 15 ml conical tube. Each sample is subjected to analytical detection of urolithin A and other urolithin metabolites as described above, and individuals that test positive for urolithin A and urolithin metabolite(s) production from ingested ellagitannin are identified as fecal material donors for experiments described below.

Measurement of the Conversion of EA to Urolithin a in Human Individuals

Fresh stool samples of approximately 1 gram each were obtained from healthy volunteers. Urolithins were extracted by adding 500 μL of 50% methanol in water, and vortexing for 1 minute. Samples were allowed to sit overnight at room temperature, then centrifuged at 14,000 rpm for 5 minutes. Supernatants were removed by a pipette, then filtered through a 0.22 micron filter.

Urolithin concentration in supernatants of liquid bacterial cultures is measured using HPLC equipped with a triple quadrupole mass spectrometer in negative ionization mode (ThermoFinnegan). A C18 POROSHELL® 120 (3×150 mm, 2.7 um particle size) is used for the separation, with mobile phases of 0.1% formic acid (A) and 0.1% formic acid in acetonitrile (B) at a flow of 0.3 mL/min ramping from 0 to 90% B over 30 minutes. Optimal mass spectrometer conditions for urolithin detection are: gas temperature 300° C., drying gas 11 L/min, nebulizer pressure 45 psi, sheath gas temperature 400° C., and sheath gas flow 12 L/min. All compounds are monitored in the multiple reaction monitoring mode (MRM) using mass transitions as indicated in Garcia-Villalba et al. (J. Chromatography (2016) 1428:162-175). In particular, urolithin A can be distinguished by a 227 to 198 mass transition, and urolithin C can be distinguished by a 243 to 187 mass transition. These are both unique among all the metabolites of interest. Also run were pure standards of urolithin A and urolithin C in methanol, at 50 uM concentration, and a pure methanol blank. Results are shown in Table 4. Units are peak area counts for each mass transition.

Isolation from fecal matter of novel clonal bacterial strains able to produce urolithin C and/or urolithin A from EA.

TABLE 4

| | Sample | |
|---|---|---|
| | Urolithin C | Urolithin A |
| Urolithin A, 50 uM | 11739 | 7075687 |
| Urolithin C, 50 uM | 9011134 | 32396 |
| Blank | 1273 | 972 |
| Sample 1 | 7497 | 58334 |
| Sample 2 | 2113 | 251593 |
| Sample 3 | 11151 | 1376365 |

Table 4 shows the urolithin concentration in supernatants of liquid bacterial cultures from healthy volunteers as measured by HPLC. Units are peak area counts for each mass transition.

An identified fecal matter donor consumes 0.6 g/Kg body weight walnuts for five days (ellagitannin source), then donates fresh fecal matter that is placed in an anaerobic chamber within 30 minutes of collection. One gram of fecal matter is placed in a 15 ml conical tube with 10 ml reduced and anoxic nutrient broth, shaken by hand for 1 minute and then allowed to stand for 15 minutes to allow large particulate matter to settle. From the top of the fecal resuspension, a 1 ml syringe and 18-gauge needle are used to remove 1.0 ml of the suspension, which is then injected through the butyl rubber bung of an anaerobic tube containing 10 ml of reduced and anoxic nutrient broth to achieve a 14-fold dilution of the suspended fecal material. Further serial dilutions are made in the same fashion to achieve 10e-2, 10e-3, 10e-4, 10e-5, 10e-6, 10e-7, 10e-8, 10e-9, 10e-10-fold dilutions. From each dilution tube, 1.0 ml is removed by syringe and needle and then 0.1 ml is applied to ABB agar plates, which are incubated at 37° C. in an anaerobic environment for 3 days until single isolated colonies are visible. This is to empirically produce plates with 100 to 300 isolated colonies per plate that are optimal for selection of single colonies.

In an anaerobic chamber, each well of four 2 ml deep-well plates are filled with 1.0 ml ABB broth. Isolated single colonies are selected and inoculated into each well, and the plate is sealed with a permeable adhesive seal (Fisher Scientific). The plates are placed in a sealed anaerobic box with a catalyst to maintain an anaerobic environment, removed from the chamber and placed in a 37° C. platform shaker at 100 rpm for three days. Once turbid, the plates are returned to the anaerobic chamber and 0.5 ml culture is removed from each well and placed in a fresh 2 ml deep-well plate. An equal volume of sterile and anoxic 50% glycerol as a cryoprotectant is then mixed with each sample before sealing the plate with an impermeable aluminum adhesive seal (Fisher Scientific). The sealed plates are removed from the anaerobic chamber and immediately stored at −80° C. as representative cryostocks for each selected single colony.

In the anaerobic chamber, four fresh 96-well 2 ml deep well plates are filled with 1 ml/well of ABB broth with 0.05 mM ellagic acid, using DMSO as a carrier (final concentration of DMSO is 0.1%). Then 0.01 ml of culture from the culture plates are used to inoculate the plate containing ABB broth plus ellagic acid (100× dilution). Wells are reserved on each plate for inclusion of clonal organisms *G. urolithinfaciens* (Selma et al. (2014) Int J Syst Evol Microbiol 64:2346-2352) (Selma et al. (2014) Food Func 5: 1779-1784), *G. pamelaeae*, (Selma et al. (2014) Food Funct 5: 1779-1784) and CEBAS 4A4 (Selma et al. (2017) Front Mirobiol 8:1521) as positive controls for EA to urolithin conversion. The plates are placed in a sealed anaerobic box with a catalyst to maintain an anaerobic environment, removed from the chamber, and placed in a 37° C. platform shaker at 100 rpm for three to five days.

The ABB plus ellagic acid culture plates in the anaerobic box are removed from the shaker, and then the culture plates are removed from the anaerobic box into the ambient environment. The culture plates are centrifuged at 3000 g in a Sorvall ST-40 swinging bucket centrifuge for 15 minutes to pellet the cells. 0.5 ml culture supernatant from each well is transferred to a fresh deep-well block for ethyl acetate extraction. The remaining culture is removed and discarded, followed by freezing of the cell pellet at −80° C. in preparation for later genotypic characterization by Next Generation Sequencing (NGS).

1 ml ethyl acetate plus 1.5% formic acid is added to each well containing 0.5 ml reserved culture supernatant. The plate is sealed with a rubber mat and then vortexed for one minute. Then the plate is centrifuged at 3000 g in a Sorvall ST-40 swinging bucket centrifuge for 10 minutes to separate the organic ethyl acetate upper phase from the aqueous lower phase. 0.5 ml of the ethyl acetate plus 1.5% formic acid organic phase is removed and transferred to a fresh 2 ml deep well plate, which is sealed with an aluminum adhesive seal. An 18 gauge needle is used to make a hole above each well and then all four plates are placed in a GENEVAC® Centrifugal Evaporator at vacuum until the ethyl acetate organic phase is eliminated. 100 ml methanol with 0.1% formic acid is then added to each well, followed by sealing of the plates with an impermeable plastic seal (Fisher Scientific). The plates are incubated at room temperature for 2 hours, then mixed by pipetting to fully resuspend the samples. The volumes in each plate are then filtered through a 96-well AcroPrep™ Advance Plate with 0.2 micron GHP membrane into a fresh 96-well plate. Then 0.05 ml filtrates from each plate are transferred to a 96 DeepWell™ plate with pre-slit well Cap Matt™ (Nunc®) in preparation for liquid chromatography-mass spectrometry (LCMS) analytical detection of urolithin metabolites.

Those isolates shown by LCMS analyses to be producing urolithin metabolites, especially urolithin A and urolithin C, are examined further. Cells from corresponding wells in the −80° C. preserved cryostocks are struck on to ABB agar medium for single colonies in an anaerobic chamber. Eight isolated colonies from each streak are each inoculated into 1 ml ABB broth in 96-well deep well blocks as described above to be restocked as anoxic cryostocks and to be retested for production of urolithin A and/or C from ellagic acid as described above. Those colonies that test positive for urolithin A and/or C from ellagic acid will be reinoculated into 7 ml ABB broth in Hungate tubes and cultured for two days in the anaerobic chamber. These cultures are then brought out of the anaerobic chamber transferred to 15 ml conical tubes, brought out of the anaerobic chamber, transferred to 15 ml conical tubes, and centrifuged at 3000 g in a Sorvall ST-40™ swinging bucket centrifuge for 15 minutes to pellet the cells. The supernatant is discarded and the pelleted cells are processed for whole genome sequencing (WGS). Resulting sequence is compared to genome sequence databases to gauge similarity or uniqueness of the isolated microbes.

Alternatively, *Gordonibacter* species bacterial colonies can be identified by colony morphology as a screen for microbes capable of conversion of EA to urolithin compounds. *G. urolithinfaciens* grows as small translucent colonies after three to five days growth on ABB agar plates in an anaerobic environment at 37° C. *G. urolithinfaciens* is also refractory to negative growth effects of the Gram-negative specific antibiotic colistin up to 0.01 mg/ml, which is used as a further selection against plate growth of Gram-negative gut microbial species. In this embodiment, fecal matter is diluted in nutrient broth as per above and plated on ABB agar plates containing 0.01 mg/ml colistin (Fisher Scientific™), and incubated in an anoxic environment at 37° C. for five days. Small translucent colonies that match the morphology of *G. urolithinfaciens* colonies are picked into 1 ml ABB broth volumes in a 96 well deepwell block along with *G. urolithinfaciens* in select wells as a control, covered with a gas permeable seal, and incubated in an anoxic environment at 37° C. After five days incubation, 0.2 ml from each well is transferred to a 96-well PCR plate which is subjected to centrifugation at 4000 g for 15 minutes to pellet the cell growth. After the supernatant is removed and discarded, the cell pellets are subjected to 16S sequencing. Those cultures identified as *Gordonibacter* or closely-related species are then tested for conversion of ellagic acid to urolithin compounds by LCMS as described above.

Example 18—Efficacy of Microbial Cocktails as an Anticancer Monotherapy Animals and Tumor Model BALB/c mice are obtained from Shanghai Lingchang Biotechnology Co., Ltd (Shanghai, China). 6-8-week-old female mice are used. For tumor growth experiments, mice are injected subcutaneously with $2.5\times10^5$ CT-26 colon cancer tumor cells (Griswold and Corbett (1975) Cancer 36:2441-2444). Tumor size is measured twice a week until endpoint, and tumor volume determined as length×width×0.5.

Tumor Cell Preparation

Cryo vials containing CT-26 tumor cells are thawed and cultured according to manufacturer's protocol (ATCC CRL-2638). On the day of injection cells are washed in serum free media, counted, and resuspended in cold serum free media at a concentration of 250,000 viable cells/100 μl.

Flow Cytometry

A whole-blood flow cytometry-based assay is utilized to assess T cell activation in response to microbial treatment. Whole blood via cardiac puncture is collected into an EDTA tube at the end of the experiment. 100 μL of whole mouse blood is transferred to a 15 mL conical tube. 1 mL of RBC Lysis Buffer is added to the tube and allowed to incubate at room temperature for 10 minutes. Lysis is quenched by adding 10 mL of cold DPBS. Samples are centrifuged at 1500 rpm for 5 minutes at 4° C. The pellet is aspirated and resuspend in another 10 mL of cold DPBS. Samples are recentrifuged at 1500 rpm for 5 minutes at 4° C. Samples are resuspended in 500 μL of FACS buffer and transferred to a 96-well plate. Samples are stained with Fixable Viability ef780™ (eBioscience), CD45-PEcy7 (BioLegend), CD3-BV605™ (BioLegend), CD8-AF700™ (BioLegend), and CD4-AF488™ (BioLegend). Stained samples are run on a BD LSRFortessa™ flow cytometer and analyses are performed with FlowJo™ (Tree Star).

Tumor Challenge and Treatment

Tumor size is routinely monitored by means of a caliper. Stool is collected on day 0 and 48 hours after each subsequent administration of treatment until the end of the study.

To test whether manipulation of the microbial community is effective as a monotherapy, Microbe Mix 4 was evaluated in the presence or absence of ellagic acid and/or ellagitannin is administered. In some groups, ellagic acid is administered separately via oral gavage (0.2 mL of a 5.5 mg/mL suspension) prior to administration of the microbe cocktails. Each mouse treated by monotherapy is given 200 l of the suspension by oral gavage three times a week for the duration of the study starting from day 1. Tumor growth and tumor-specific T cell responses are compared among the different treatment groups.

GI Tract Removal and Analysis

After mice are euthanized at the termination of the study, the intact digestive tract of each mouse from stomach to rectum are removed and kept in a 5 ml Eppendorf tube on ice prior to dissection. Forceps are sterilized by soaking in 100% ethanol and then used to remove the intestine length and stretch it on a work surface covered with cellophane. With the use of ethanol-sterilized dissection scissors, 3 cm lengths of the jejunum nearest to the stomach and the ilium nearest to the cecum/large intestine are excised and then each placed with forceps in a 1.5 ml Eppendorf tube and placed on ice. A 2 cm segment of the cecum/ascending colon is then excised, as are 2 cm segments of the transcending colon and the descending colon, and all are placed in 1.5 ml Eppendorf tubes on ice. Dissection instruments are sterilized by dipping in 100% ethanol between each intestine fragment removal. To each tube containing dissected intestinal segments is added 0.5 ml ice cold PBS buffer. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice and then stored at −80° C. for later analysis.

Tumor size is measured in all animals receiving the different microbial treatments. On average, the animals receiving Microbe Mix 4 (equal amounts of *F. prausnitzii, C. coccoides, R. gnavus, C. scindens, E. lenta*, and *G. urolith-*

Figure 9:
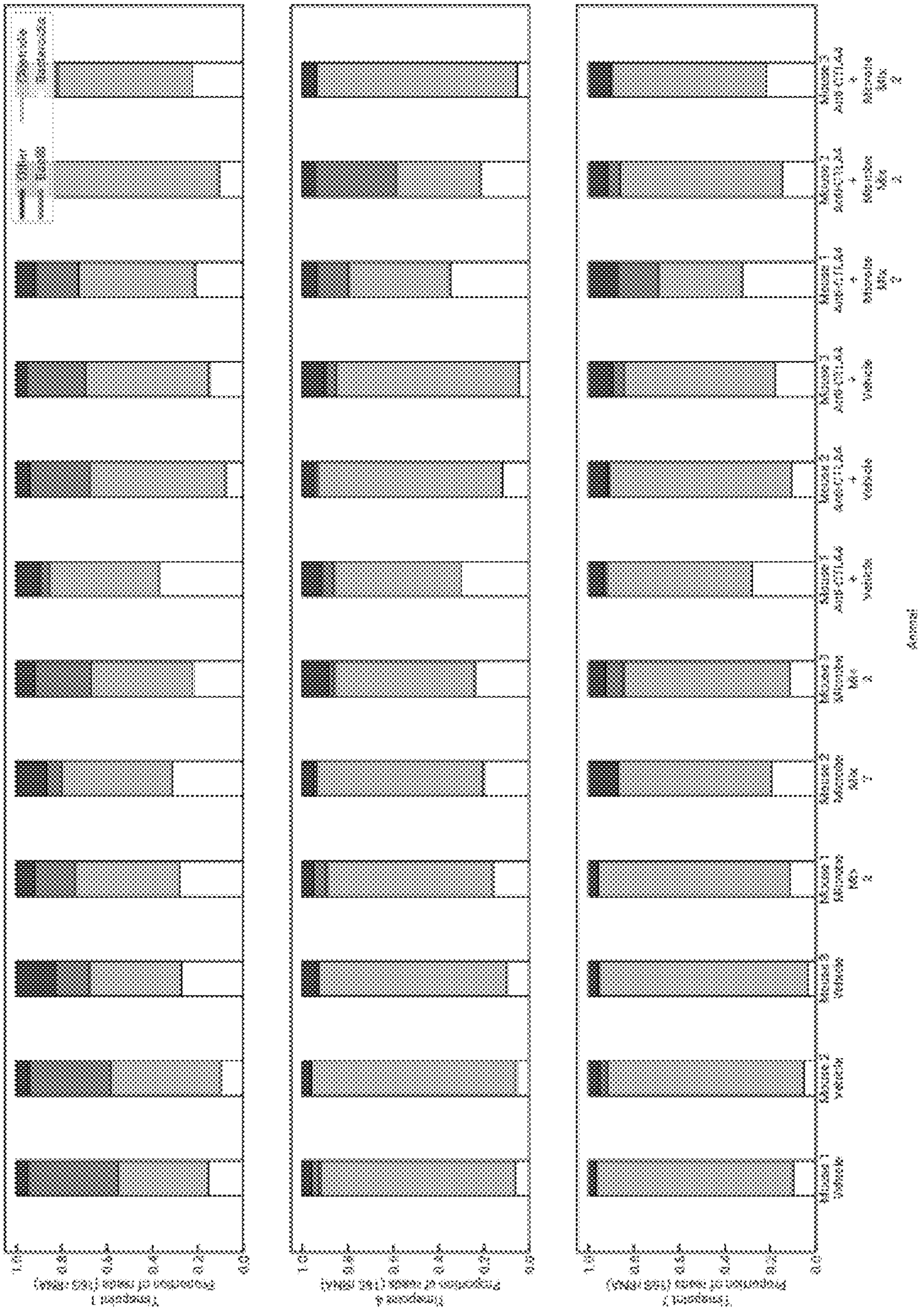
FIG. 9, lists the 16S rRNA analysis of fecal samples from mice treated with vehicle, microbe mix 2 and the anti-CTLA4 checkpoint inhibitor. Taxonomic indicators are listed as class, discussed in detail in Example 6, below.

*infaciens*) alone or in conjunction with ellagic acid have a reduction in tumor size compared to those receiving vehicle as illustrated in FIG. 9.

Specific genes differentially present or expressed among the cultures are identified using commercial expression analysis software such as SPOTFIRE® (TIBCO Software) or free tools such as BioConductor™. This approach is used to identify genes overrepresented in samples from mice receiving microbial cocktail 4 [equal amounts of *F. prausnitzii, C. coccoides, R. gnavus, C. scindens, E. lenta*, and *G. urolithinfaciens*] in conjunction with or without ellagic acid. Similarly, LCMS peaks from the metabolomics analysis are identified that have significantly higher or lower concentration in the samples from mice receiving microbial cocktail 4 alone or in conjunction with ellagic acid. These represent candidate metabolites either produced or degraded by these microbes that are important for stimulating immune function and thus contribute to anticancer function.

Figure 10:
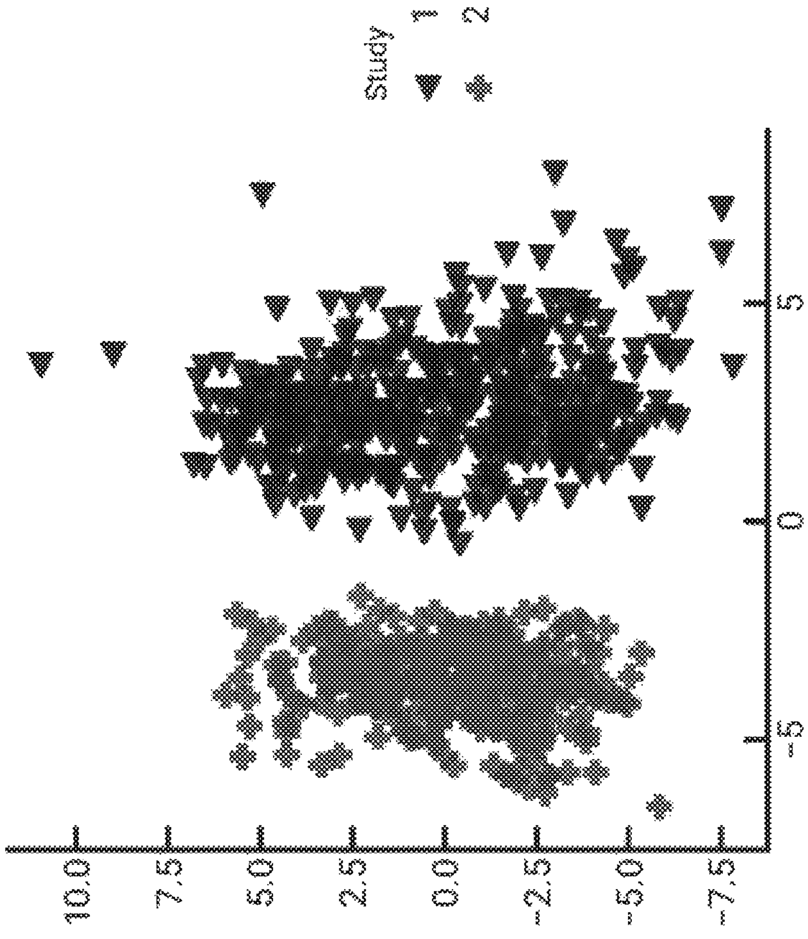
FIG. 10, graphically shows the Principal Components Analysis (PCA) of the 16S RNA analysis of fecal samples collected from mice treated in FIG. 6 and FIG. 8, discussed in detail in Example 6, below.

Flow cytometry is used to perform immunophenotyping of mice subjected to cancer receiving the different microbial treatments. Measurements are conducted on both peripheral blood and on the tumor itself, with stains for various cell surface markers. The results show that CD3+ cells, which includes both helper and killer T cells, are upregulated in mice that respond better to therapy. Furthermore, the results also show that mice receiving the therapy had both higher CD3+ proportions as well as much lower final tumor volumes. CD8+T-lymphocytes are also upregulated in the presence of the microbial treatments. Combined together, the results provided evidence that the microbe mix therapeutic impacts tumor volume via a mechanism of stimulating the CD3+ cells of the immune system. Flow cytometry results are graphically presented in FIG. 10.

Example 19: Computational Methods and Machine Learning Approaches for Analyzing Patient or Mouse Derived Data Machine learning techniques including but not limited to deep neural networks and random forests are deployed to better characterize microbiomes and identify putative therapeutic consortia. These learning techniques work off a data set that includes multiple types of -omics (proteomics, metabolomics, shotgun metagenomics, transcriptomics, 16S rRNA sequencing, etc.) in addition to patient metadata, data on cancer treatment outcome, and data from literature.

Characterization of Public Data

Deep learning is used to build an autoencoder for dimensionality reduction of microbiome data, including public databases such as the Human Microbiome Project or TwinsUK. The autoencoder allows for characterization of the space of human microbiomes with a few critical parameters. These parameters are varied and leveraged to create a set of microbiome archetypes. The microbiome therapeutic is tested in animal models carrying these different archetypes in order to verify or characterize its efficacy across the population.

Literature Mining

Automatic literature searches are performed using available databases (e.g. Google Scholar) to query scientific literature for small molecules, bacterial strains or species, cancer types, immune cell types, or other biological quantities of interest. Techniques including natural language processing, sentiment analysis, or just direct data scraping are used to distill literature information into a format that can be introduced into a machine learning algorithm for designing and predicting efficacy of microbiome therapies.

Meta-Omics Data Integration

Sequencing results (both RNA-seq and DNA-seq) are characterized for content at multiple levels and against multiple databases. RNA-seq reads are filtered against databases of ribosomal RNA to remove non-mRNA reads. Sequencing reads are trimmed using existing tools and aligned using existing alignment tools against organism and protein level databases. The results characterize microbiome content at the genomic and proteomic level. Because a large proportion of metagenomic sequence reads do not map to known databases, the unknown reads are assembled using a metagenomic assembly algorithm, and the assembly is used to predict hypothetical proteins and their associated functions. The meta-assembly and predicted protein information is used to augment the proprietary database going forward. In the specific case where metagenomics and transcriptomics are performed on the same sample, the combination of metagenomic assembly and RNA reads is used to improve gene prediction. Furthermore, in order to capture other missed information, raw sequence level features are also tracked from sample to sample, including but not limited to kmer counts for abundant kmers. Long read sequencing is used as required to improve the quality of metagenomic assembly.

In order to estimate species abundance from read level information, maximum likelihood estimation is performed leveraging convex optimization to solve for the global optimal point, corresponding to the most likely proportion of strains in the sample.

Computational Characterization of Isolated Fecal Bacteria

Strains are isolated from acquired samples by plating on varying types of media followed by anaerobic culture. The strains are screened by Sanger sequencing for 16S rRNA sequences of interest. Interesting strains are sent for whole genome sequencing, and genomes are assembled from the resulting sequencing data. The resulting contigs are used to predict proteins and associated functions. Using a metabolic scoring algorithm based on relevance to the live biotherapeutic, strains with interesting metabolic properties are further selected for long read sequencing to generate a fully characterized circular full genome. Strains at any point in the discovery process may be used in microbial consortia composing the live biotherapeutic.

Deep Learning Approaches for Therapeutic Design

The data for learning is collected from in vivo experiments in mice, public databases, literature mining, sequencing and characterization of strains both genomically and metabolically, metabolic modeling results on strains and consortia, and from ex vivo experiments on metabolism of strains and consortia and their impact on tumor cells and immune cells. A model is trained to predict the impact of different consortia of strains or of different metabolites on tumor cell growth and immune cell stimulation ex vivo, and for the same quantities and response to cancer therapy in vivo. The learned network is used to identify combinations of strains predicted to have a strong anti-cancer effect for further screening in animal studies. A large volume of high throughput ex vivo experiments along with in silico modeling results is used to generate sufficient amounts of data for the learning algorithm. Identified consortia may be validated ex vivo to verify impact on tumor cell growth or immune cell function before they are tested in an animal study.

Example 20: Gene Expression Analysis of Microbial Treatment in Co-Culture

Microbe mixes (1-7) are evaluated in co-culture for immunomodulatory effects. Microbe mixes are co-cultured with human colonic cells (CaCo2) to investigate the effects of the bacteria on the host. Microbe mixes are also co-cultured on CaCo2 cells that were stimulated with IL1 to mimic the effect of the bacteria in an inflammatory environment. The effects in both scenarios are evaluated through gene expression analysis either by PCR or by next generation sequencing approaches.

Cytokine Production in THP-1 Cells Induced by Microbial Mixes

Microbial mixes as provided herein (e.g., mixes 1-7) are evaluated alone and in combination with lipopolysaccharide (LPS) on cytokine production in THP-1 cells, a model cell line for monocytes and macrophages.

THE-1 cells are differentiated into M0 medium for 48 h with 5 ng/mL phorbol-12-myristate-13-acetate (PMA). These cells are subsequently incubated with the microbe mix at a final concentration of $10^8$/ml, with or without the addition of LPS at a final concentration of 100 ng/ml. The bacteria are then washed off and the cells allowed to incubate under normal growing conditions for 24 h. The cells are then spun down and the resulting supernatant is analyzed for cytokine content.

Cytokine Production in Immature Dendritic Cells Induced by Microbial Mixes

Microbial mixes (1-7) are evaluated alone and in combination with LPS on cytokine production in immature dendritic cells. A monocyte population is isolated from peripheral blood mononuclear cells (PBMCs). The monocyte cells are subsequently differentiated into immature dendritic cells. The immature dendritic cells are plated out at 200,000 cells/well and incubated with the microbe mix at a final concentration of $10^7$/ml, with the optional addition of LPS at a final concentration of 100 ng/ml. The negative control involved incubating the cells with RPMI media alone and positive controls incubated the cells with LPS at a final concentration of 100 ng/ml. The cytokine content of the cells is then analyzed.

Example 21: Stability Testing

A composition described herein of the family or genus (or class): Clostridiaceae, *Faecalibacterium* containing at least one bacterial strain described herein is stored in a sealed container at 25° C. or 4° C. and the container is placed in an atmosphere having 30%, 40%, 50%, 60%, 70%, 75%, 80%, 90% or 95% relative humidity. After 1 month, 2 months, 3 months, 6 months, 1 year, 1.5 years, 2 years, 2.5 years or 3 years, at least 50%, 60%, 70%, 80% or 90% of the bacterial strain shall remain as measured in colony forming units determined by standard protocols.

Example 22—Therapeutic Effect of Microbes on Efficacy of Cancer Immunotherapy with Antibiotic Pretreatment Anaerobe Basal Broth Supplemented with Rumen Fluid (ABB+RF)

34.5 grams of anaerobic basal broth dry powder (Fisher Scientific/Oxoid) is combined with 600 ml distilled water and is brought to a gentle boil while stirring on a heated stirplate until the solution clarifies. 150 ml of rumen fluid (Bar Diamond Inc., Parma Idaho) that has been centrifuge-clarified is then added, along with 1 ml 2.5 mg/ml resazurin (ACROS Organics™) solution followed by distilled water to one-liter final volume. The medium is kept at 55° C. in a water bath while it is dispensed in 50 ml volumes into 100 ml serum bottles. Nitrogen is bubbled through a metal canula into each bottle for 15 minutes to displace oxygen from the medium, then the bottles are quickly sealed by insertion of a butyl-rubber bung that is secured by a crimped collar. The medium bottles are then sterilized by autoclaving and then stored in the dark until use. L-cysteine is added to 1 mM final concentration to each ABB+RF bottle one hour prior to use to fully reduce the medium prior to inoculation with microorganisms.

Preparation of Centrifuge-Clarified Rumen Fluid

Rumen fluid is the liquid obtained from the rumen of fistulated cows and is obtained in one-liter volumes from Bar Diamond Inc., Parma Idaho. The rumen fluid is aliquoted in 50 ml volumes into 50 ml conical tubes and centrifuged at 4000 g for 30 minutes at 4° C. to pellet large fibrous material. After centrifugation the supernatant is decanted into fresh 50 ml conical tubes that are then subjected to centrifugation at 34,000 g for 90 minutes at 4° C. The supernatant from this centrifugation is then decanted into fresh 50 ml conical tubes and stored at −20° C. until use.

Microorganisms in Mouse Study

The following obligate anaerobic microbes are obtained from the American Type Culture Collection (ATCC): *Faecalibacterium prausnitzii* (ATCC-27768), *Clostridium coccoides* (ATCC-29236), *Ruminococcus gnavus* (ATCC-29149), *Clostridium scindens* (ATCC-35704), *Akkermansia muciniphila* (BAA-835), *Enterococcus hirae* (ATCC-9790), *Bacteroides thetaiotamicron* (ATCC-29148), *Bacteroides caccae* (ATCC-43185), *Bifidobacterium breve* (ATCC-15700), *Bifidobacterium longum* (ATCC BAA-999) and *Gemmiger formicilis* (ATCC-27749). *Eggerthella lenta* (DSM-2243), *Gordonibacter urolithinfaciens* (DSM-27213), *Gordonibacter* species CEBAS 4A4*; Alistipes indistinctus* (DSM-22520), *Dorea formicigenerans* (DSM-3992), *Senegalimassilia anaerobia* (DSM-25959), *Collinsella aerofaciens* (DSM-3979), *Adlercreutzia* equolifaciens (DSM-19450), *Ellagibacter isourolithinifaciens* (DSM-104140), *Slackia isoflavoniconvertens* (DSM-22006), *Slackia equohfaciens* (DSM-2485) and *Paraeggerthella hongkongensis* (DSM-16106) are obtained from the Leibnitz Institute-German Collection of Microorganisms and Cell Cultures (DSMZ).

The following organisms were obtained from stool of healthy donors as described in Example 16*: Dorea longicatena* and *Blautia* sp. SG-772. Whole genome sequencing of these organisms indicated they are more than 95% identical to the published strains.

Culture of Individual Microbes for Mouse Study 0.5 ml starter cultures of *C. coccoides, R. gnavus, C. scindens, A. muciniphila, E. hirae, B. thetaiotamicron, B. caccae, B. breve, B. longum, G. formicilis, E. lenta, G. urolithinfaciens, A. indistinctus, D. formicigenerans, S. anaerobia, C. aerofaciens, A. equohfaciens, E. isourolithinfaciens, S. isoflavoniconvertens, S. equolifaciens* and *P. hongkongensis, E. hallii, D. longicatena*, and *Blautia* sp. SG-772 are each inoculated into four 50 ml anaerobic bottles of fully reduced ABB+RF anaerobic medium and cultured at 37° C. *F. prausnitzii* is inoculated into fifteen 7 ml tubes of YCFAC (Anaerobe Systems) and cultured at 37° C. Cultures are harvested after 48 hours when they achieve 0.1 to $1.0\times10^9$ cells/ml as measured by optical absorbance at 600 nm by spectrophotometer (1 $OD_{600}=1.0\times10^9$ cells/ml). Bacterial starter cultures may be modified to achieve $1.0\times10^{10}$ cells/ml, $1.0\times10^{11}$ cells/ml or $1.0\times10^{12}$ cell/ml.

To harvest cultures, they are first brought into the anaerobic chamber where they are opened and decanted into 50 ml conical tubes that are tightly capped and sealed by wrapping the caps in parafilm. These are brought out of the anaerobic chamber and then centrifuged at 4000 g for 15 minutes at 4° C. The centrifuged tubes are brought back into the anaerobic chamber where the supernatant is decanted and discarded. The cell pellets are each combined with anoxic Phosphate Buffered Saline with 2.5 mM L-Cysteine and 15% glycerol (PBS-C-G) followed by tight capping and parafilm seal. The capped and sealed tubes are brought out of the anaerobic chamber and are centrifuged at 4000 g for 15 minutes. The culture tubes are again brought into the anaerobic chamber where the supernatant is decanted and discarded. Pelleted cells are resuspended in volumes of PBS-C-G to attain effective cell densities of each microbial strain at $1\times10^9$ cells/ml, $1.0\times10^{10}$ cells/ml, $1.0\times10^{11}$ cells/ml or $1.0\times10^{12}$ cell/ml.

Assembly of Microbe Mixes

The PBS-C-G suspended microbe cultures are mixed together to form 20 ml of the following microbe mixes to attain $1\times10^9$, $1.0\times10^{10}$ cells/ml, $1.0\times10^{11}$ cells/ml or $1.0\times10^{12}$ total microbial cells/ml, see Table 5, below (see also Table 1, Example 1).

Microbe Mix 1 consists of 5 ml each of *F. prausnitzii, C. coccoides, R. gnavus*, and *C. scindens* cultures.

Microbe Mix 2 consists of 3.3 ml each of *F. prausnitzii, C. coccoides, R. gnavus, C. scindens, A. muciniphila*, and *E. hirae* cultures.

Microbe Mix 3 consists of 10 ml each of *E. lenta* and *G. urolithinfaciens* cultures.

Microbe Mix 4 consists of 3.3 ml each of *F. prausnitzii, C. coccoides, R. gnavus, C. scindens, E. lenta*, and *G. urolithinfaciens* cultures.

Microbe Mix 5 consists of 2.9 ml each of *F. prausnitzii, C. coccoides, R. gnavus, C. scindens, B. thetaiotamicron, B. caccae*, and *G. formicilis* cultures.

Microbe Mix 6 consists of 3.3 ml each of *F. prausnitzii, C. coccoides, R. gnavus, C. scindens, A. indistinctus* and *D. formicigenerans* cultures.

Microbe Mix 7 consists of 3.3 ml each of *F. prausnitzii, C. coccoides, R. gnavus, C. scindens, B. longum* and *B. breve* cultures.

Microbe Mix 8 consists of 2.85 ml each of *F. prausnitzii, C. coccoides, R. gnavus, C. scindens, E. lenta, G. urolithinfaciens* and A. equolifaciens cultures.

Microbe Mix 9 consists of 2.5 ml each of *F. prausnitzii, C. coccoides, R. gnavus, C. scindens, E. lenta, G. urolithinfaciens, A. equohfaciens* and *S. anaerobia* cultures.

Microbe Mix 10 consists of 2.2 ml each of *F. prausnitzii, C. coccoides, R. gnavus, C. scindens, E. lenta, G. urolithinfaciens, A. equohfaciens, S. anaerobia* and *E. isourolithinfaciens* cultures.

Microbe Mix 11 consists of 2.5 ml each of *F. prausnitzii, C. coccoides, R. gnavus, C. scindens, E. lenta, G. urolithinfaciens, A. equohfaciens* and *E. isourolithinfaciens* cultures.

Microbe Mix 12 consists of 4 ml each of *E. lenta, G. urolithinfaciens, A. equohfaciens, S. anaerobia* and *E. isourolithinifaciens* cultures.

Microbe Mix 13 consists of 3.3 ml each of *E. lenta, G. urolithinfaciens, A. equohfaciens, S. anaerobia, E. isourolithinifaciens* and *C. aerofaciens* cultures.

Microbe Mix 14 consists of 2.2 ml each of *F. prausnitzii, C. coccoides, R. gnavus, C. scindens, E. lenta, G. urolithinfaciens, A. equohfaciens, S. anaerobia* and *C. aerofaciens* cultures.

Microbe Mix 15 consists of 2 ml each of *F. prausnitzii, C. coccoides, R. gnavus, C. scindens, E. lenta, G. urolithinfaciens, A. equohfaciens, S. anaerobia, C. aerofaciens* and *E. isourolithinfaciens* cultures.

Microbe Mix 16 consists of 2.85 ml each of *F. prausnitzii, C. coccoides, R. gnavus, C. scindens, E. lenta, G. urolithinfaciens and E. isourolithinifaciens* cultures.

Microbe Mix 17 consists of 6.6 ml each of *E. lenta, G. urolithinfaciens* and *E. isourolithinfaciens* cultures.

Microbe Mix 18 consists of 2.85 ml each of *F. prausnitzii, C. coccoides, R. gnavus, C. scindens, E. lenta, G. urolithinfaciens and P. hongkongensis* cultures.

Microbe Mix 19 consists of 2.2 ml each of *F. prausnitzii, C. coccoides, R. gnavus, C. scindens, E. lenta, G. urolithinfaciens, P. hongkongensis, S. isoflavoniconvertens* and *S. equohfaciens* cultures.

After assembly, 20 ml of PBS-C-G is added to each microbe mix to double the volume to 40 ml and to reduce the total cell density of each microbe mix to attain a gavage dosage of $1\times10^8$/0.2 ml, $1\times10^9$/0.2 ml, $1\times10^{10}$/0.2 ml or $1\times10^{11}$/0.2 ml.

Microbe mixes are aliquoted into eight 5.0 ml volumes into 15 ml conical tubes and stored at −20° C. until required.

Microbe Mix 33 consists of 10 mL each of *A. muciniphilia* and *F. prausnitzii* cultures.

Microbe Mix 34 consists of 6.7 mL each of *E. hallii, D. longicatena*, and *Blautia* sp. SG-772 cultures.

Microbe Mix 35 consists of 4 mL each of *A. muciniphilia, F. prausnmitzii, E. hallii, D. longicatena*, and *Blautia* sp. SG-772 cultures.

Animals and Tumor Model

BALB/c mice are obtained from Jackson laboratory, Taconic farms or Shanghai Lingchang Biotechnology Co., Ltd (Shanghai, China). 6-8-week-old female mice are used. For tumor growth experiments, mice are injected subcutaneously with $2.5\times10^5$ CT-26 colon cancer tumor cells (Griswold and Corbett (1975) Cancer 36:2441-2444). Tumor size is measured twice a week until endpoint, and tumor volume determined as length×width×0.5.

Tumor Cell Preparation

Cryo vials containing CT-26 tumor cells are thawed and cultured according to manufacturer's protocol (ATCC CRL-2638). On the day of injection cells are washed in serum free media, counted, and resuspended in cold serum free media at a concentration of 250,000 viable cells/100 μl. Cells will be prepared for injections by withdrawing 100 μL cell suspension into a 1 ml syringe. The cell suspension and filled syringes will be kept on ice.

Tumor Implantation

Animals will be prepared for injection using standard approved anesthesia, the mice will be shaved prior to injection. Once mouse at a time will be immobilized and the site of injection will be disinfected with an alcohol swab. 100 μl of the cell suspension will be subcutaneously injected into the rear flank of the mouse. During implantation, a new syringe and needle will be used for every mouse inoculated to minimize tumor ulceration. The cells will be drawn up into a 1 mL syringe (no needle attached) to 150 μL with the 50 μL nearest to the plunger being air and 100 μL of cell suspension. Once the cells are drawn up the needle will be attached (without priming the needle). For implant, lift up or tent the skin using forceps to ensure a subcutaneous injection. Inject the cells, twist the syringe/needle and then pull the needle out. Mice will be marked by ear tagging.

Antibiotics Protocols

Mice are treated daily with 200 μL of water or antibiotics via oral gavage 1-2 weeks before tumor implantation and continued for a duration of 2-3 weeks. Mouse fecal samples were collected twice a week for 5 collections in total (timepoints 1-5). Animals are given a mix of ampicillin (1 mg/mL)(Alfa Aesar J6380706), gentamicin (1 mg/mL)(Acros Organics AC455310050), metronidazole (1 mg/mL) (Acros Organics AC210440050), neomycin (1 mg/mL)(Alfa Aesar AAJ6149922), and vancomycin (0.5 mg/mL)(Alfa Aesar J6279006) via oral gavage. Antibiotic activity is analyzed by macroscopic changes observed at the level of caecum (dilatation) and by cultivating the fecal pellets resuspended in BHI+15% glycerol on blood agar and anaerobic blood agar plates for 48 h at 37° C. with 5% CO2 for aerobic conditions or in anaerobic conditions respectively. 16S RNA and Whole Genome Sequencing are applied to determine the distribution of organisms in fecal samples collected from the water and antibiotic treated groups at both the phylum and genus level, and the distribution is compared across all collected fecal samples. PCA is used to classify all samples of mice without antibiotic treatment, showing that samples with the same microbial treatment type cluster together. Mice are treated with antibiotics or water for two weeks and fecal samples are collected at three different time points.

16S RNA Sequencing

Figure 28:
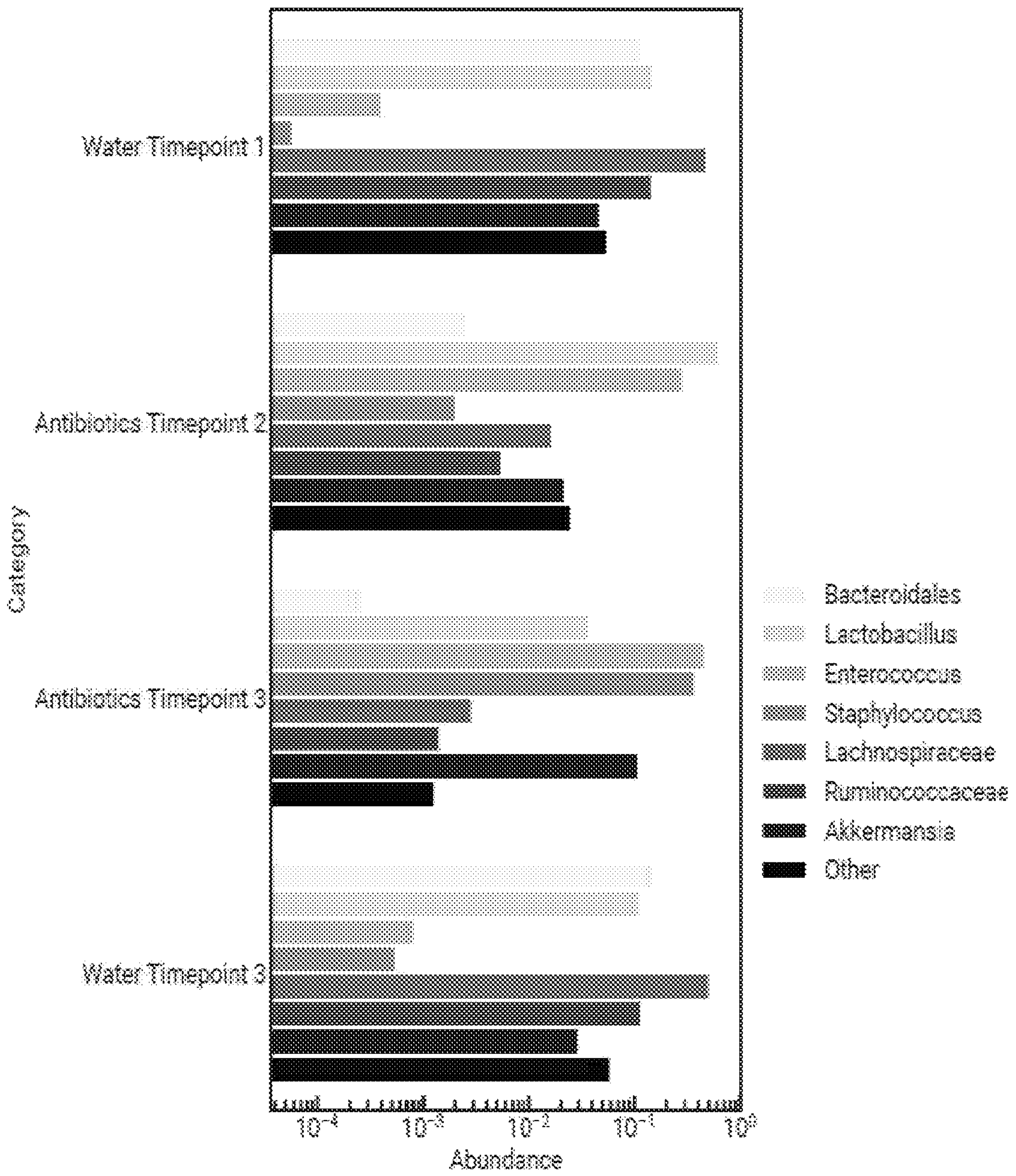
FIG. 28 graphically illustrates the 16S RNA OTU abundances for each treatment group and time point—with OTU's not shown captured in the Other category; as discussed in detail in Example 22, below.

Fecal gDNA was extracted and 16S RNA sequencing and classification was performed after antibiotic treatment. 16S OTU abundances are shown in FIG. 28 for each treatment group and time point, with OTU's not shown captured in the "Other" category. Mice treated with water maintain a similar microbiome from time point 1 to 3, while there is a shift in the composition of the microbiome of mice treated with antibiotics from a diverse mix of bacteria at time point 1 to a microbiome dominated by *Lactobacillus* and *Enterococcus* at time point 2, and by *Enterococcus* and *Staphylococcus* at time point 3.

Isolation of Lamina Propria Cells from Small Intestine

Whole duodenum and ileum are harvested, Peyer's patches are removed, as well as all fat residues and fecal content. Small fragments are obtained by cutting them first longitudinally along the length and then transversally into pieces of 1-2 cm length. After removing the intra-epithelial lymphocytes (IELs), the gut pieces are further cut and incubated with 0.25 mg/ml collagenase VIII and 10 U/ml DNaseI for 40 min at 37° C. under shaking to isolate lamina propria cells (LPCs). After digestion, intestinal pieces are mashed on a cell strainer. For FACS analysis, cell suspensions are subjected to a percoll gradient for 20 min at 2100 RPM, while for RNA extraction, cells are directly lysed in RNALater buffer (Thermo Fisher Scientific) and frozen at −80° C.

Analyses of Dendritic Cell Subsets in Treated Mice

Cell suspensions from mouse spleen and lymph nodes are prepared by digestion with collagenase and DNase for 60 min and subsequently strained through a 70 mm mesh. Colonic and small intestinal lymphocytes are isolated as previously described (Viaud, S. et al. Science (80-.). 342, 971-976 (2013). In brief, cecum, colon and small intestine are digested in PBS containing 5 mM EDTA and 2 mM DTT shaking at 37° C. A plastic pestle is used to press and massage the intestinal segment in each tube to expel ruminal matter, which is then removed by pipette and placed in a fresh Eppendorf tube. Tubes containing expelled ruminal matter from each intestinal segment are immediately placed on dry ice and then stored for later analyses at −80° C. Remaining intestinal tissues are then rinsed twice by adding and then removing 0.5 ml ice cold PBS. Rinsed intestinal fragment tissues are then frozen on dry ice in RNALater (Thermo Fisher Scientific) and then stored at −80° C. for later analysis.

After initial digestion colonic and small intestinal tissue pieces are digested in collagenase/Dnase containing RPMI medium for 30 min. Tissue pieces are further strained through a 70 mm mesh. For flow cytometry analyses, cell suspensions are stained with antibodies against the following surface markers: CD11c (N418), CD11b (M1/70), Ly6c (HK1.4), MHC class II (M5/114.15.2), CD24 (M1/69), CD64 (X54-5/7.1), CD317 (ebio927), CD45 (30-F11), F4/80 (C1:A3-1), CD8a (53-6.7). DAPI is used for dead cell exclusion. Antibodies are purchased from eBiosciences, BD Biosciences or BioLegend respectively. Cell populations are gated as follows: small intestine (migratory fraction): CD103+DC (CD45+CD11c+MHC-II+CD103+CD24+), CD11b+CD103+(CD45+CD11c+MHC-II+CD103+ CD11b+CD24+), CD11b+(CD45+CD11c+MHC-II+ CD11b+CD24+), inflammatory DC (CD45+CD11c+MHC-II+CD11b+CD64+Ly6c+), large intestine: CD103+DC (CD45+CD11c+MHC-II+CD103+CD24+), CD11b+ (CD45+CD11c+MHC-II+CD11b+CD24+), inflammatory DC (CD45+CD11c+MHC-II+CD11b+CD64+Ly6c+).

Figure 39:
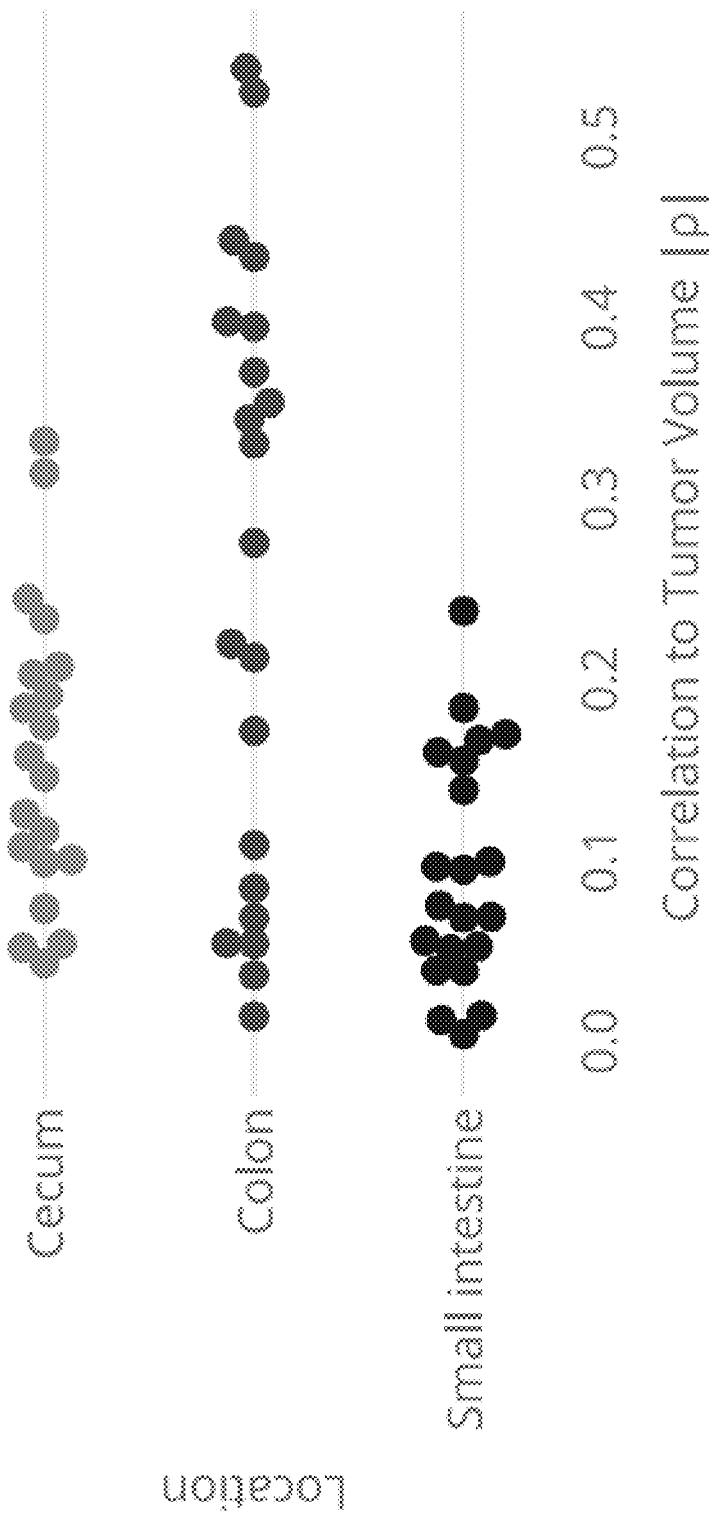
FIG. 39 graphically illustrates Spearman correlations between immune cell populations and final tumor volume for all treatment groups and magnitude is plotted by GI location (small instestine, cecum and colon); as discussed in detail in Example 22, below.
Figure 40:
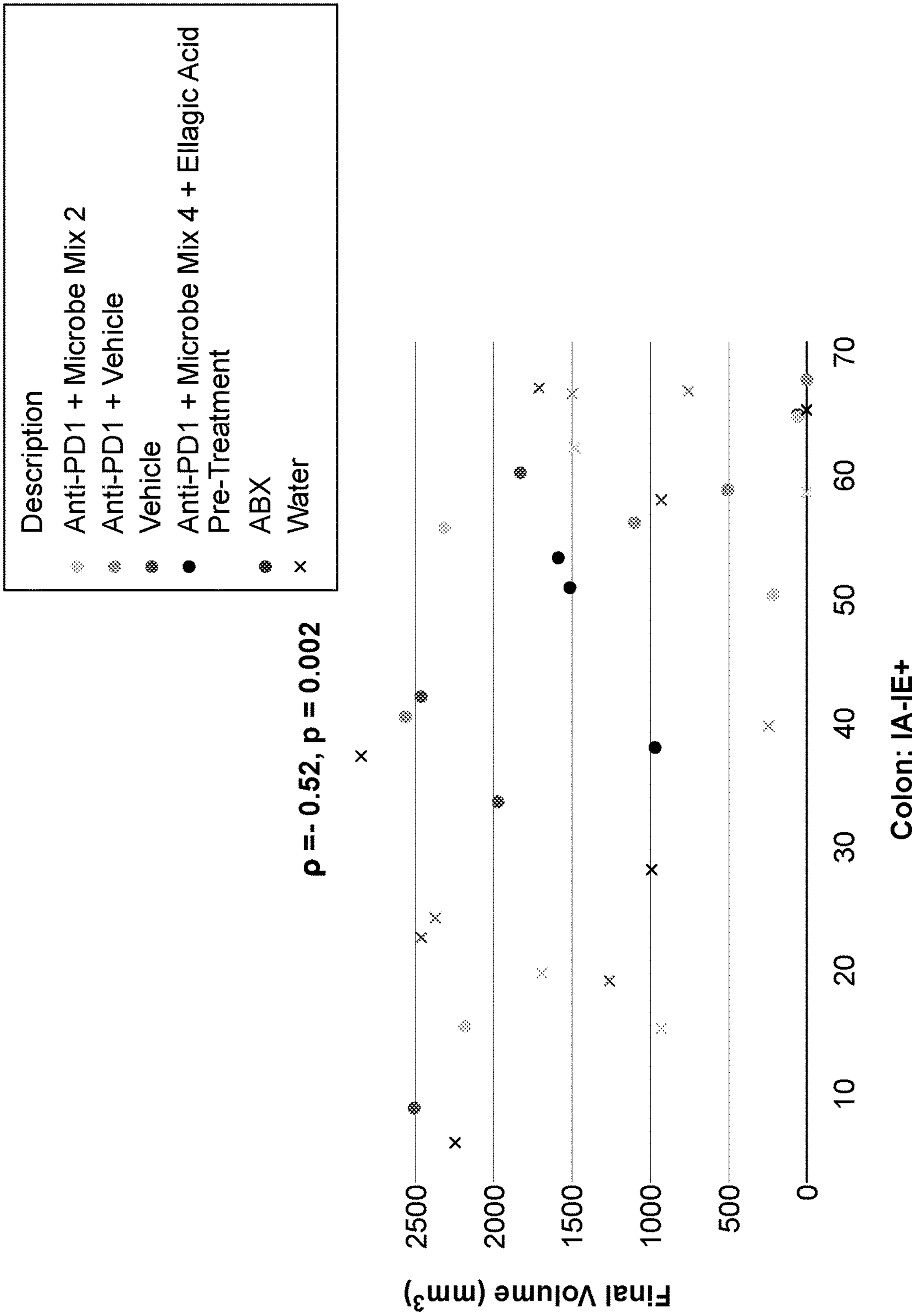
FIG. 40 graphically illustrates the stastically significant correlation between final tumor volume for all treatment groups and the IA/IE (MHC II) immune cell populations in the colon for all treatment groups; as discussed in detail in Example 22, below.
Figure 41A:
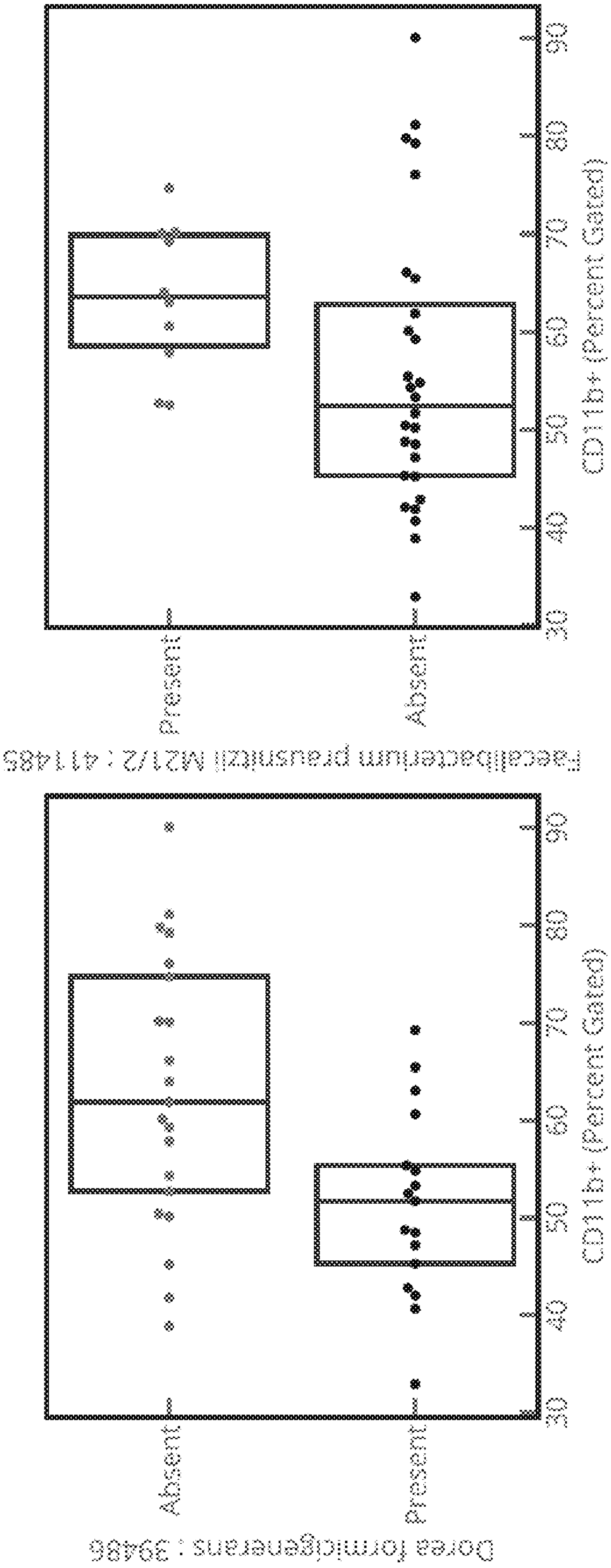
FIG. 41A-D graphically illustrates flow cytometry gated percentages for CD11b+, CD3+, CD8-HLADR+ and FoxP3+ populations with respect to whether an organism is present in the microbiome above a certain threshold abundance; as discussed in detail in Example 7, below.
Figure 41B:
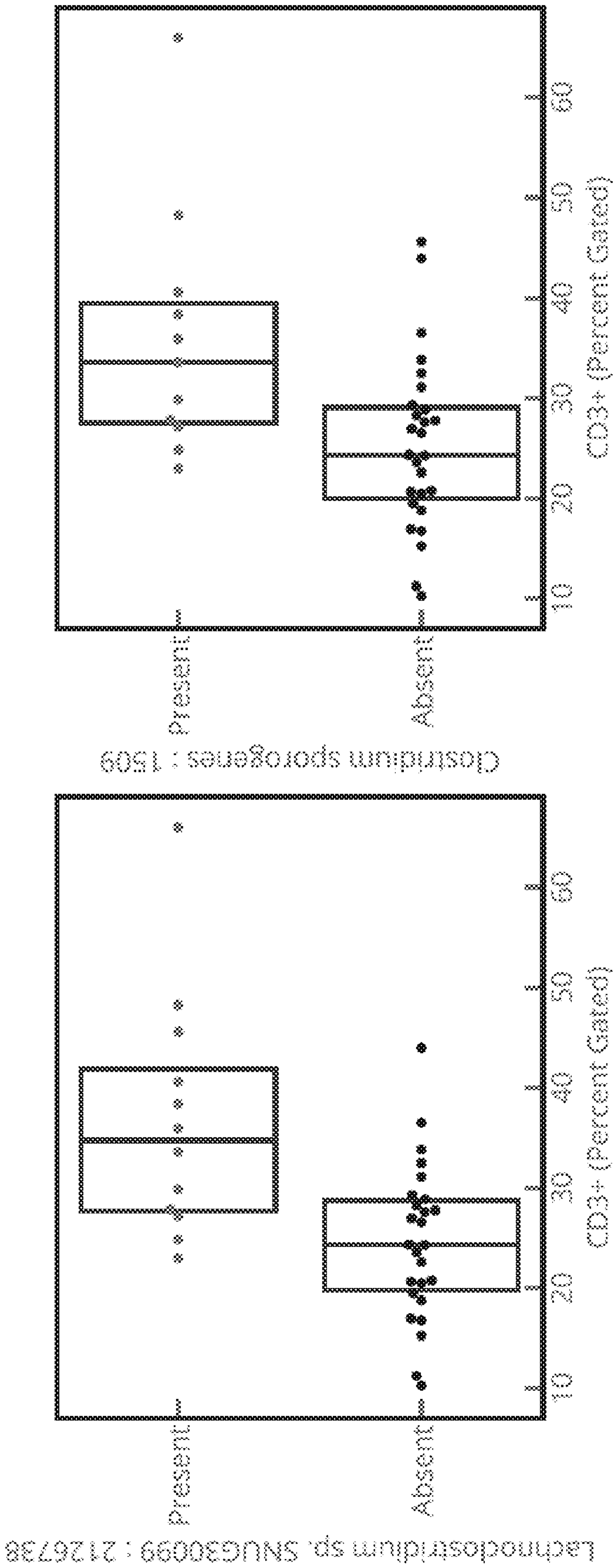
Figure 41C:
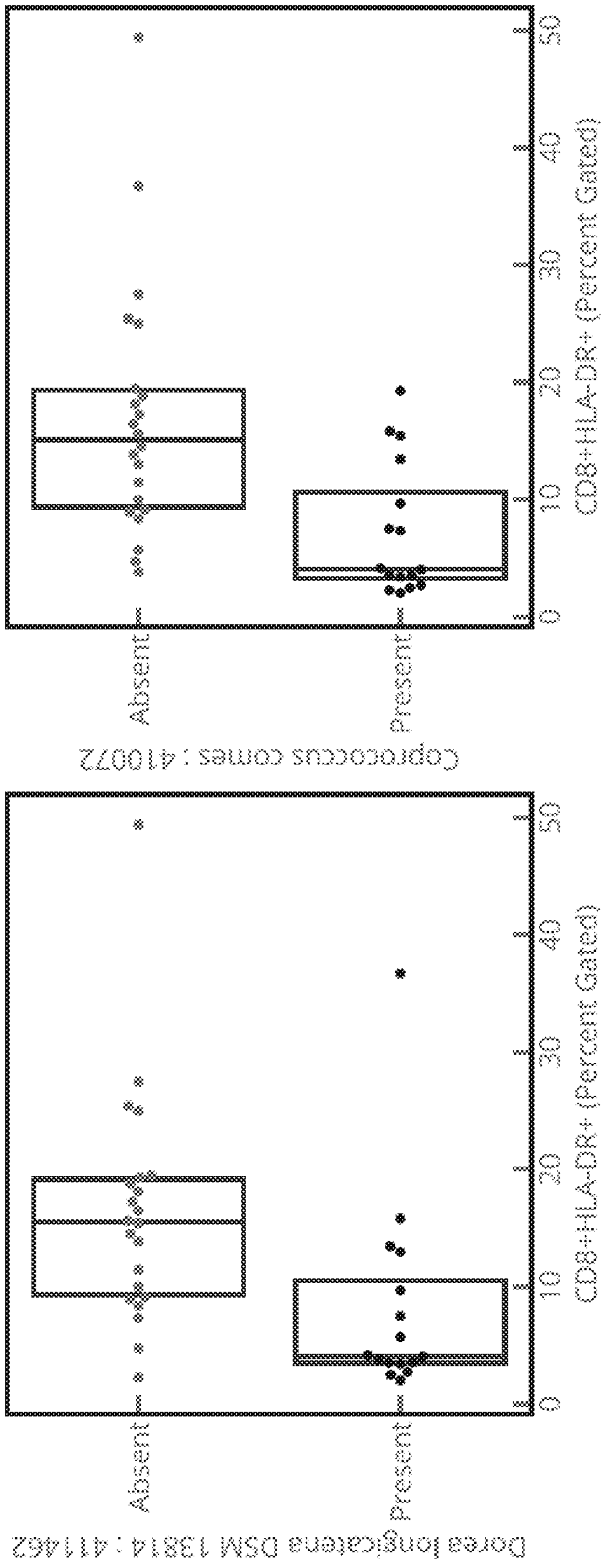
Figure 41D:
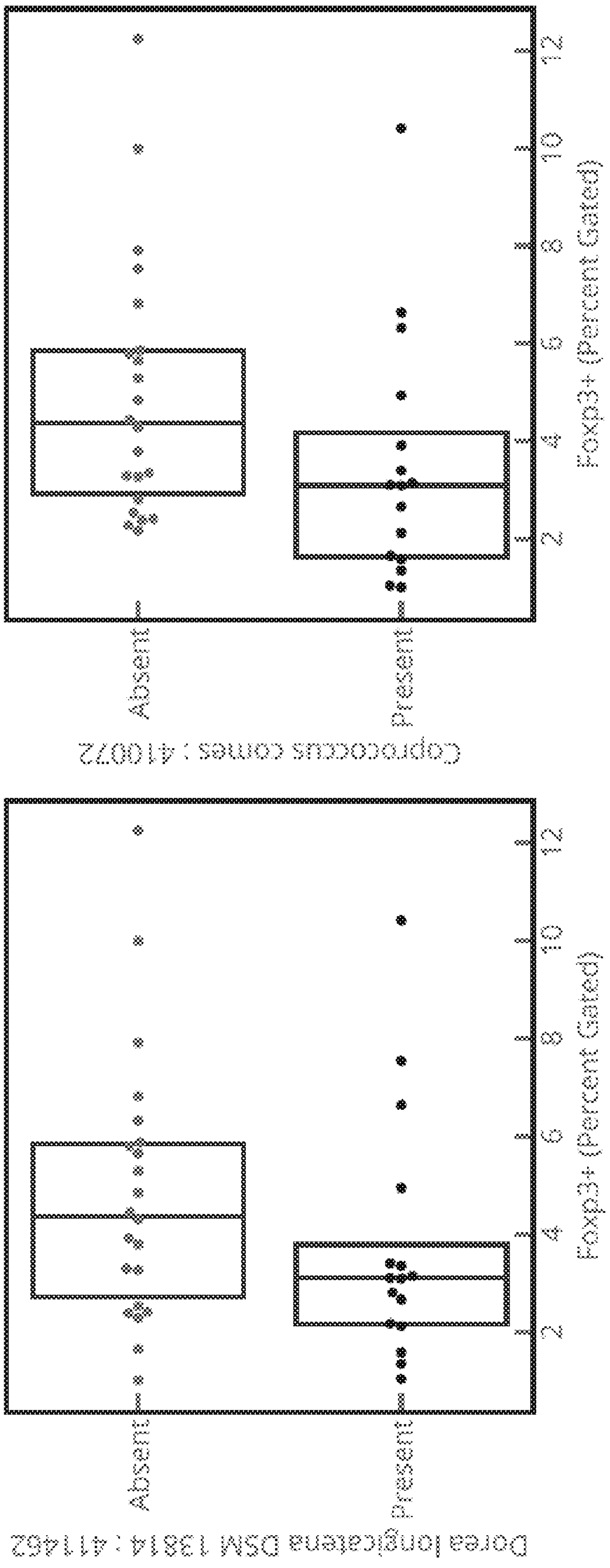

Flow cytometry analyses were performed on small intestine, cecum and colon tissue collected from mice pretreated with water and antibiotics and treatments including vechicle, anti-PD-1 and vehicle, anti-PD-1 in combination with microbe mix 4 and ellagic acid and anti-PD-1 in combination with mix 2. Spearman correlation was computed between final tumor volume and each flow gate for all treatments in each GI location. Correlations passing a false discovery rate threshold of 0.25 are reported in Table 23. Spearman correlations between each flow gate, final tumor volume and their magnitude by GI location is reported in FIG. 39. The strongest correlations between final tumor volume and the flow results occur in the colon. Final tumor volume for all treatment groups was plotted against the IA/IE (MHC Class II) immune population in the colon, which revealed a statistically significant negative correlation as reported in FIG. 40.

TABLE 23

| | Category | | |
|---|---|---|---|
| | P | rho | location |
| Colon: CD11b-IA-IE+ | 0.001495129 | −0.537953832 | Colon |
| Colon: IA-IE+ | 0.002046607 | −0.524752511 | Colon |
| Colon: Monocytes | 0.011114461 | −0.442977661 | Colon |
| Colon: cDC | 0.013117759 | 0.433810077 | Colon |

Fecal Microbiota Transplantation (FMT)

Fecal Microbiota Transplantation (FMT) of a favorable gut microbiome into antibiotic treated mice is a method for standardizing microbiome composition. FMT is performed in some experiments with fecal material derived from healthy and cancer patients, as well as mouse stools. Colonization is performed by oral gavage with 200 μl of suspension obtained by homogenizing the fecal samples in PBS. Efficient colonization is first checked before tumor inoculation. Mouse fecal samples are collected 1-2 times during this period. So that the efficacy of the FMT can be evaluated. Following FMT, a rest period of 5-7 days is allowed to pass prior to checkpoint inhibitor and/or microbe dosing. Blood and fecal pellets are collected at different time points during the experiment.

Flow Cytometry of Peripheral Blood

A whole-blood flow cytometry-based assay is utilized to assess T cell activation in response to anti-CTLA4, anti-PD-1 and microbial treatment. Whole blood via cardiac puncture is collected into an EDTA tube at the end of the experiment. 100 μL of whole mouse blood is transferred to a 15 mL conical tube. 1 mL of RBC Lysis Buffer is added to the tube and allowed to incubate at room temperature for 10 minutes. Lysis is quenched by adding 10 mL of cold DPBS. Samples are centrifuged at 1500 rpm for 5 minutes at 4° C. The pellet is aspirated and resuspend in another 10 mL of cold DPBS. Samples are recentrifuged at 1500 rpm for 5 minutes at 4° C. Samples are resuspended in 500 µL of FACS buffer and transferred to a 96-well plate. Samples are stained with Fixable Viability ef780 (eBioscience), CD45-PEcy7 (BioLegend), CD3-BV605 (BioLegend), CD8-AF700 (BioLegend), and CD4-AF488 (BioLegend). Stained samples are run on a BD LSRFortessa™ flow cytometer and analyses are performed with FlowJo™ (Tree Star).

Figure 31:
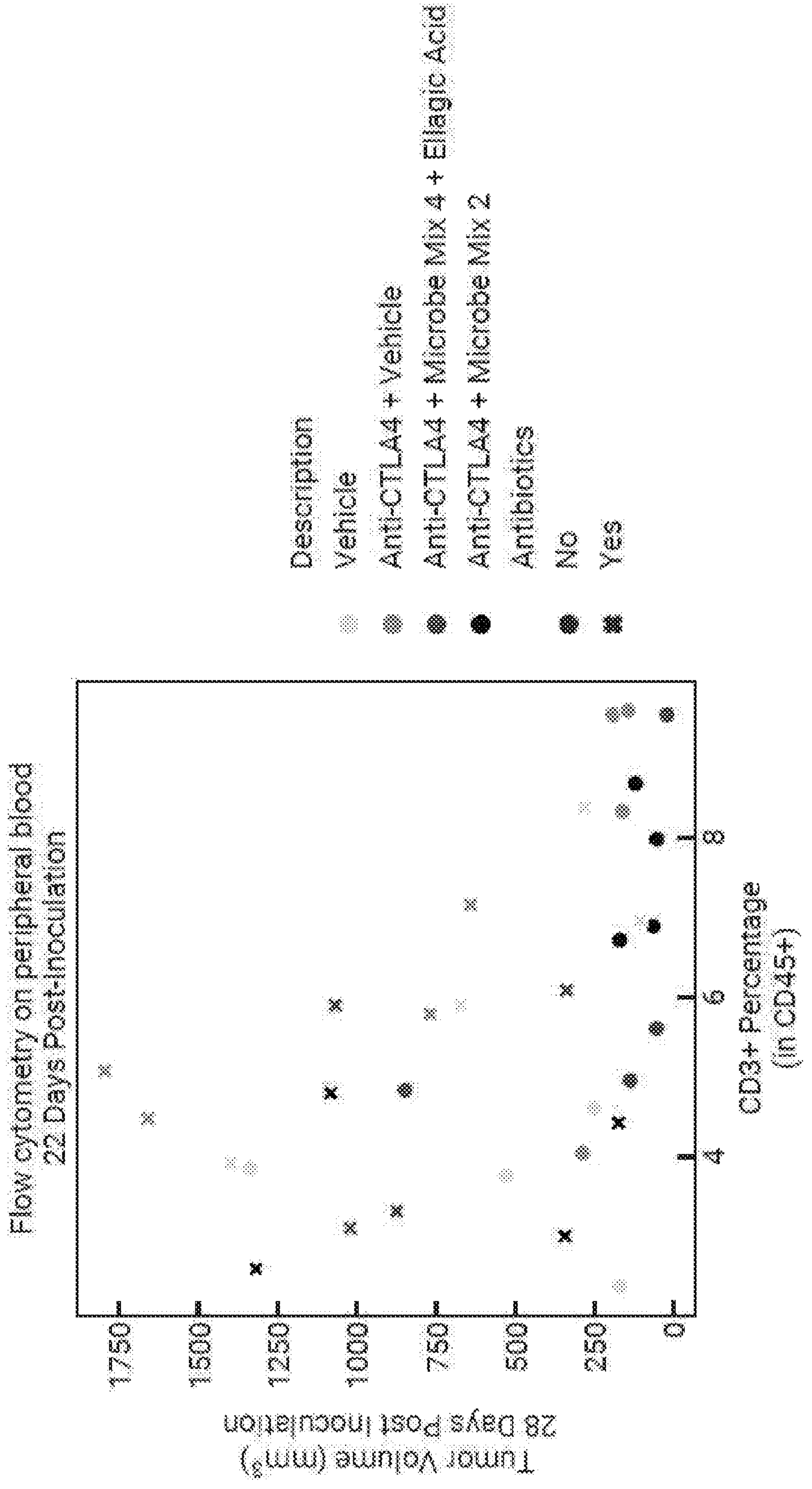
FIG. 31 graphically illustrates flow cytometry data on mice 22 days post-inoculation and CD3+ percentage is displayed against tumor volume at day 28 post-inoculation; as discussed in detail in Example 22, below.

Flow cytometry analysis was performed on mice and CD3+ percentage is displayed against tumor volume at day 28 post-inoculation as shown in FIG. 31. There is a strong inverse relationship between CD3+ percentage and tumor volume where CD3+ cells are increased by treatment with mixes 2 and 4.

Tumor Challenge and Treatment

After pre-treatment is complete, animals will be randomized when average tumor volume reaches 40-60 mm3 (Study Day 0). Dosing of Microbes, Vehicle, anti-CTLA 4, anti-PD1 and Ellagic Acid will begin the following day (Study Day 1) below and continue for 3 weeks. Animals are given at least 48 hrs of no treatment between antibiotic pre-treatment and regular study treatment to allow for antibiotics to go through system. Mice are divided into immunotherapy treatment and non-treatment groups. The treatment group is injected intraperitoneally once the tumor reached a size of 40 to 60 $mm^3$ (day 0) with 100 g anti-PD1 mAb (BioXCell), or with 100 µg anti-PD-L1 mAb, or with 100 µg anti-CTLA-4 mAb (BioXCell) in 100 µl PBS twice a week for three weeks starting from day 1. Tumor size is routinely monitored by means of a caliper. Stool is collected on day 0 and 8 hours after each subsequent administration of treatment until the end of the study.

To test whether manipulation of the microbial community is effective as a combination therapy, microbial cocktails 1-19 and 20-42 (Table 1 and as described in Example 22 and Table 5, Example 22) in the presence or absence of ellagic acid and/or ellagitannin is administered. In some groups, ellagic acid is administered separately via oral gavage (0.2 mL of a 5.5 mg/mL suspension) prior to administration of the microbe cocktails. In other groups, urolithin A is administered alone via oral gavage (0.2 mL of a 5.5 mg/mL suspension), without microbe cocktails. Each mouse treated by combination therapy is given 200 l of the suspension by oral gavage three times a week for the duration of the study starting from day 1. Tumor growth and tumor-specific T cell responses are compared among the different treatment groups.

Mice with and without tumors are given microbial cocktails by oral gavage, as described in the example above. The 16S RNA sequencing results are used to determine the distribution of organisms in each sample at both the phylum and genus level, and the distribution is compared across all fecal samples from mice without tumors to determine how these microbes colonize the gut. PCA is used to classify all samples of mice without tumors, showing that samples with the same microbial treatment type cluster together. In addition, the genera represented by each microbial treatment have increased representation in those samples compared to those of different treatment type.

Figure 29:
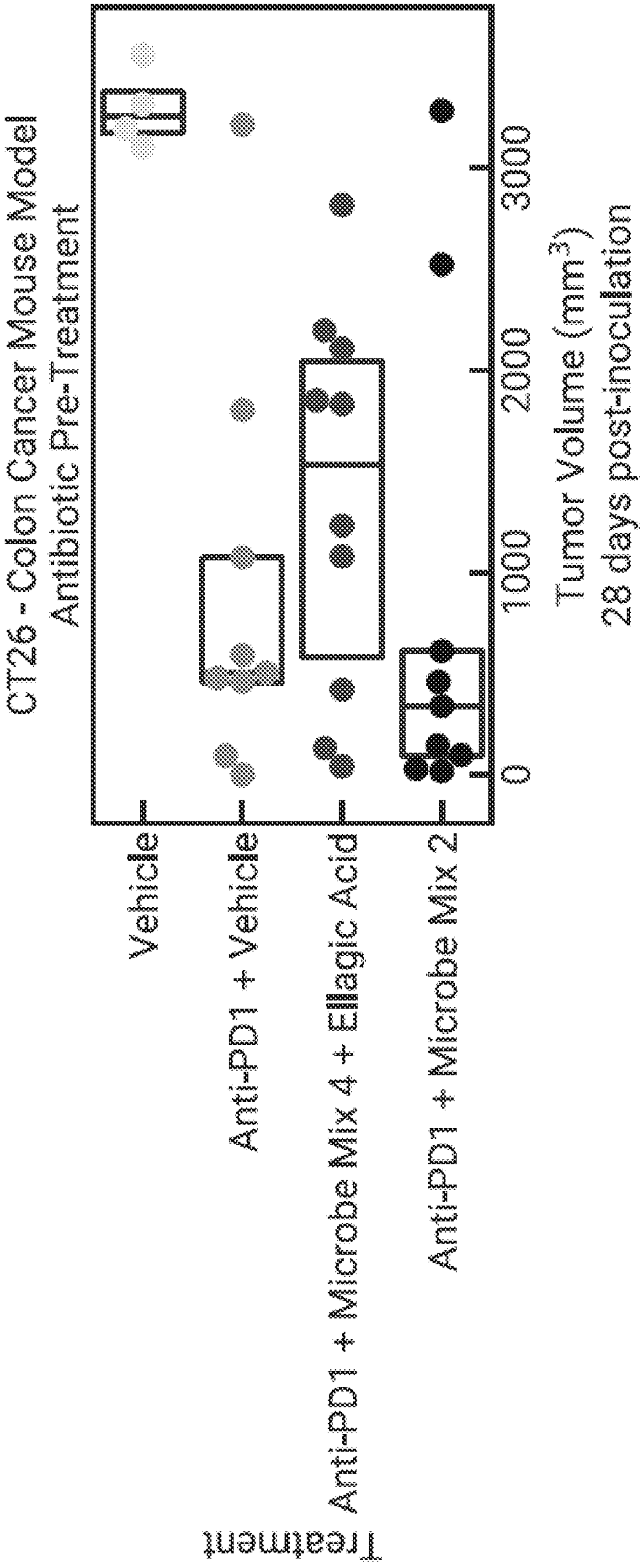
FIG. 29 graphically illustrates tumor volumes for mice remaining alive (10 mice initially per group) 28 days post tumor inoculation; as discussed in detail in Example 22, below.
Figure 30:
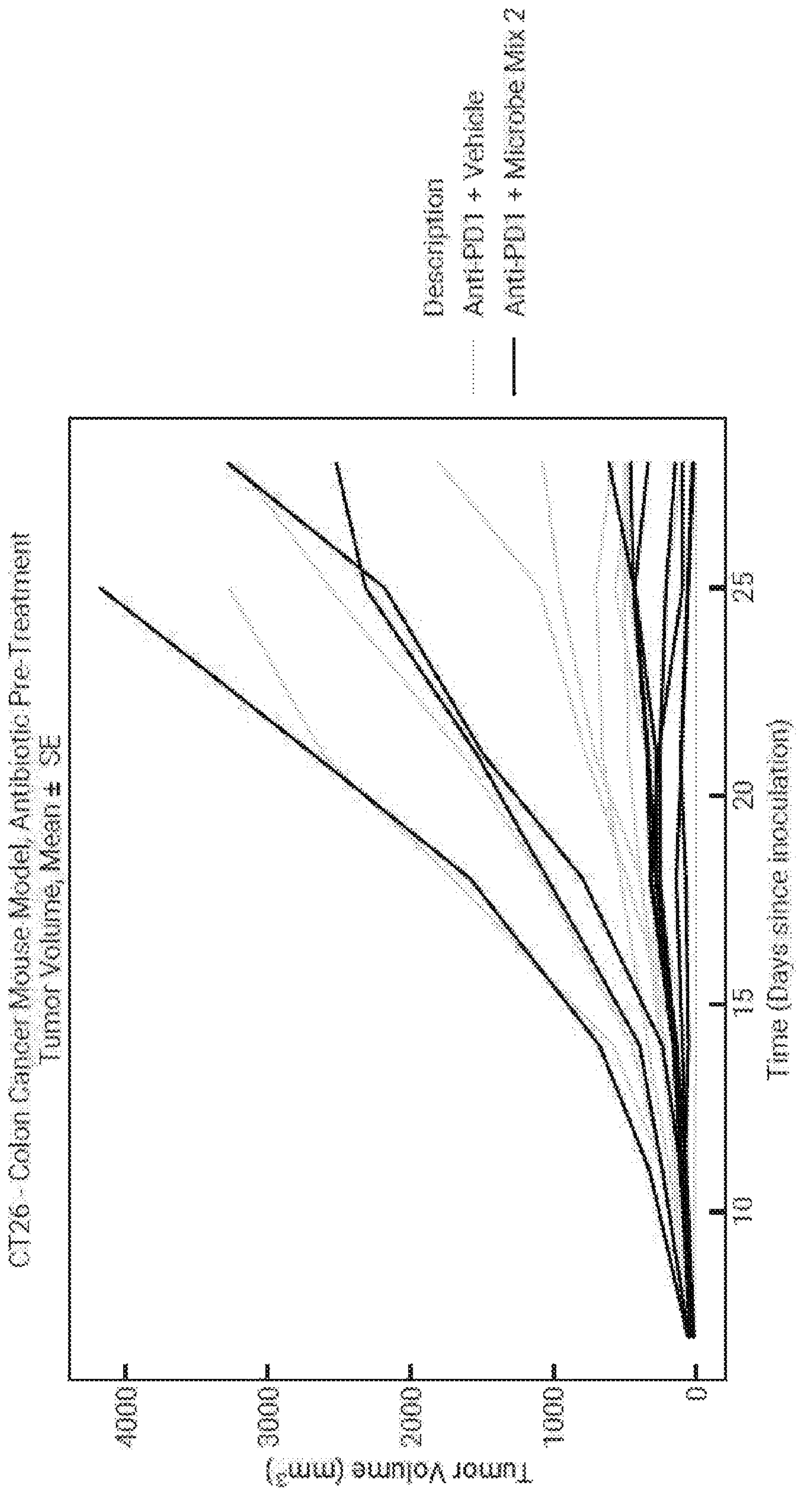
FIG. 30 graphically illustrates tumor volumes over time for mice treated with anti-PD1 alone or in conjunction with mix 2; as discussed in detail in Example 22, below.
Figure 32:
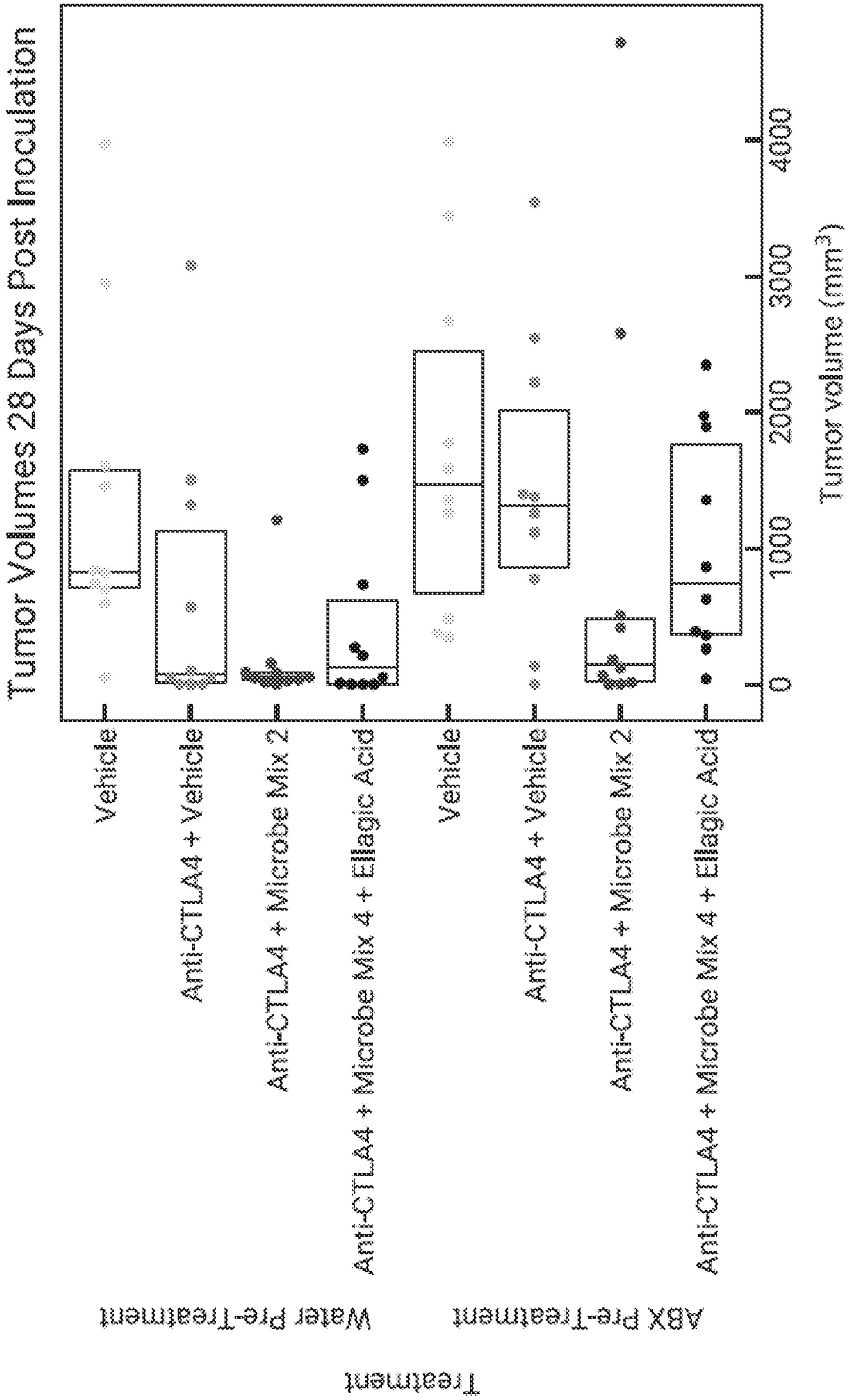
FIG. 32 graphically illustrates tumor volumes that were measured 28 days post inoculation and displayed by both pre-treatment and treatment groups; as discussed in detail in Example 22, below.
Figure 33A:
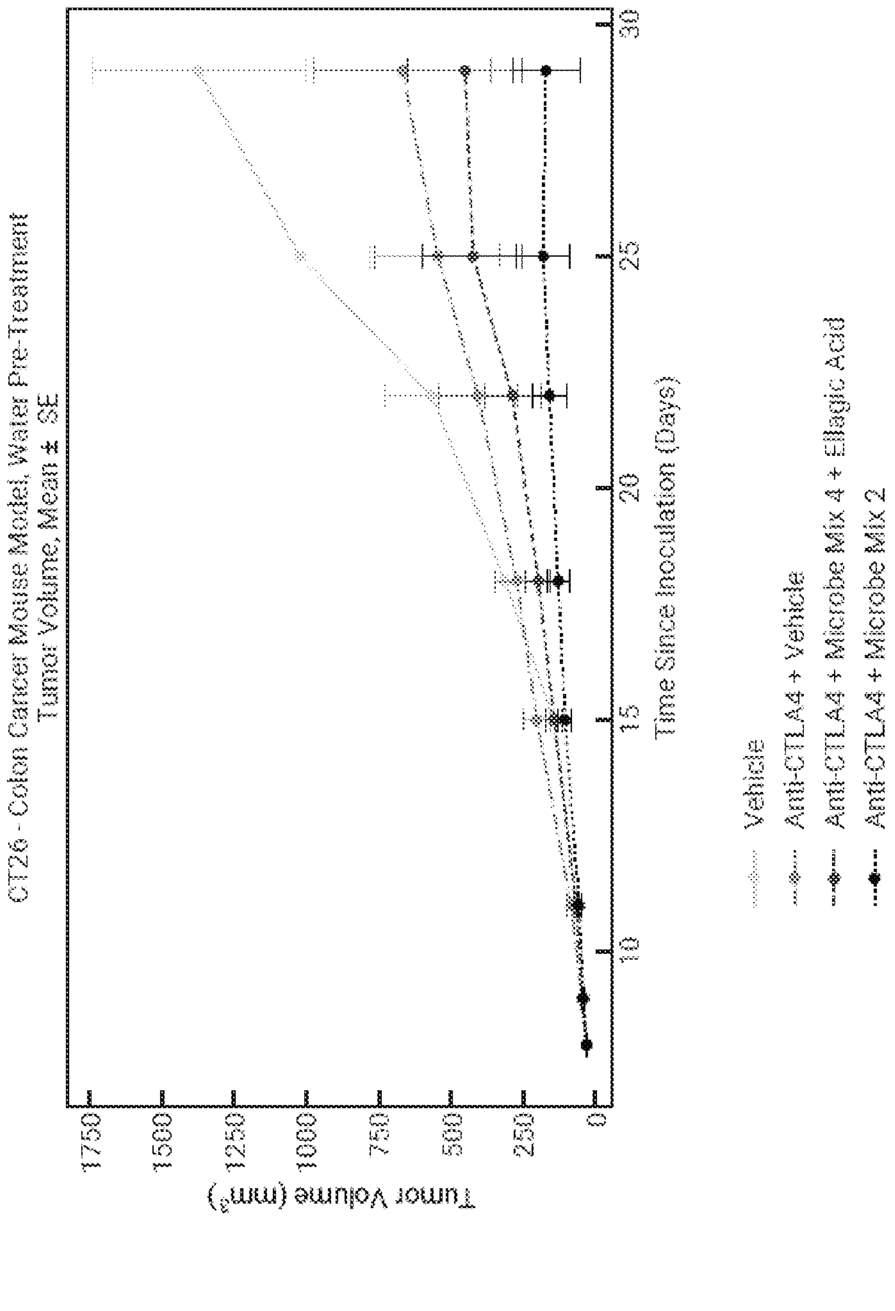
FIG. 33A-B graphically illustrates tumor volumes that were measured at multiple time points post-inoculation. Mean and standard error of the mean are displayed for each treatment group within water (FIG. 33A) and antibiotic (FIG. 33B) pre-treatment groups; as discussed in detail in Example, 22 below.
Figure 33B:
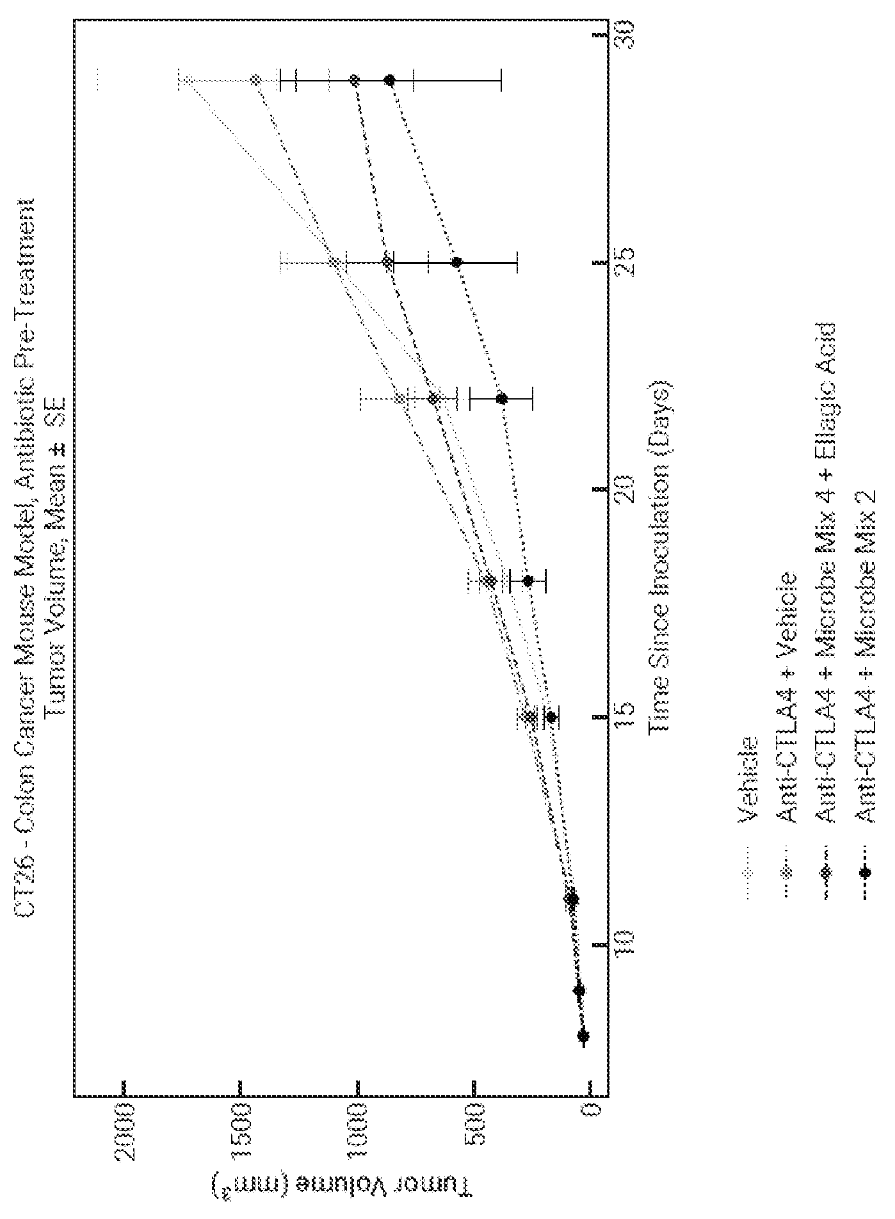

Tumor size was measured in all animals receiving the different microbial treatments, with and without anti-CTLA4, anti-PD1 or anti-PD-L1 therapy. On average, the animals receiving Microbe Mix 2 (equal amounts of *F. prausnitzii, C. coccoides, R. gnavus, C. scindens, A. muciniphila*, and *E. hirae*) in conjunction with anti-PD1 have a reduction in tumor size compared to those with other microbes or not receiving any anti-PD1 treatment, as illustrated in FIG. 29. Mice treated with mix 2 and the anti-PD1 therapy had reduced tumor growth in contrast to the anti-PD1 monotherapy as shown in FIG. 30. Tumor volumes were measured 28 days post inoculation and displayed by both pre-treatment and treatment groups as shown in FIG. 32. On average, the animals receiving Microbe Mix 2 (equal amounts of *F. prausnitzii, C. coccoides, R. gnavus, C. scindens, A. muciniphila*, and *E. hirae*) in conjunction with anti-CTLA4 in both pre-treatment groups, have a reduction in tumor size compared to those with other microbes or the anti-CTLA4 monotherapy. Tumor volumes were measured at multiple time points post-inoculation. Mean and standard error of the mean are displayed for each treatment group within water and antibiotic pre-treatment groups are shown in FIG. 33.

Figure 45:
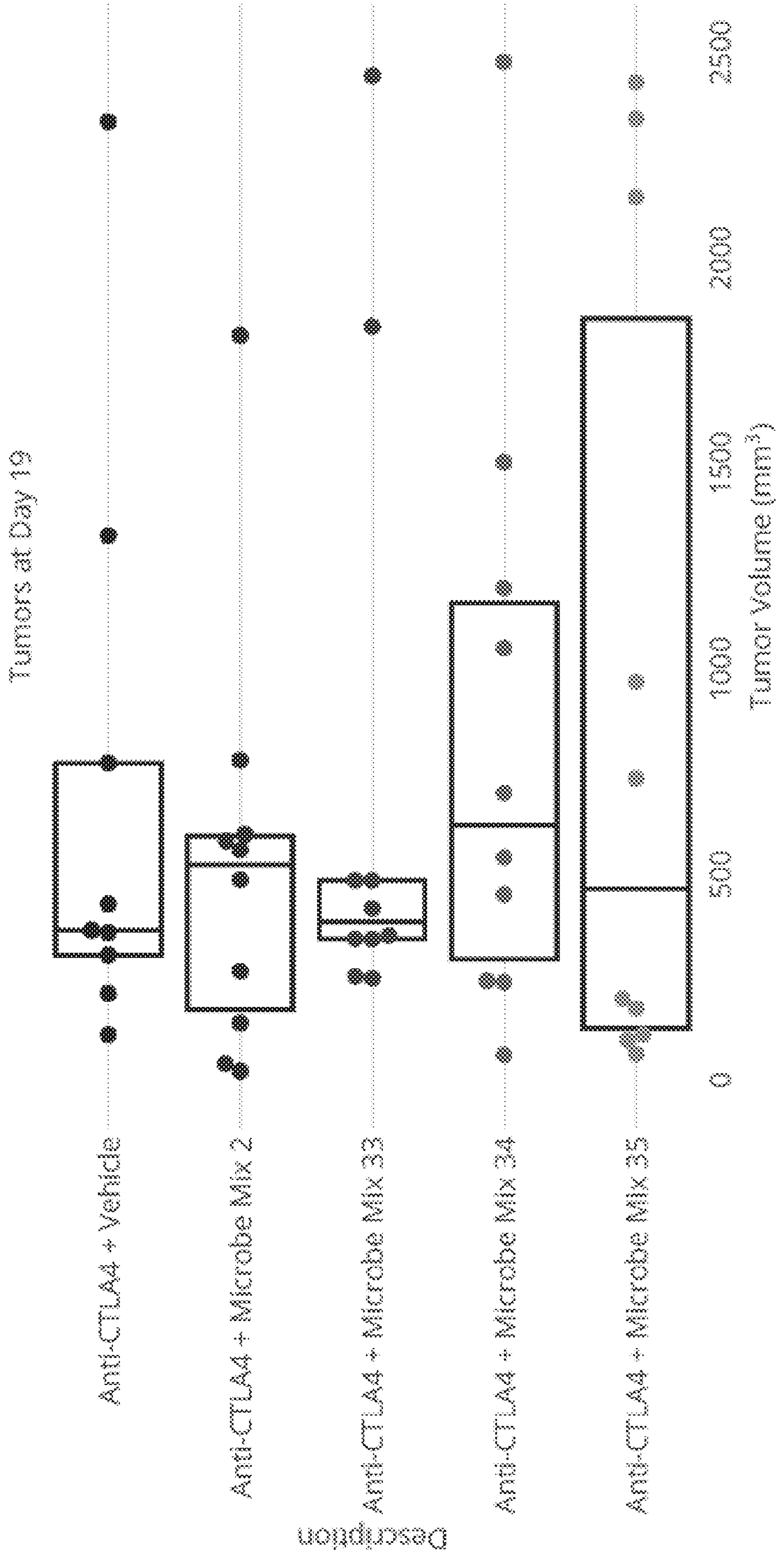
FIG. 45 graphically illustrates tumor volume distributions at day 19 after randomization for each treatment. The box denotes the 25th, 50th, and 75th percentiles of the data, and each point is a single mouse; as discussed in detail in Example 22, below.
Figure 46:
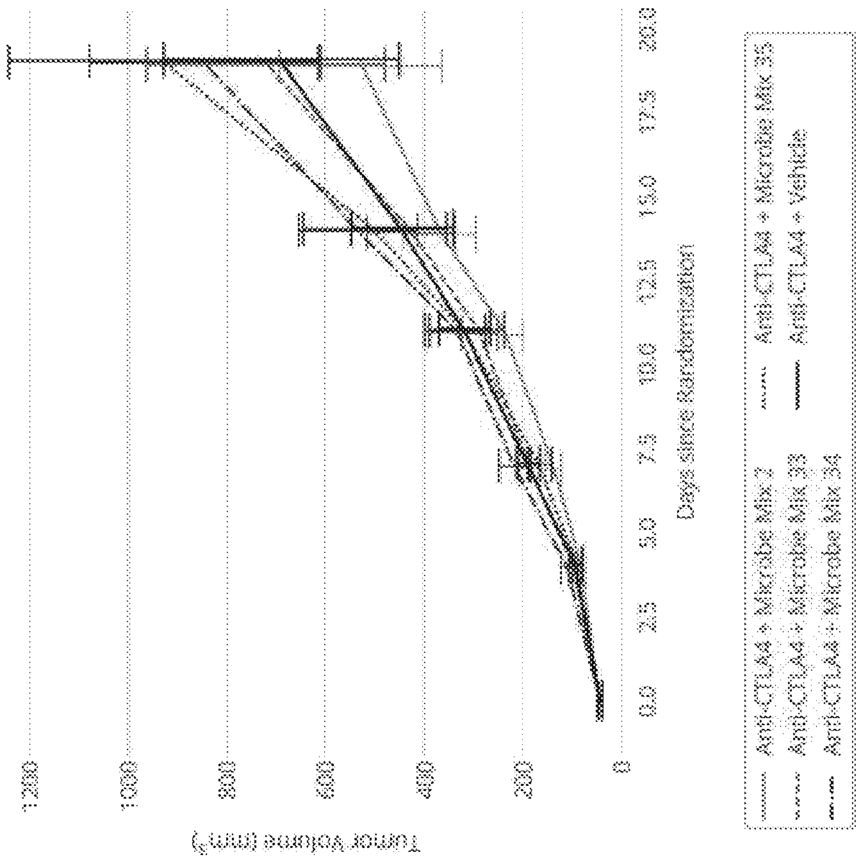
FIG. 46 graphically illustrates tumor volumes that were measured at multiple time points post-inoculation. Mean and standard error of the mean are displayed for each treatment group within the antibiotic pre-treatment groups; as discussed in detail in Example, 22 below.

Mice were pre-treated with antibiotics and inoculated with tumors and randomization occurs and treatment begins at a tumor volume of 50 $mm^3$. Tumor size is measured in all animals receiving the different microbial treatments and antibiotic pre-treatment with and without anti-CTLA4, anti-PD1 or anti-PD-L1 therapy. On average, the animals receiving Microbe Mix 2 (equal amounts of *F. prausnitzii, C. coccoides, R. gnavus, C. scindens, A. muciniphila*, and *E. hirae*) in conjunction with anti-CTLA4 and those receiving Microbe Mix 35 (equal amounts of *A. muciniphilia, F. prausnmitzii, E. hallii, D. longicatena*, and *Blautia* sp. SG-772) have a reduction in tumor size compared to those with other microbes or the anti-CTLA4 monotherapy, as illustrated in FIG. 45. Mean and standard error of the mean are displayed for each treatment group within the antibiotic pre-treatment groups are shown in FIG. 46.

Figure 47:
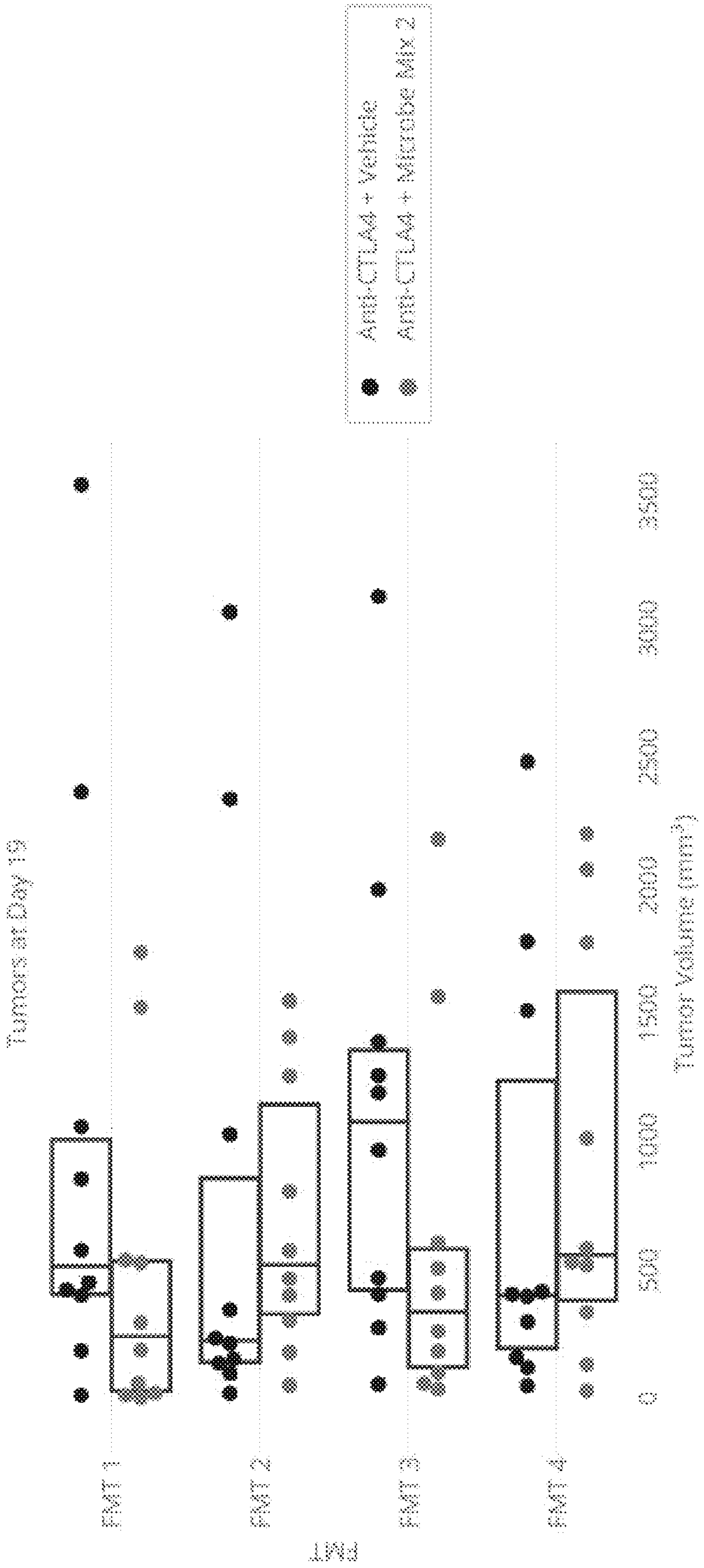
FIG. 47 graphically illustrates tumor volume distribution with and without Microbe Mix 2 being administered for each FMT donor. The box denotes the 25th, 50th, and 75th percentiles of the data, and each point is a single mouse; as discussed in detail in Example 22, below.
Figure 48:
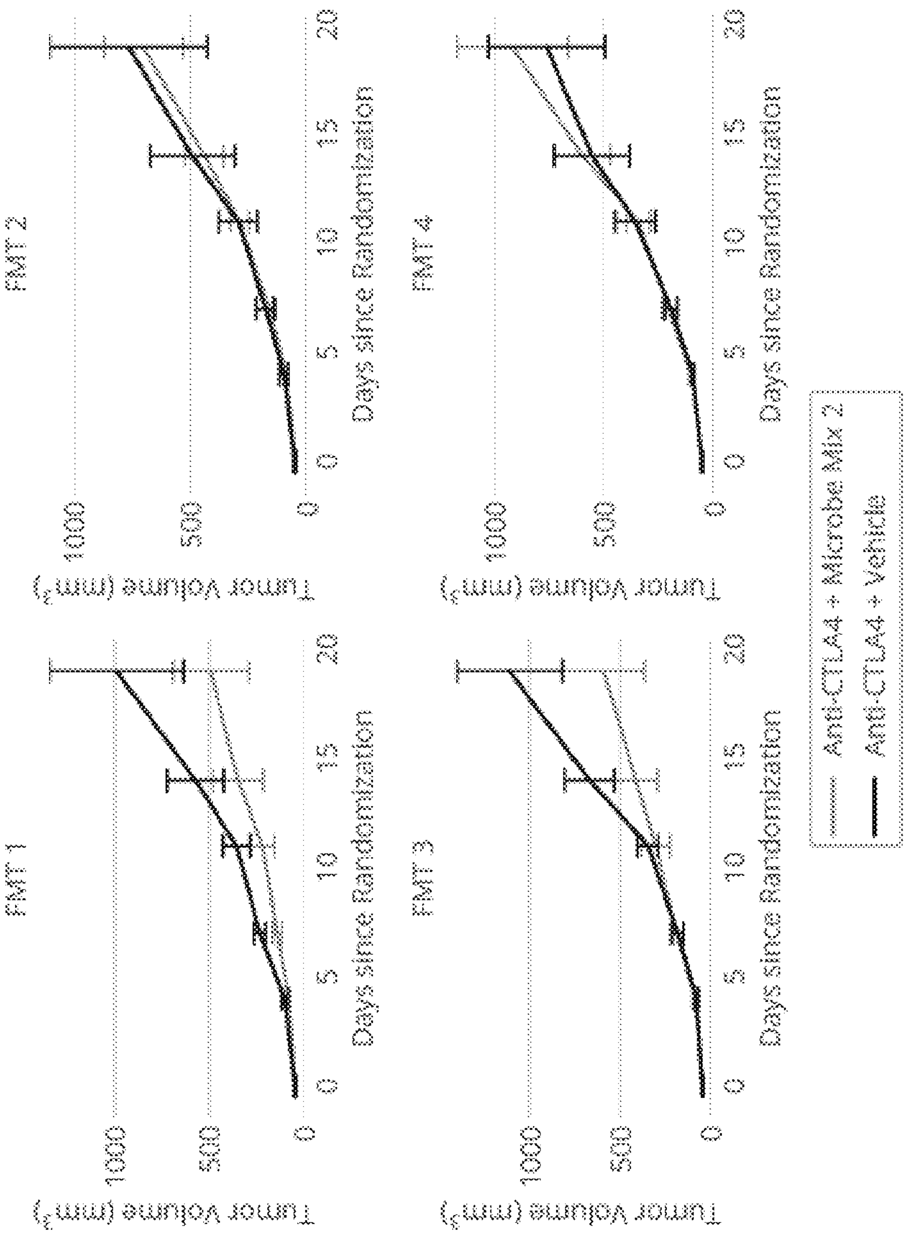
FIG. 48 graphically illustrates the mean tumor volume over time for mice receiving Microbe Mix 2 vs Vehicle for each fecal transplant donor. Error bars are standard error of the mean; as discussed in detail in Example 22, below.
Figure 49:
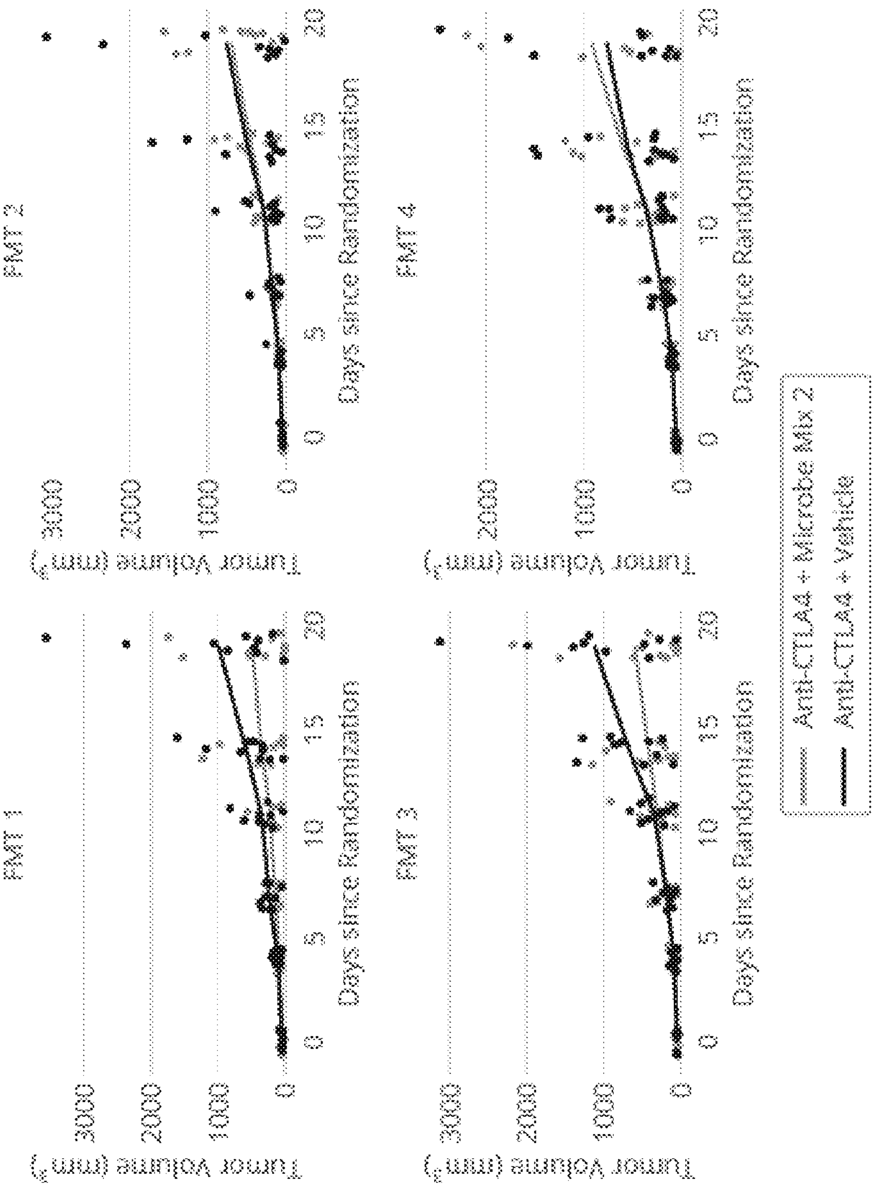
FIG. 49 graphically illustrates the mean tumor volume over time for mice receiving Microbe Mix 2 vs Vehicle for each fecal transplant donor. Each dot denotes an individual mouse's tumor volume; as discussed in detail in Example, 22 below.

Mice were pre-treated with antibiotics, fecal microbiota transplantation (FMT) was performed, and tumors were inoculated. Randomization and treatment began at a tumor volume of 50 $mm^3$. Tumor size was measured in all animals receiving microbial treatments, antibiotic pre-treatment, followed by FMT transfer from cancer patients with and without anti-CTLA4, anti-PD1 or anti-PD-L1 therapy. Four FMTs (1-4) were selected for administration to the mice based on donor cancer patient response to therapy. FMTs 1 and 3 are derived from non-responding cancer patients and FMTs 2 and 4 are from cancer patients that respond to immunotherapy. On average, the mice receiving FMTs 1 and 3 from non-responding cancer patients had larger overall tumors than those receiving FMTs 2 and 4 from responding cancer patients, as illustrated in FIG. 47. On average, the animals receiving Microbe Mix 2 (equal amounts of *F. prausnitzii, C. coccoides, R. gnavus, C. scindens, A. muciniphila*, and *E. hirae*) in conjunction with anti-CTLA4 and FMTs 1 and 3 have a reduction in tumor size compared to those only receiving FMTs 1 and 3 in combination with anti-CTLA4 as illustrated in FIG. 47. Tumor volume mean and standard error of the mean are displayed for each treatment group, as illustrated in FIG. 48. Tumor volume mean curves and individual tumor sizes plotted as dots are displayed for each treatment group, as illustrated in FIG. 49.

Specific genes differentially present or expressed among the cultures are identified using commercial expression analysis software such as SPOTFIRE® (TIBCO Software) or free tools such as BioConductor™. This approach is used to identify genes overrepresented in samples from mice receiving microbial cocktail 2 [equal amounts of *F. praus-* nitzii, C. coccoides, R. gnavus, C. scindens, A. muciniphila, and E. hirae] and microbial cocktail 4 [equal amounts of F. prausnitzii, C. coccoides, R. gnavus, C. scindens, E. lenta, and G. urolithinfaciens] in conjunction with ellagic acid, anti-CTLA4 and anti-PD1. Similarly, LCMS peaks from the metabolomics analysis are identified that have significantly higher or lower concentration in the samples from mice receiving microbial cocktails 2 and 4, ellagic acid, anti-CTLA4 and anti-PD1. These represent candidate metabolites either produced or degraded by these microbes that are important for stimulating immune function and thus contribute to anti-CTLA4 and anti-PD1 function.

Antibiotic induced depletion of mouse microbiota has been shown to significantly reduce the diversity of the microbiota, gut motility and increase the weight and size of the gastrointestina tract (Ge et al. J Transl Med (2017) 15:13). Images of the gastrointestinal tract (GI) for mice in both water and antibiotic pre-treatment groups are shown in FIG. 38A-D. The GI tract for antibiotic pre-treatment groups with vehicle or anti-CTLA-4 treatments was enlarged compared to the equivalent water pre-treatment groups. Treatment groups with microbe mix 2 in combination with anti-CTLA-4 and microbe mix 4+ellagic acid in combination with anti-CTLA-4 had similar sized GI tracts for both pre-treatment groups. The normal size of the GI tract suggests that microbe mixes 2 and 4 have anti-inflammatory properties that may contribute to the observed anti-cancer efficacy.

TABLE 5

| Microbe Mix | Strains |
|---|---|
| 1 | *Faecalibacterium prausnitzii* |
| | *Clostridium coccoides* |
| | *Ruminococcus gnavus* |
| | *Clostridium scindens* |
| 2 | *Faecalibacterium prausnitzii* |
| | *Clostridium coccoides* |
| | *Ruminococcus gnavus* |
| | *Clostridium scindens* |
| | *Akkermansia mucimphila* |
| | *Enterococcus hirae* |
| 3 | *Eggerthella lento* |
| | *Gordonibacter urolithinfaciensans* |
| 4 | *Faecalibacterium prausnitzii* |
| | *Clostridium coccoides* |
| | *Ruminococcus gnavus* |
| | *Clostridium scindens* |
| | *Eggerthella lento* |
| | *Gordonibacter urolithinfaciens* |
| 5 | *Faecalibacterium prausnitzii* |
| | *Clostridium coccoides* |
| | *Ruminococcus gnavus* |
| | *Clostridium scindens* |
| | *Bacteroides thetaiotamicron* |
| | *Bacteroides caccae* |
| | *Gemmiger formicilis* |
| 6 | *Faecalibacterium prausnitzii* |
| | *Clostridium coccoides* |
| | *Ruminococcus gnavus* |
| | *Clostridium scindens* |
| | *Alistipes indistinctus* |
| | *Dorea formicigenerans* |
| 7 | *Faecalibacterium prausnitzii* |
| | *Clostridium coccoides* |
| | *Ruminococcus gnavus* |
| | *Clostridium scindens* |
| | *Bifidobacterium longum* |
| | *Bifidobacterium breve* |
| 8 | *Faecalibacterium prausnitzii* |
| | *Clostridium coccoides* |
| | *Ruminococcus gnavus* |
| | *Clostridium scindens* |
| | *Eggerthella lenta* |

TABLE 5-continued

| Microbe Mix | Strains |
|---|---|
| | *Gordonibacter urolithinfaciens* |
| | *Adlercreutzia equolifaciens* |
| 9 | *Faecabbacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Adlercreutzia equolifaciens* |
| | *Senegalimassilia anaerobia* |
| 10 | *Faecabbacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Adlercreutzia equolifaciens* |
| | *Senegalimassilia anaerobia* |
| | *Ellagibacter isourolithinifaciens* |
| 11 | *Faecabbacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Adlercreutzia equolifaciens* |
| | *Ellagibacter isourolithinifaciens* |
| 12 | *Eggerthella lenta* |
| | *Gordonibacter urolithinfaciens* |
| | *Adlercreutzia equolifaciens* |
| | *Senegalimassilia anaerobia* |
| | *Ellagibacter isourolithinifaciens* |
| 13 | *Eggerthella lenta* |
| | *Gordonibacter urolithinfaciens* |
| | *Adlercreutzia equolifaciens* |
| | *Senegalimassilia anaerobia* |
| | *Ellagibacter isourolithinifaciens* |
| | *Collinsella aerofaciens* |
| 14 | *Faecabbacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Adlercreutzia equolifaciens* |
| | *Senegalimassilia anaerobia* |
| | *Collinsella aerofaciens* |
| 15 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Adlercreutzia equolifaciens* |
| | *Senegalimassilia anaerobia* |
| | *Collinsella aerofaciens* |
| | *Ellagibacter isourolithimfaciens* |
| 16 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Ellagibacter isourolithinifaciens* |
| 17 | *Eggerthella lenta* |
| | *Gordonibacter urolithinfaciens* |
| | *Ellagibacter isourolithinifaciens* |
| 18 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Paraeggerthella hongkongensis* |
| 19 | *Faecalibacterium prausnitzii* |
| | *Clostridium coccoides* |
| | *Ruminococcus gnavus* |
| | *Clostridium scindens* |

TABLE 5-continued

| Microbe Mix | Strains |
|---|---|
| | *Eggerthella lenta* |
| | *Gordonibacter urolithinfaciens* |
| | *Paraeggerthella hongkongensis* |
| | *Slackia isoflavoniconvertens* |
| | *Slackia equolifaciens* |
| 20 | *Faecalibacterium prausnitzii* |
| | *Clostridium coccoides* |
| | *Ruminococcus gnavus* |
| | *Clostridium scindens* |
| | *Gordonibacter urolithinfaciens* |
| 21 | *Eubacterium hallii* |
| 22 | *Faecalibacterium prausnitzii* |
| | *Clostridium coccoides* |
| | *Ruminococcus gnavus* |
| | *Clostridium scindens* |
| | *Eubacterium hallii* |
| 23 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Eubacterium hallii* |
| 24 | *Faecalibacterium prausnitzii* |
| | *Clostridium coccoides* |
| | *Ruminococcus gnavus* |
| | *Clostridium scindens* |
| | *Akkermansia muciniphila* |
| | *Enterococcus hirae* |
| | *Eubacterium hallii* |
| 25 | *Blautia massiliensis* |
| 26 | *Faecalibacterium prausnitzii* |
| | *Clostridium coccoides* |
| | *Ruminococcus gnavus* |
| | *Clostridium scindens* |
| | *Blautia massiliensis* |
| 27 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Blautia massiliensis* |
| 28 | *Faecalibacterium prausnitzii* |
| | *Clostridium coccoides* |
| | *Ruminococcus gnavus* |
| | *Clostridium scindens* |
| | *Akkermansia muciniphila* |
| | *Enterococcus hirae* |
| | *Blautia massiliensis* |
| 29 | *Faecalibacterium prausnitzii* |
| | *Clostridium coccoides* |
| | *Ruminococcus gnavus* |
| | *Clostridium scindens* |
| | *Eggerthella lenta* |
| | *Gordonibacter urolithinfaciens* |
| | *Blautia massiliensis* |
| | *Eubacterium hallii* |
| 30 | *Faecalibacterium prausnitzii* |
| | *Clostridium coccoides* |
| | *Ruminococcus gnavus* |
| | *Clostridium scindens* |
| | *Akkermansia muciniphila* |
| | *Enterococcus hirae* |
| | *Blautia massiliensis* |
| | *Eubacterium hallii* |
| 31 | *Faecalibacterium prausnitzii* |
| | *Clostridium coccoides* |
| | *Ruminococcus gnavus* |
| | *Clostridium scindens* |
| | *Gordonibacter urolithinfaciens* |
| | *Eubacterium hallii* |
| 32 | *Faecalibacterium prausnitzii* |
| | *Clostridium coccoides* |
| | *Ruminococcus gnavus* |
| | *Clostridium scindens* |

TABLE 5-continued

| Microbe Mix | Strains |
|---|---|
| | *Gordonibacter urolithinfaciens* |
| | *Eubacterium hallii* |
| | *Blautia massiliensis* |
| 33 | *Akkermansia muciniphila* |
| | *Faecalibacterium prausnitzii* |
| 34 | *Eubacterium Hallii* |
| | *Dorea Longicatena* |
| | *Blautia* sp. SG-772 |
| 35 | *Akkermansia muciniphila* |
| | *Faecalibacterium prausnitzii* |
| | *Eubacterium Hallii* |
| | *Dorea Longicatena* |
| | *Blautia* sp. SG-772 |
| 36 | *Akkermansia muciniphila* |
| | *Faecalibacterium prausnitzii* |
| | *Ruminococcus gnavus* |
| 37 | *Dorea Longicatena* |
| | *Dorea formicigenerans* |
| | *Blautia* sp. SG-772 |
| | *Eubacterium Hallii* |
| | *Ruminococcus faecis* |
| | *Coprococcus comes* |
| 38 | *Faecalibacterium prausnitzii* |
| | *Ruminococcus gnavus* |
| 39 | *Ruminococcus gnavus* |
| | *Eubacterium ramulus* |
| | *Gemmiger formicilis* |
| 40 | *Anaerostipes hadrus* |
| | *Dorea formicigenerans* |
| | *Dorea longicatena* |
| | *Coprococcus comes* |
| | *Ruminococcus faecis* |
| 41 | *Anaerostipes hadrus* |
| | *Dorea formicigenerans* |
| | *Dorea longicatena* |
| | *Coprococcus comes* |
| | *Ruminococcus faecis* |
| | *Ruminococcus gnavus* |
| 42 | *Anaerostipes hadrus* |
| | *Dorea formicigenerans* |
| | *Dorea longicatena* |
| | *Coprococcus comes* |
| | *Ruminococcus faecis* |
| | *Akkermansia muciniphila* |
| 43 | *Akkermansia muciniphila* |
| | *Eubacterium ramulus* |
| | *Gemmiger formicilis* |
| 44 | *Akkermansia muciniphila* |
| | *Ruminococcus gnavus* |
| | *Ruminococcus torques* |
| | *Bifidobacterium bifidum* |
| 45 | *Akkermansia muciniphila* |
| | *Ruminococcus gnavus* |
| | *Ruminococcus torques* |
| 46 | *Akkermansia muciniphila* |
| | *Ruminococcus torques* |
| | *Dorea longicatena* |
| | *Coprococcus comes* |
| | *Anaerostipes hadrus* |
| 47 | *Akkermansia muciniphila* |
| | *Roseburia inulivorans* |
| | *Dorea longicatena* |
| | *Coprococcus comes* |
| | *Anaerostipes hadrus* |
| 48 | *Dorea longicatena* |
| | *Coprococcus comes* |
| | *Anaerostipes hadrus* |
| | *Eubacterium Hallii* |
| | *Faecalibacterium prausnitzii* |
| | *Collinsella aerofaciens* |
| 49 | *Dorea longicatena* |
| | *Coprococcus comes* |
| | *Anaerostipes hadrus* |
| | *Eubacterium Hallii* |
| | *Faecalibacterium prausnitzii* |
| | *Blautia obeum* |
| 50 | *Akkermansia muciniphila* |
| | *Ruminococcus gnavus* |

TABLE 5-continued

| Microbe Mix | Strains |
|---|---|
| | *Dorea longicatena* |
| | *Coprococcus comes* |
| | *Anaerostipes hadrus* |
| 51 | *Akkermansia muciniphila* |
| | *Gemmiger formicilis* |
| | *Asacharobacter celatus* |
| | *Collinsella aerofaciens* |
| | *Alistipes putredinis* |
| | *Gordonibacter urolithinfaciens* |
| 52 | *Akkermansia muciniphila* |
| | *Mono globus pectinilyticus* |
| | *Bacteroides galacturonicus* |
| | *Collinsella aerofaciens* |
| | *Ruminococcus gnavus* |
| | *Dorea longicatena* |
| 53 | *Akkermansia muciniphila* |
| | *Mono globus pectinilyticus* |
| | *Bacteroides galacturonicus* |
| | *Collinsella aerofaciens* |
| | *Ruminococcus torques* |
| | *Dorea longicatena* |

Example 23: Characterization of Urolithin Production in Actinobacteria

*Gordonibacter urolithinfaciens* DSM 27213, *Gordonibacter* pamelaeae DSM 19378, *Senegalimassilia anaerobia* DSM 25959, *Collinsella aerofaciens* DSM 3979, *Adlercreutzia* equolifaciens DSM 19450, *Ellagibacter isourolithinifaciens* DSM 104140, *Slackia isoflavoniconvertens* DSM 22006, *Slackia* equolifaciens DSM 2485, *Paraeggerthella hongkongensis* DSM 16106 and *Eggerthella lenta* DSM 2243 are tested for the ability to bioconvert ellagic acid and urolithin C into downstream urolithin species in liquid culture, as described in Selma et al. 2017 Front Microbiol 8:1521, with the following modifications:

1. Ellagic acid (Millipore Sigma) and urolithin C (Dalton Research Molecules) are each added to propylene glycol to make 1.5 mM stock solutions in 1.5 ml Eppendorf tubes. A 1.5 ml size plastic pestle is used to fully suspend and solubilize the compounds in the propylene glycol.
2. Prepare reduced anaerobe basal broth (ABB) medium as 10 ml sterilized aliquots in Hungate tubes.
3. Inoculate six ABB hungate tubes each with 0.1 ml bacteria to final density of $1E^6$ cfu/ml.
4. To two of the six inoculated tubes for each strain, add 0.1 ml ellagic acid stock solution to final concentration of 0.015 mM.
5. To two of the remaining inoculated tubes for each strain, add 0.1 ml urolithin C stock solution to final concentration of 0.015 mM.
6. To the last two inoculated tubes for each strain, both ellagic acid and urolithin C are withheld. These "no compound" tubes will serve as background controls for downstream LCMS analyses.
7. Once assembled, all tubes are placed horizontally in a 37° C. environmental shaker set at 100 rpm.
8. At seven day and fourteen-day intervals, one ellagic acid, urolithin C and no compound tube representing each inoculated strain is removed from the incubator and processed as follows:
   a. Hungate culture tubes are opened and decanted into 15 ml conical tubes, then centrifuged at 4000 g for 10 minutes in a swinging bucket centrifuge to pellet cell growth.

b. 9 ml of the culture supernatant is removed by pipette and then transferred into two 4.5 ml volumes each in a fresh 15 ml conical tube.
   c. To each 4.5 ml volume is added an equal volume of ethyl acetate acidified by adding HCl to 0.1 mM.
   d. The tubes are vortexed for one minute, then centrifuged at 4000 g for 10 minutes in a swinging bucket centrifuge to separate the solvent and aqueous phases.
   e. Three ml of the top ethyl acetate phase is removed by pipette and transferred into two 1.5 ml volumes in 2 ml Eppendorf tubes.
   f. A hole is made in the lid of the 2 ml Eppendorf tubes using an 18-gauge needle, then the tubes are placed in a rotary evaporator (GeneVac) at the low boiling point setting for 2 hours to remove all solvent.
   g. Dried material remaining in the tube is solubilized with 50 acidified methanol in preparation for injection and analysis by LCMS to determine remaining concentrations of ellagic acid and urolithin C and evidence of bioconversion of these compounds to downstream urolithin species.

Example 24: Method of Treating a Subject with a Microbial Cocktail

A patient is suffering from cancer. The patient is administered one of the present microbial cocktails (Tables 1, and as described in Examples 16 and 22) in combination with a checkpoint inhibitor, CAR-T or other immunotherapy for the duration of treatment. Specifically, the patient is administered a microbial cocktail at a dose of $10^8$, $10^9$ or $10^{10}$ bacteria total in a lyophilized form formulated in an enteric coated capsule. The patient takes the capsule by mouth and resumes a normal diet after 4, 8, 12, or 24 hours. In another embodiment, the patient may take the capsule by mouth before, during, or immediately after a meal. In another embodiment, the patient is given a course of antibiotics one to two weeks prior to the first dose of microbial cocktail, or three weeks prior, or four weeks prior, or up to 6 months prior to the first dose of microbial cocktail. Patient response to the combination therapy is a measure of success and is based on radiographic assessment using the Response Evaluation Criteria in Solid Tumors (RECIST 1.1) criteria (Schwartz L H, et al. Eur. J. Cancer. 2016; 62:132-137) at 6 months after treatment initiation. Patients are classified as responders if they achieved an objective response (complete or partial response or stable disease lasting at least 6 months), versus non-responders if they progressed on therapy or had stable disease lasting less than 6 months.

Figure 17:
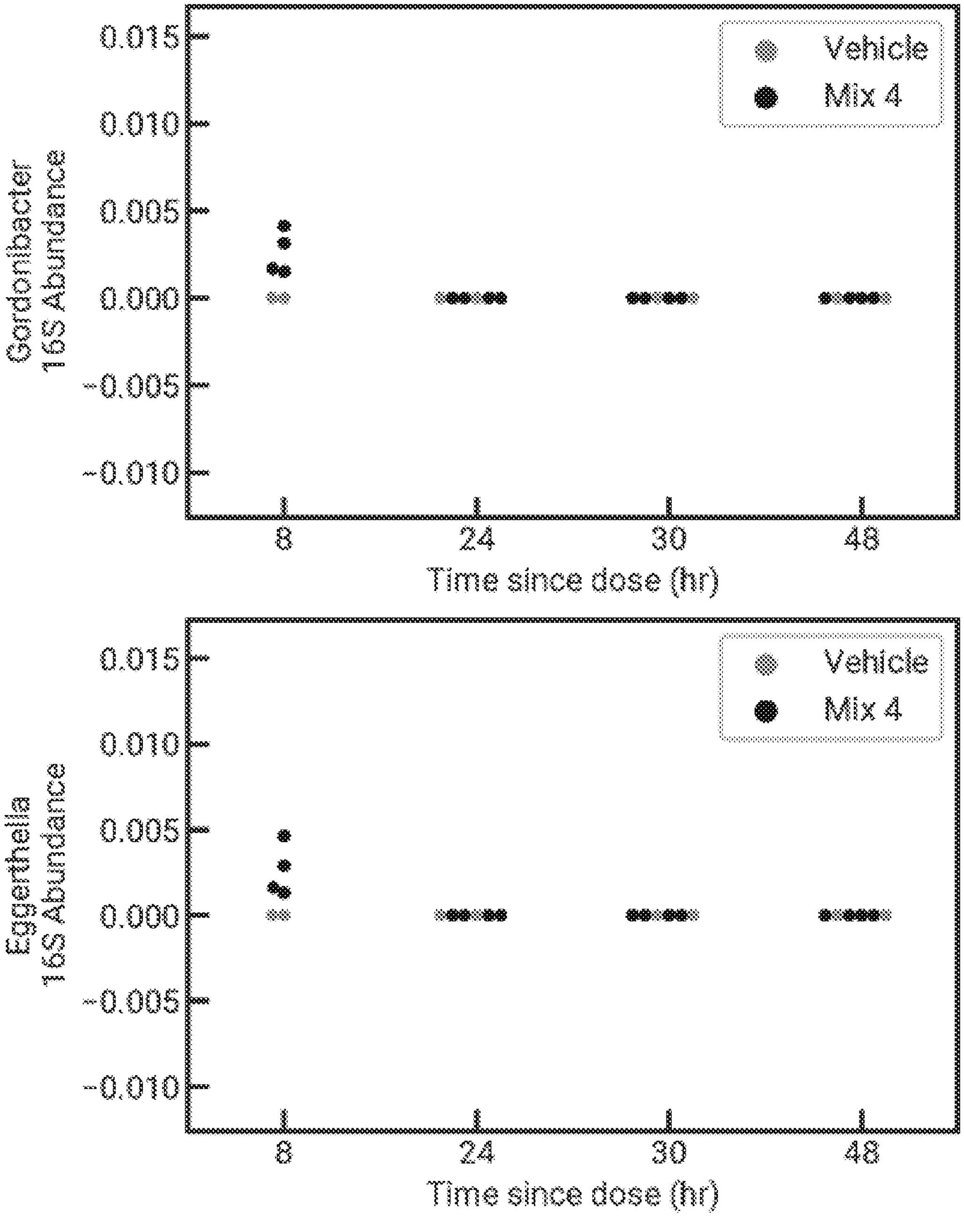
FIG. 17 graphically illustrates the 16S rRNA relative read abundance by time point for two genera, *Eggerthella* and *Gordonibacter* from mouse stool samples collected overtime. Microbe mix 4 contains organisms in both *Eggerthella* and *Gordonibacter*, and as expected, these genera have a non-zero read abundance at the 8-hour time point only when microbial cocktail 4 is administered; as discussed in detail in Example 25, below.

Example 25—Fecal Composition Analysis of Non-Tumor Bearing Mice Treated with Microbial Cocktails BALB/c mice were obtained from the Jackson laboratory and 6-8-week-old female mice were used. Stool was collected from non-tumor bearing Balb/c mice at 8 h, 24 h, 30 h, and 48 hours treated with vehicle or microbe mix 4. Mice were treated with either vehicle or microbe mix 4 for a total of 3 doses on a biweekly schedule starting on Day 1. 16S rRNA analysis of collected fecal samples was performed to evaluate detection of the individual microbes in mix 4. The qiime2 pipeline was used in conjunction with the SILVA rRNA database to assign a phylogenetic identity to each read. FIG. 17 shows the relative read abundance by time point for two genera, *Eggerthella* and *Gordonibacter*.

Microbe Mix 4 contains organisms in both *Eggerthella* and *Gordonibacter*, and as expected, these genera have a non-zero read abundance at the 8-hour time point only when microbe mix 4 is administered.

Example 26: Method of Stratifying Subjects Prior to Treating with a Microbial Cocktail A patient is suffering from cancer. A stool sample is collected and whole genome sequencing performed as described in Example 7. Centered-log-ratio transformed abundances are calculated, and principal components determined using the loadings used to generate FIG. 55, FIG. 56, or analogous plot. The patient's sample is plotted on the same axes and compared to the other points for both cancer patients and healthy subjects. In another embodiment, the stool sample is subjected to metabolomics analysis as described in Example 7. Principal components are determined using the loadings used to generate FIG. 57*b*, or analogous plot. In yet another embodiment, the patient's blood is taken and plasma isolated as described in Example 7. The plasma is subjected to metabolomics analysis, and principal components are determined using the loadings used to generate FIG. 57*a*, or analogous plot. If the patient's sample fits within the cluster composed primarily of cancer patients for any of these analyses, this patient is projected to be non-responsive and thus a good candidate for co-treatment with a live biotherapeutic. If the sample clusters with primarily healthy individuals, the patient is likely to naturally be a responder to treatment. In yet another embodiment, the immune profile of the patient's blood is identified by flow cytometery, single cell proteomics (CyTOF), single cell RNA sequencing, or other method. Specifically, the fraction of T cells identified as CD8+HLA-DR+ is determined. If this value falls above the mean value identified by analysis of a cohort of cancer patients (e.g., FIG. 50), then this patient is projected to be non-responsive, and thus considered a good candidate for co-treatment with live biotherapeutic. Finally, any combination of these methods may be used for patient stratification. The examples given here are using principal components analysis, but in general any machine learning algorithm or correlation analysis can be done to determine if the patient sample identifies with non-responders to treatment. Patients stratified as such are therefore administered one of the present microbial cocktails (Tables 1, and as described in Examples 16 and 22) in combination with a checkpoint inhibitor, CAR-T, other immunotherapy, or chemotherapy for the duration of treatment. Specifically, the patient is administered a microbial cocktail at a dose of $10^8$, $10^9$ or $10^{10}$ bacteria total in a lyophilized form formulated in an enteric coated capsule. The patient takes the capsule by mouth and resumes a normal diet after 4, 8, 12, or 24 hours. In another embodiment, the patient may take the capsule by mouth before, during, or immediately after a meal. In another embodiment, the patient is given a course of antibiotics two weeks prior to the first dose of microbial cocktail, three weeks prior, four weeks prior, or up to 6 months prior to the first dose of microbial cocktail. Patient response to the combination therapy is a measure of success and is based on radiographic assessment using the Response Evaluation Criteria in Solid Tumors (RECIST 1.1) criteria (Schwartz L H, et al. Eur. J. Cancer. 2016; 62:132-137) at 6 months after treatment initiation. Patients are classified as responders if they achieved an objective response (complete or partial response or stable disease lasting at least 6 months), versus non-responders if they progressed on therapy or had stable disease lasting less than 6 months.

A number of embodiments of the invention have been described. Nevertheless, it can be understood that various modifications may be made without departing from the spirit and scope of the invention. Accordingly, other embodiments are within the scope of the following claims.

What is claimed is:

1. A method for controlling, ameliorating or treating a cancer in an individual in need thereof, comprising administering or having administered to an individual in need thereof:

(a) an inhibitor of an inhibitory immune checkpoint molecule; and (b) a formulation comprising a combination of bacteria which are: *Faecalibacterium prausnitzii, Clostridium coccoides, Ruminococcus gnavus, Clostridium scindens, Eggerthella lenta* and *Gordonibacter urolithinfaciens.*

2. The method of claim 1, wherein:

(a) the formulation comprises an inner core surrounded by an outer layer of polymeric material enveloping the inner core, wherein the combination of bacteria is in the inner core;

(b) the formulation is formulated or manufactured as or in: a nano-suspension delivery system; an encochleated formulation; or, as a multilayer crystalline, spiral structure with no internal aqueous space;

(c) the formulation is formulated or manufactured as a delayed or gradual enteric release composition or formulation, (d) the formulation comprises a gastro-resistant coating designed to dissolve at a pH of 7 in the terminal ileum, (e) the formulation is coated with an acrylic based resin, (f) the formulation is coated with a poly(meth)acrylate, optionally a methacrylic acid copolymer Type B-NF, which dissolves at pH 7 or greater, (g) the formulation is a multimatrix (MMX) formulation, or (h) the formulation is manufactured as an enteric coated formulation to bypass the acid of the stomach and bile of the duodenum.

3. The method of claim 1, wherein:

(a) the bacteria in the combination are substantially dormant, or (b) the combination of bacteria comprises dormant colony forming live bacteria which are live vegetative bacterial cells that have been rendered dormant by lyophilization or freeze drying.

4. The method of claim 1, wherein the formulation comprises at least about $1\times10^4$ colony forming units (CFUs), or between about $1\times10^1$ and $1\times10^{13}$ CFUs, of the combination of bacteria.

5. The method of claim 4, wherein the formulation comprises between about $1\times10^2$ and $1\times10^{10}$ CFUs, $1\times10^2$ and $1\times10^8$ CFUs, $1\times10^3$ and $1\times10^7$ CFUs, or $11\times10^4$ and $1\times10^6$ CFUs, of the combination of bacteria.

6. The method of claim 1, wherein:

(a) the formulation further comprises water, saline, a pharmaceutically acceptable preservative, a carrier, a buffer, a diluent, an adjuvant or a combination thereof, (b) the formulation is administered orally or rectally, or is formulated as a liquid, a food, a gel, a candy, an ice, a lozenge, a tablet, pill or capsule, or a suppository or as an enema formulation, or for any form of intra-rectal or intra-colonic administration;

(c) the formulation is administered to the subject in one, two, three, or four or more doses, and wherein the one, two, three, or four or more doses are administered once a day, bid or tid, or every other day, every third day, or about once a week, or the two, three, or four or more doses are administered at least a week apart, or doses are separated by about a week; or (d) the formulation further comprises an antibiotic, or the method further comprises administration of an antibiotic, and optionally at least one dose of the antibiotic is administered before a first administration of the formulation, optionally at least one dose of the antibiotic is administered one day or two days, or more, before a first administration of the formulation.

7. The method of claim 1, wherein:

(a) the inhibitor of the inhibitory immune checkpoint molecule comprises a protein or polypeptide that binds to an inhibitory immune checkpoint protein, and optionally the inhibitor of the inhibitory immune checkpoint protein is an antibody or an antigen binding fragment thereof that specifically binds to the inhibitory immune checkpoint protein;

(b) the inhibitor of the inhibitory immune checkpoint molecule targets a compound or protein comprising: a CTLA4 or CTLA-4 (cytotoxic T-lymphocyte-associated protein 4, also known as CD152, or cluster of differentiation 152); Programmed cell Death protein 1, also known as PD-1 or CD279; Programmed Death-Ligand 1 (PD-L1), also known as cluster of differentiation 274 (CD274) or B7 homolog 1 (B7-H1); PD-L2; A2AR (adenosine A2A receptor, also known as ADORA2A); B7-H3; B7-H4; BTLA (B- and T-lymphocyte attenuator protein); KIR (Killer-cell Immunoglobulin-like Receptor); IDO (Indoleamine-pyrrole 2,3-dioxygenase); LAG3 (Lymphocyte-Activation Gene 3 protein); TIM-3; VISTA (V-domain Ig suppressor of T cell activation protein); or any combination thereof;

(c) the inhibitor of the inhibitory immune checkpoint molecule comprises: ipilimumab; pembrolizumab; nivolumab; atezolizumab; avelumab; durvalumab; or any combination thereof; or (d) the inhibitor of the inhibitory immune checkpoint molecule is administered by: intravenous (IV) injection, intramuscular (IM) injection, intratumoral injection or subcutaneous injection; or, is administered orally or by suppository.

8. The method of claim 1, wherein the cancer is advanced melanoma, non-small-cell lung cancer or renal cell carcinoma.

9. The method of claim 1, further comprising administering, or having administered, or delivering an ellagic acid and/or an ellagitannin, or a benzo-coumarin or a dibenzo-α-pyrone.

10. The method of claim 9, further comprising administering, or having administered, or delivering an urolithin A, or any polycyclic aromatic compound containing a 1-benzopyran moiety with a ketone group at the C2 carbon atom, or a 1-benzopyran-2-one.

11. The method of claim 10, wherein the ellagic acid and/or the ellagitannin, or the benzo-coumarin or dibenzo-α-pyrone or urolithin A is administered or delivered before administration of, simultaneously with, and/or after administration or delivery of the formulation.

12. The method of claim 1, further administering, or having administered, or delivering, a genetically engineered cell.

13. The method of claim 12, wherein the genetically engineered cell is a lymphocyte.

14. The method of claim 13, wherein the lymphocyte is a B cell or a T cell (CAR-T cell).

15. The method of claim 13, wherein the lymphocyte is a tumor infiltrating lymphocyte (TIL).

16. The method of claim 12, wherein the genetically engineered cell expresses a chimeric antigen receptor (CAR).

17. The method of claim 12, wherein the genetically engineered cell is administered or delivered before administration of, simultaneously with, and/or after administration or delivery of the formulation.

18. The method of claim 1, wherein the combination of bacteria can individually or together metabolize urolithin A from ellagic acid, or can individually or together synthesize urolithin A.

19. The method of claim 1, wherein the combination of bacteria comprise at least about 1%, 5%, 10%, 20%, 30%, 40%, or 50% or more spore forms based on the total amount of the combination of bacteria.

20. The method of claim 1, wherein the formulation consists of a combination of *Faecalibacterium prausnitzii, Clostridium coccoides, Ruminococcus gnavus, Clostridium scindens, Eggerthella lenta* and *Gordonibacter urolithinfaciens*.

21. The method of claim 2, wherein the polymeric material comprises a natural polymeric material.

* * * * *